(12) United States Patent
Ito et al.

(10) Patent No.: US 11,053,229 B2
(45) Date of Patent: Jul. 6, 2021

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Hirokatsu Ito, Ichihara (JP); Tasuku Haketa, Chiba (JP); Yu Kudo, Chiba (JP); Yumiko Mizuki, Bunkyo-ku (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 49 days.

(21) Appl. No.: 16/491,370

(22) PCT Filed: Mar. 7, 2018

(86) PCT No.: PCT/JP2018/008855
§ 371 (c)(1),
(2) Date: Sep. 5, 2019

(87) PCT Pub. No.: WO2018/164201
PCT Pub. Date: Sep. 13, 2018

(65) Prior Publication Data
US 2020/0392122 A1 Dec. 17, 2020

(30) Foreign Application Priority Data
Mar. 8, 2017 (JP) .............................. JP2017-044367

(51) Int. Cl.
*C07D 407/12* (2006.01)
*H01L 51/00* (2006.01)
*H01L 51/50* (2006.01)

(52) U.S. Cl.
CPC .......... *C07D 407/12* (2013.01); *H01L 51/006* (2013.01); *H01L 51/0052* (2013.01);
(Continued)

(58) Field of Classification Search
CPC ........ C07D 407/12; H01L 51/50; H01L 51/00
See application file for complete search history.

(56) References Cited

U.S. PATENT DOCUMENTS

2007/0278938 A1 12/2007 Yabunouchi et al.
2008/0106190 A1 5/2008 Yabunouchi et al.
(Continued)

FOREIGN PATENT DOCUMENTS

JP 2010-92940 A 4/2010
JP 2011-51936 A 3/2011
(Continued)

OTHER PUBLICATIONS

International Search Report dated Apr. 24, 2018 in PCT/JP2018/008855 filed on Mar. 7, 2018.

*Primary Examiner* — Sheng-Bai Zhu
(74) *Attorney, Agent, or Firm* — Oblon, McClelland, Maier & Neustadt, L.L.P.

(57) ABSTRACT

A compound represented by formula (1):

(Continued)

wherein $R^1$ to $R^7$, $R^{11}$ to $R^{18}$, $L^1$ to $L^3$, a to c, n, and Ar are as defined in the description, provides an organic electroluminescence device having an emission efficiency and a device lifetime further improved.

32 Claims, 1 Drawing Sheet

(52) U.S. Cl.
CPC ...... *H01L 51/0072* (2013.01); *H01L 51/0073* (2013.01); *H01L 51/5012* (2013.01); *H01L 51/5056* (2013.01)

(56) References Cited

U.S. PATENT DOCUMENTS

| | | |
|---|---|---|
| 2009/0066235 A1 | 3/2009 | Yabunouchi et al. |
| 2011/0315964 A1 | 12/2011 | Eida et al. |
| 2012/0018710 A1 | 1/2012 | Eida et al. |
| 2012/0074395 A1 | 3/2012 | Yabunouchi et al. |
| 2012/0146014 A1 | 6/2012 | Kato |
| 2012/0187391 A1 | 6/2012 | Kato et al. |
| 2012/0292606 A1 | 11/2012 | Kato |
| 2013/0105771 A1 | 5/2013 | Ryu et al. |
| 2014/0061602 A1 | 3/2014 | Kato et al. |
| 2014/0159023 A1 | 6/2014 | Matsumoto et al. |
| 2015/0171356 A1 | 6/2015 | Nakamura et al. |
| 2015/0221874 A1 | 8/2015 | Kim et al. |
| 2015/0287921 A1 | 10/2015 | Kato et al. |
| 2015/0287931 A1 | 10/2015 | Kato et al. |
| 2016/0126469 A1 | 5/2016 | Nakano |
| 2016/0181525 A1 | 6/2016 | Kato et al. |
| 2016/0190477 A1 | 6/2016 | Kawakami et al. |
| 2016/0197277 A1 | 7/2016 | Kato et al. |
| 2016/0260905 A1 | 9/2016 | Lee et al. |
| 2018/0179206 A1* | 6/2018 | Haketa ................ C07D 471/10 |
| 2019/0088879 A1* | 3/2019 | Haketa ................ C07D 335/12 |
| 2020/0024263 A1* | 1/2020 | Ito ........................ C07D 405/12 |

FOREIGN PATENT DOCUMENTS

| | | |
|---|---|---|
| JP | 2012-111719 A | 6/2012 |
| KR | 10-2015-0068282 A | 6/2015 |
| KR | 10-2015-0070661 A | 6/2015 |
| KR | 10-2016-002790 A | 3/2016 |
| KR | 10-2016-0059602 A | 5/2016 |
| KR | 10-2016-0059609 A | 5/2016 |
| WO | WO 2010/061824 A1 | 6/2010 |
| WO | WO 2010/114017 A1 | 10/2010 |
| WO | WO 2011/024922 A1 | 3/2011 |
| WO | WO 2013/118812 A1 | 8/2013 |
| WO | WO 2014/132636 A1 | 9/2014 |
| WO | WO 2016/006708 A1 | 1/2016 |
| WO | WO 2016/006711 A1 | 1/2016 |
| WO | WO 2016/032066 A1 | 3/2016 |
| WO | WO 2016/064111 A1 | 4/2016 |

* cited by examiner

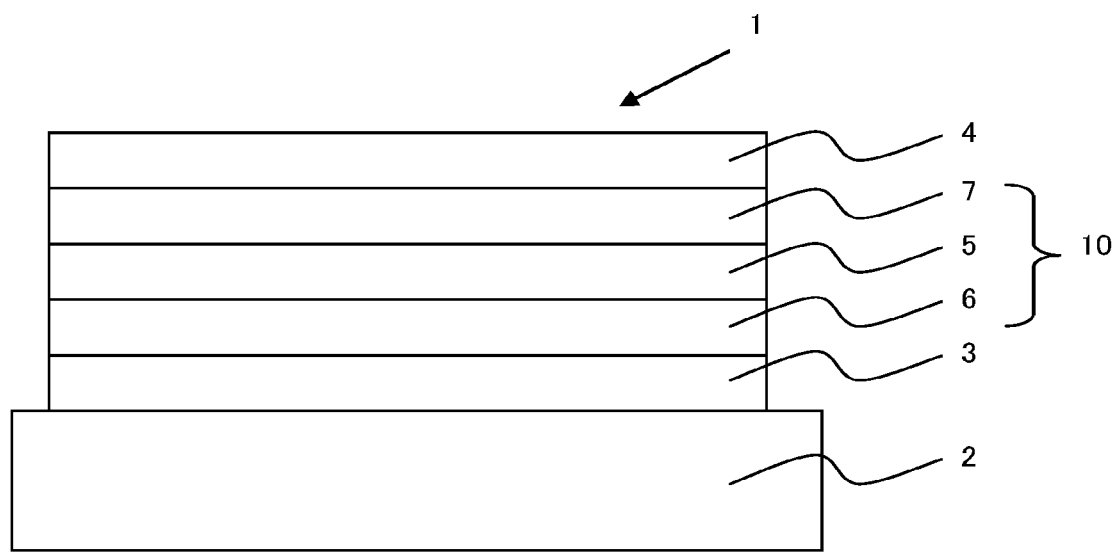

COMPOUND, MATERIAL FOR ORGANIC ELECTROLUMINESCENT ELEMENT, ORGANIC ELECTROLUMINESCENT ELEMENT, AND ELECTRONIC DEVICE

TECHNICAL FIELD

The present invention relates to compounds, materials for organic electroluminescence devices comprising the compounds, organic electroluminescence devices comprising the compounds, and electronic devices comprising the organic electroluminescence devices.

BACKGROUND ART

An organic electroluminescence device ("organic EL device") is generally composed of an anode, a cathode, and an organic layer sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for obtaining an organic EL device with a high efficiency to develop a compound that transports electrons or holes into the light emitting region efficiently and facilitates the recombination of electrons and holes.

Patent Literature 1 describes a compound wherein a 9,9-diphenylfluorenyl group is bonded to the central nitrogen atom directly or via a linker and two groups selected from a dibenzofuranyl group, a dibenzothiophenyl group, and a carbazolyl group are bonded to the central nitrogen atom each directly or via a linker. The compound is used in a hole transporting layer.

Patent Literature 2 discloses the use of a composition in a hole transporting layer, wherein the composition comprises an amine compound (1) including a C-carbazolyl group bonded to the central nitrogen atom directly or via a linker and an amine compound (2) including a N-carbazolyl group bonded to the central nitrogen atom directly or via a linker. As an example of the amine compound (2), a compound wherein a dibenzofuranyl group and/or a dibenzothiophenyl group is directly bonded to the central nitrogen group is described.

Patent Literature 3 discloses an amine compound wherein a group represented by formula (1), a group represented by formula (2) or (3), and a group selected from a group represented by formula (2) or (3) and a substituted or unsubstituted aryl group are bonded to the central nitrogen atom:

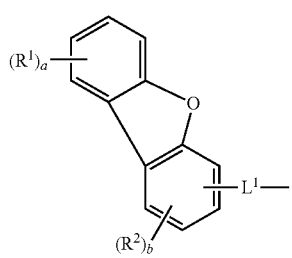

(1)

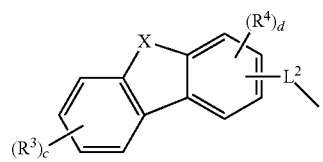

(2)

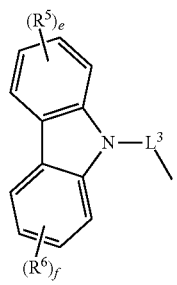

(3)

wherein, X is an oxygen atom or NAr$^1$ and Ar$^1$ is a substituted or unsubstituted aryl group.

The amine compound is used in a hole transporting layer or a hole injecting layer.

However, Patent Literature 3 fails to describe a compound having a 1-benzofuranyl group.

CITATION LIST

Patent Literature

Patent Literature 1: WO 2016/006711
Patent Literature 2: KR10-2016-0059602A
Patent Literature 3: WO 2010/061824

SUMMARY OF INVENTION

Technical Problem

Various compounds useful for the production of organic EL devices have been reported. However, a compound that further improves the performance of organic EL devices has been still demanded.

The present invention has been made to solve the above problem and an object of the invention is to provide organic EL devices that are further improved in emission efficiency and device lifetime and provide novel compounds for achieving such organic EL devices.

Solution to Problem

As a result of extensive research for achieving the above object, the inventors have found that a compound represented by formula (1) provides an organic EL device having a further improved emission efficiency and device lifetime.

In an aspect, the invention provides a compound represented by formula (1) (hereinafter also referred to as "compound (1)"):

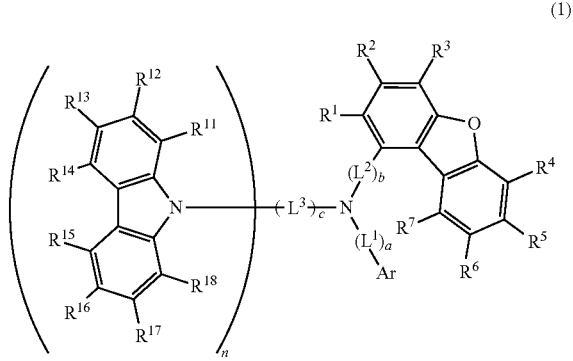

(1)

wherein:

$R^1$ to $R^7$ and $R^{11}$ to $R^{18}$ are each independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted aralkyl group having 7 to 36 carbon atoms, a substituted or unsubstituted alkoxy group having 1 to 30 carbon atoms, a substituted or unsubstituted aryloxy group having 6 to 30 ring carbon atoms, a mono-, di- or tri-substituted silyl group having a substituent selected from the group consisting of a substituted or unsubstituted alkyl group having 1 to 30 carbon atoms and a substituted or unsubstituted aryl group having 6 to 30 ring carbon atoms, a substituted or unsubstituted haloalkyl group having 1 to 30 carbon atoms, a substituted or unsubstituted haloalkoxy group having 1 to 30 carbon atoms, a substituted or unsubstituted heteroaryl group having 5 to 30 ring atoms, a halogen atom, a cyano group, or a nitro group;

adjacent two selected from $R^1$ to $R^3$, adjacent two selected from $R^4$ to $R^7$, adjacent two selected from $R^{11}$ to $R^{14}$, and adjacent two selected from $R^{15}$ to $R^{18}$ may be bonded to each other to form a ring structure;

Ar is a substituted or unsubstituted aryl group having 6 to 30 ring carbon atoms, wherein the aryl group is composed of only a six-membered ring;

a is 0, 1, 2, or 3;

when a is 0, Ar is directly bonded to the central nitrogen atom;

when a is 2 or 3, two or three $L^1$'s may be the same or different;

b is 1, 2, or 3;

when b is 2 or 3, two or three $L^2$'s may be the same or different;

c is 1, 2, or 3;

when c is 2 or 3, two or three L's may be the same or different;

n is 1 or 2;

when n is 1, $L^1$, $L^2$, and L are each independently a substituted or unsubstituted arylene group having 6 to 18 ring carbon atoms;

when n is 2, $L^3$ directly bonded to the nitrogen atom of the carbazole structure is a three-valent residue of an aromatic hydrocarbon having 6 to 18 ring carbon atoms, which may have a substituent, and $L^1$, $L^2$, and $L^3$ that is not directly bonded to the nitrogen atom of the carbazole structure are each independently a substituted or unsubstituted arylene group having 6 to 18 ring carbon atom.

In another aspect, the invention provides a material for organic electroluminescence device comprising the compound (1).

In still another aspect, the invention provides an organic electroluminescence device comprising a cathode, an anode, and an organic layer disposed between the cathode and the anode, wherein the organic layer comprises a light emitting layer and at least one layer of the organic layer comprises the compound (1).

In still another aspect, the invention provides an electronic device comprising the organic electroluminescence device.

Advantageous Effects of Invention

The compound (1) provides an organic EL device having further improved emission efficiency and device lifetime.

BRIEF DESCRIPTION OF DRAWINGS

FIG. 1 is a schematic view showing the structure of an organic EL device in an embodiment of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms that form the ring itself of a compound in which a series of atoms is bonded to form a ring, for example, a monocyclic compound, a fused ring compound, a cross-linked compound, a carbocyclic compound, and a heterocyclic compound. If the ring has a substituent, the carbon atom in the substituent is not included in the ring carbon atom. Unless otherwise noted, the same applies to the number of "ring carbon atoms" mentioned below. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirobifluorene ring), the carbon atom in the fluorene substituent is not counted as the ring carbon atom of the fluorene ring.

The number of "ring atom" referred to herein means the number of the atoms that form the ring itself of a compound in which a series of atoms is bonded to form a ring, for example, a monocyclic compound, a fused ring compound, a cross-linked compound, a carbocyclic compound, and a heterocyclic compound. The atom not forming the ring, for example, hydrogen atom bonding to the atom that forms the ring and the atom in the substituent bonding to the atom that forms the ring are not counted as the ring atom. Unless otherwise noted, the same applies to the number of "ring atoms" mentioned below. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent on the ring carbon atom of a pyridine ring or a quinazoline ring are not counted as the ring atom. In case of a fluorene ring to which a fluorene substituent is bonded (inclusive of a spirobifluorene ring), the atom in the fluorene substituent is not counted as the ring atom of the fluorene ring.

The compound in an aspect of the invention ("compound (1)") is represented by formula (1):

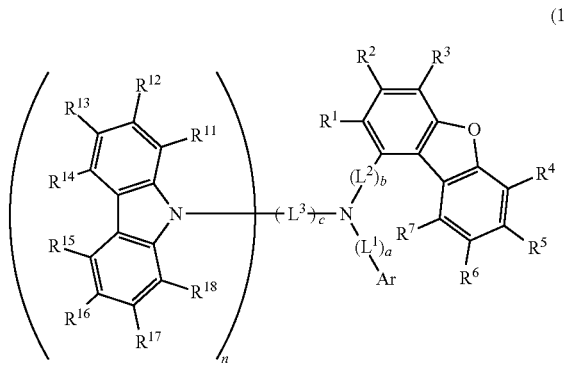

The compound (1) is preferably represented by formula (2):

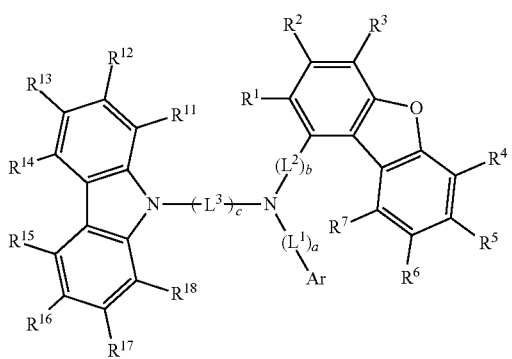

Each symbol in formulae (1) and (2) will be described below.

$R^1$ to $R^7$ and $R^{11}$ to $R^{18}$ are each independently a hydrogen atom; a substituted or unsubstituted alkyl group having 1 to 30, preferably 1 to 18, and more preferably 1 to 8 carbon atoms; a substituted or unsubstituted cycloalkyl group having 3 to 30, preferably 3 to 10, more preferably 3 to 8, and still more preferably 5 or 6 ring carbon atoms; a substituted or unsubstituted aryl group having 6 to 30, preferably 6 to 25, and more preferably 6 to 18 ring carbon atoms; a substituted or unsubstituted aralkyl group having 7 to 36, preferably 7 to 26, and more preferably 7 to 20 carbon atoms; a substituted or unsubstituted alkoxy group having 1 to 30, preferably 1 to 18, and more preferably 1 to 8 carbon atoms; a substituted or unsubstituted aryloxy group having 6 to 30, preferably 6 to 25, and more preferably 6 to 18 ring carbon atoms; a mono-, di- or tri-substituted silyl group having a substituent selected from the group consisting of a substituted or unsubstituted alkyl group having 1 to 30, preferably 1 to 18, and more preferably 1 to 8 carbon atoms and a substituted or unsubstituted aryl group having 6 to 30, preferably 6 to 25, and more preferably 6 to 18 ring carbon atoms; a substituted or unsubstituted haloalkyl group having 1 to 30, preferably 1 to 18, and more preferably 1 to 8 carbon atoms; a substituted or unsubstituted haloalkoxy group having 1 to 30, preferably 1 to 18, and more preferably 1 to 8 carbon atoms; a substituted or unsubstituted heteroaryl group having 5 to 30, preferably 5 to 24, and more preferably 5 to 13 ring atoms; a halogen atom; a cyano group; or a nitro group.

The alkyl group of the substituted or unsubstituted alkyl group having 1 to 30 carbon atoms is, for example, a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), or a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), more preferred are a methyl group, an ethyl group, a n-propyl group, an isopropyl group, a n-butyl group, an isobutyl group, a s-butyl group, and a t-butyl group, and still more preferred are a methyl group and a t-butyl group.

The cycloalkyl group of the substituted or unsubstituted cycloalkyl group having 3 to 30 ring carbon atoms is, for example, a cyclopropyl group, a cyclobutyl group, a cyclopentyl group, a cyclohexyl group, or a cycloheptyl group. Preferred are a cyclopentyl group and a cyclohexyl group.

The aryl group of the substituted or unsubstituted aryl group having 6 to 30 ring carbon atoms is, for example, a phenyl group, a biphenylyl group, a terphenylyl group, a biphenylenyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group. Preferred are a phenyl group, a biphenylyl group, a terphenylyl group, and a naphthyl group, more preferred are a phenyl group, a biphenylyl group, and a naphthyl group, and still more preferred is a phenyl group.

The aryl portion in the aralkyl group of the substituted or unsubstituted aralkyl group having 7 to 36 ring carbon atoms is selected from the aryl group having 6 to 30, preferably 6 to 25, and more preferably 6 to 18 ring carbon atoms which is mentioned above, and the alkyl portion is selected from the alkyl group having 1 to 30, preferably 1 to 18, and more preferably 1 to 8 carbon atoms which is mentioned above. The aralkyl group is, for example, a benzyl group, a phenethyl group or a phenylpropyl group, with a benzyl group being preferred.

The alkyl portion in the alkoxy group of the substituted or unsubstituted alkoxy group having 1 to 30 carbon atoms is selected from the alkyl group having 1 to 30, preferably 1 to 18, and more preferably 1 to 8 carbon atoms which is mentioned above. The alkoxy group is preferably a t-butoxy group, a propoxy group, an ethoxy group, or a methoxy group, with an ethoxy group and a methoxy group being more preferred and a methoxy group being still more preferred.

The aryl portion in the aryloxy group of the substituted or unsubstituted aryloxy group having 6 to 30 ring carbon atoms is selected from the aryl group having 6 to 30, preferably 6 to 25, and more preferably 6 to 18 ring carbon atoms which is mentioned above. The aryloxy group is preferably a terphenyloxy group, a biphenyloxy group, or a phenoxy group, with a biphenyloxy group and a phenoxy group being preferred and a phenoxy group being more preferred.

The substituent of the mono-, di- or tri-substituted silyl group is selected from the alkyl group having 1 to 30, preferably 1 to 18, and more preferably 1 to 8 carbon atoms which is mentioned above and the aryl group having 6 to 30, preferably 6 to 25, and more preferably 6 to 18 ring carbon atoms which is mentioned above. Preferred is a tri-substituted silyl group, for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group.

The haloalkyl group of the substituted or unsubstituted haloalkyl group having 1 to 30 carbon atoms is an alkyl group having 1 to 30, preferably 1 to 18, and more preferably 1 to 8 carbon atoms, wherein at least one hydrogen atom, preferably 1 to 7 hydrogen atoms, or all hydrogen atoms are replaced by a halogen atom. The halogen atom is selected from a fluorine atom, a chlorine atom, a bromine atom, and an iodine atom, and preferably a fluorine atom.

The haloalkyl group is preferably a fluoroalkyl group having 1 to 30, preferably 1 to 18, more preferably 1 to 8 carbon atoms, more preferably a heptafluoropropyl group (inclusive of isomeric groups), a pentafluoroethyl group, a 2,2,2-trifluoroethyl group, or a trifluoromethyl group, still more preferably a pentafluoroethyl group, a 2,2,2-trifluoroethyl group, or a trifluoromethyl group, and particularly preferably a trifluoromethyl group.

The haloalkyl portion in the haloalkoxy group of the substituted or unsubstituted haloalkoxy group is selected from the haloalkyl group having 1 to 30, preferably 1 to 18, and more preferably 1 to 8 carbon atoms which is mentioned above. The haloalkoxy group is preferably a fluoroalkoxy group having 1 to 30, preferably 1 to 18, more preferably 1 to 8 carbon atoms, more preferably a heptafluoropropoxy group (inclusive of isomeric groups), a pentafluoroethoxy group, a 2,2,2-trifluoroethoxy group, or a trifluoromethoxy group, still more preferably a pentafluoroethoxy group, a 2,2,2-trifluoroethoxy group, or a trifluoromethoxy group, and particularly preferably a trifluoromethoxy group.

The heteroaryl group of the substituted or unsubstituted heteroaryl group having 5 to 30 ring atoms comprises 1 to 5, preferably 1 to 3, and more preferably 1 to 2 ring hetero atoms, which is selected, for example, from a nitrogen atom, a sulfur atom, and an oxygen atom. The free valance of the heteroaryl group is present on a ring carbon atom or may be present on a ring nitrogen atom, if structurally possible.

The heteroaryl group is, for example, a pyrrolyl group, a furyl group, a thienyl group, a pyridyl group, an imidazolyl group, a pyrazolyl group, an indolyl group, an isoindolyl group, a benzofuranyl group, an isobenzofuranyl group, a benzothiophenyl group (a benzothienyl group, the same applies below), an indolizinyl group, a benzimidazolyl group, an indazolyl group, a dibenzofuranyl group, a naphthobenzofuranyl group, a dibenzothiophenyl group (a dibenzothienyl group, the same applies below), a naphthobenzothiophenyl group (a naphthobenzothienyl group, the same applies below), a carbazolyl group, or a benzocarbazolyl group. Preferred are a furyl group, a thienyl group, a benzofuranyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group, and more preferred are a thienyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group. The substituted heteroaryl group is, for example, a 9-phenylcarbazolyl group, a 9-biphenylylcarbazolyl group, a 9-phenylphenyla carbazolyl group, a 9-naphthylcarbazolyl group, a phenyldibenzofuranyl group, or a phenyldibenzothiophenyl group (a phenyldibenzothienyl group).

The halogen atom is a fluorine atom, a chlorine atom, a bromine atom, or an iodine atom, with a fluorine atom being preferred.

Adjacent two selected from $R^1$ to $R^3$, adjacent two selected from $R^4$ to $R^7$, adjacent two selected from $R^{11}$ to $R^{14}$, and adjacent two selected from $R^{15}$ to $R^{18}$ may be bonded to each other to form a ring structure.

In an embodiment of the invention, the adjacent two mentioned above may be not bonded to each other, thereby failing to form a ring structure.

Examples of the ring structure include a substituted or unsubstituted aromatic hydrocarbon ring having 6 to 18 ring carbon atoms, a substituted or unsubstituted aliphatic hydrocarbon ring having 5 to 18 ring carbon atoms, a substituted or unsubstituted aromatic heterocyclic ring having 6 to 18 ring atoms, and a substituted or unsubstituted aliphatic heterocyclic ring having 5 to 18 ring atoms.

Examples of the aromatic hydrocarbon ring having 6 to 18 ring carbon atoms include benzene, biphenylene, naphthalene, anthracene, benzanthracene, phenanthrene, benzophenanthrene, phenalene, pyrene, chrysene, and triphenylene.

Examples of the aliphatic hydrocarbon ring having 5 to 18 ring carbon atoms include a cyclopentene ring, a cyclopentadiene ring, a cyclohexene ring, a cyclohexadiene ring, and an aliphatic hydrocarbon ring obtained by partially hydrogenating the aromatic hydrocarbon ring having 6 to 18 ring carbon atoms.

Examples of the aromatic heterocyclic ring having 5 to 18 ring atoms include pyrrole, furan, thiophene, pyridine, imidazole, pyrazole, indole, isoindole, benzofuran, isobenzofuran, benzothiophene, benzimidazole, indazole, dibenzofuran, naphthobenzofuran, dibenzothiophene, naphthobenzothiophene, carbazole, and benzocarbazole.

Examples of the aliphatic heterocyclic ring having 5 to 18 ring atoms includes an aliphatic heterocyclic ring obtained by partially hydrogenating the aromatic heterocyclic ring having 5 to 18 ring atoms.

Preferably $R^1$ to $R^7$ and $R^{11}$ to $R^{18}$ are each independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted heteroaryl group having 5 to 30 ring atoms, a halogen atom, or a cyano group, and more preferably a hydrogen atom, a substituted or unsubstituted alkyl group having 1 to 30 carbon atoms, a substituted or unsubstituted aryl group having 6 to 30 ring carbon atoms, a substituted or unsubstituted heteroaryl group having 5 to 30 ring atoms, a halogen atom, or a cyano group.

In an embodiment of the invention, $R^1$ to $R^7$ and $R^{11}$ to $R^{18}$ may be all hydrogen atoms.

Ar is a substituted or unsubstituted aryl group having 6 to 30, preferably 6 to 25, and more preferably 6 to 18 ring carbon atoms. The aryl group is composed of only a six-membered ring (benzene ring), i.e., the aryl group is a single ring group of a six-membered ring, a fused ring group composed of only a six-membered ring, or a ring assembly group composed of only a six-membered ring.

The single ring group of a six-membered ring is a phenyl group.

The fused ring group composed of only a six-membered ring is a monovalent group of a ring system wherein two or more benzene rings are fused. Examples thereof include a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, a perylenyl group, and a triphenylenyl group.

The ring assembly group composed of only a six-membered ring is a monovalent group of a ring system wherein two or more benzene rings are bonded to each other via a single bond. Examples thereof include a monovalent residue of biphenyl and terphenyl.

The aryl group containing a five-membered ring is, for example, a fluorene-type aryl group and a fluoranthene-type aryl group. The fluorene-type aryl group has a benzylic alkyl group at its 9-position. The benzylic alkyl group is considered to easily form a radical, thereby reducing the durability (stability) of a compound containing a fluorene-type aryl group. Therefore, the device lifetime may be decreased if a device contains such a compound particularly in a layer adjacent to a light emitting layer. The fluoranthene-type aryl group has an extremely high electron acceptability. If a compound containing the fluoranthene-type aryl group is used in a hole transporting layer adjacent to a light emitting layer, electrons from a cathode are not blocked at the interface between the light emitting layer and the hole transporting layer and enter into the hole transporting layer. This may reduce the device lifetime. For the above reasons, the aryl group and the arylene group in the compound (1) are preferably composed of only a six-membered ring.

The aryl group of the substituted or unsubstituted aryl group having 6 to 30 ring carbon atoms represented by Ar is, for example, a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, a perylenyl group, or a triphenylenyl group; more preferably a phenyl group, a biphenylyl group, a terphenylyl group, a naphthyl group, a phenanthryl group, or a triphenylenyl group; still more preferably a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4- or 9-phenanthryl group, or a 2-triphenylenyl group.

The subscript a is 0, 1, 2, or 3, preferably 0, 1, or 2, and more preferably 0 or 1. In an embodiment of the invention, a is preferably 0. In another embodiment of the invention, a is preferably 1. When a is 0, Ar is directly bonded to the central nitrogen atom. When a is 2 or 3, two or three $L^1$'s may be the same or different. Two optional substituents that may be respectively present on each of adjacent two L's are preferably not bonded to each other, i.e., adjacent two $L^1$'s are preferably not crosslinked by optional substituents.

The subscript b is 1, 2, or 3, preferably is 1 or 2, and more preferably 1. When b is 2 or 3, two or three $L^2$'s may be the same or different. Two optional substituents that may be respectively present on each of adjacent two U's are preferably not bonded to each other, i.e., adjacent two $L^2$'s are preferably not crosslinked by optional substituents.

The subscript c is 1, 2, or 3, preferably 1 or 2, and more preferably 1. When c is 2, two L's may be the same or different. Two optional substituents that may be respectively present on each of adjacent two L's are preferably not bonded to each other, i.e., adjacent two L's are preferably not crosslinked by optional substituents.

The subscript n is 1 or 2, preferably 1.

$L^1$ is a substituted or unsubstituted arylene group having 6 to 18 ring carbon atoms.

The arylene group is, for example, a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group; preferably a phenylene group, a biphenylylene group, a terphenylylene group, a naphthylene group, or a phenanthrylene group; more preferably an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group; and still more preferably a phenylene group, i.e., an o-phenylene group, a m-phenylene group, or a p-phenylene group.

One of the two free valences of the arylene group is directly or indirectly bonded to the central nitrogen atom and the other is directly or indirectly bonded to Ar.

$L^2$ is a substituted or unsubstituted arylene group having 6 to 18 ring carbon atoms.

The arylene group is, for example, a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group; preferably a phenylene group, a biphenylylene group, a terphenylylene group, a naphthylene group, or a phenanthrylene group; more preferably an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group; still more preferably an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group; and particularly preferably an o-phenylene group, a m-phenylene group, a p-phenylene group, a 4,4'-biphenylylene group, a 4,3'-biphenylylene group, or a 4,2'-biphenylylene group.

One of the two free valences of the arylene group is directly or indirectly bonded to the central nitrogen atom and the other is directly or indirectly bonded to the 1-position of the dibenzofluorene structure.

$L^3$ is a substituted or unsubstituted arylene group having 6 to 18 ring carbon atoms, provided that when n is 2, $L^3$ that is directly bonded to the nitrogen atom of the carbazole structure is a three-valent residue of an aromatic hydrocarbon having 6 to 18 ring carbon atoms which is optionally substituted.

The arylene group is, for example, a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group; preferably a phenylene group, a biphenylylene group, a terphenylylene group, a naphthylene group, or a phenanthrylene group; and more preferably a phenylene group, a biphenylylene group, or a terphenylylene group.

One of two free valences of the arylene group is directly or indirectly bonded to the central nitrogen atom and the other is directly or indirectly bonded to the nitrogen atom of the carbazole structure.

In an embodiment of the invention, the arylene group for $L^3$ is more preferably a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group; and more preferably selected from the following arylene groups:

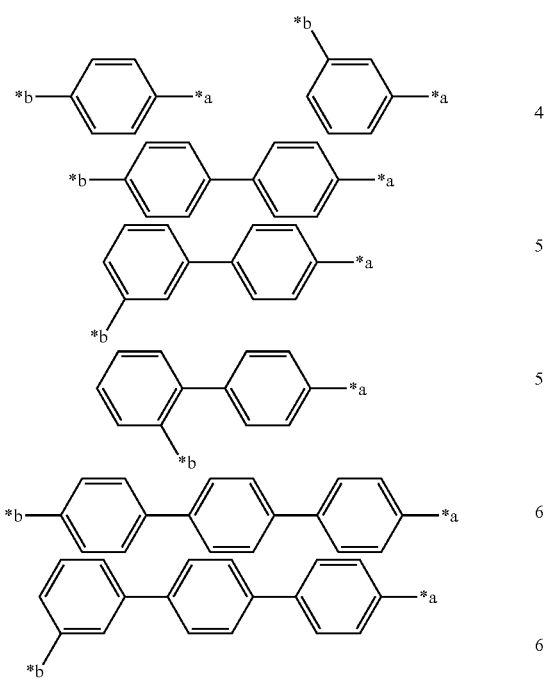

wherein *a is directly or indirectly bonded to the central nitrogen atom, and *b is directly or indirectly bonded to the nitrogen atom of the carbazole structure.

In another embodiment of the invention, the arylene group for $L^3$ is more preferably a p-phenylene group, a 4,4'-biphenylylene group, or a 4,4"-p-terphenylylene group; and particularly preferably a p-phenylene group or a 4,4'-biphenylylene group.

In still another embodiment of the invention, the arylene group for $L^3$ is more preferably a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group; and more preferably selected from the following arylene groups:

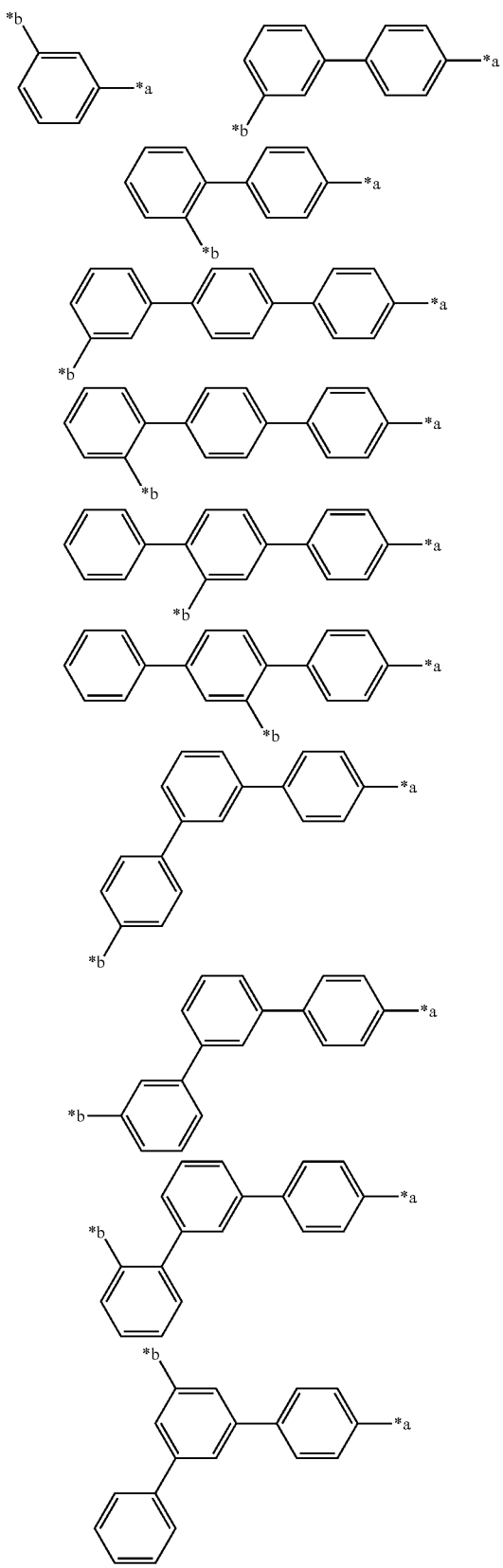

wherein *a is directly or indirectly bonded to the central nitrogen atom, and *b is directly or indirectly bonded to the nitrogen atom of the carbazole structure; and particularly preferably selected from the following arylene groups:

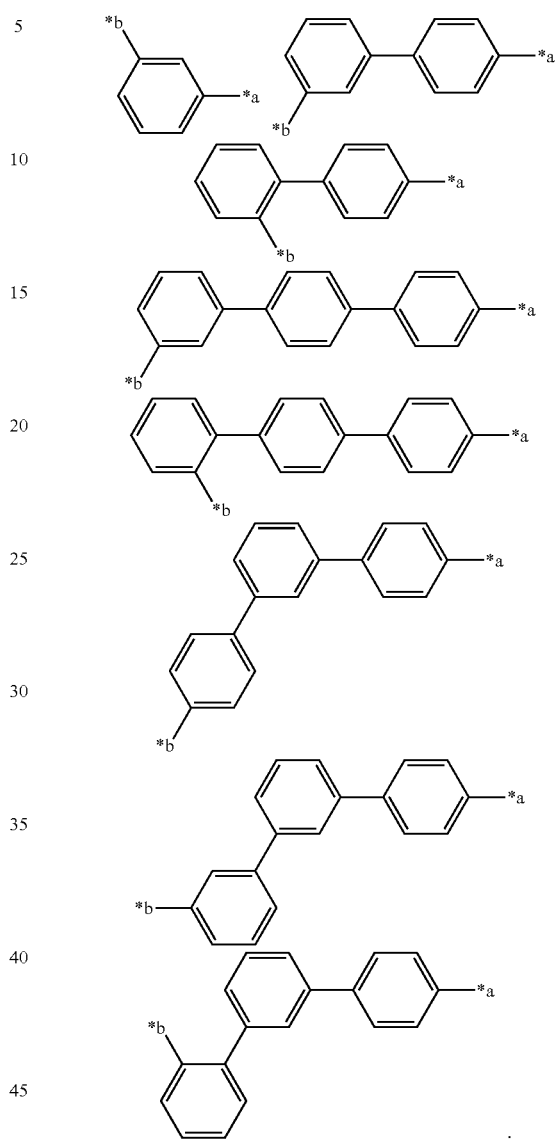

When n is 2, $L^3$ that is directly bonded to the nitrogen atom of the carbazole structure is a three-valent residue of an aromatic hydrocarbon having 6 to 18 ring carbon atoms which may be optionally substituted.

Examples of the three-valent residue may include three-valent residues of aromatic hydrocarbons selected from benzene, biphenyl, terphenyl, naphthalene, anthracene, benzanthracene, phenanthrene, benzophenanthrene, phenalene, picene, pentaphene, pyrene, chrysene, benzochrysene, and triphenylene.

The compound (1) of the invention includes the following compounds (11) to (36).

Compound (11):
a compound of formula (2), wherein:
a is 0 or 1, b is 1, and c is 1;
$L^1$ is a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, or a triphenylenylene group;

$L^2$ is a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, or a triphenylenylene group;

$L^3$ is a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, or a triphenylenylene group;

Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group; and $R^1$ to $R^7$ and $R^{11}$ to $R^{18}$ are all hydrogen atoms.

Compound (12):

a compound of formula (2), wherein:

a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a phenylene group, a biphenylylene group, a terphenylylene group, a naphthylene group, or a phenanthrylene group;

Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group; and $R^1$ to $R^7$ and $R^{11}$ to $R^{18}$ are all hydrogen atoms.

Compound (13):

a compound of formula (2), wherein:

a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a phenylene group, a biphenylylene group, or a terphenylylene group;

Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group; and $R^1$ to $R^7$ and $R^{11}$ to $R^{18}$ are all hydrogen atoms.

Compound (14):

a compound of formula (2), wherein:

a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a p-phenylene group, a 4,4'-biphenylylene group, or a 4,4"-p-terphenylylene group;

Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group; and $R^1$ to $R^7$ and $R^{11}$ to $R^{18}$ are all hydrogen atoms.

Compound (15):

a compound of formula (2), wherein a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group;

Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group; and $R^1$ to $R^7$ and $R^{11}$ to $R^{18}$ are all hydrogen atoms.

Compound (16):

a compound of formula (2), wherein:

a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a phenylene group, a biphenylylene group, a terphenylylene group, a naphthylene group, or a phenanthrylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Compound (17):

a compound of formula (2), wherein a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a phenylene group, a biphenylylene group, or a terphenylylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Compound (18):

a compound of formula (2), wherein:

a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a p-phenylene group, a 4,4'-biphenylylene group, or a 4,4"-p-terphenylylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Compound (19):

a compound of formula (2), wherein:

a is 0 or 1, b is 1, and c is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

$L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Compound (20):

a compound of formula (2), wherein:

a is 0 or 1, b is 1, and c is 1;

$L^1$ is a phenylene group;

$L^2$ is a phenylene group, a biphenylylene group, a naphthylene group, or a phenanthrylene group;

$L^3$ is a phenylene group, a biphenylylene group, or a terphenylylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Compound (21):

a compound of formula (2), wherein:

a is 0 or 1, b is 1, and c is 1;

$L^1$ is a phenylene group;

$L^2$ is a phenylene group, a biphenylylene group, a naphthylene group, or a phenanthrylene group;

$L^3$ is a p-phenylene group, a 4,4'-biphenylylene group, or a 4,4"-p-terphenylylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Compound (22):

a compound of formula (2), wherein:

a is 0 or 1, b is 1, and c is 1;

$L^1$ is a phenylene group;

$L^2$ is a phenylene group, a biphenylylene group, a naphthylene group, or a phenanthrylene group;

$L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Compound (23):

a compound of formula (2), wherein:

a is 0 or 1, b is 1, and c is 1;

$L^1$ is an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group;

$L^2$ is an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group;

$L^3$ is a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (24):

a compound of formula (2), wherein:

a is 0 or 1, b is 1, and c is 1;

$L^1$ is an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group;

$L^2$ is an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group;

$L^3$ is a p-phenylene group, a 4,4'-biphenylylene group, or a 4,4"-p-terphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (25):
a compound of formula (2), wherein:
a is 0 or 1, b is 1, and c is 1;
$L^1$ is an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group;

$L^2$ is an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group;

$L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (26):
a compound of formula (2), wherein:
a is 0 or 1, b is 1, and c is 1;
$L^1$ is an o-phenylene group, a m-phenylene group, or a p-phenylene group;
$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group;
$L^3$ is a phenylene group, a biphenylylene group, or a terphenylylene group;
Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (27):
a compound of formula (2), wherein:
a is 0 or 1, b is 1, and c is 1;
$L^1$ is an o-phenylene group, a m-phenylene group, or a p-phenylene group;
$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;

$L^3$ is a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (28)
a compound of formula (2), wherein:
a is 0 or 1, b is 1, and c is 1;
$L^1$ is an o-phenylene group, a m-phenylene group, or a p-phenylene group;
$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;

$L^3$ is selected from the following arylene groups:

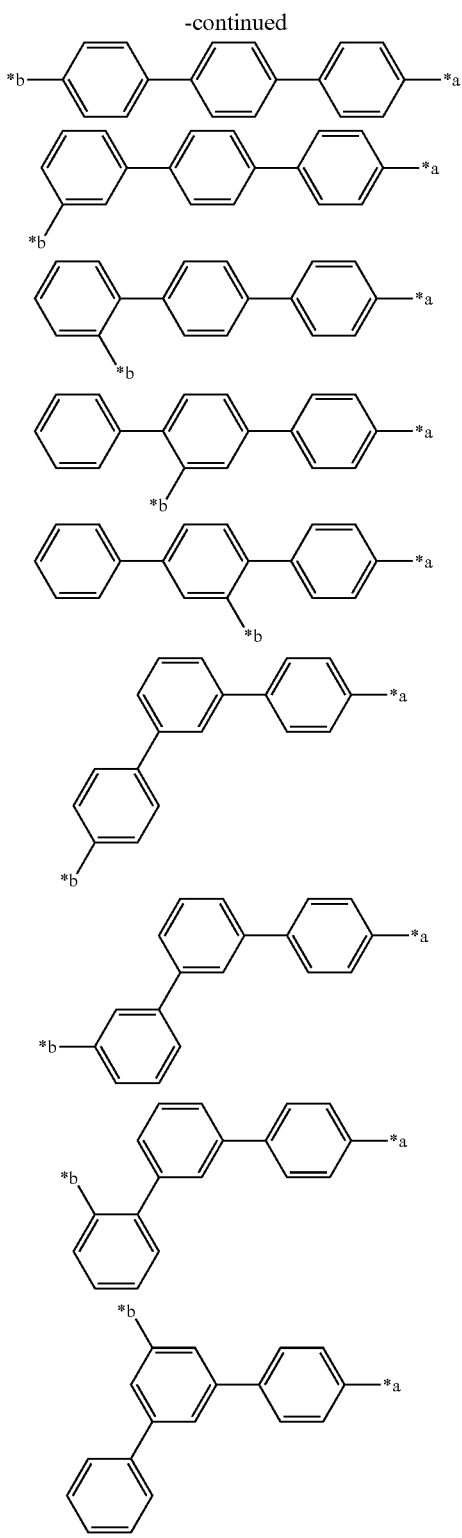

wherein *a is bonded to the central nitrogen atom, and *b is bonded to the nitrogen atom of the carbazole structure;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (29)
a compound of formula (2), wherein:
a is 0 or 1, b is 1, and c is 1;
$L^1$ is an o-phenylene group, a m-phenylene group, or a p-phenylene group;
$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;
$L^3$ is a p-phenylene group, a 4,4'-biphenylylene group, or a 4,4"-p-terphenylylene group, preferably a p-phenylene group or a 4,4'-biphenylylene group;
Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and
$R^1$ to $R^7$ and $R^{11}$ to $R^{18}$ are all hydrogen atoms.

Compound (30):
a compound of formula (2), wherein:
a is 0 or 1, b is 1, and c is 1;
$L^1$ is an o-phenylene group, a m-phenylene group, or a p-phenylene group;
$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;
$L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group;
Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and
$R^1$ to $R^7$ and $R^{11}$ to $R^{18}$ are all hydrogen atoms.

Compound (31):
a compound of formula (2), wherein:
a is 0 or 1, b is 1, and c is 1;
$L^1$ is an o-phenylene group, a m-phenylene group, or a p-phenylene group;
$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;
$L^3$ is selected from the following arylene groups:

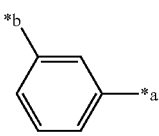 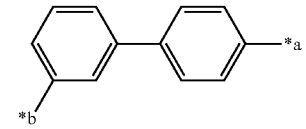

-continued

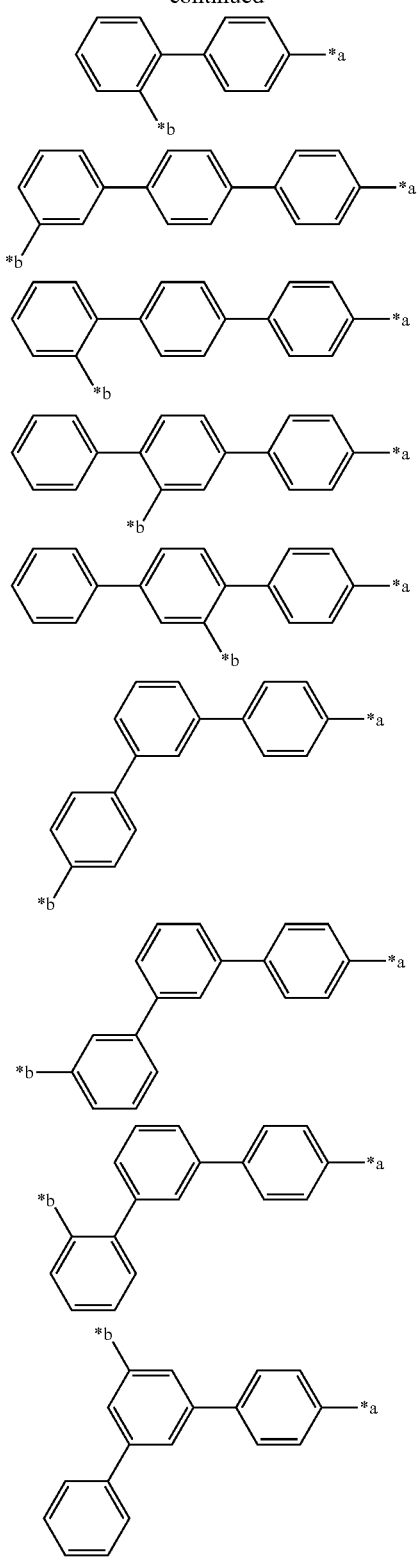

wherein *a is bonded to the central nitrogen atom, and *b is bonded to the nitrogen atom of the carbazole structure;

preferably selected from the following arylene groups:

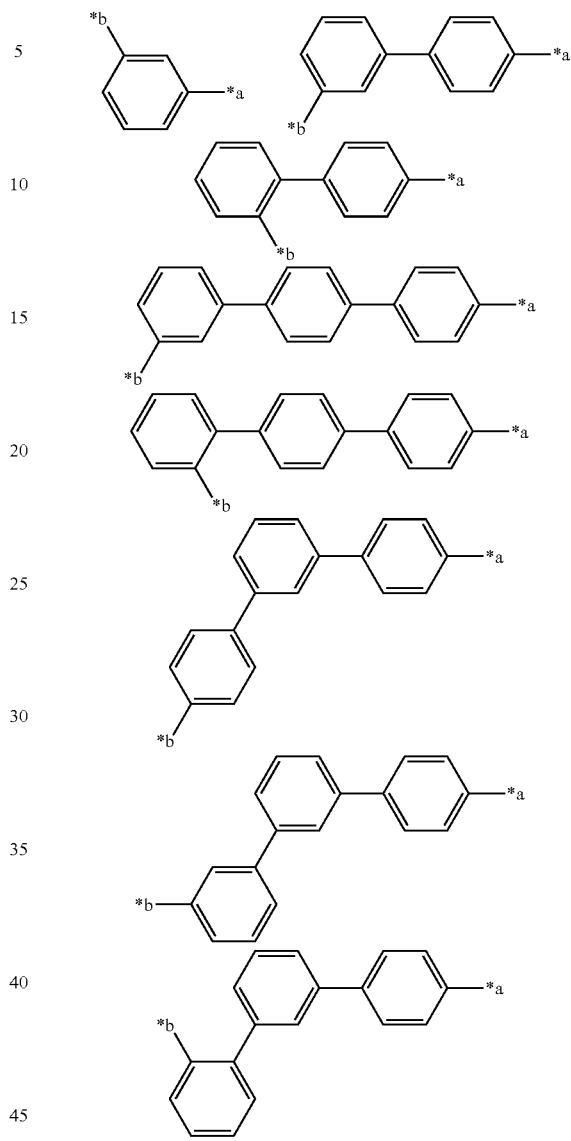

wherein *a is directly or indirectly bonded to the central nitrogen atom, and *b is directly or indirectly bonded to the nitrogen atom of the carbazole structure;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (32):
a compound of formula (2), wherein:
a is 0, b is 1, and c is 1;
$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;

$L^3$ is a p-phenylene group, a 4,4'-biphenylylene group, or a 4,4''-p-terphenylylene group, preferably a p-phenylene group or a 4,4'-biphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (33):

a compound of formula (2), wherein:

a is 0, b is 1, and c is 1;

$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;

$L^3$ is selected from the following arylene groups:

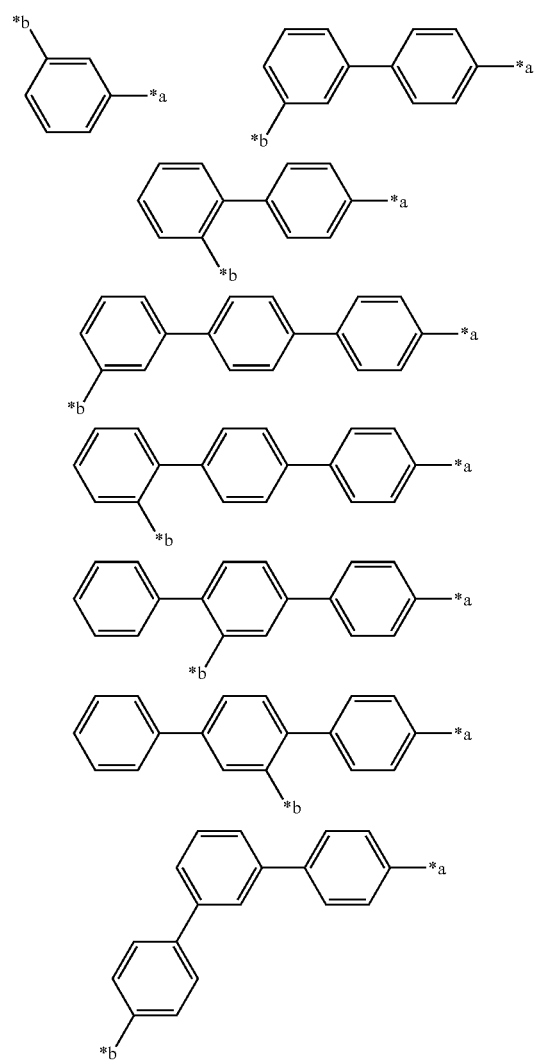

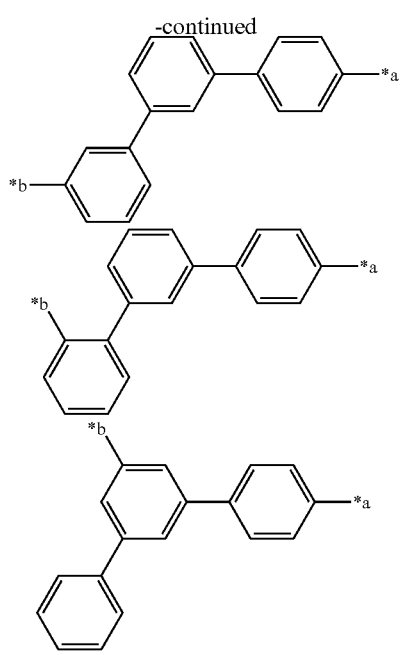

wherein *a is bonded to the central nitrogen atom, and *b is bonded to the nitrogen atom of the carbazole structure; preferably selected from the following arylene groups:

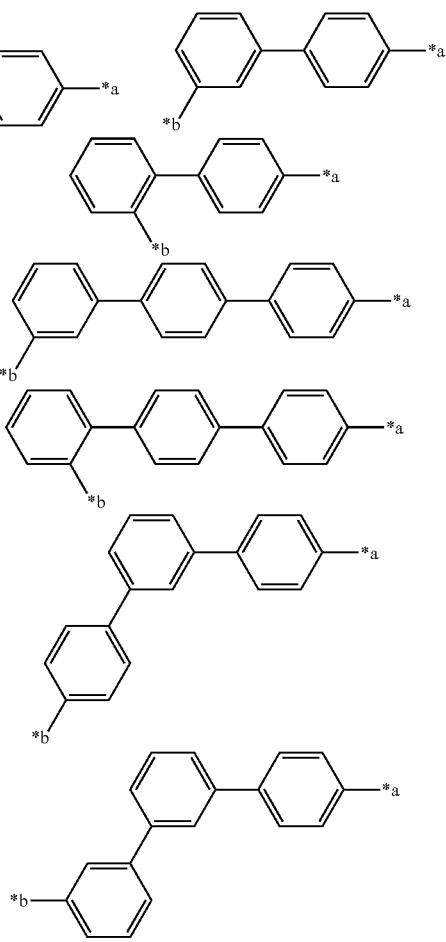

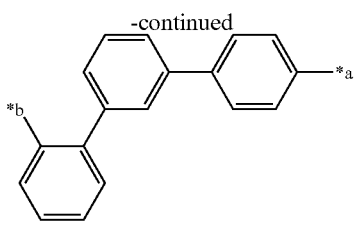

wherein *a is directly or indirectly bonded to the central nitrogen atom, and *b is directly or indirectly bonded to the nitrogen atom of the carbazole structure;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (34):
 a compound of formula (2), wherein:
 a is 1, b is 1, and c is 1;
 $L^1$ is an o-phenylene group, a m-phenylene group, or a p-phenylene group;
 $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;
 $L^8$ is a p-phenylene group, a 4,4'-biphenylylene group, or a 4,4''-p-terphenylylene group, preferably a p-phenylene group or a 4,4'-biphenylylene group;
 Ar is a 1- or 2-naphthyl group, a 2-, 3-, 4-, or 9-phenanthryl group, or a 2-triphenylenyl group; and
 $R^1$ to $R^7$ and $R^{11}$ to $R^{18}$ are all hydrogen atoms.

Compound (35):
 a compound of formula (2), wherein:
 a is 1, b is 1, and c is 1;
 $L^1$ is an o-phenylene group, a m-phenylene group, or a p-phenylene group;
 $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;
 $L^3$ is selected from the following arylene groups:

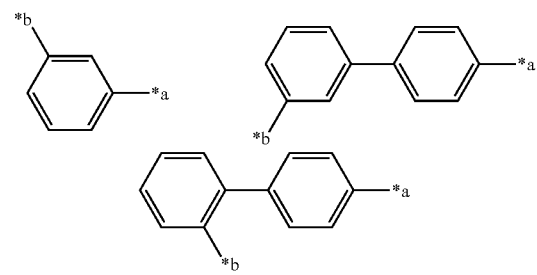

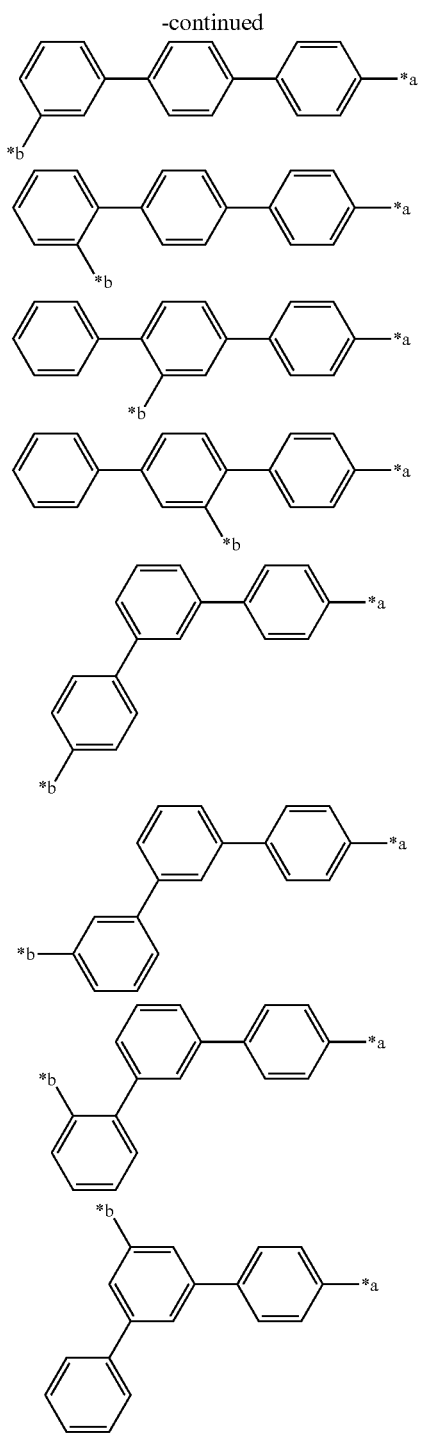

wherein *a is bonded to the central nitrogen atom, and *b is bonded to the nitrogen atom of the carbazole structure;

preferably selected from the following arylene groups:

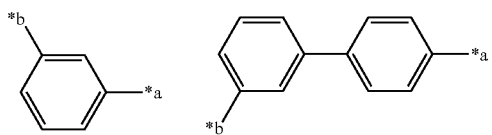

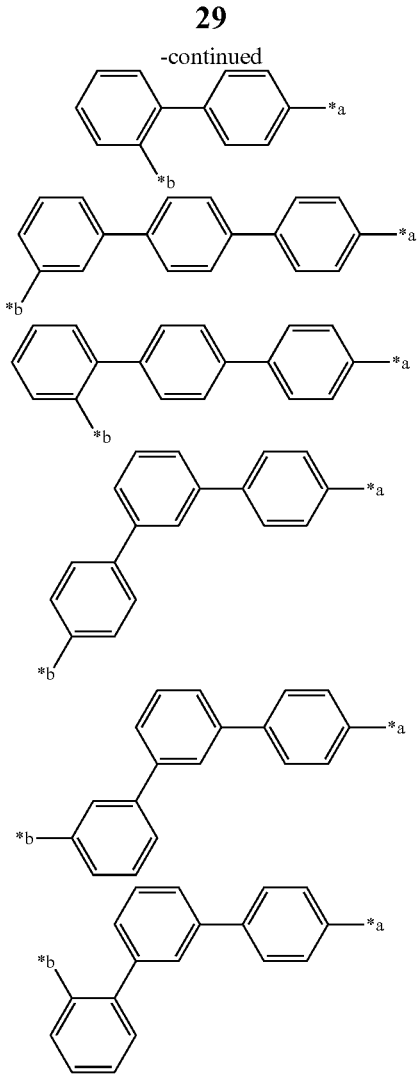

wherein *a is directly or indirectly bonded to the central nitrogen atom, and *b is directly or indirectly bonded to the nitrogen atom of the carbazole structure;

Ar is a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Compound (36):
a compound of formula (2), wherein:
a is 0, b is 1, and c is 1;
$L^2$ is a p-phenylene group;
$L^3$ is selected from the following arylene groups:

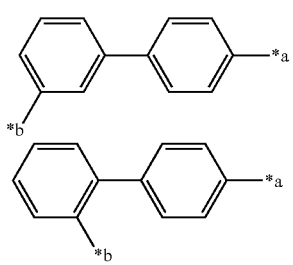

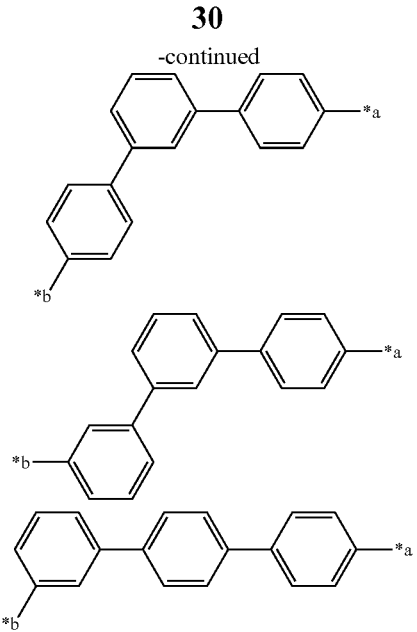

wherein *a is bonded to the central nitrogen atom, and *b is bonded to the nitrogen atom of the carbazole structure;

Ar is a 4-biphenylyl group; and $R^1$ to $R^7$ and $R^{11}$ to $R^{18}$ are all hydrogen atoms.

The optional substituent referred to by "substituted or unsubstituted" herein is, unless otherwise noted, selected from the group consisting of a substituted or unsubstituted alkyl group having 1 to 30, preferably 1 to 18, more preferably 1 to 8 carbon atoms; a substituted or unsubstituted cycloalkyl group having 3 to 30, preferably 3 to 10, more preferably 3 to 8, still more preferably 5 or 6 ring carbon atoms; a substituted or unsubstituted aryl group having 6 to 30, preferably 6 to 25, more preferably 6 to 18 ring carbon atoms; a substituted or unsubstituted aralkyl group having 7 to 36, preferably 7 to 26, more preferably 7 to 20 ring carbon atoms; a substituted or unsubstituted alkoxy group having 1 to 30, preferably 1 to 18, more preferably 1 to 8 carbon atoms; a substituted or unsubstituted aryloxy group having 6 to 30, preferably 6 to 25, more preferably 6 to 18 ring carbon atoms; a mono-, di-, or tri-substituted silyl group having a substituent selected from a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms; a substituted or unsubstituted haloalkyl group having 1 to 30, preferably 1 to 18, more preferably 1 to 8 carbon atoms; a substituted or unsubstituted haloalkoxy group having 1 to 30, preferably 1 to 18, more preferably 1 to 8 carbon atoms; a substituted or unsubstituted heteroaryl group having 5 to 30, preferably 5 to 24, more preferably 5 to 13 ring atoms; a halogen atom; a cyano group; and a nitro group.

The details of the optional substituents are as described above with respect to $R^1$ to $R^7$ and $R^{11}$ to $R^{18}$. Unless otherwise noted, adjacent optional groups may be bonded to each other to form a ring.

Examples of the compound (1) of the invention are shown below, although not limited thereto.

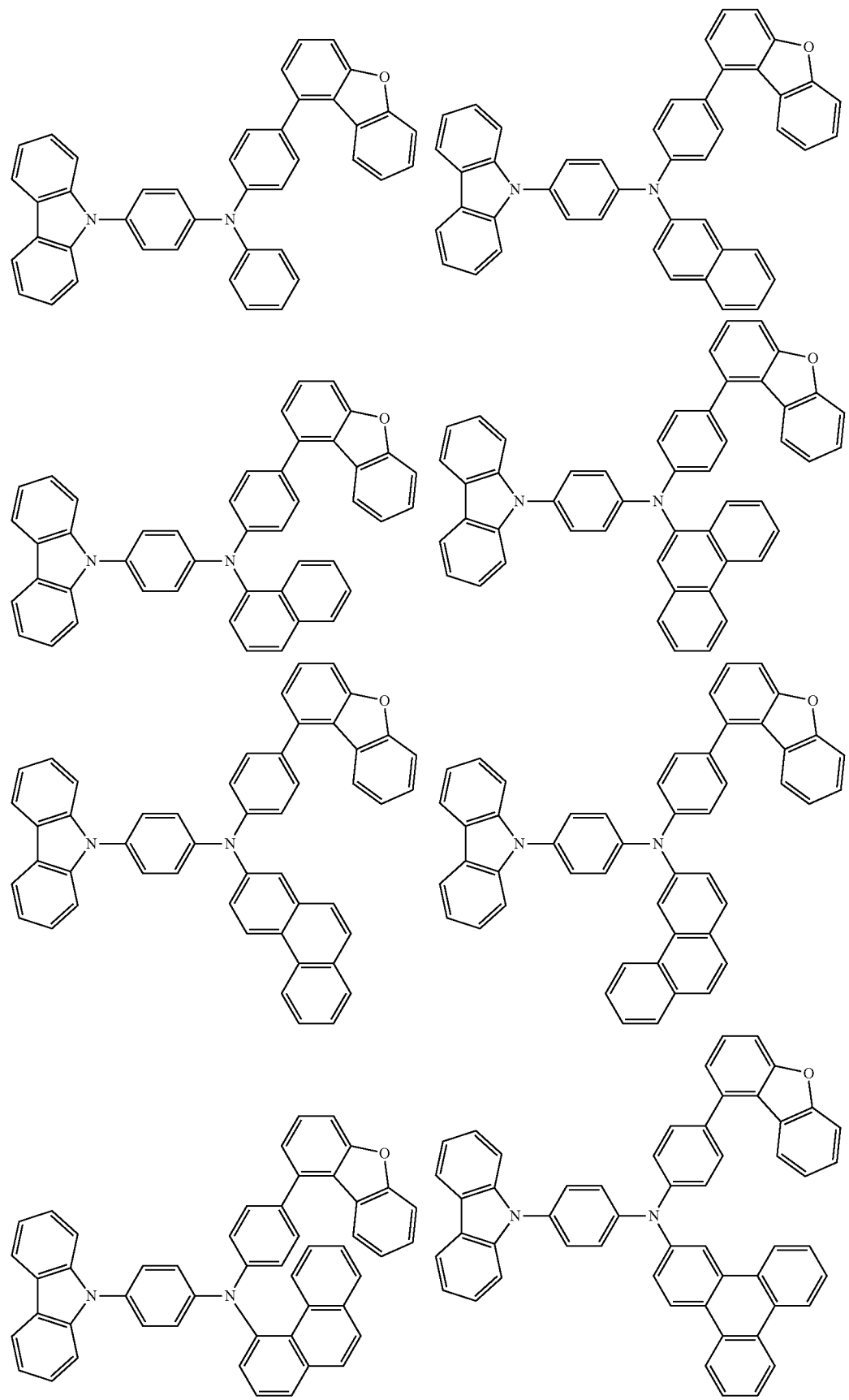

-continued
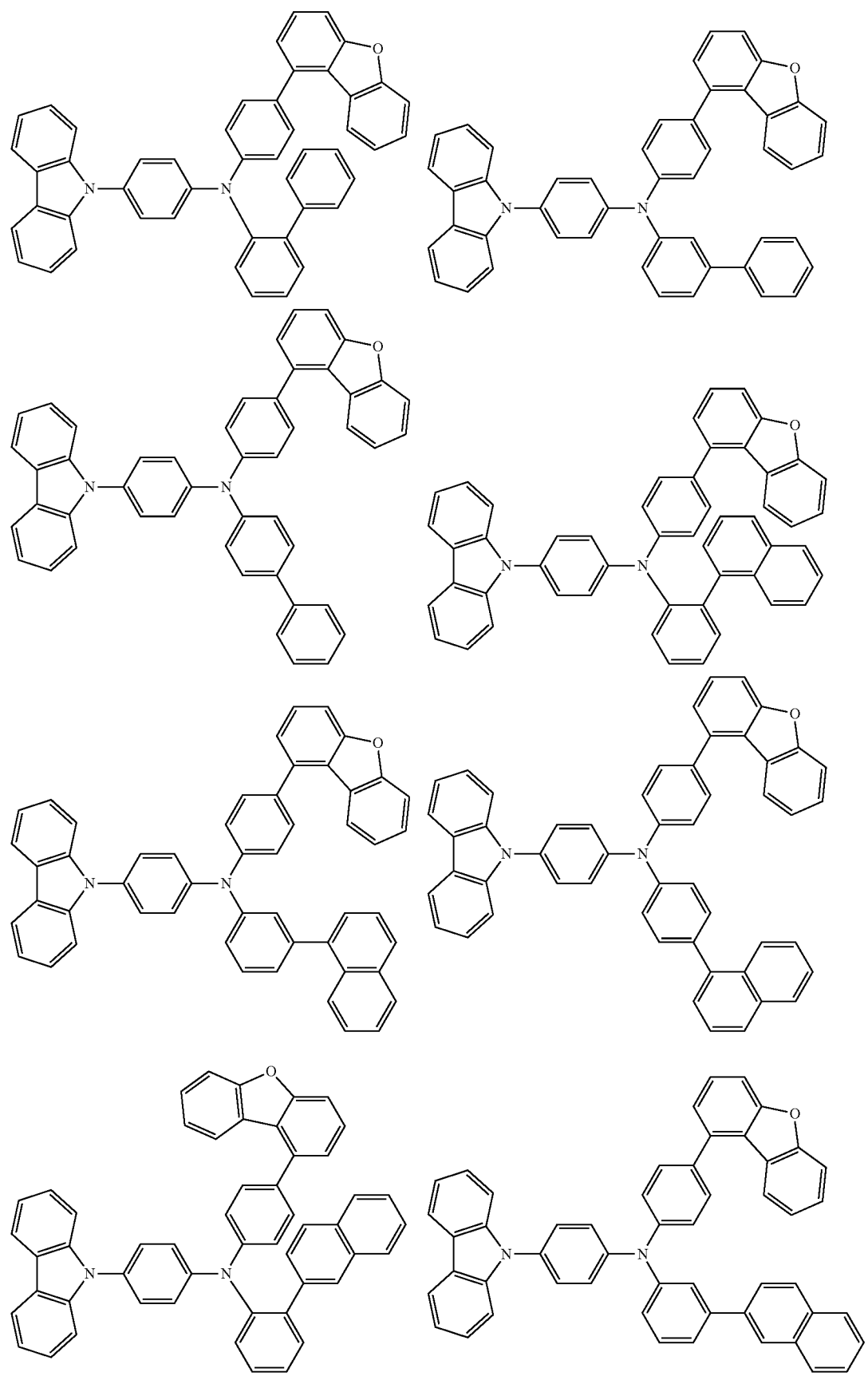

-continued
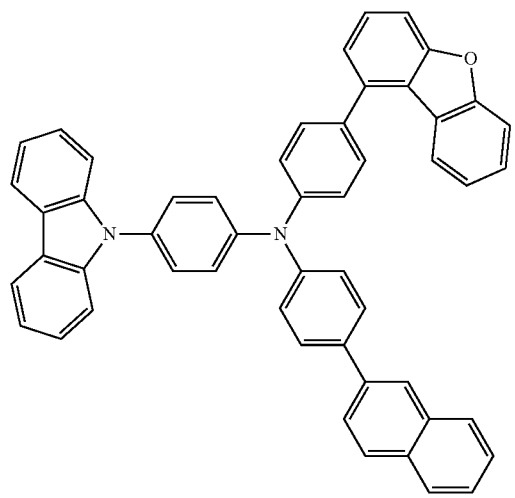
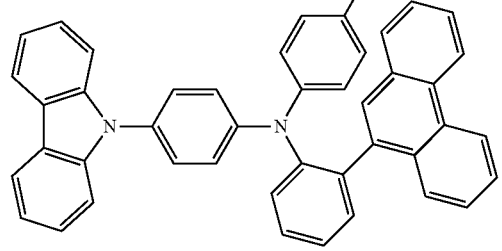
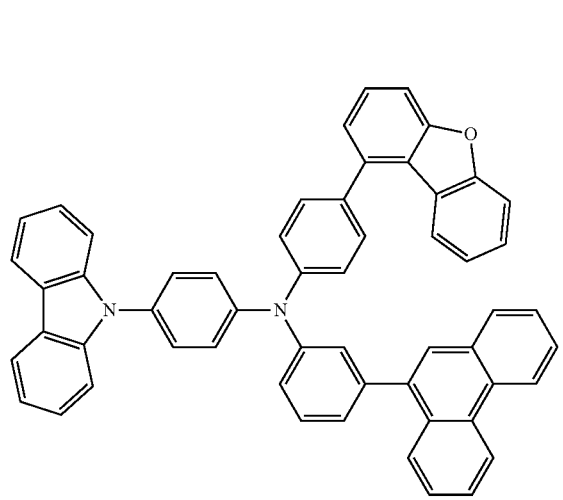
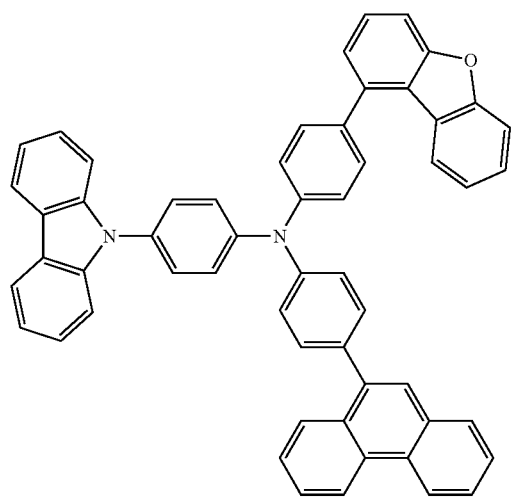
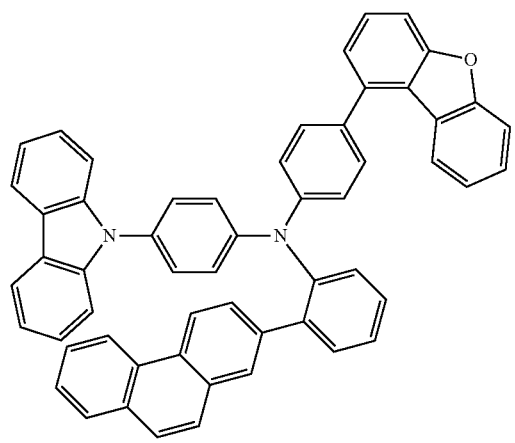
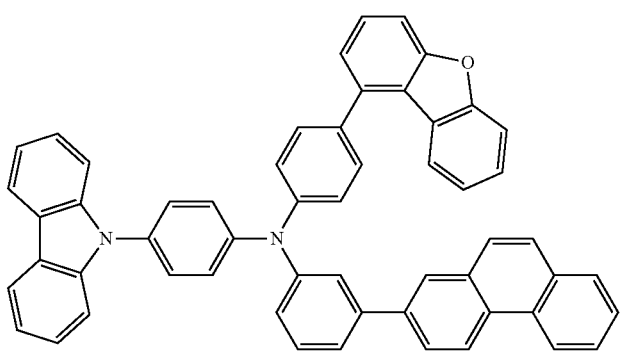

-continued
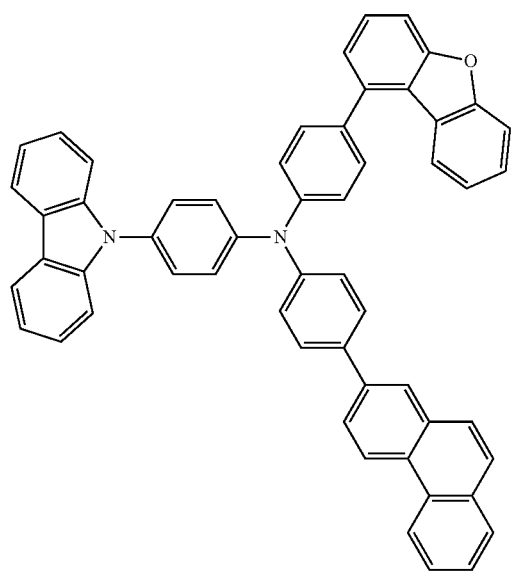
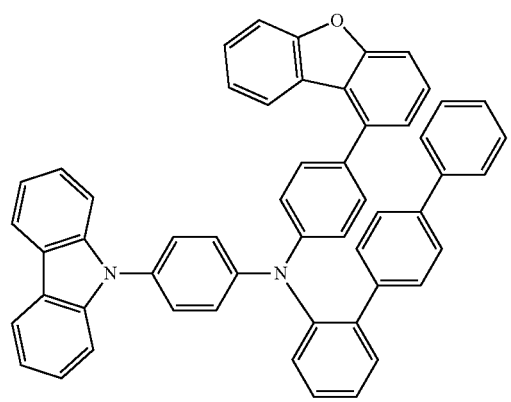
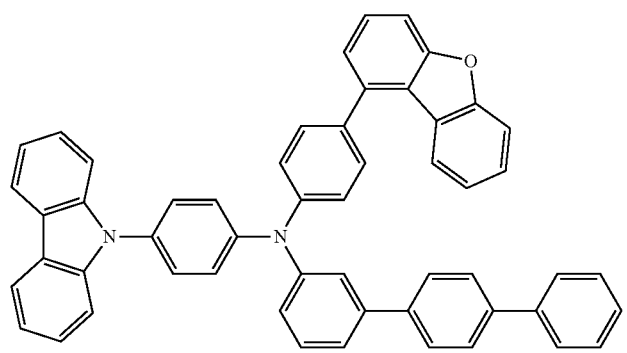
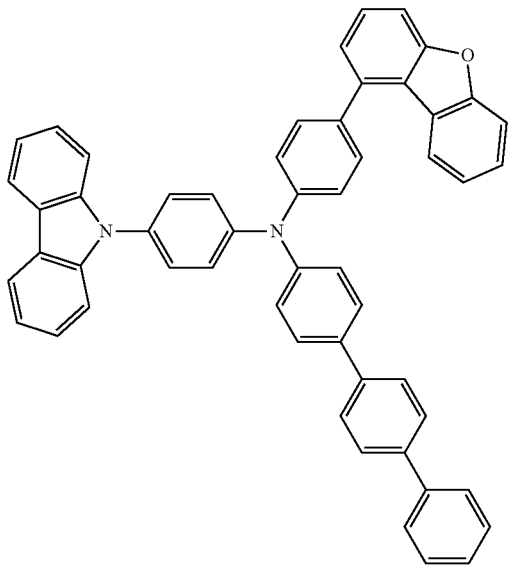
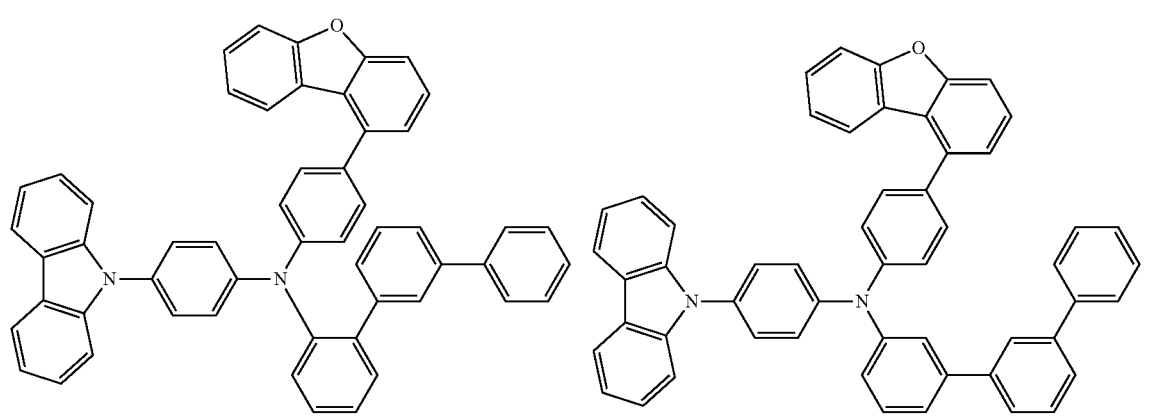

-continued
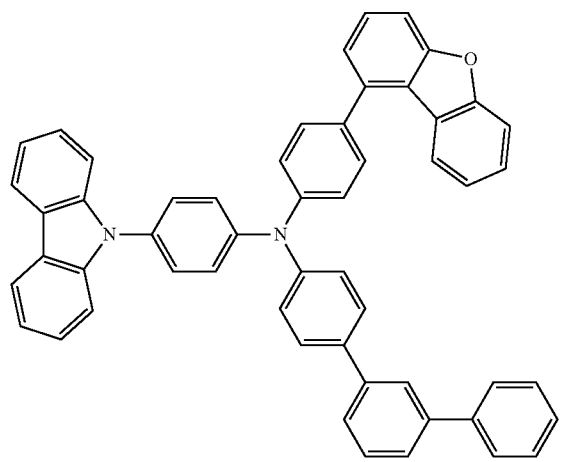
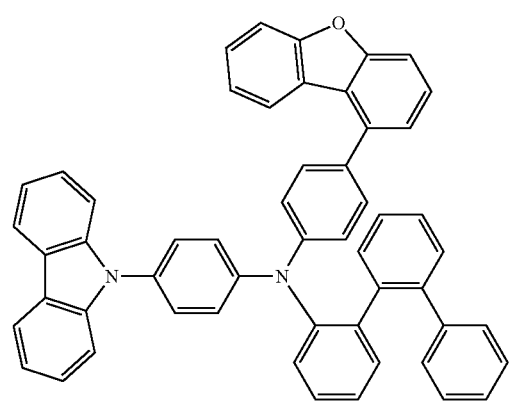
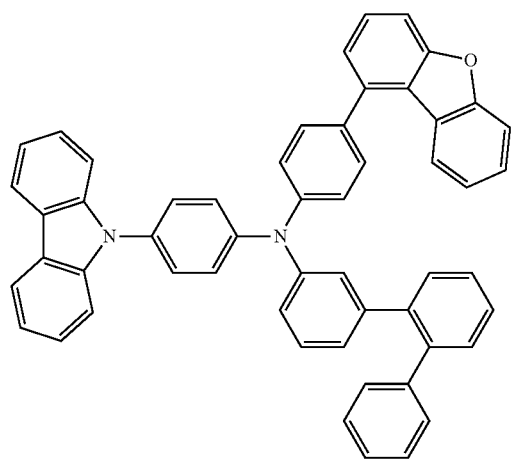
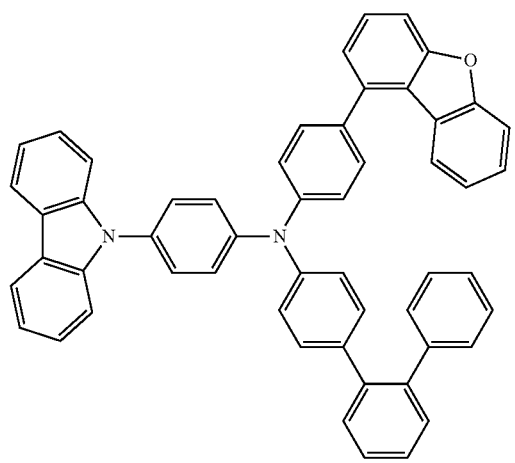
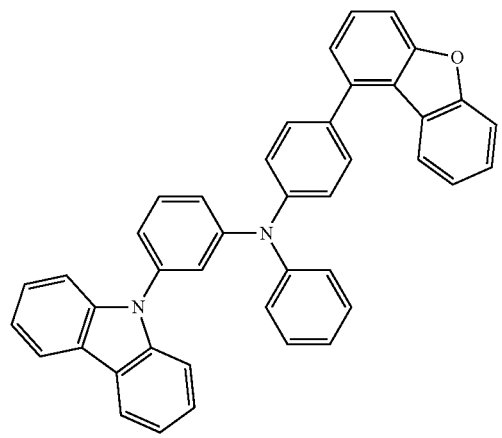
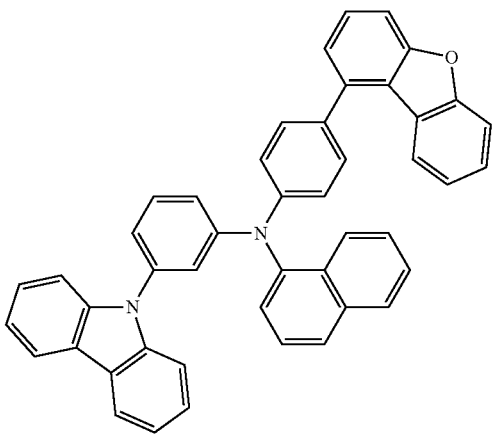

| 41 | 42 |
|---|---|
| 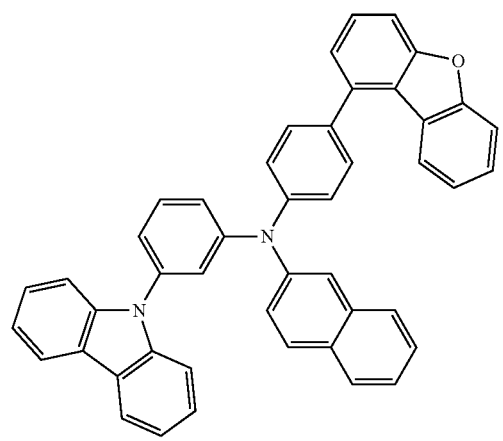 | 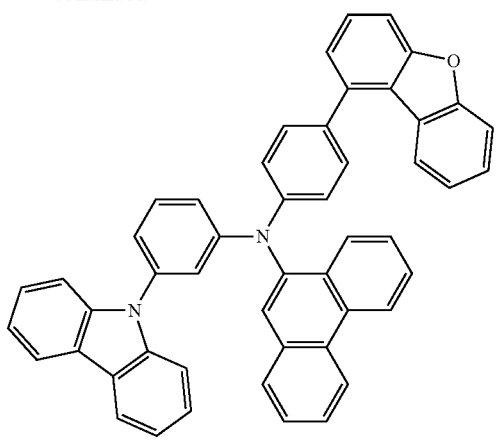 |
| 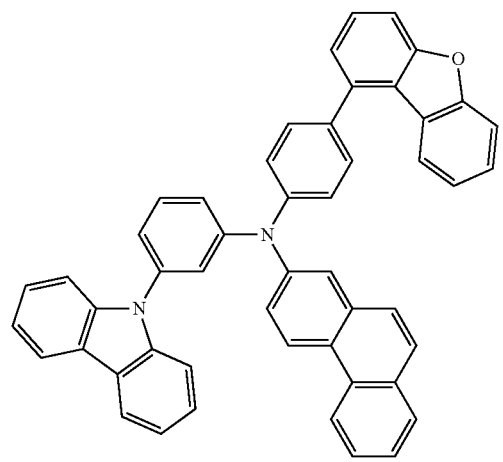 | 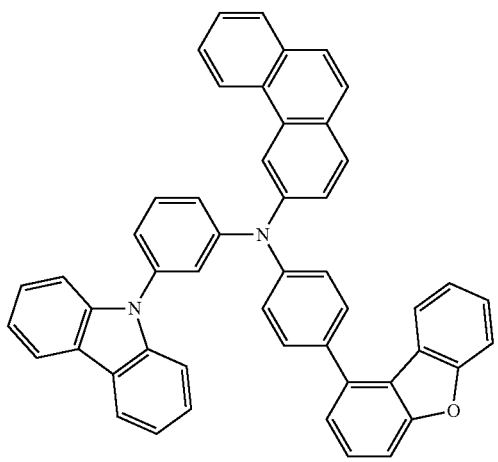 |
| 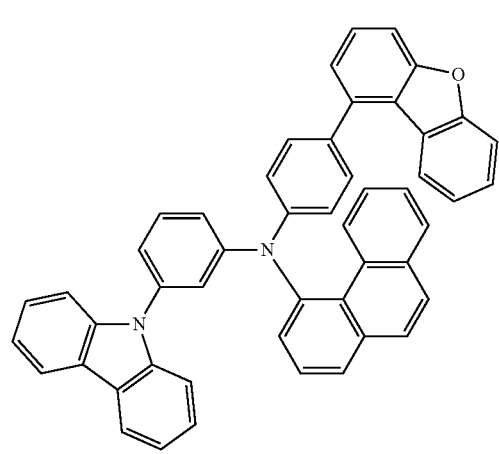 | 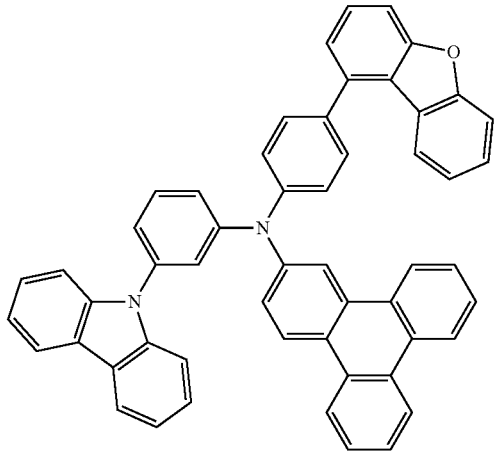 |

43
44
-continued
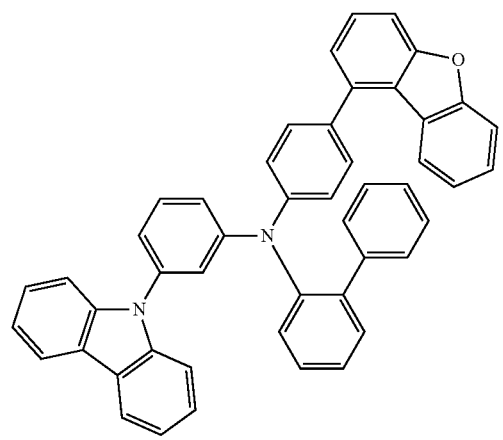
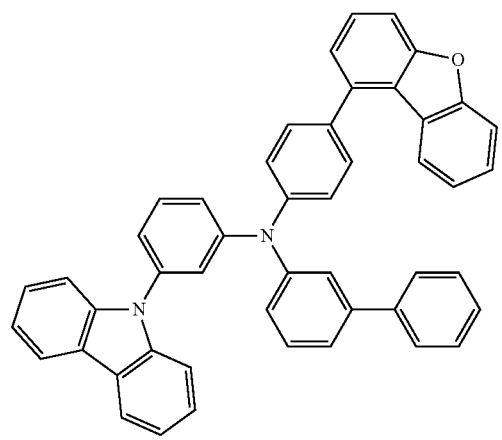
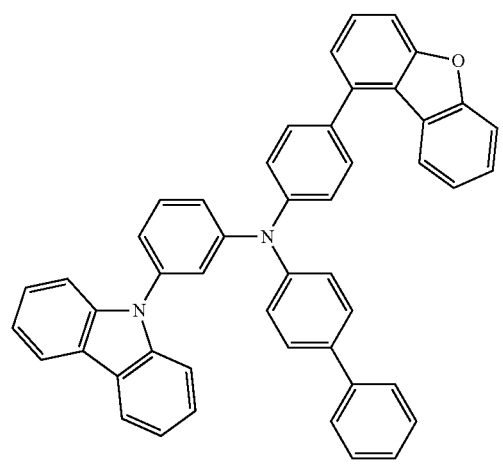
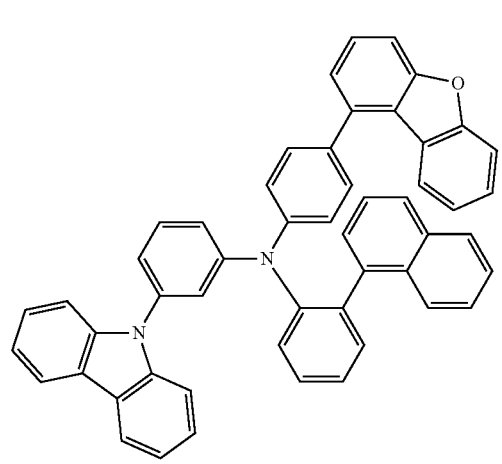
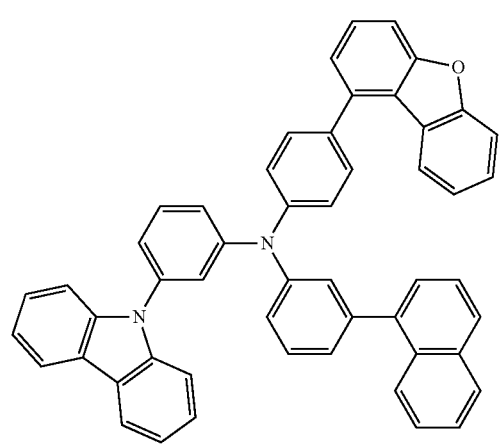
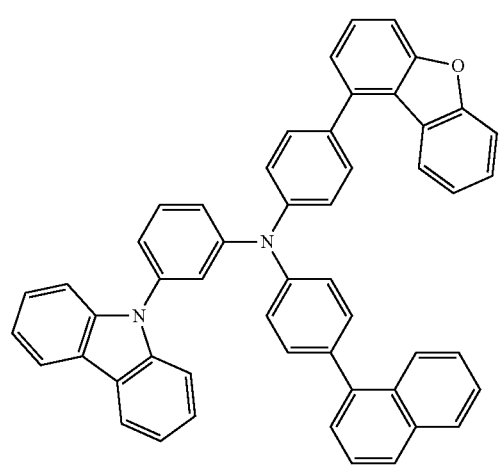

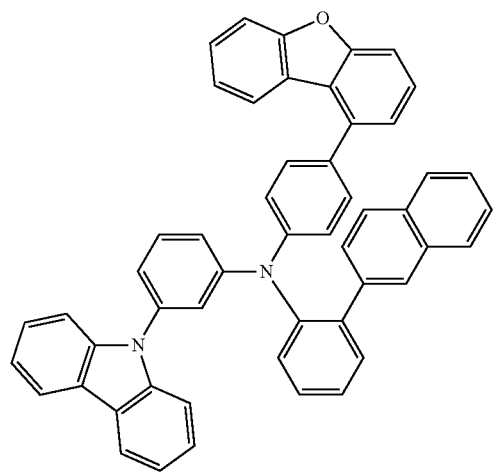
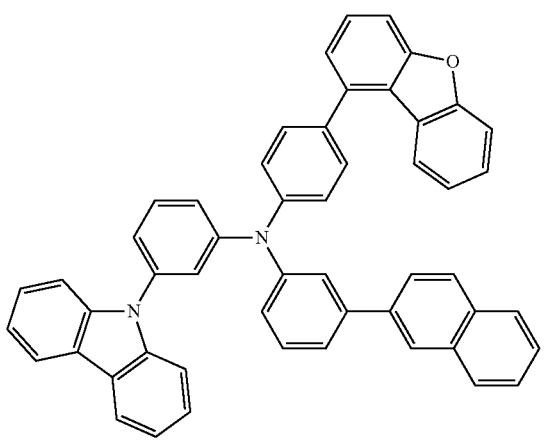
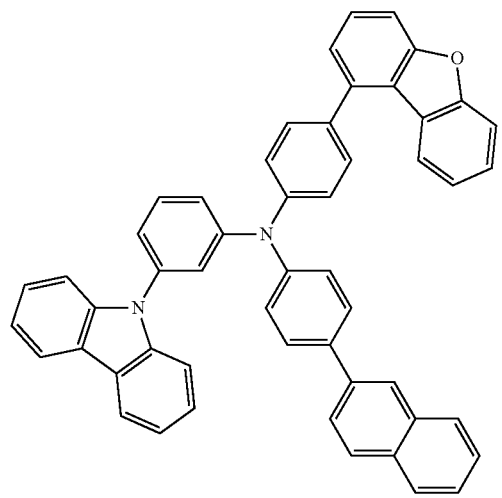
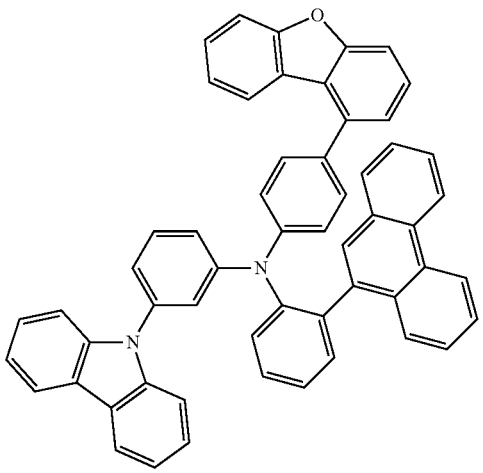
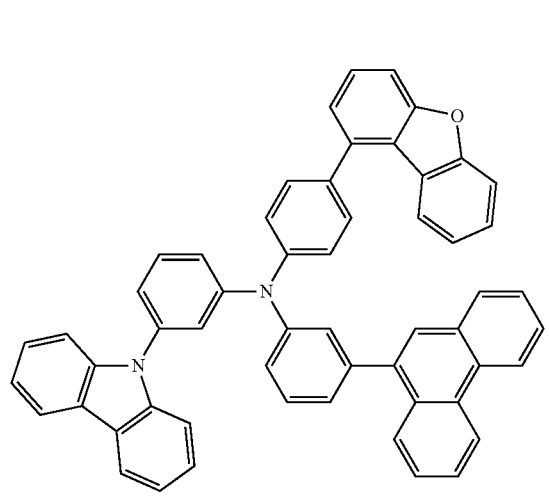
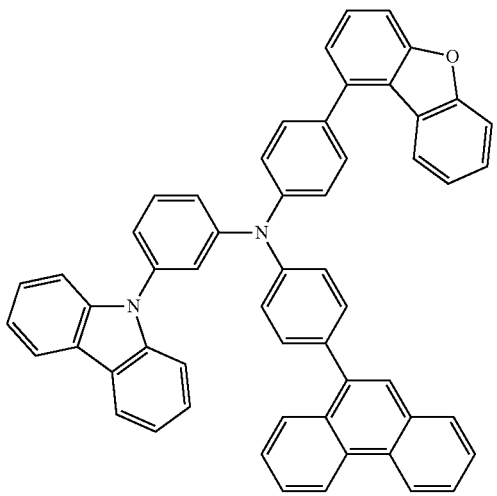

47 48
-continued
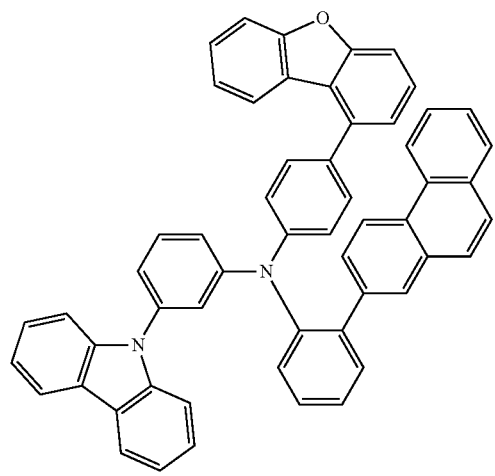
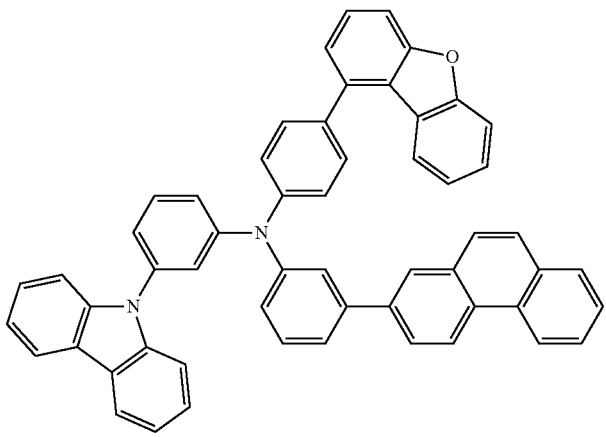
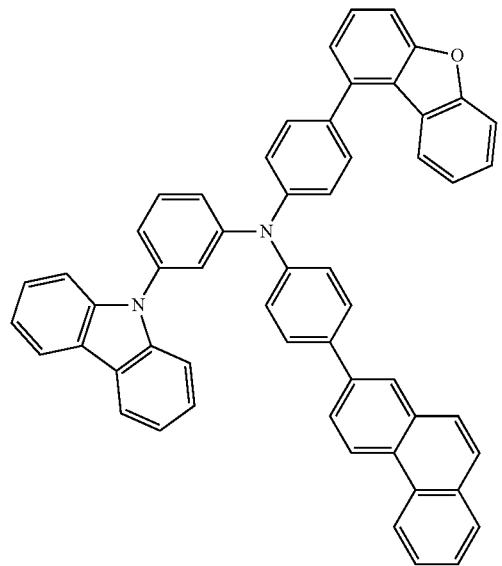
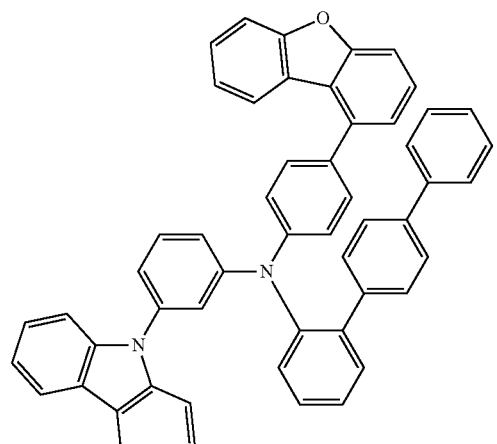
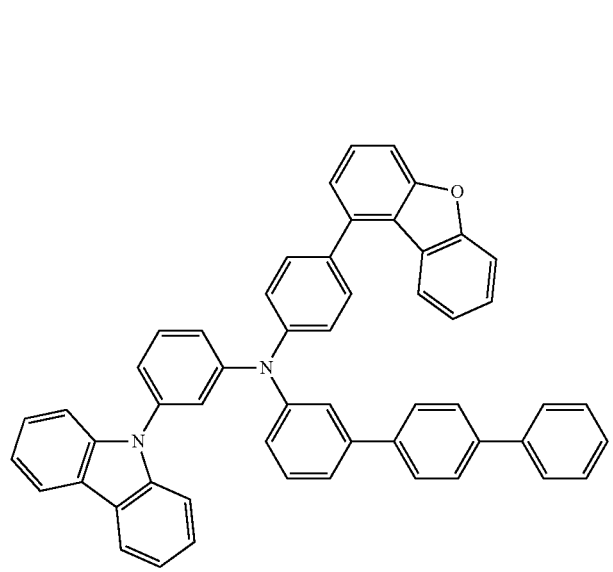
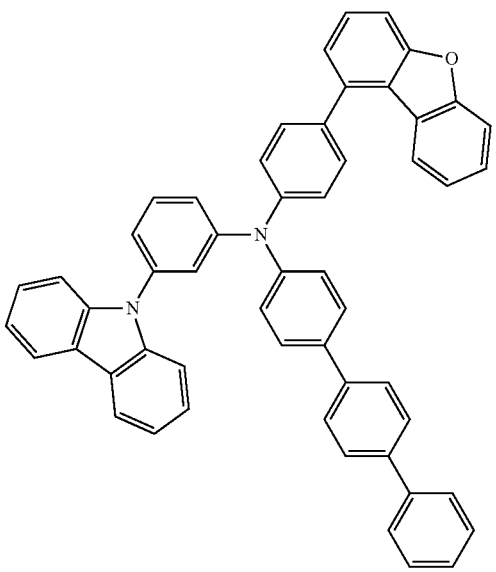

-continued
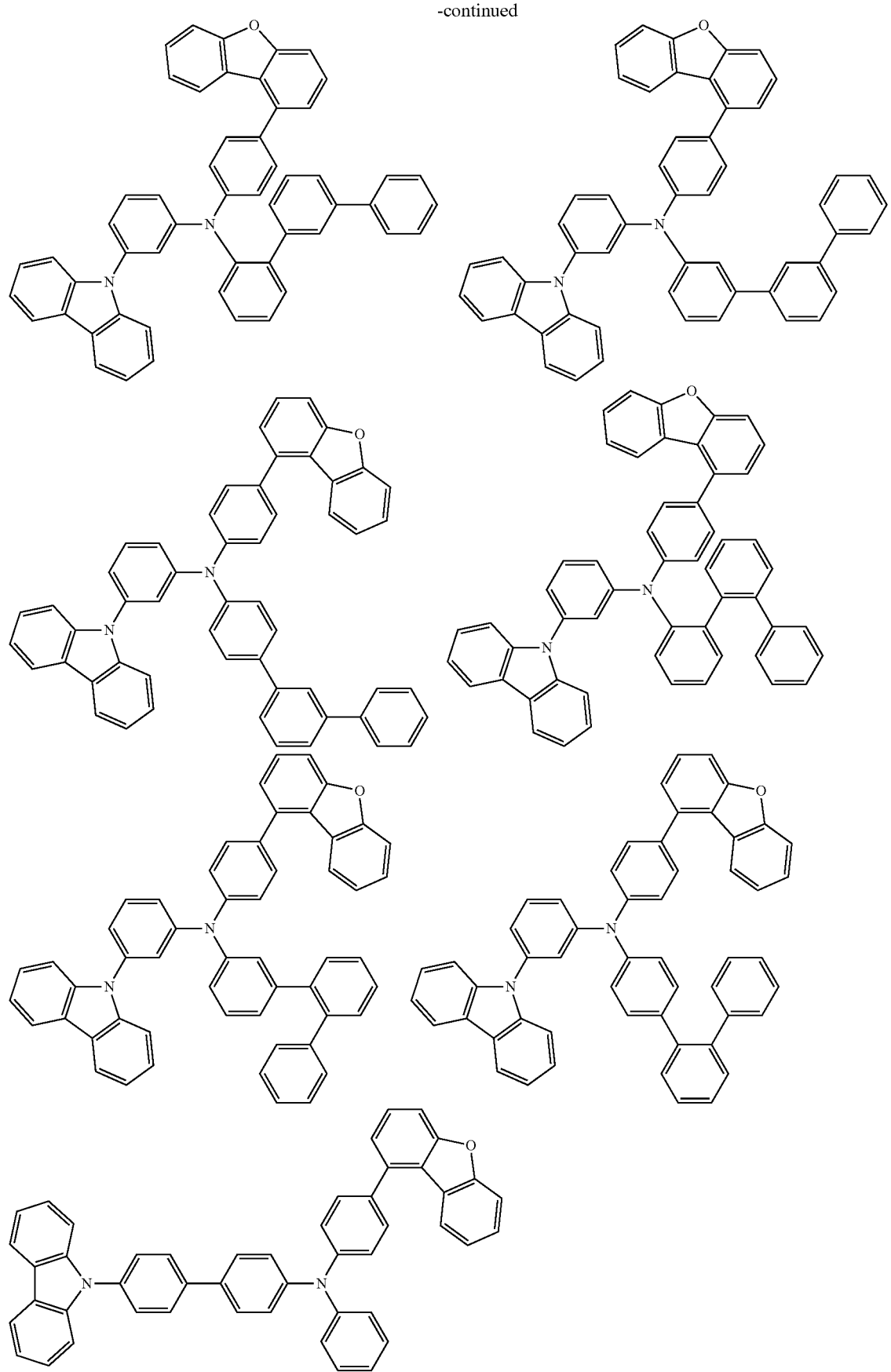

-continued
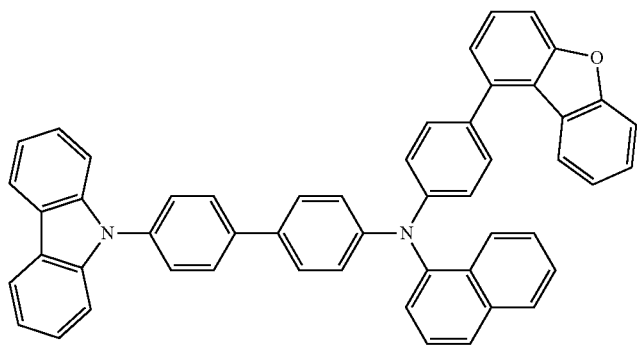
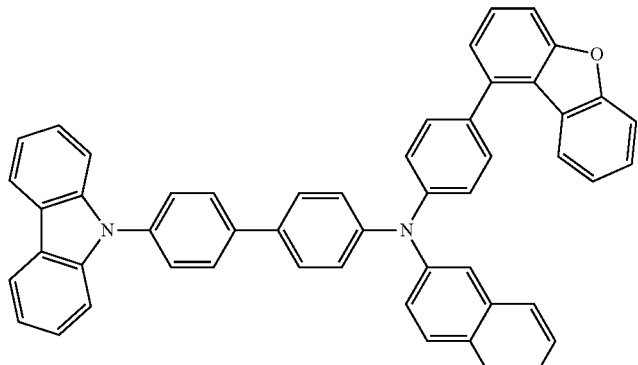
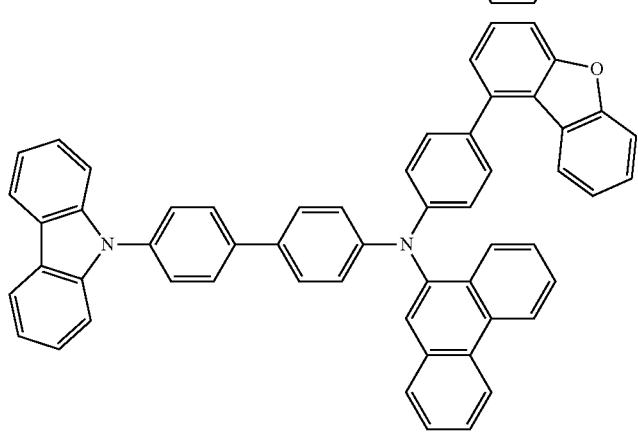
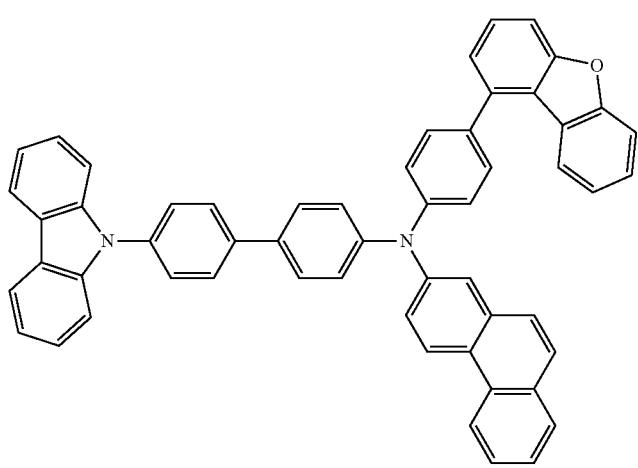

-continued
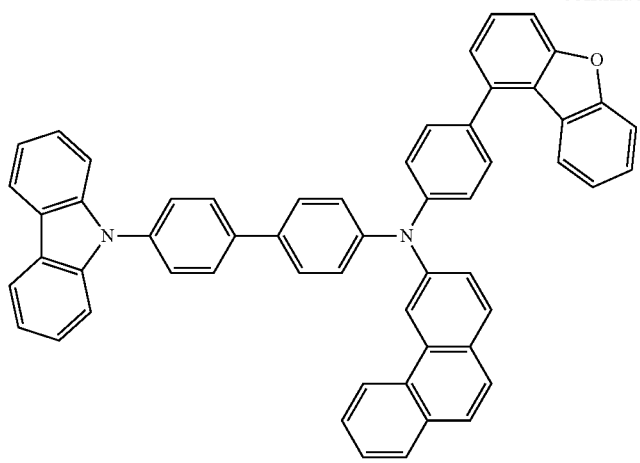
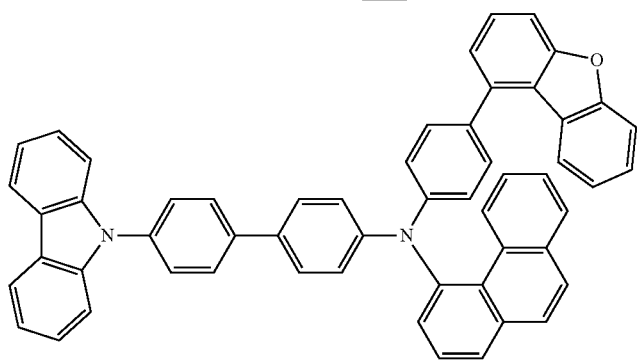
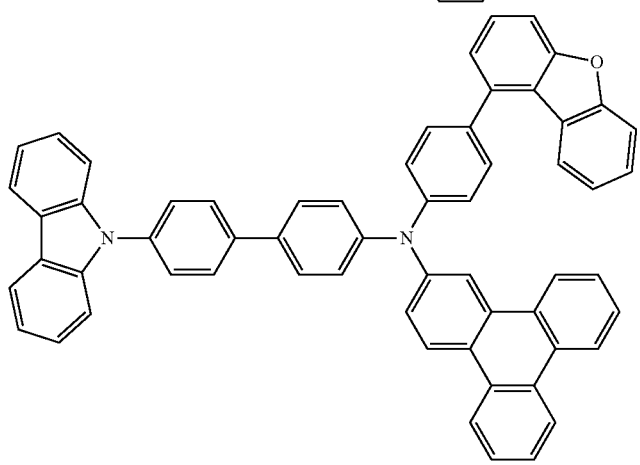
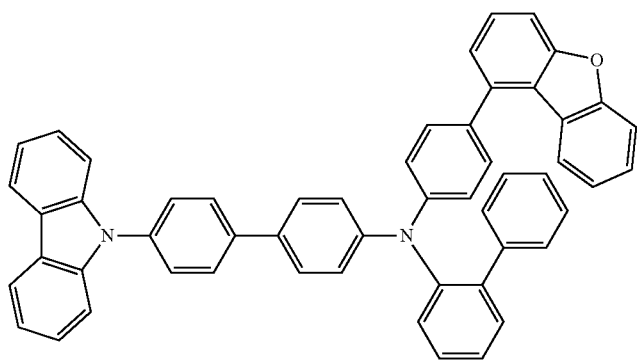

-continued
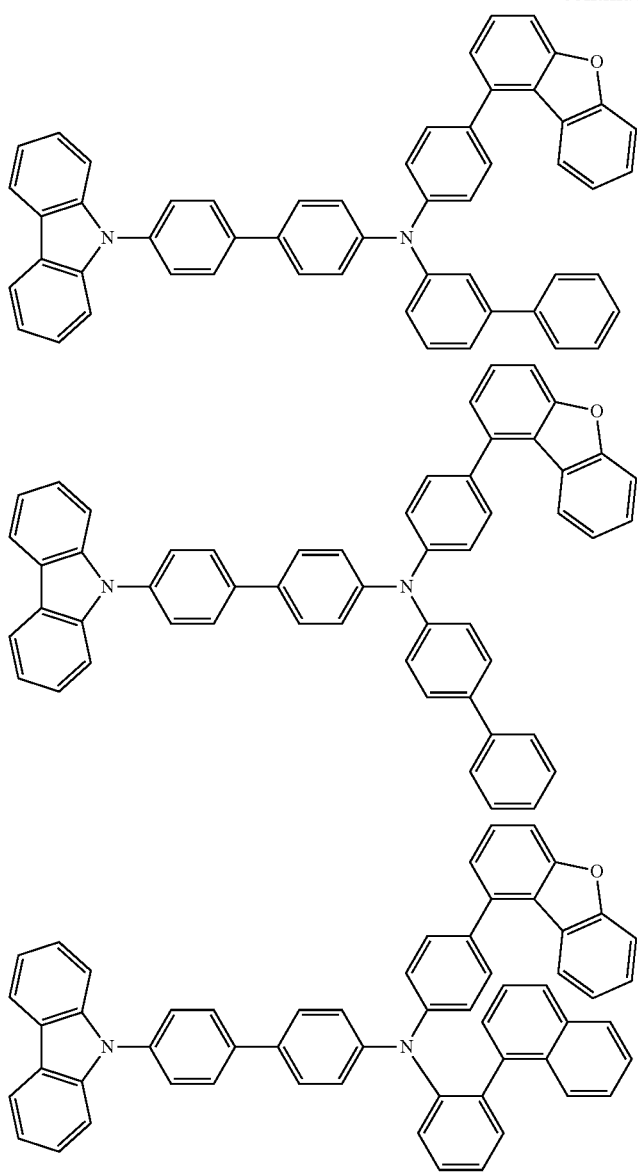
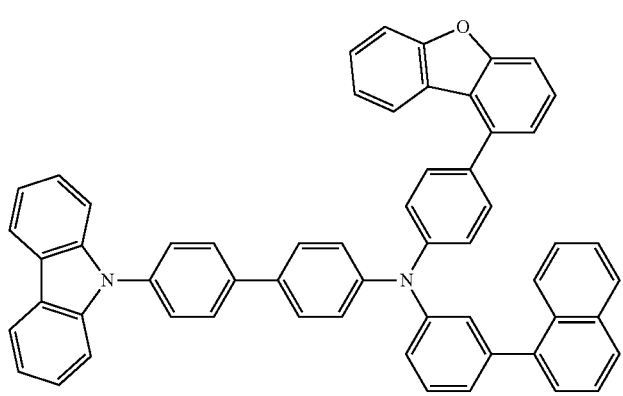

-continued
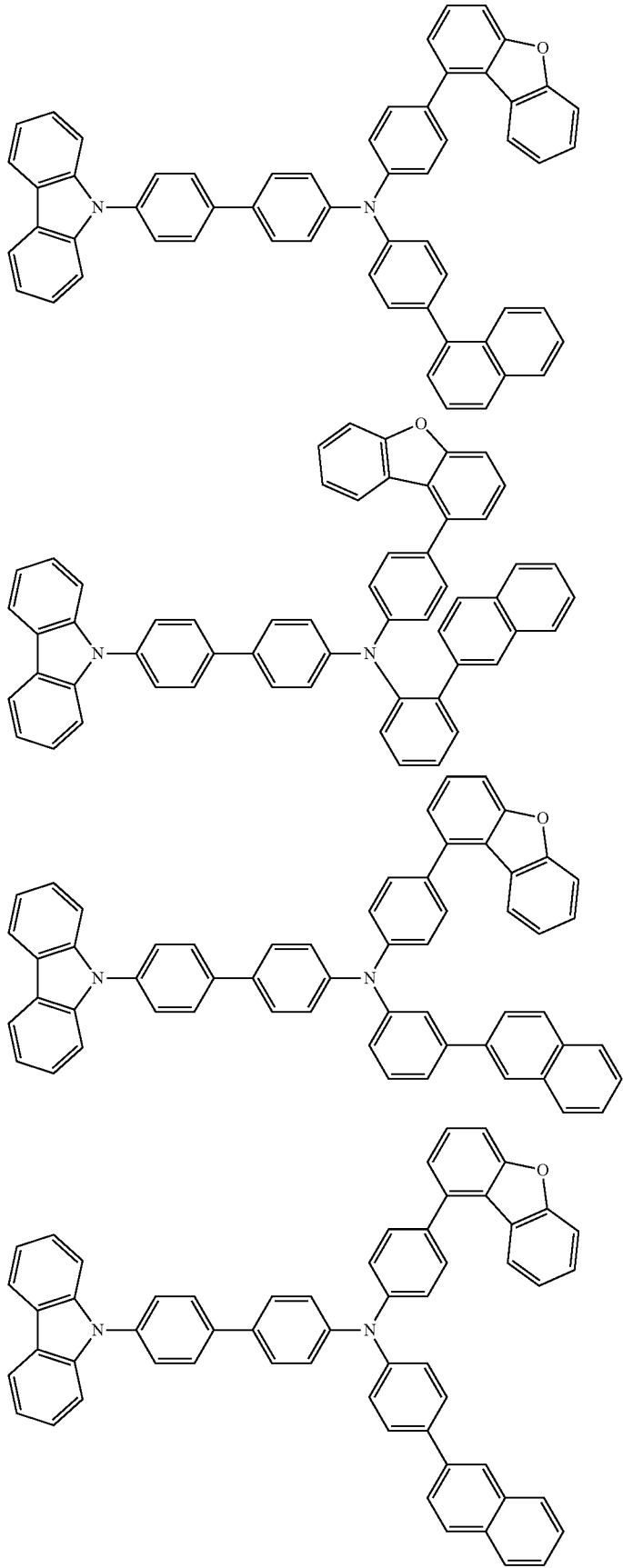

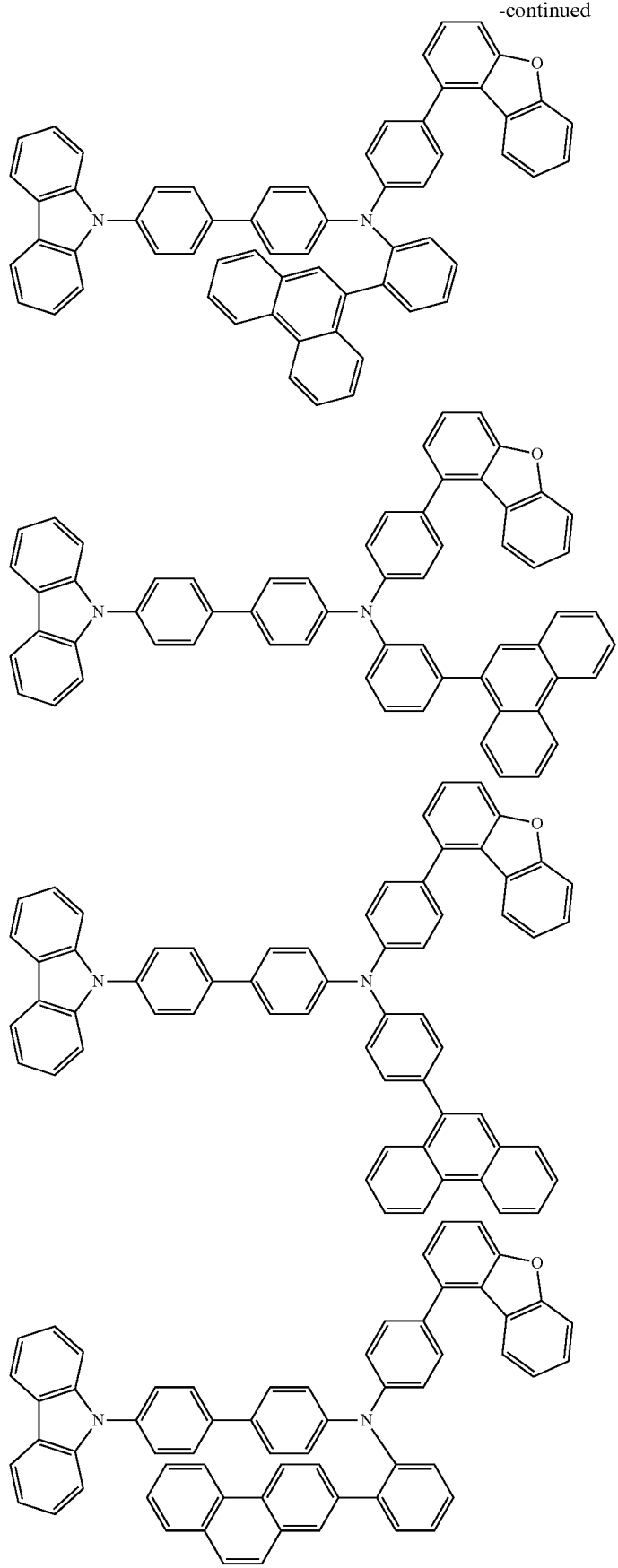

-continued
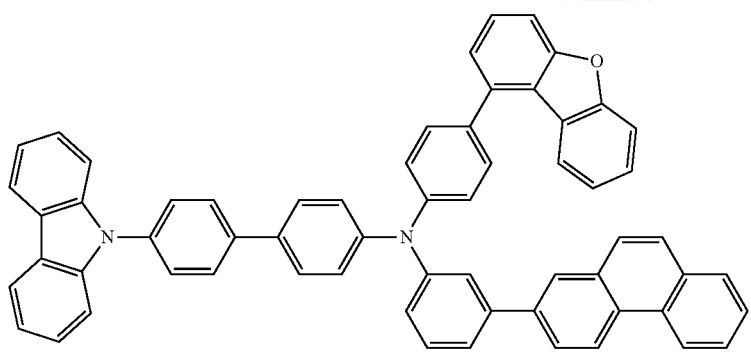
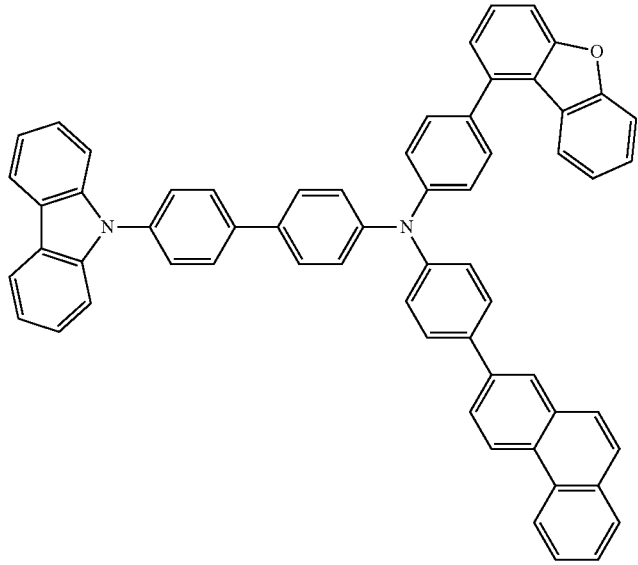
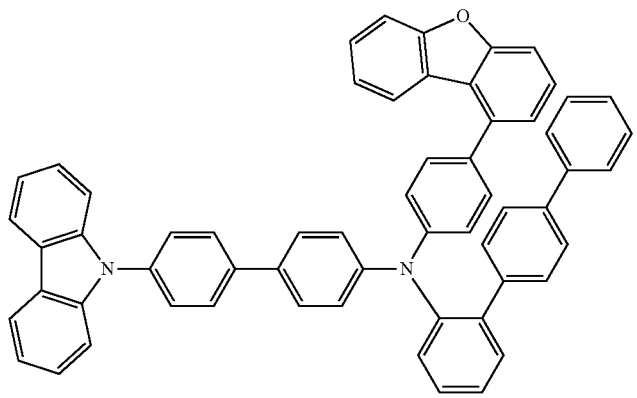
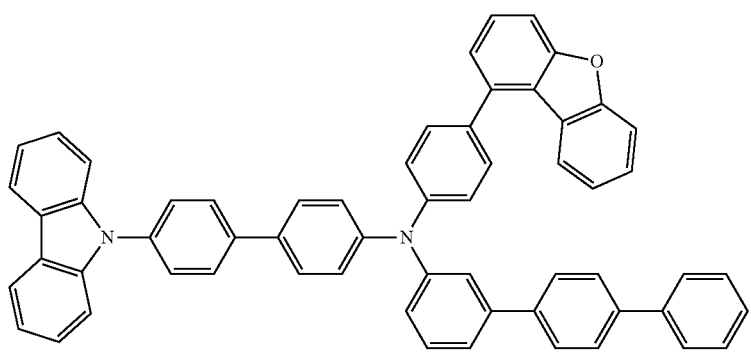

-continued
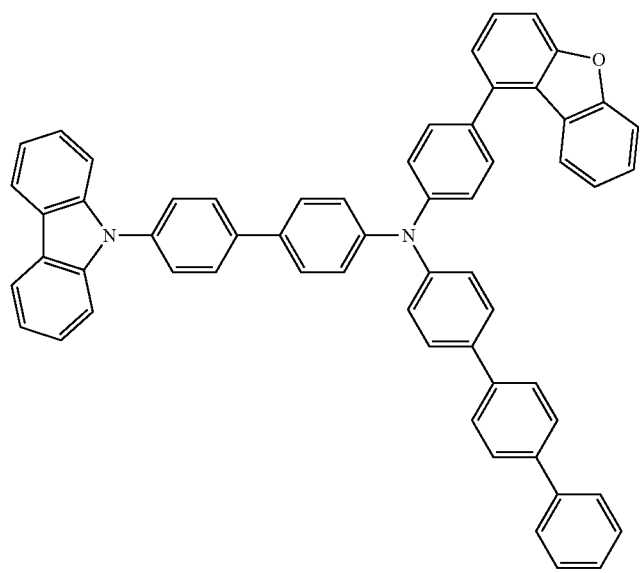
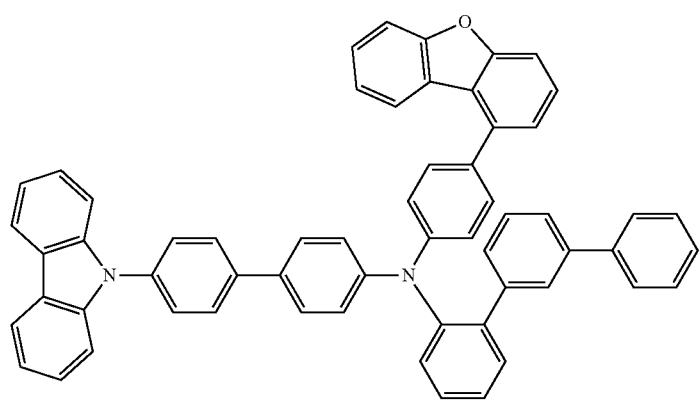
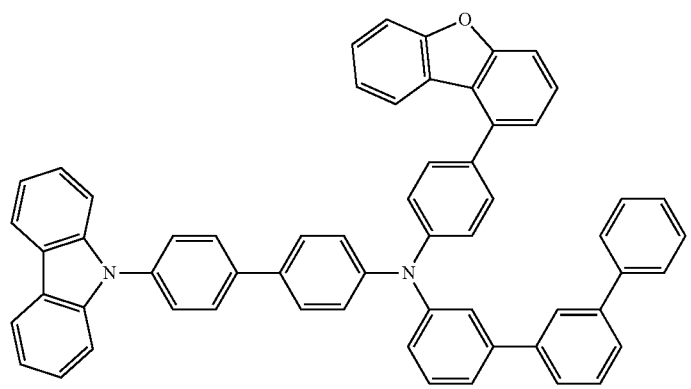

-continued
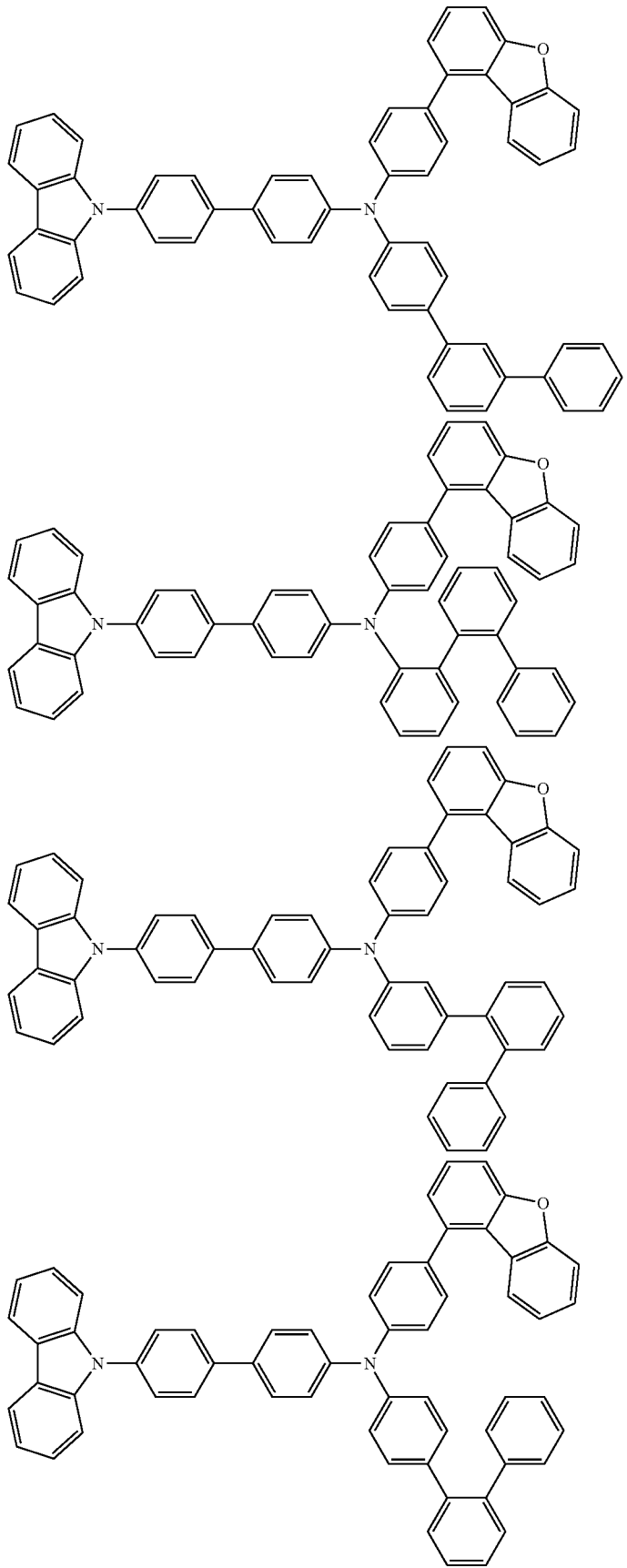

-continued
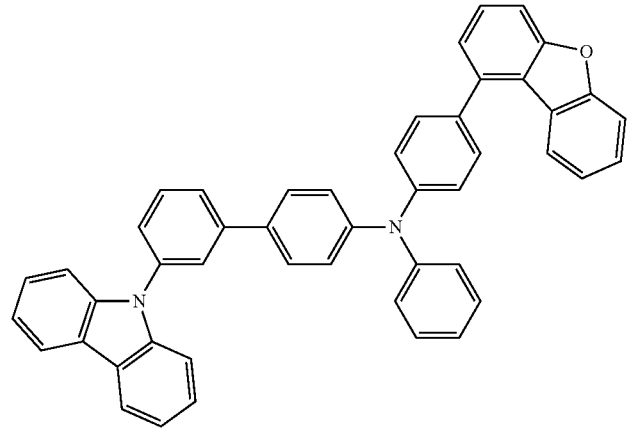
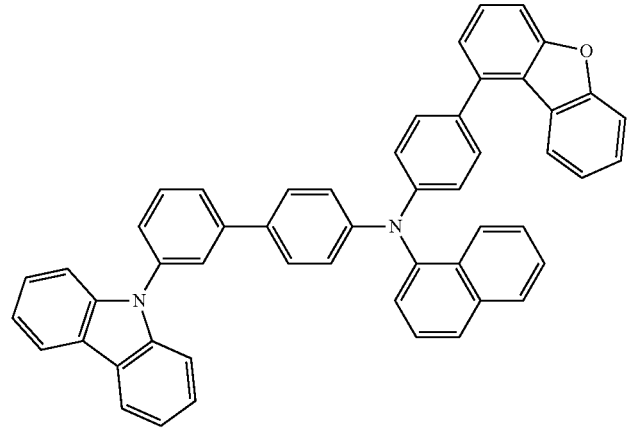
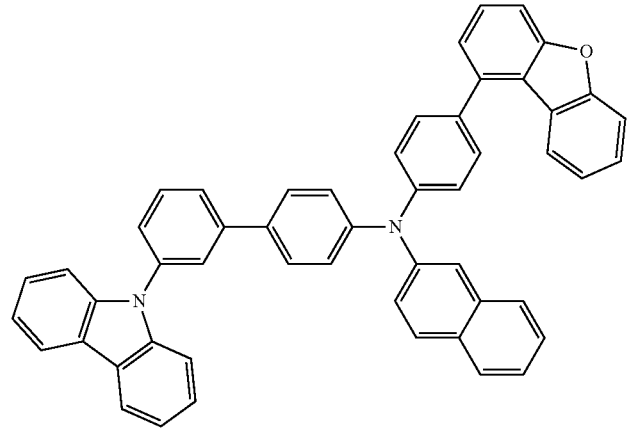
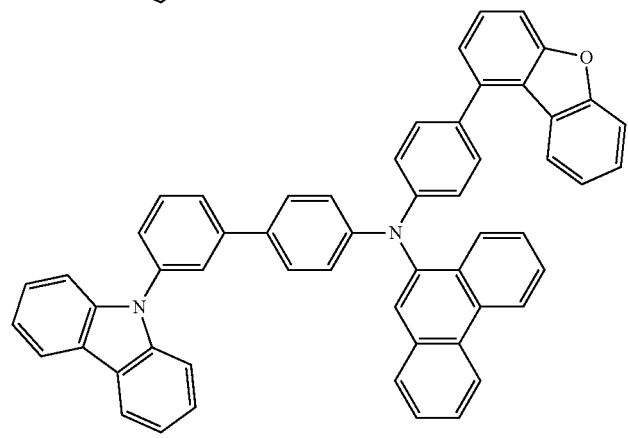

-continued
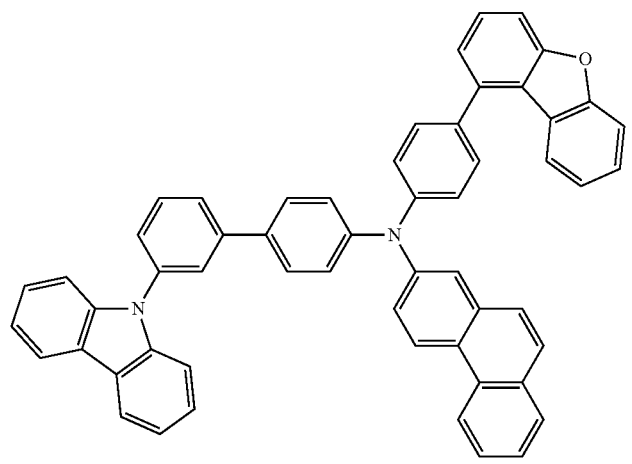
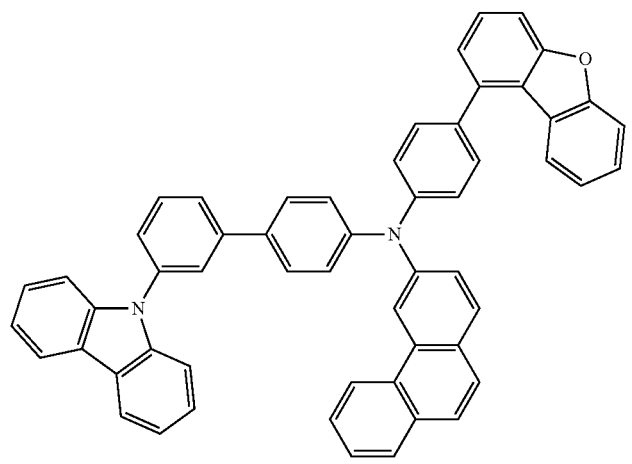
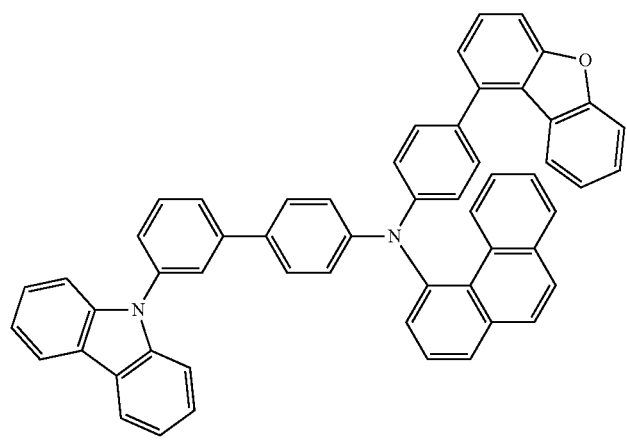

-continued
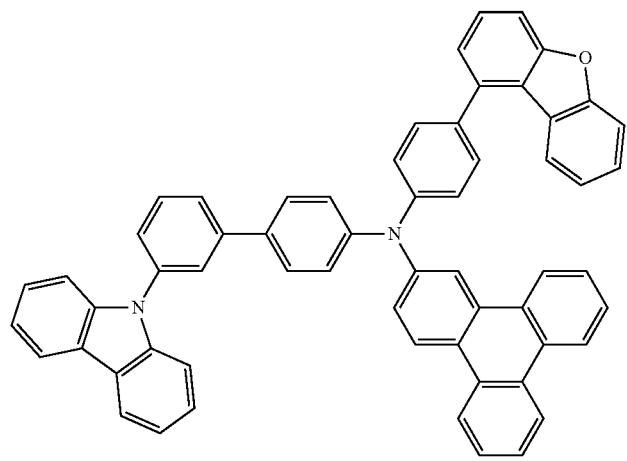
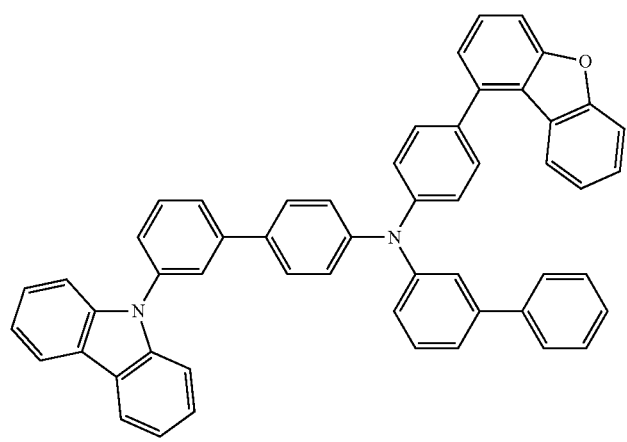
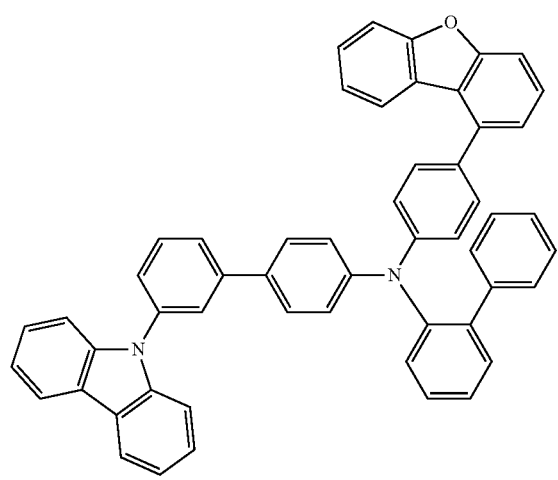

-continued
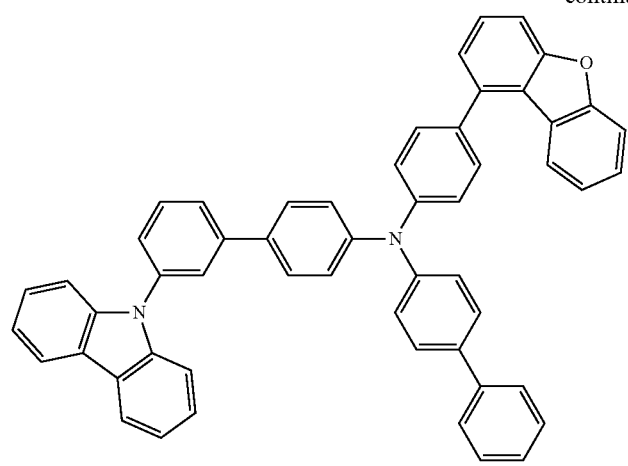
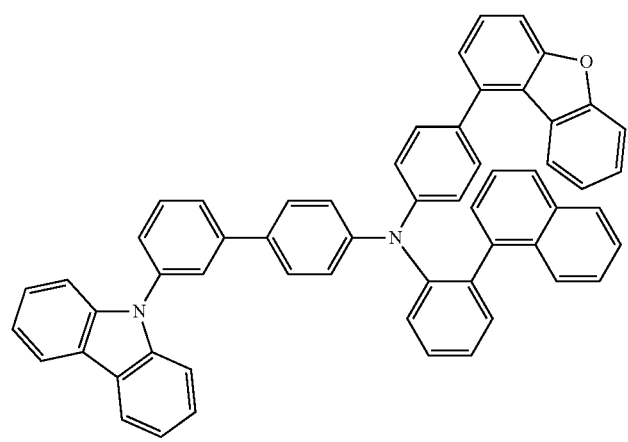
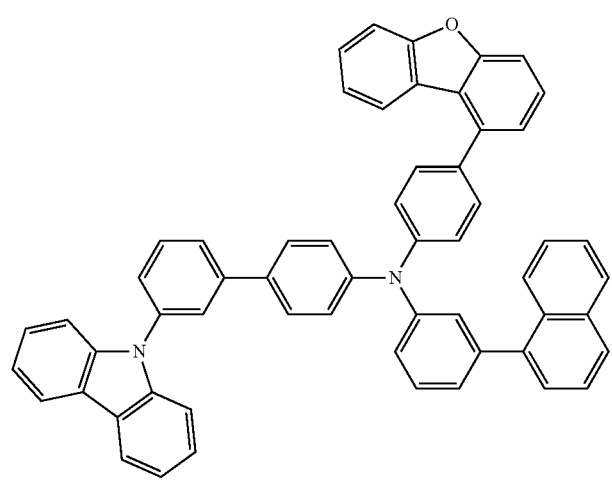

-continued
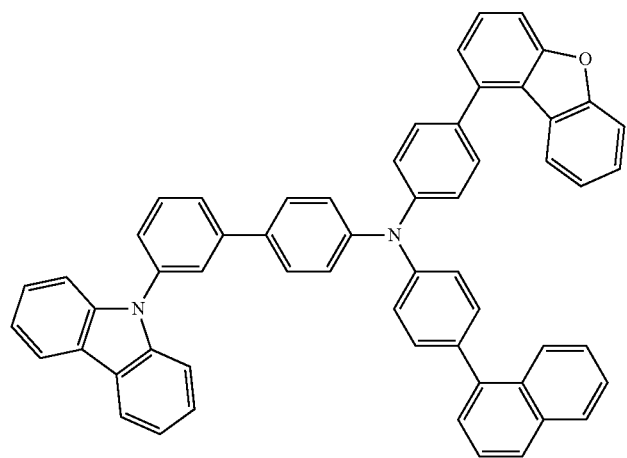
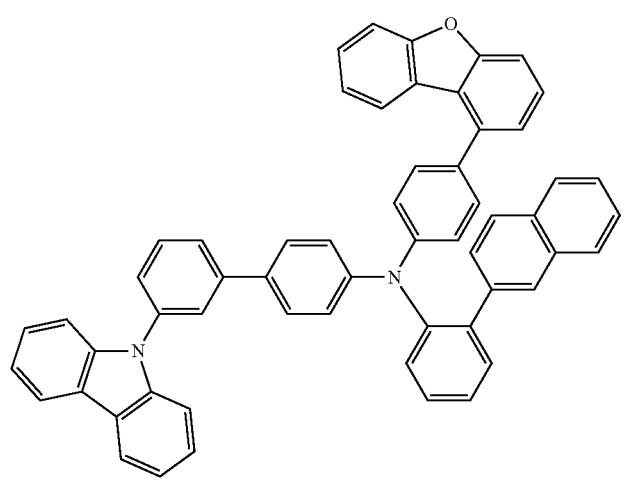
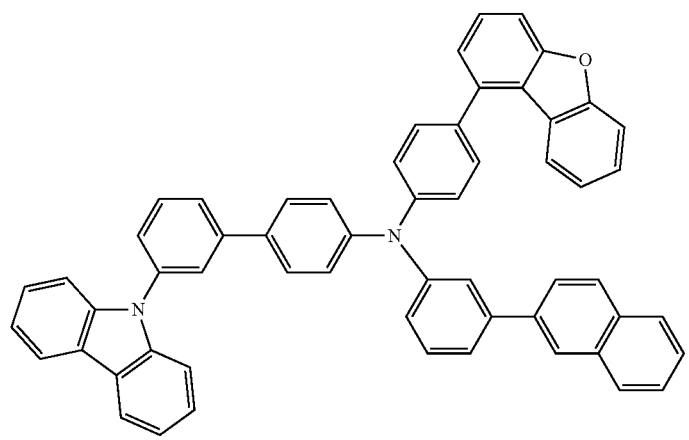

-continued
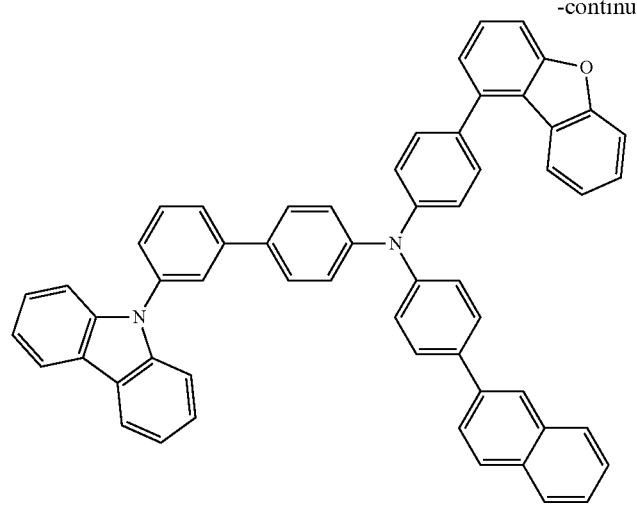
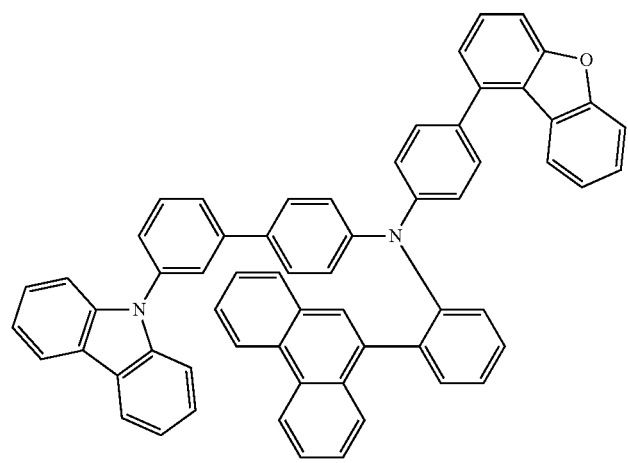
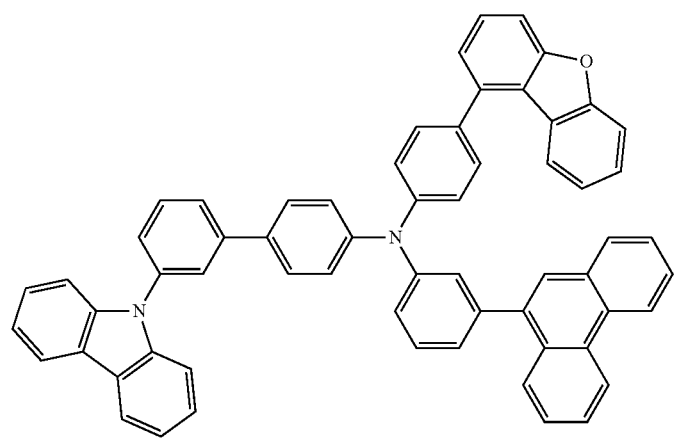

-continued
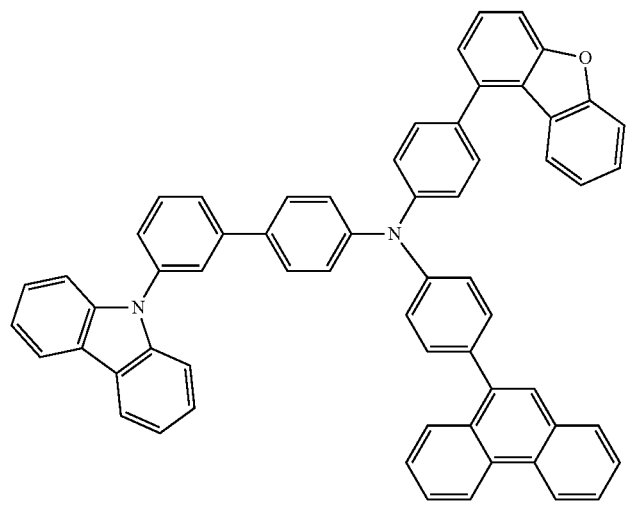
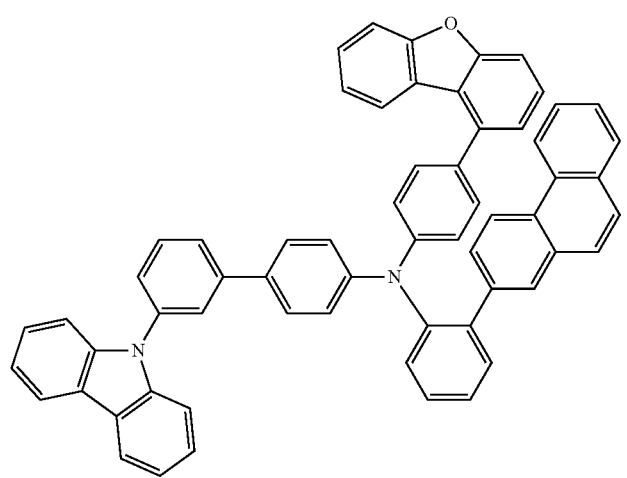
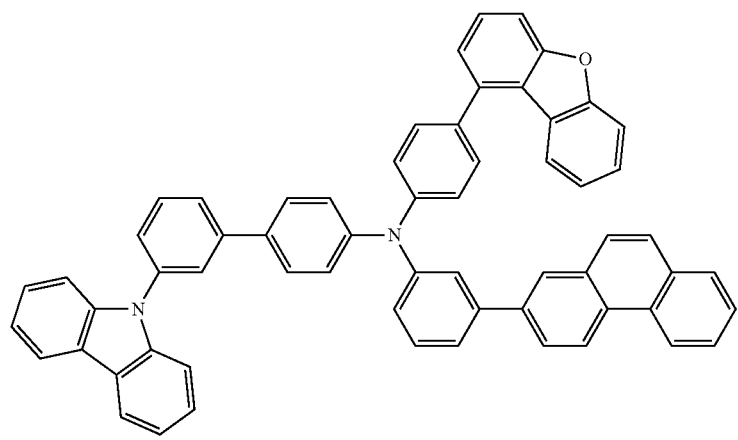

-continued
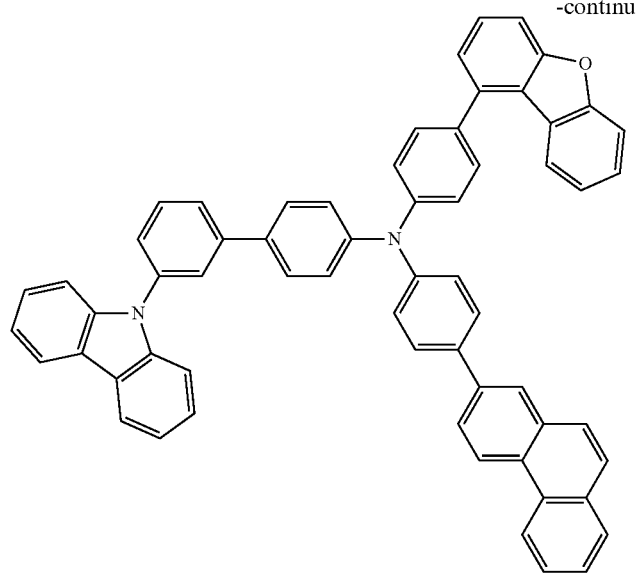
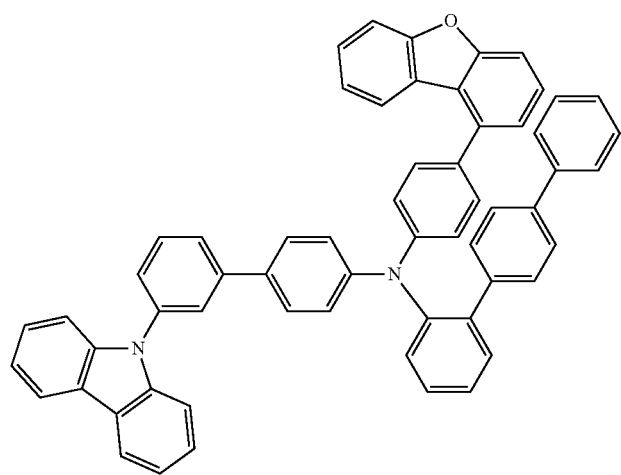
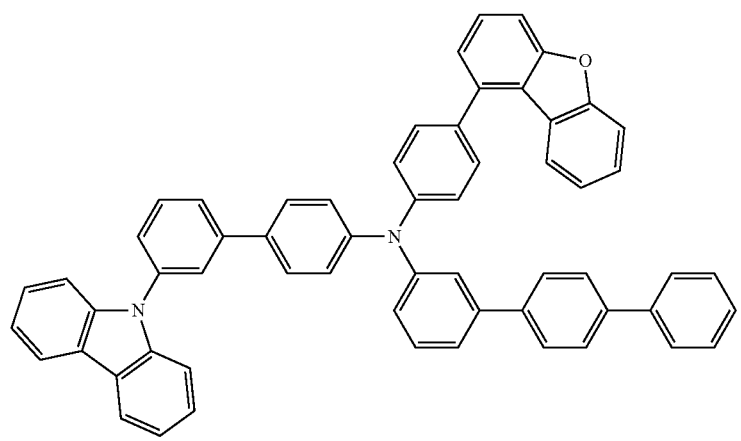

-continued
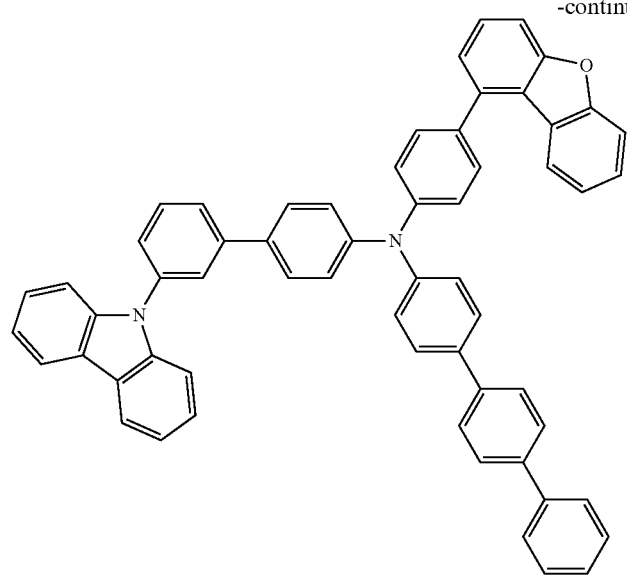
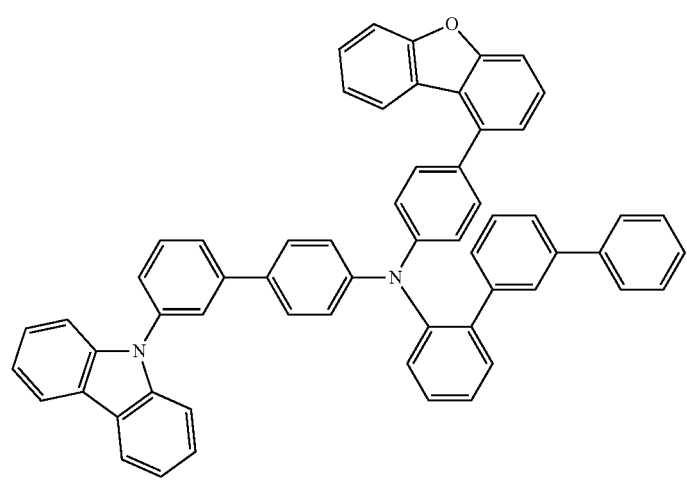
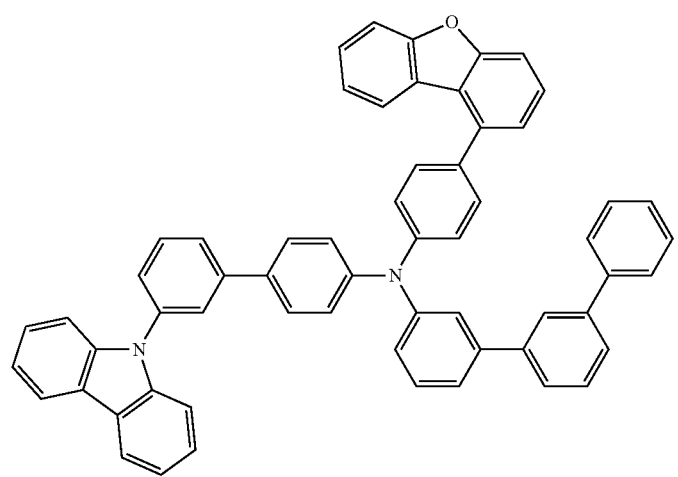

-continued
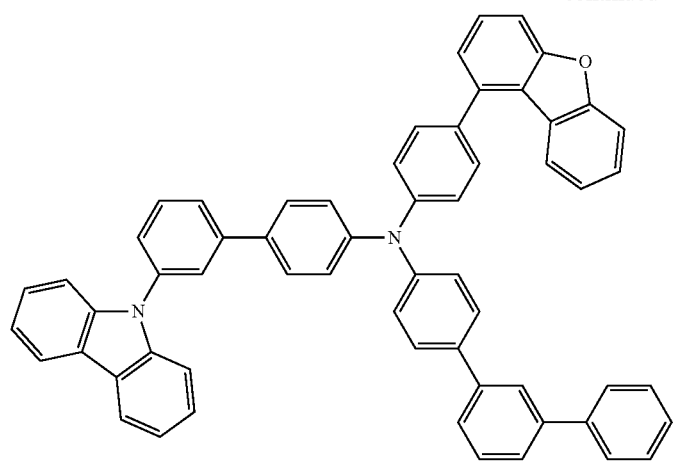
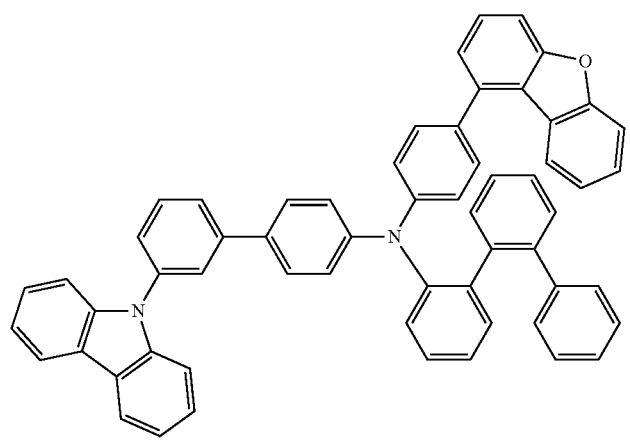
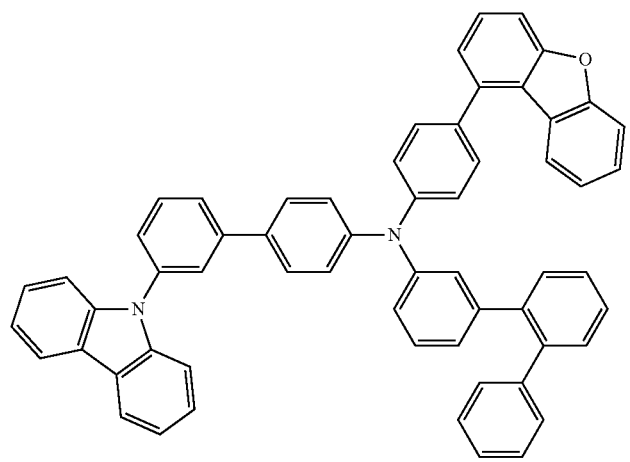

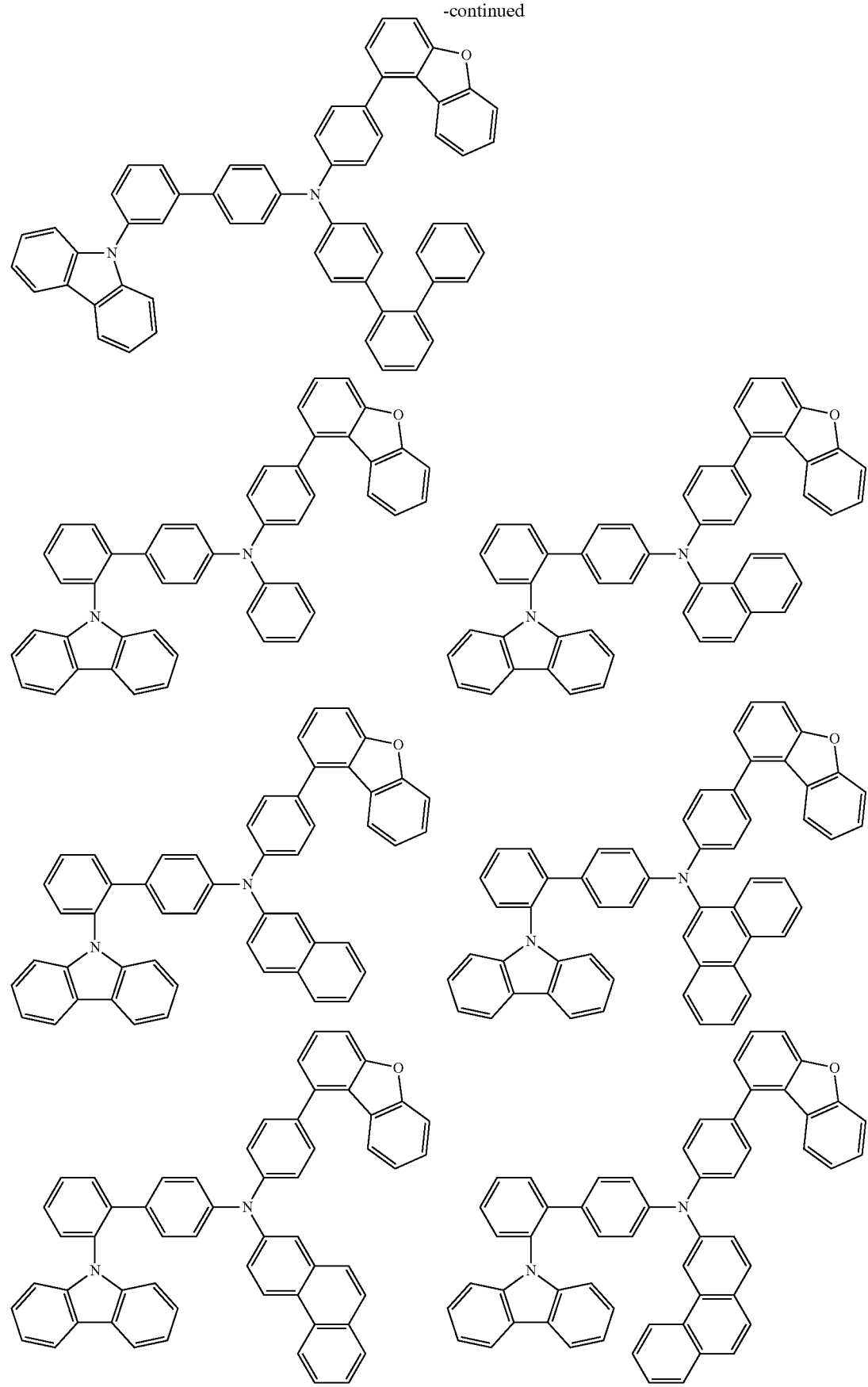

-continued
| 89 | 90 |
|---|---|
| 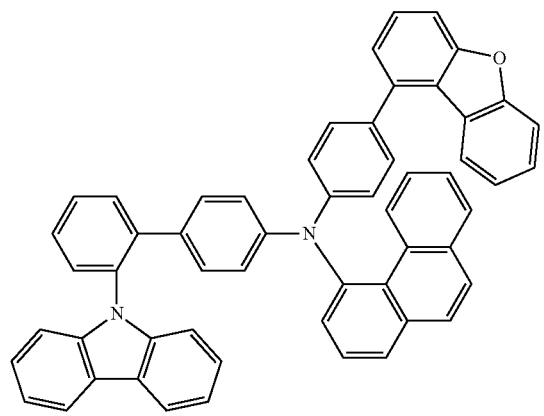 | 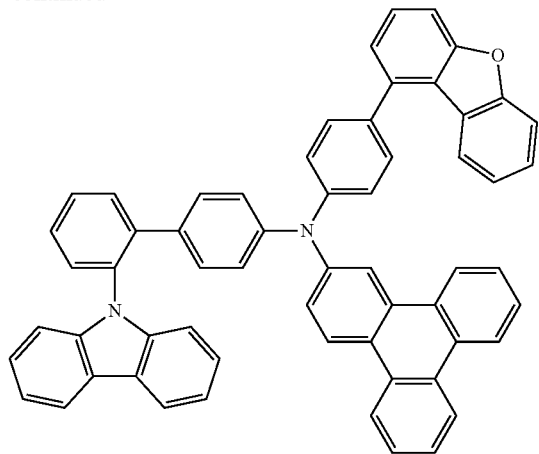 |
| 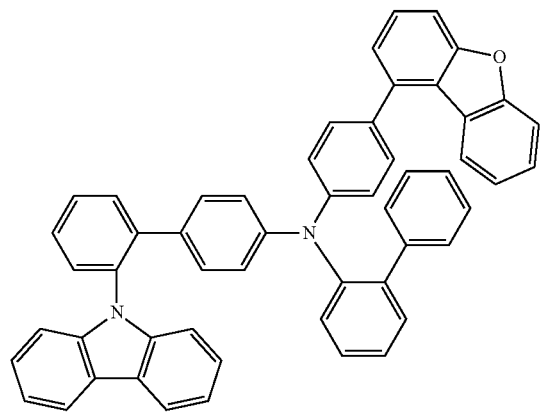 | 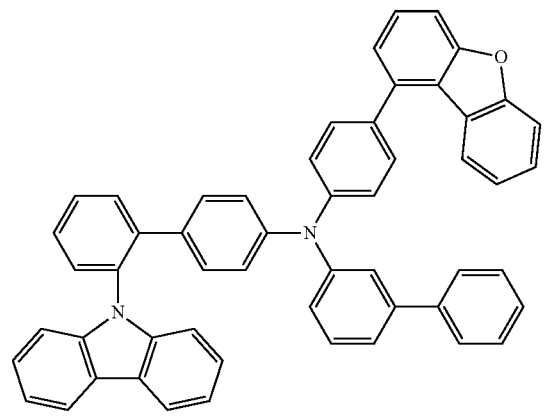 |
| 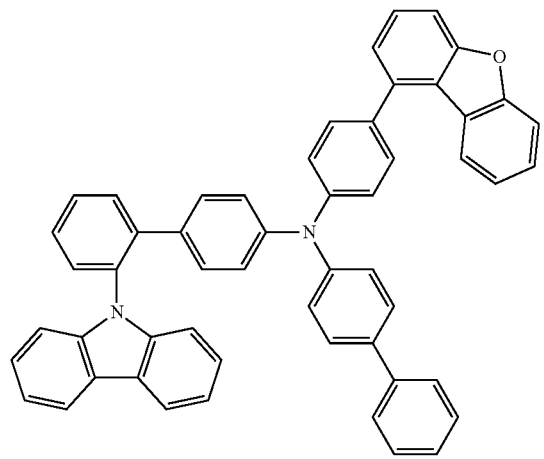 | 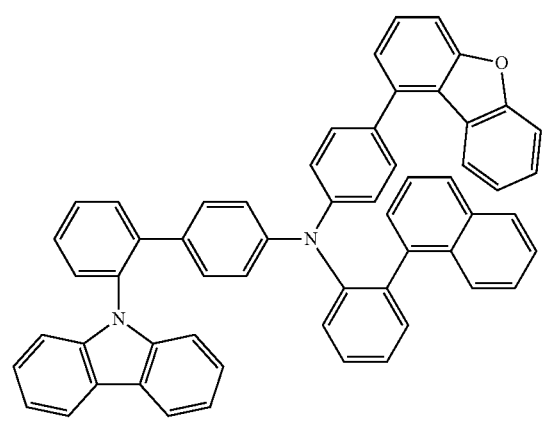 |

-continued
91
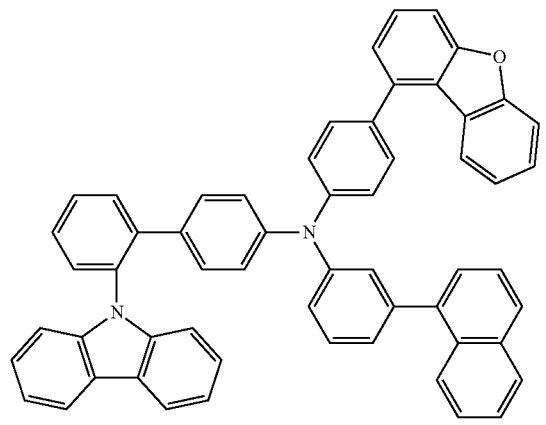
92
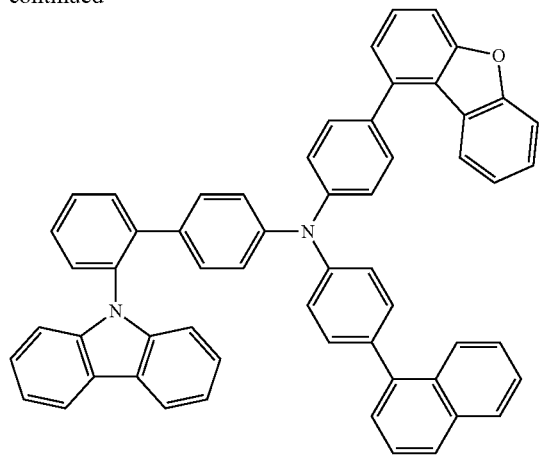
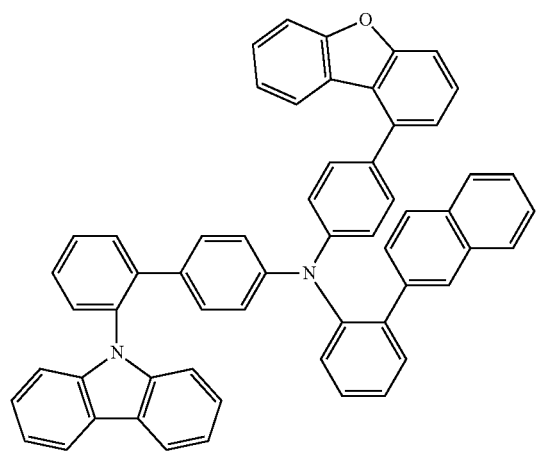
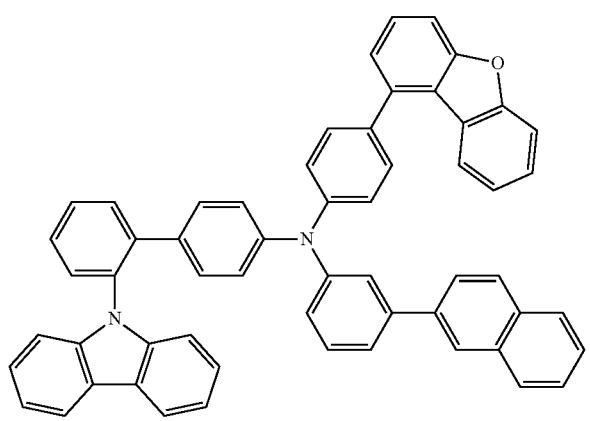
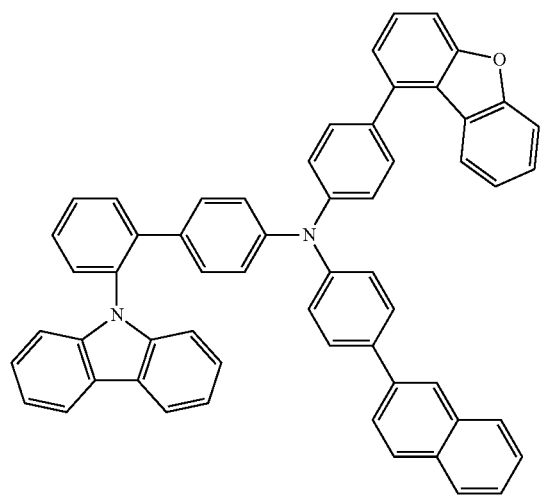
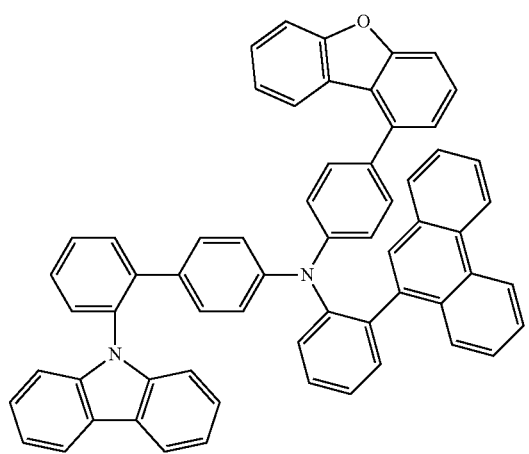

-continued
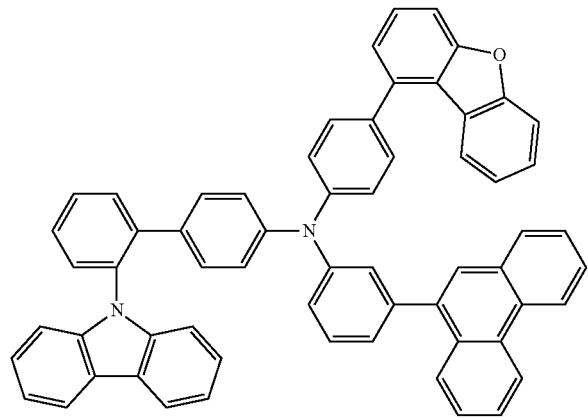
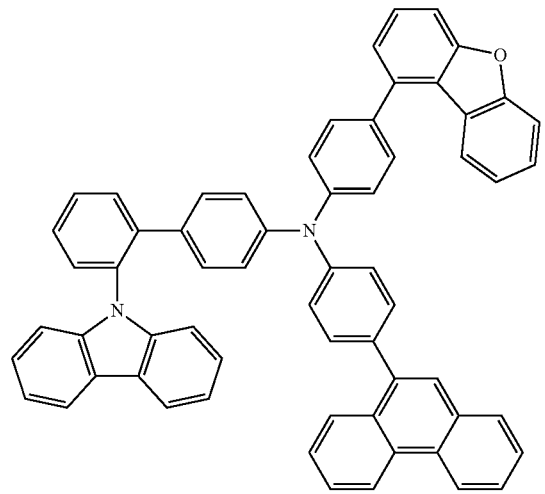
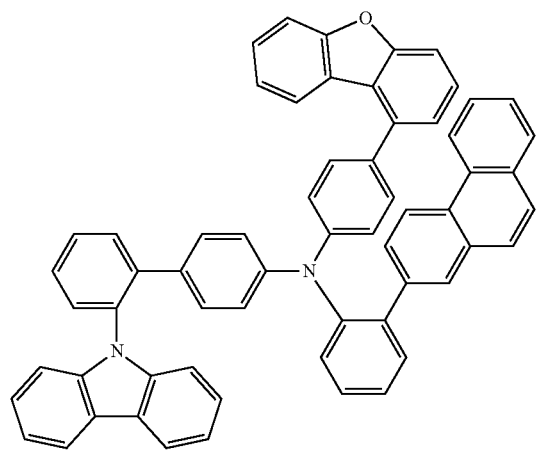
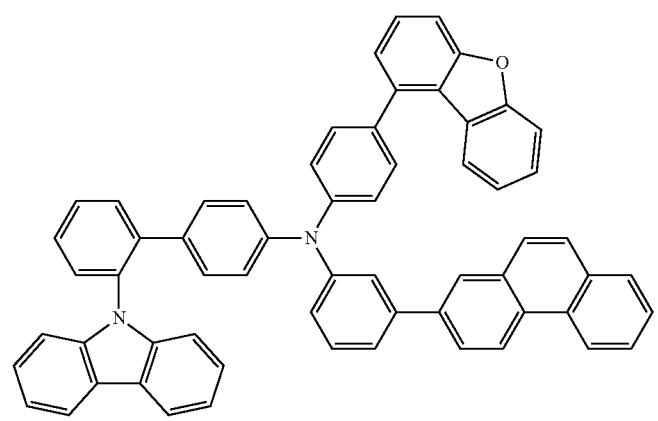
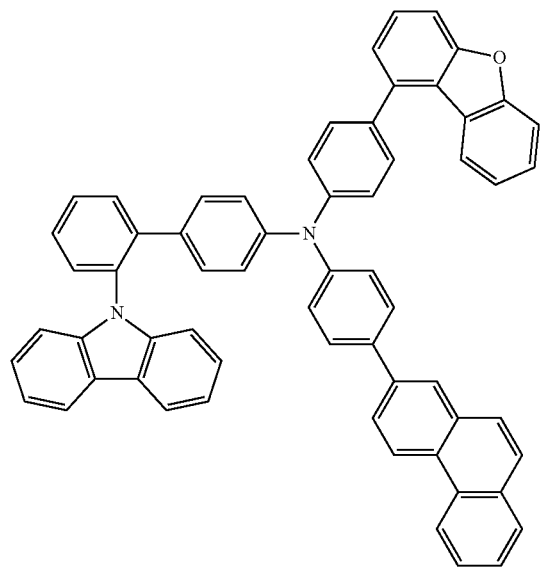
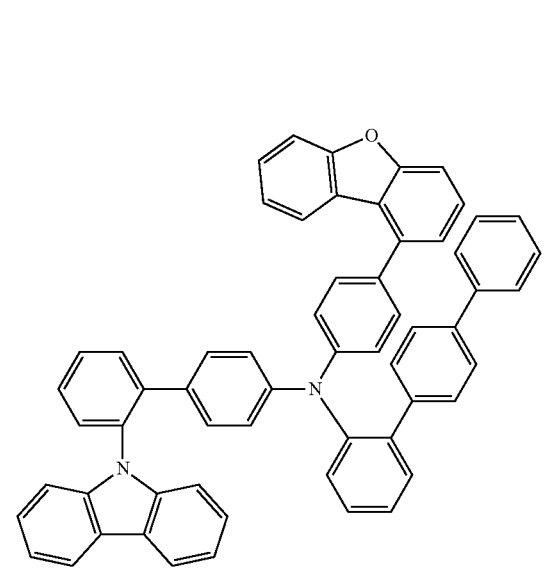

-continued
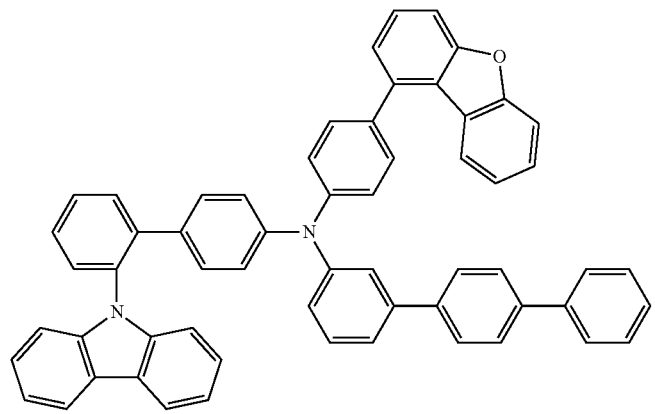
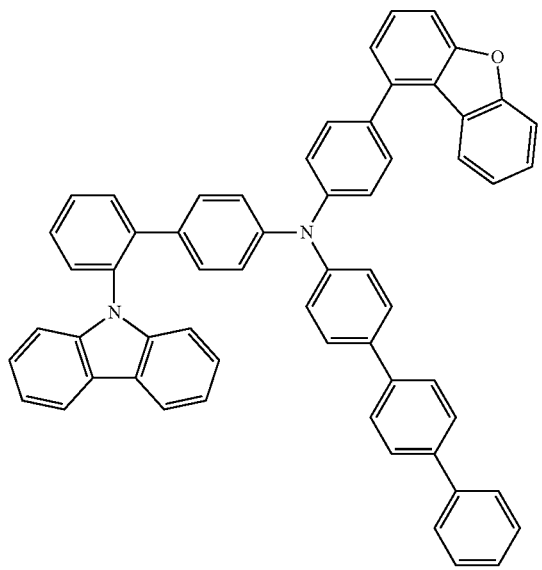
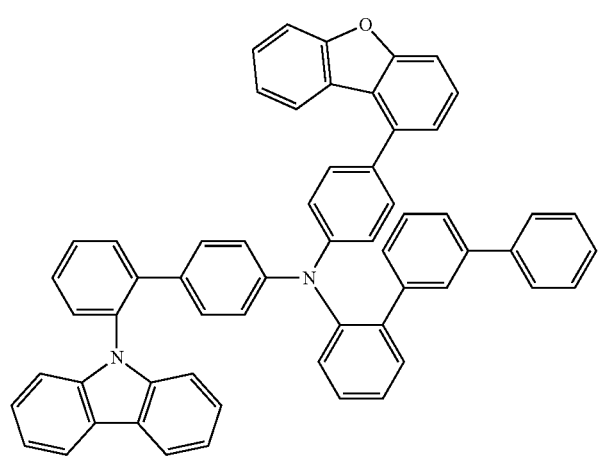
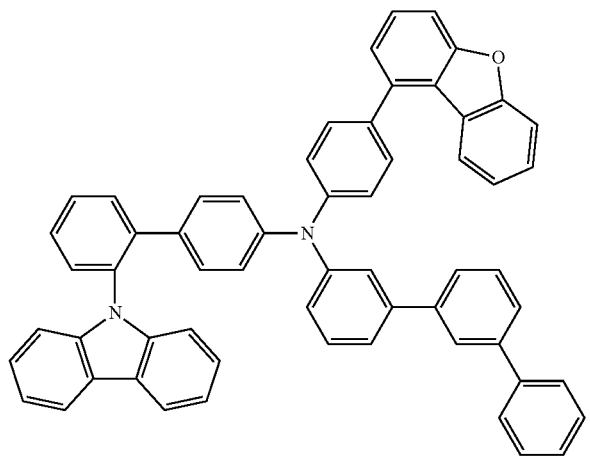
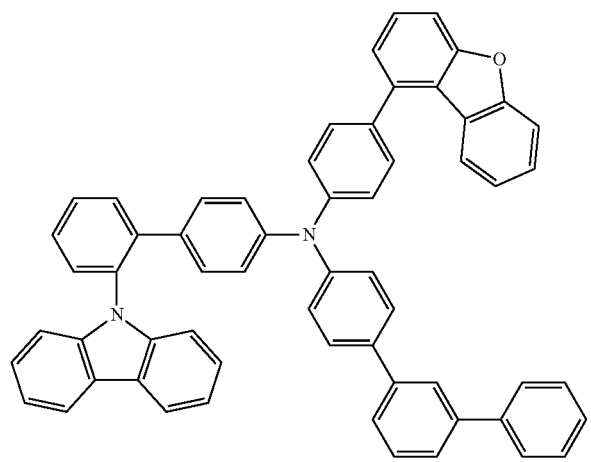
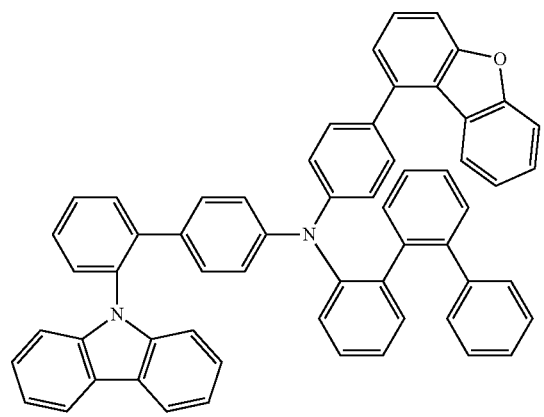

-continued
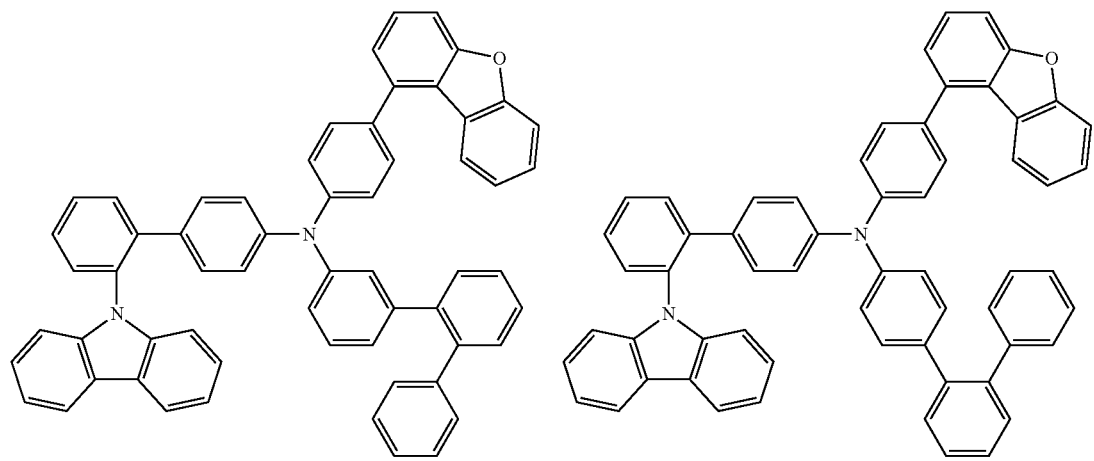
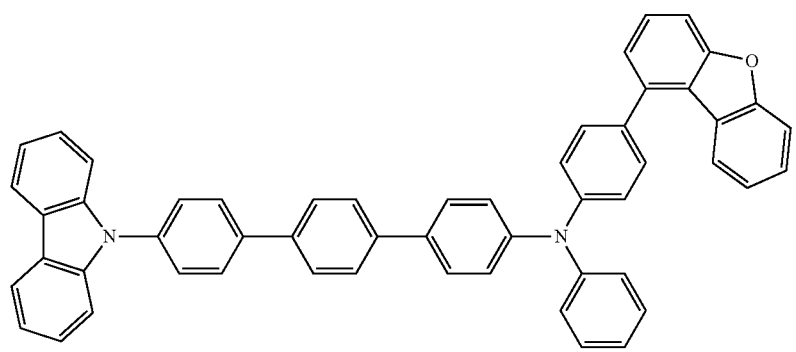
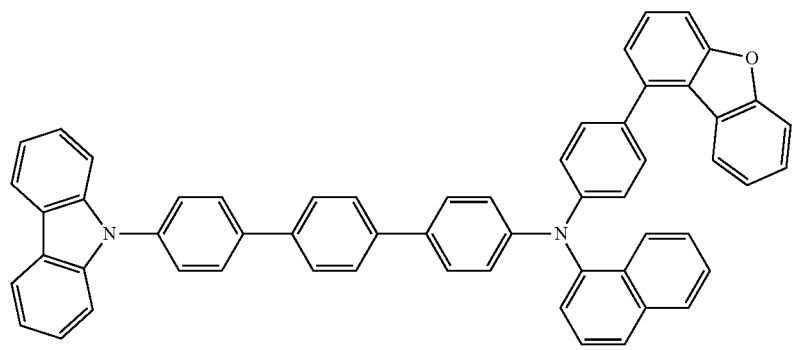
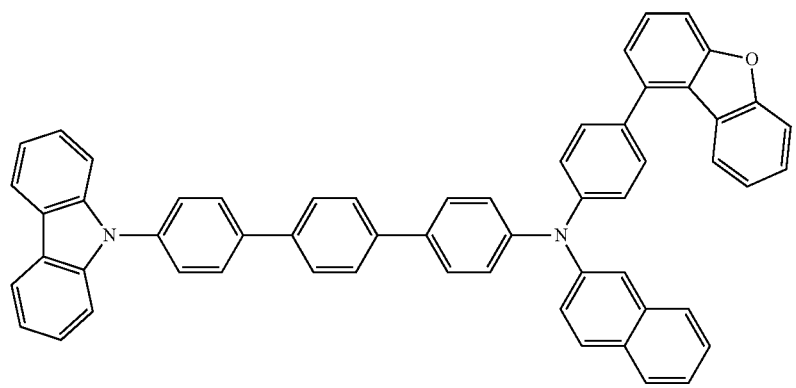

-continued
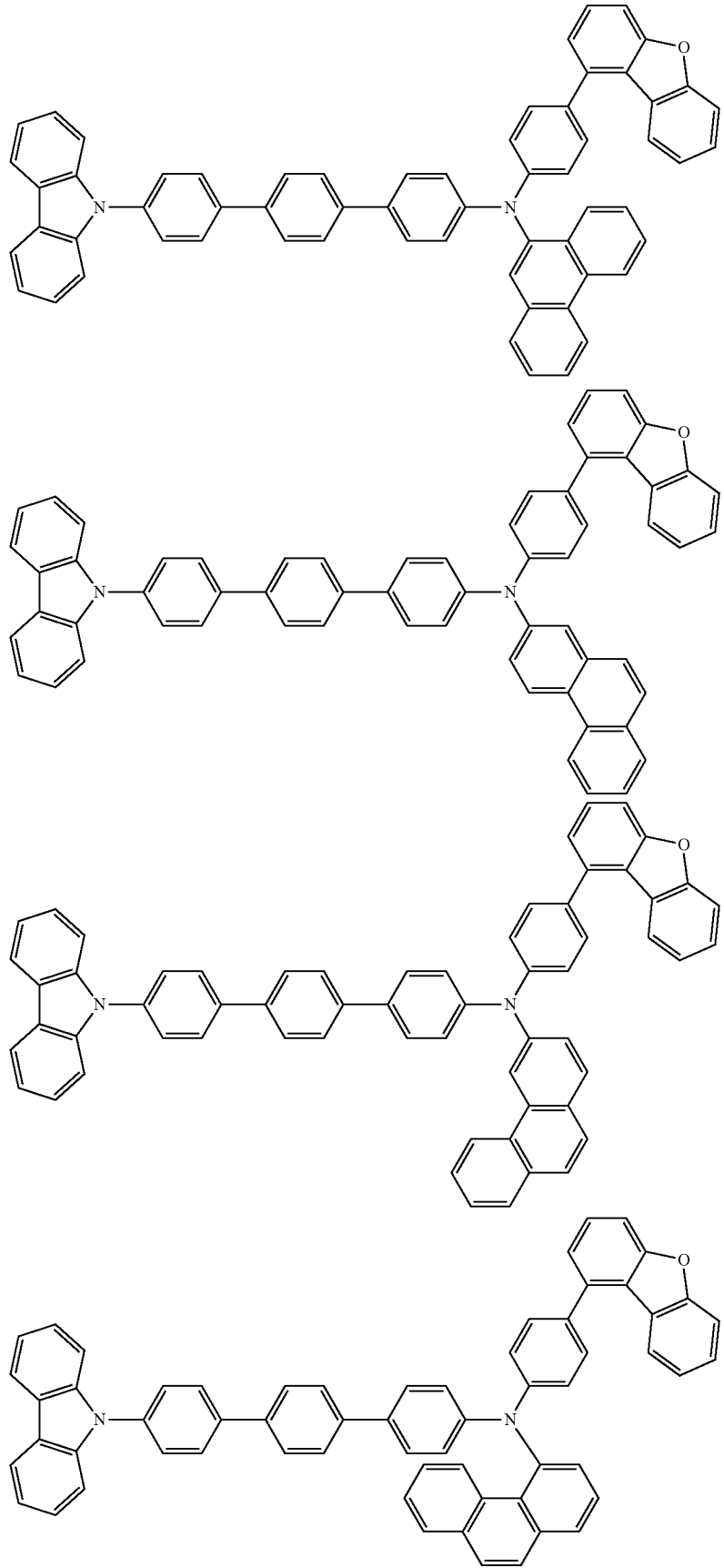

-continued
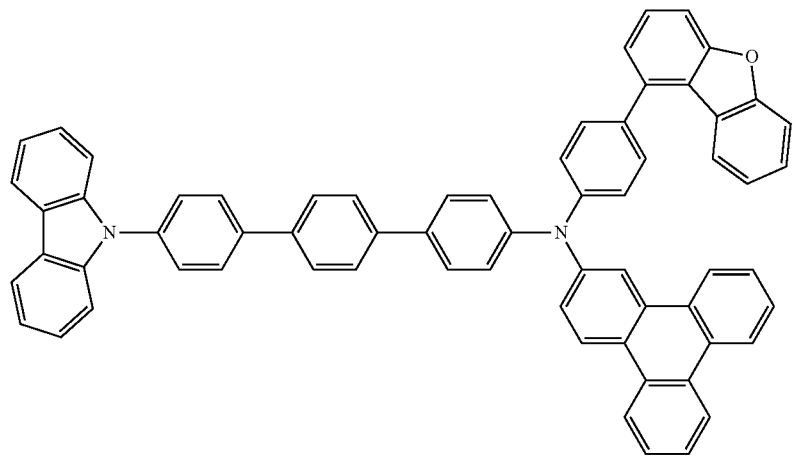
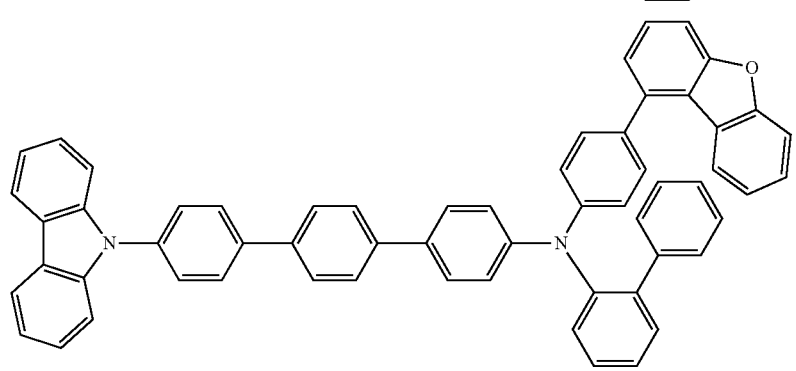
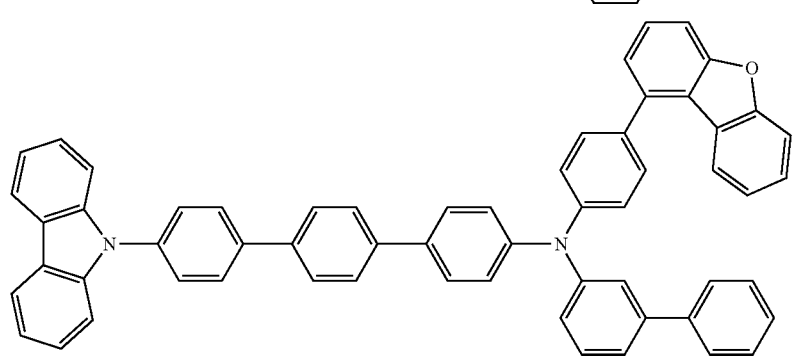
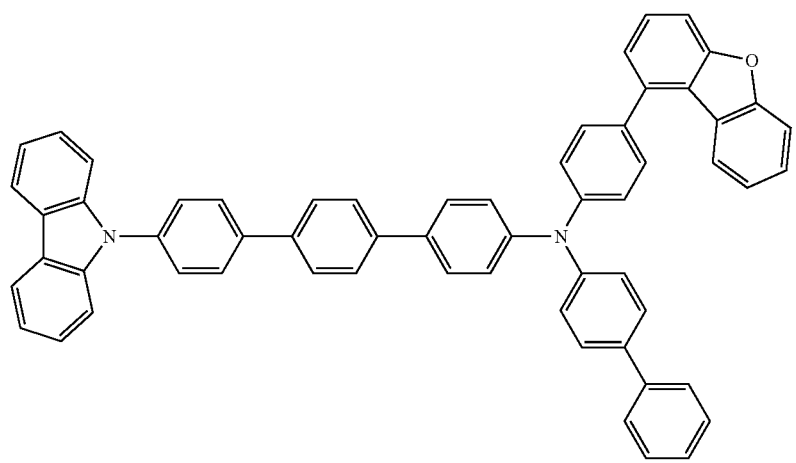

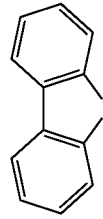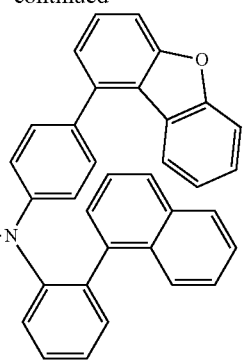
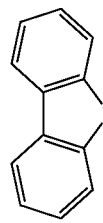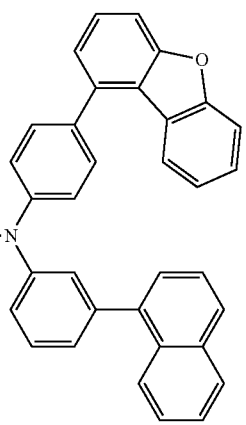
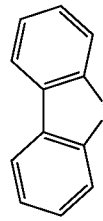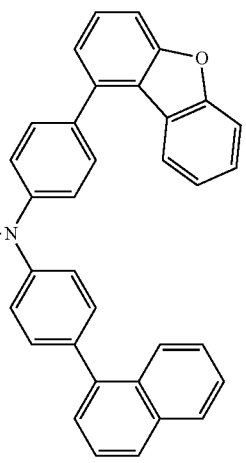
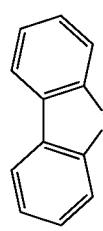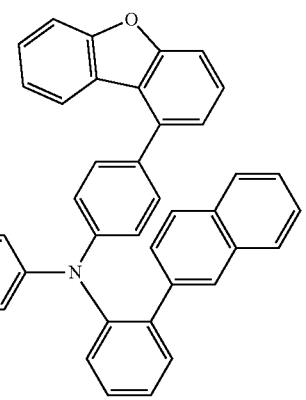

-continued
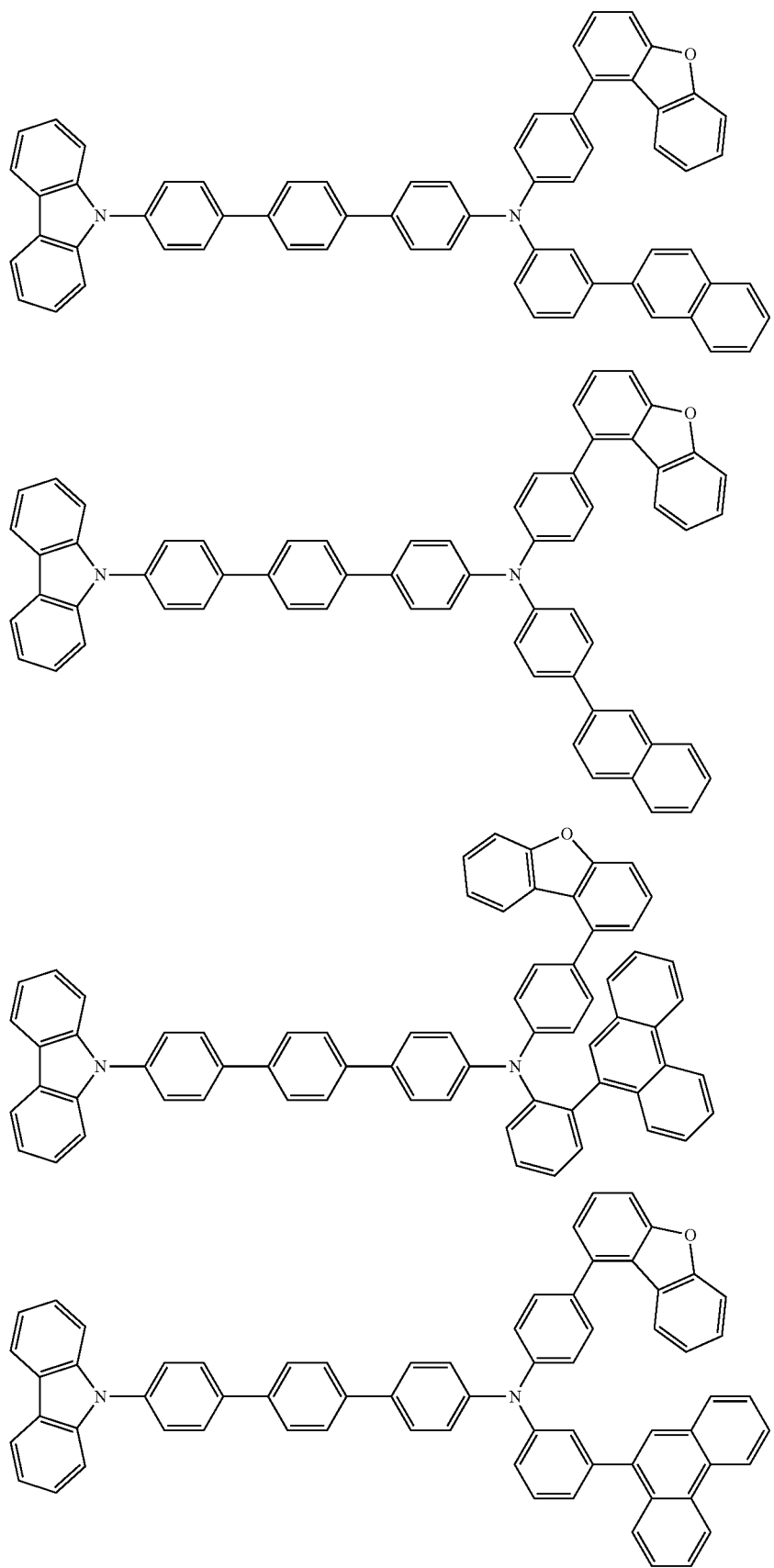

-continued
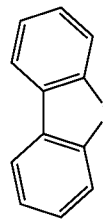
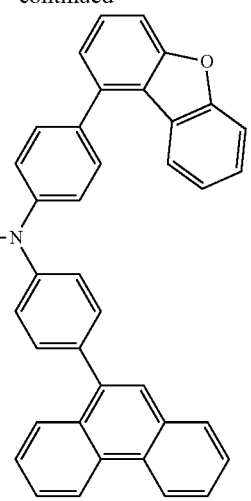
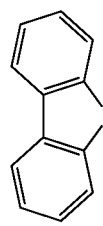
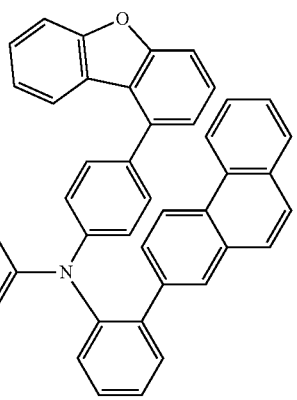
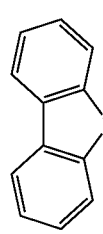
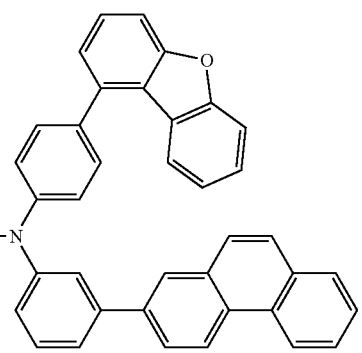

-continued
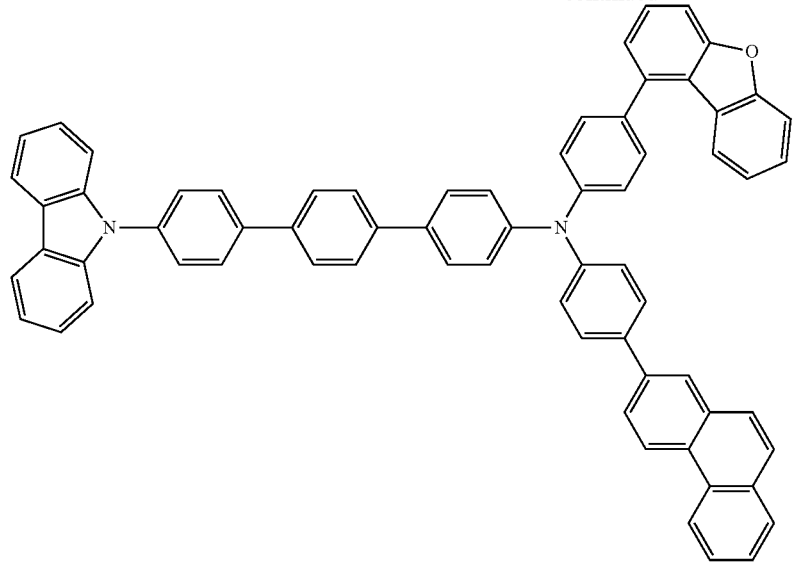
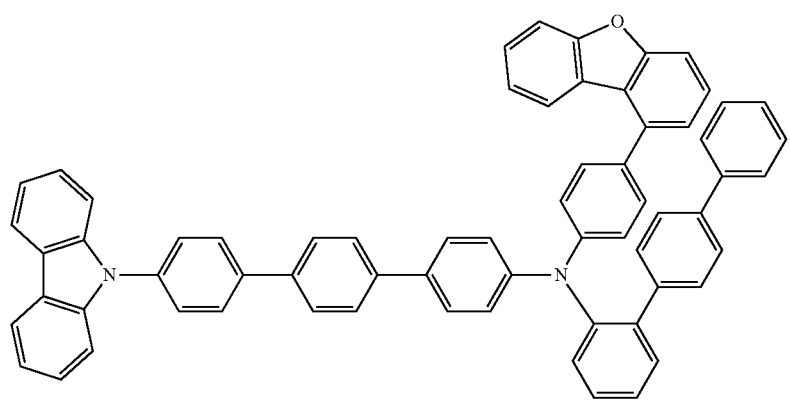
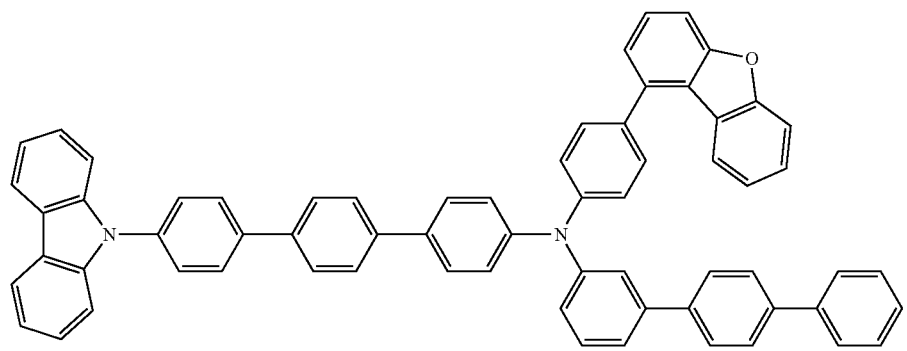

-continued
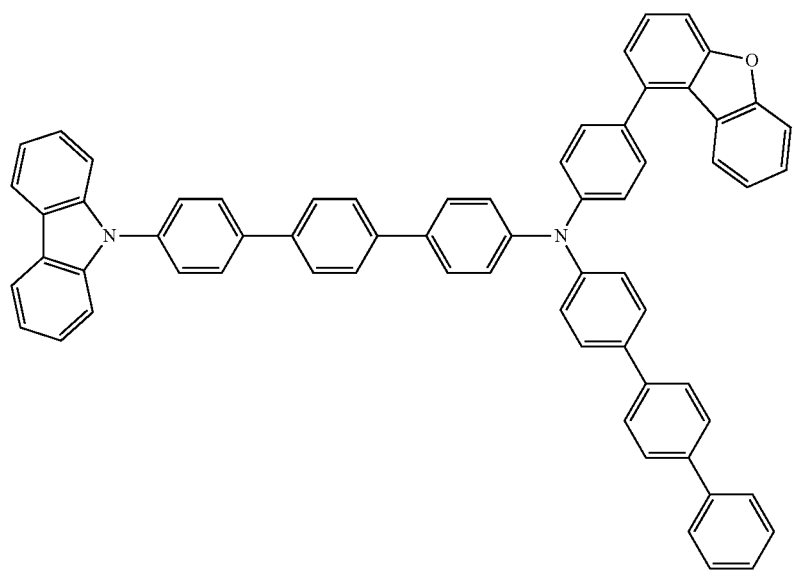
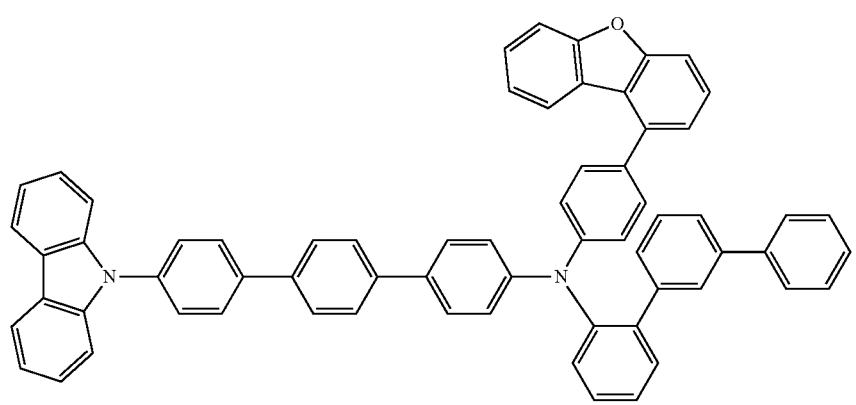
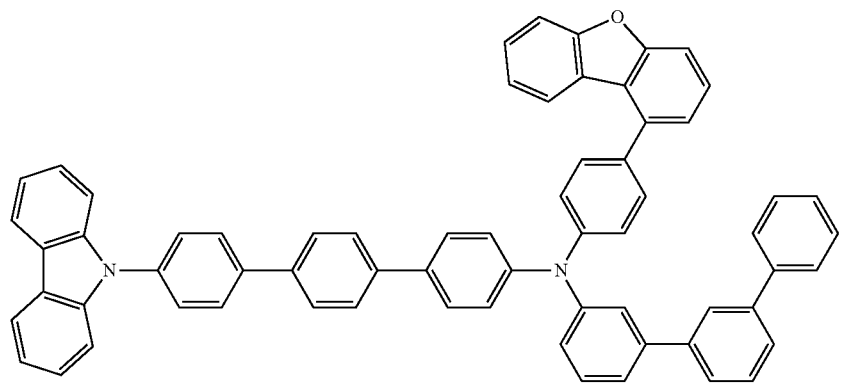

-continued
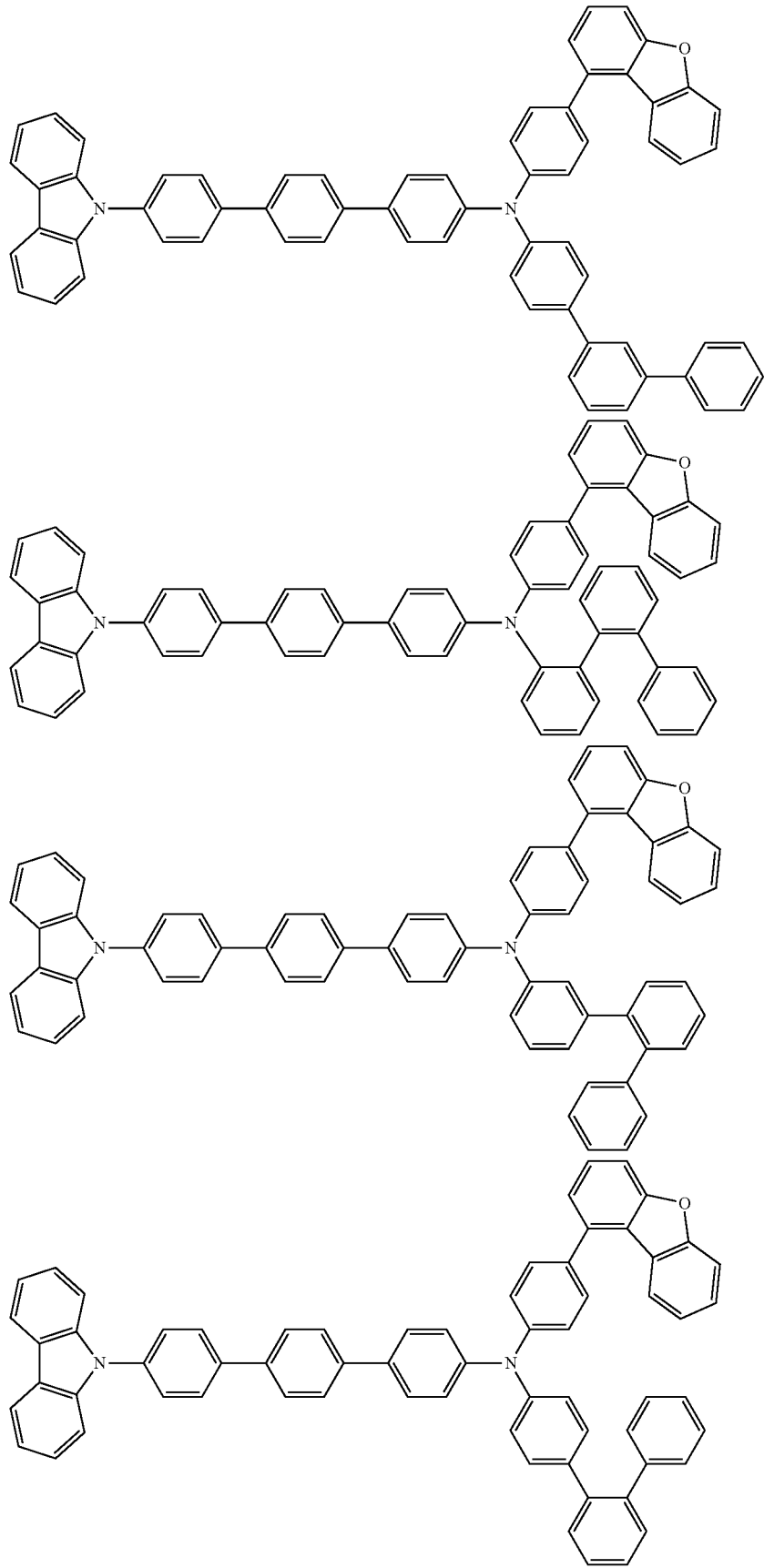

-continued
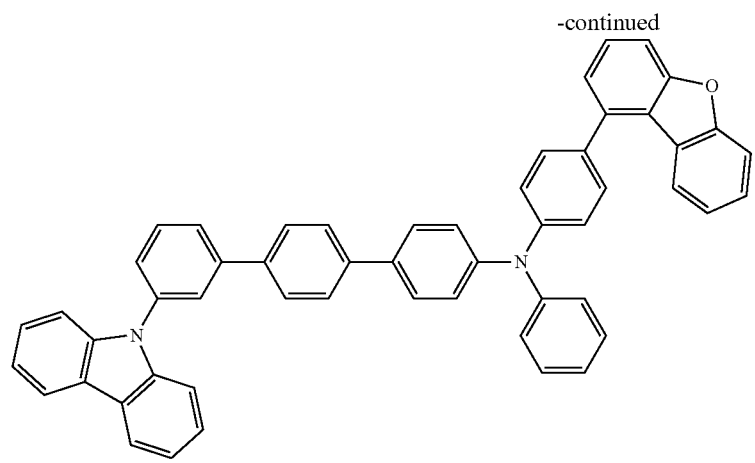
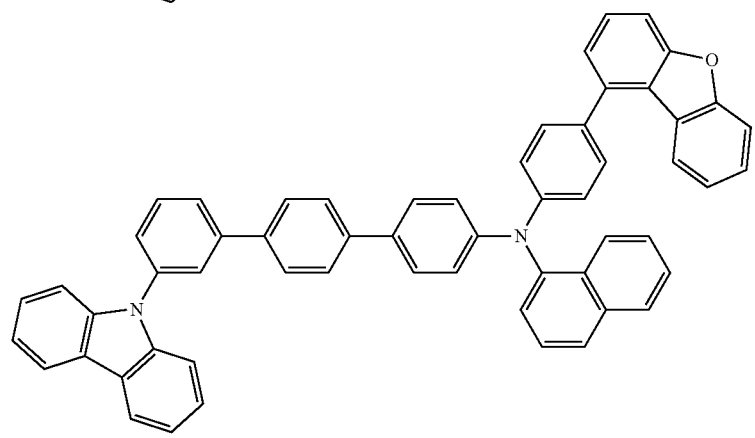
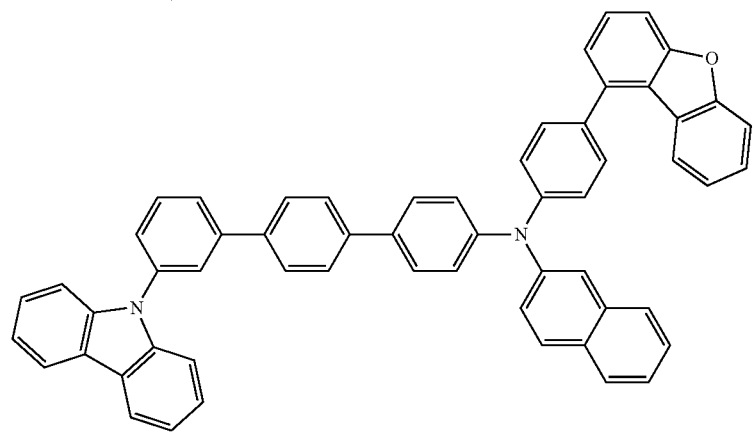
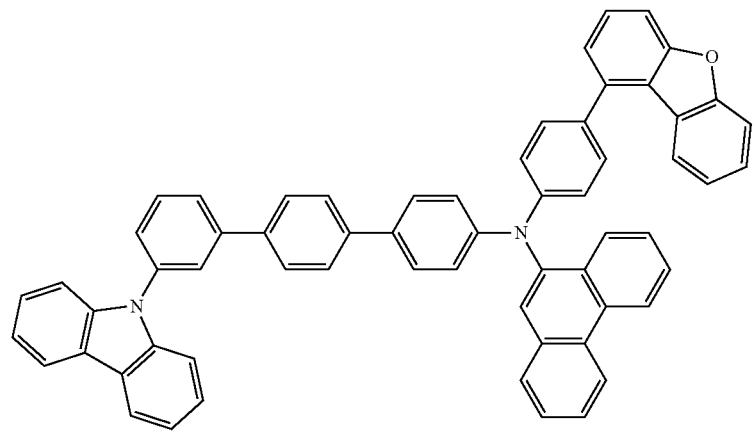

-continued
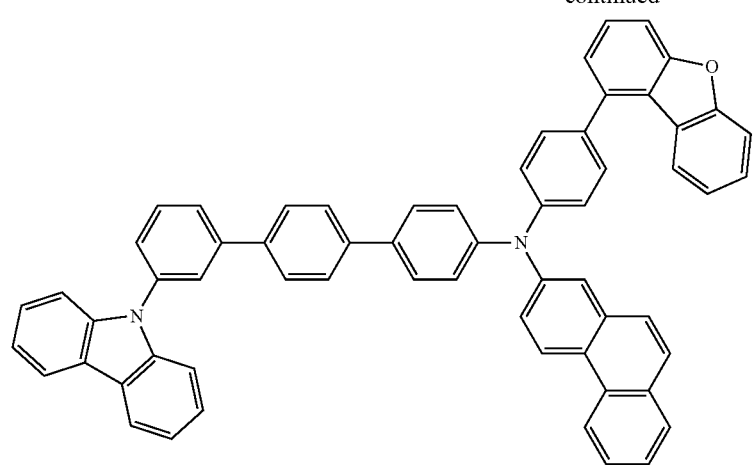
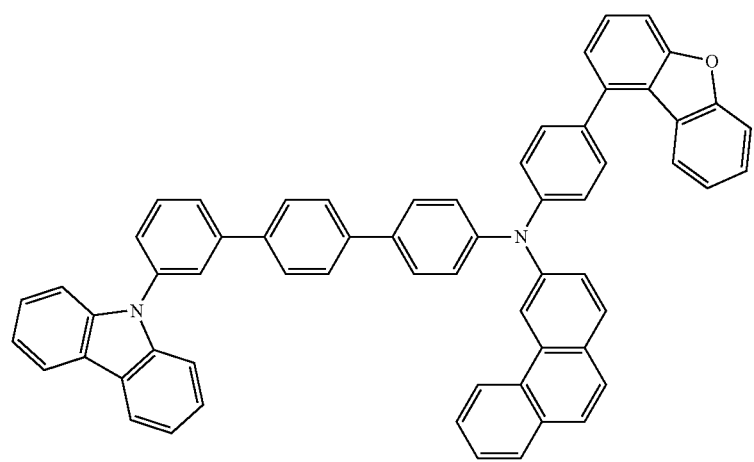
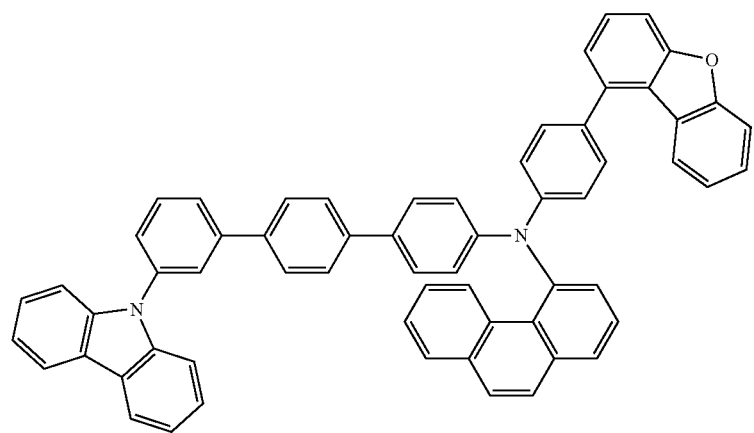

-continued
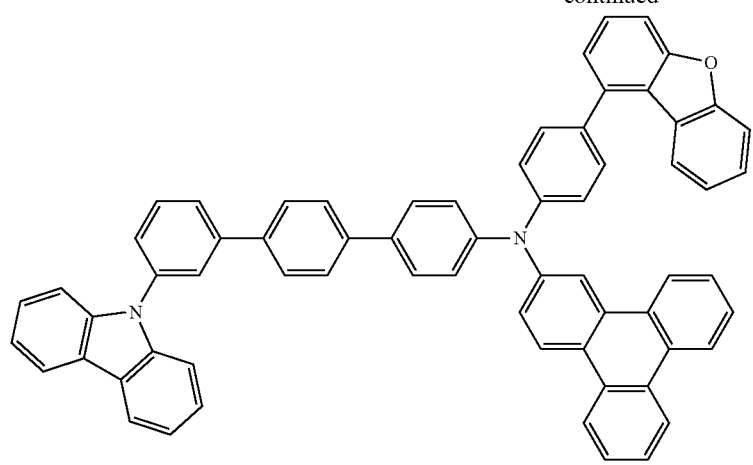
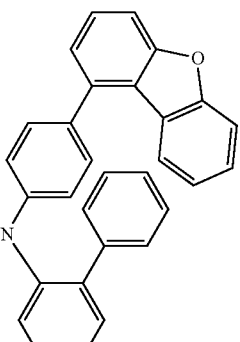
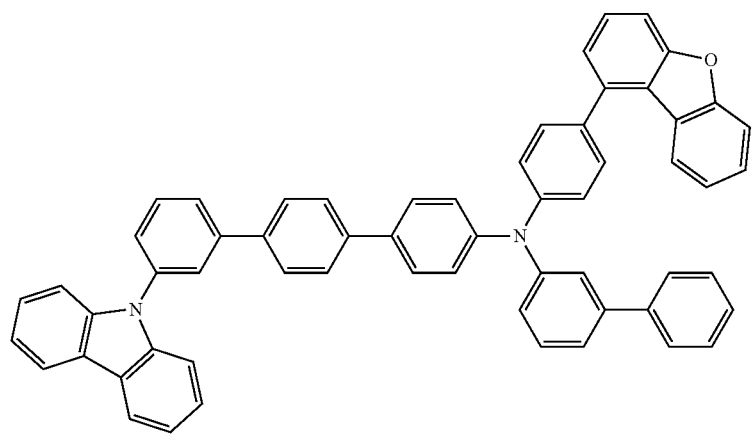

-continued
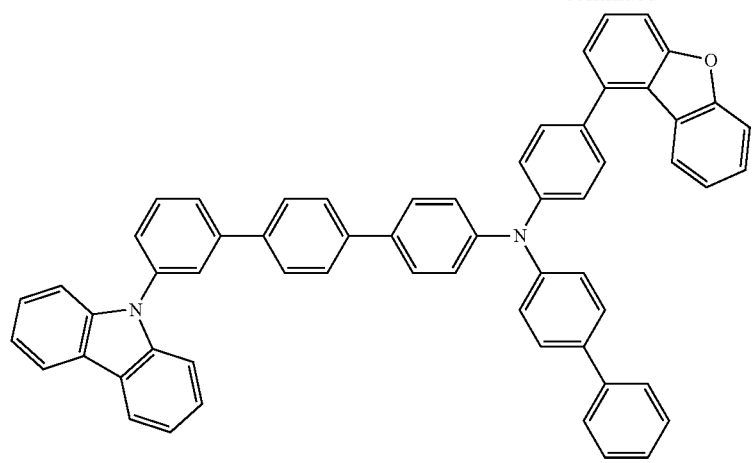
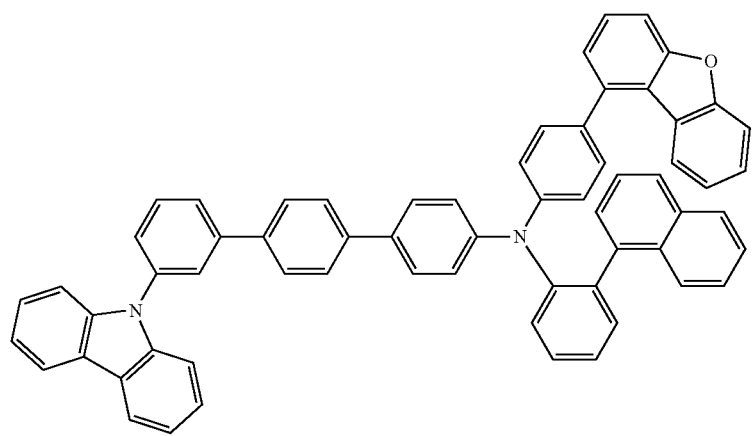
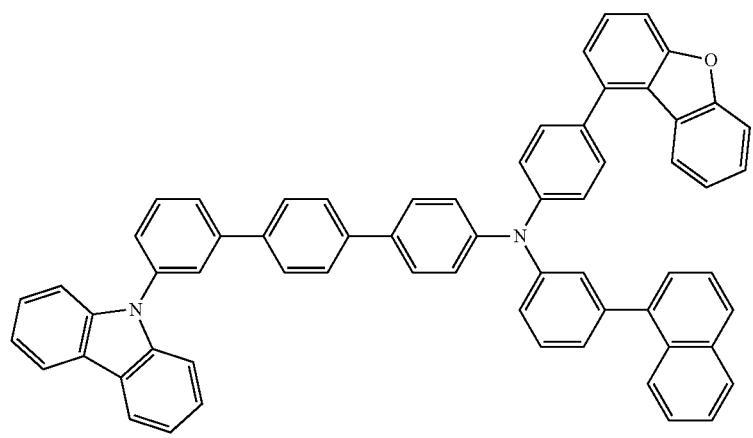

-continued
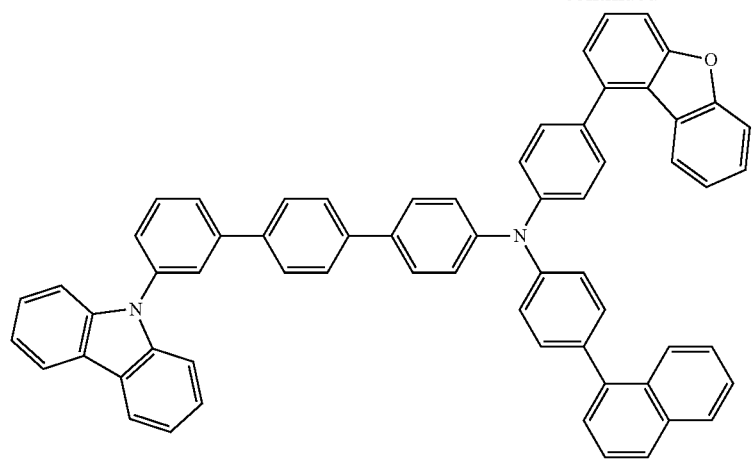
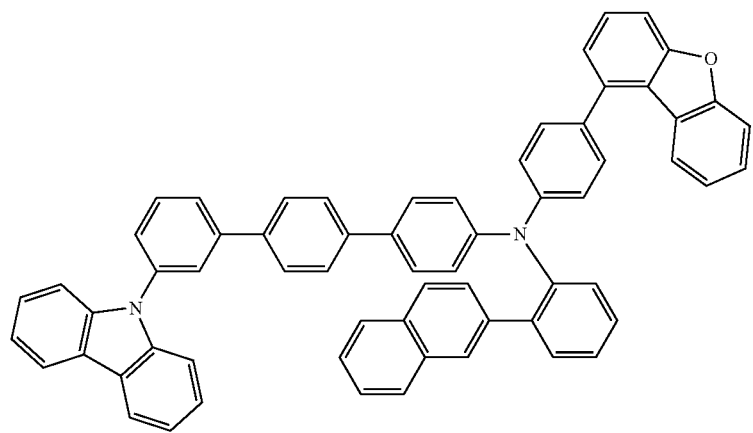
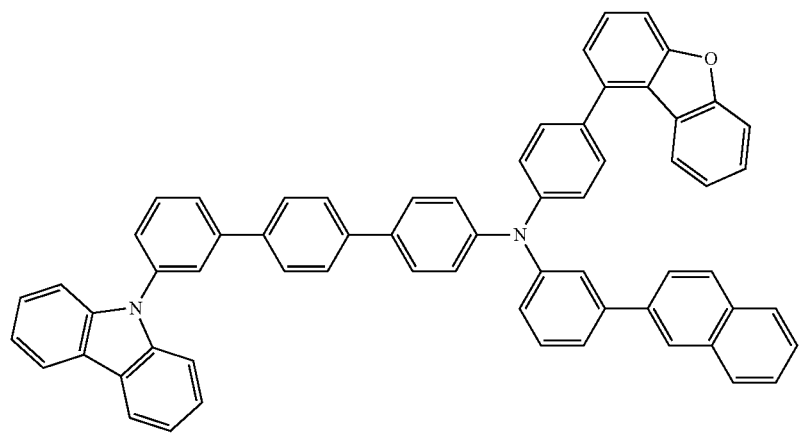

-continued
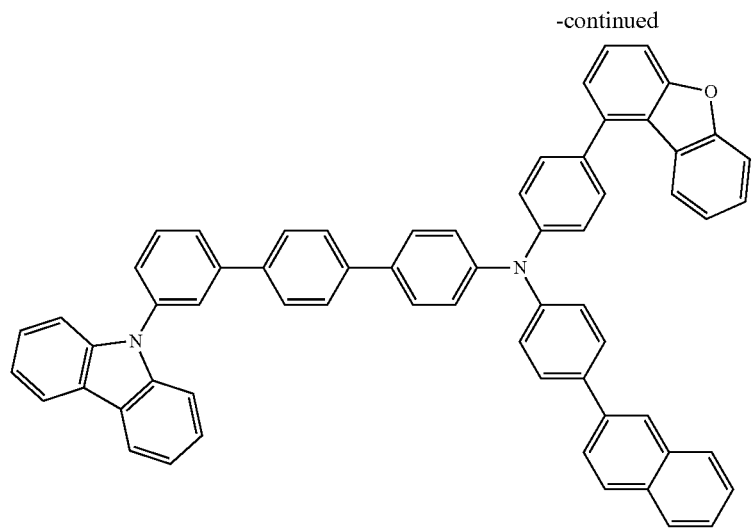
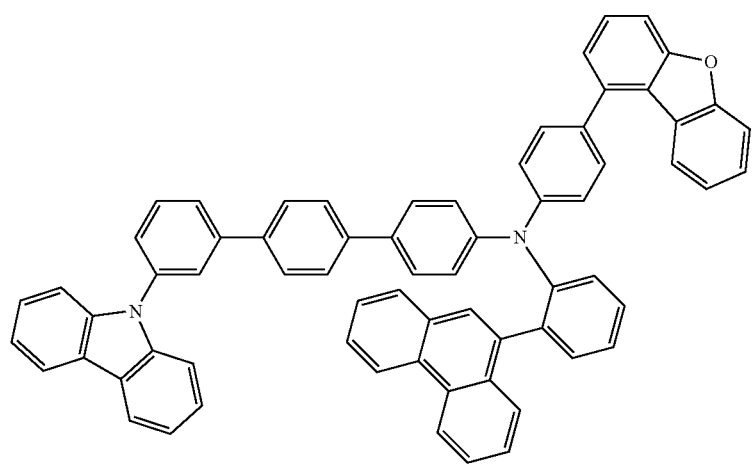
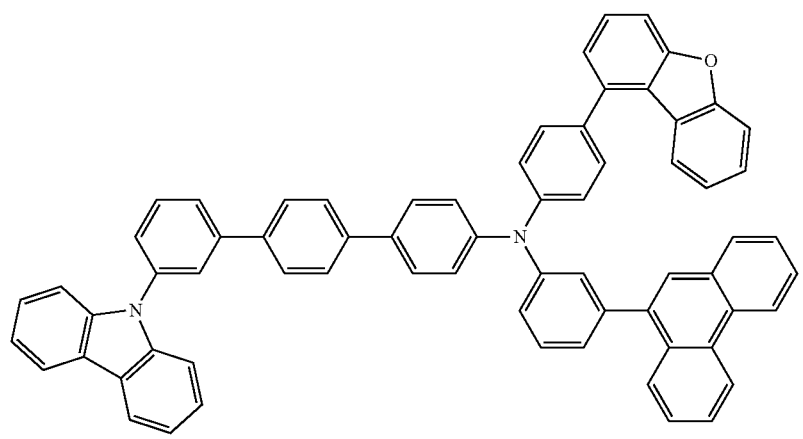

-continued
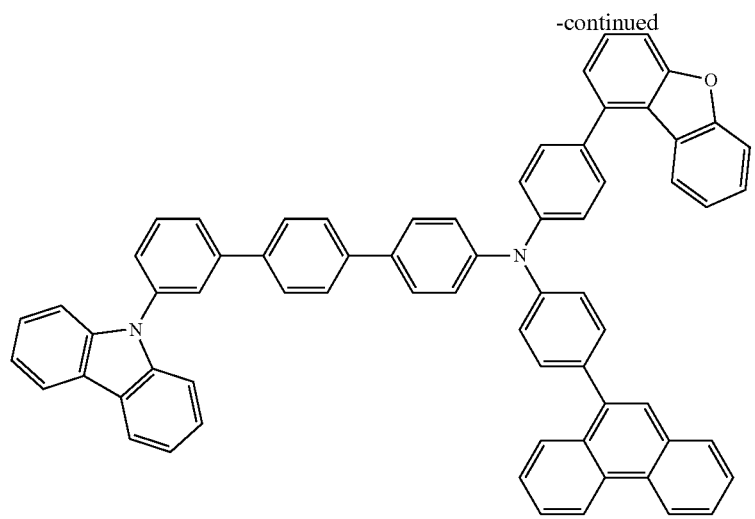
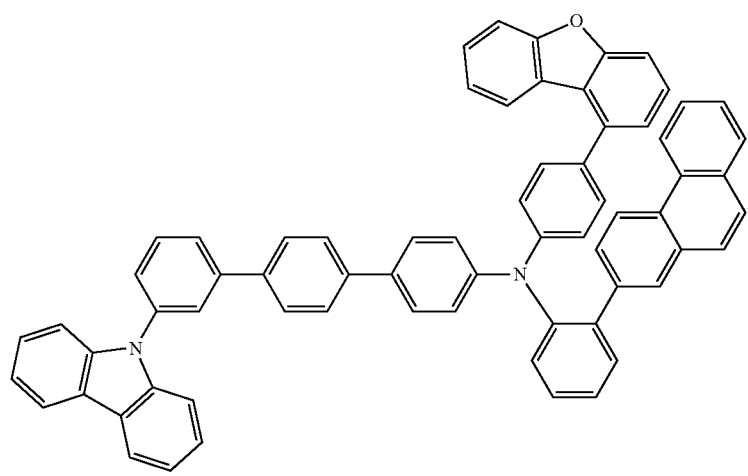
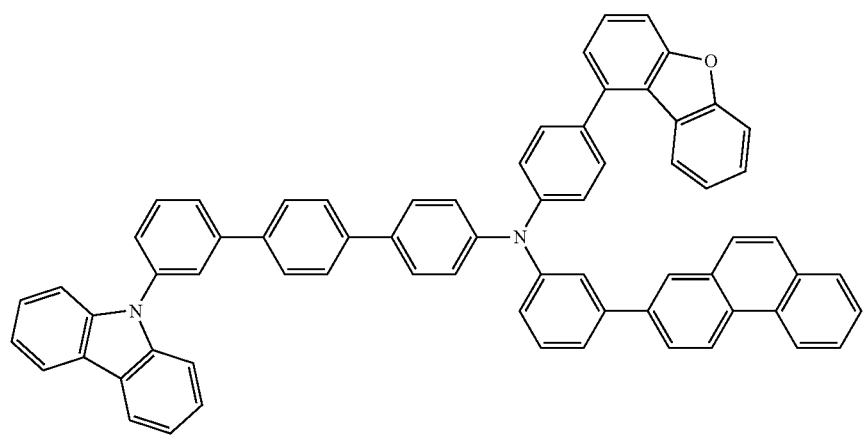

-continued
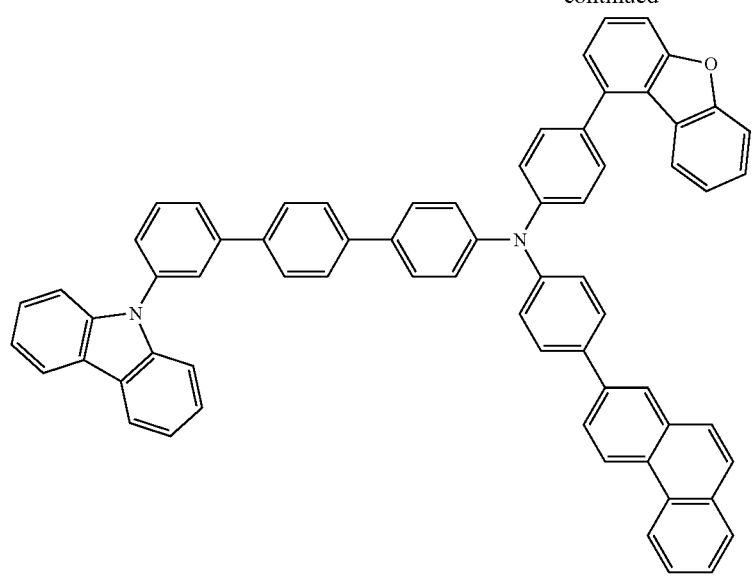
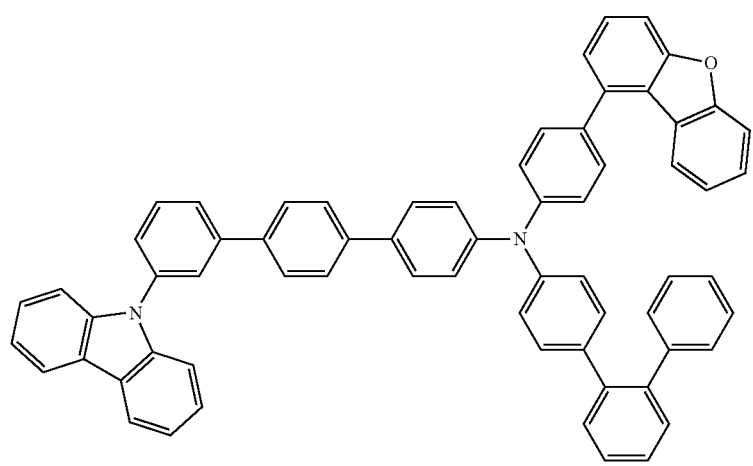
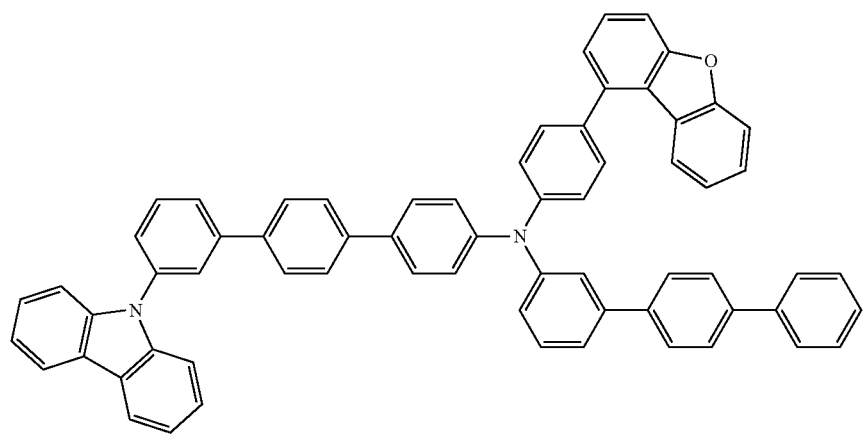

-continued
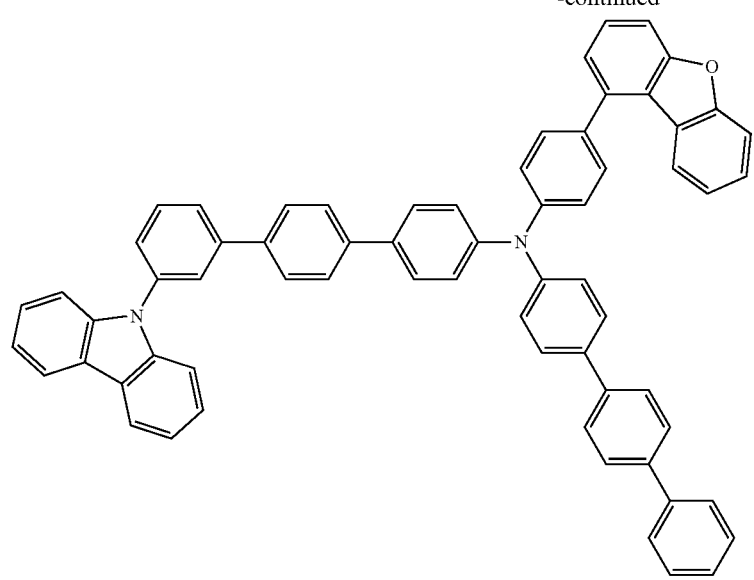
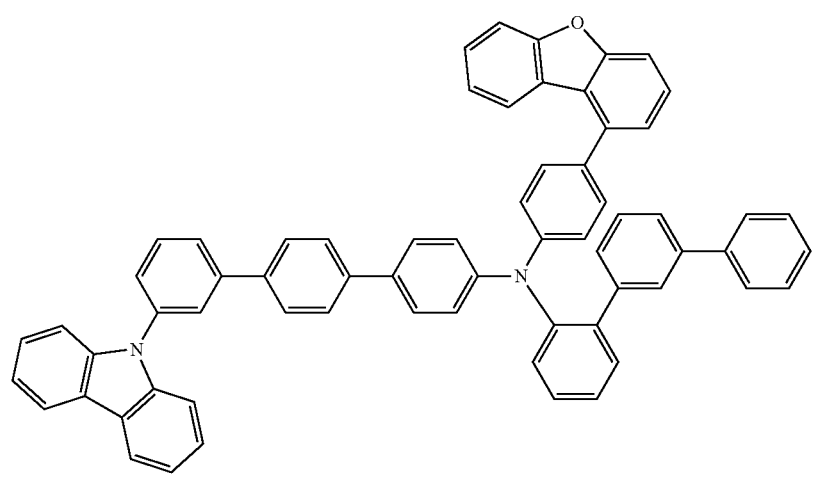
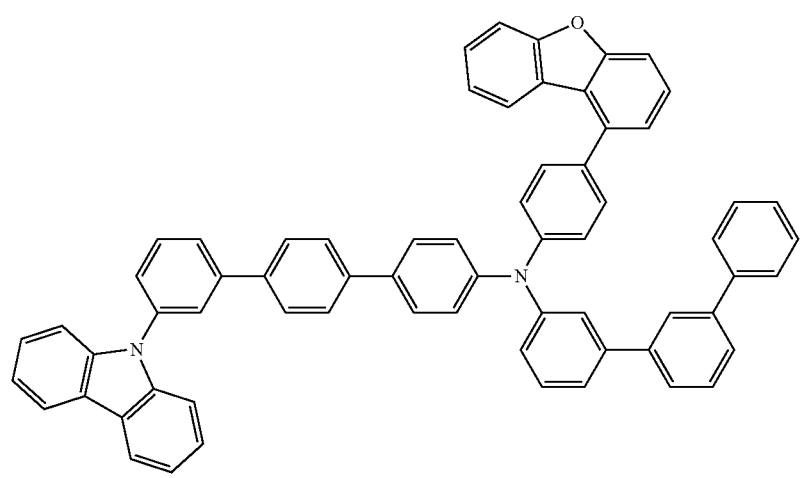

-continued
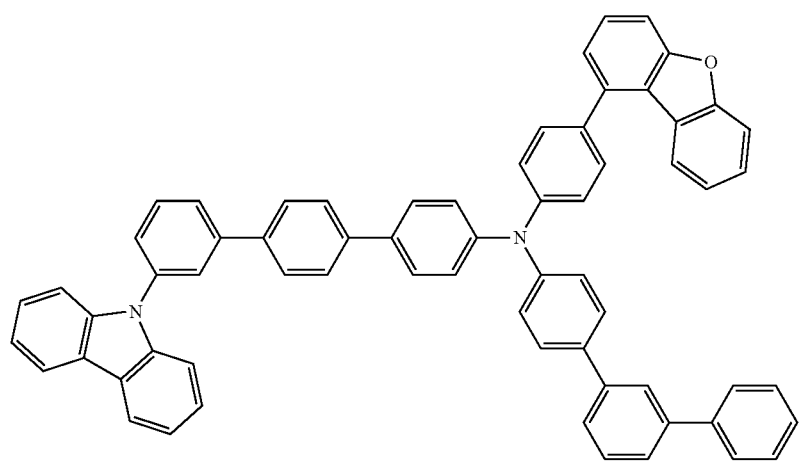
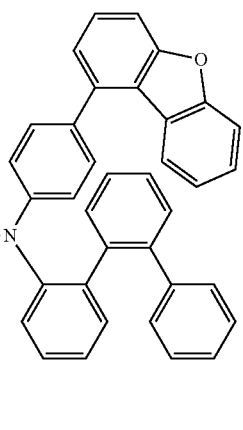
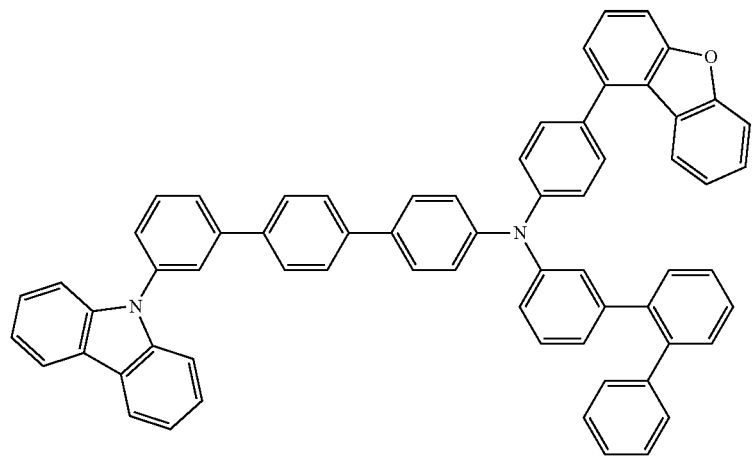

-continued
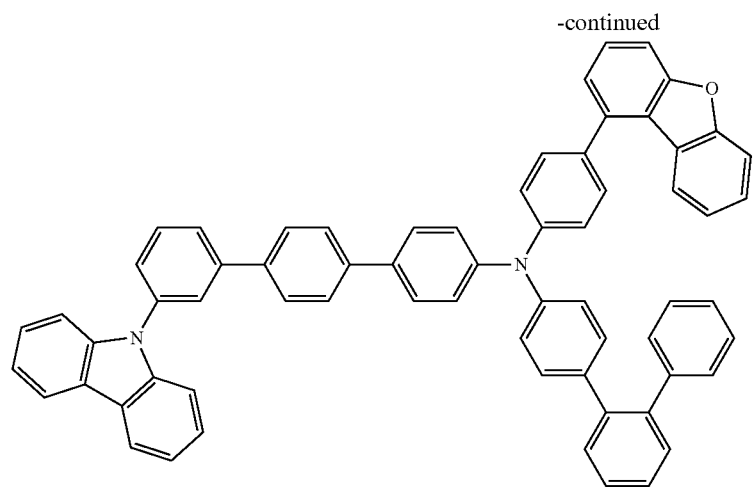
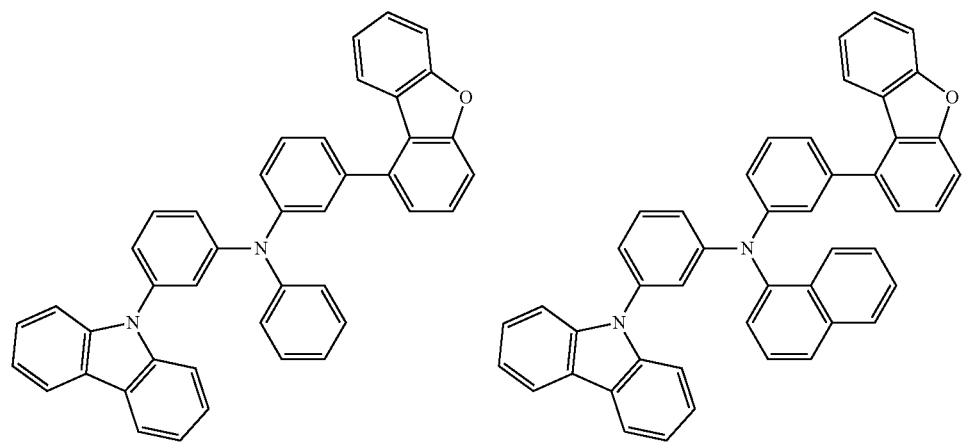

-continued
| 137 | 138 |
|---|---|
| 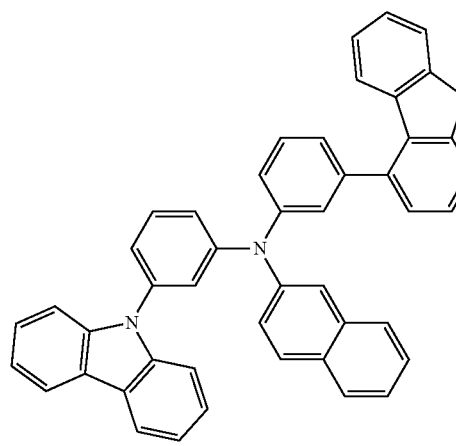 | 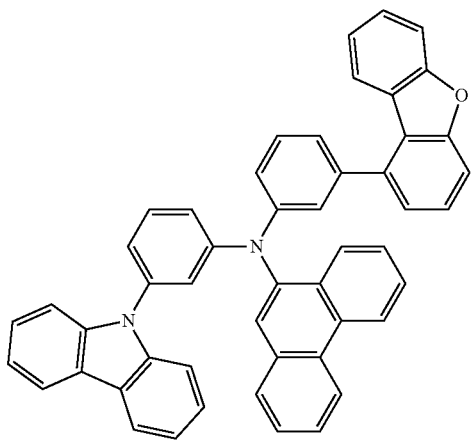 |
| 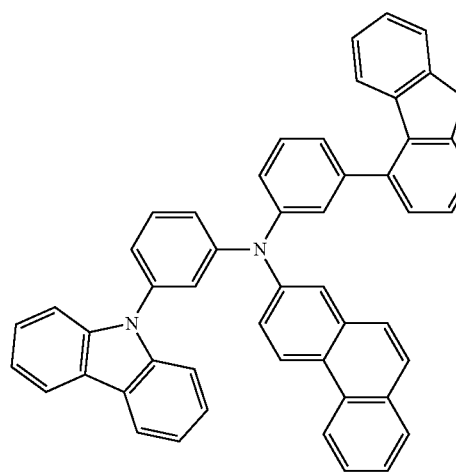 | 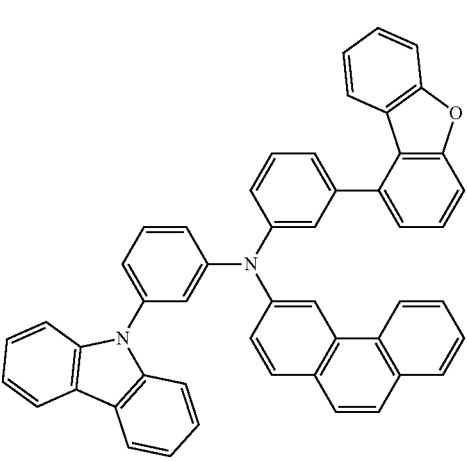 |
| 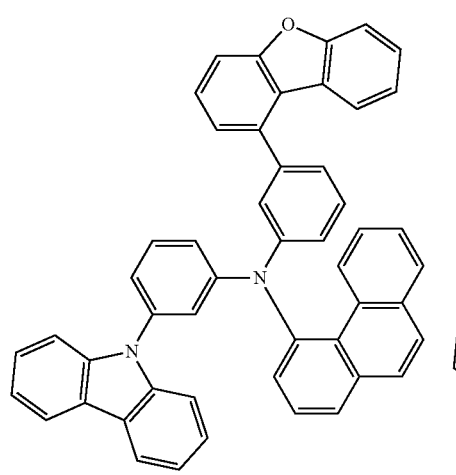 | 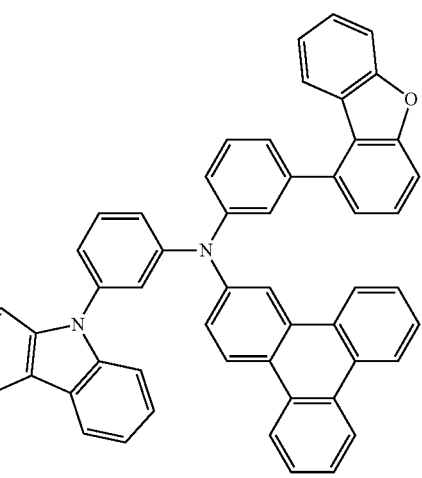 |

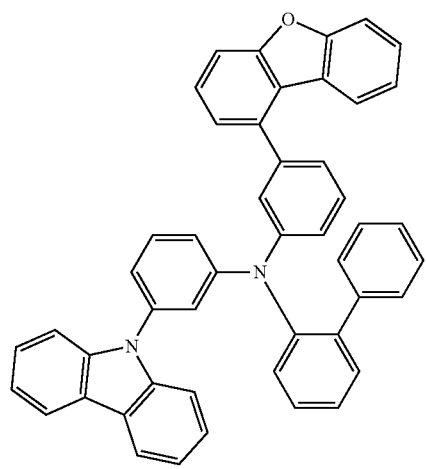
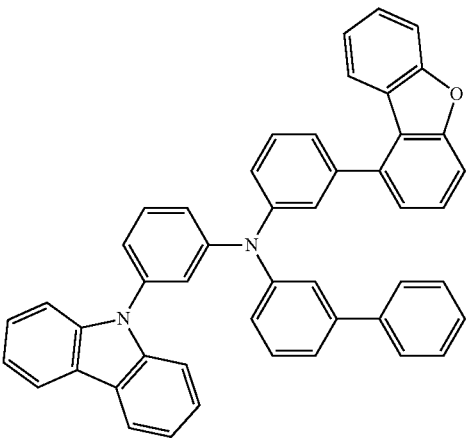
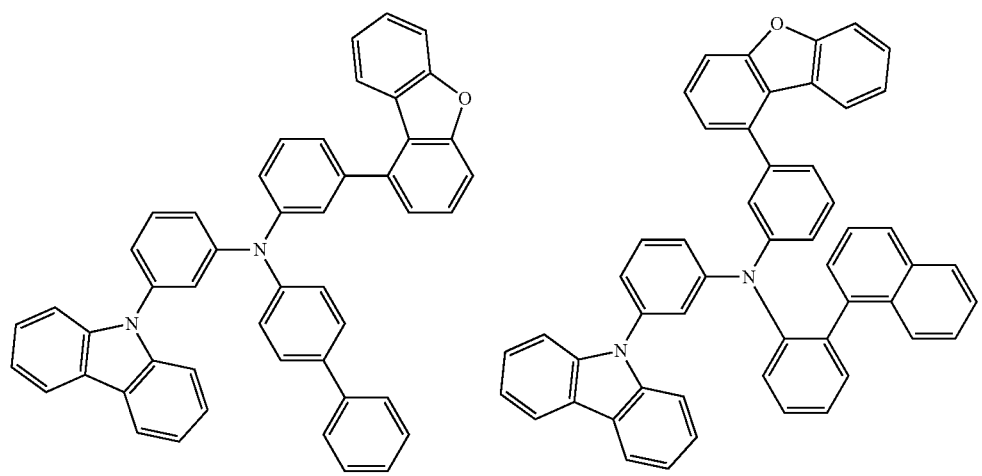
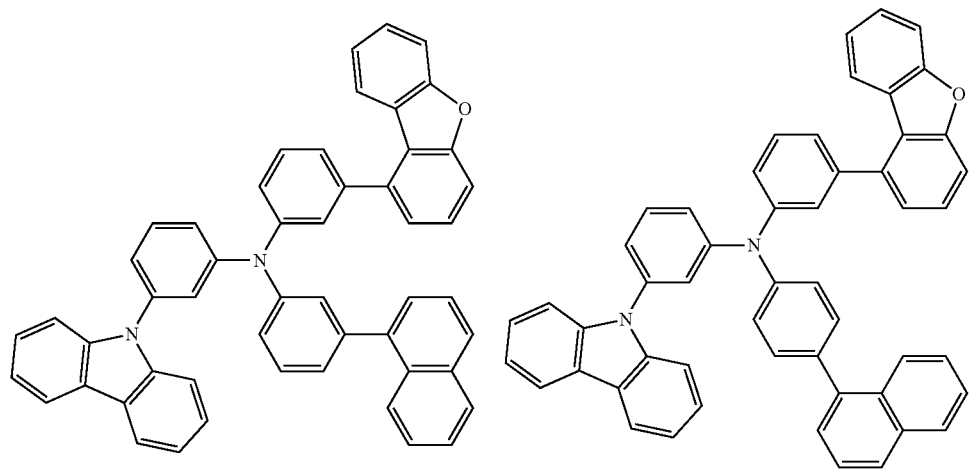

-continued
141 142
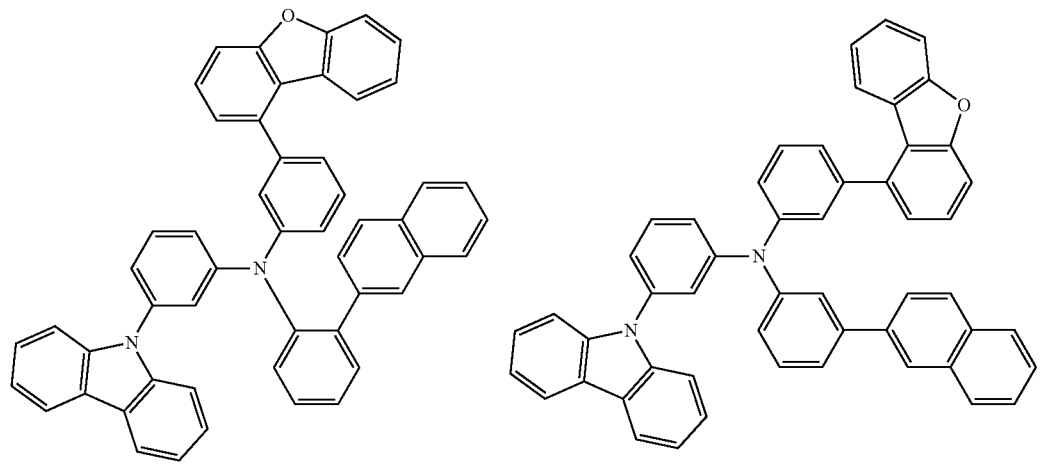
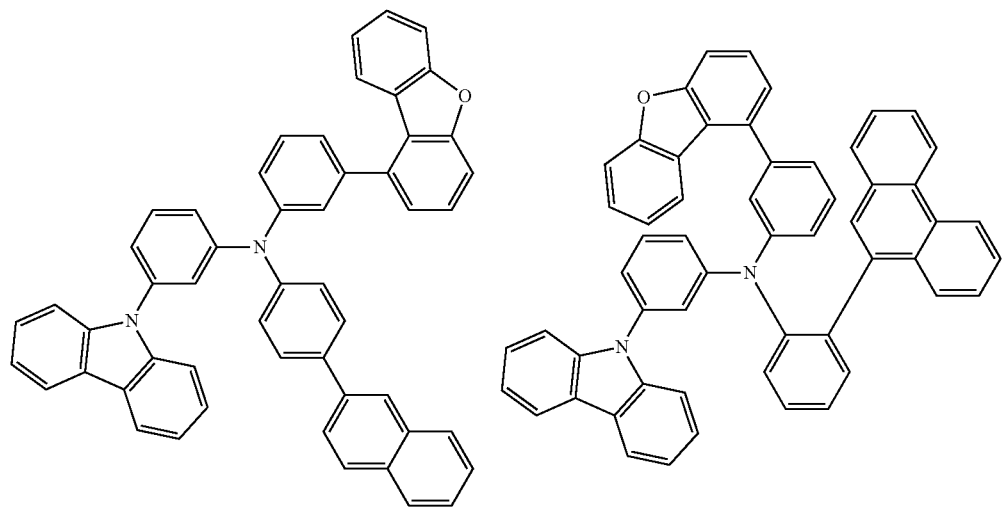
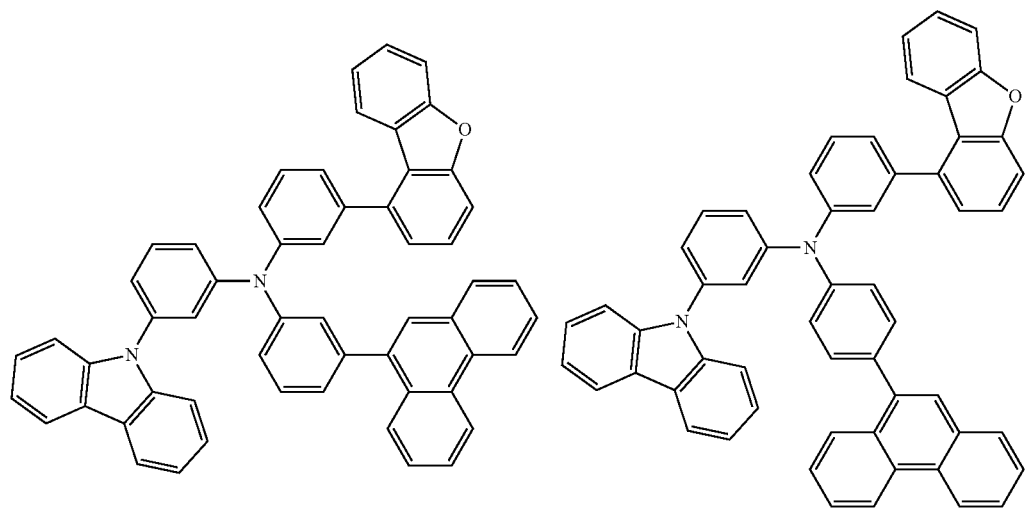

-continued
143
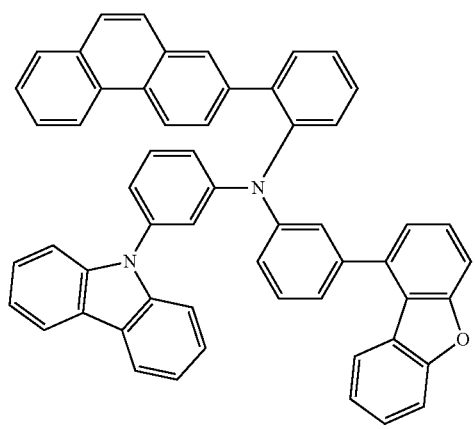
144
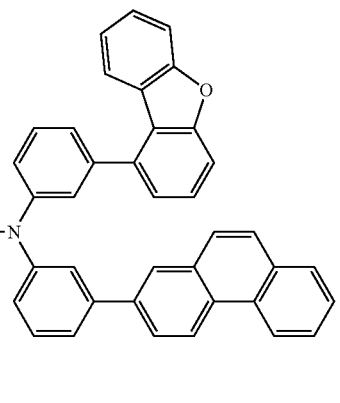
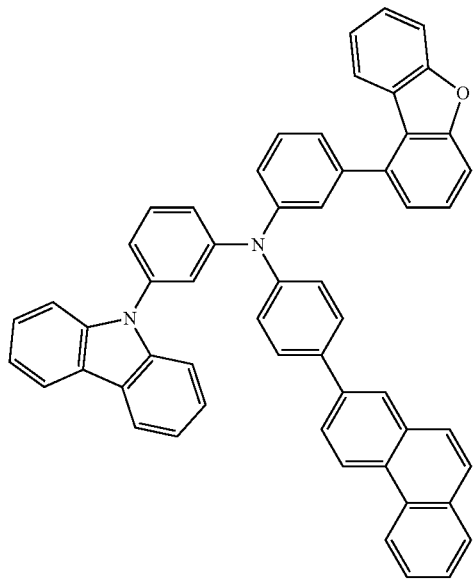
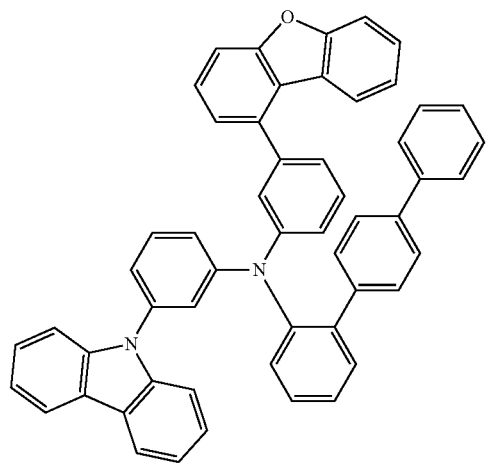
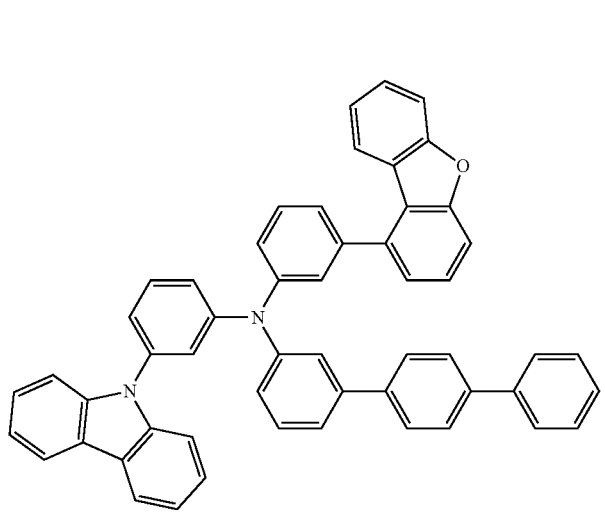
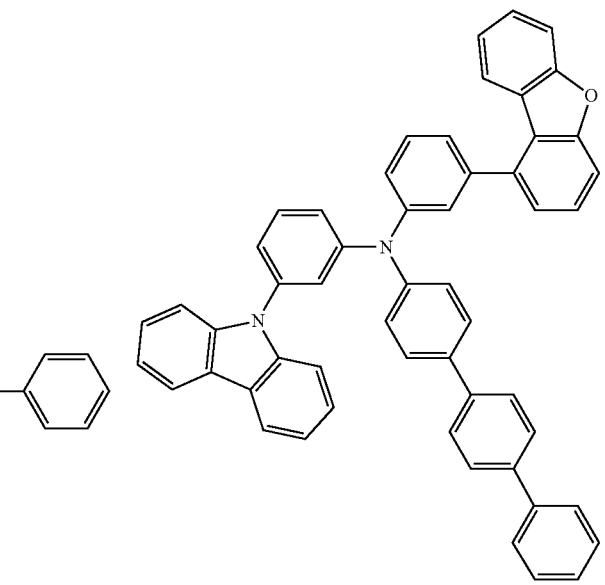

145
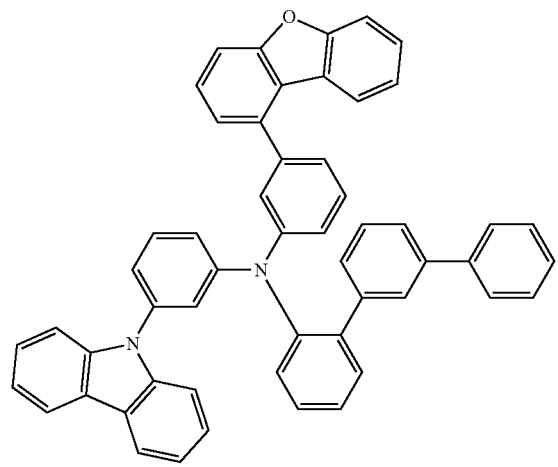
146
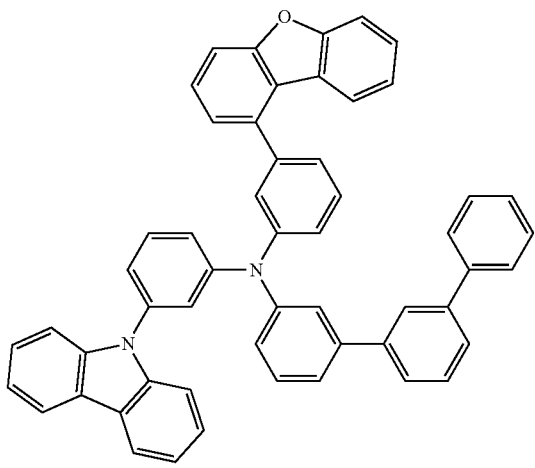
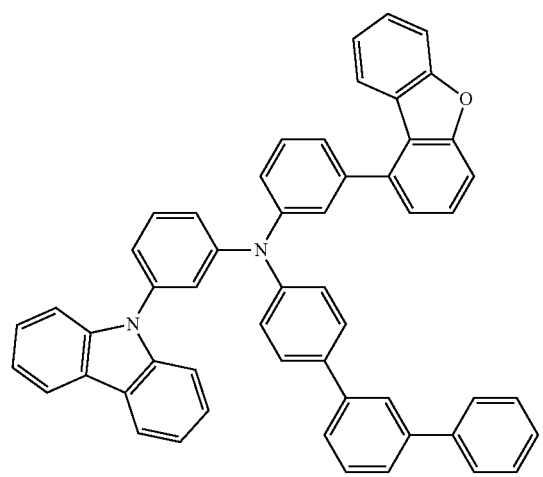
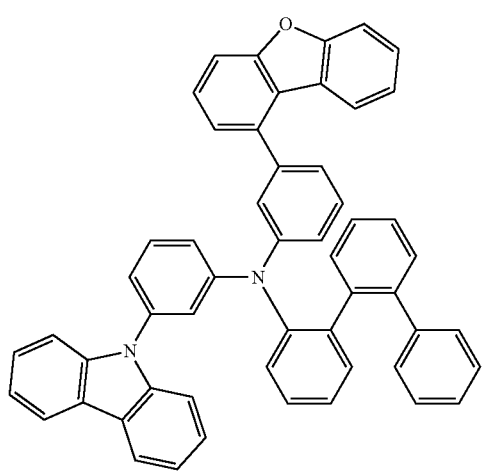
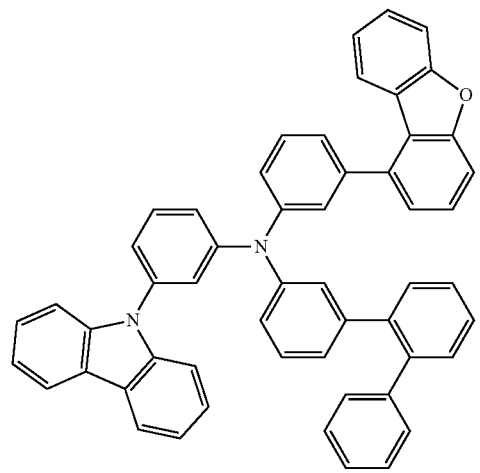
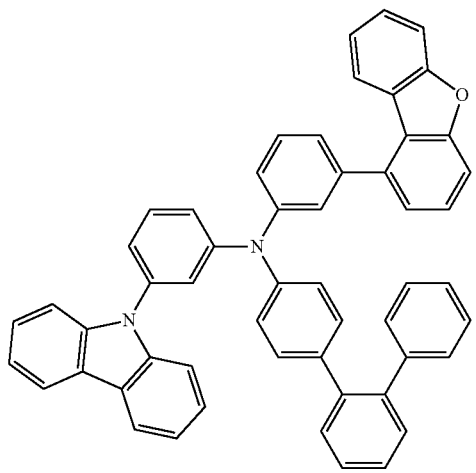

-continued
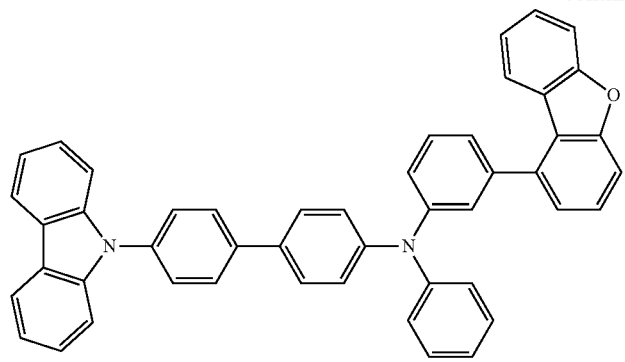
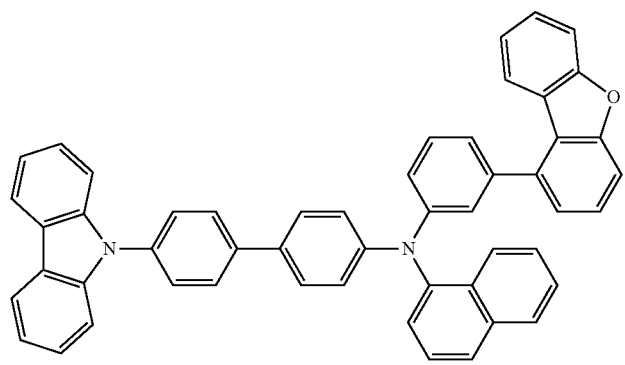
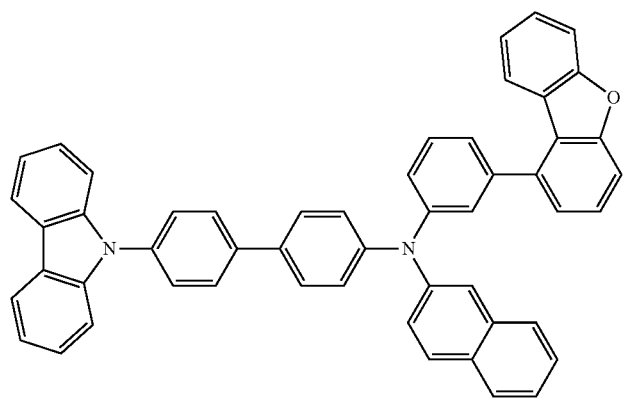
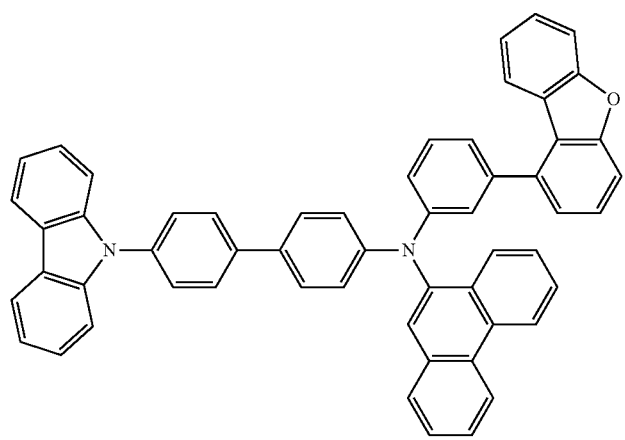

-continued
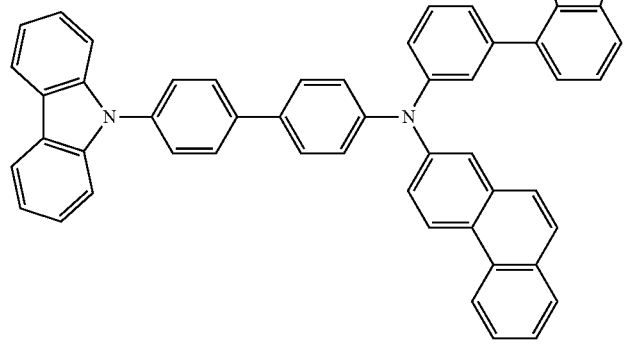
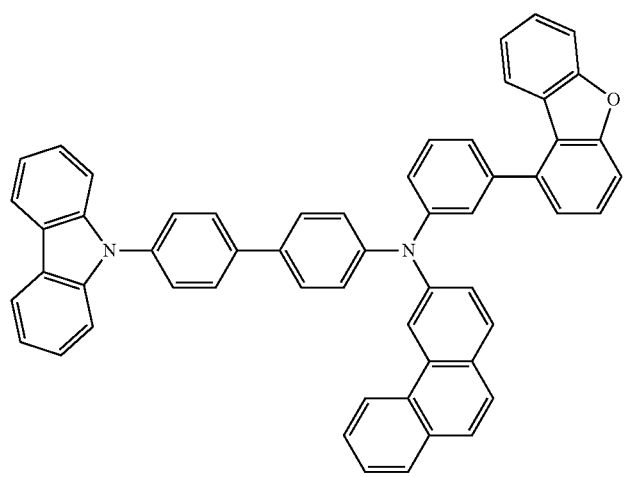
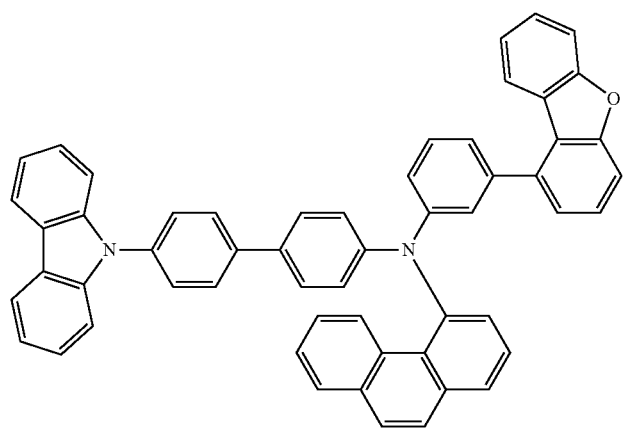

-continued
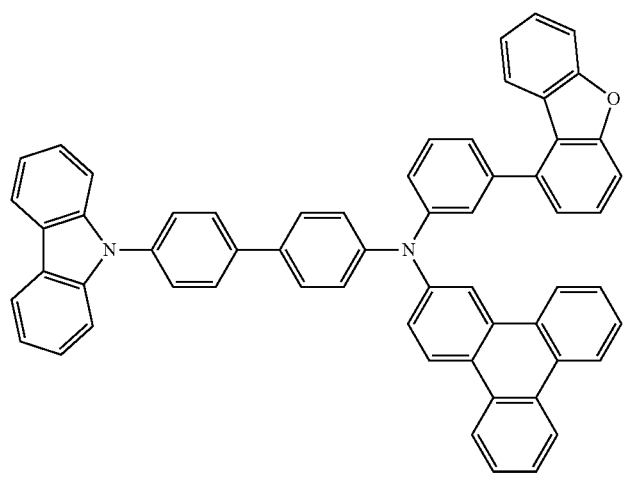
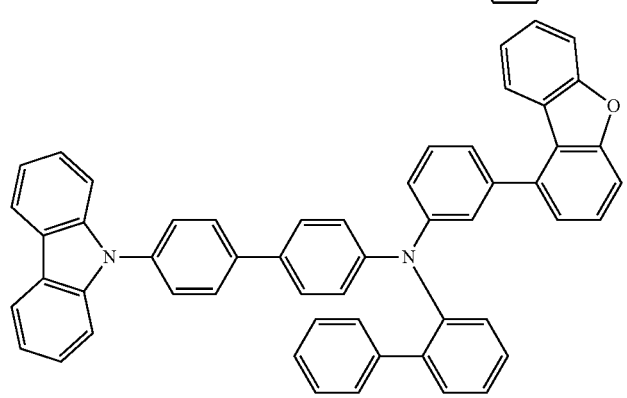
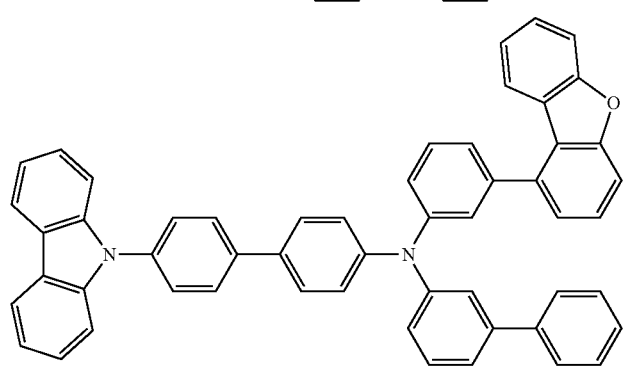
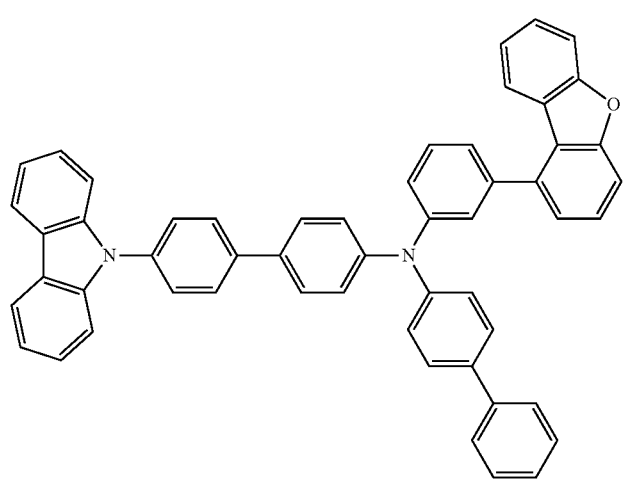

-continued
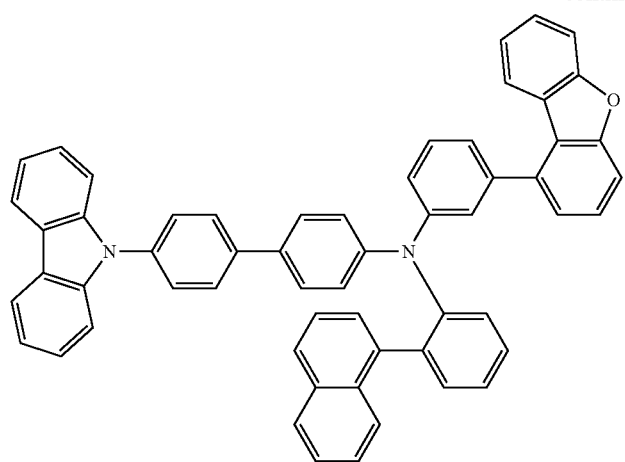
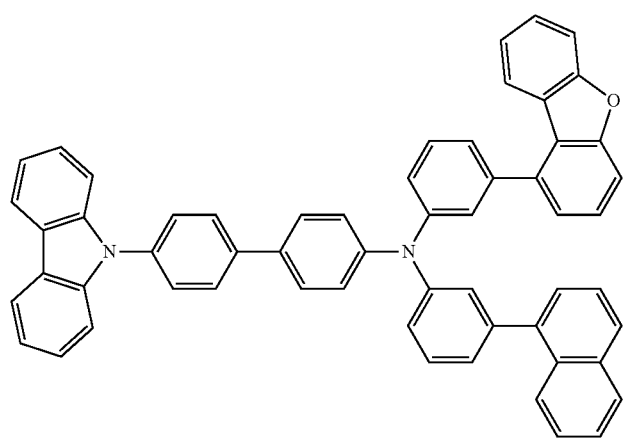
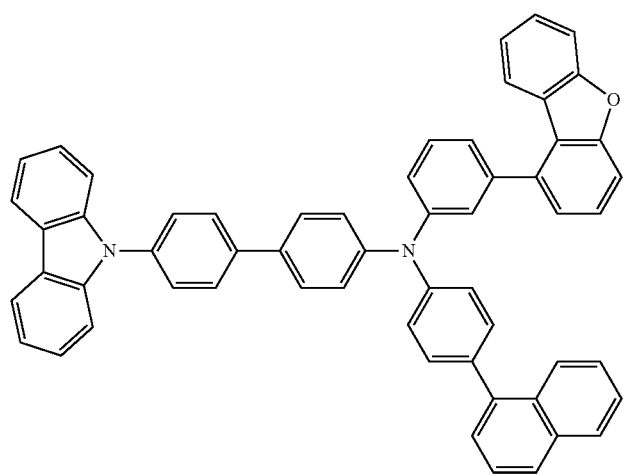

-continued
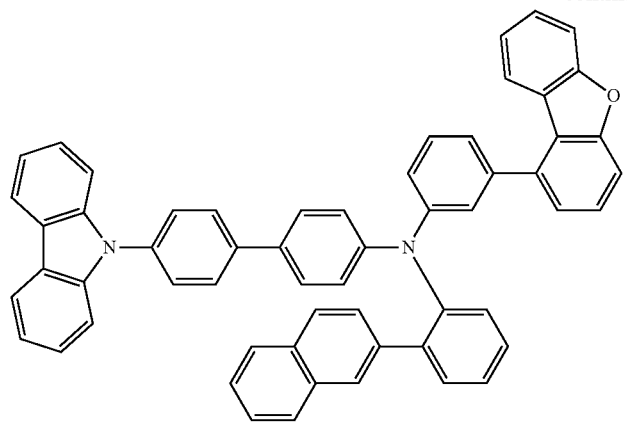
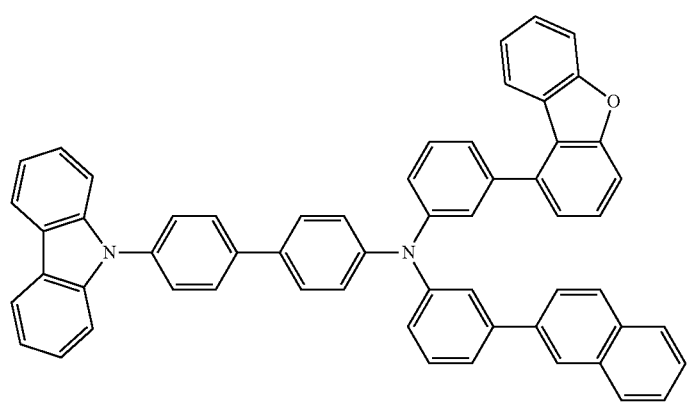
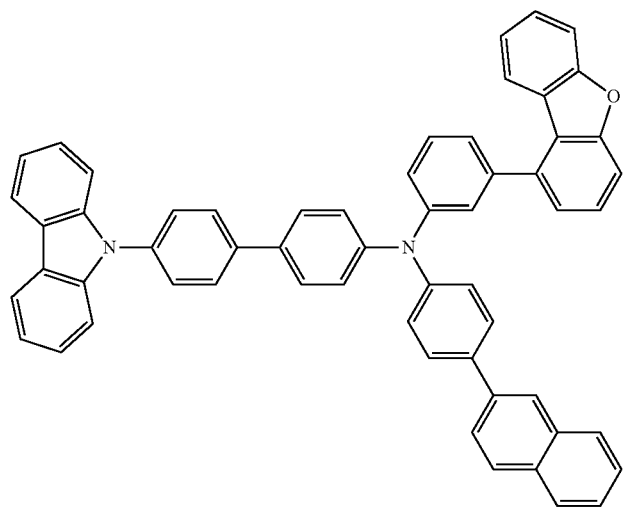

-continued
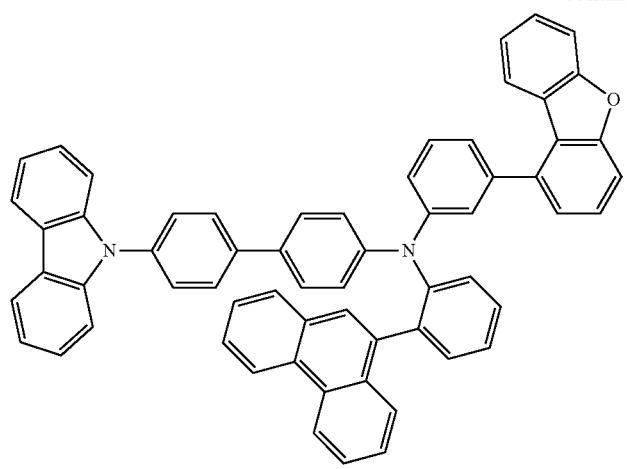
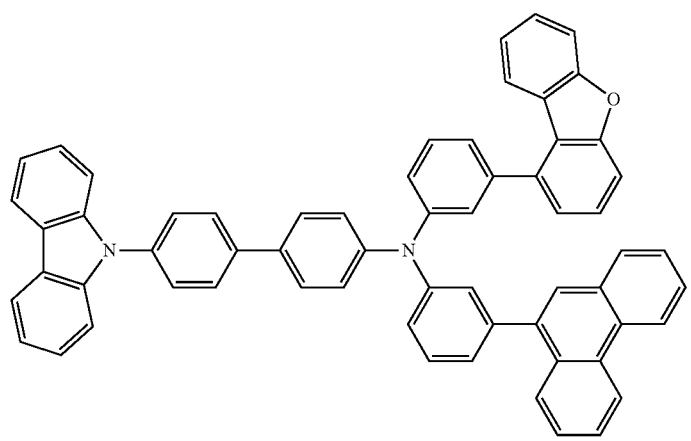
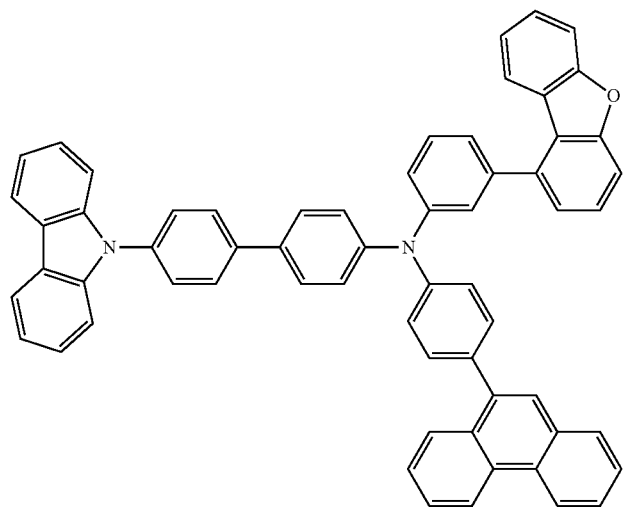

-continued
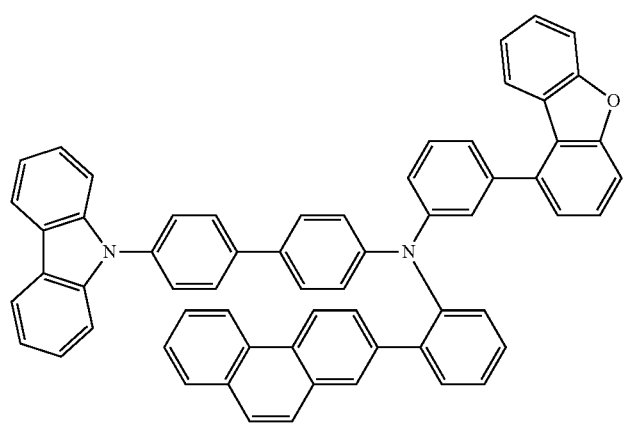
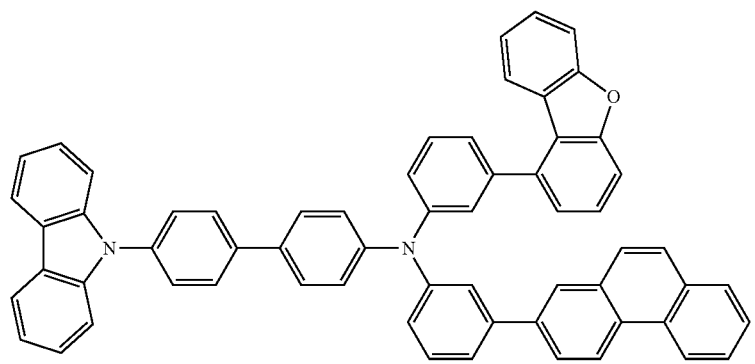
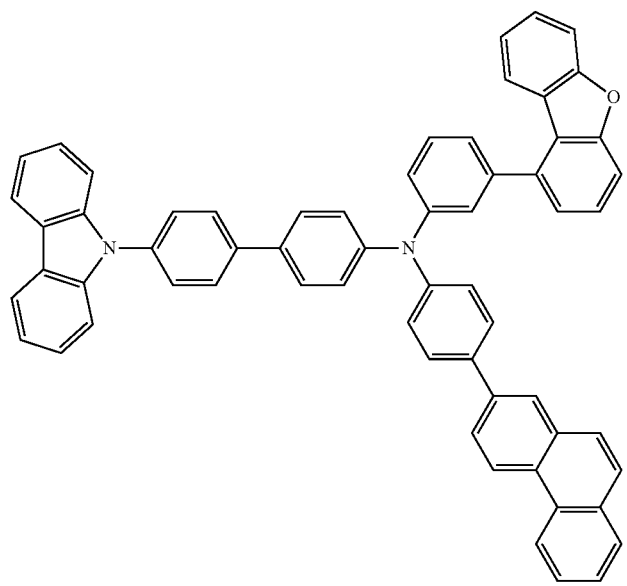

-continued
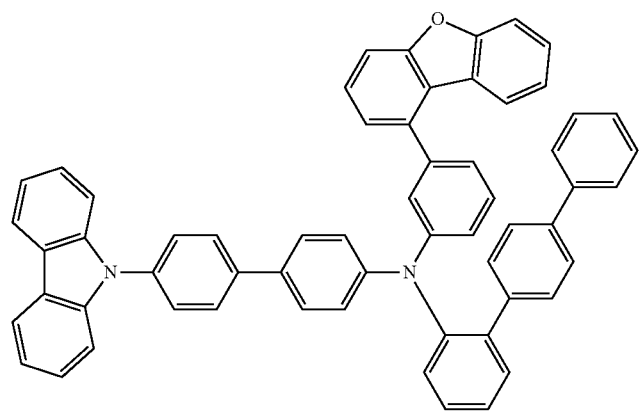
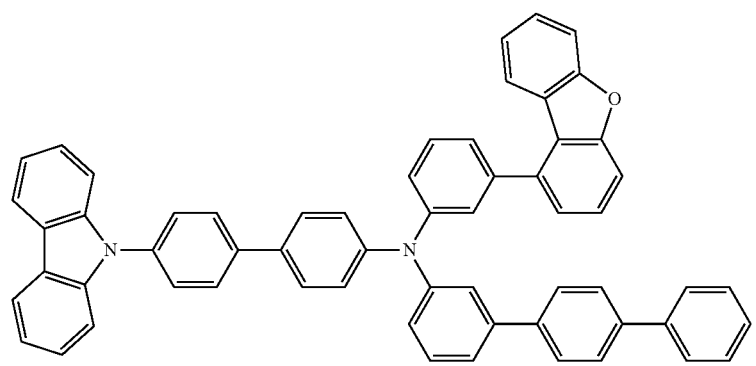
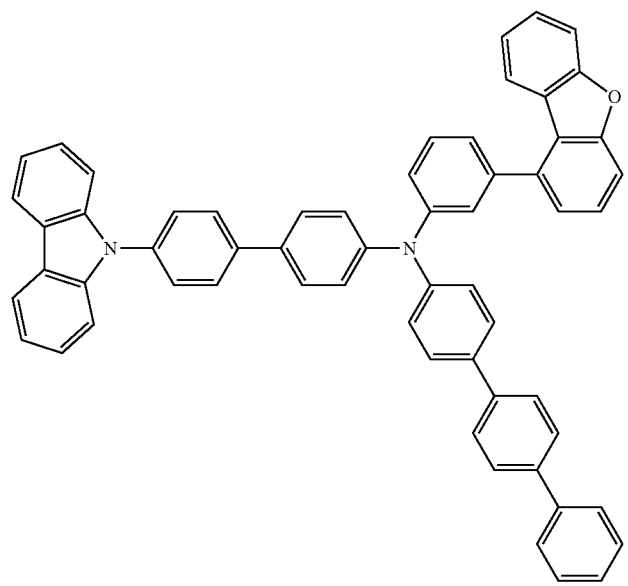

-continued
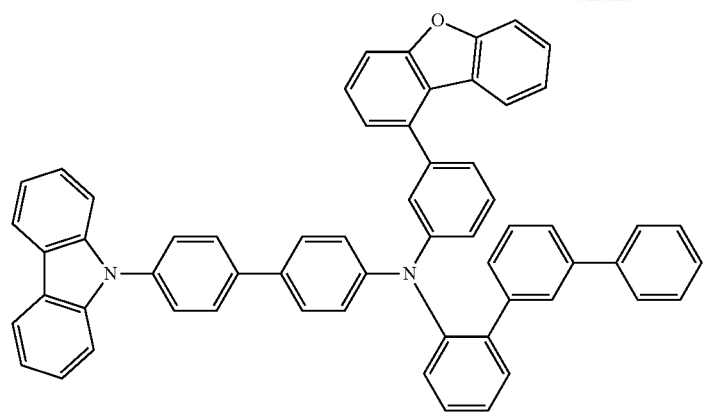
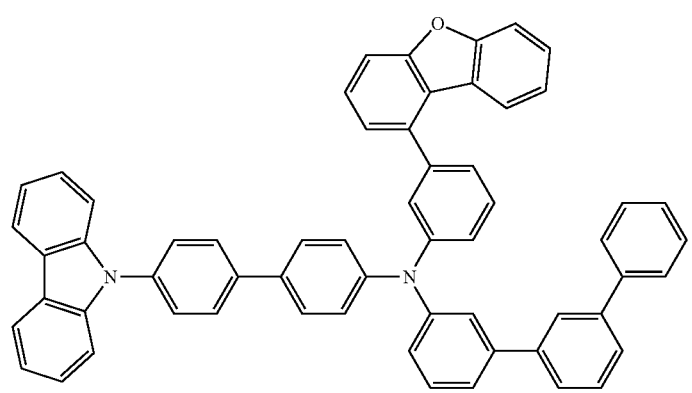
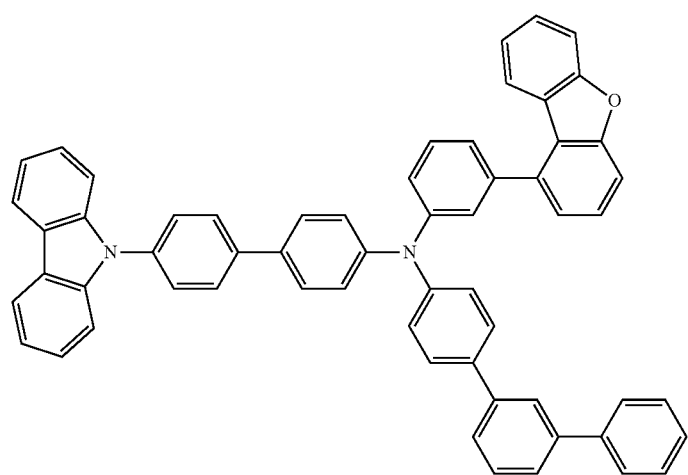

-continued
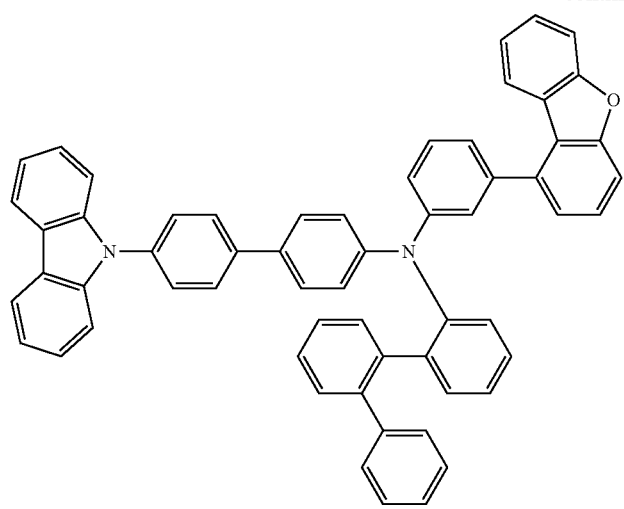
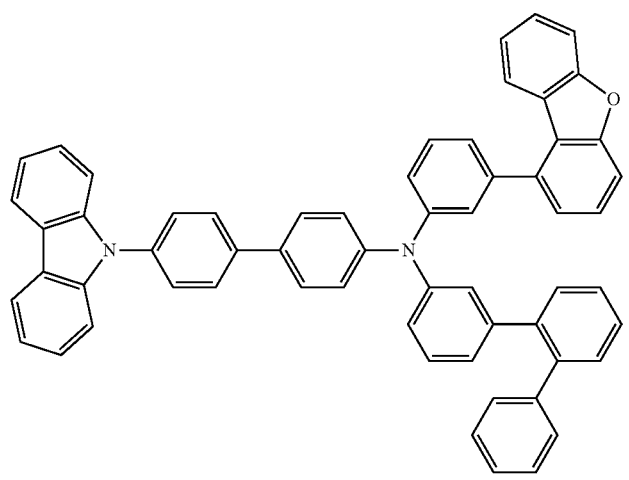
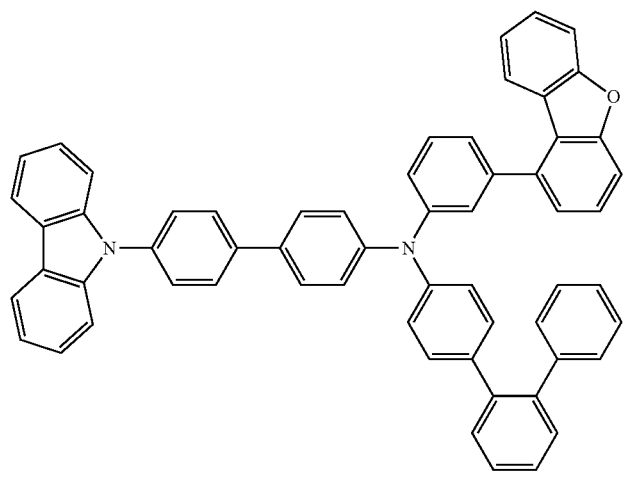

-continued
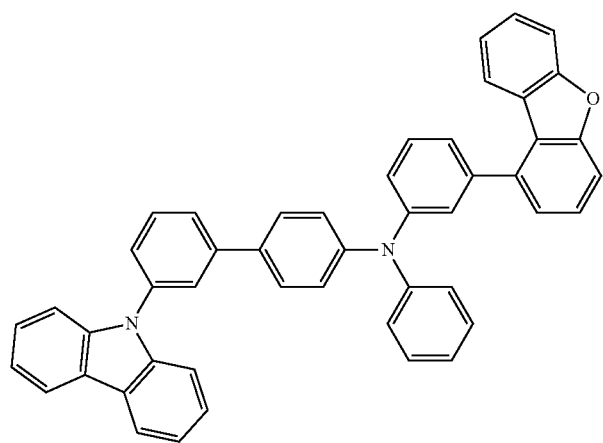
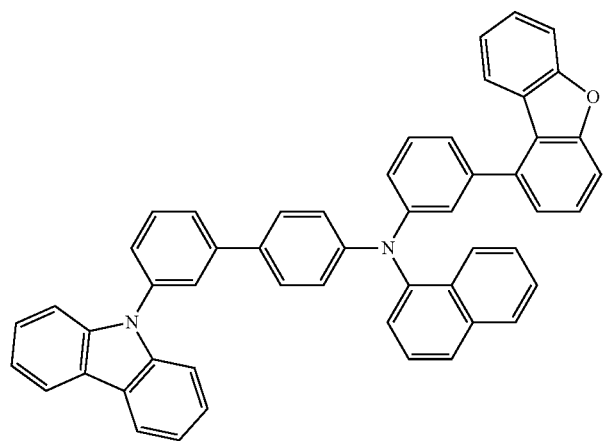
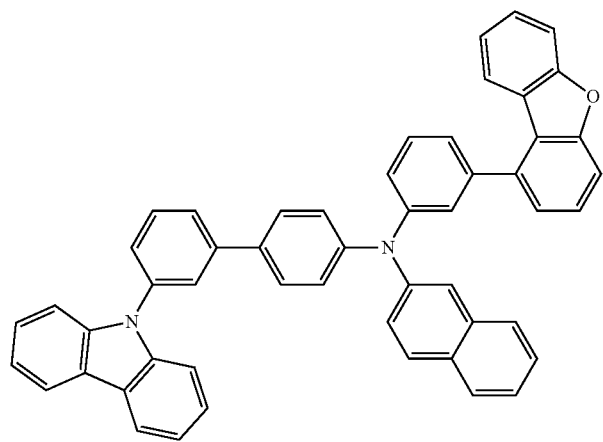

-continued
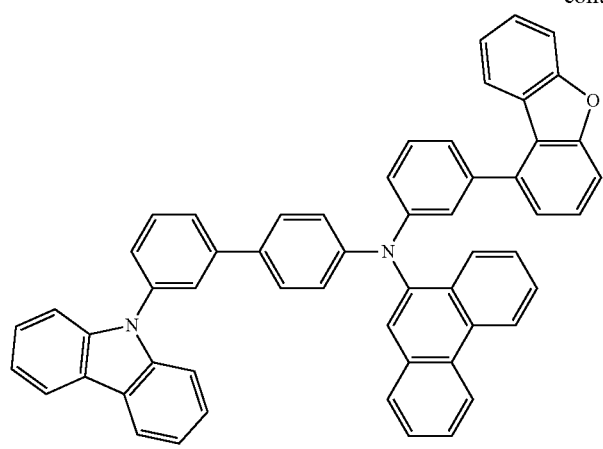
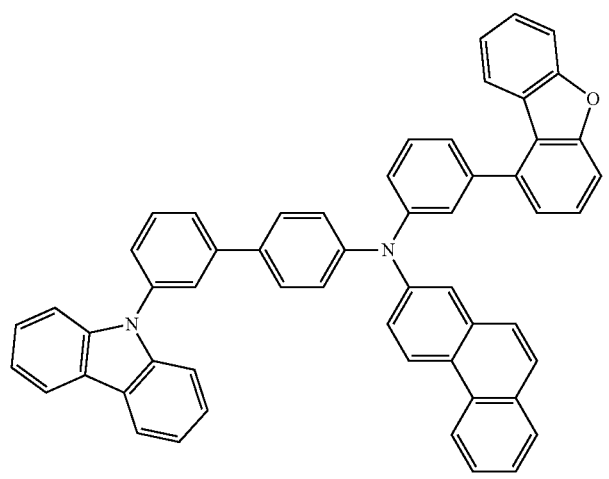
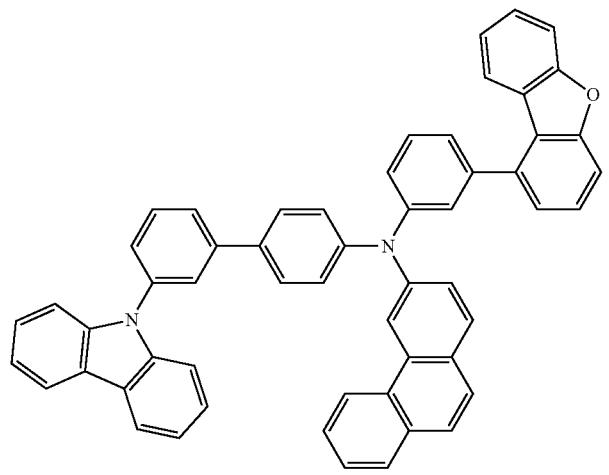

-continued
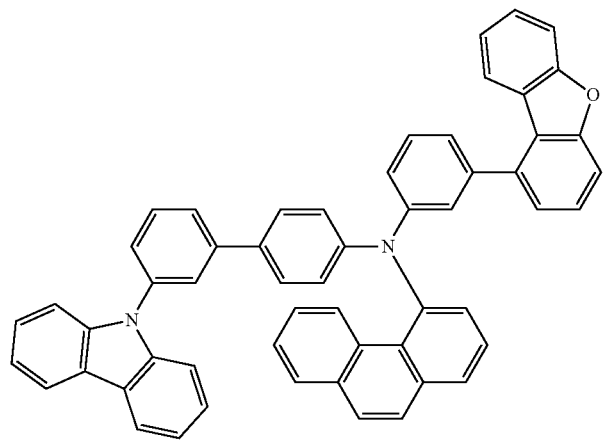
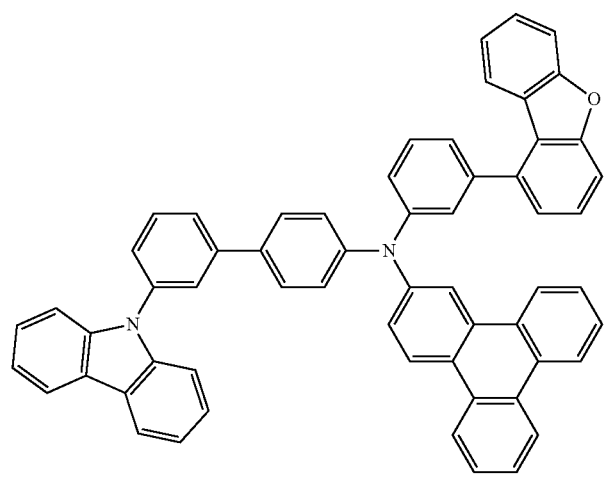
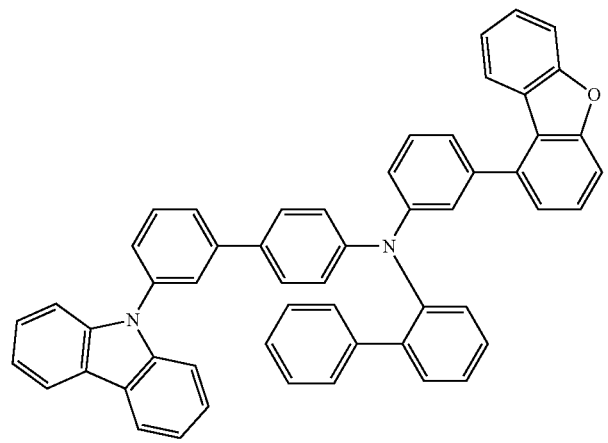

-continued
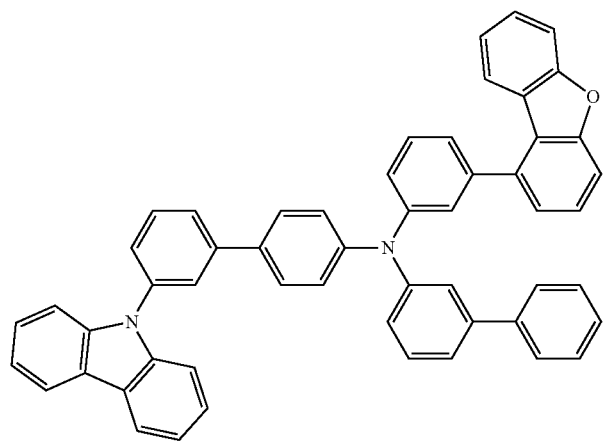
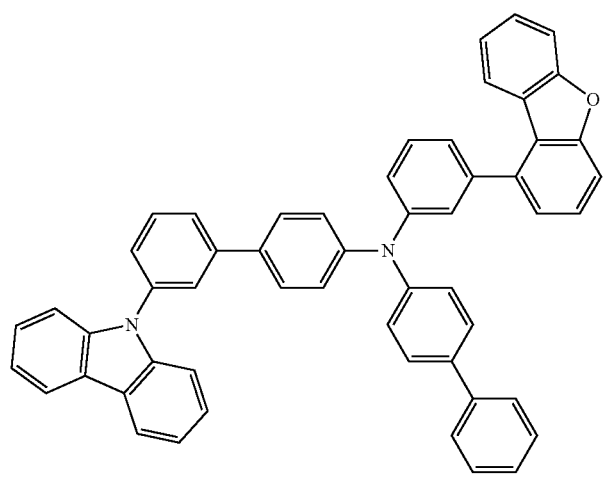
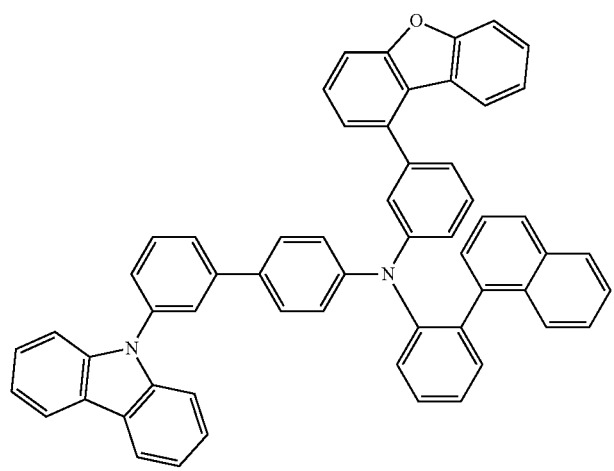

-continued
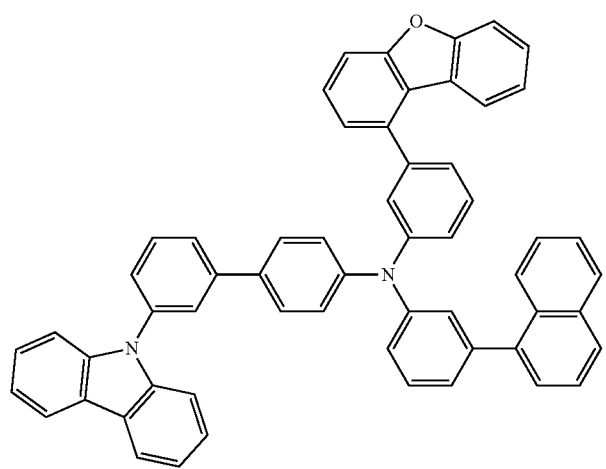
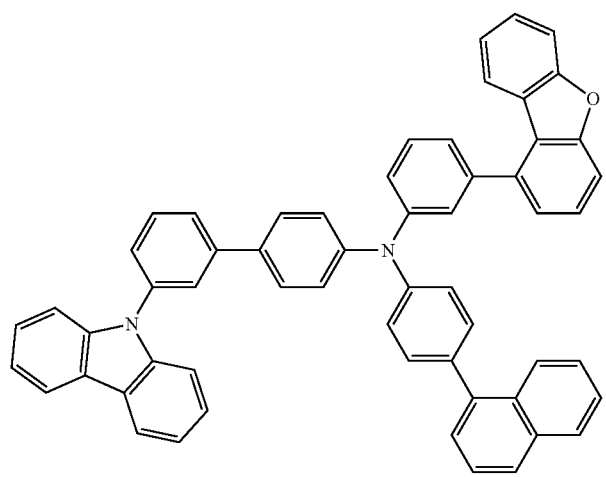

-continued
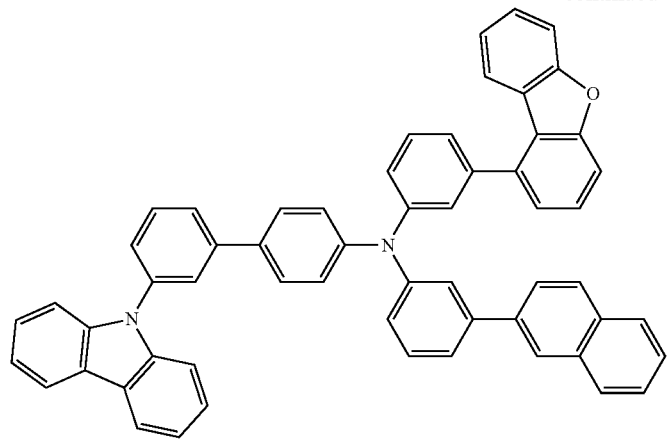
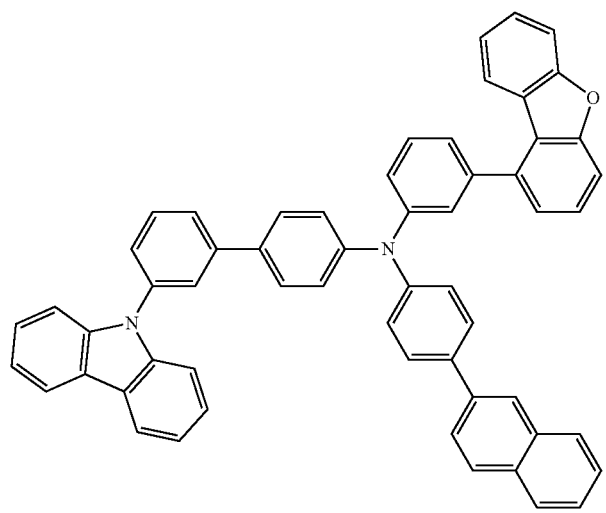
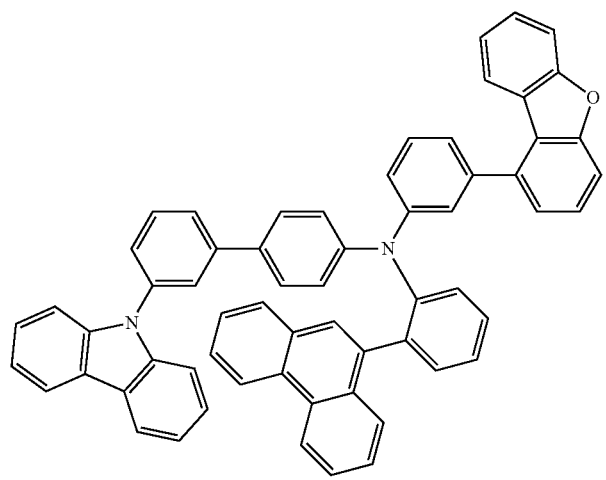

-continued
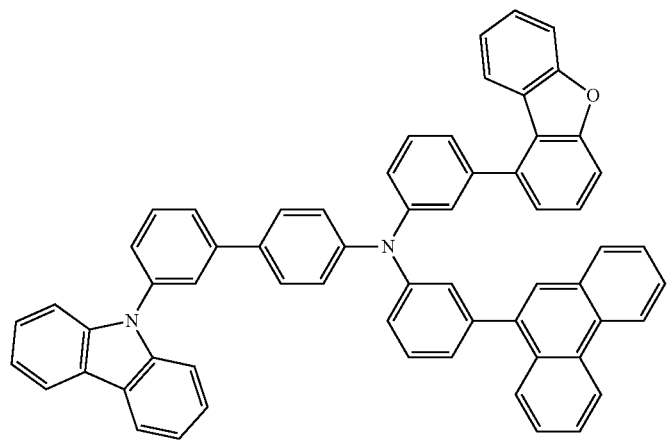
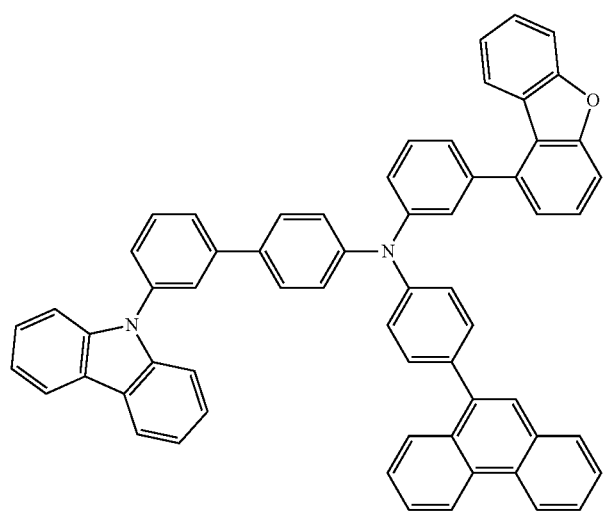
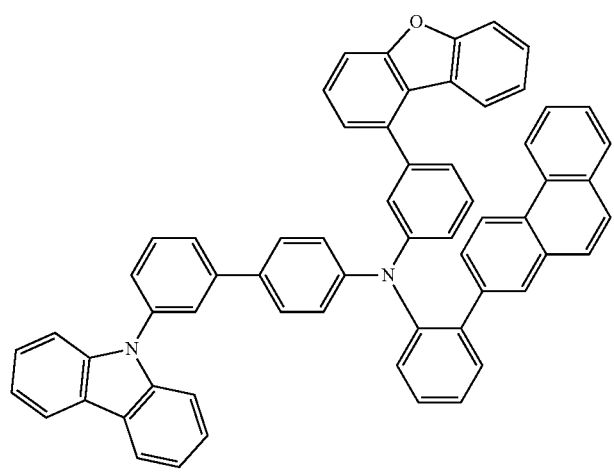

-continued
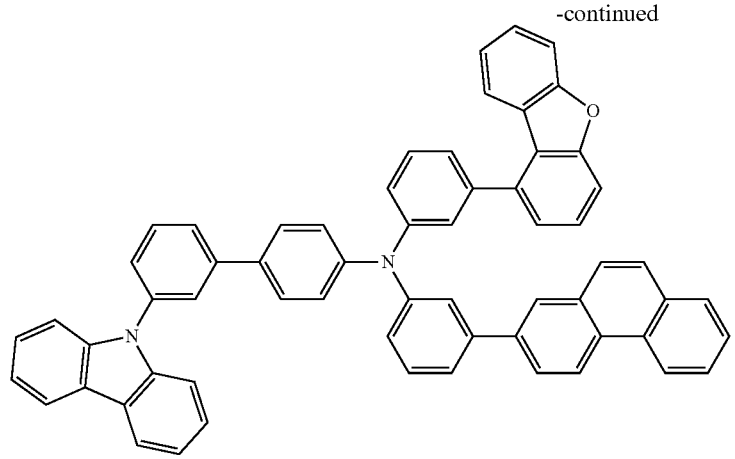
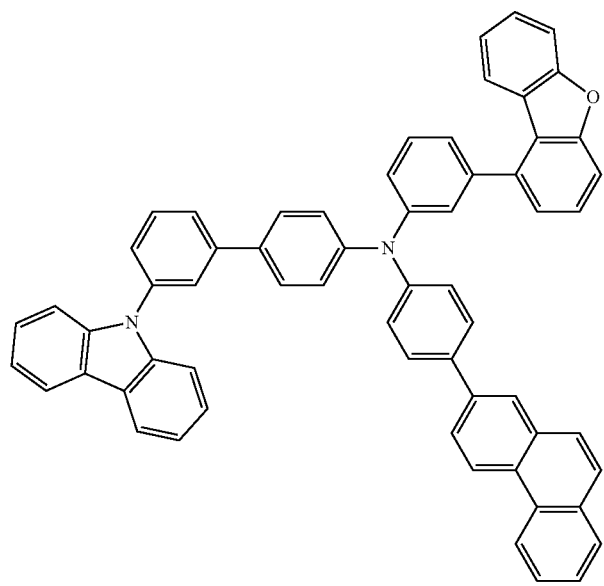
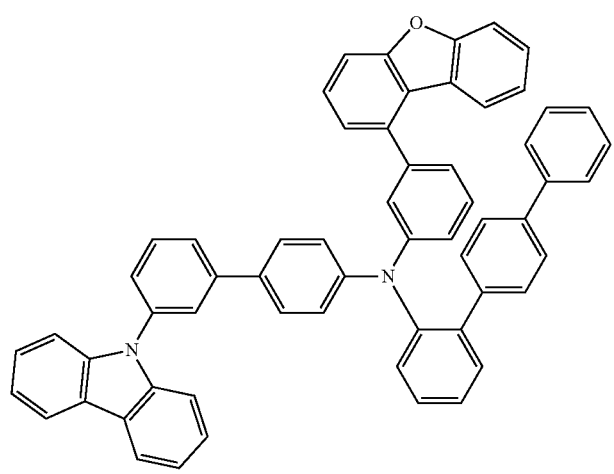

-continued
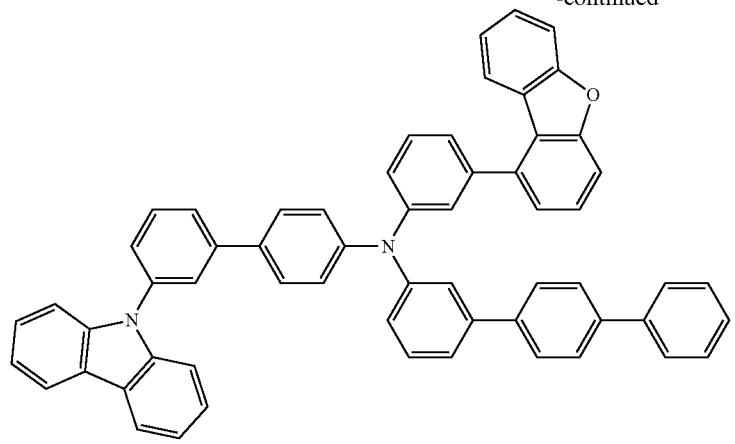
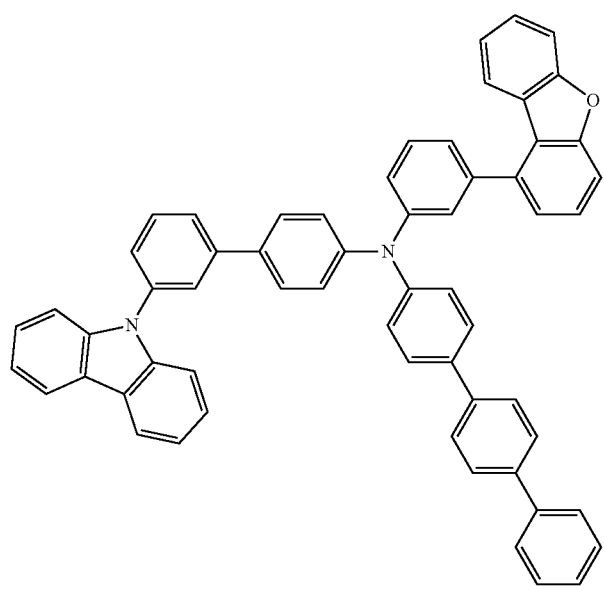
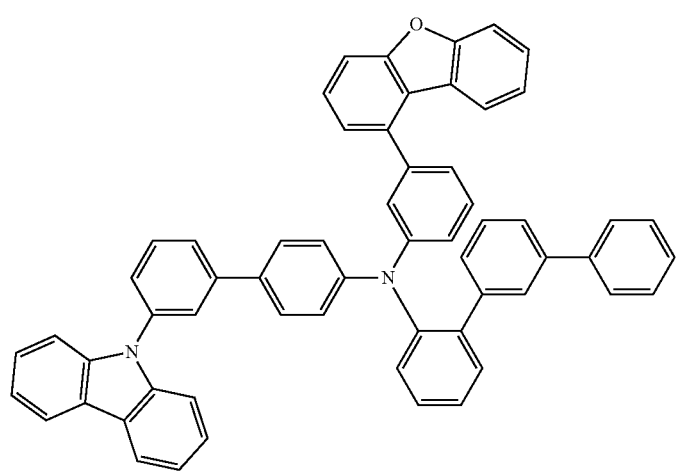

-continued
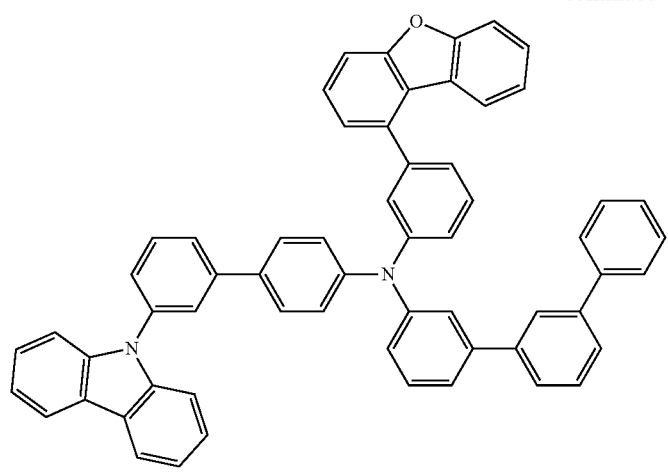
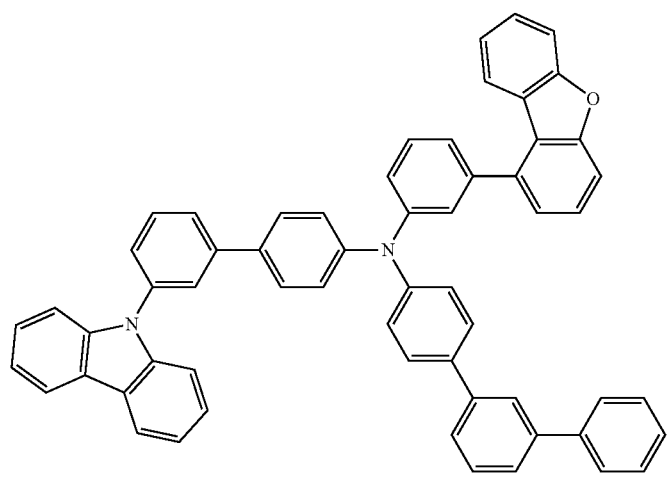
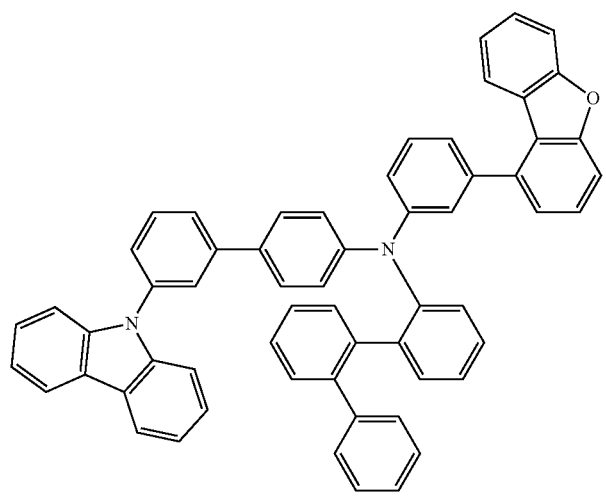

-continued
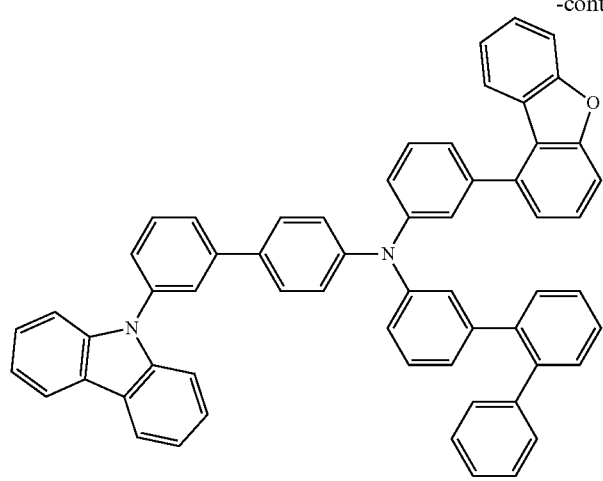
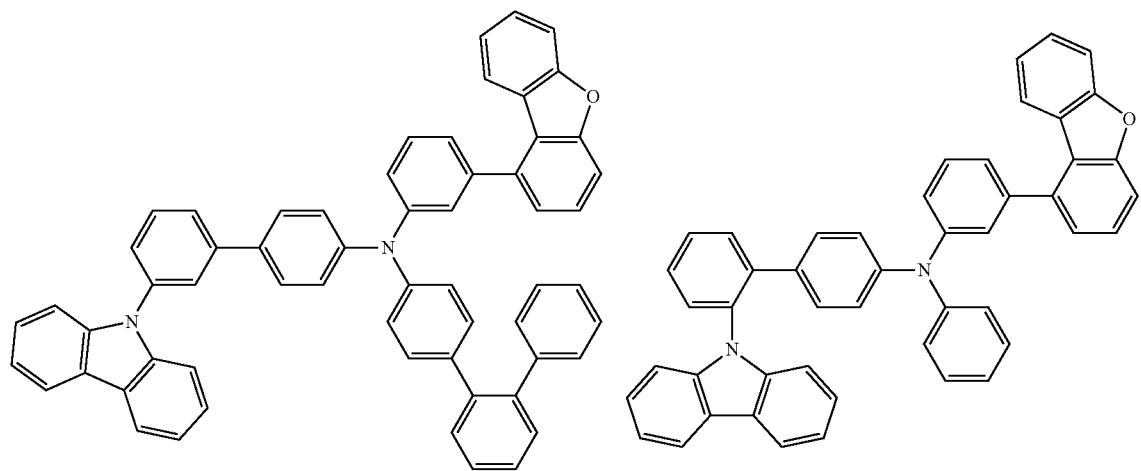
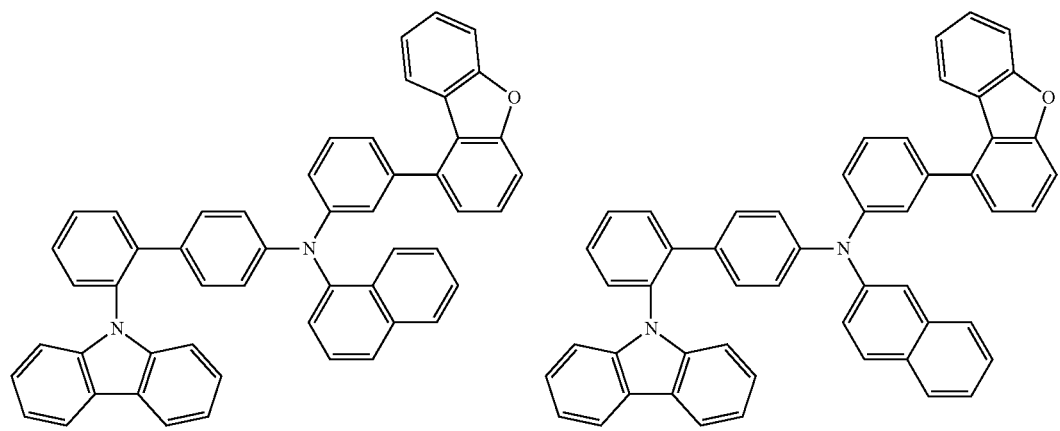

-continued
189
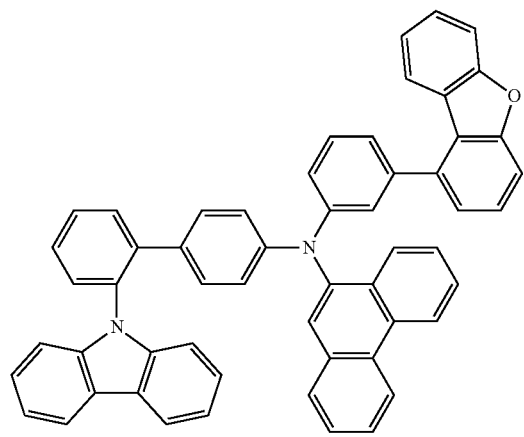
190
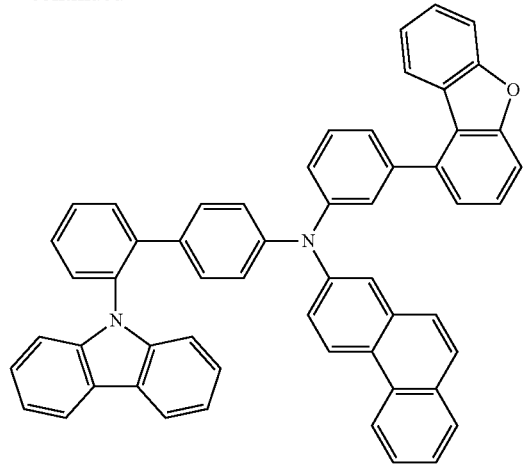
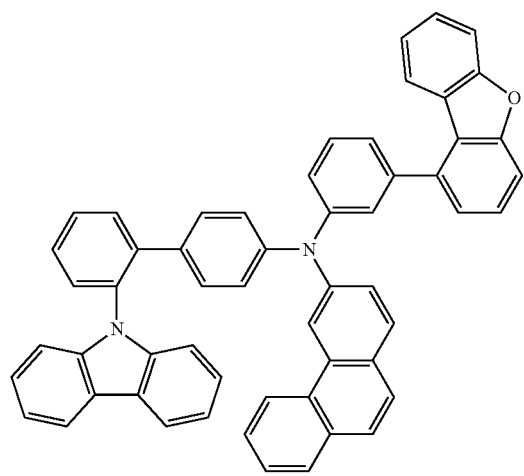
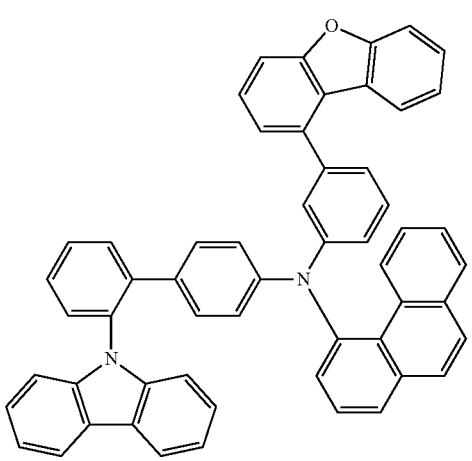
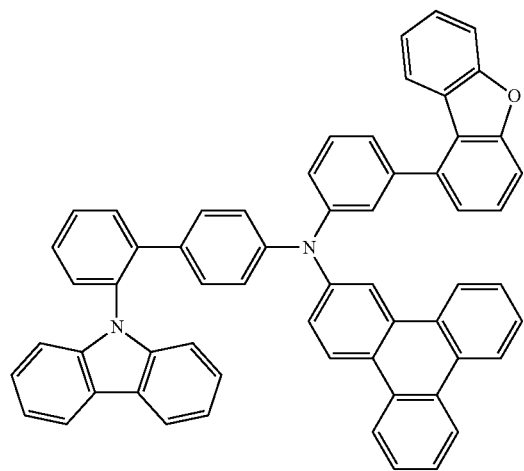
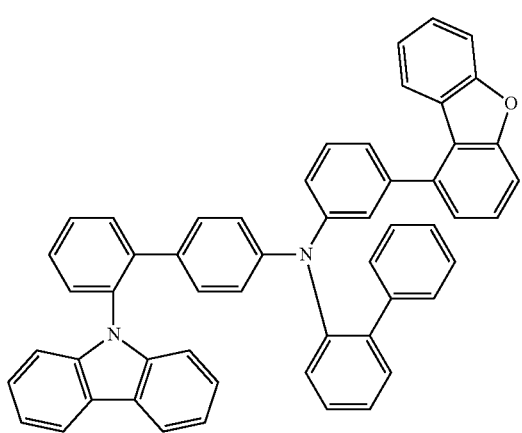

191 192
-continued
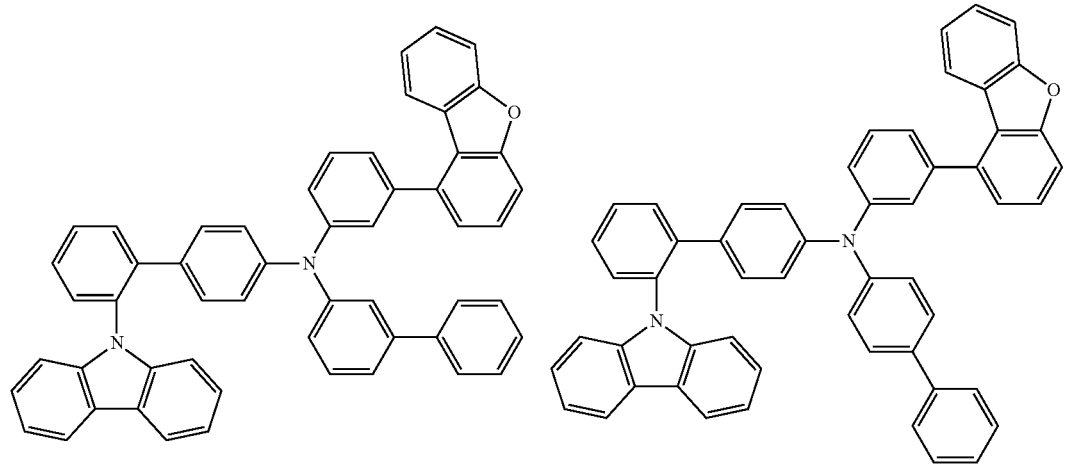
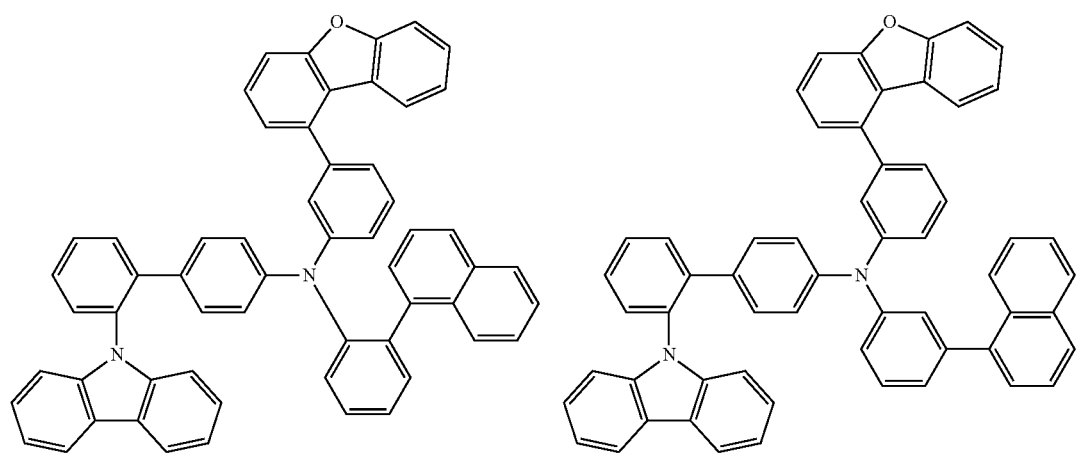
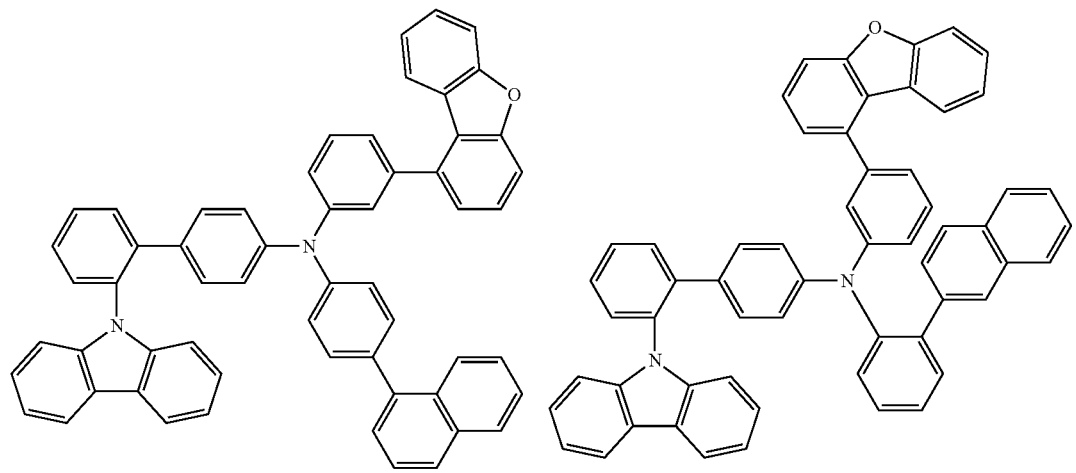

-continued
193
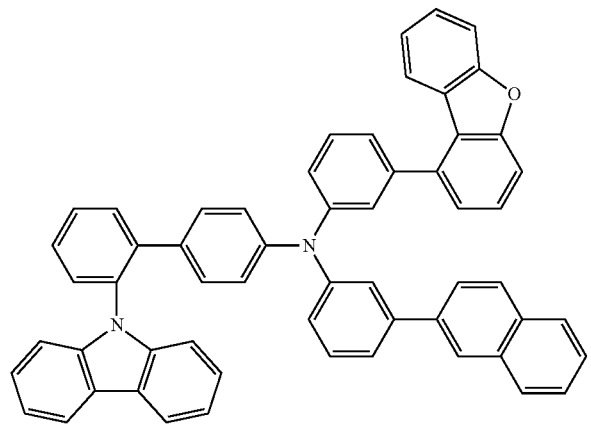
194
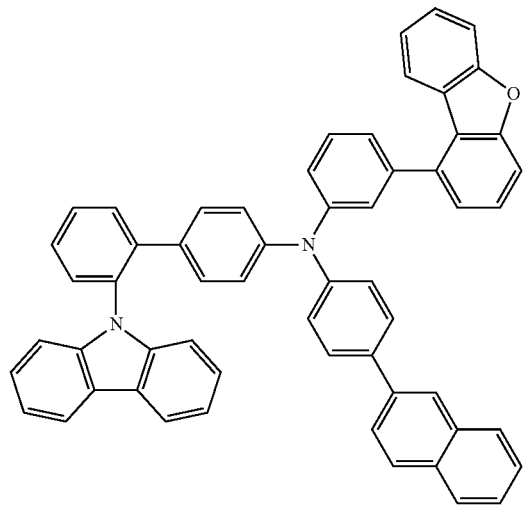
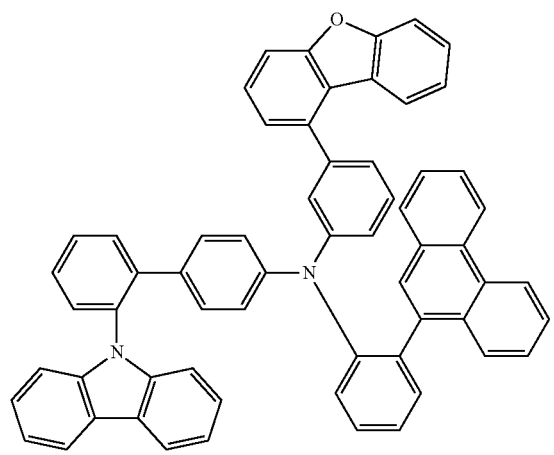
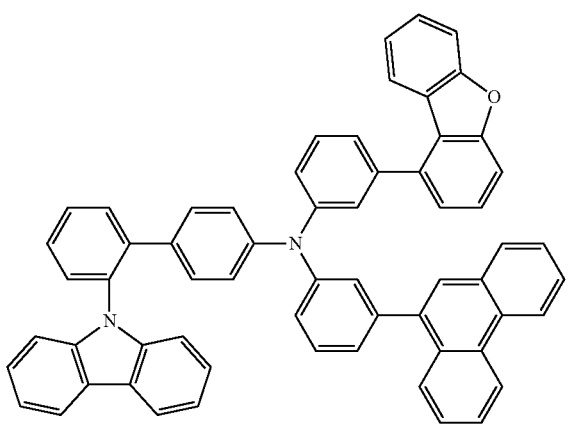
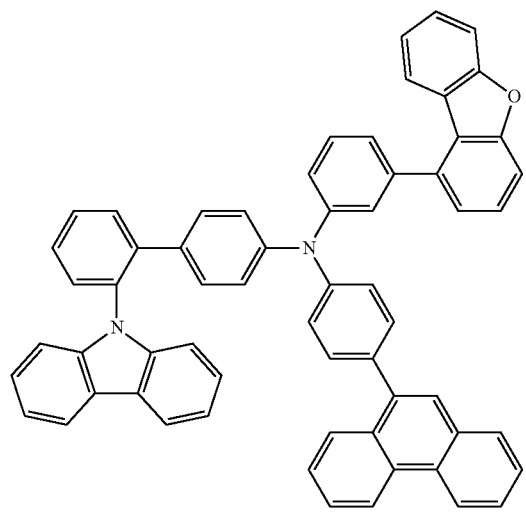
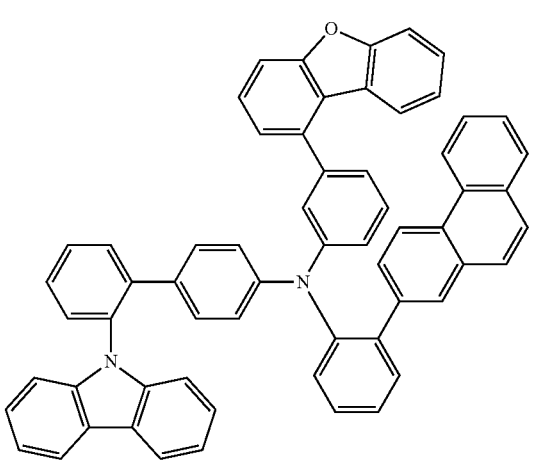

195 196
-continued
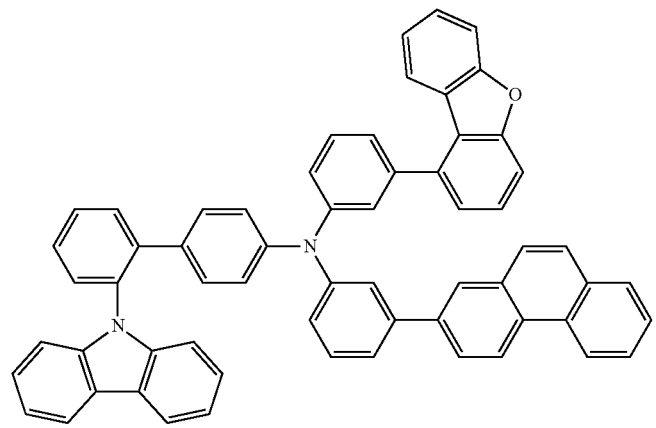
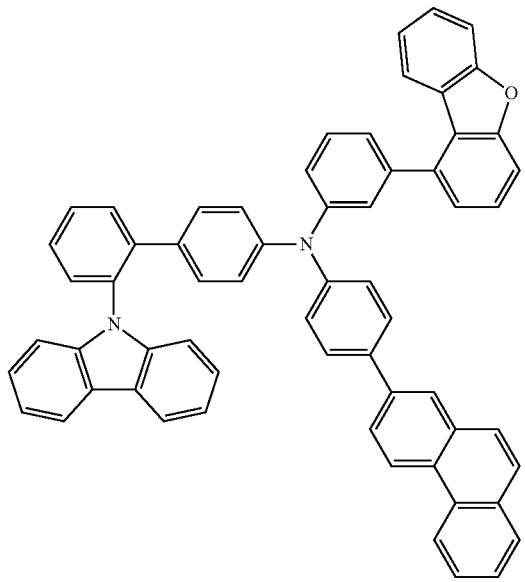
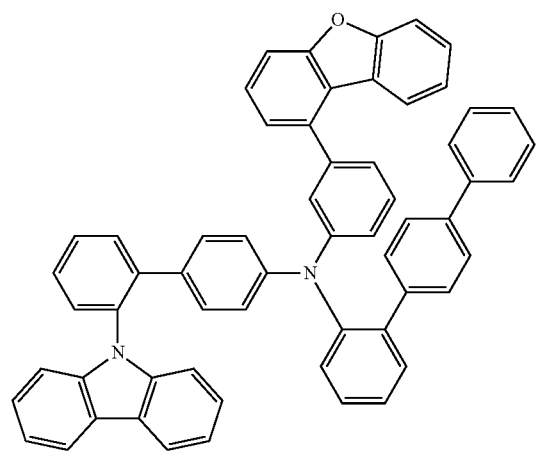
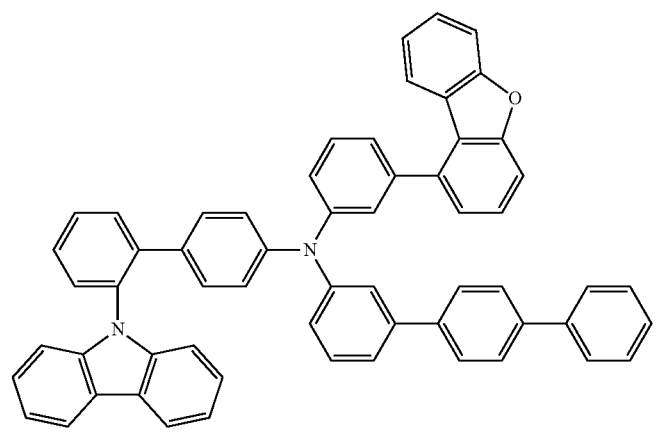
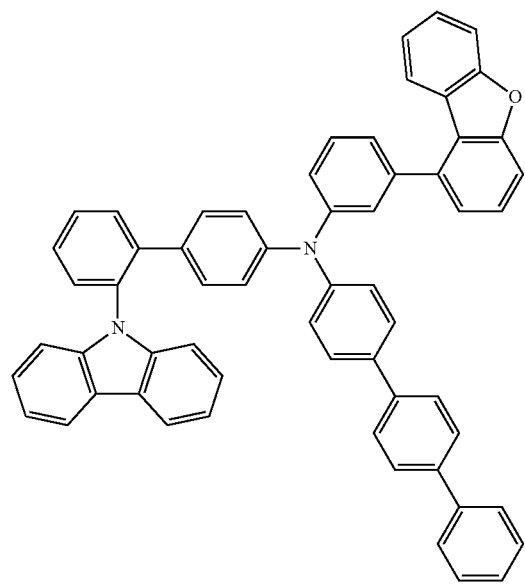
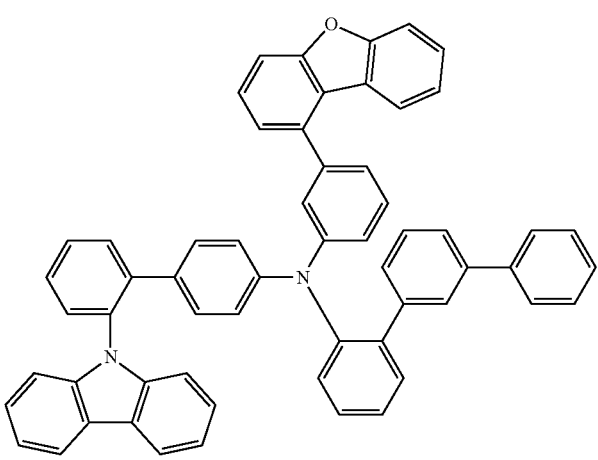

197
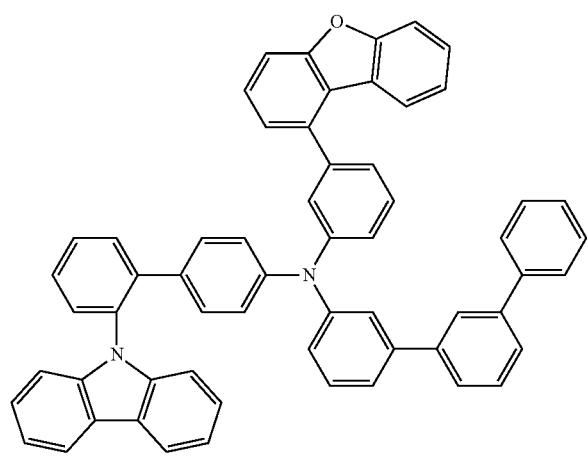
198
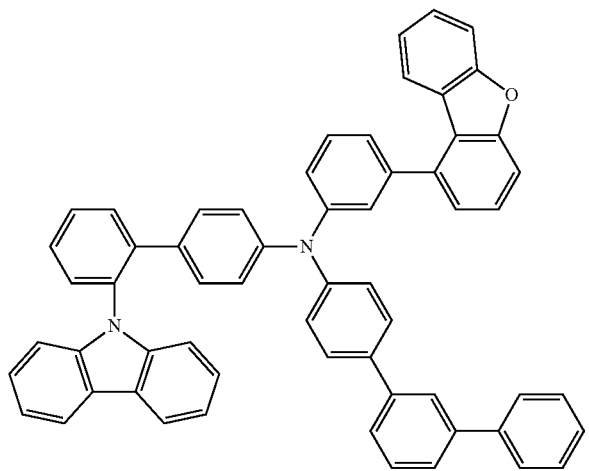
-continued
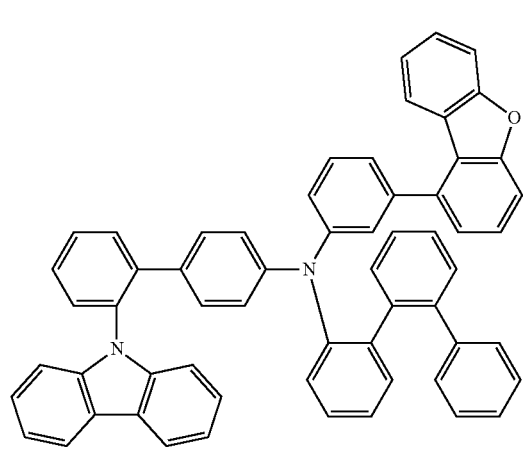
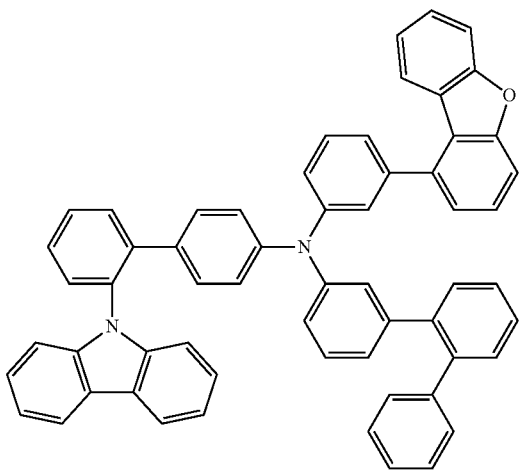
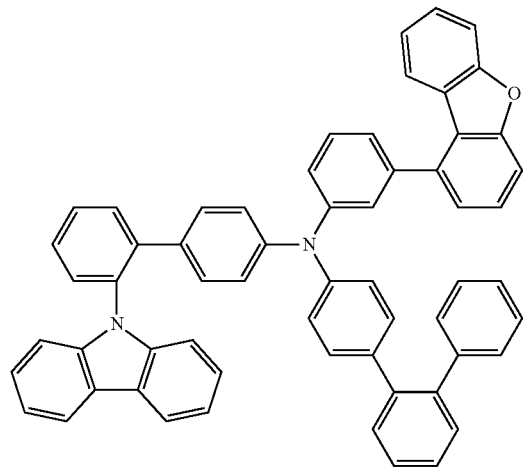

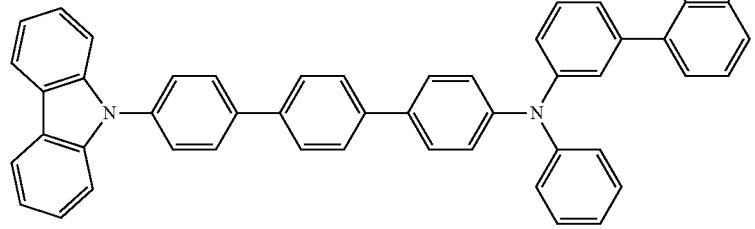
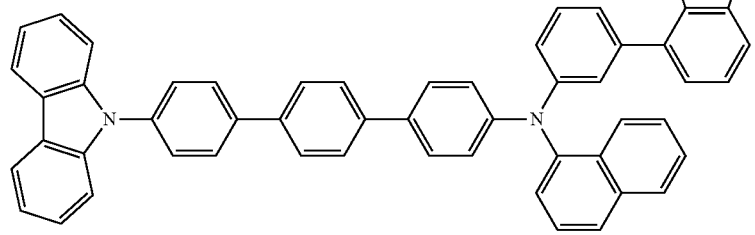
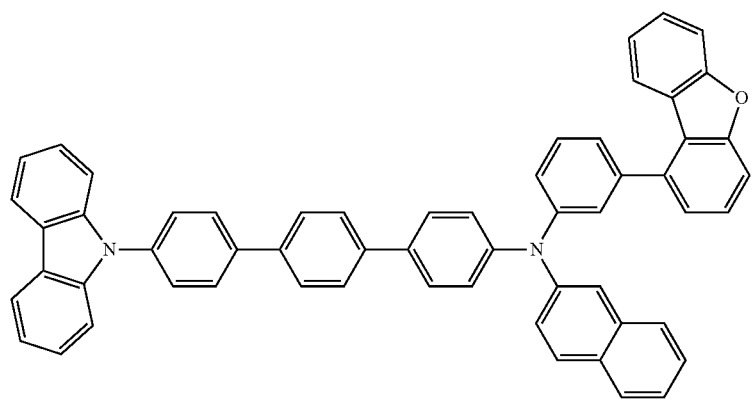
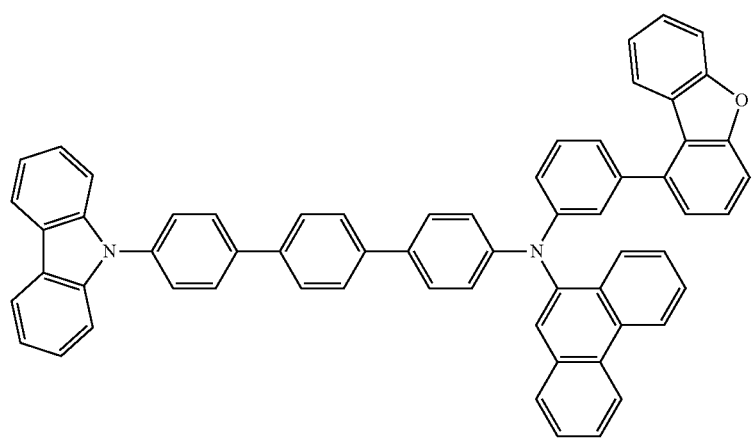

-continued
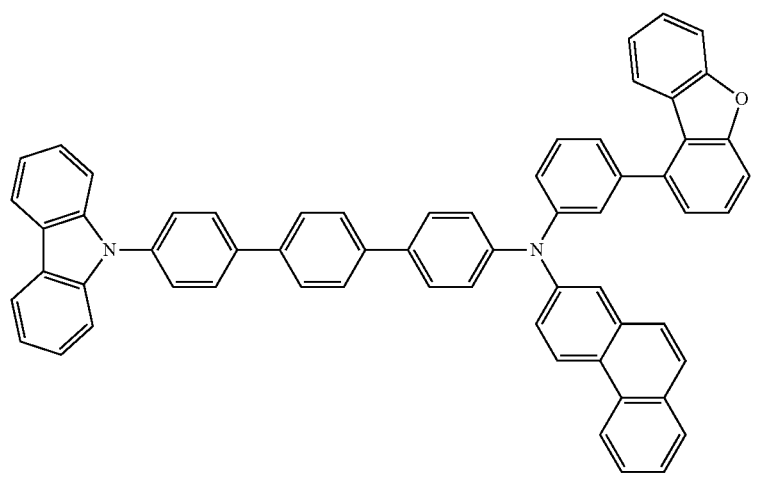
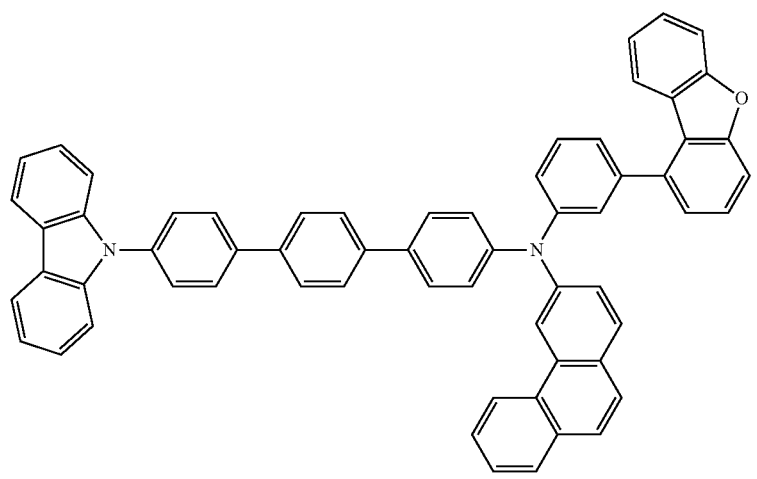
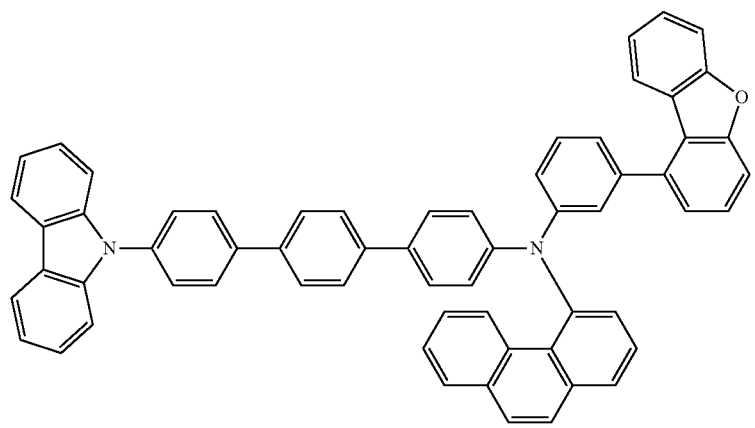

-continued
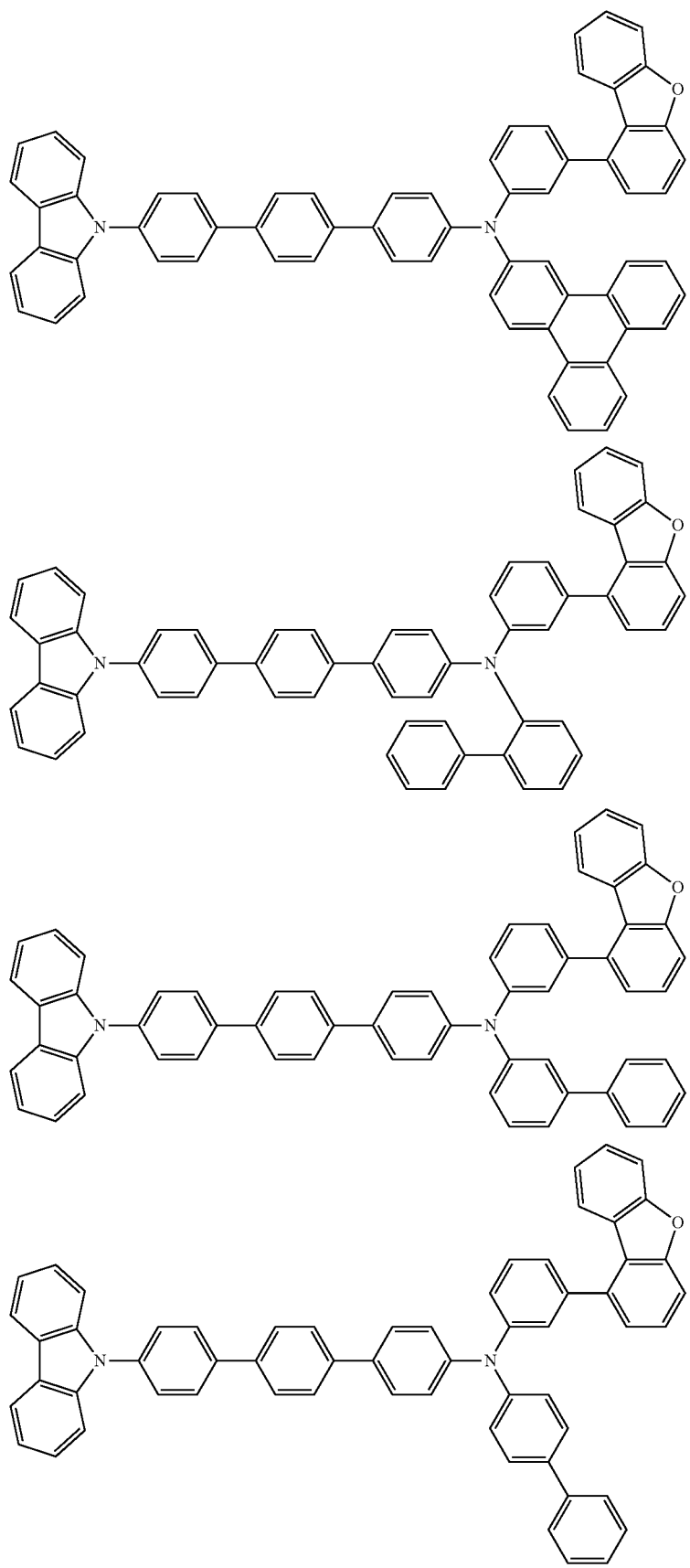

-continued
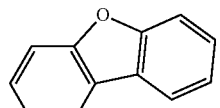
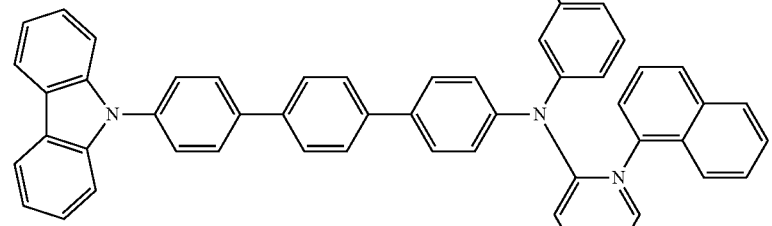
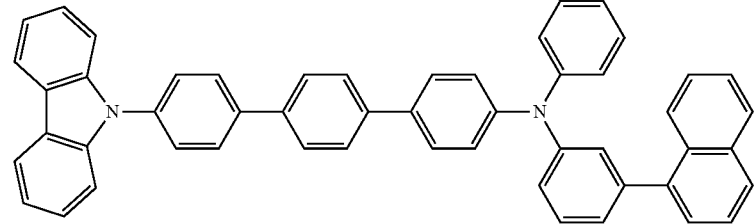
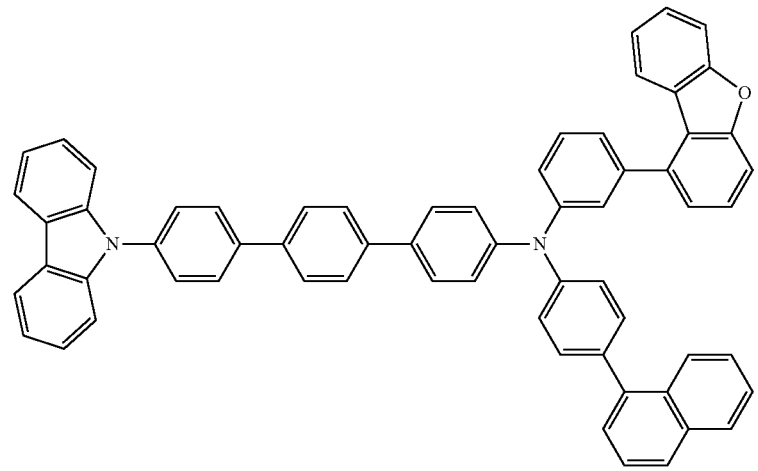
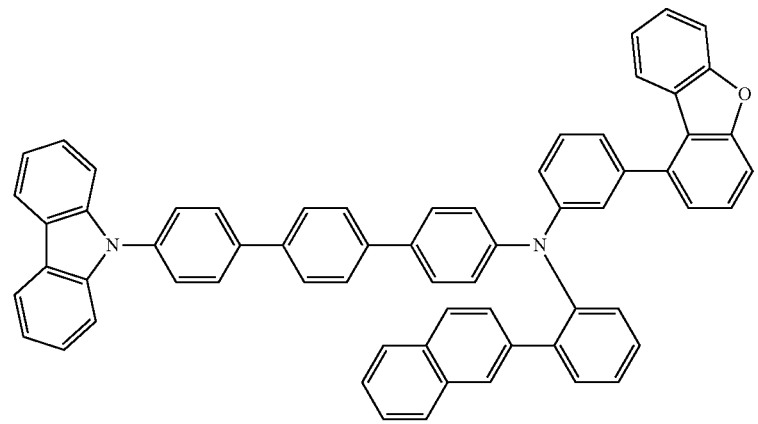

-continued
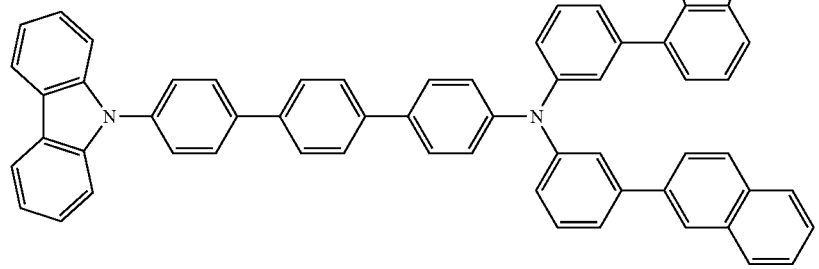
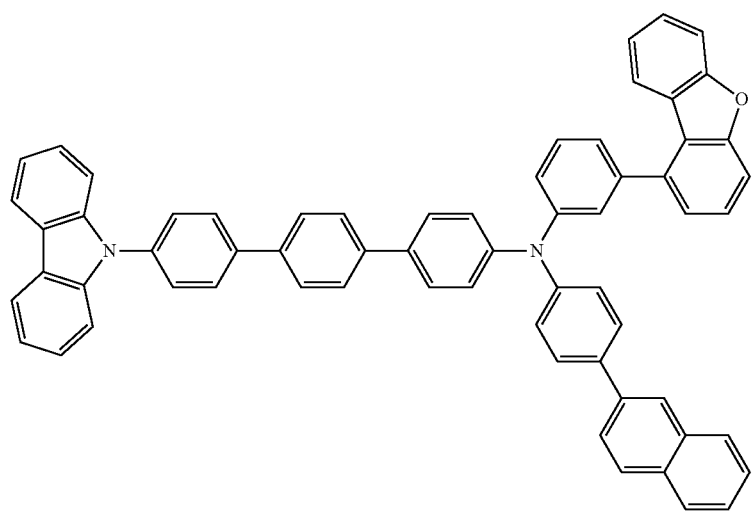
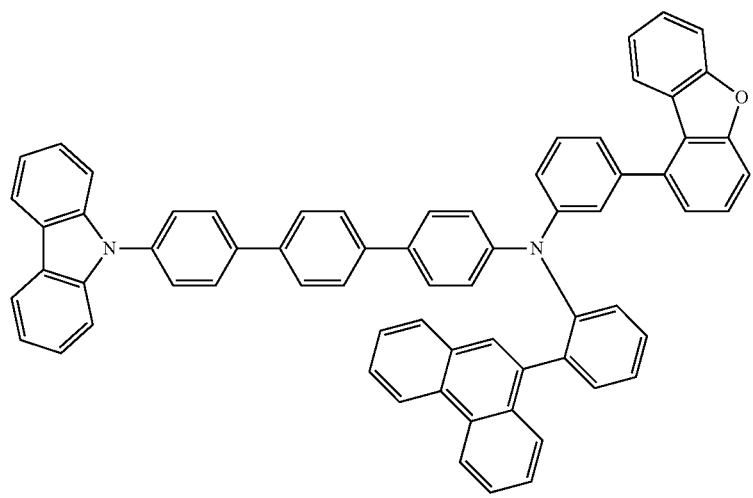

-continued
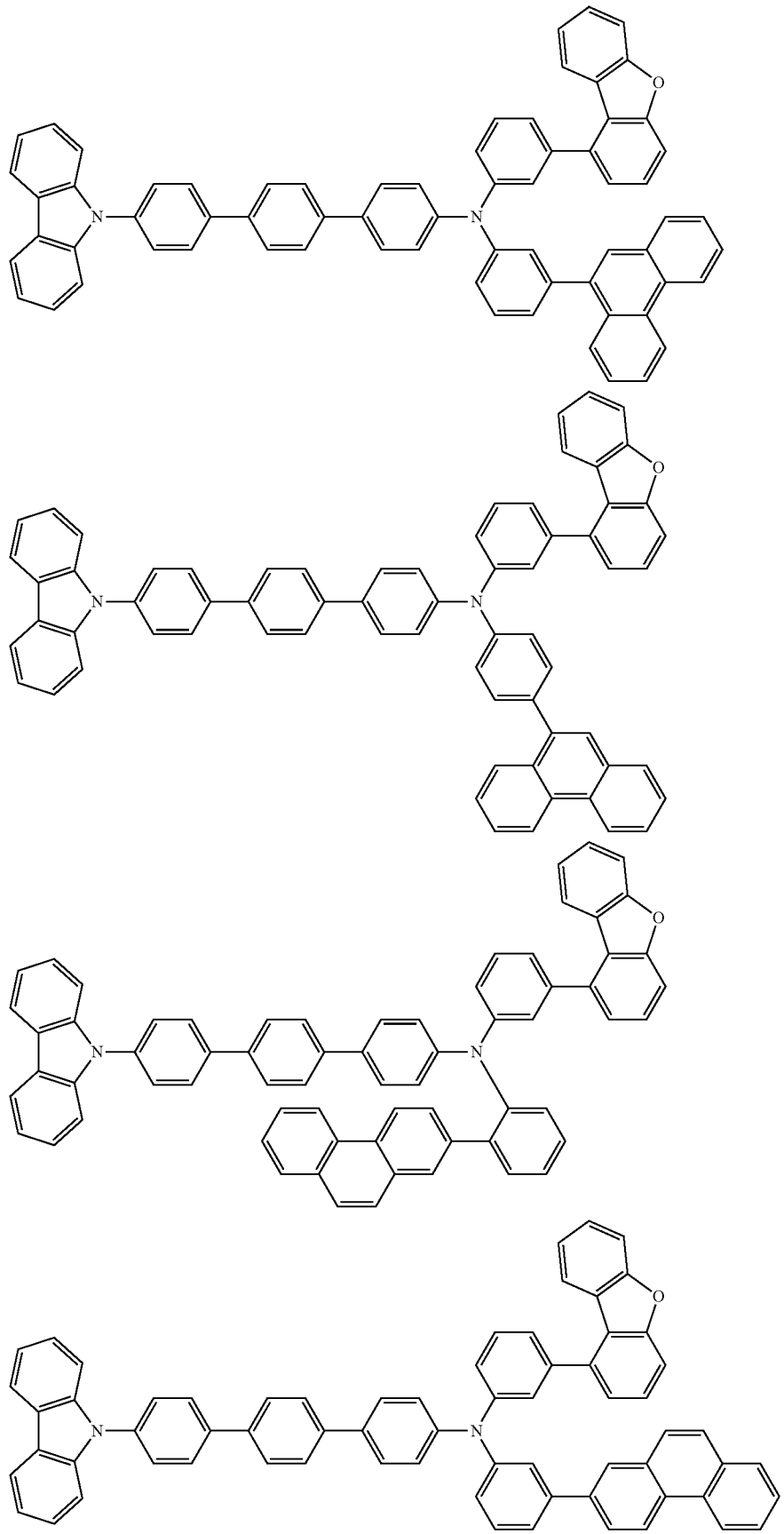

-continued
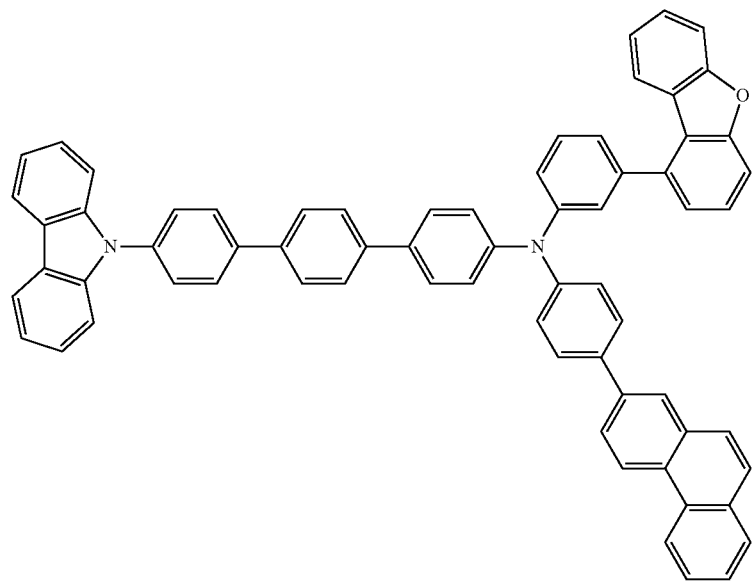
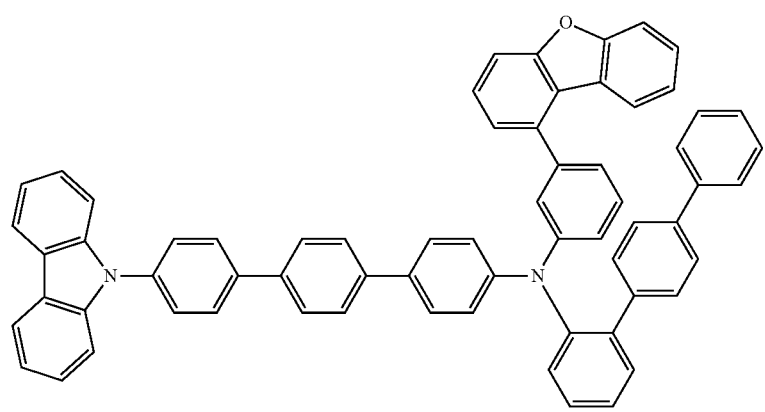
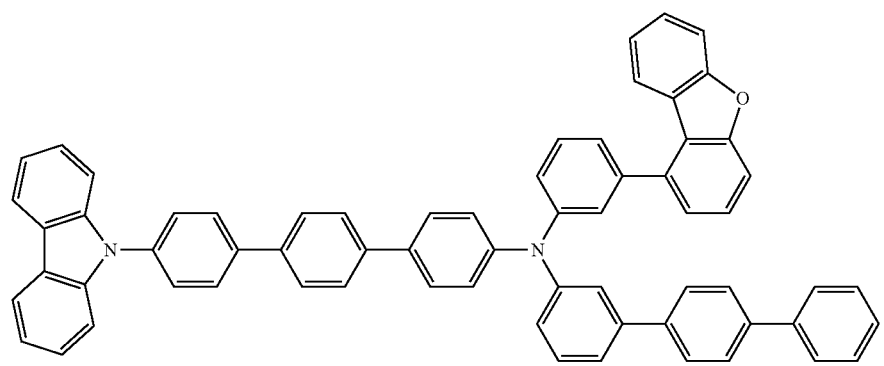

-continued
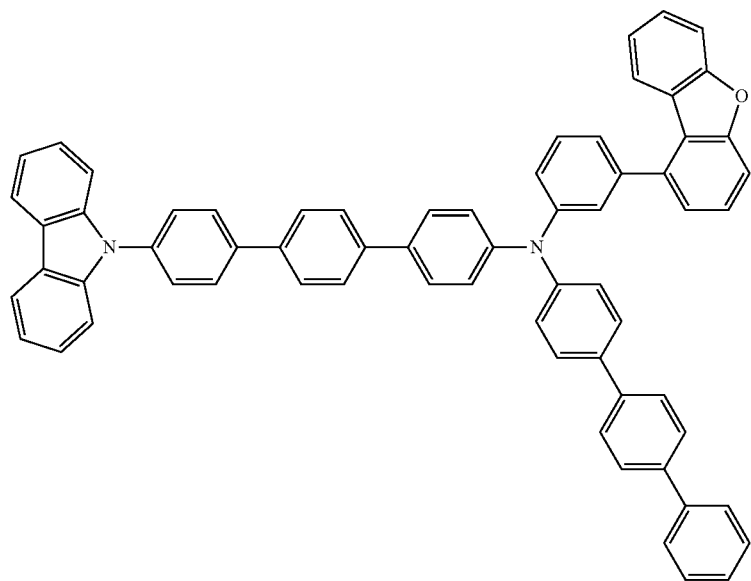
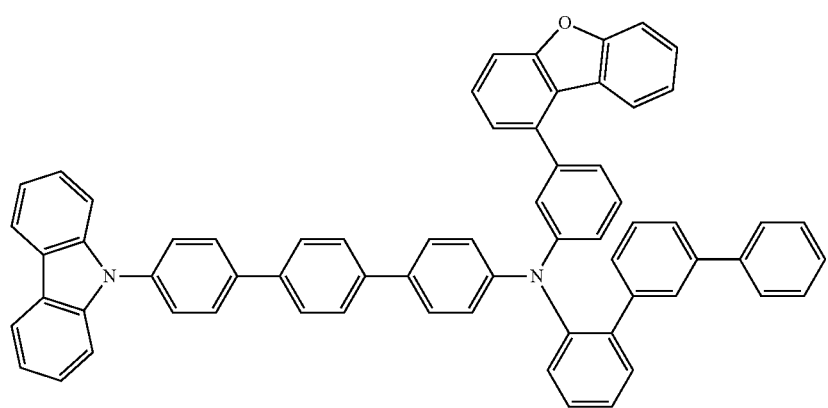
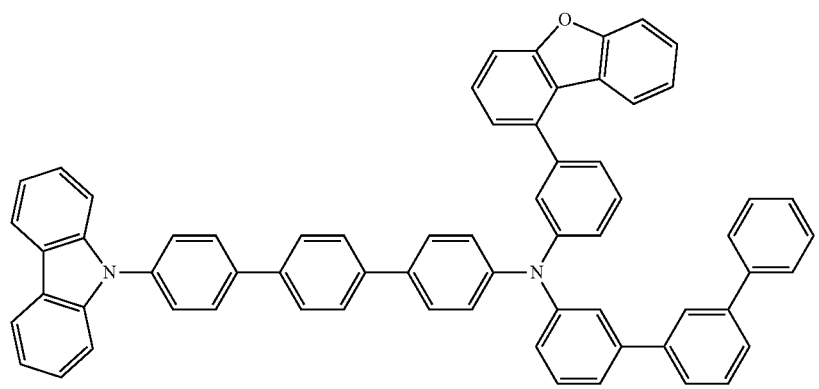

-continued
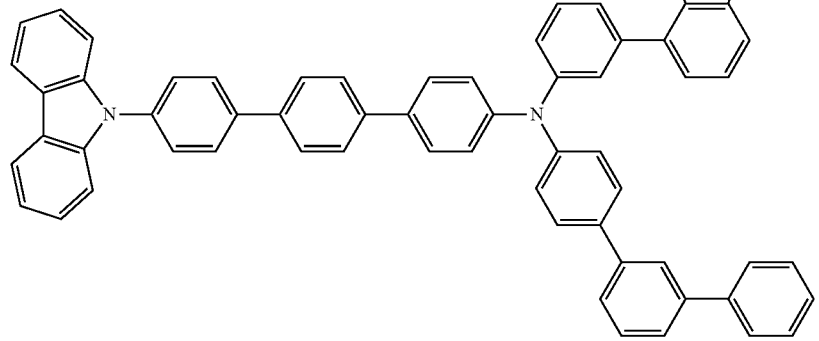
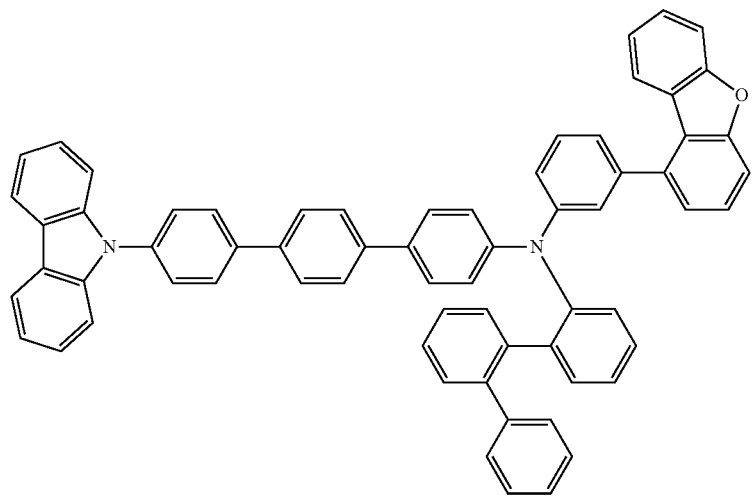
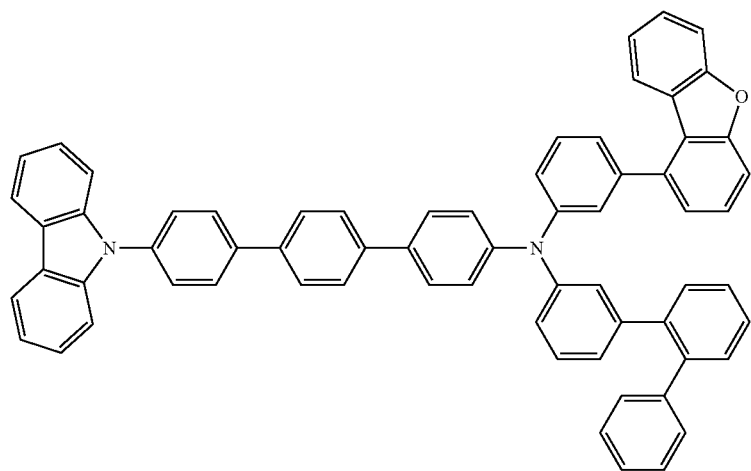

-continued
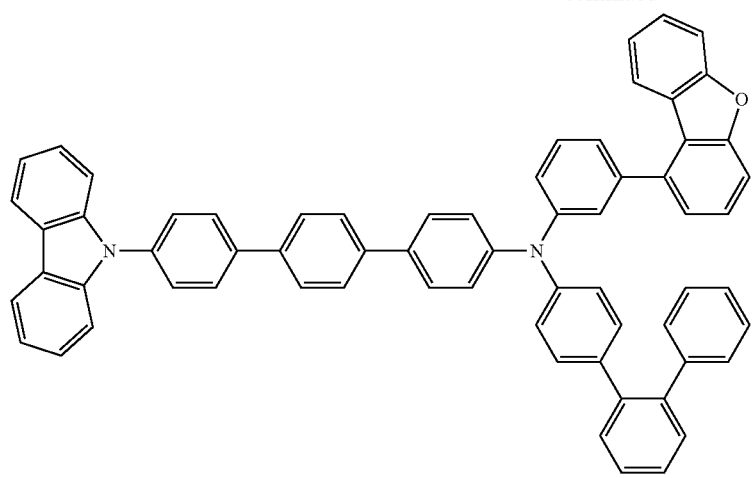
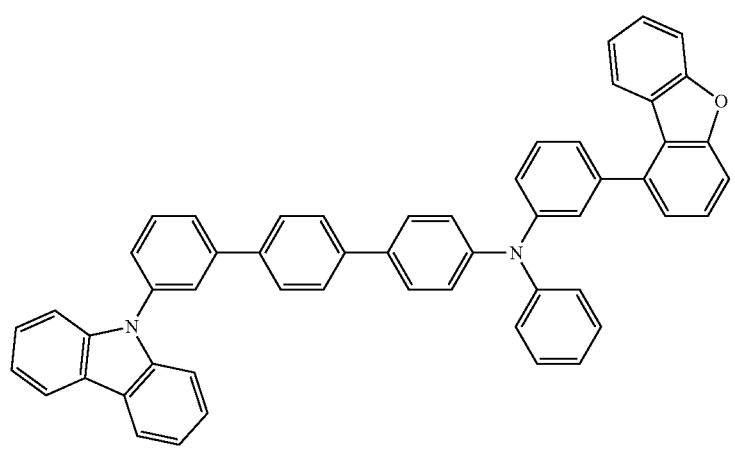
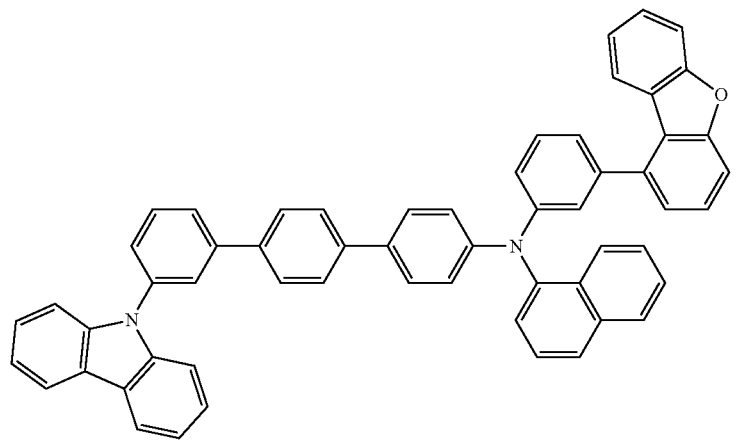

-continued
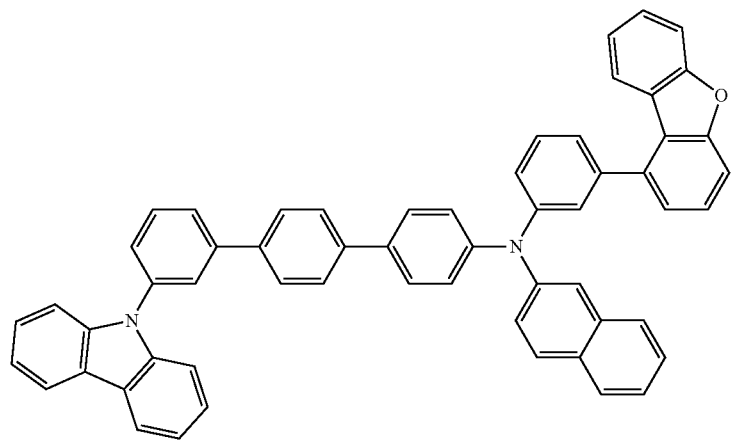
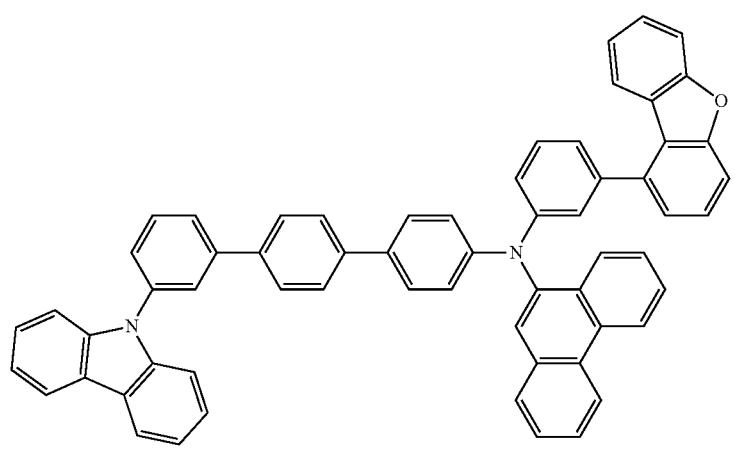
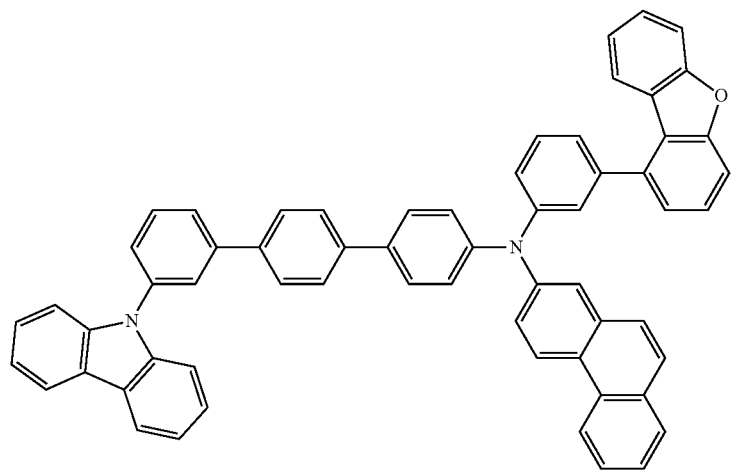

-continued
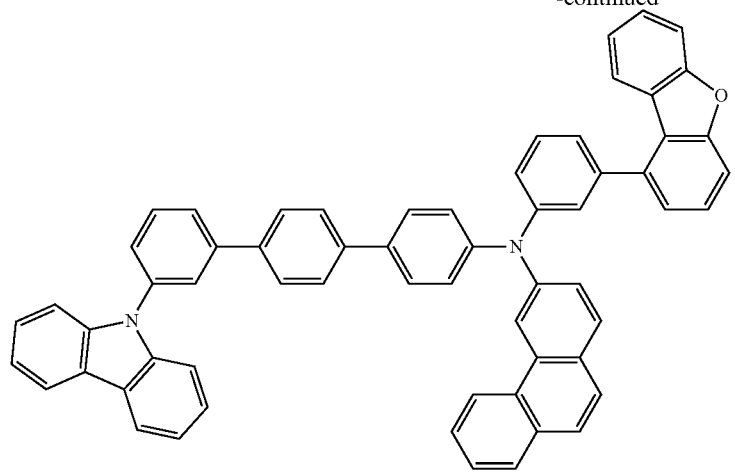
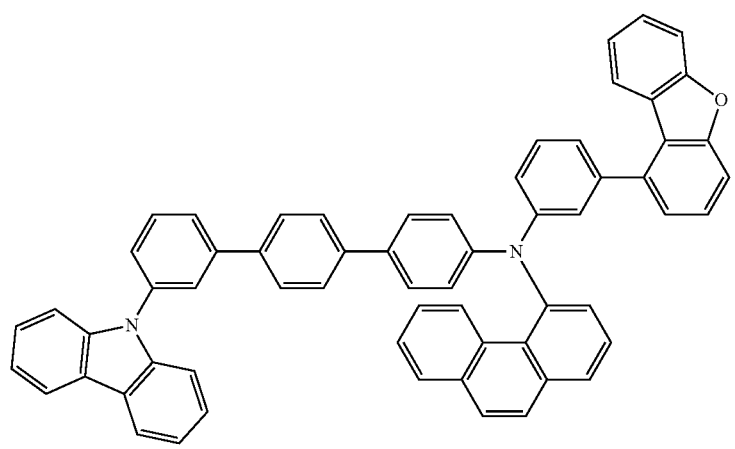
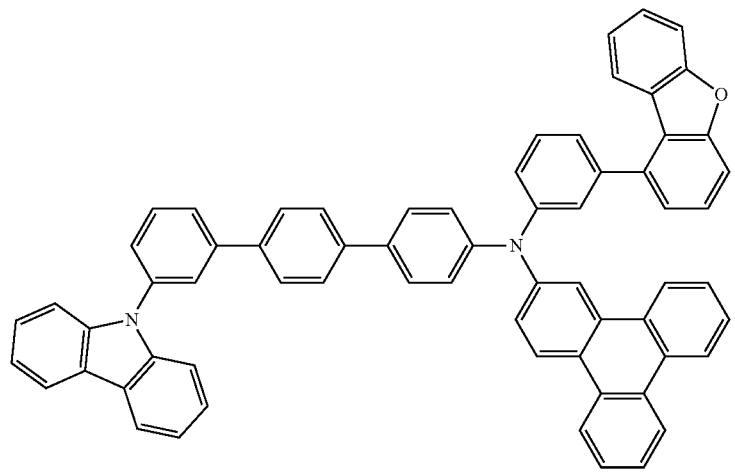

-continued
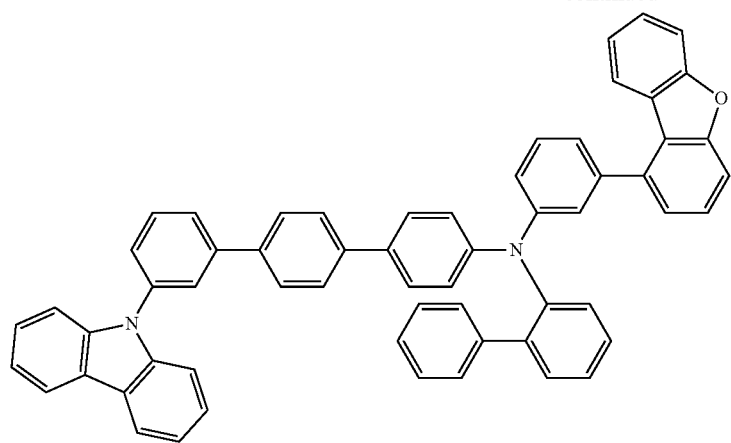
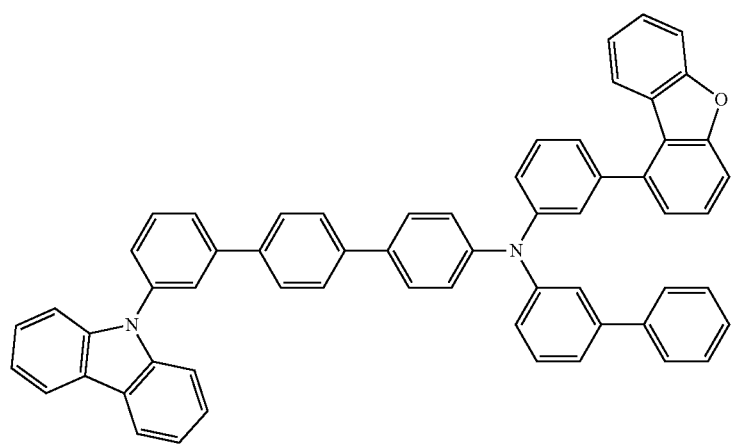
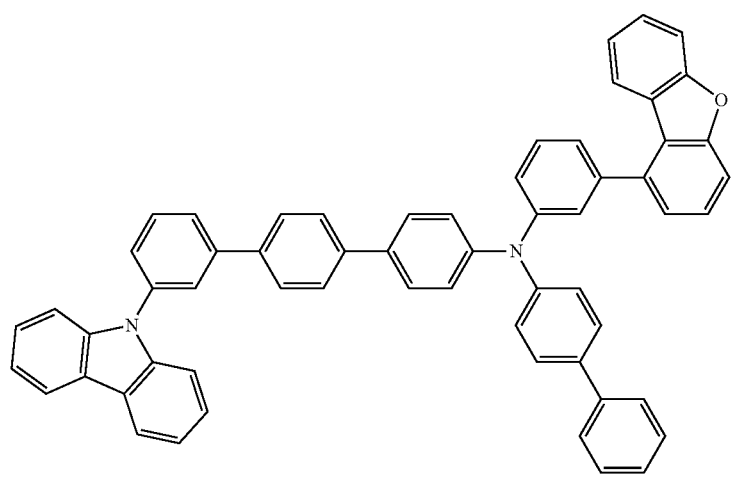

-continued
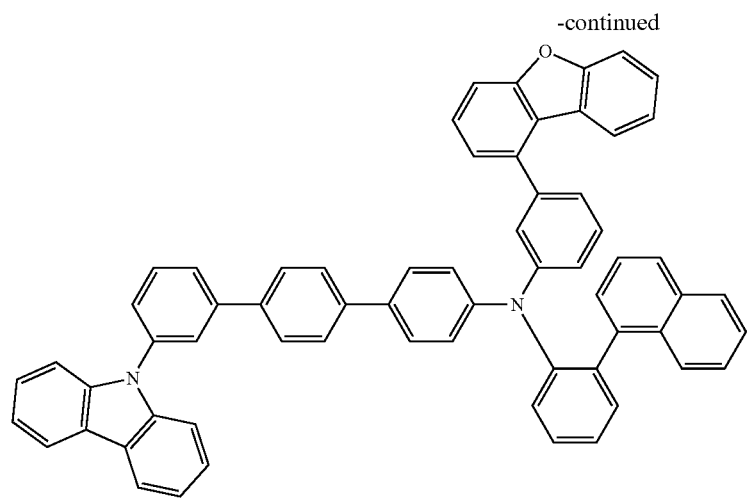
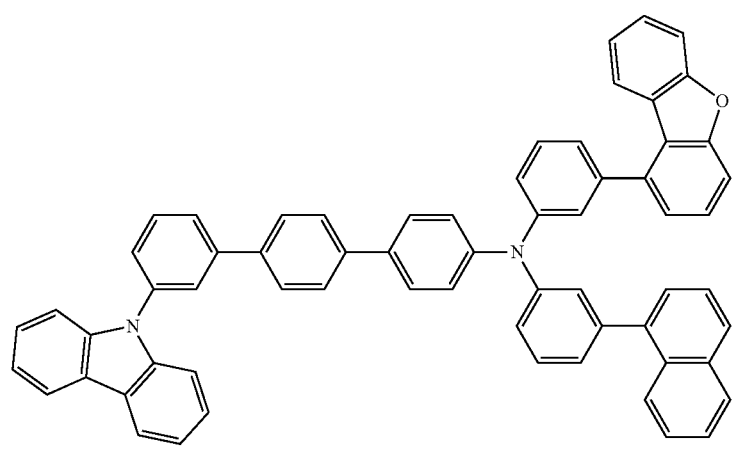
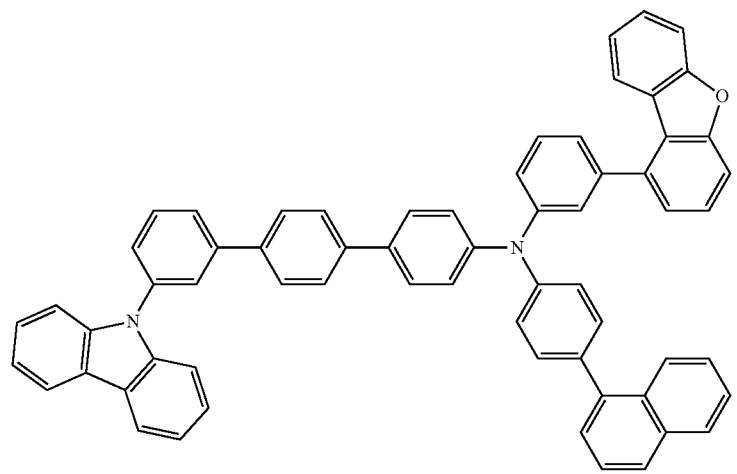

-continued
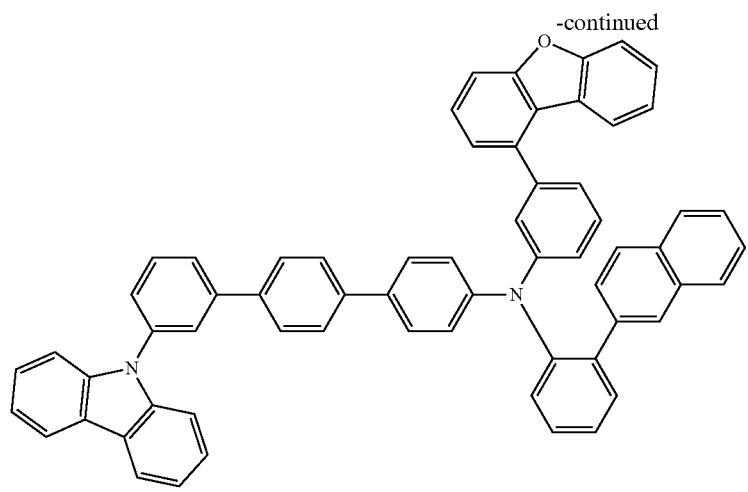
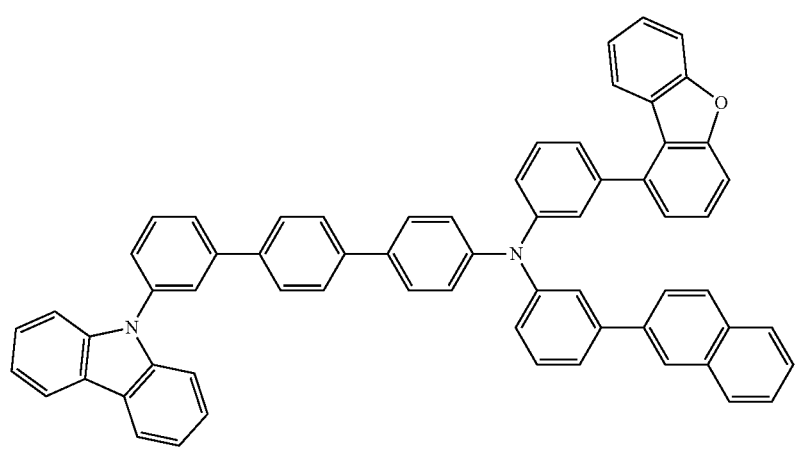
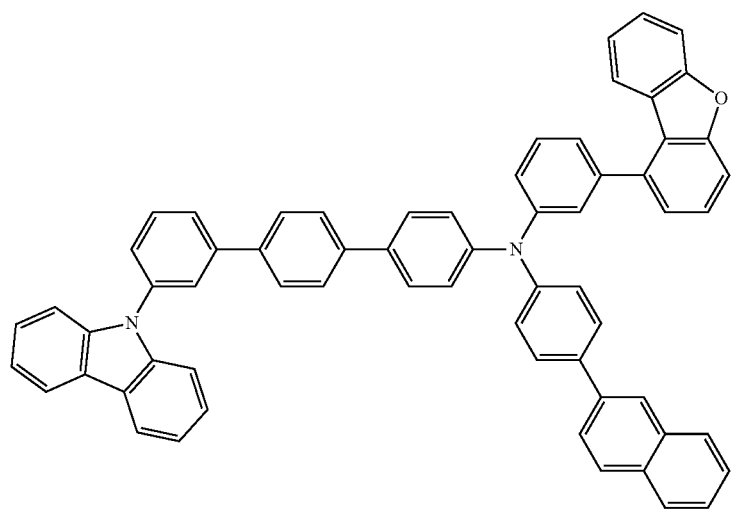

-continued
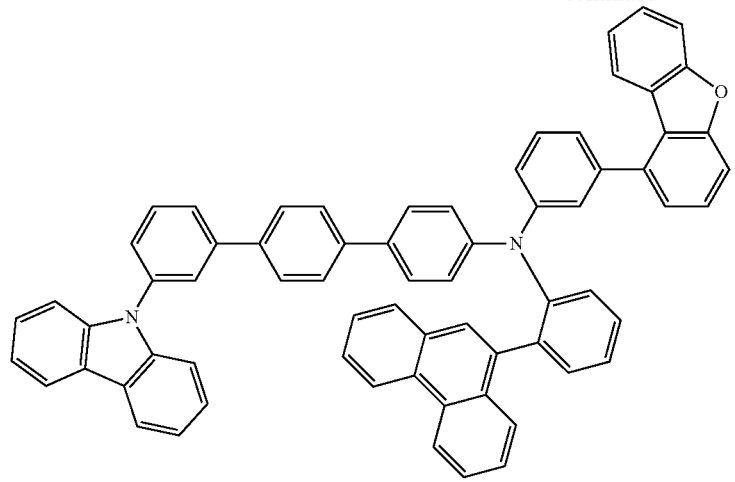
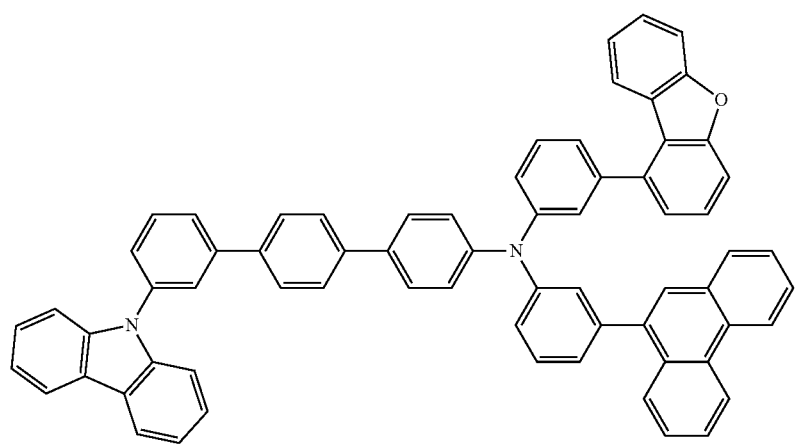
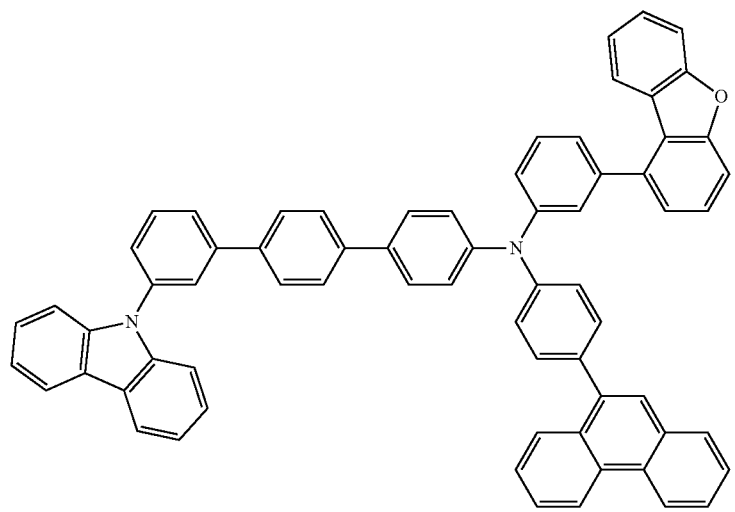

-continued
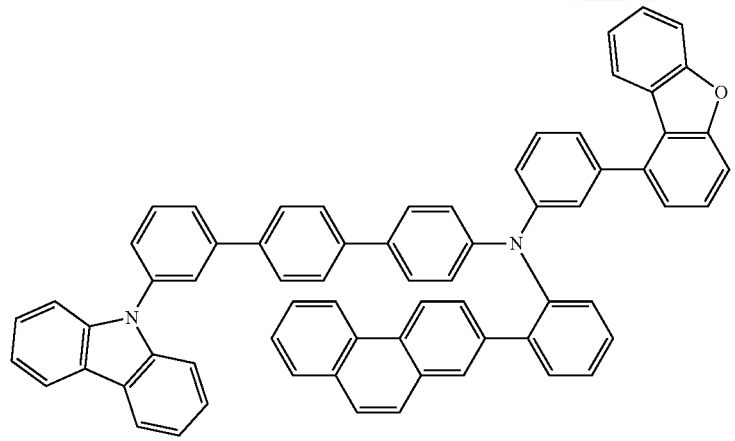
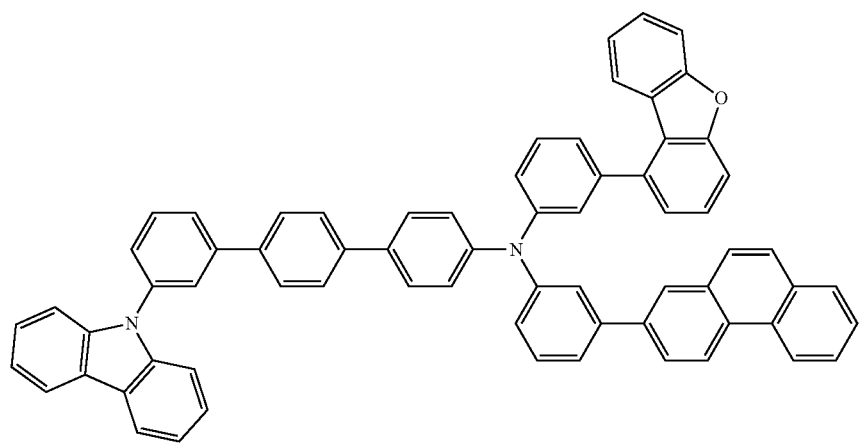
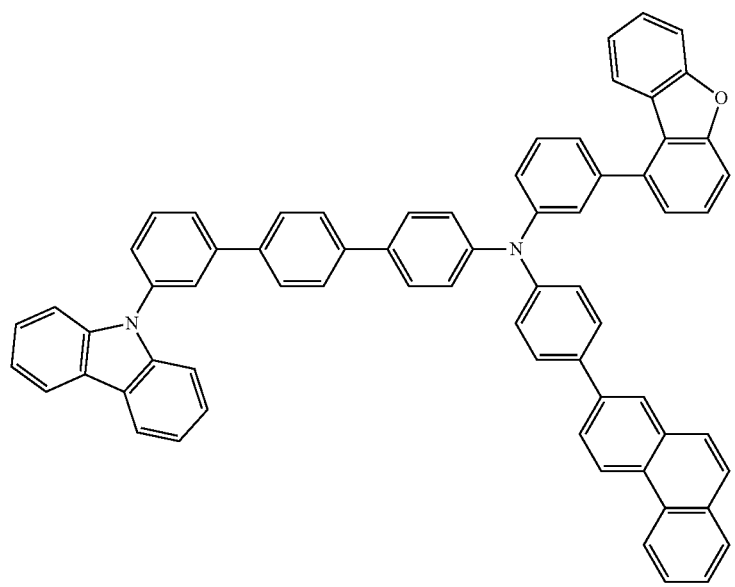

-continued
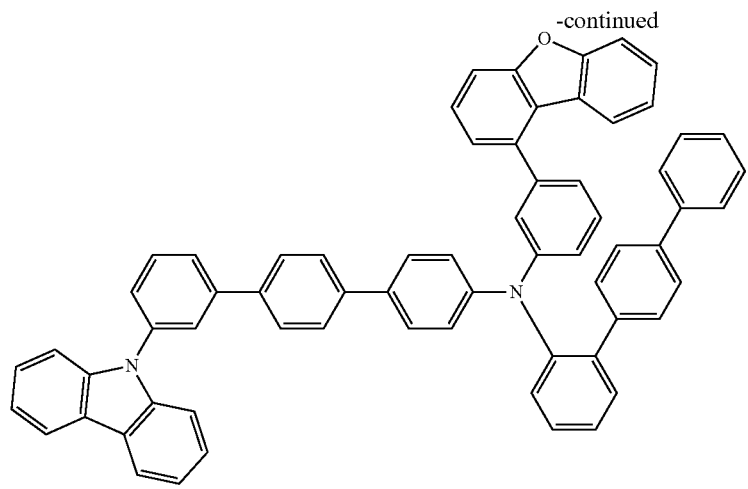
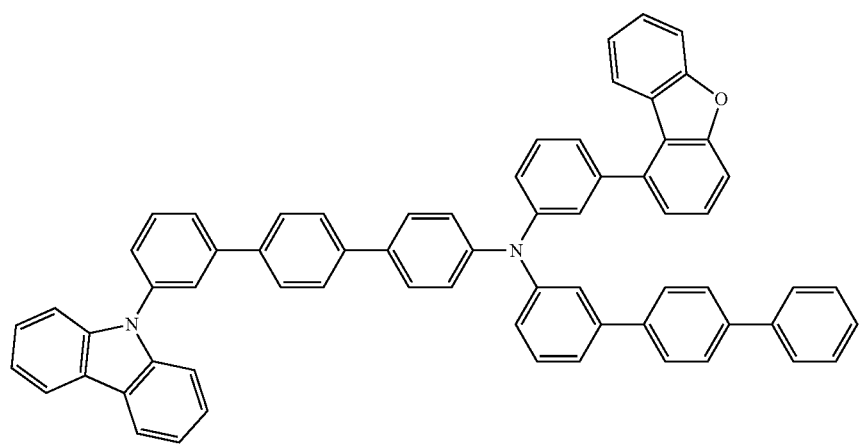
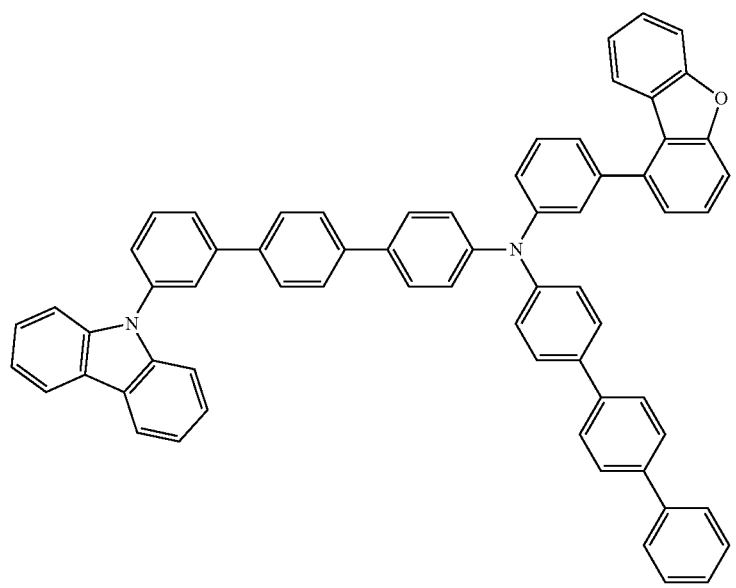

-continued
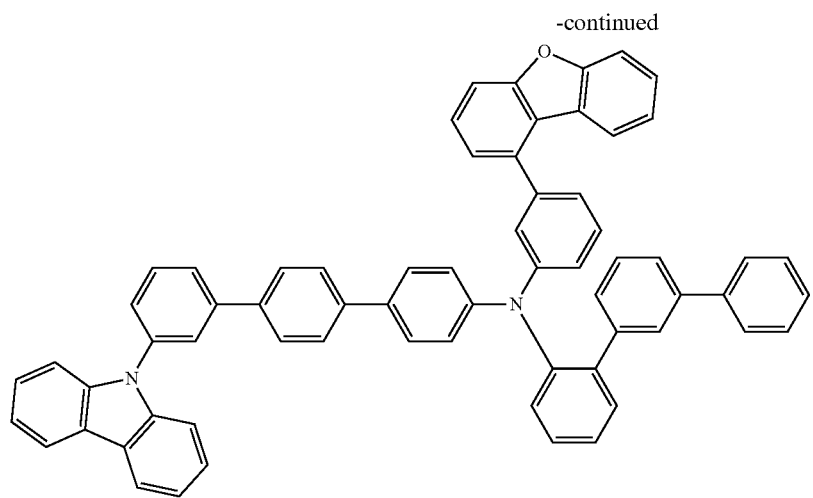
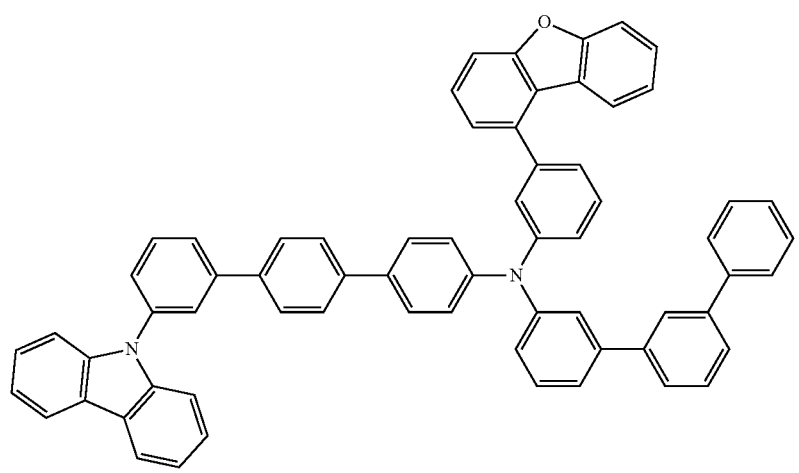
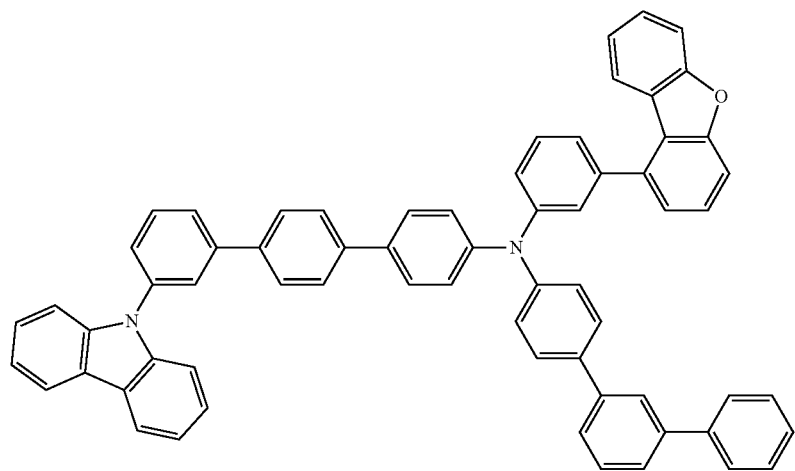

-continued
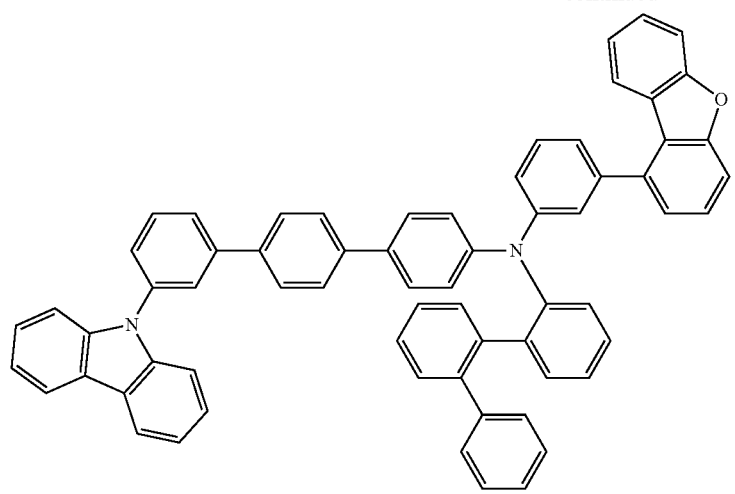
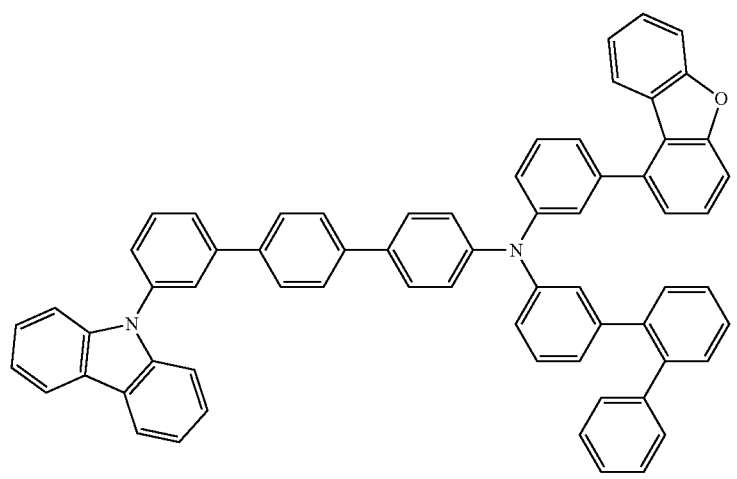
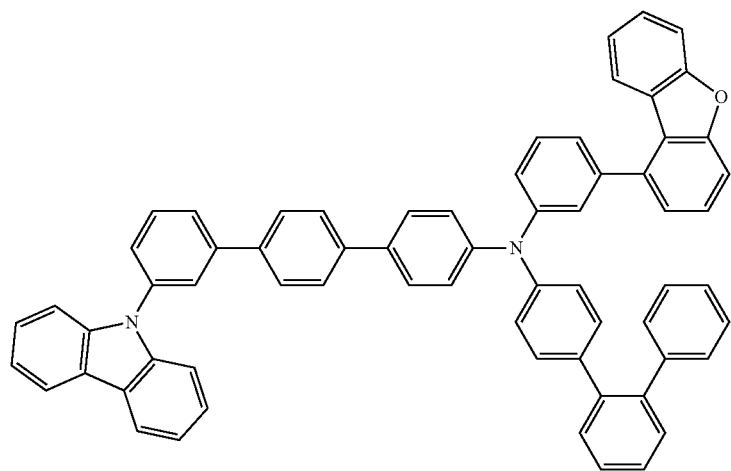

-continued
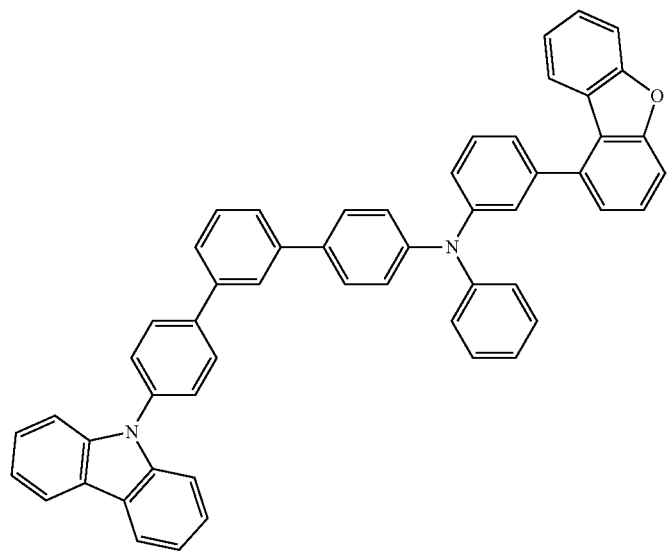
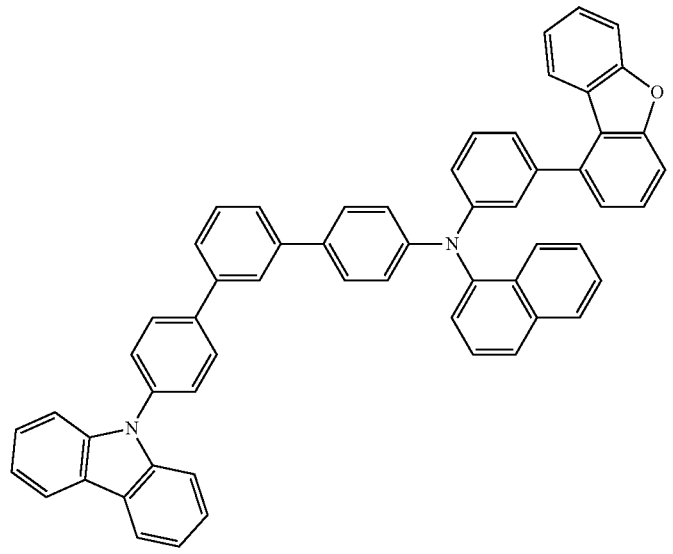
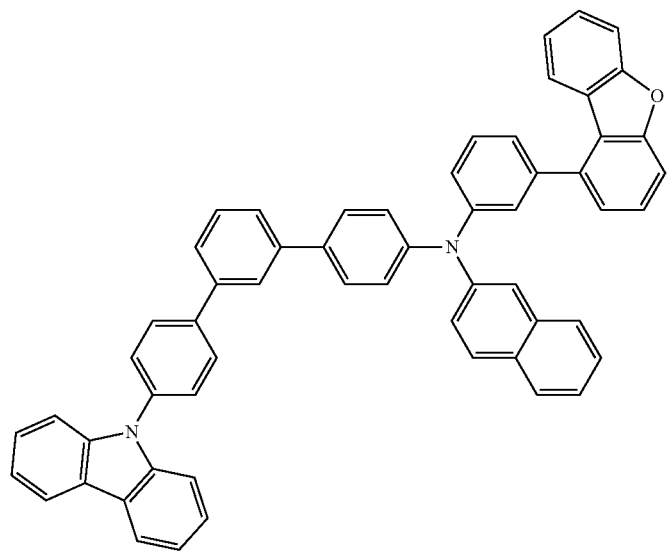

-continued
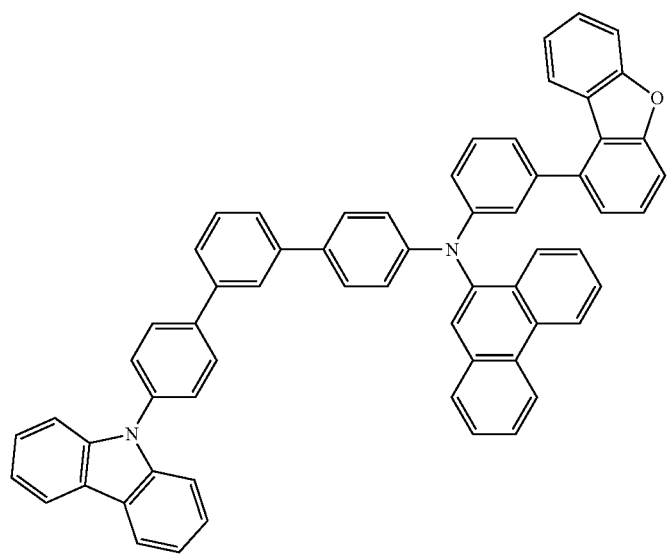
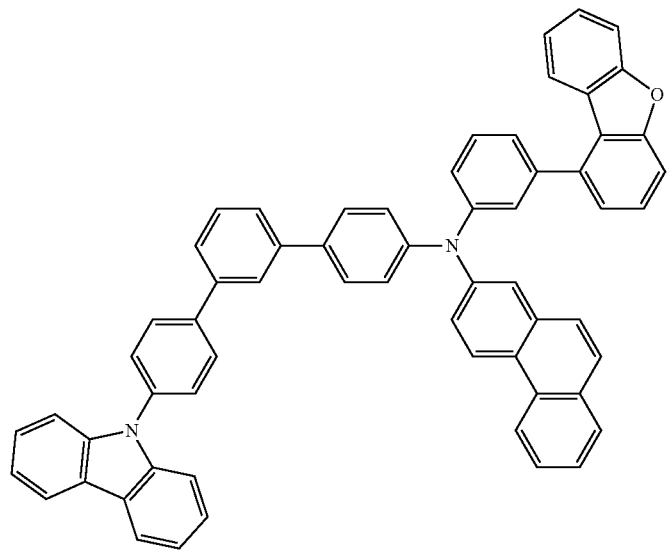
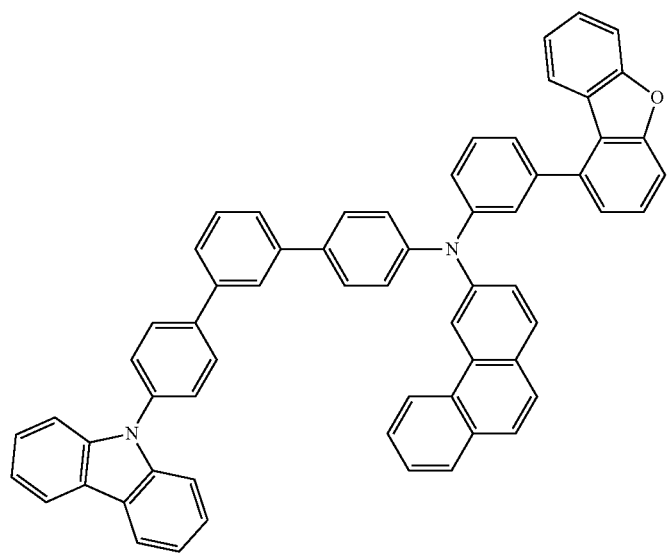

-continued
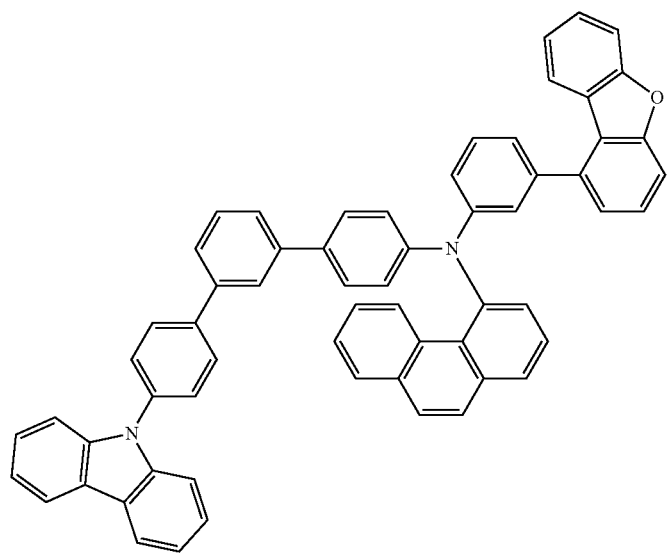
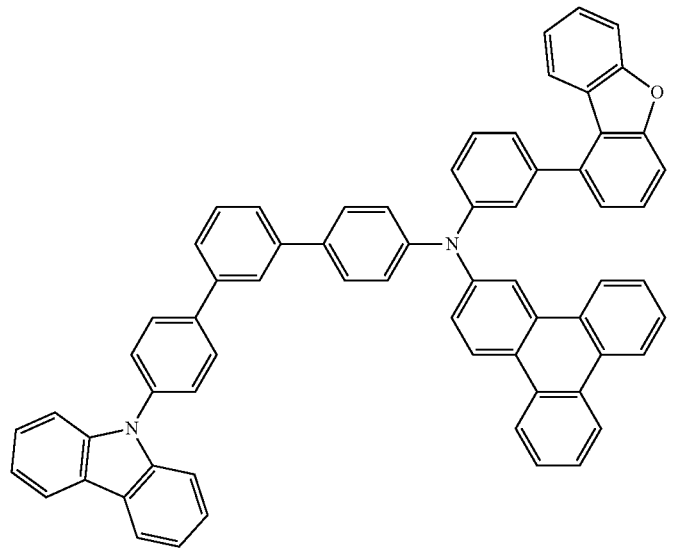
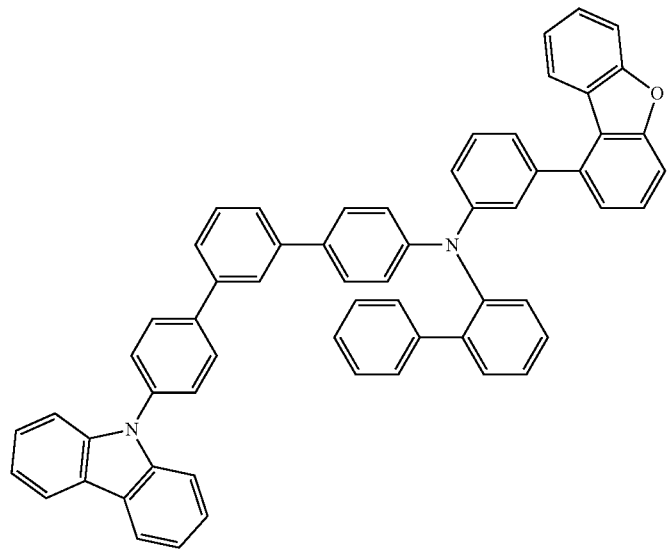

-continued
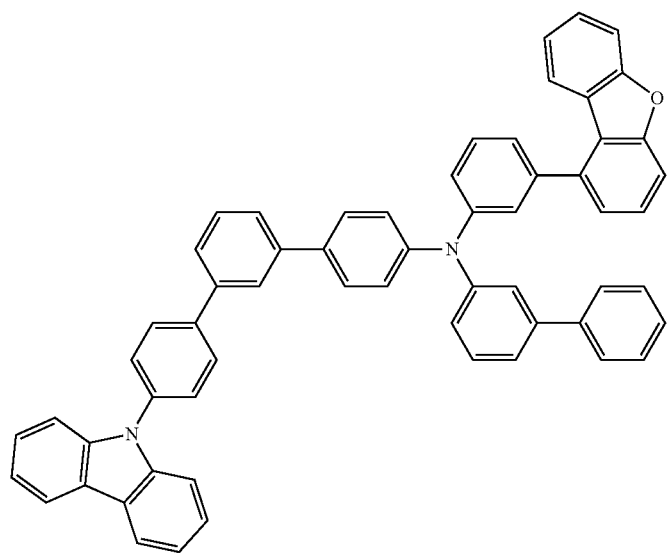
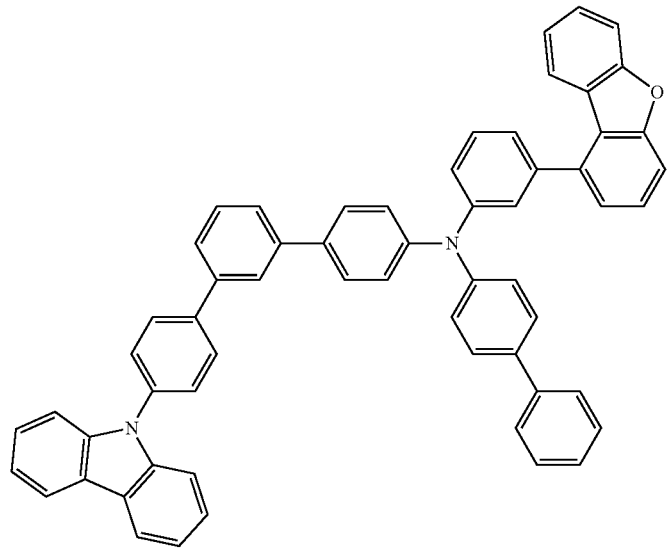
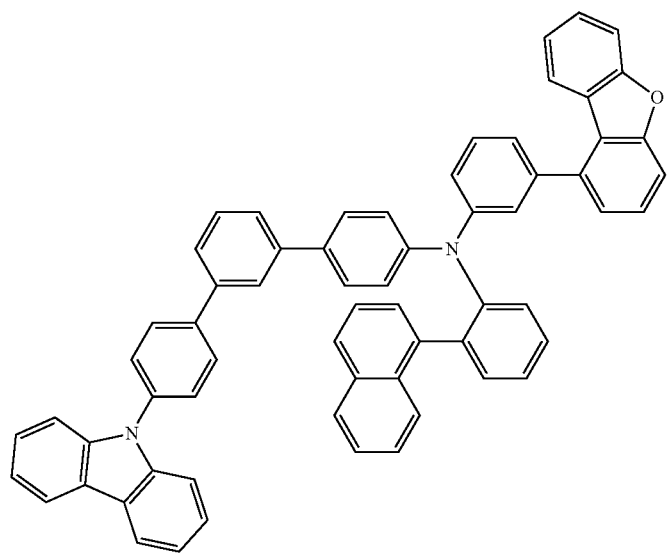

-continued
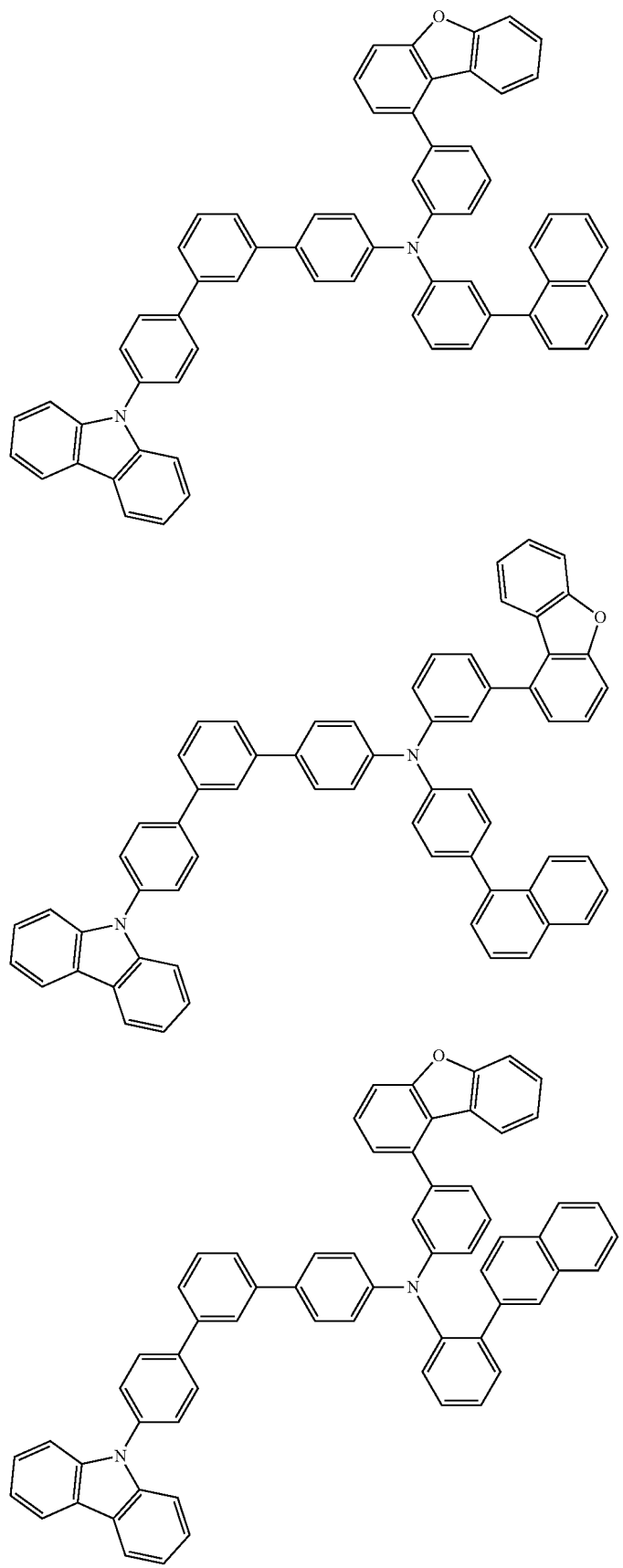

-continued
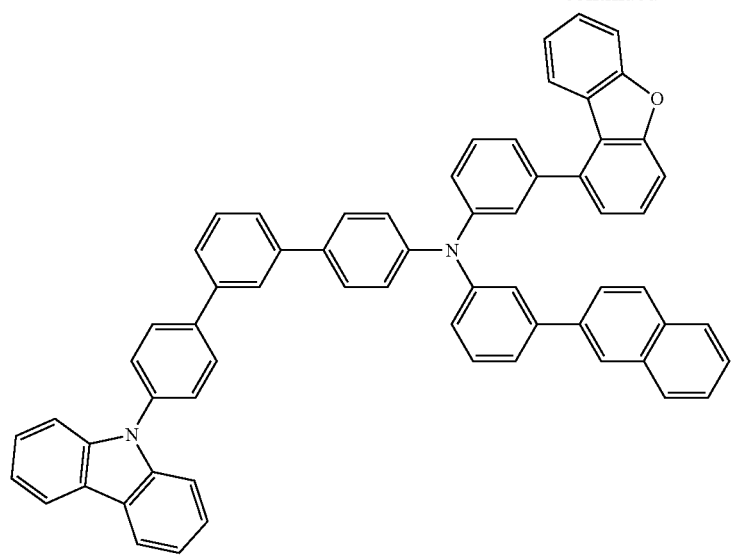
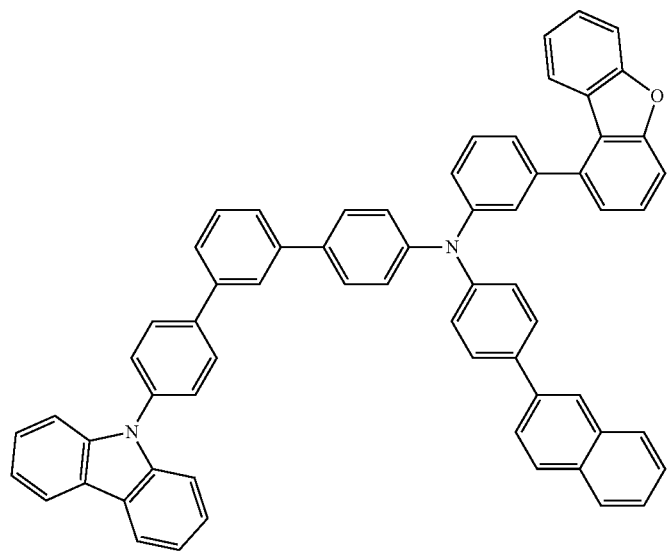
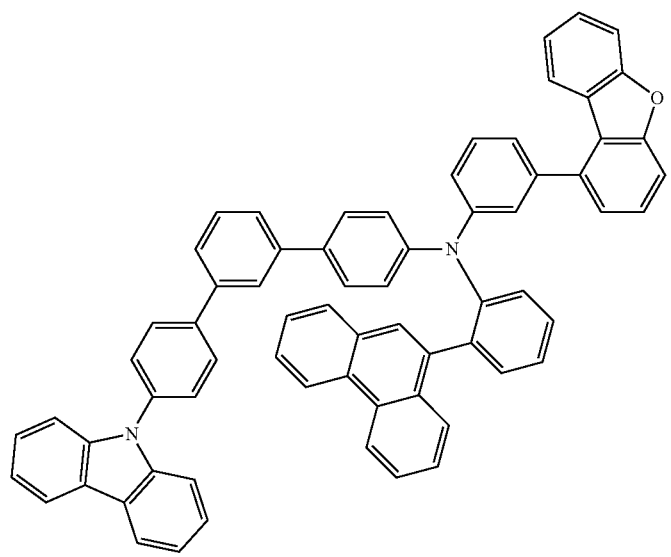

-continued
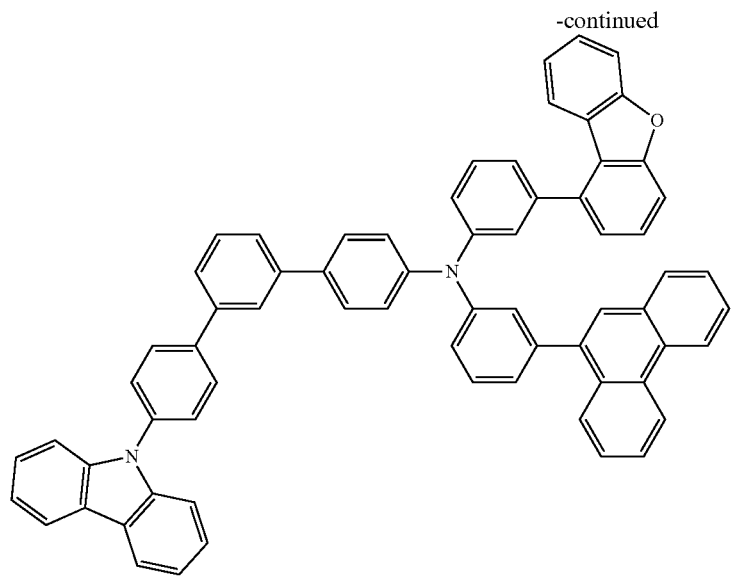
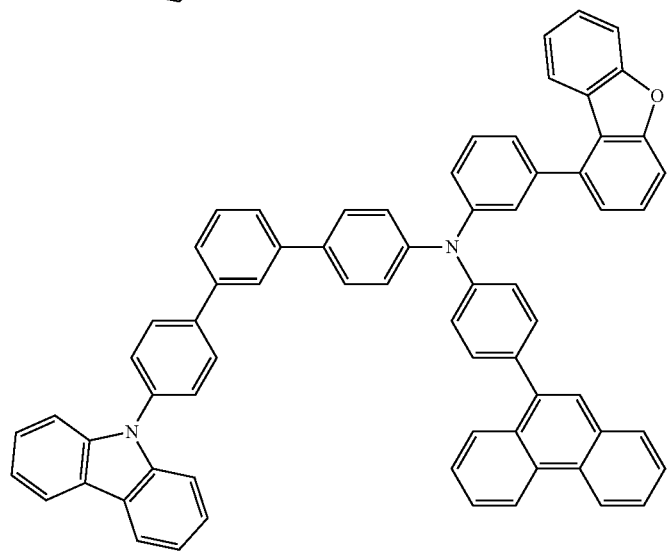
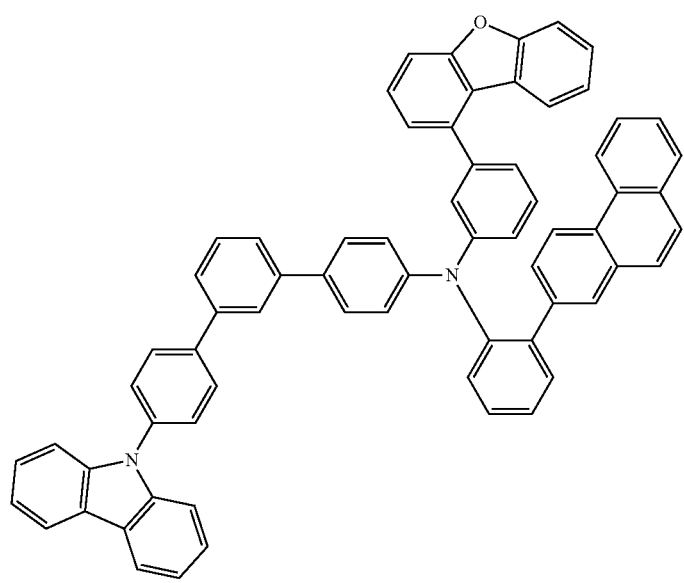

-continued
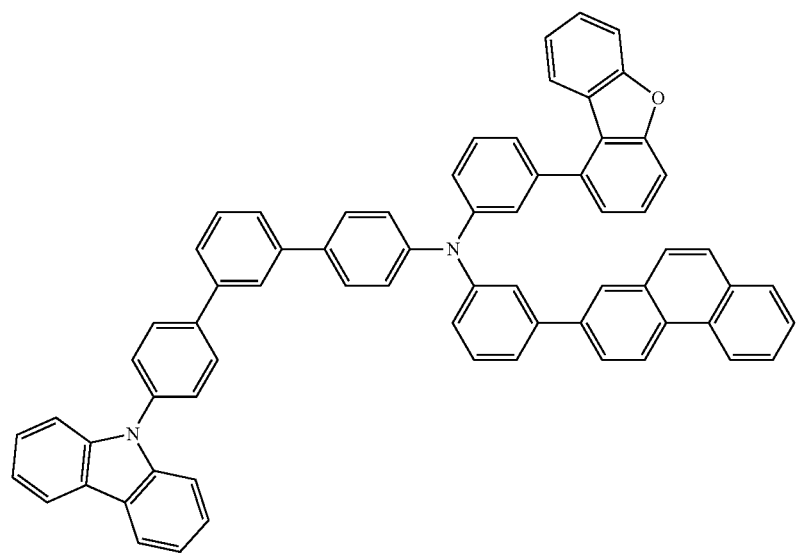
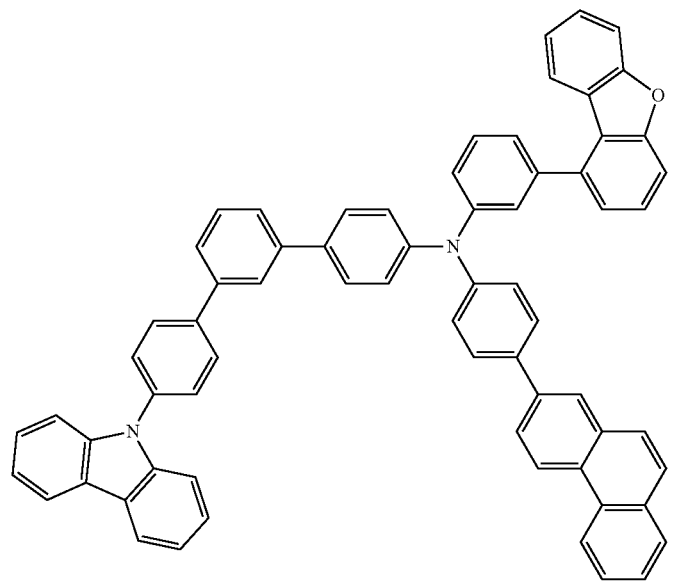
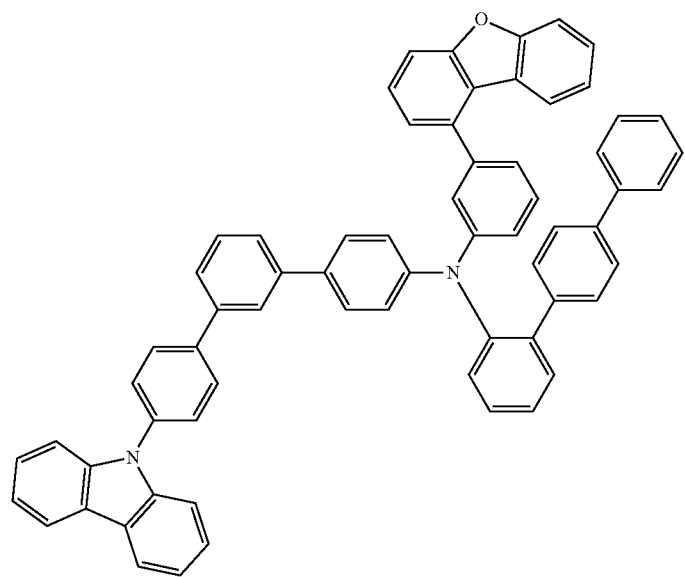

-continued
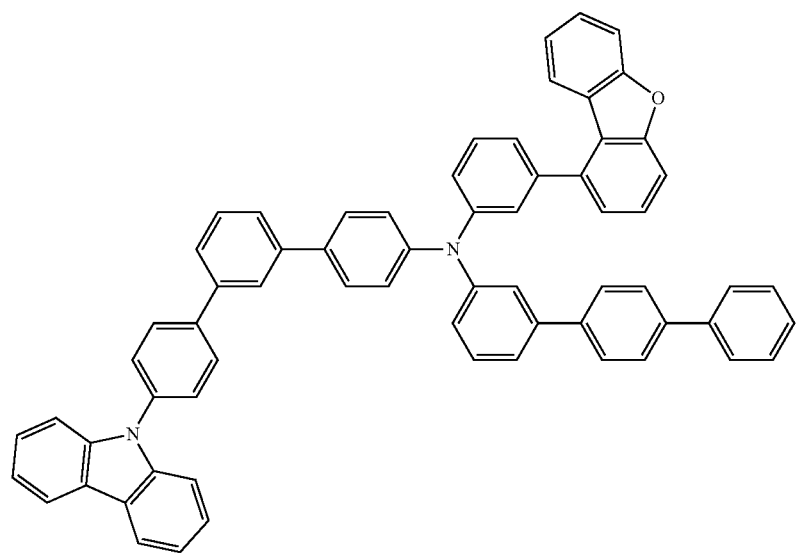
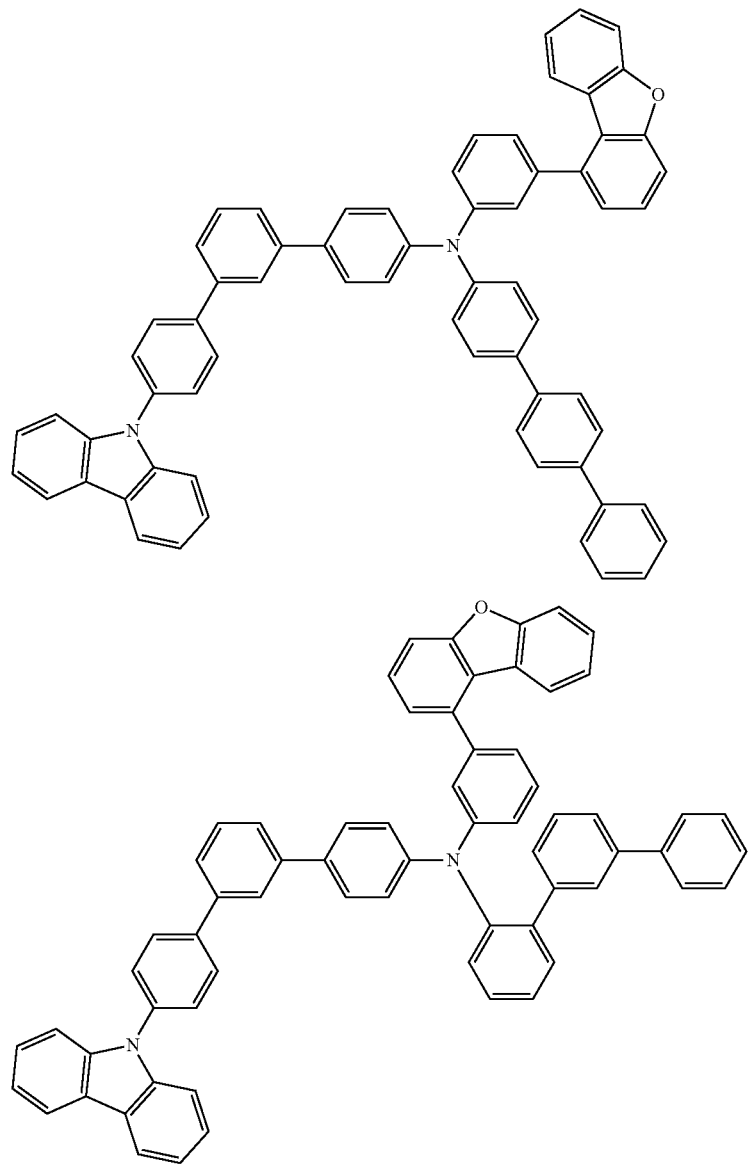

-continued
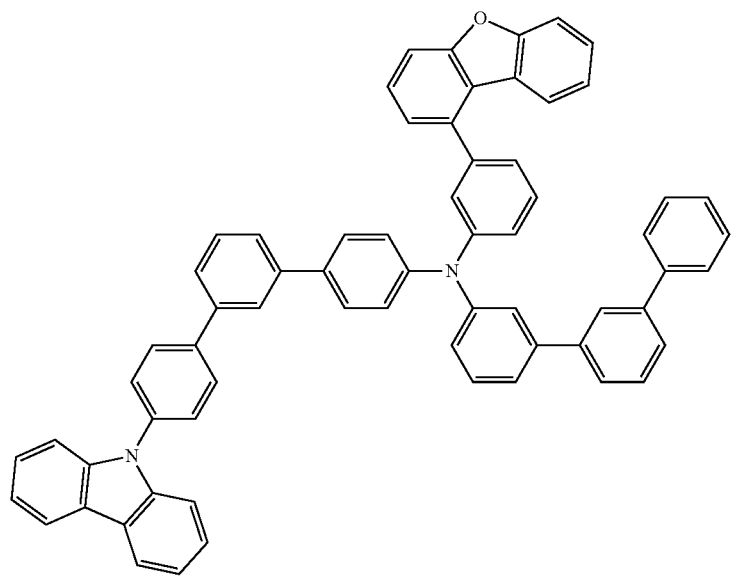
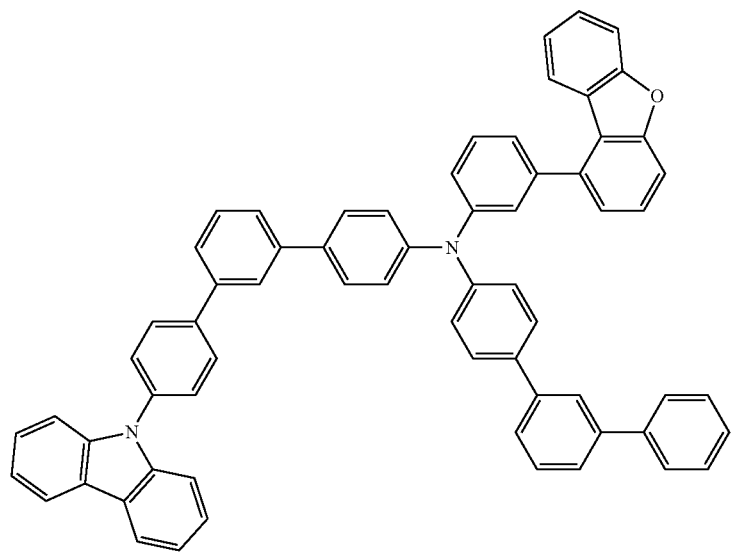
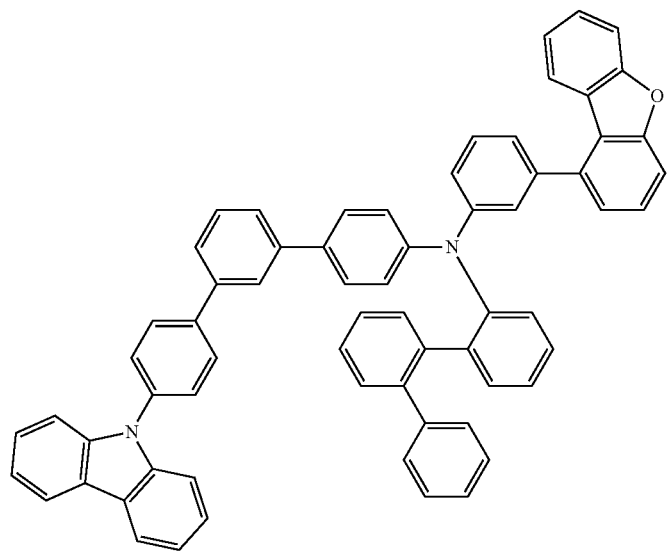

-continued
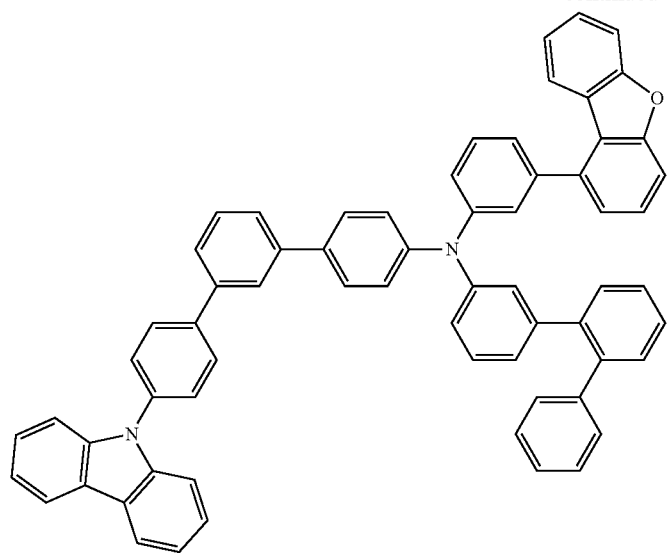
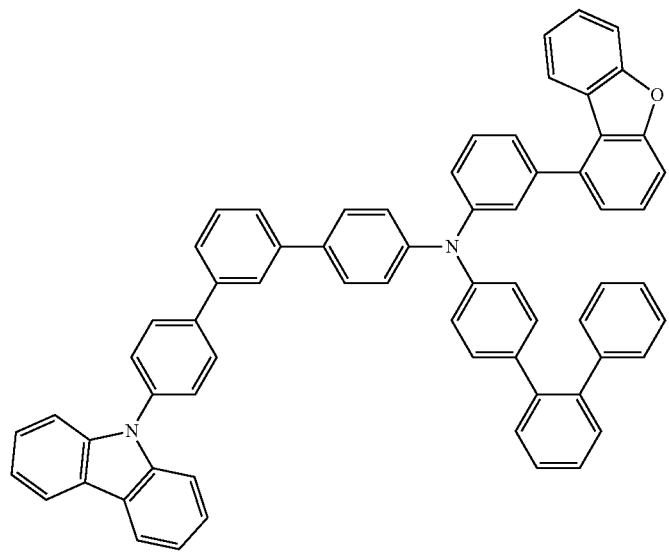
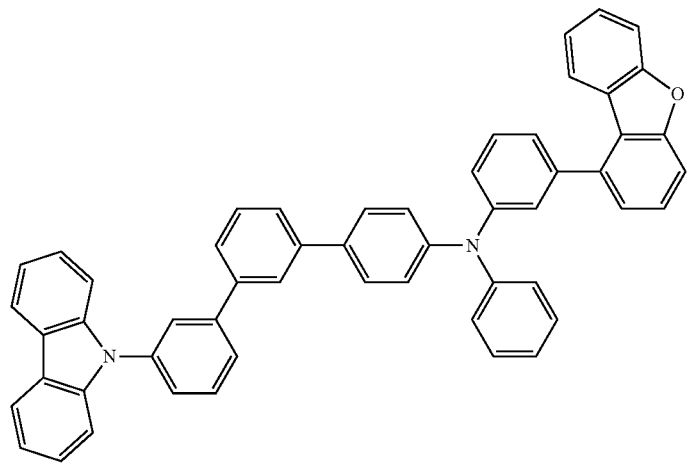

-continued
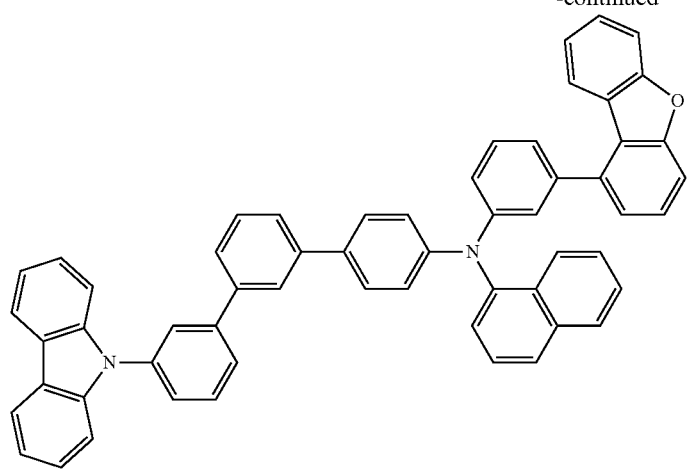
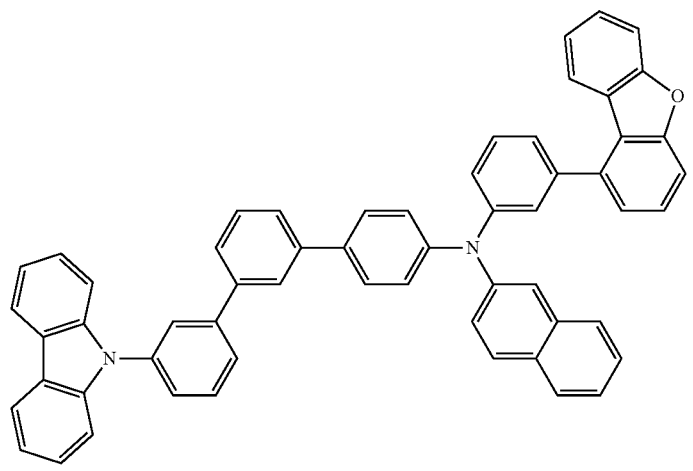
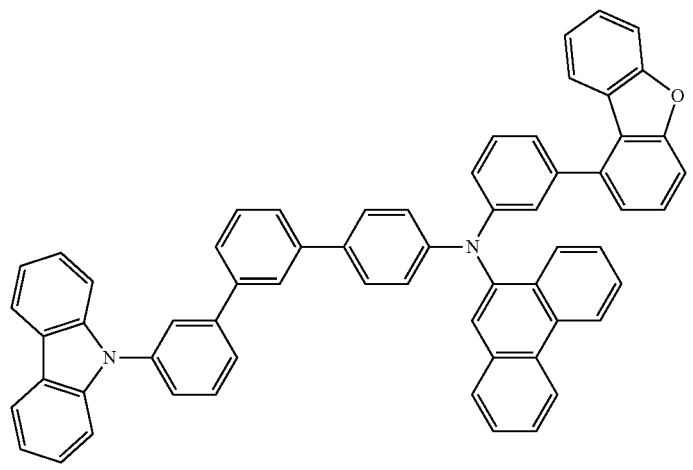

-continued
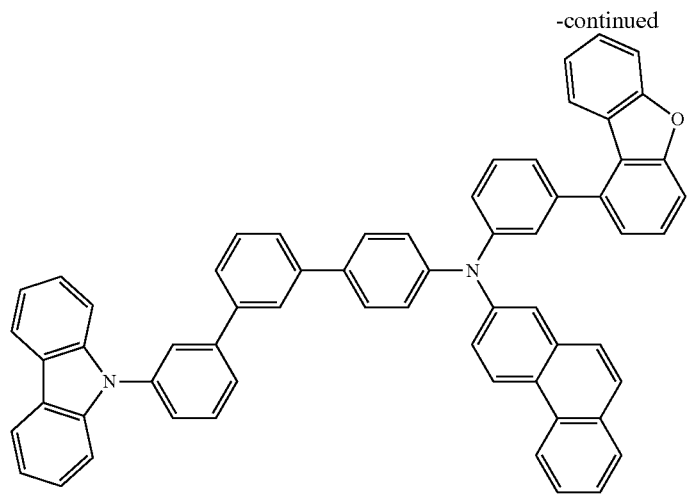
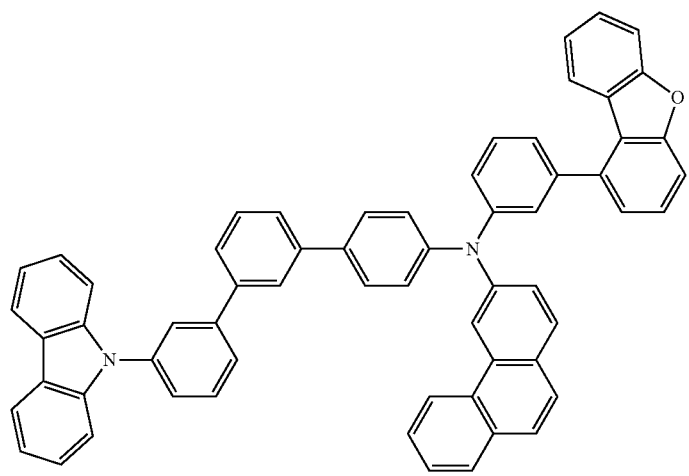
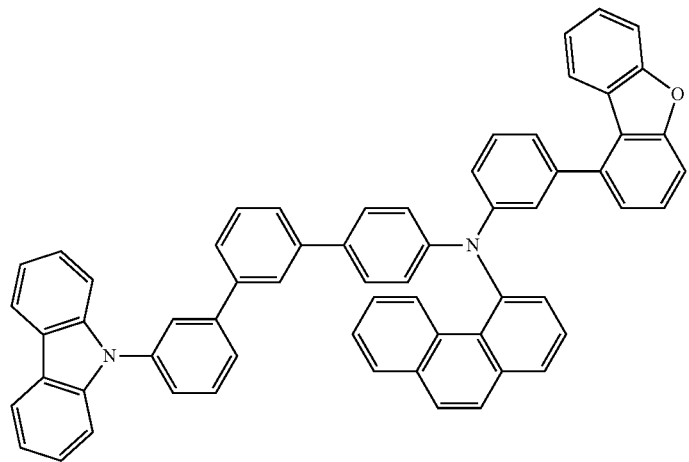

-continued
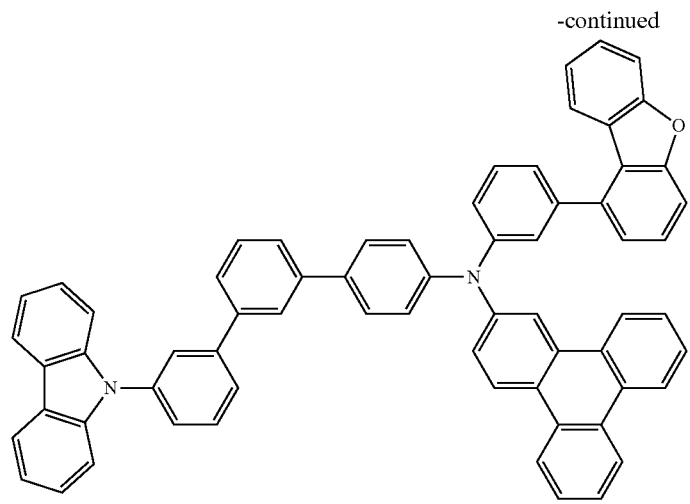
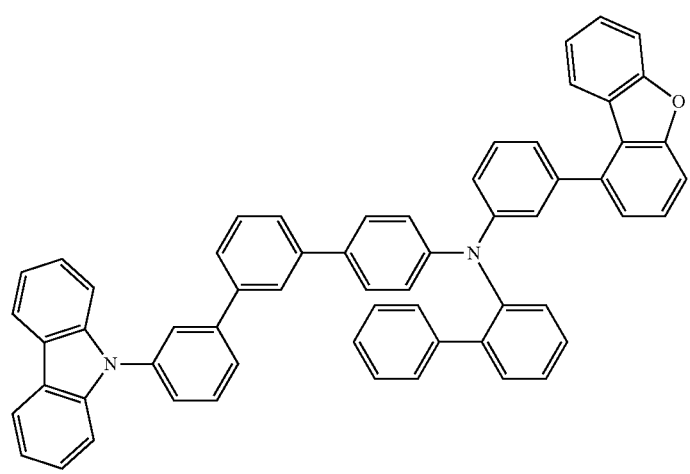
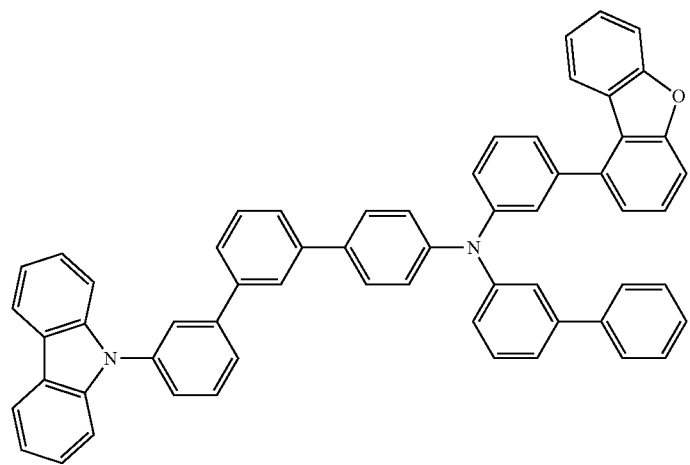

-continued
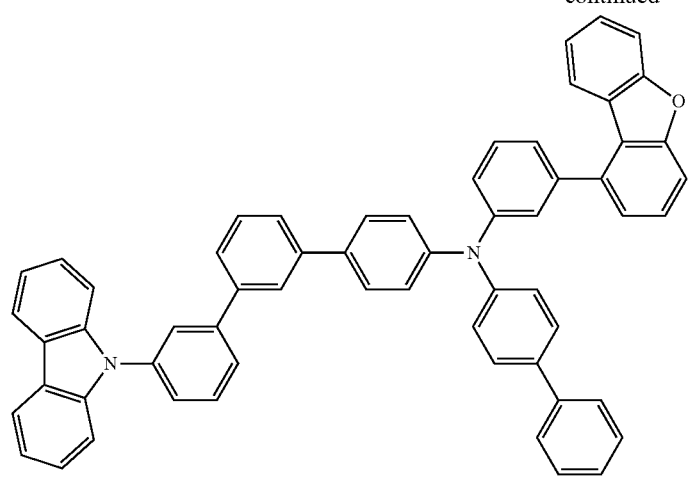
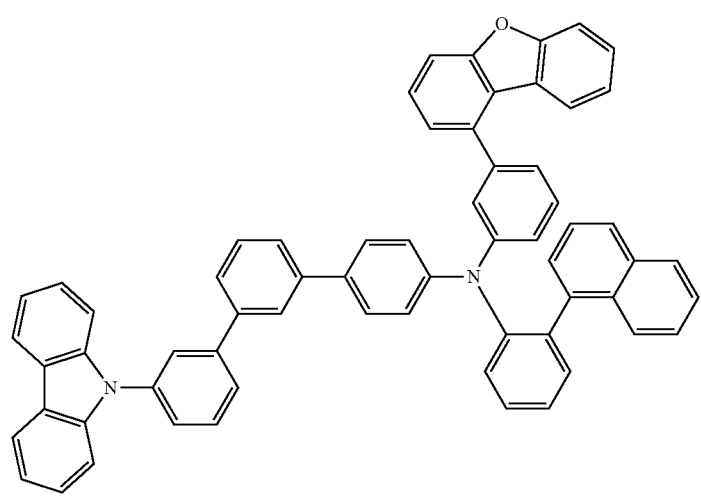
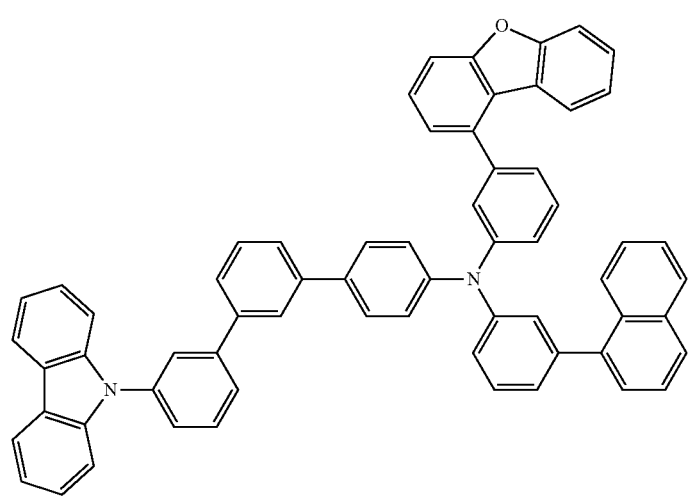

-continued
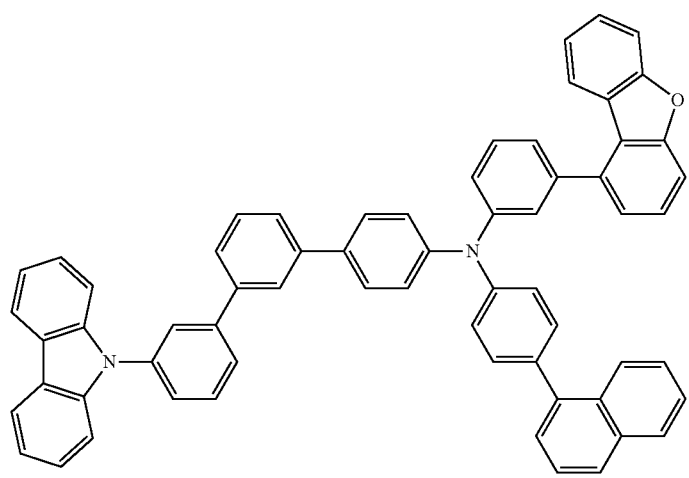
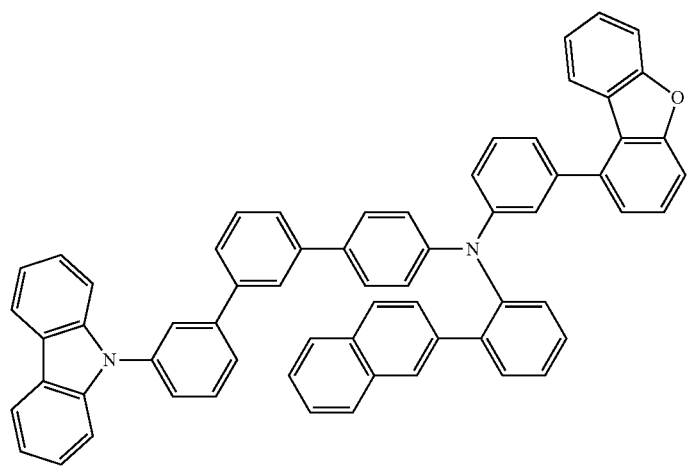
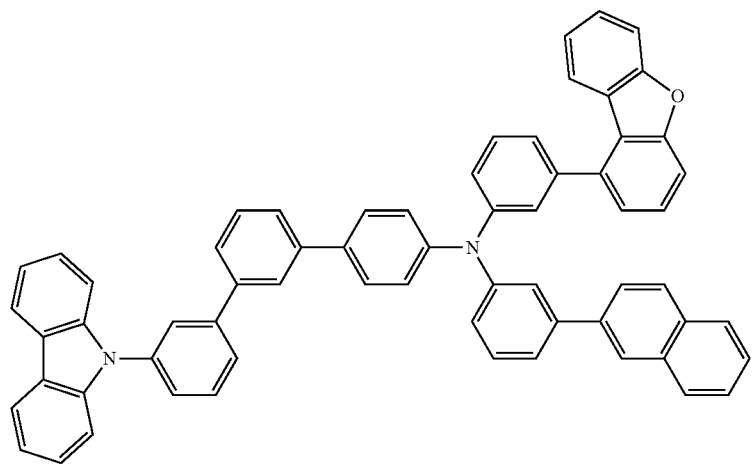

-continued
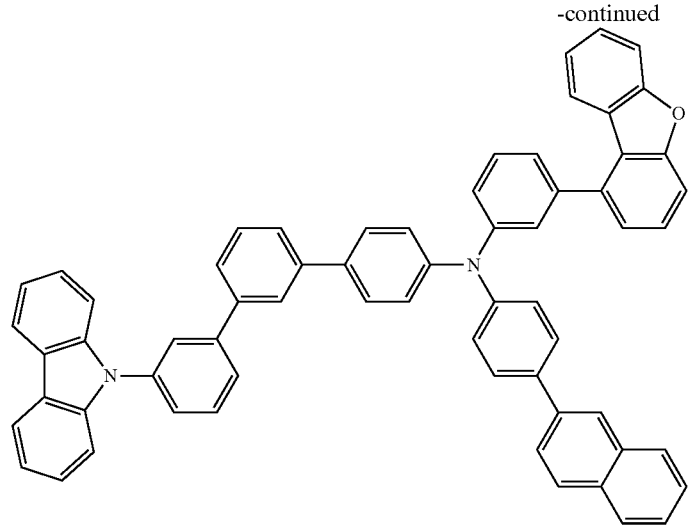
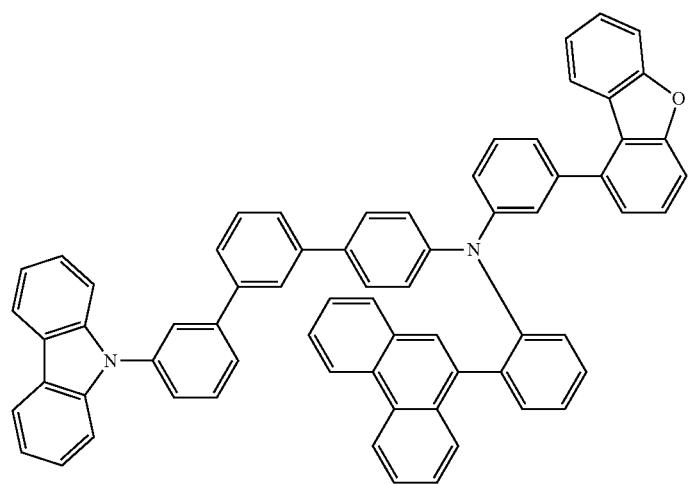
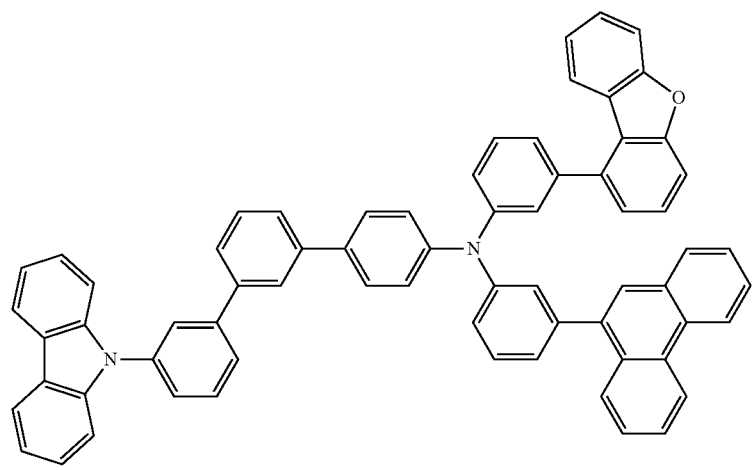

-continued
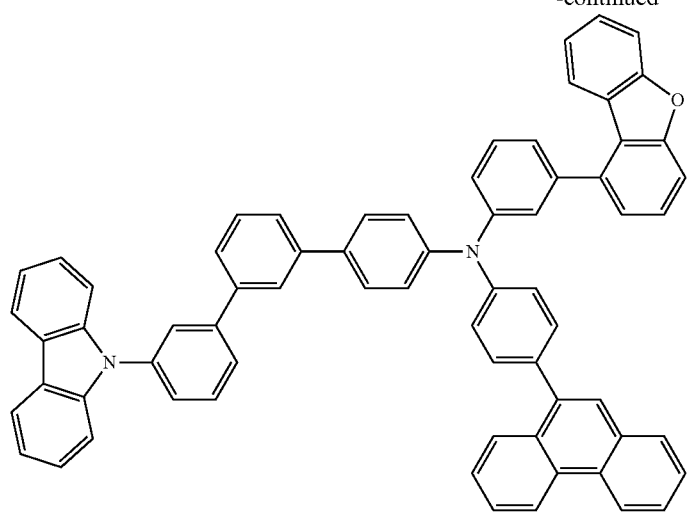
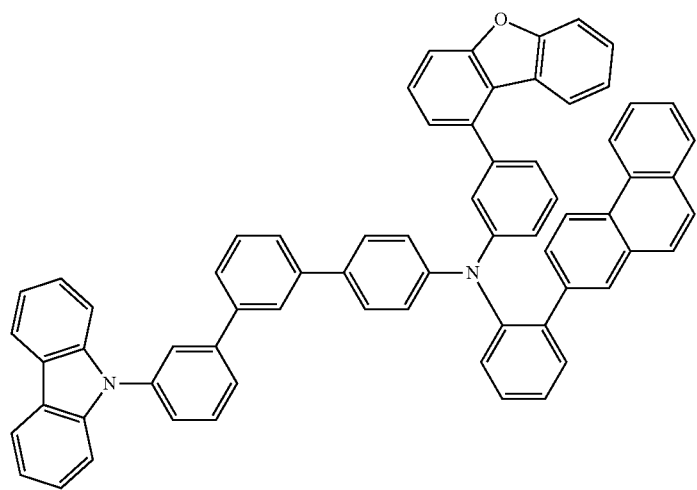
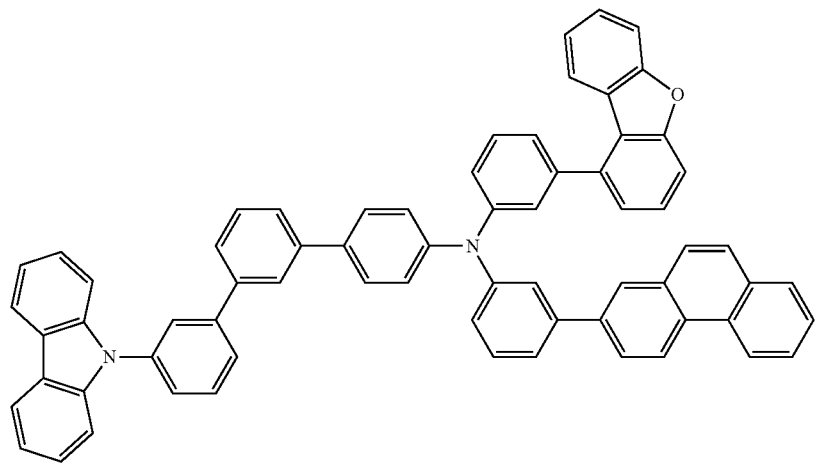

-continued
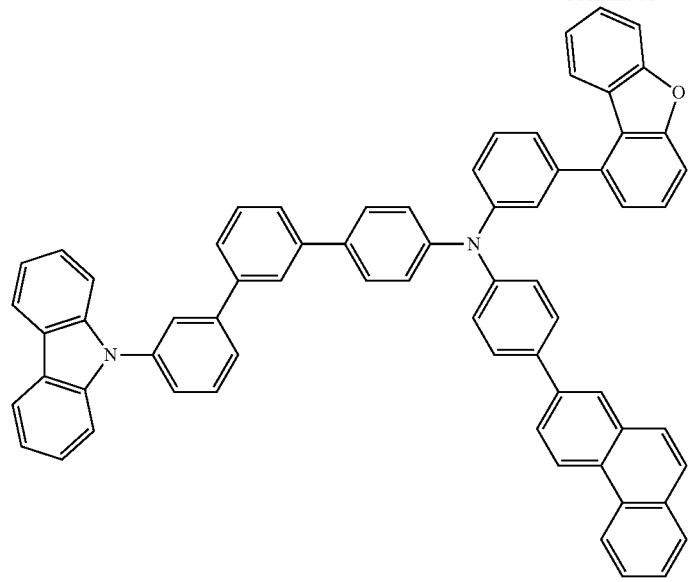
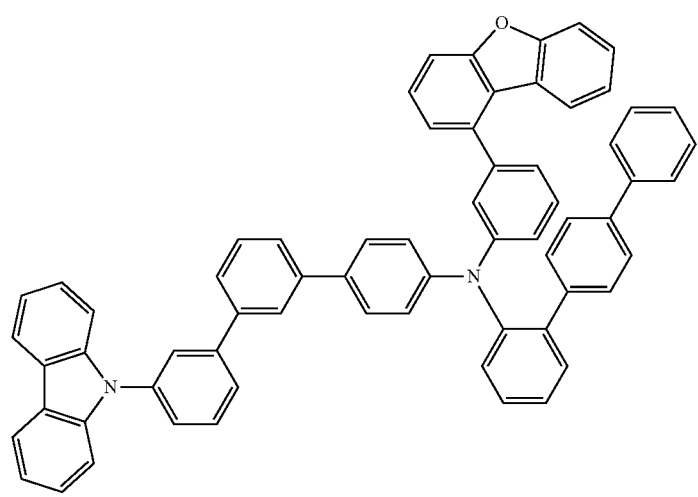
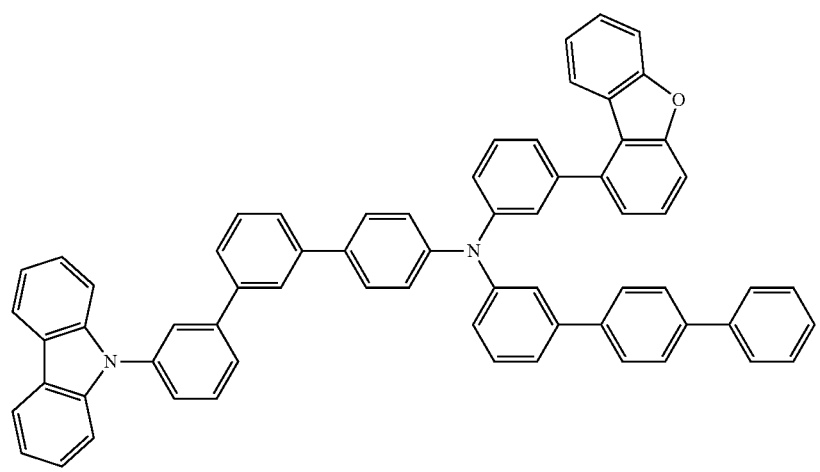

-continued
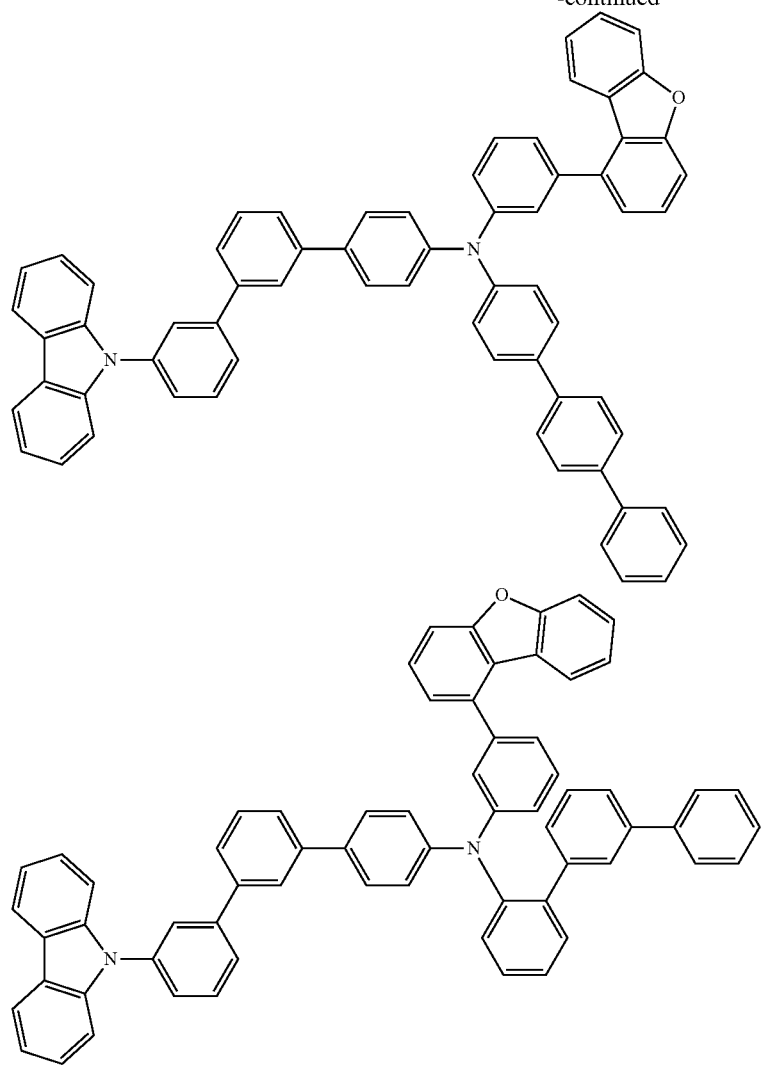
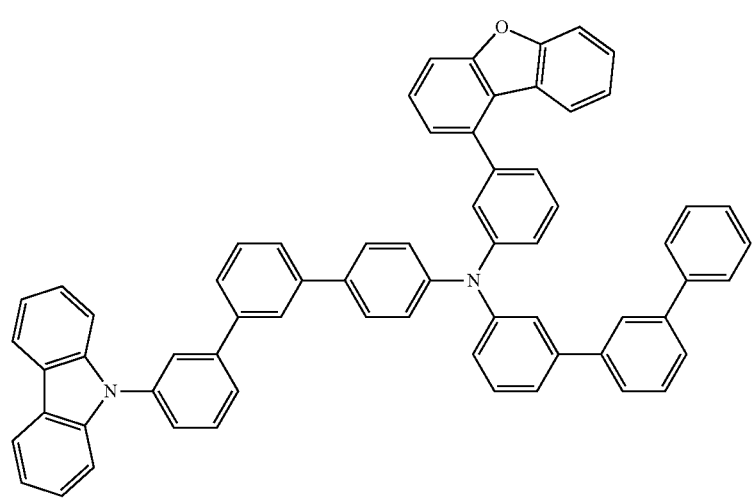

-continued
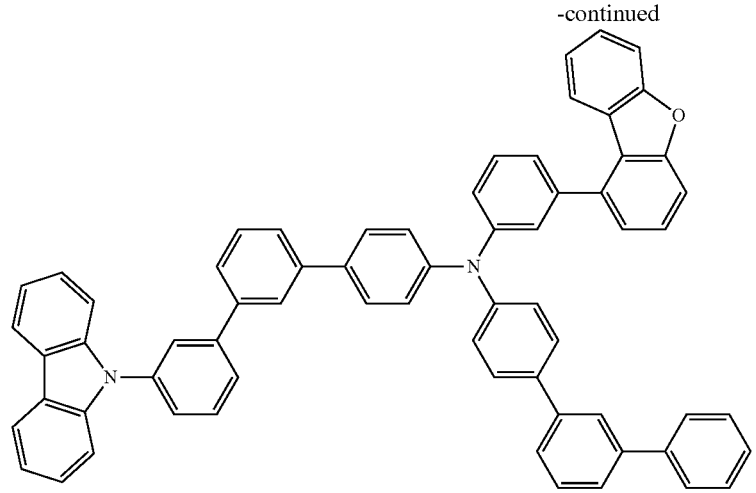
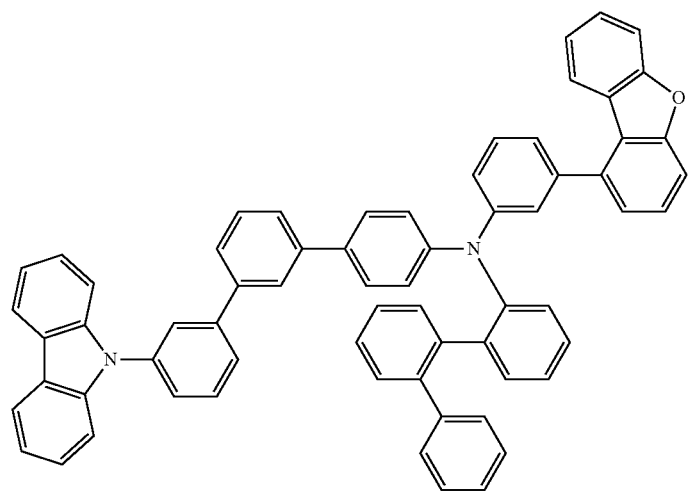
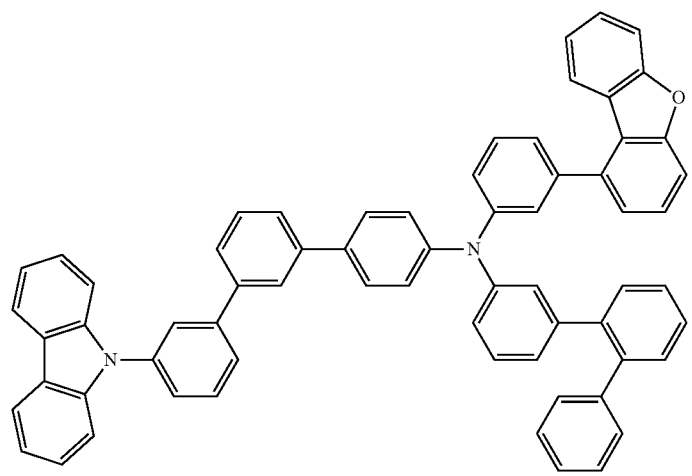

-continued
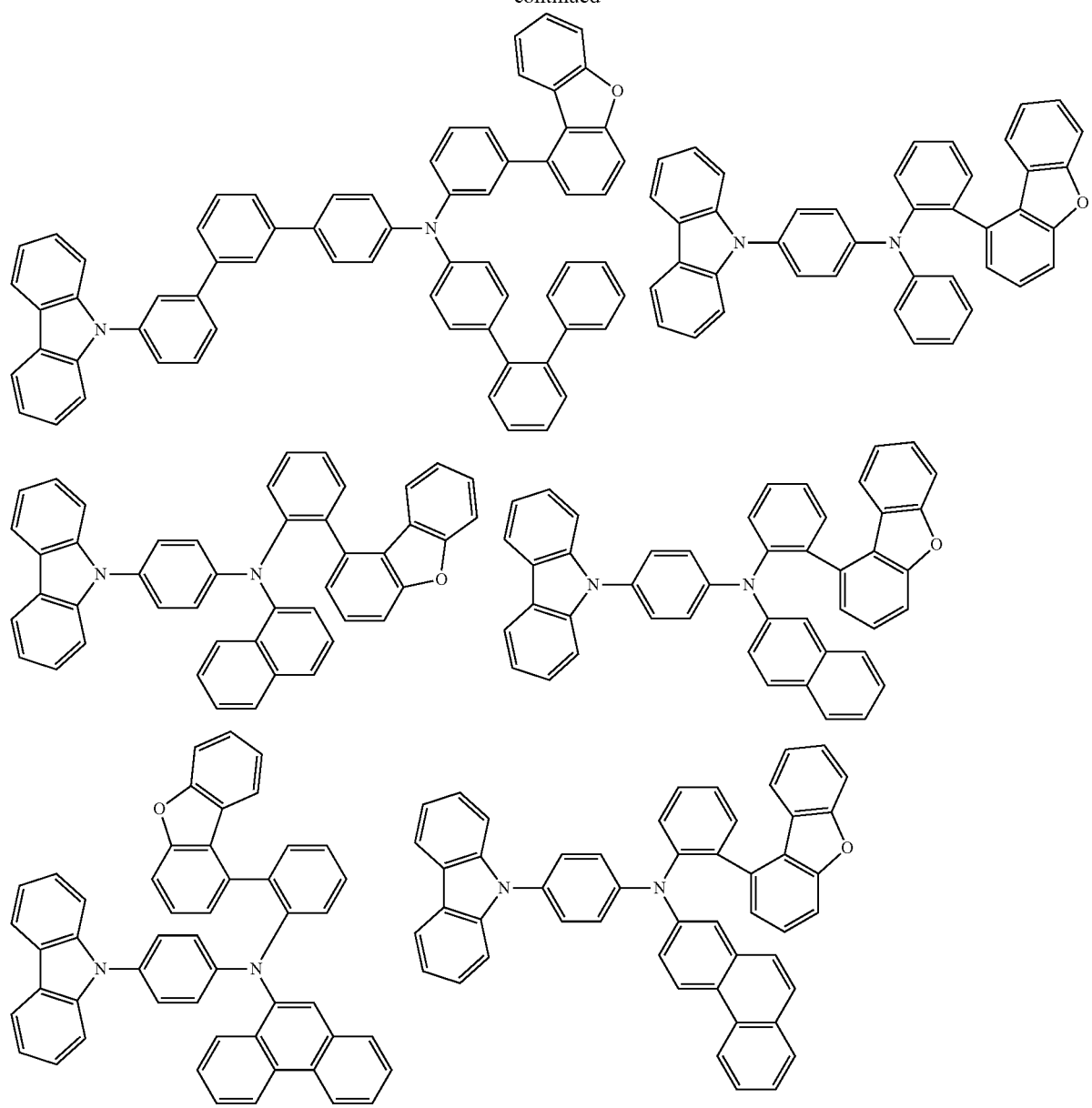
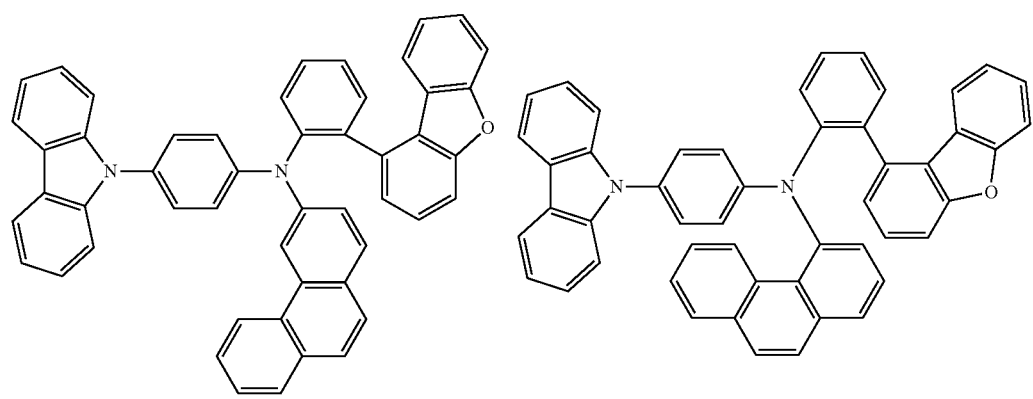

-continued
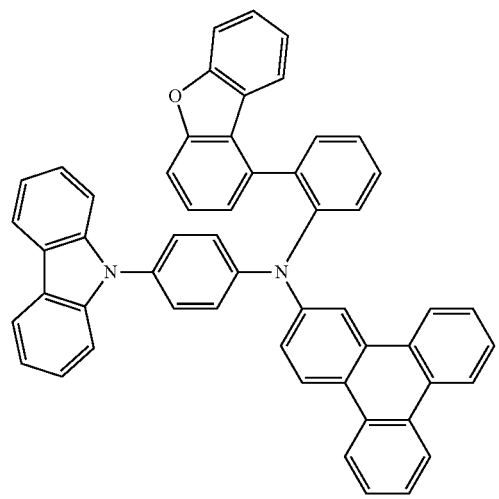
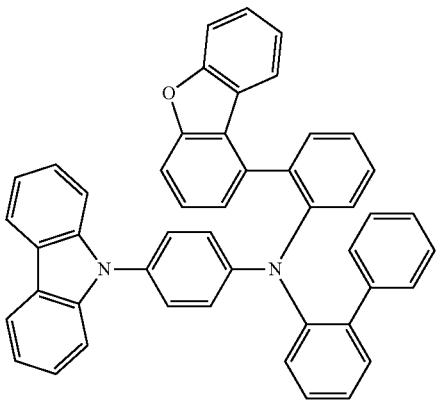
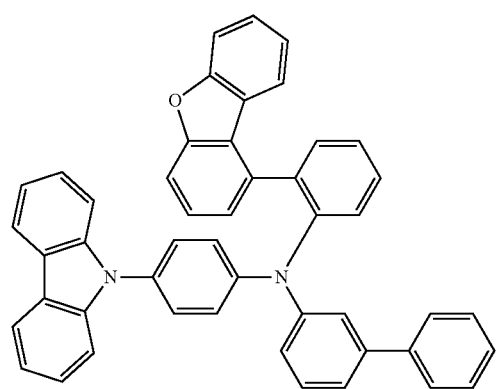
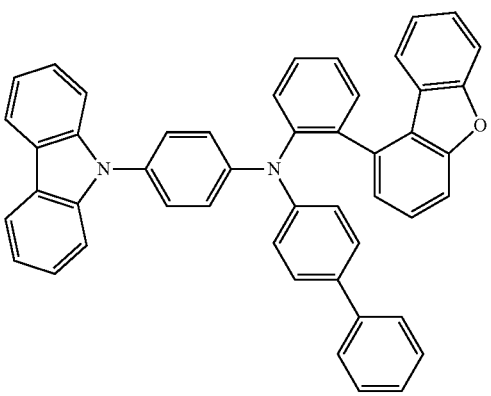
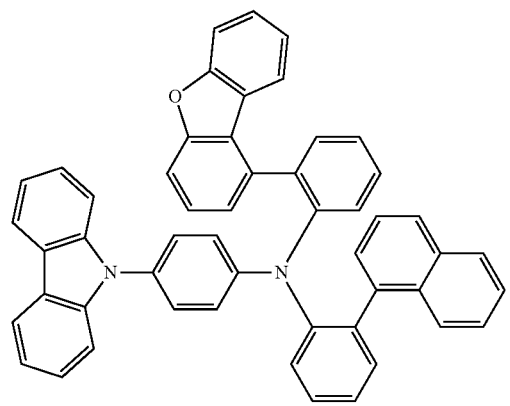
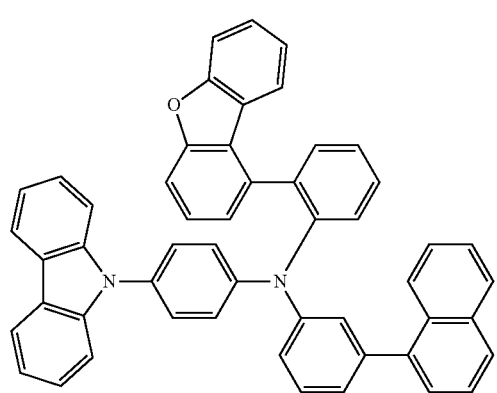
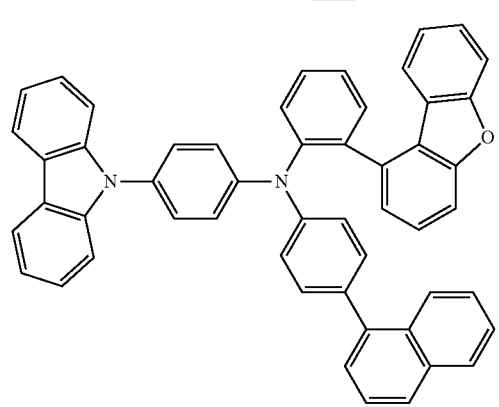
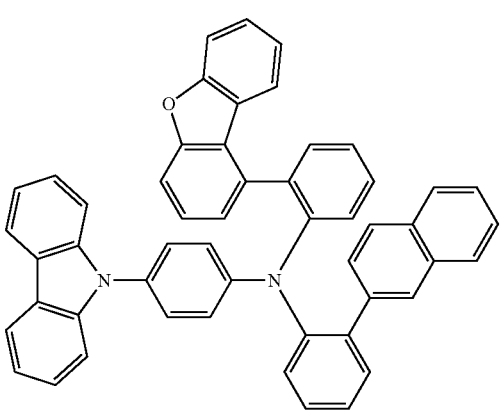

-continued
285 286
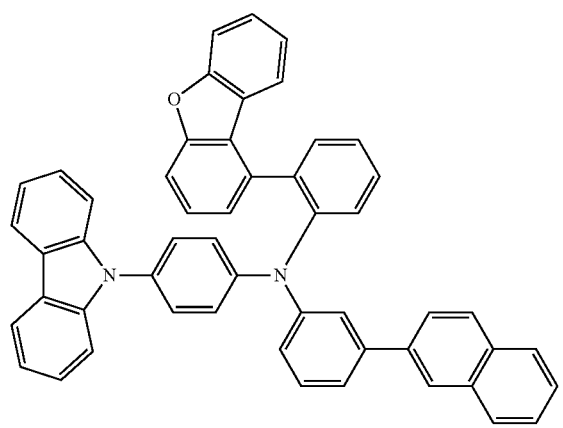
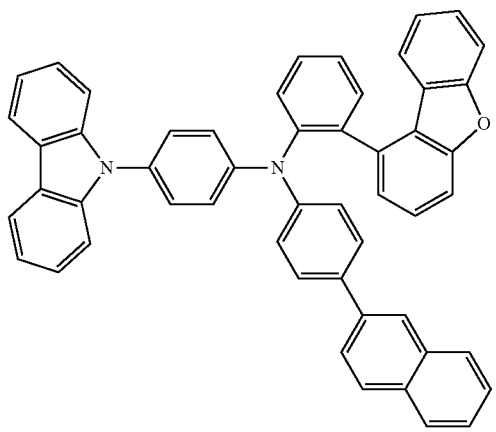
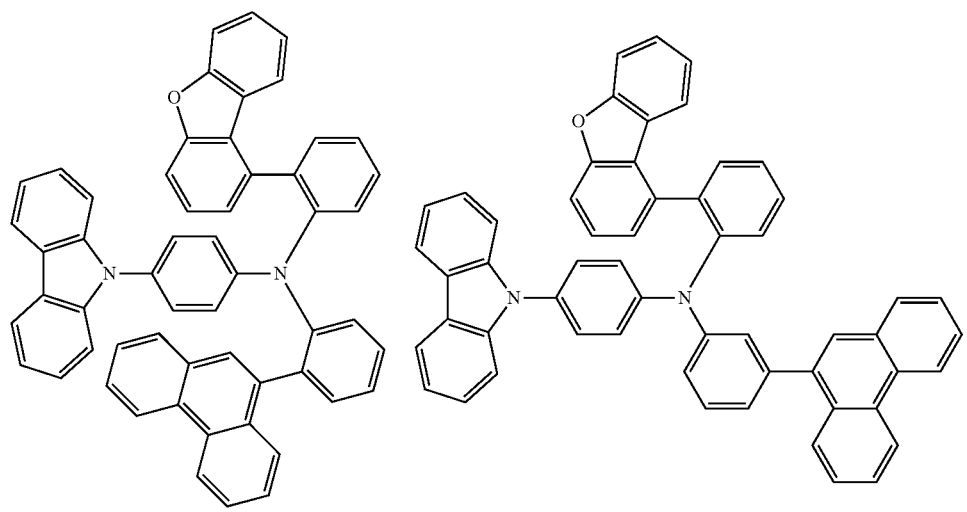
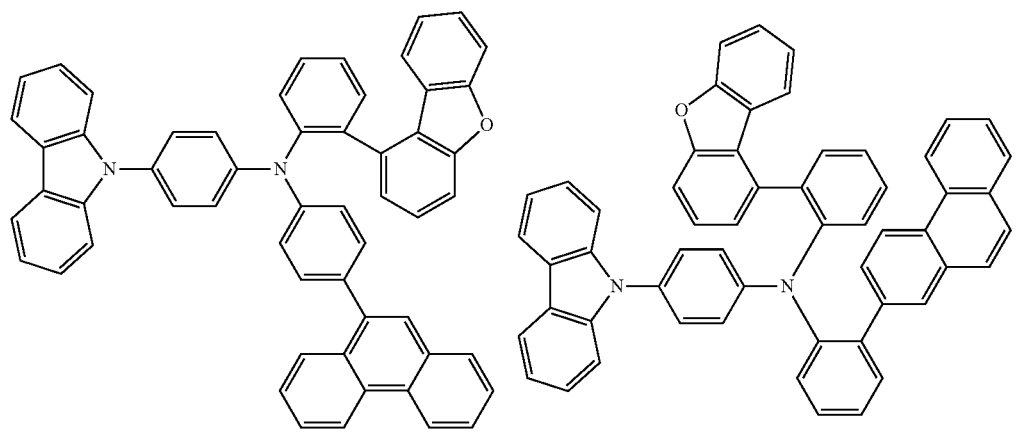

287
288
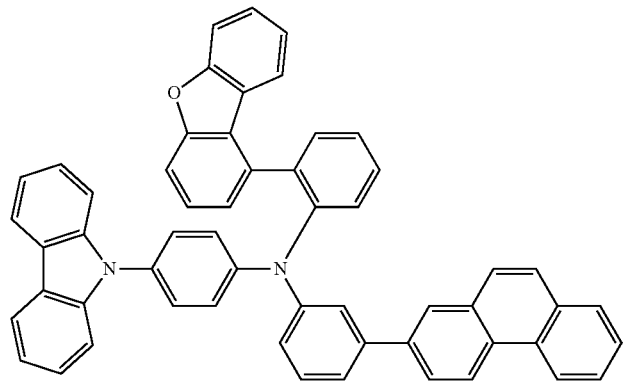
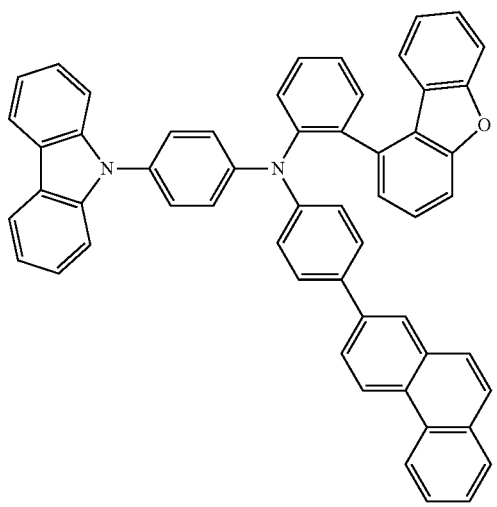
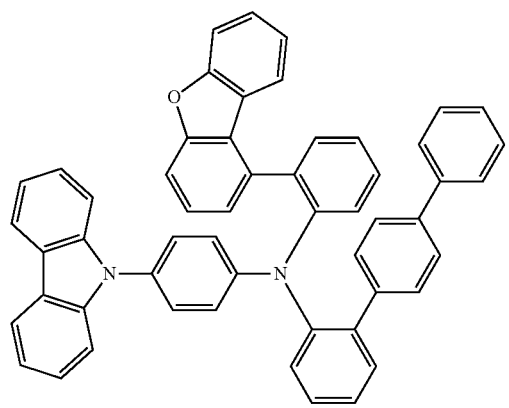
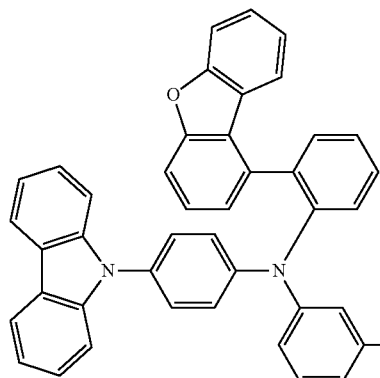
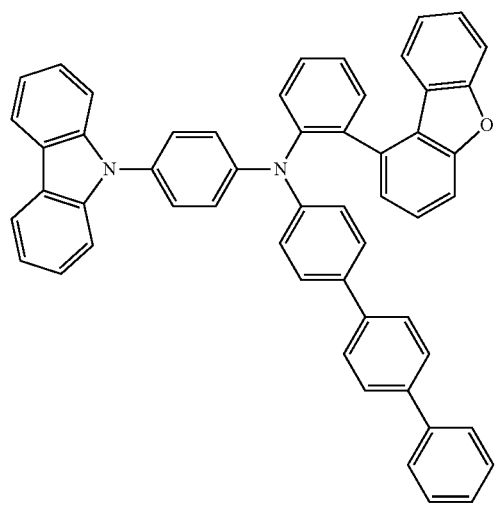
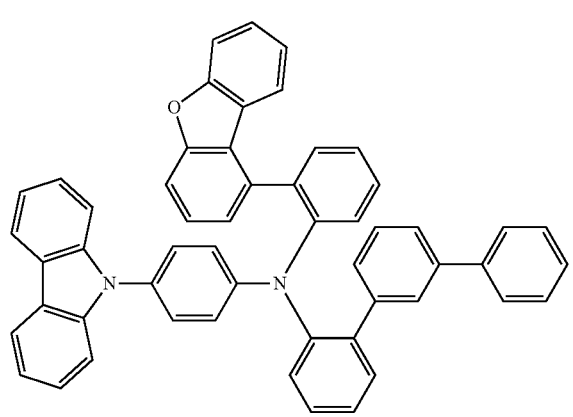

-continued
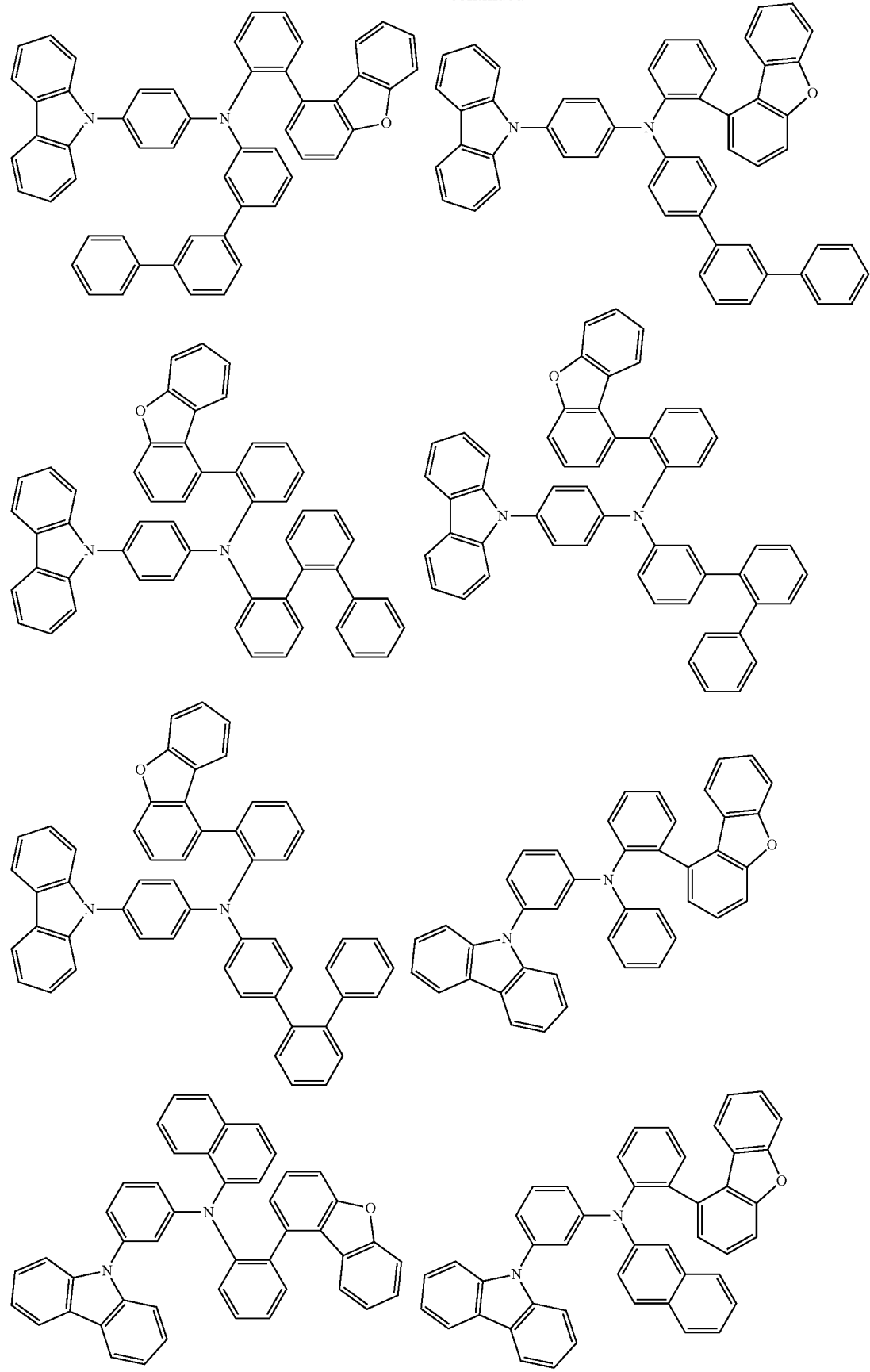

291 292
-continued
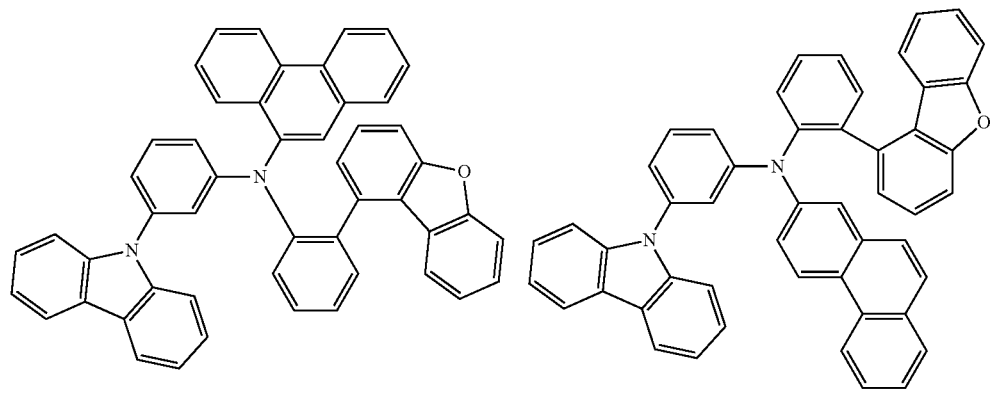
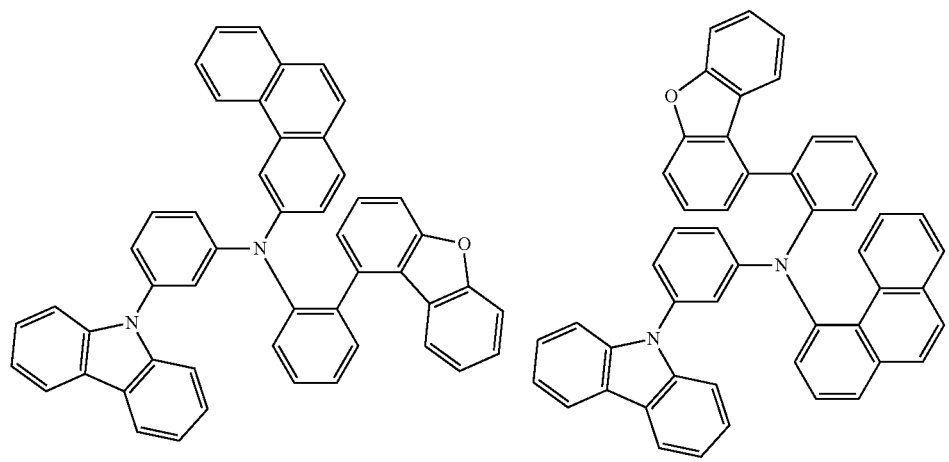
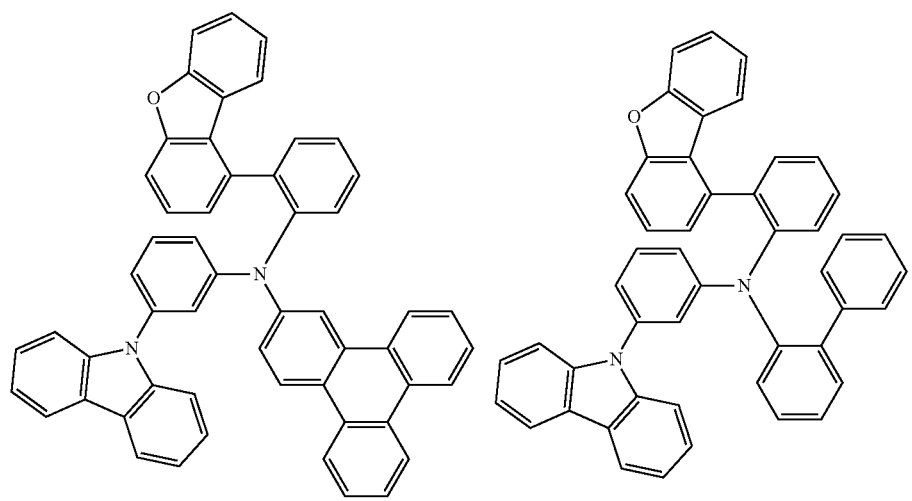

-continued
293
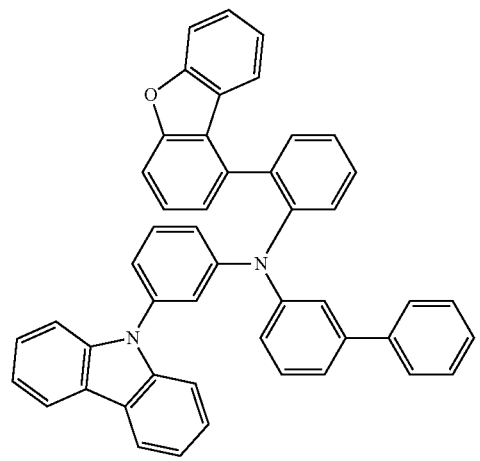
294
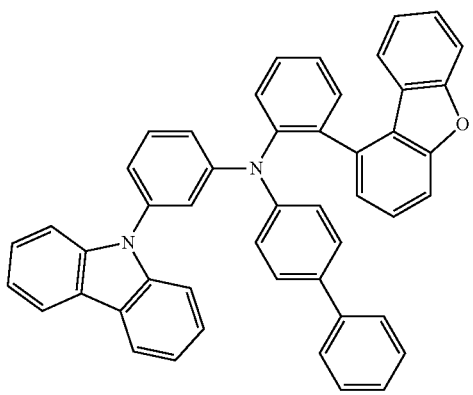
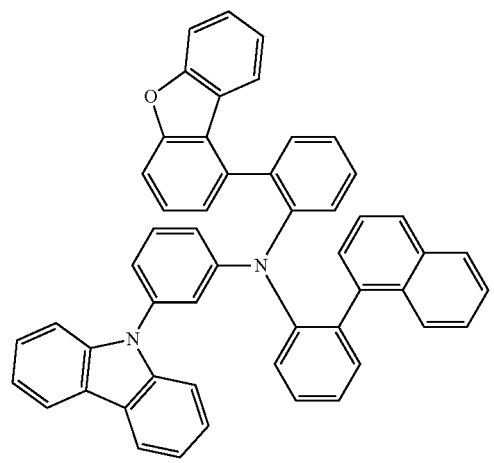
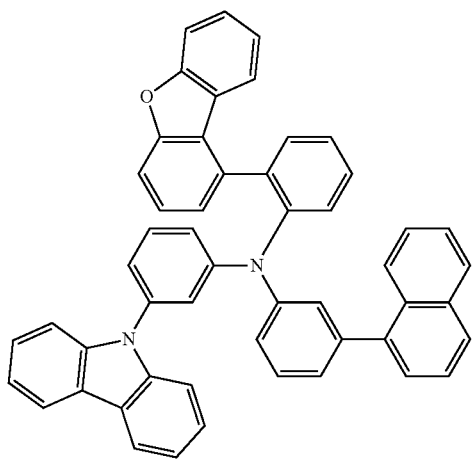
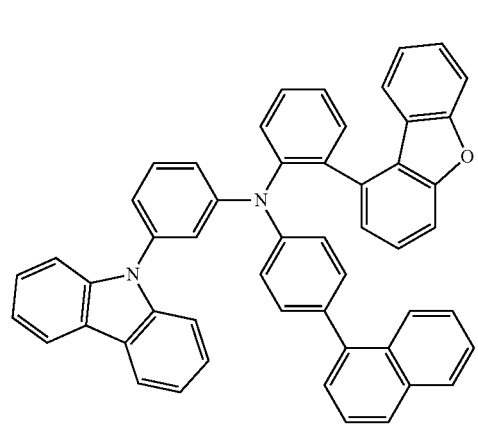
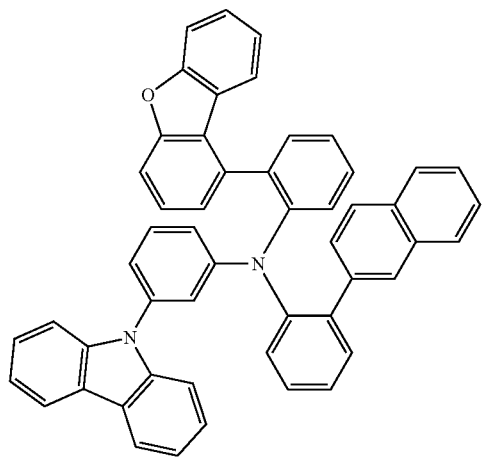

-continued
295
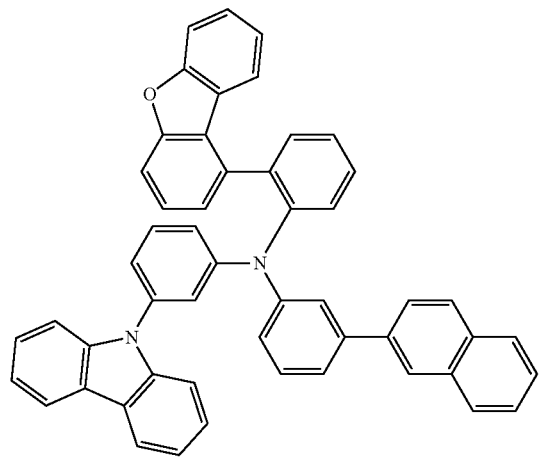
296
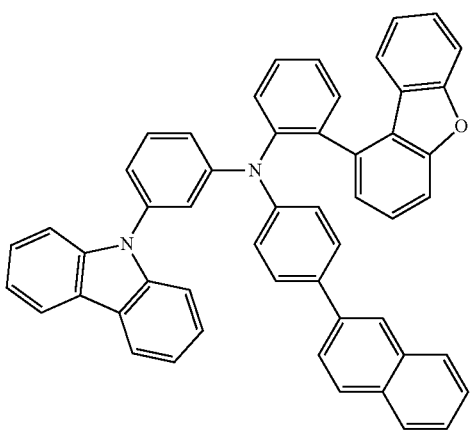
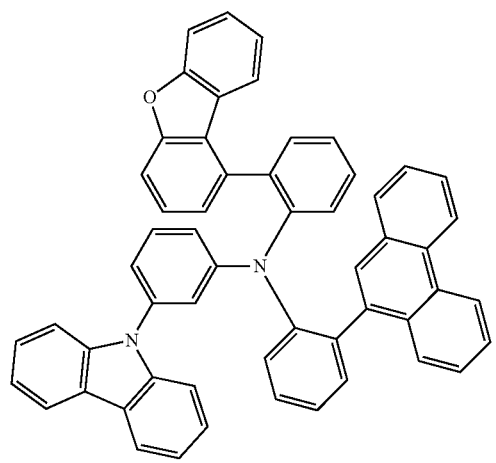
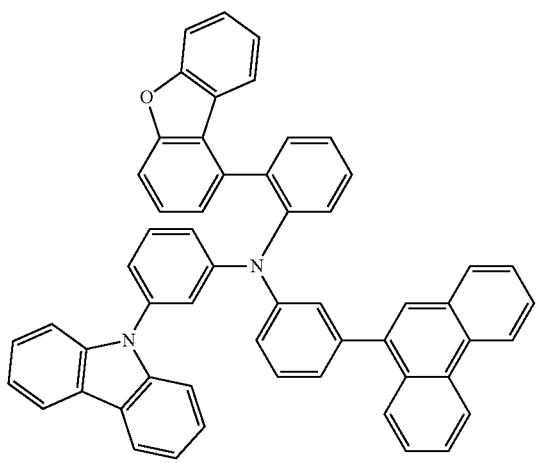
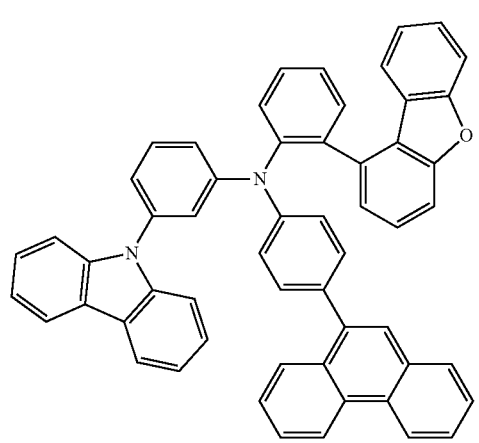
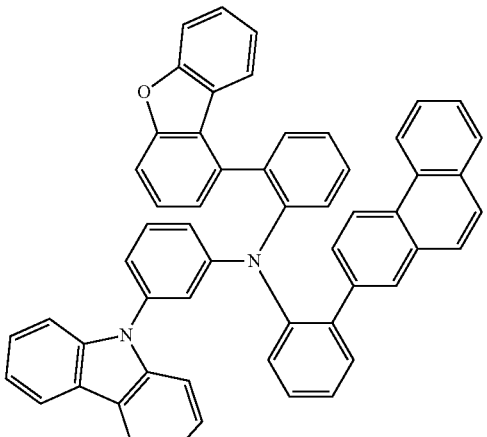

-continued
297
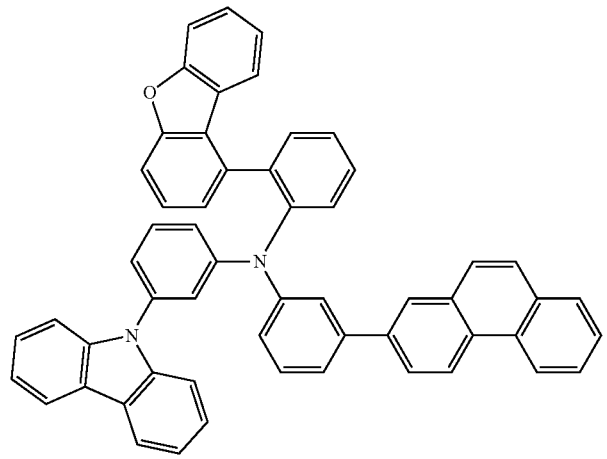
298
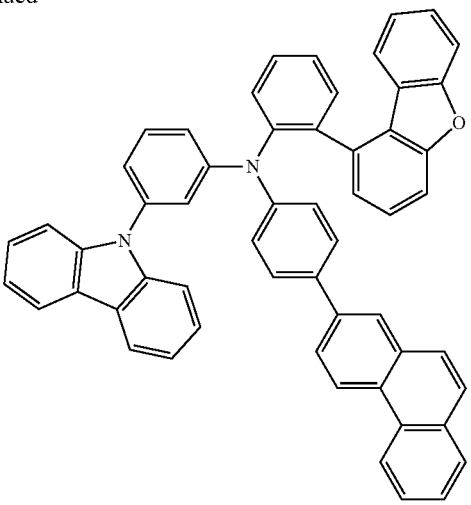
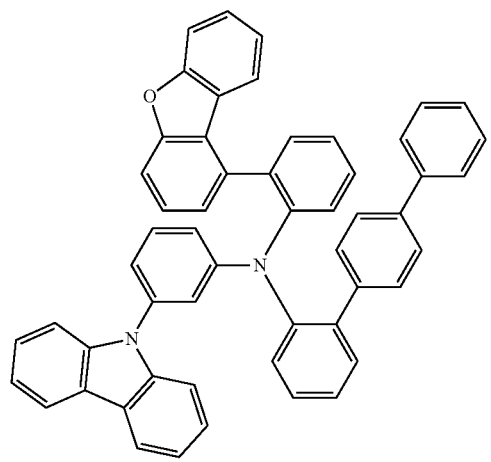
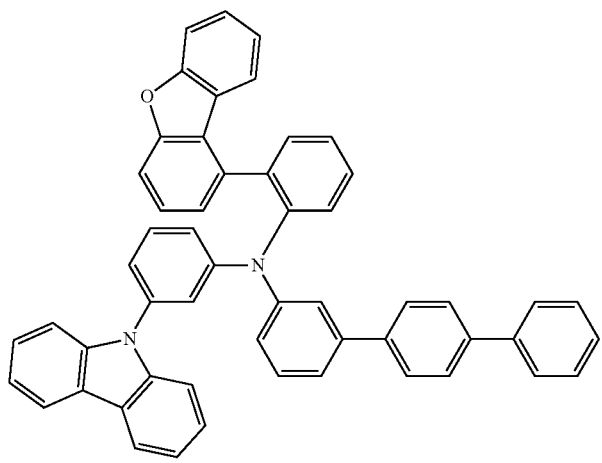
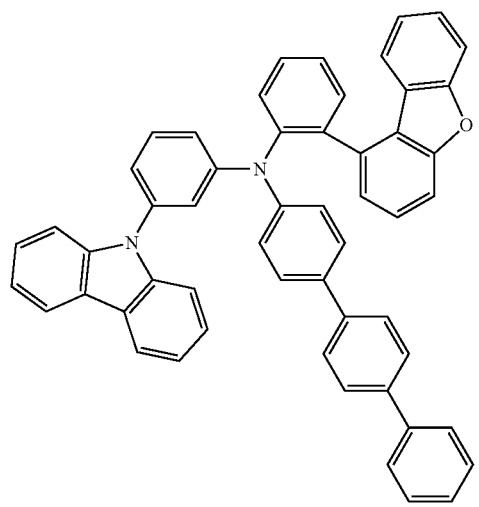
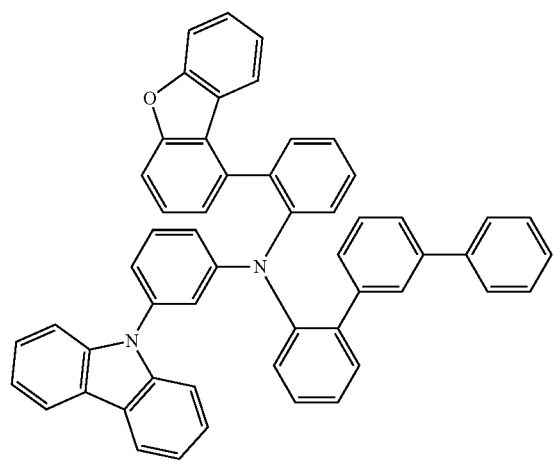

-continued
299
300
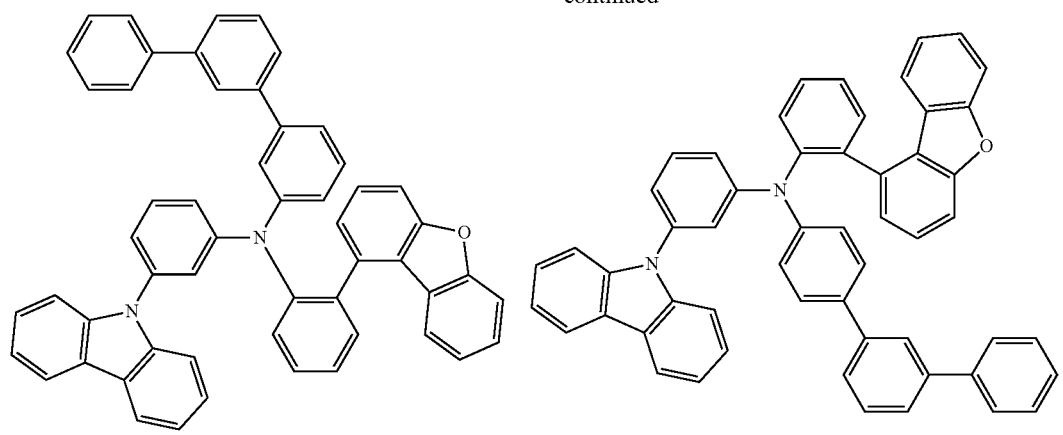
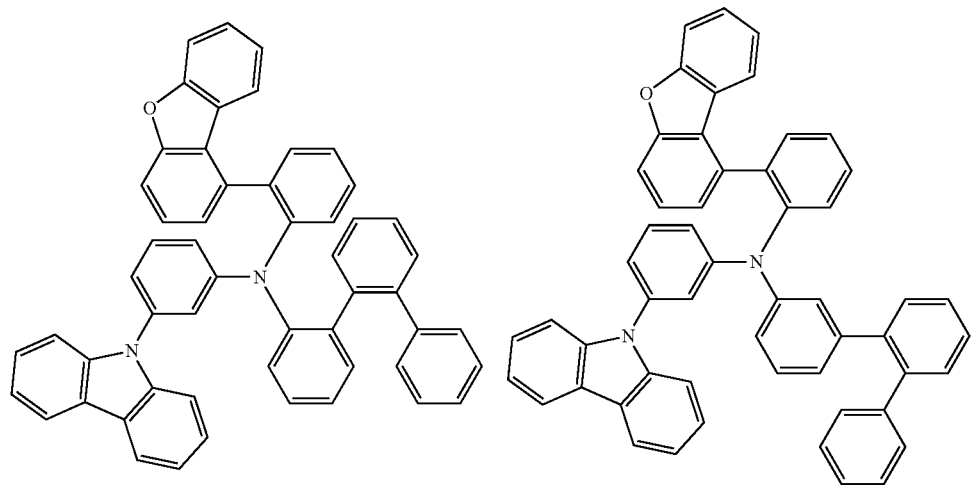
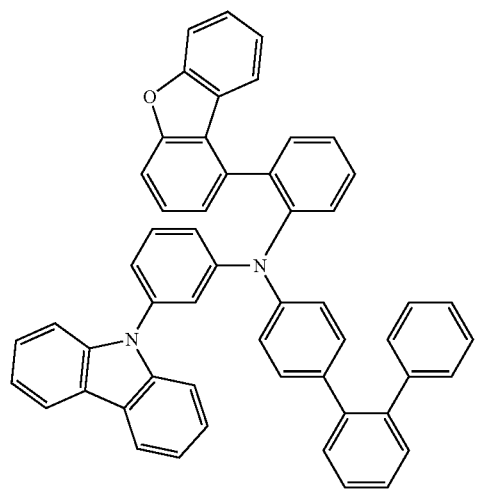

301
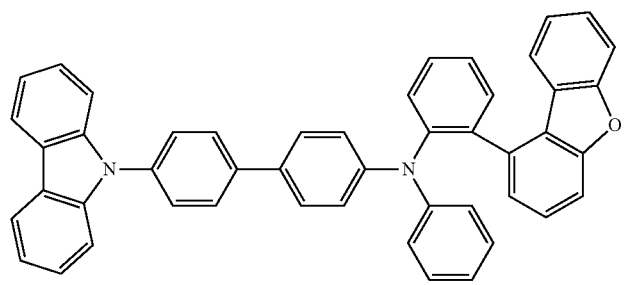
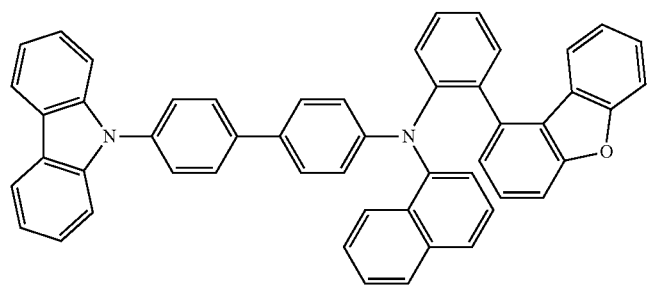
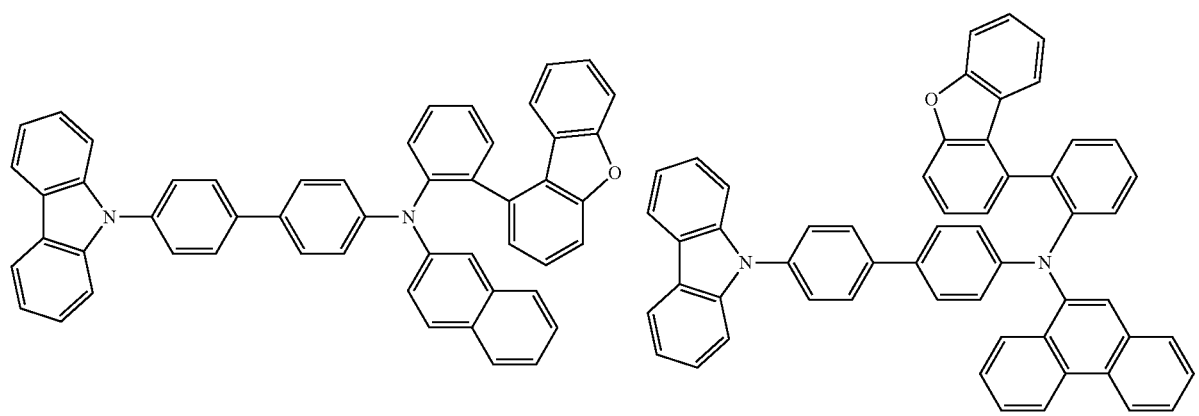
302
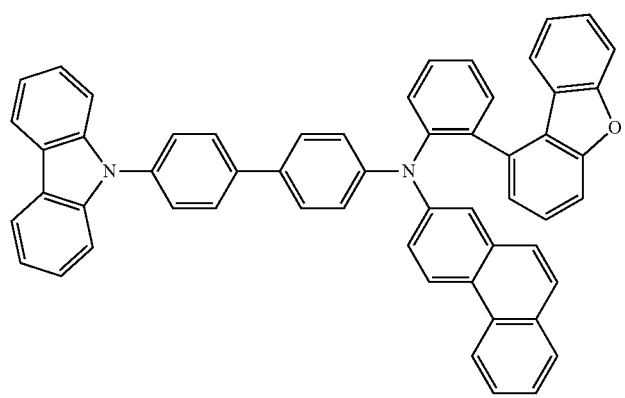

303
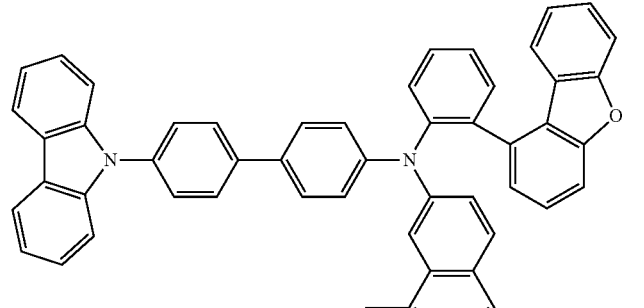
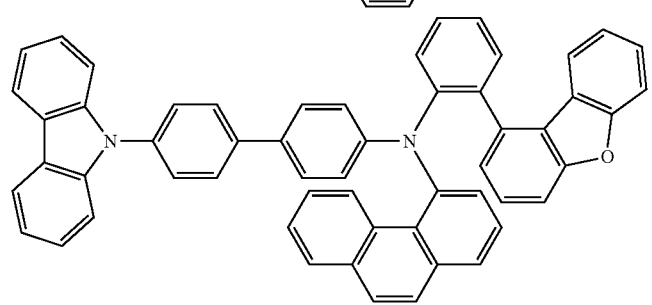
-continued
304
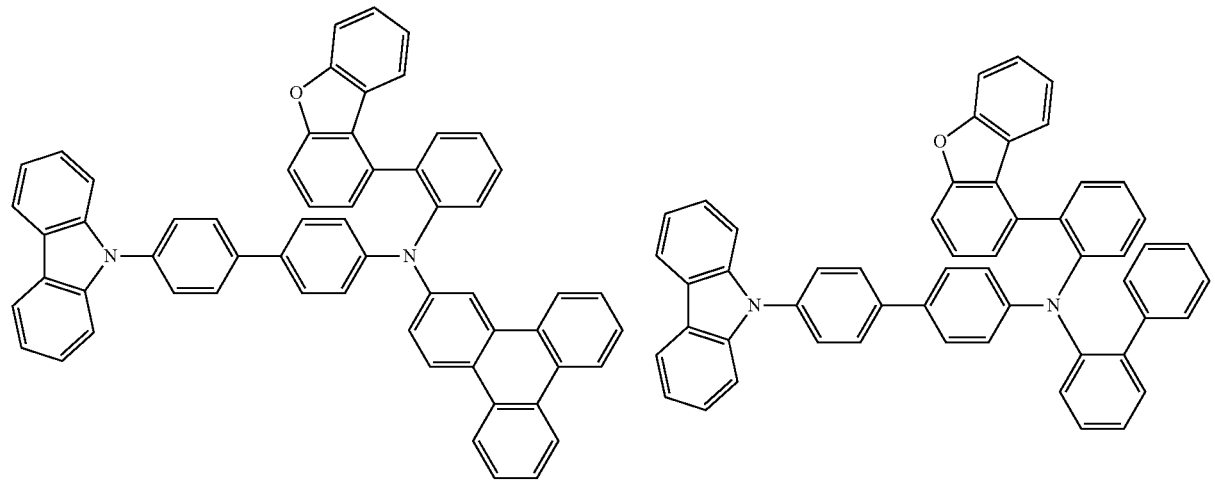
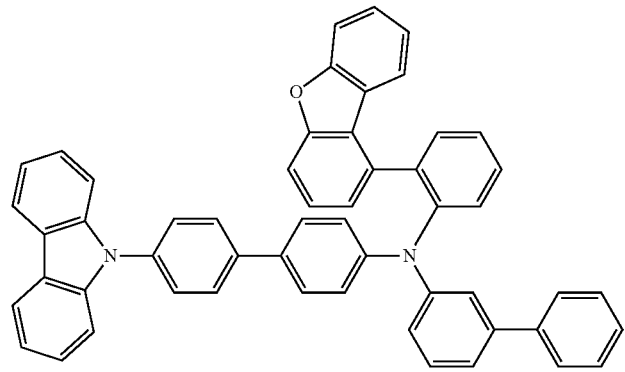

-continued
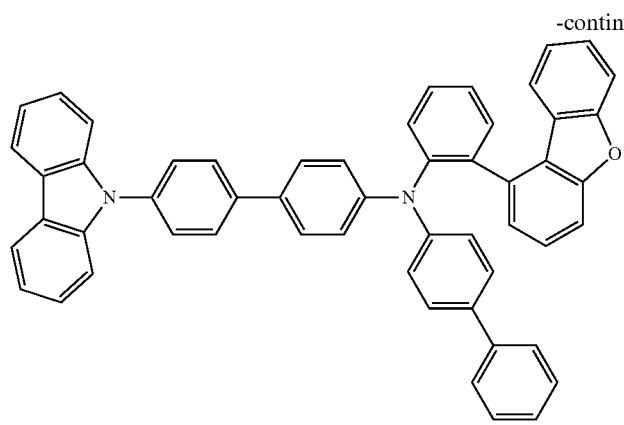
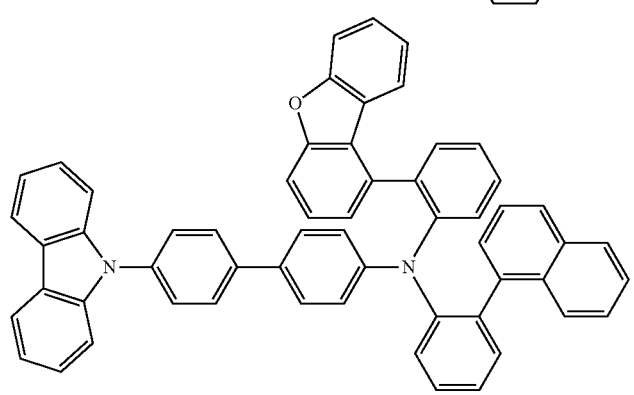
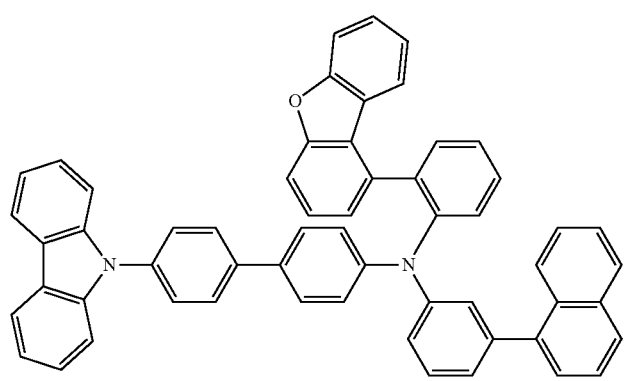
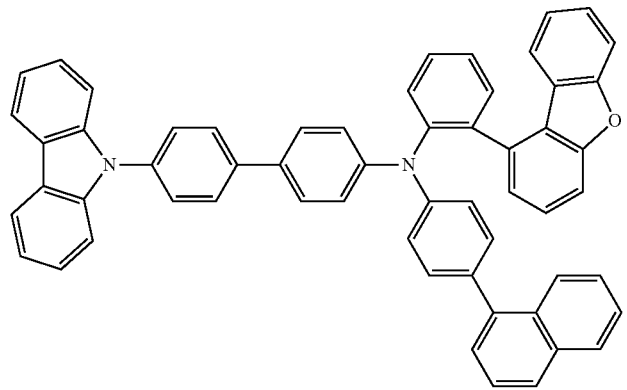

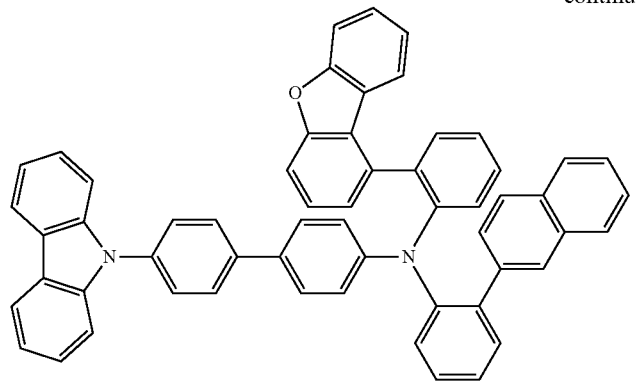
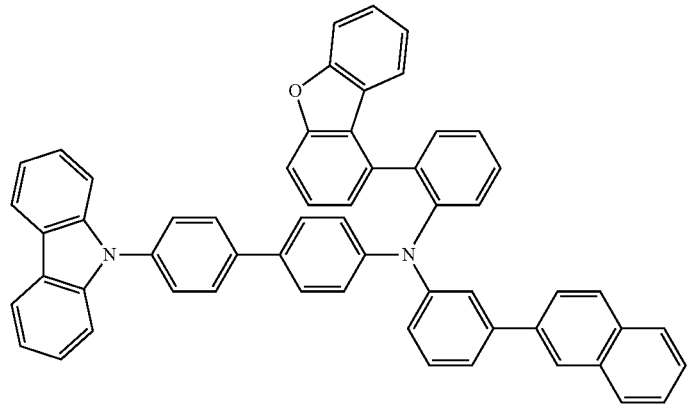
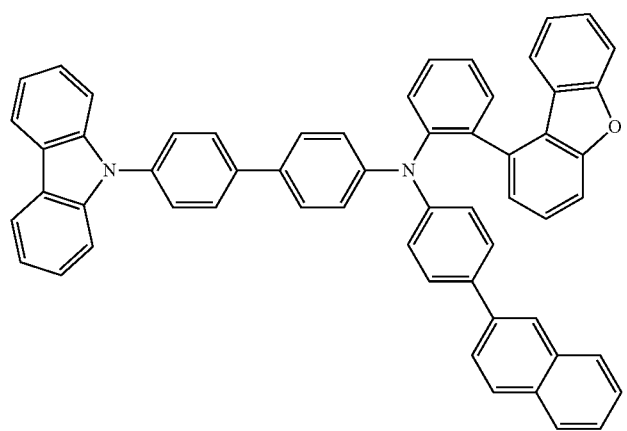
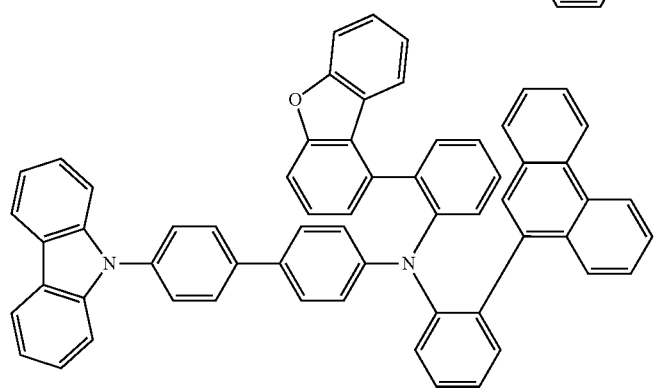

-continued
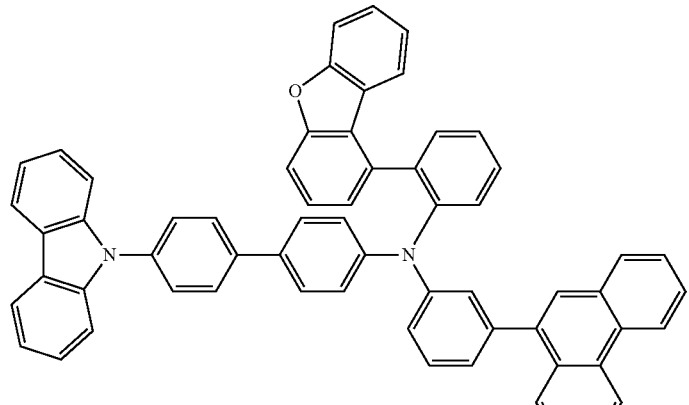
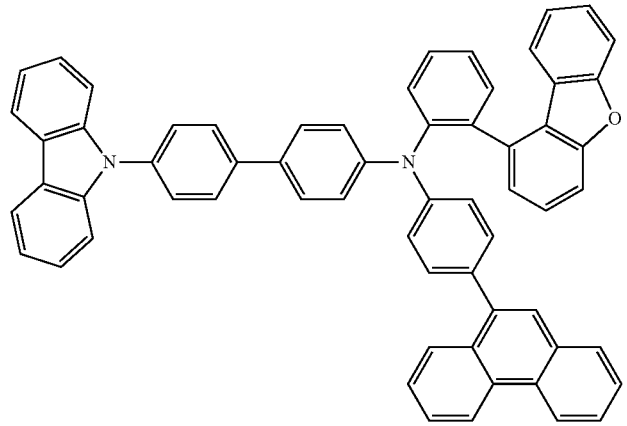
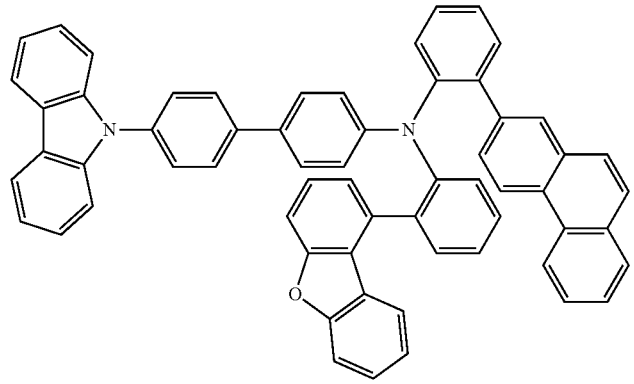
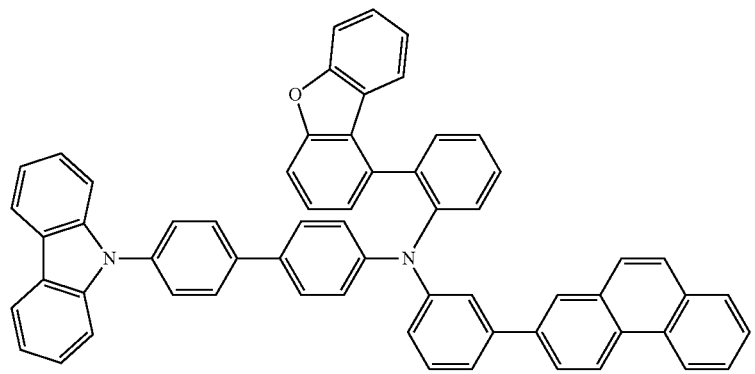

-continued
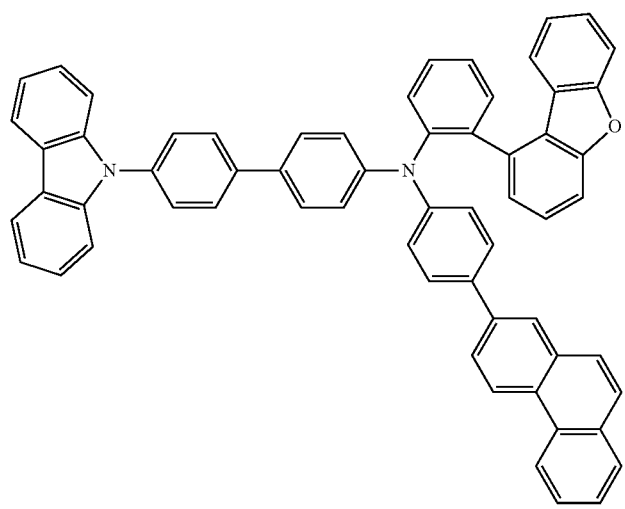
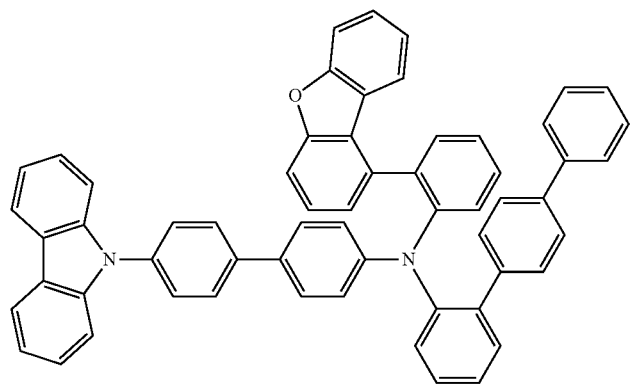
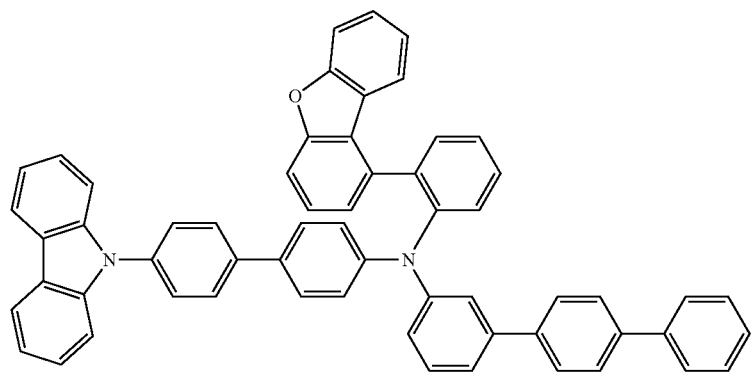

-continued
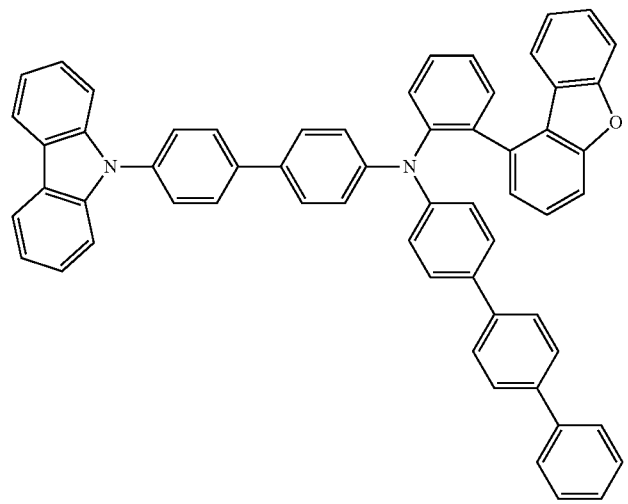
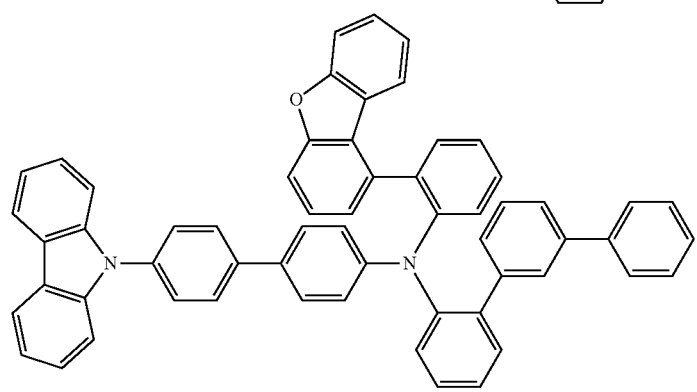
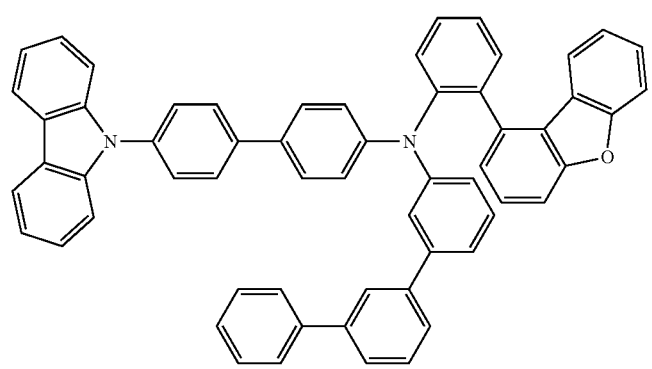
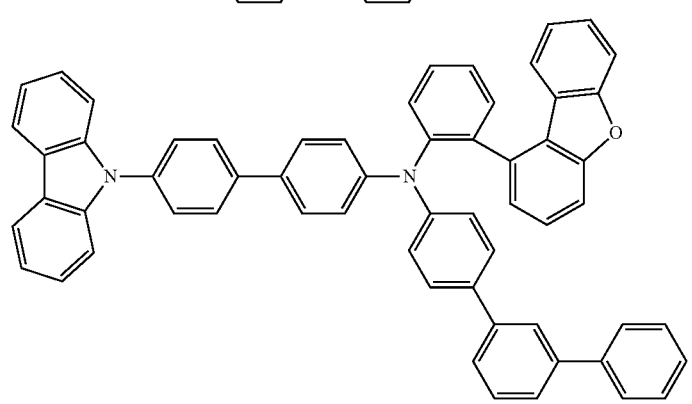

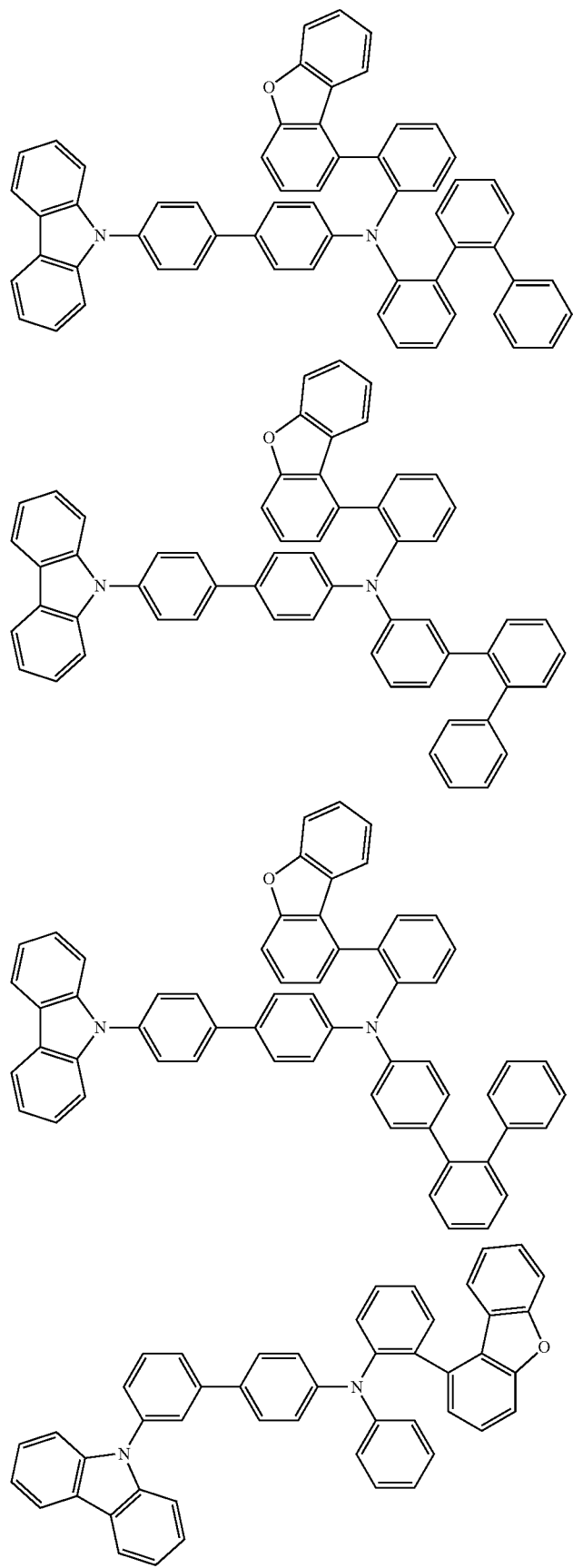

317
-continued
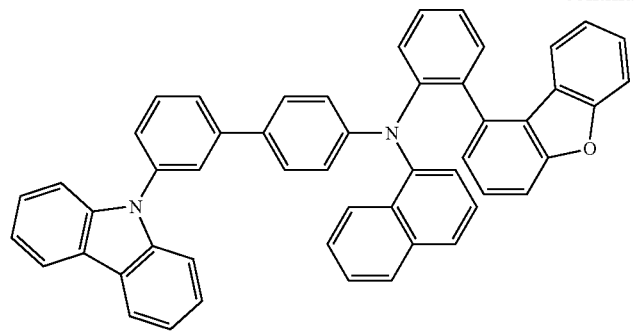
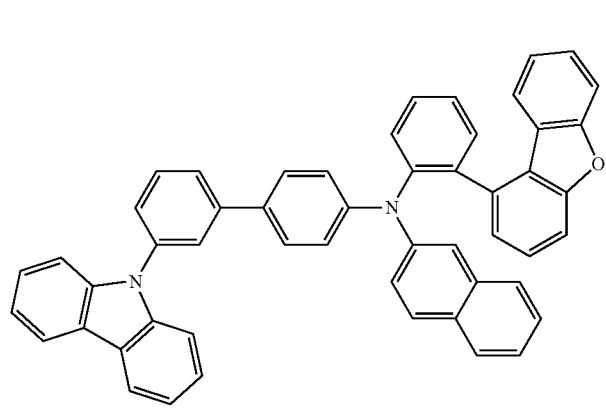
318
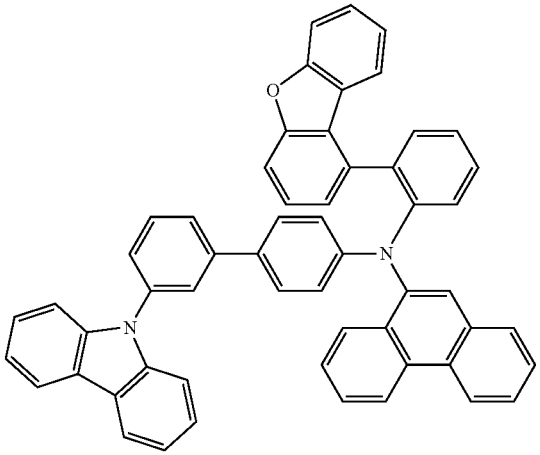
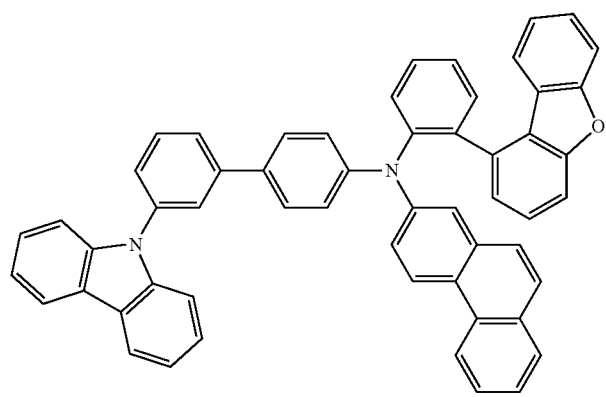
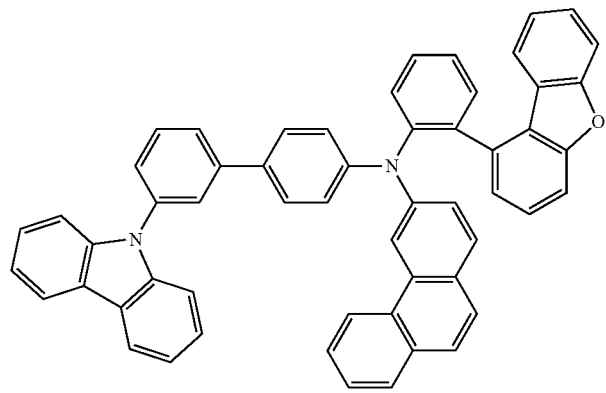

319
320
-continued
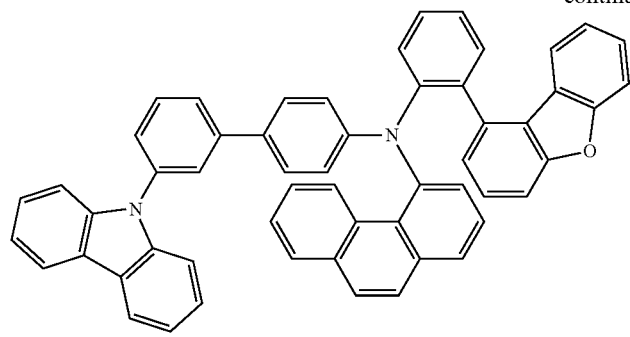
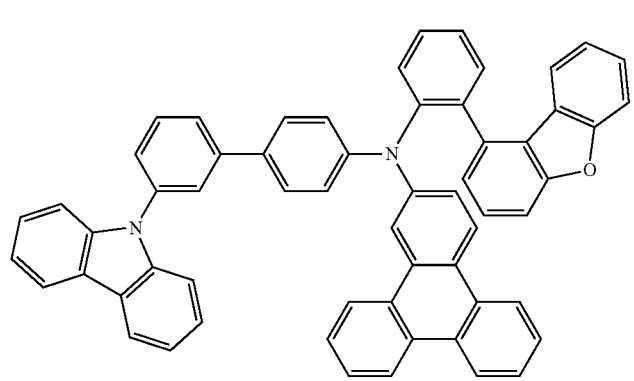
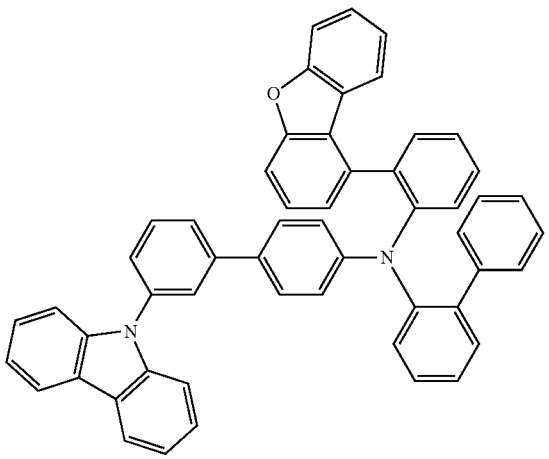
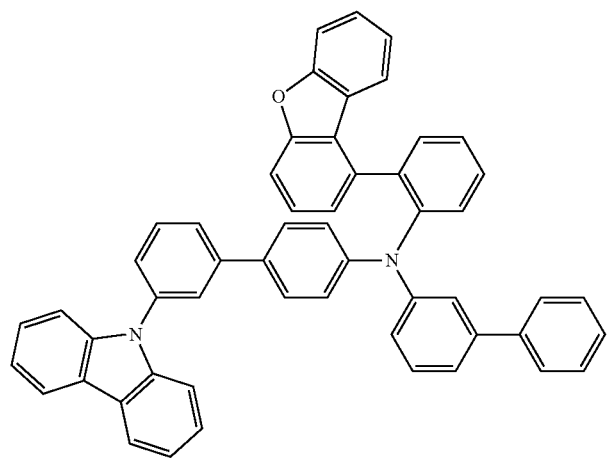
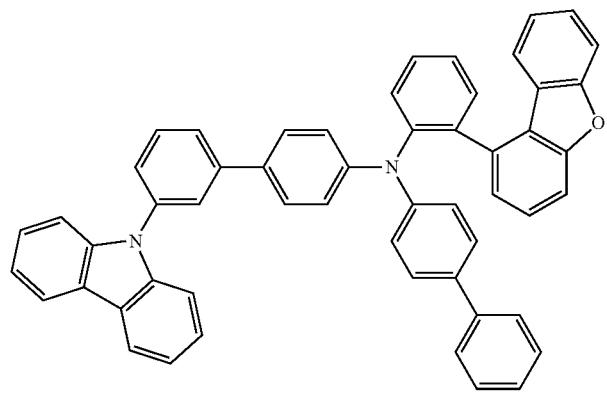

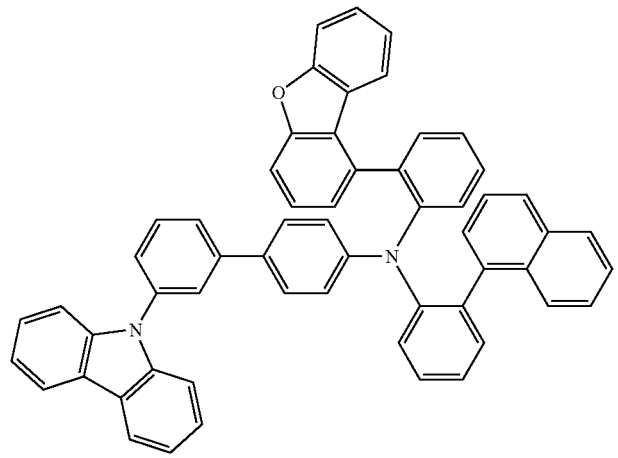
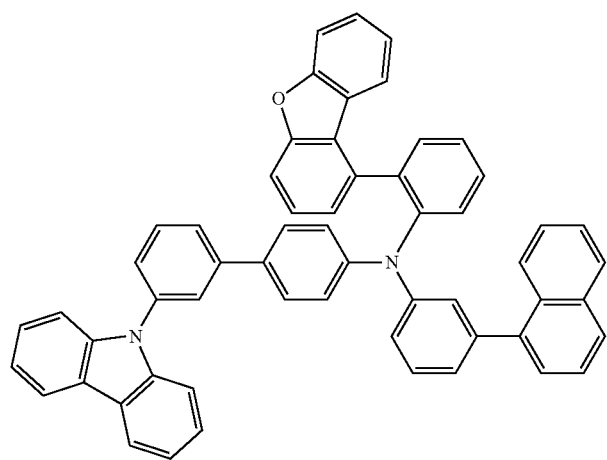
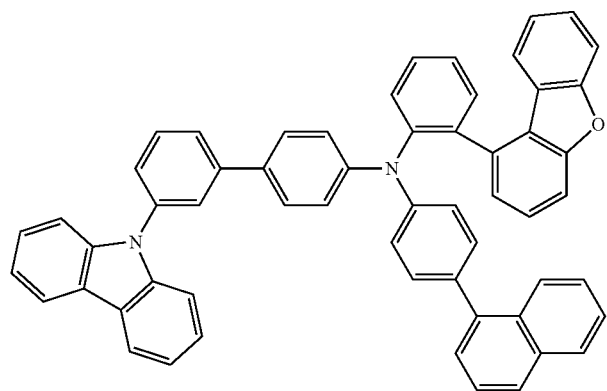

-continued
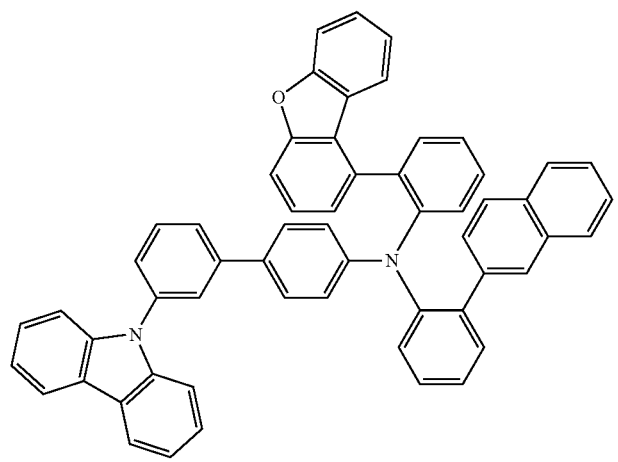
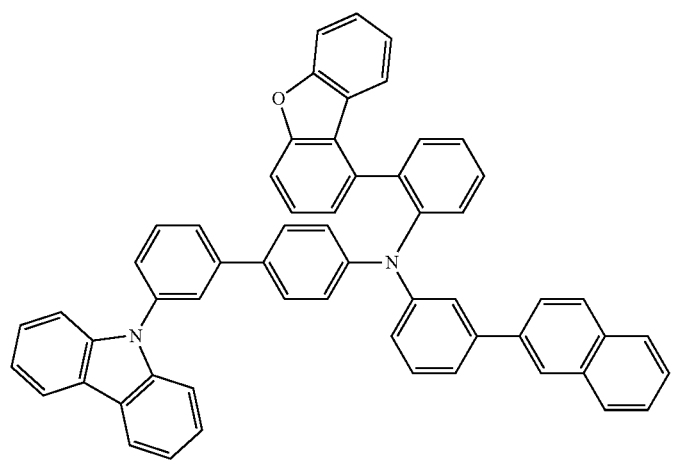
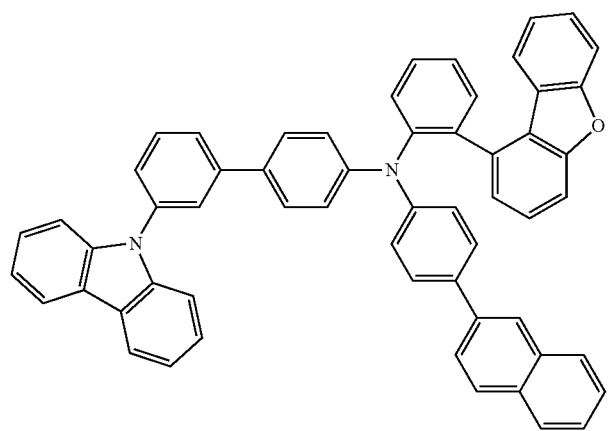

-continued
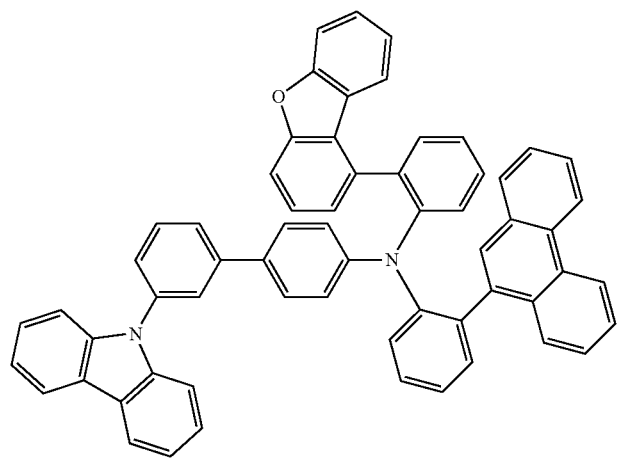
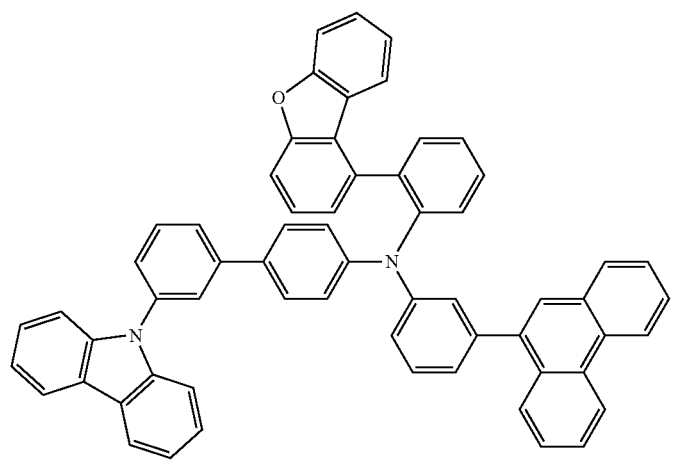
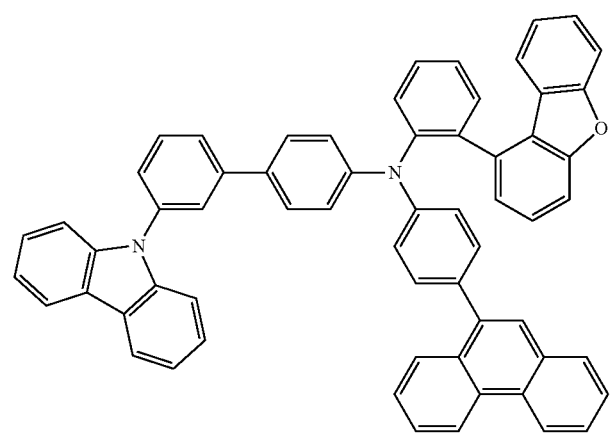

-continued
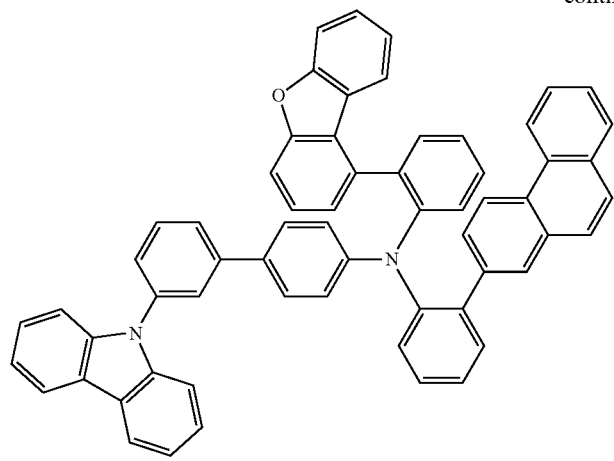
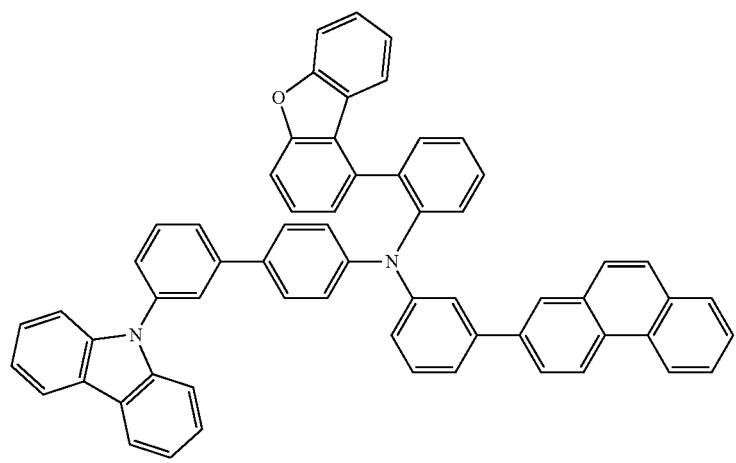
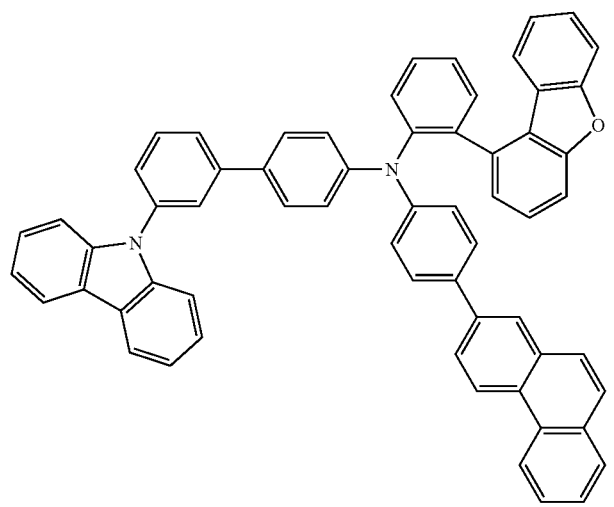

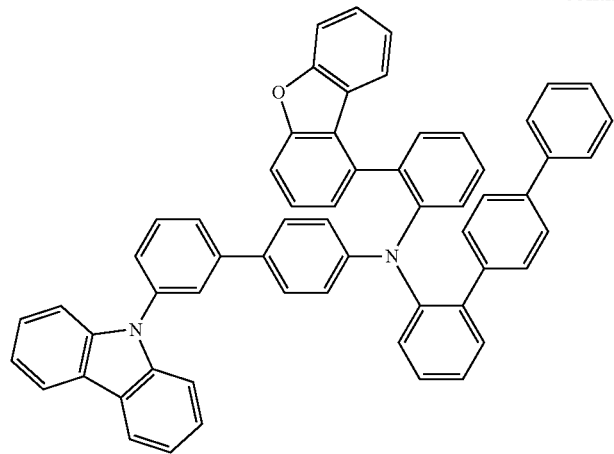
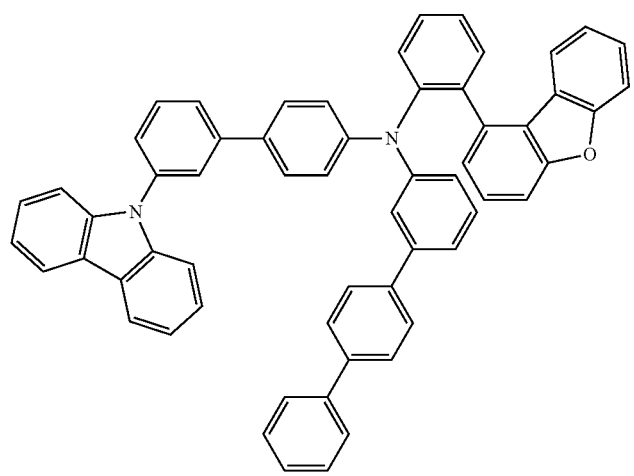
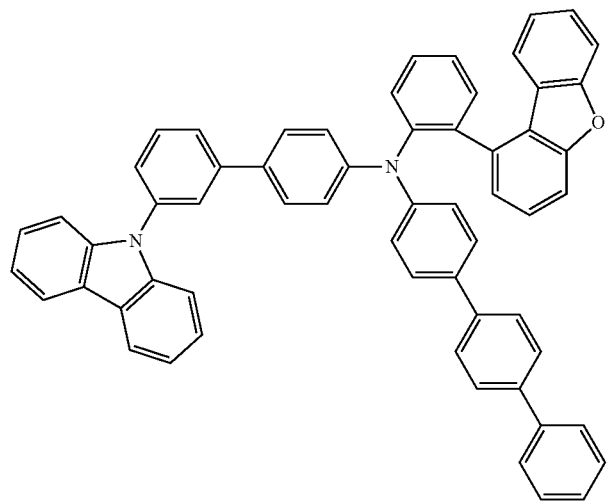

-continued
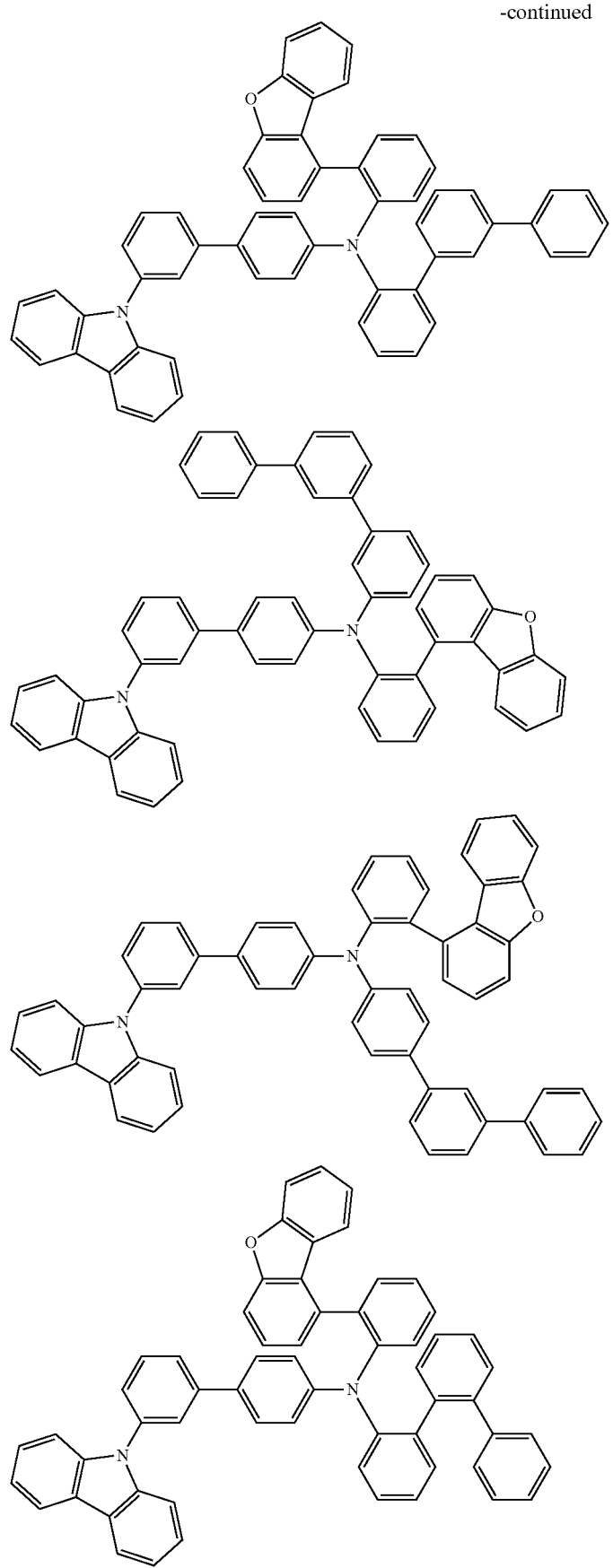

333 334
-continued
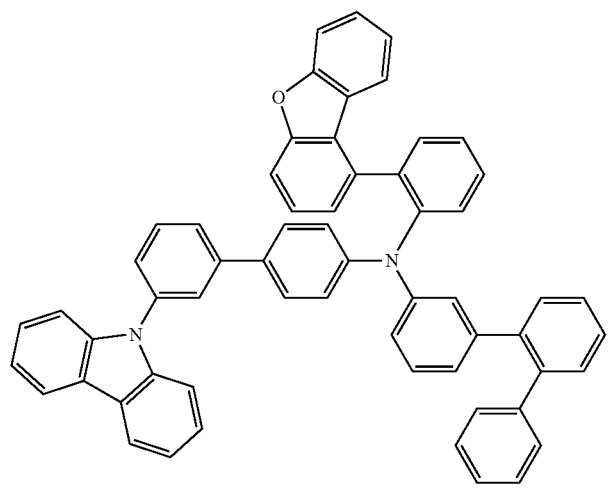
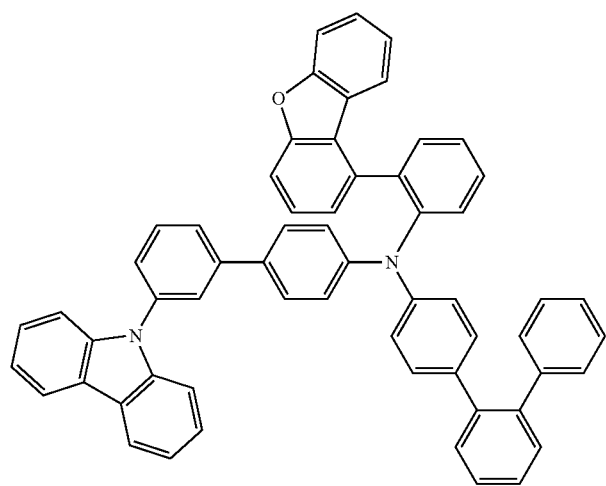
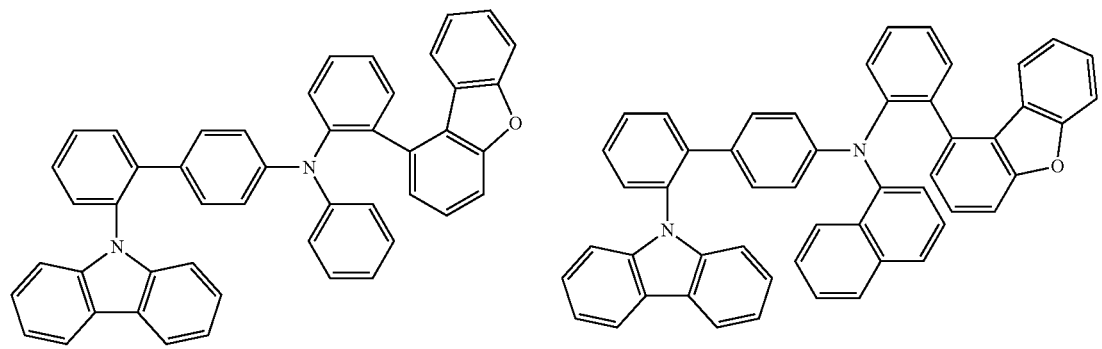

-continued
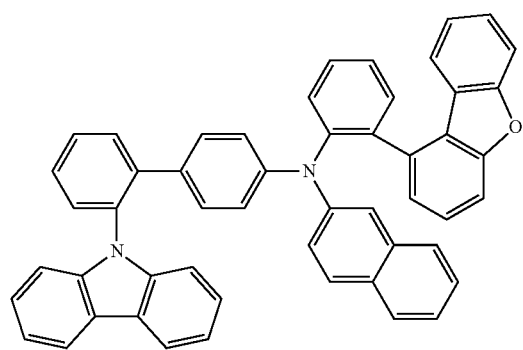
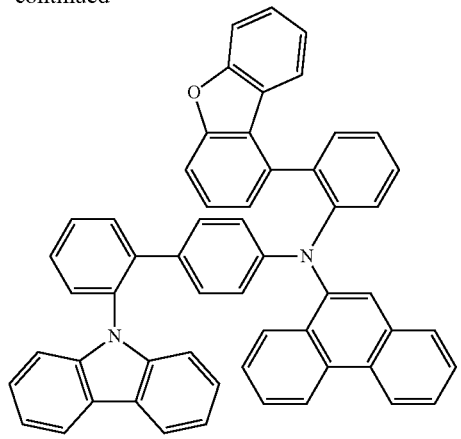
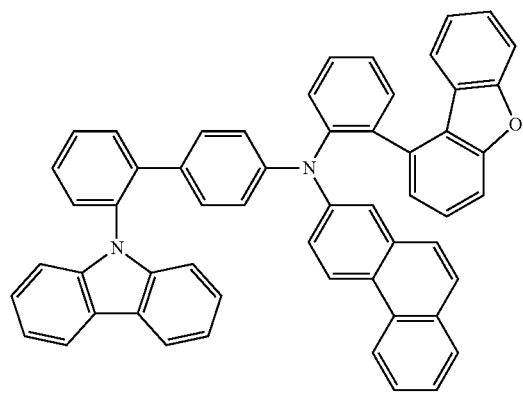
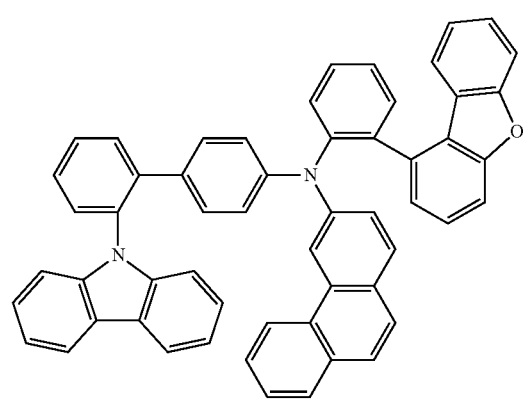
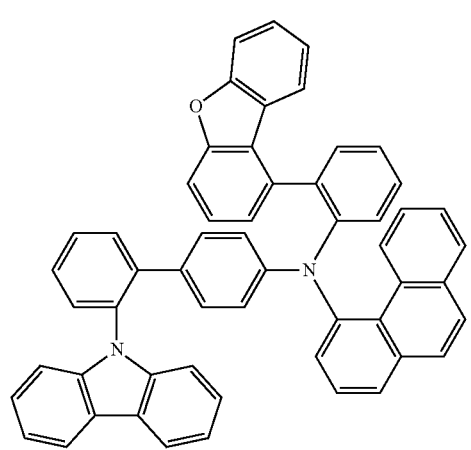
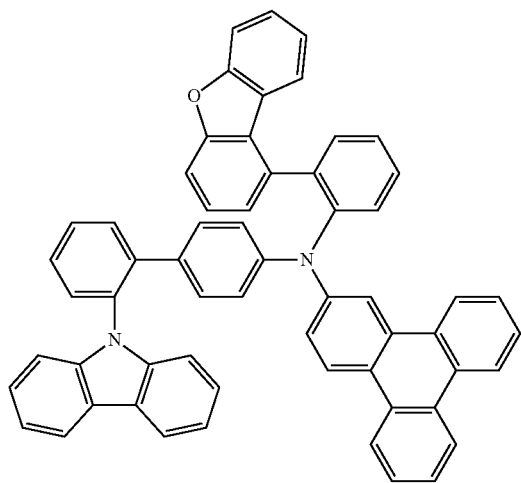

-continued
337
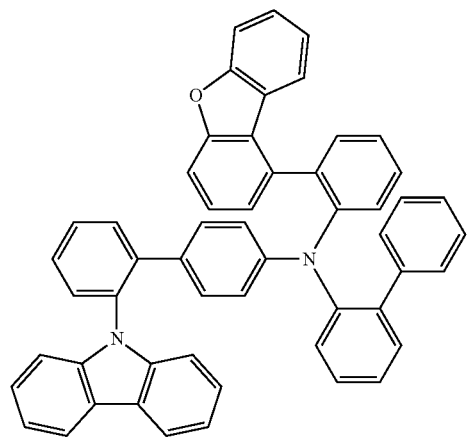
338
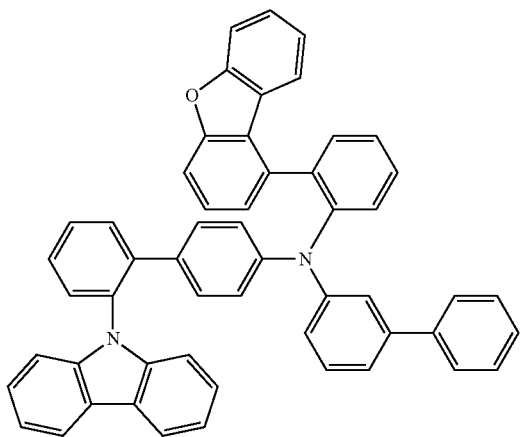
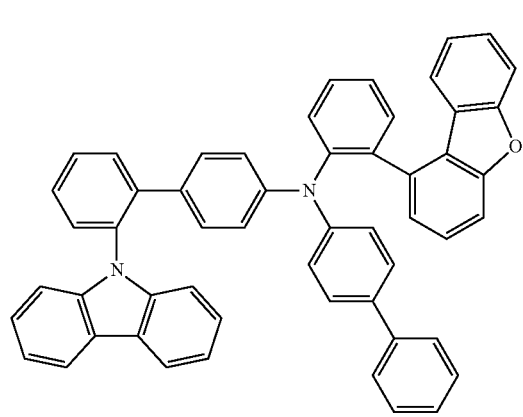
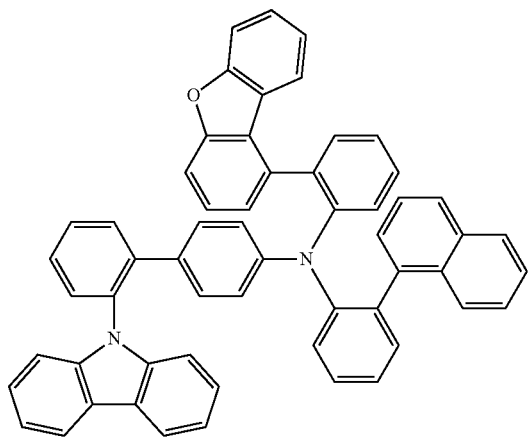
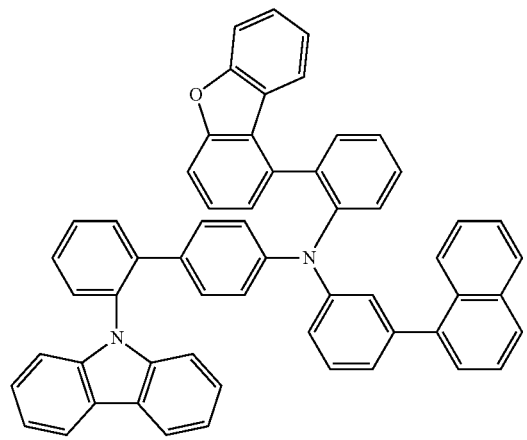
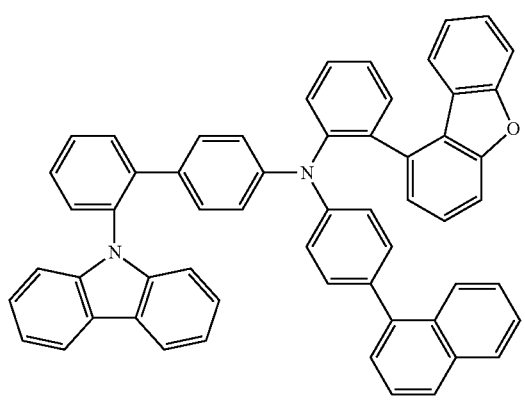

-continued
| 339 | 340 |
|---|---|
| 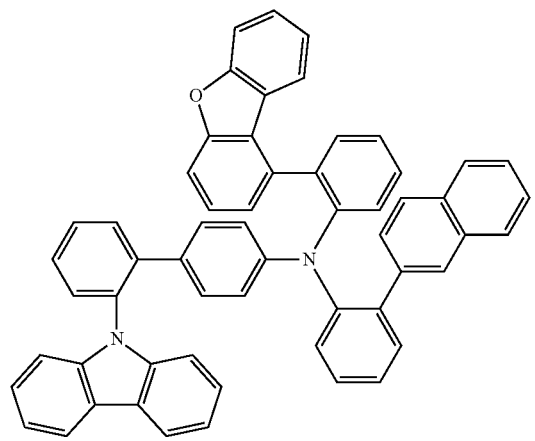 | 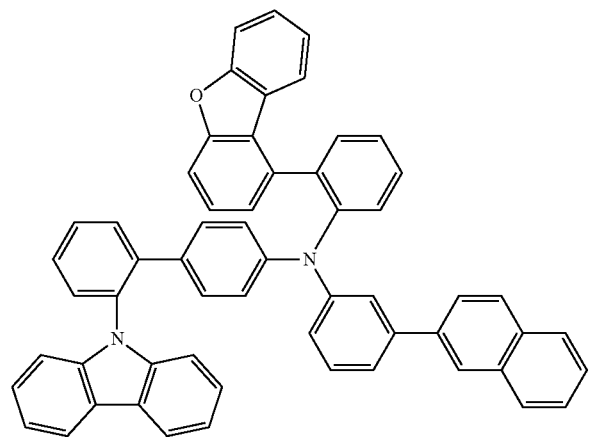 |
| 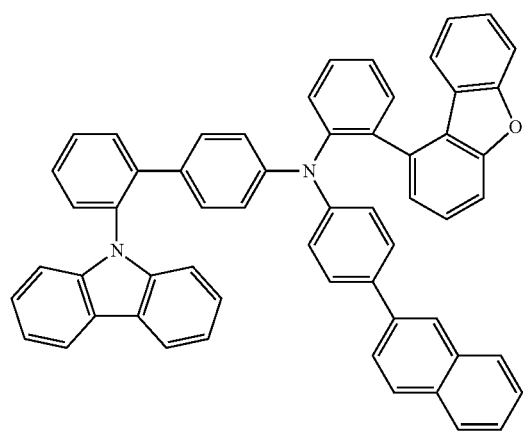 | 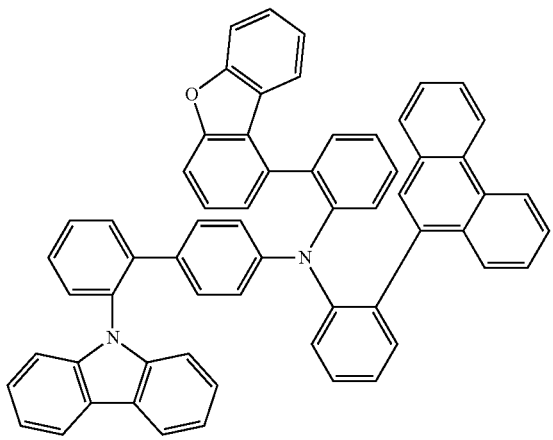 |
| 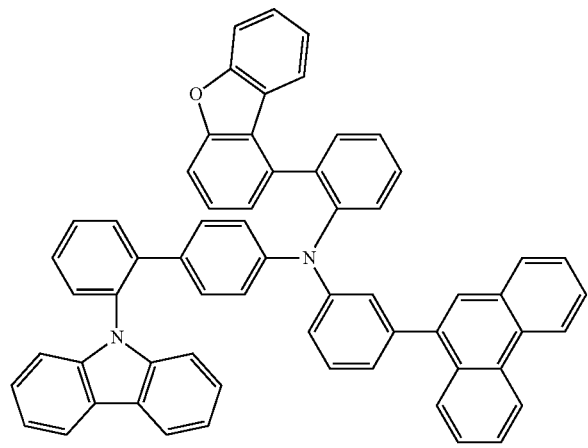 | 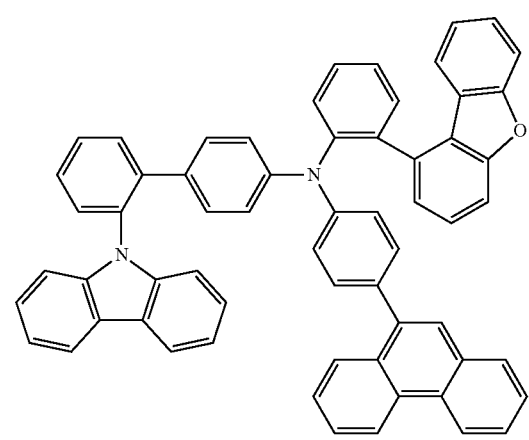 |

-continued
341
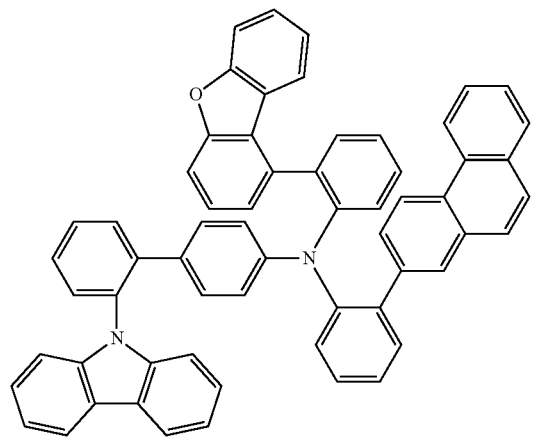
342
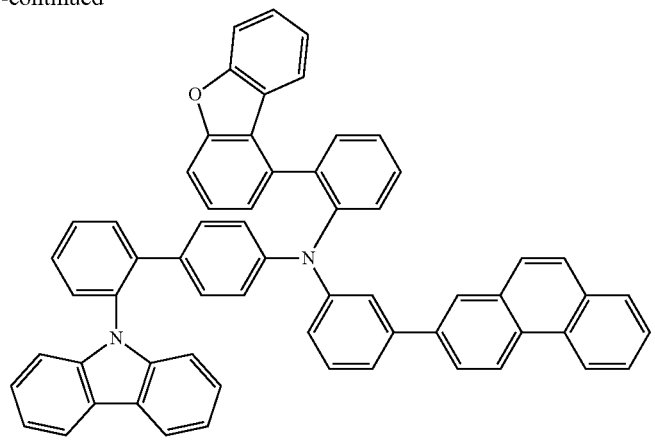
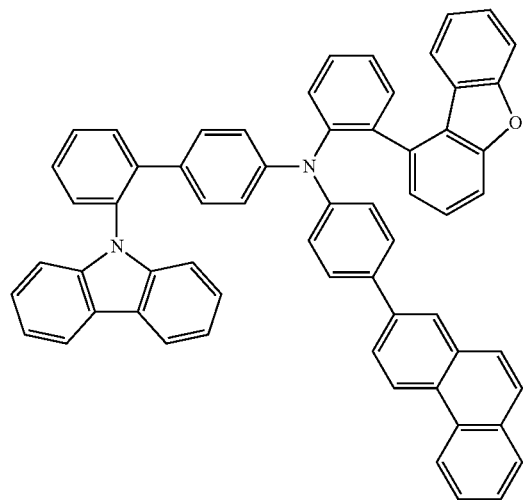
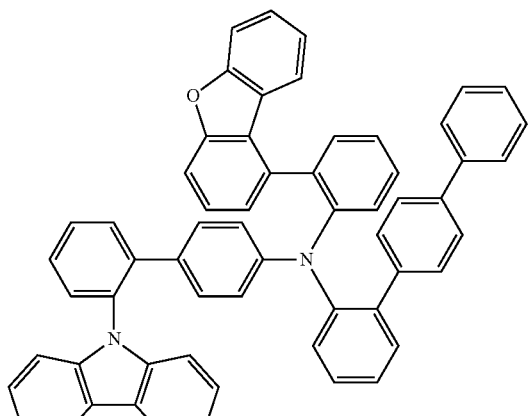
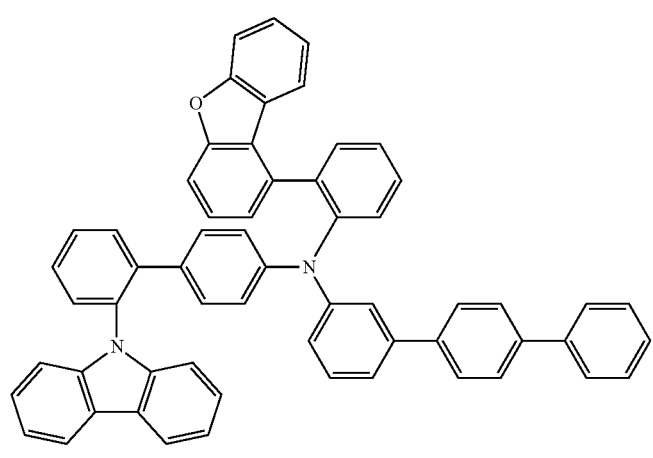
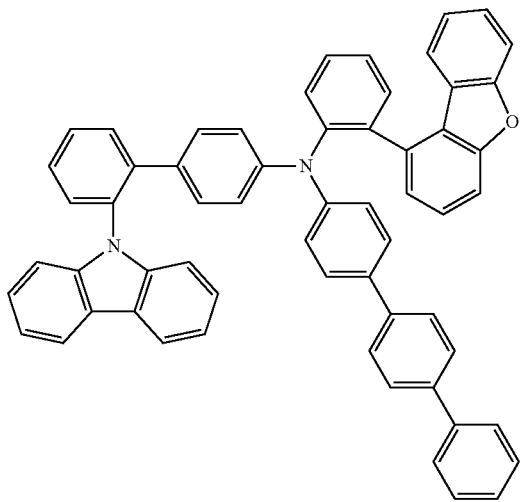

-continued
| 343 | 344 |
|---|---|
| 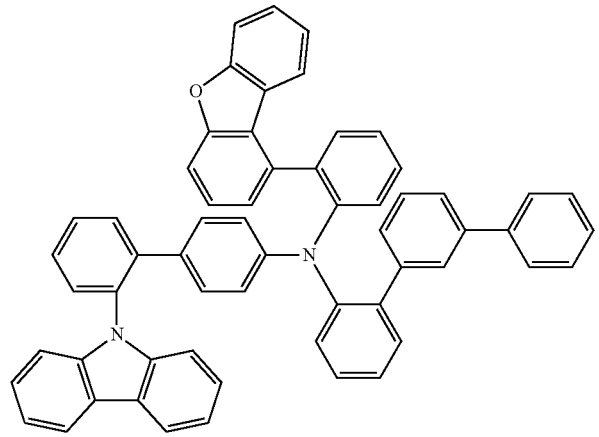 | 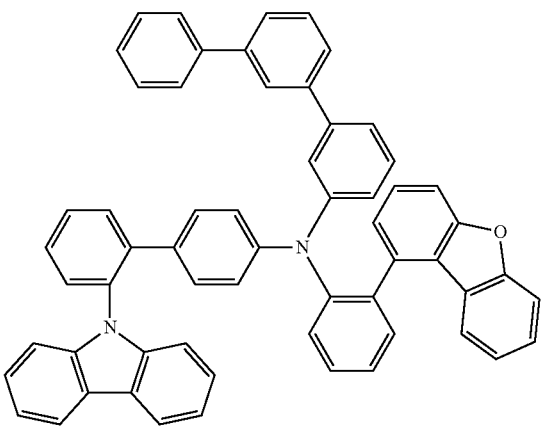 |
| 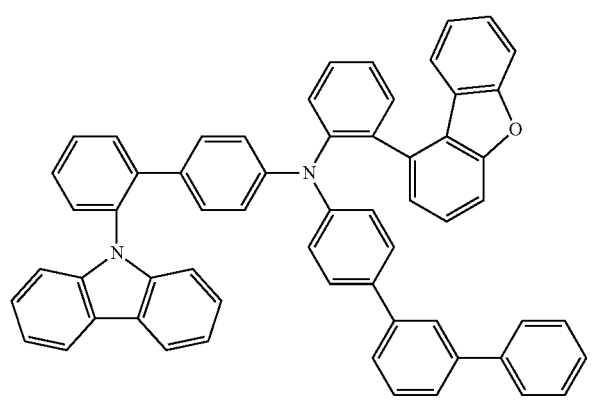 | 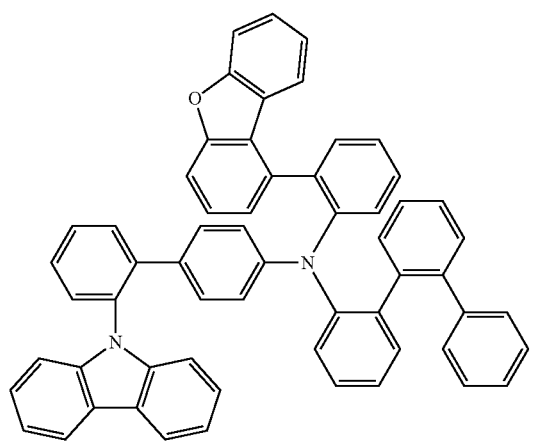 |
| 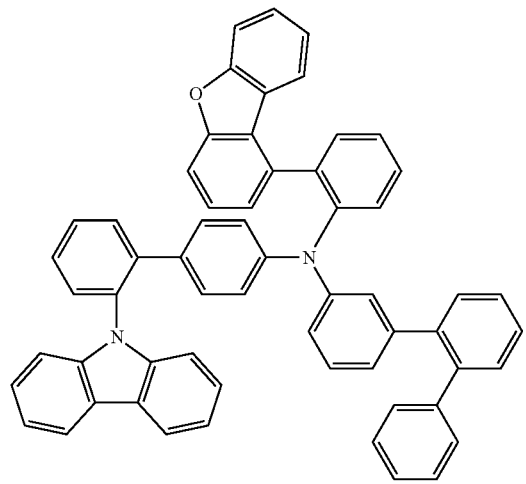 | 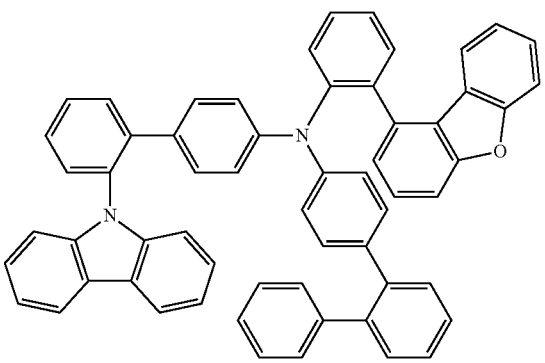 |
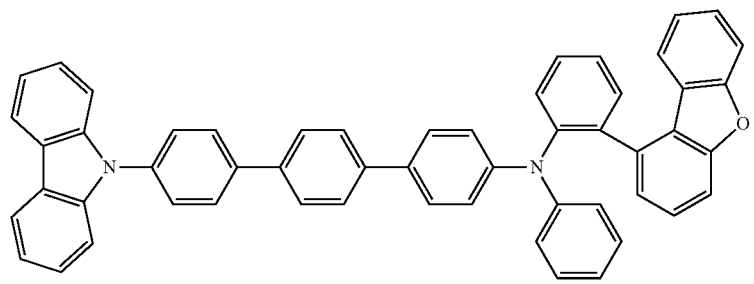

-continued
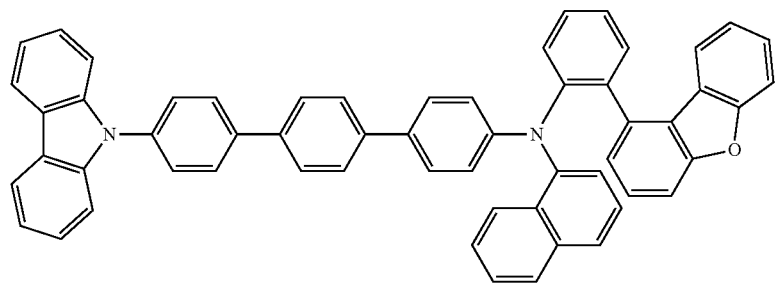
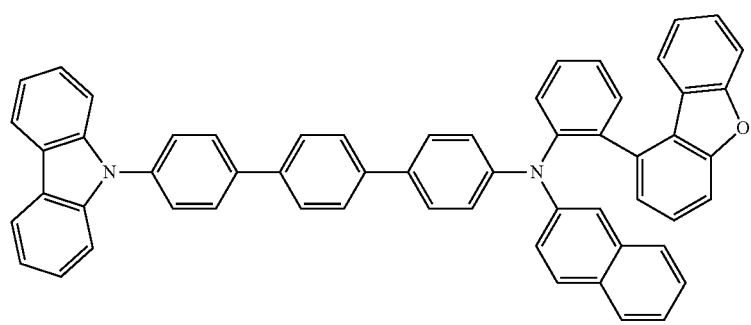
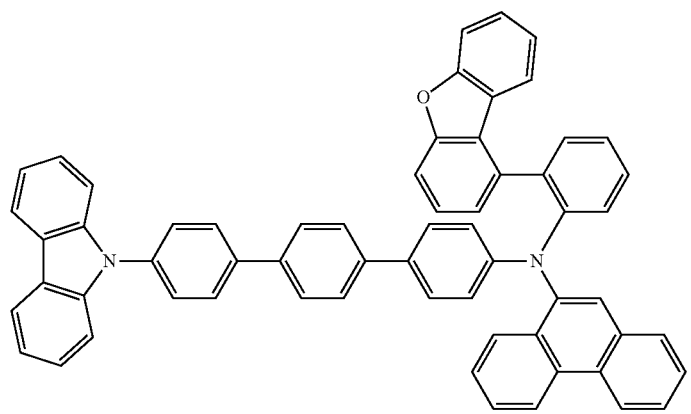
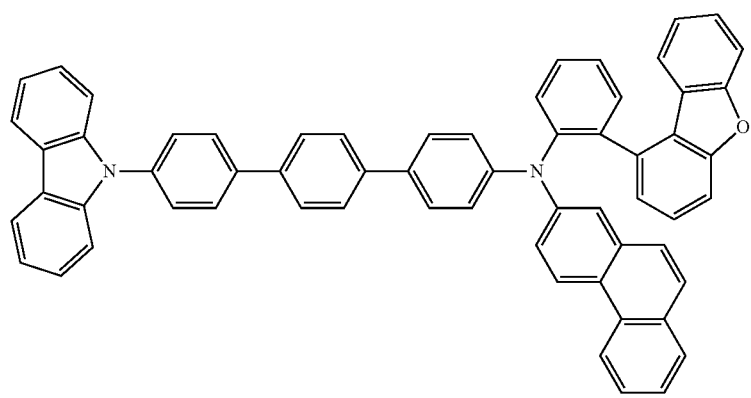

-continued
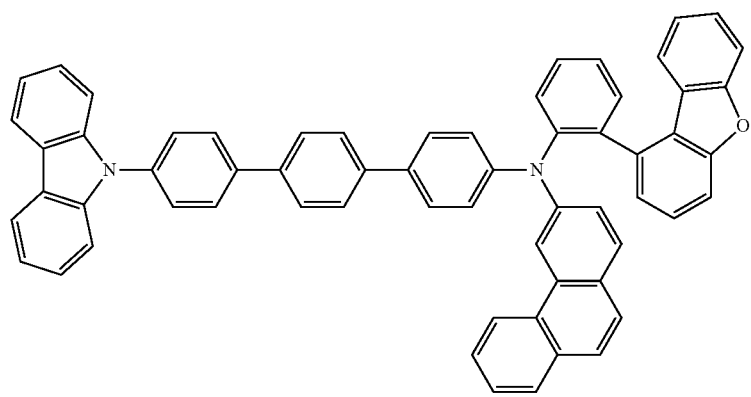
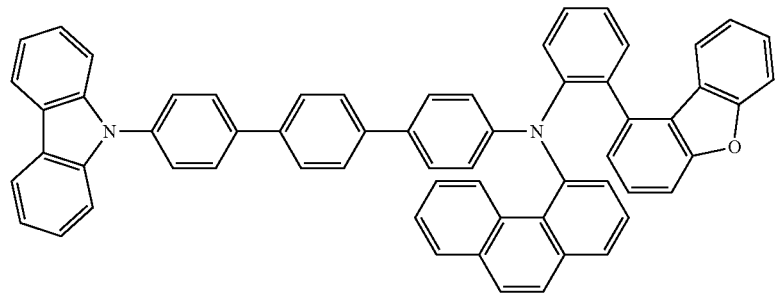
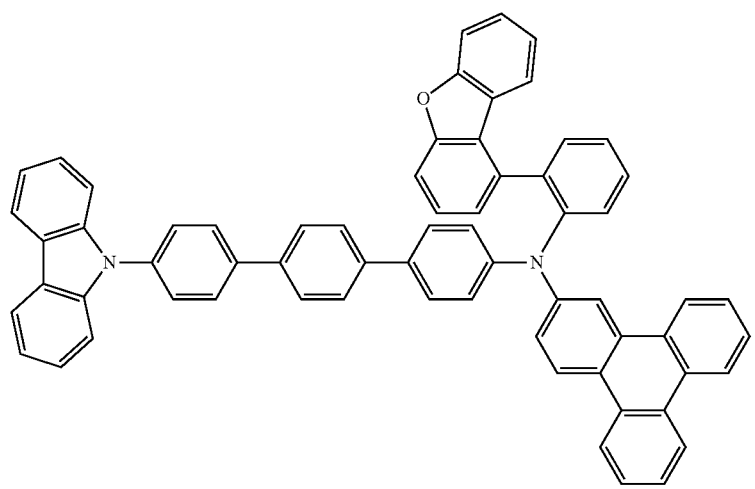
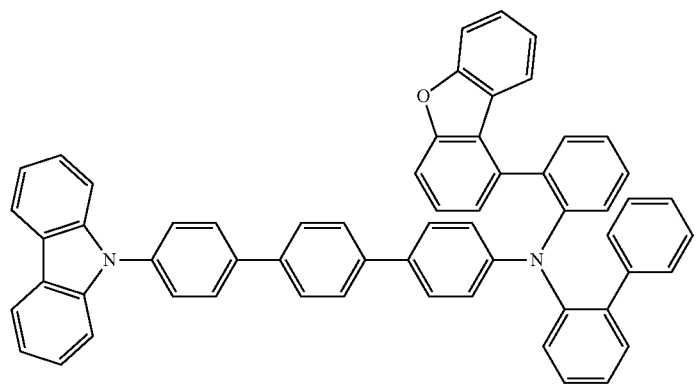

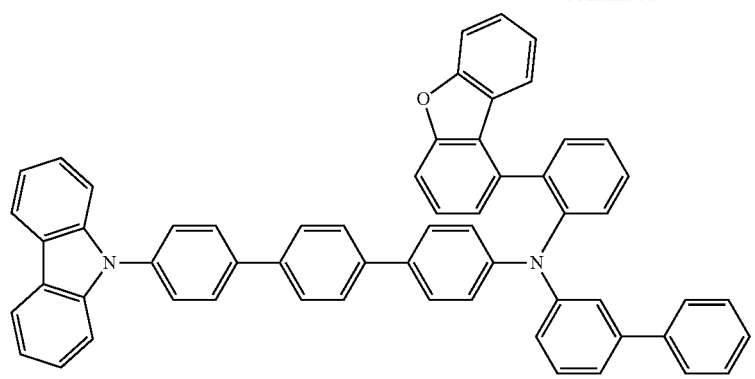
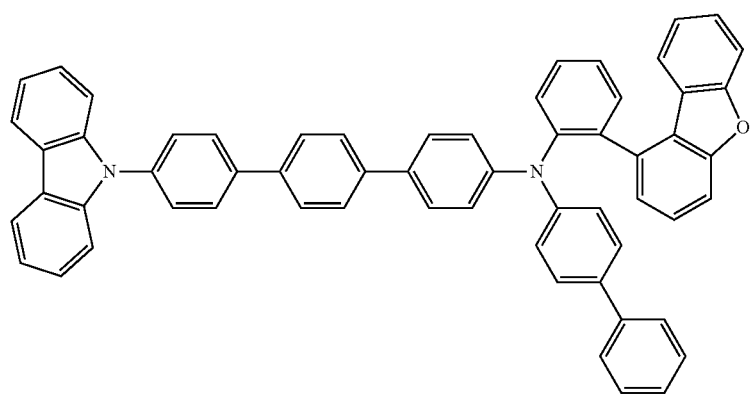
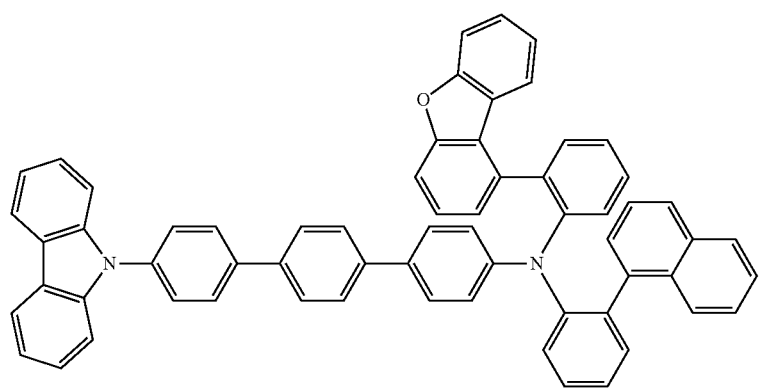
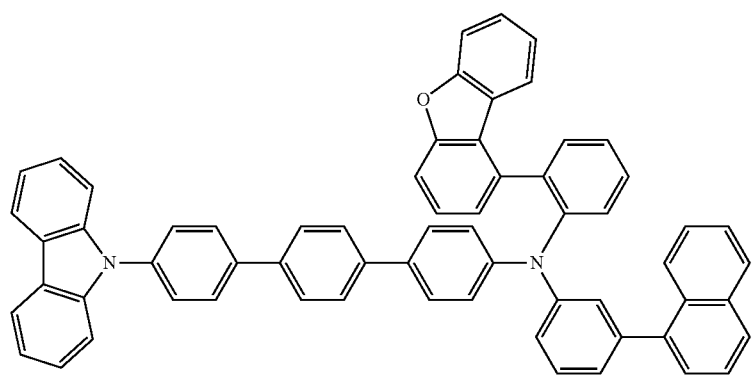

-continued
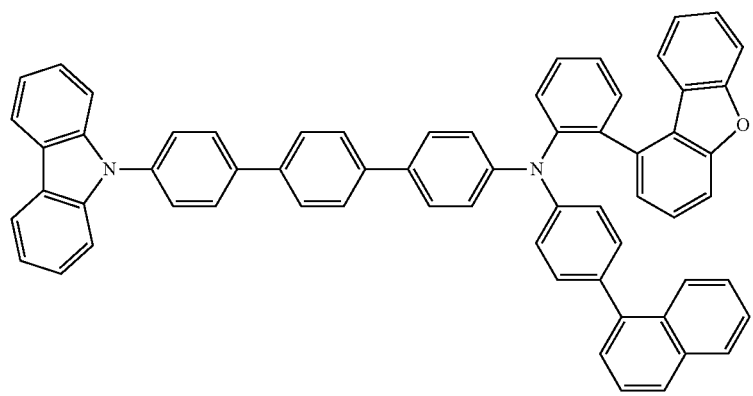
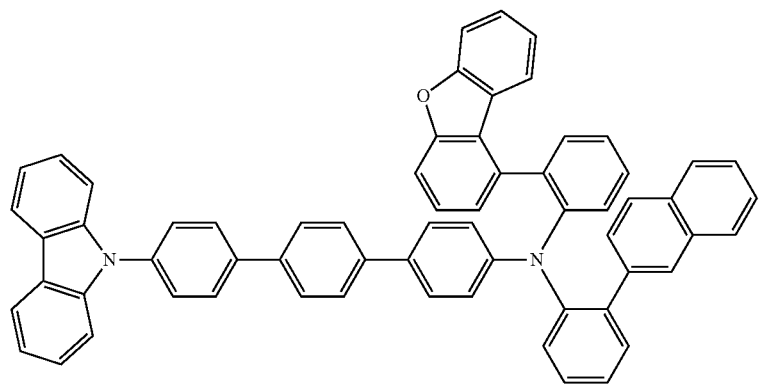
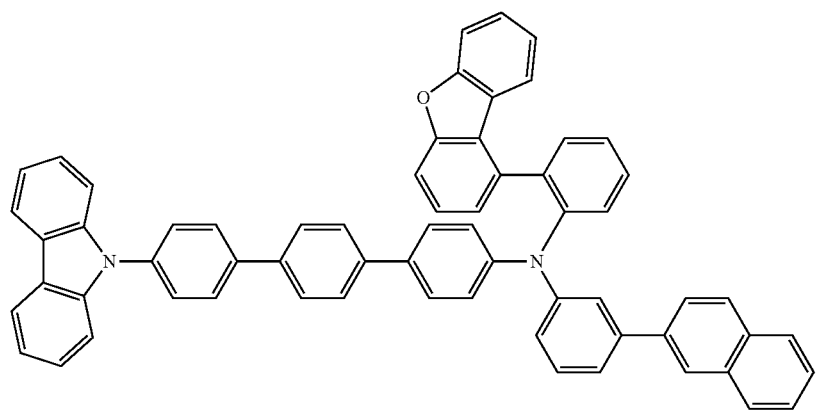
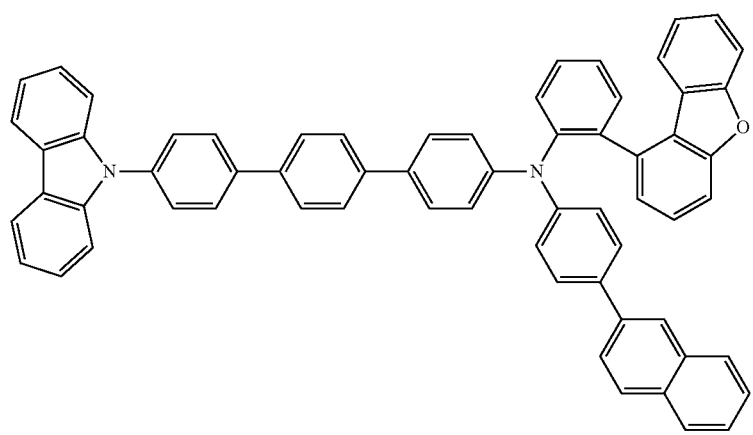

-continued
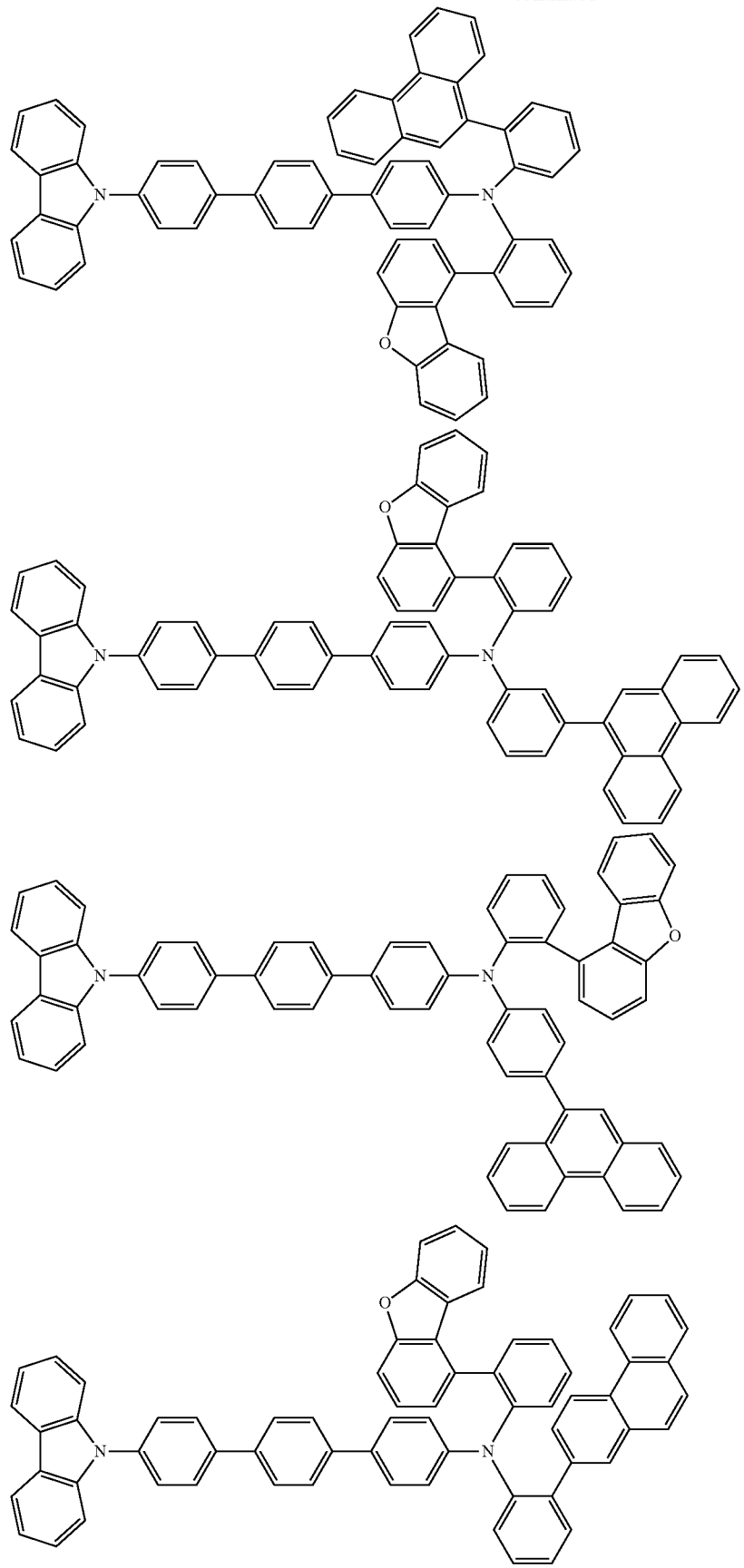

-continued
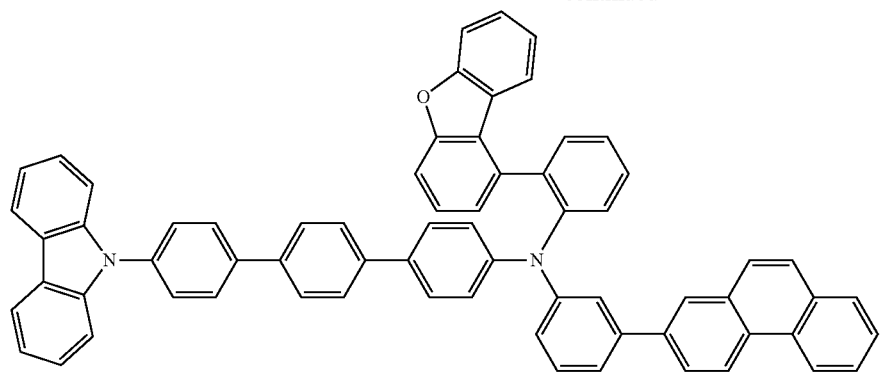
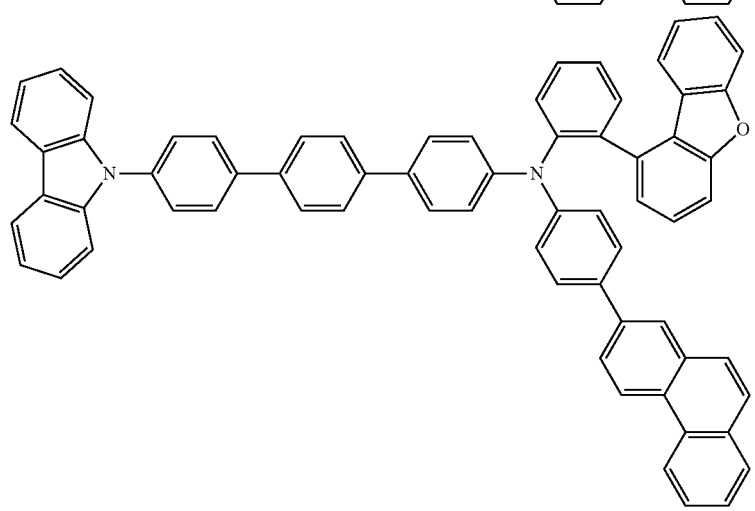
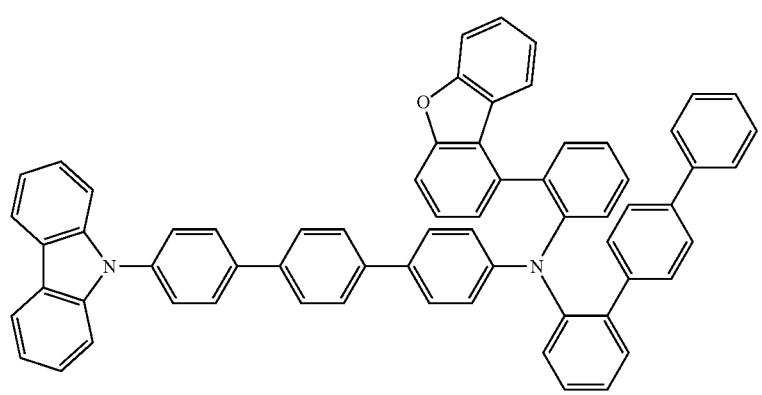
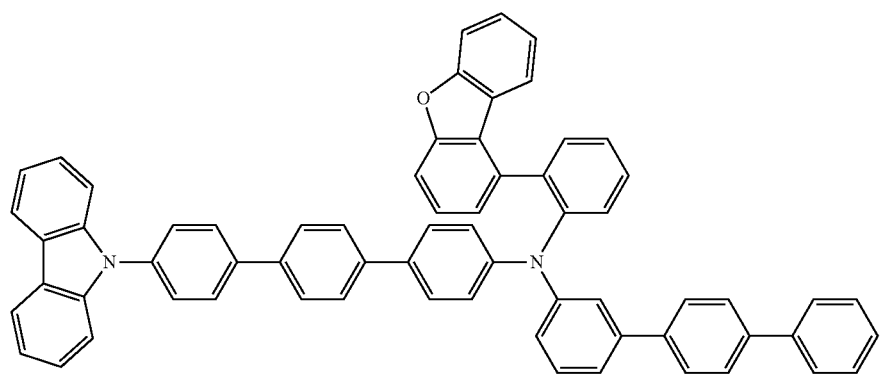

-continued
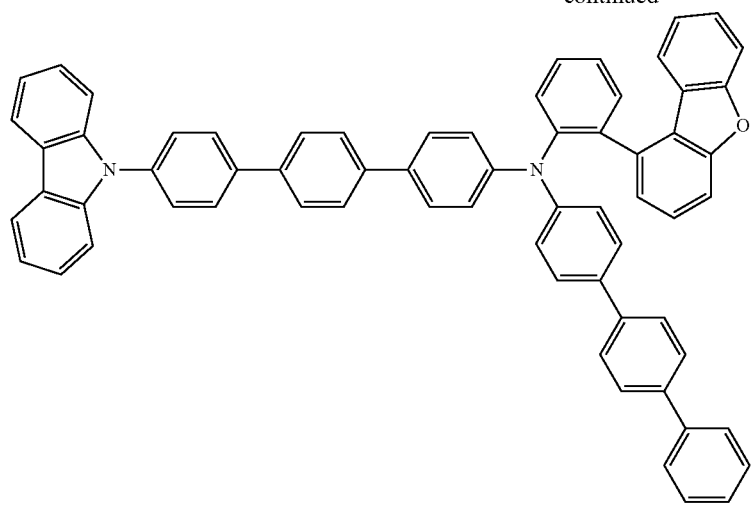
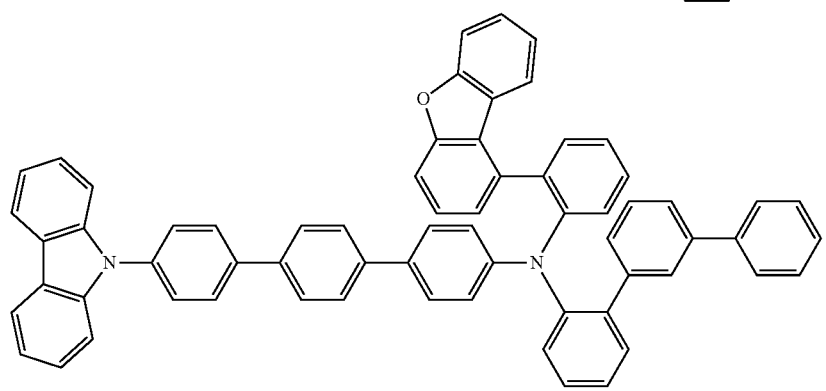
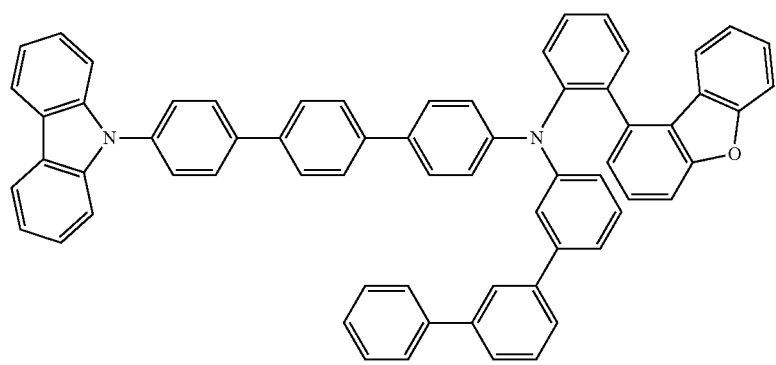
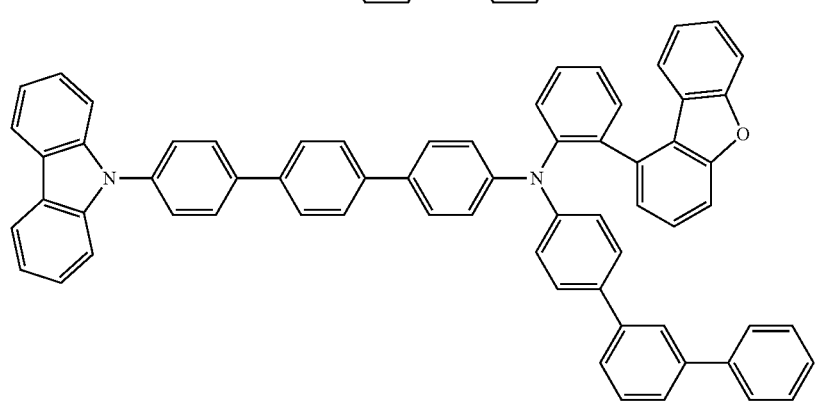

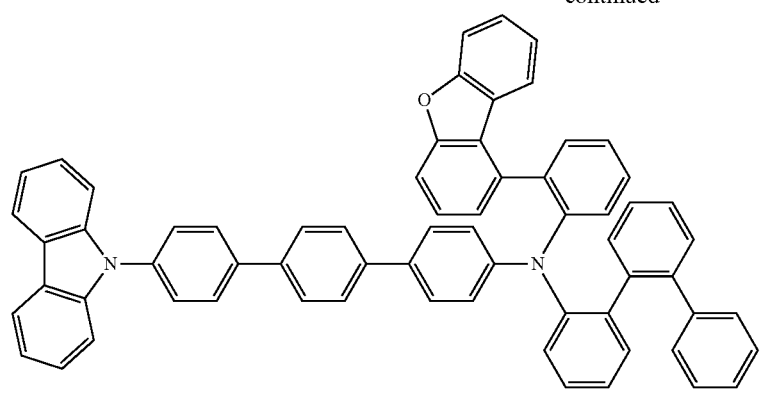
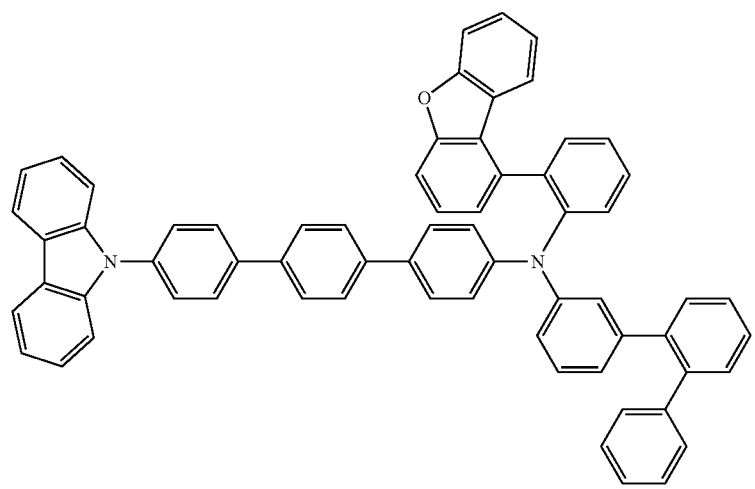
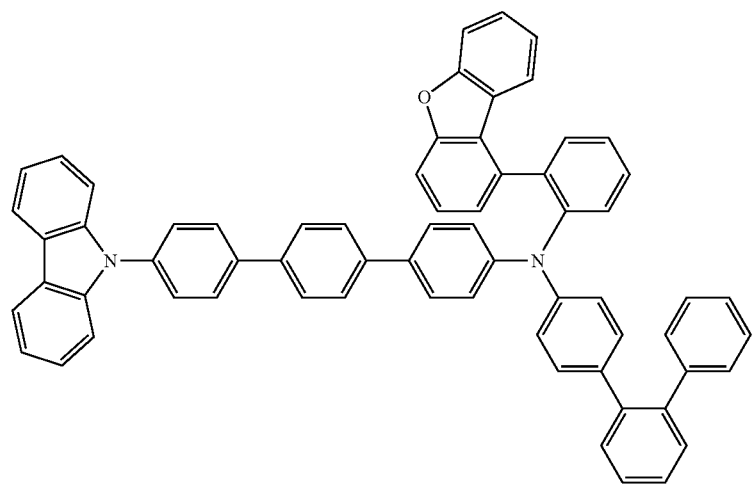
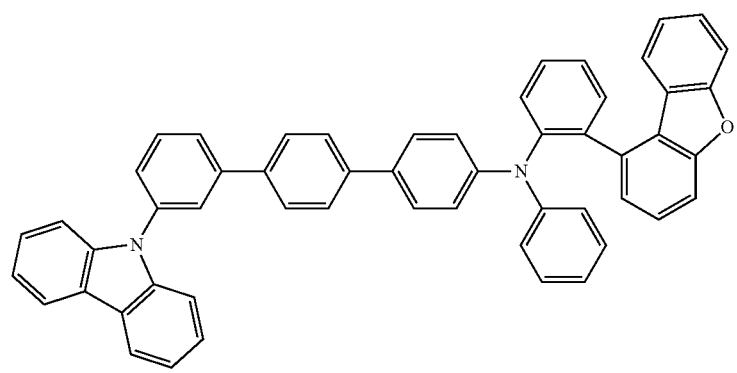

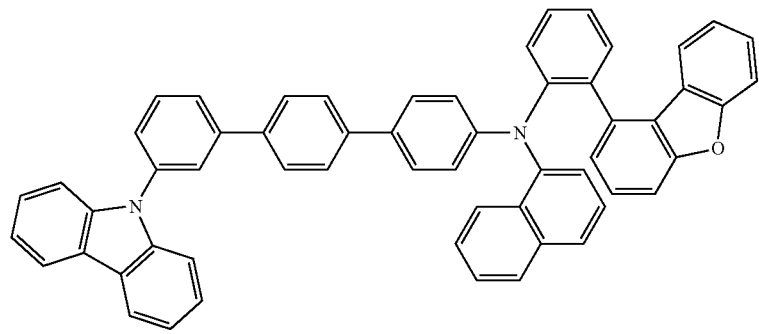
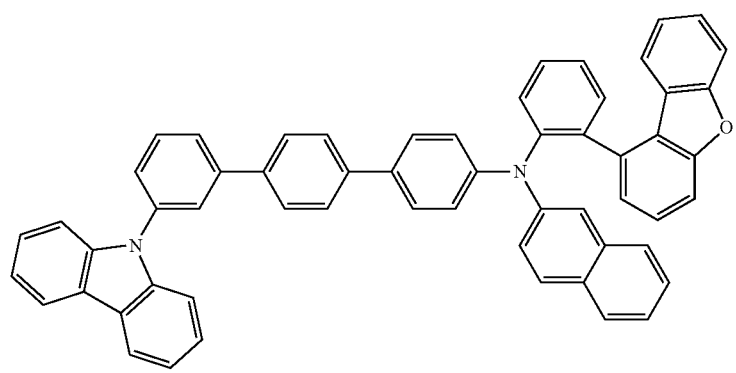
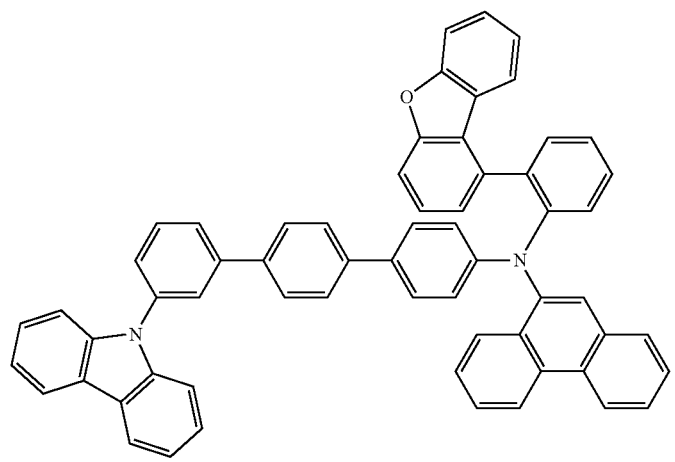
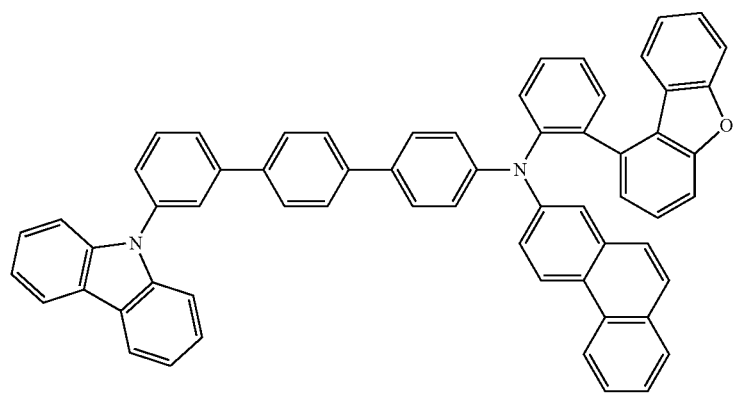

-continued
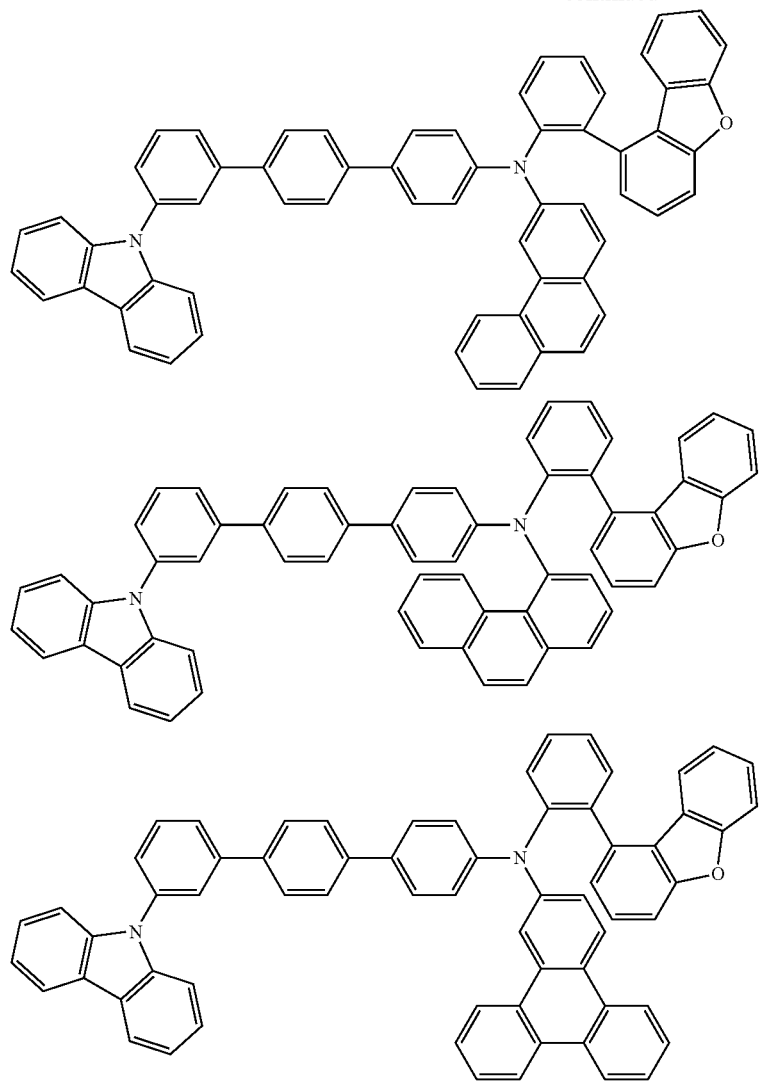
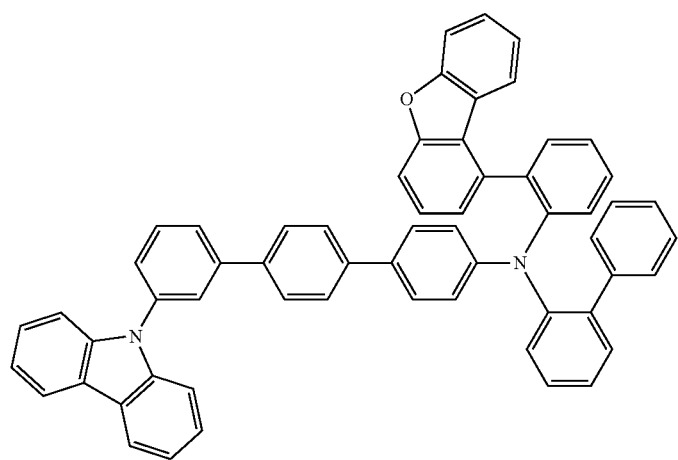

-continued
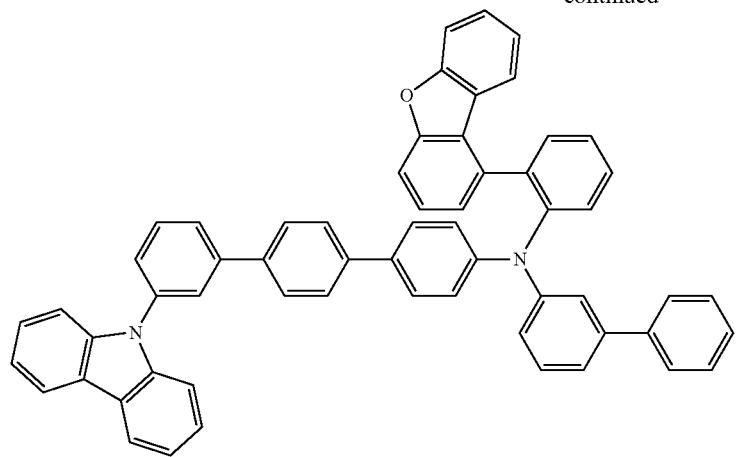
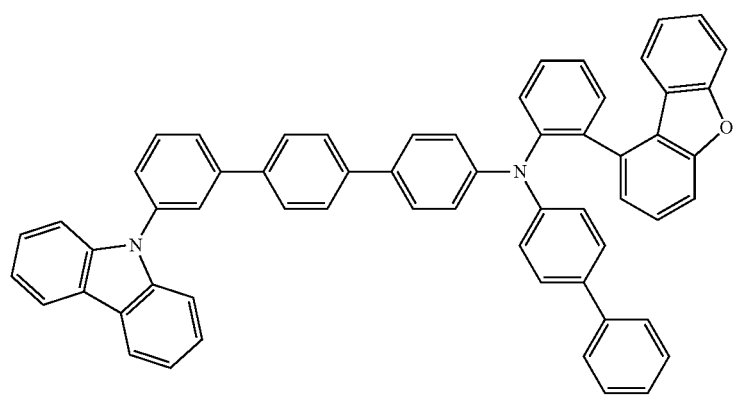
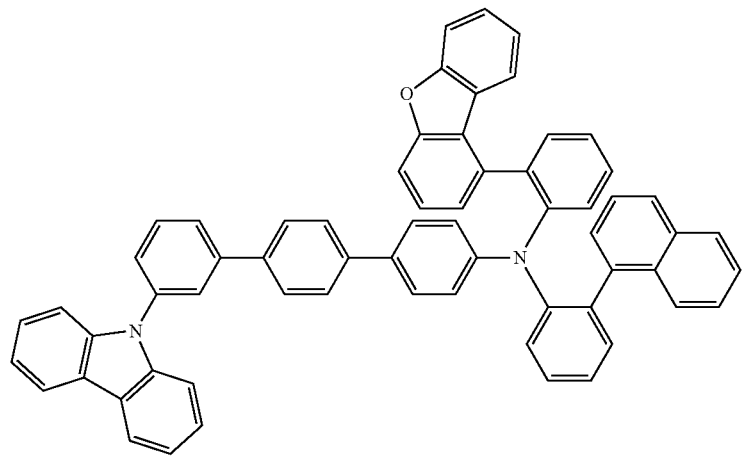

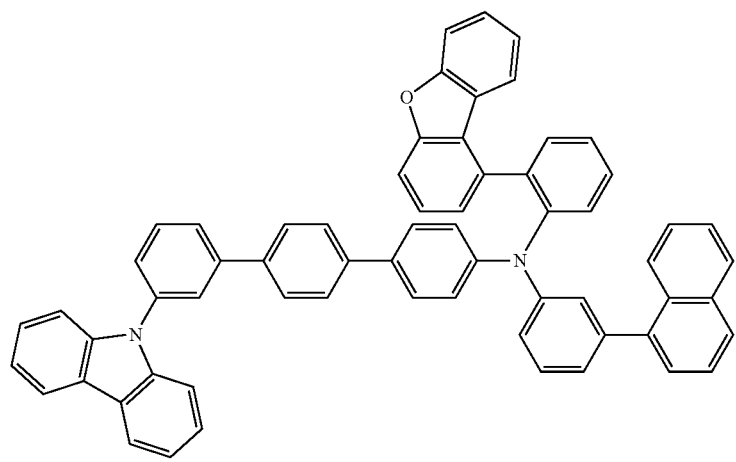
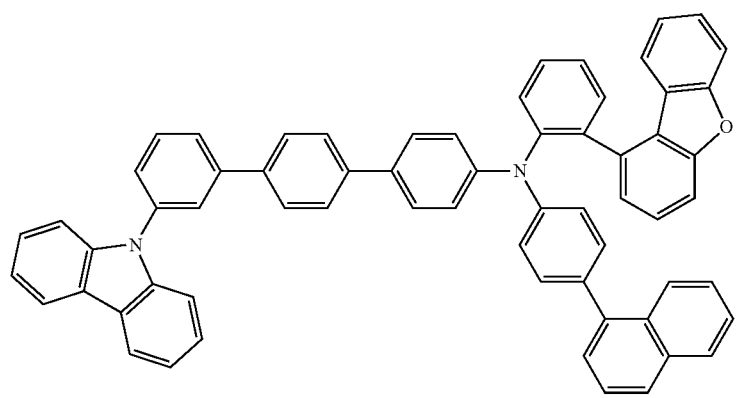
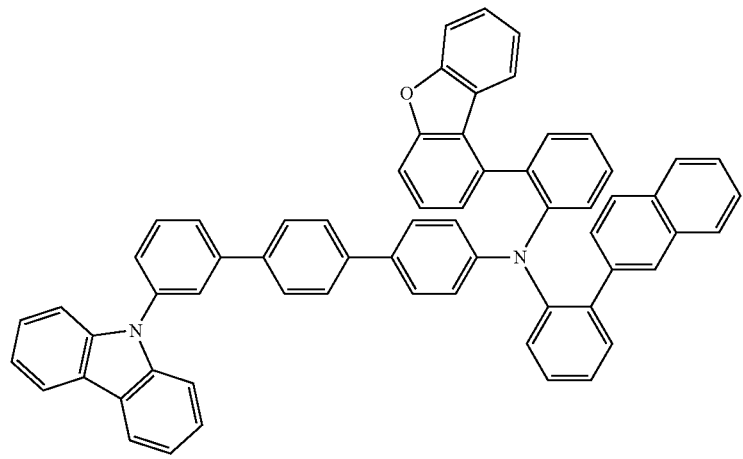

-continued
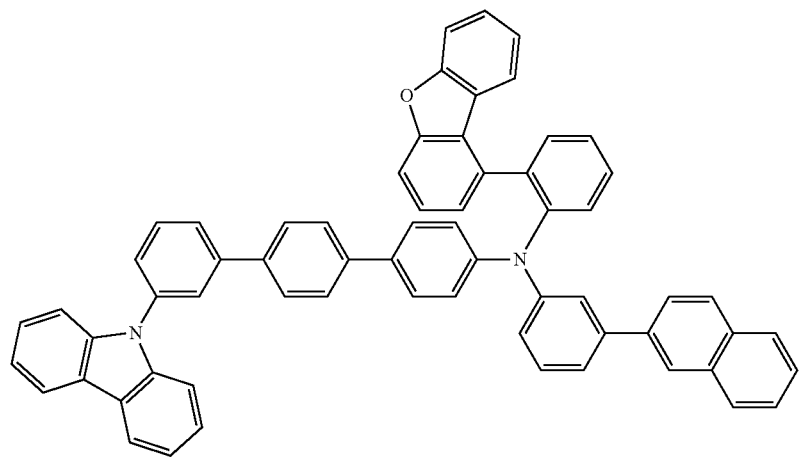
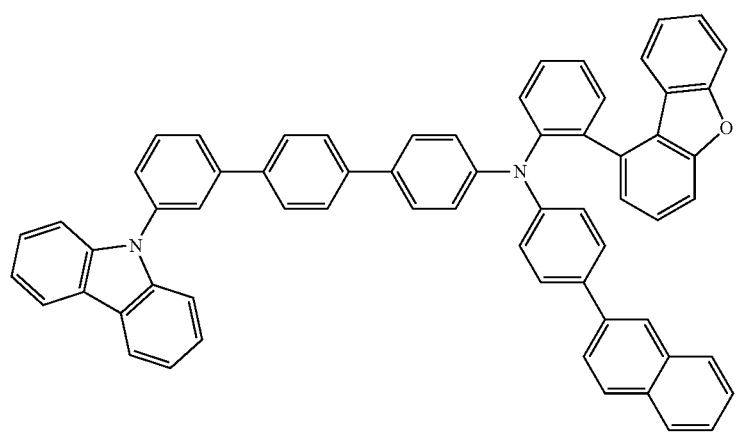
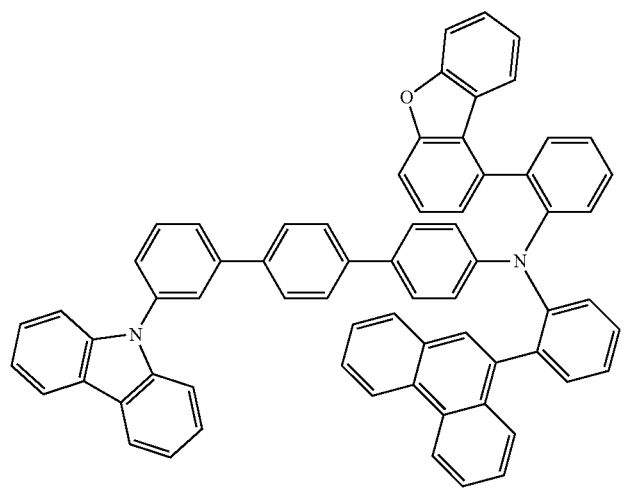

-continued
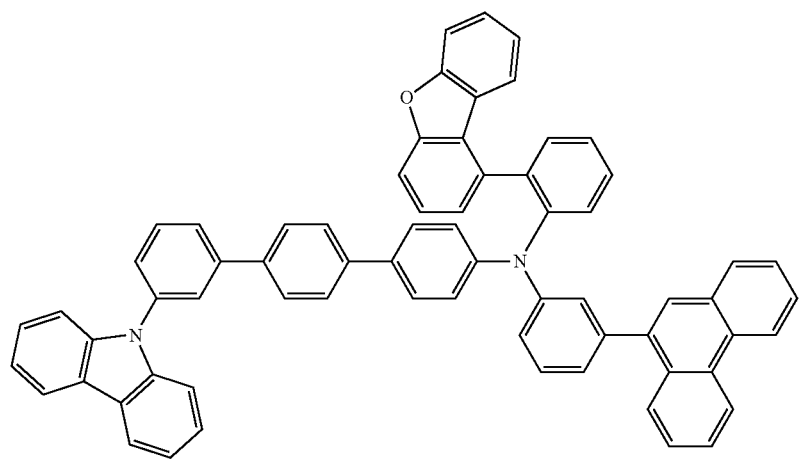
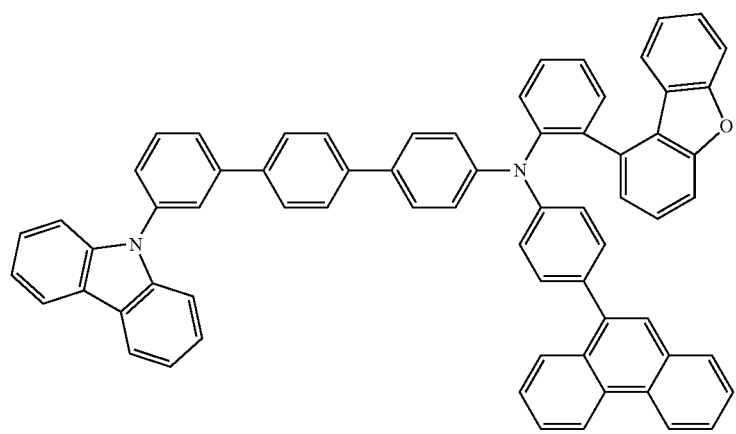
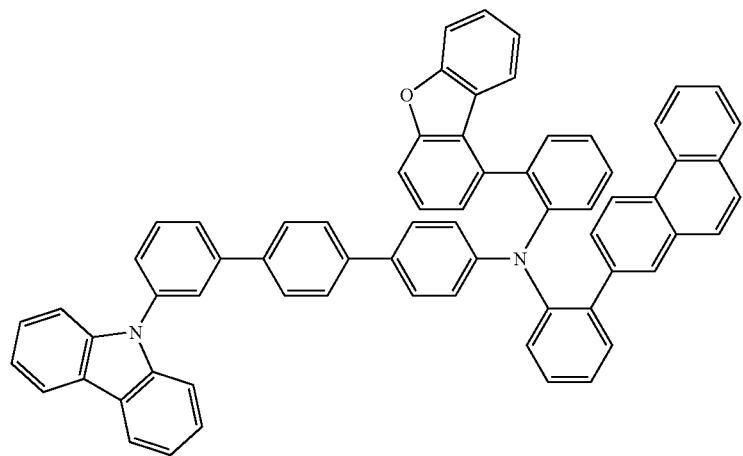

-continued
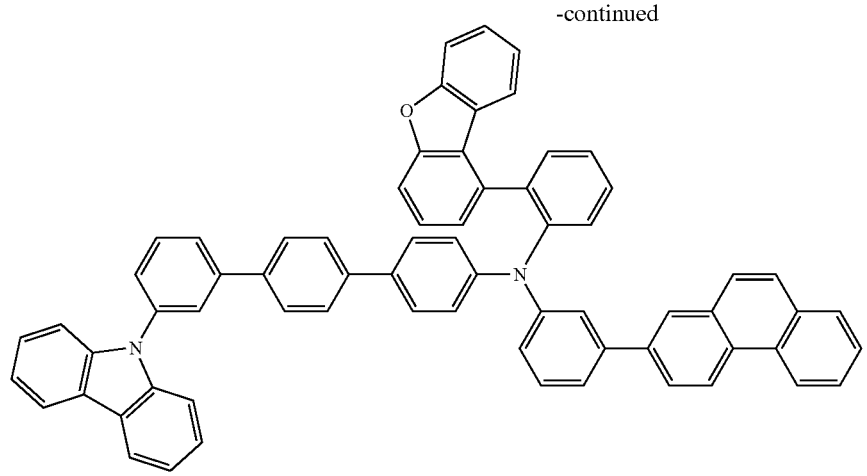
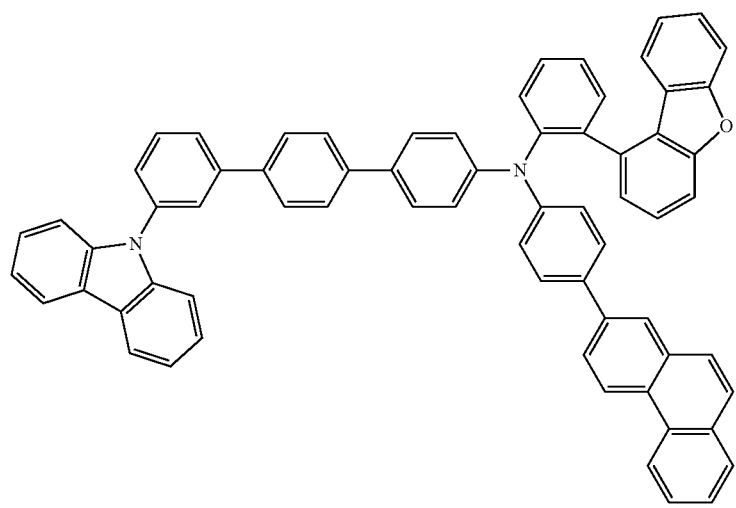
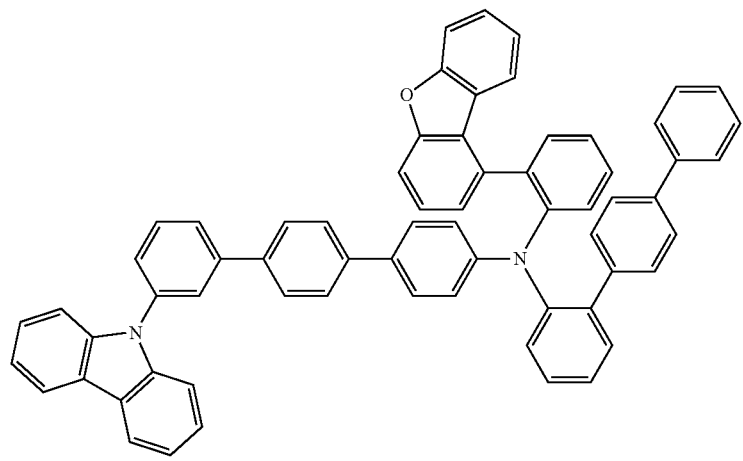 [SMILES: c1ccc(-c2ccc(-c3ccccc3N(c3ccc(-c4ccc(-c5cccc(-n6c7ccccc7c7ccccc76)c5)cc4)cc3)c3ccccc3-c3cccc4oc5ccccc5c34)cc2)cc1]

-continued
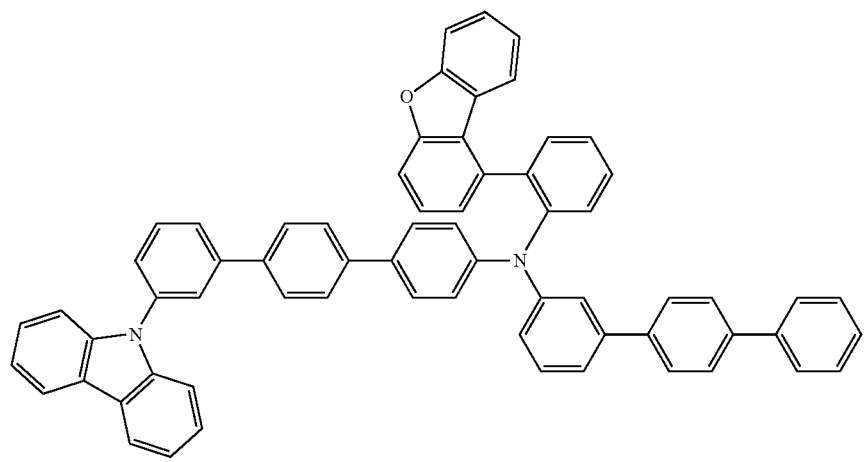
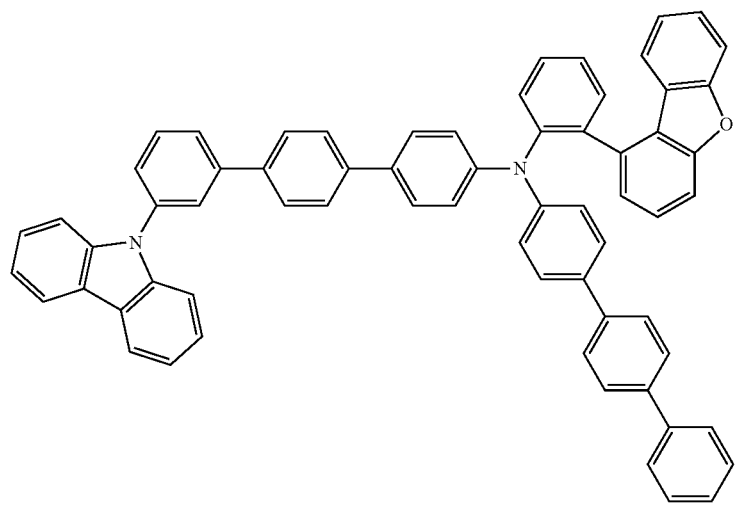

-continued
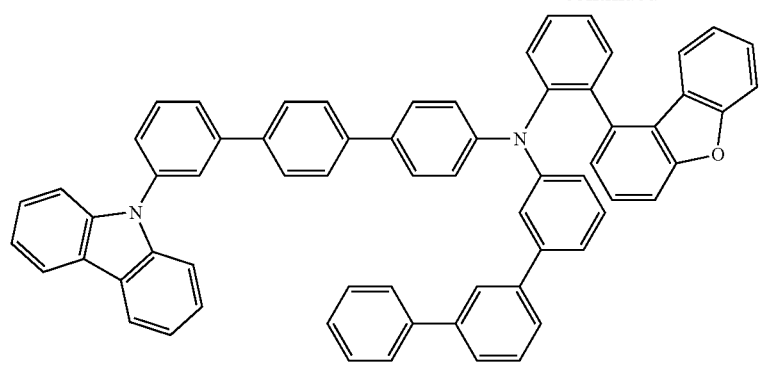
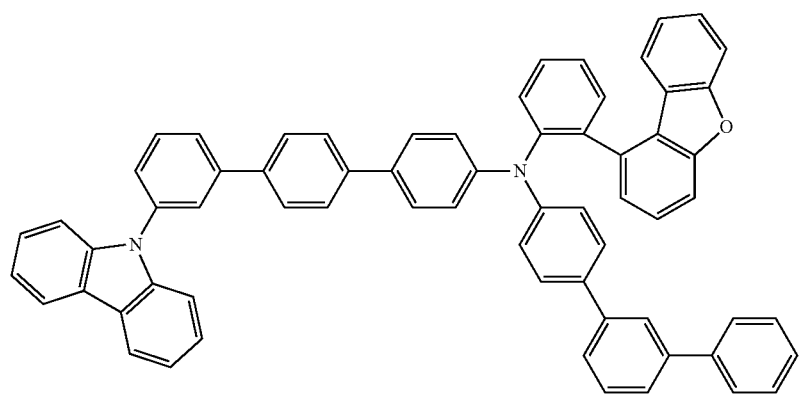
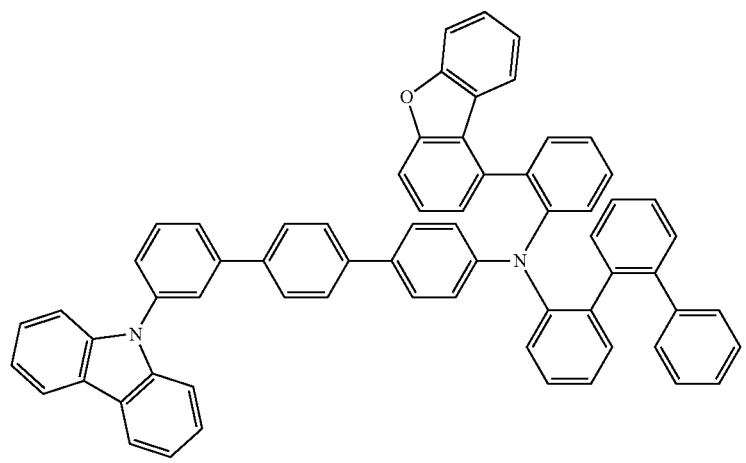
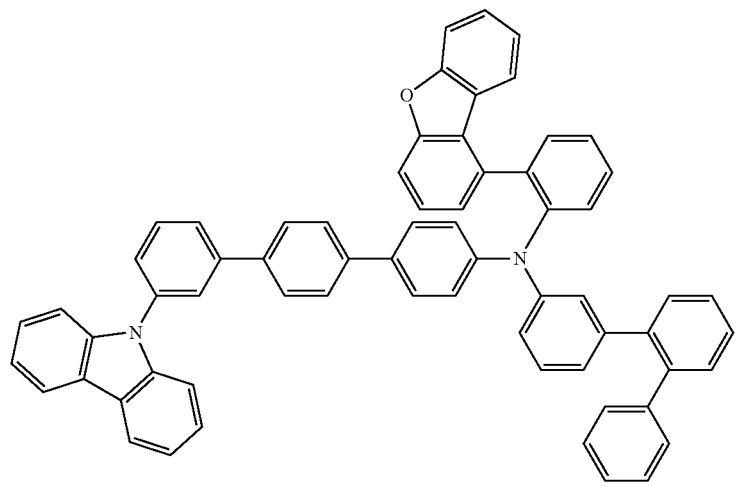

-continued
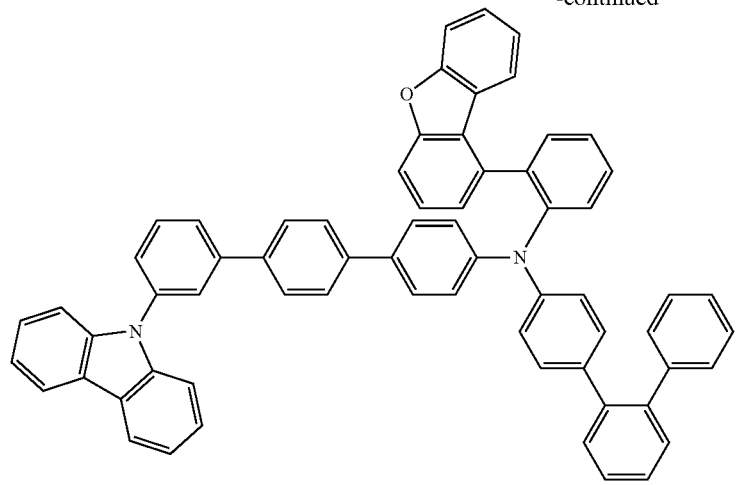
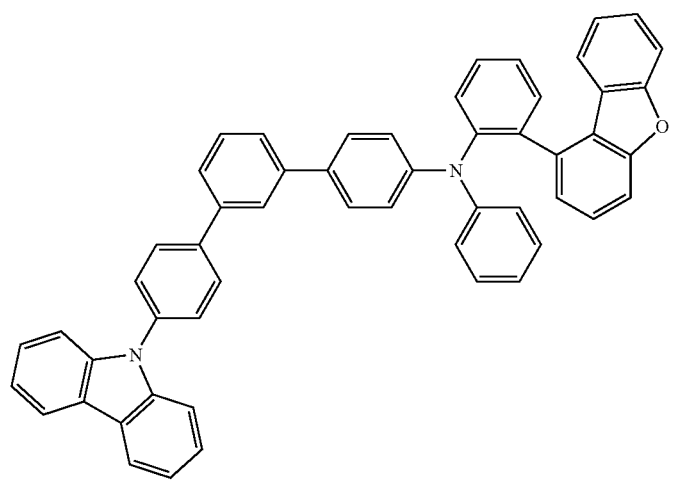
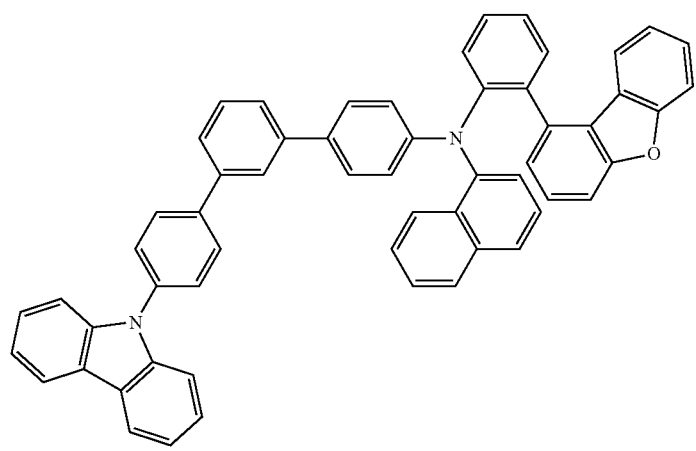

-continued
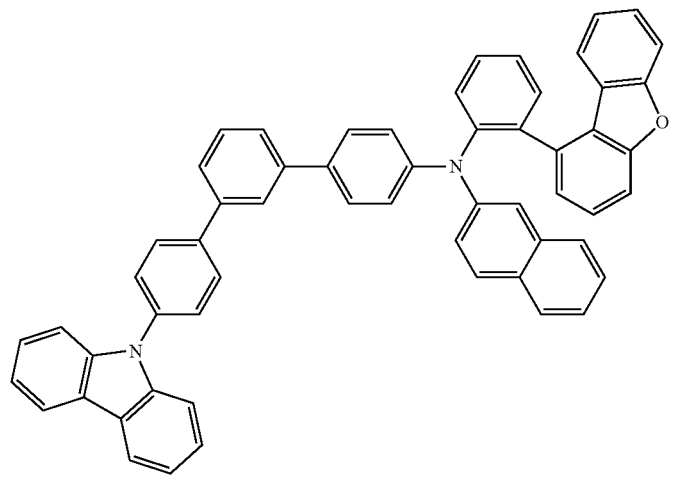
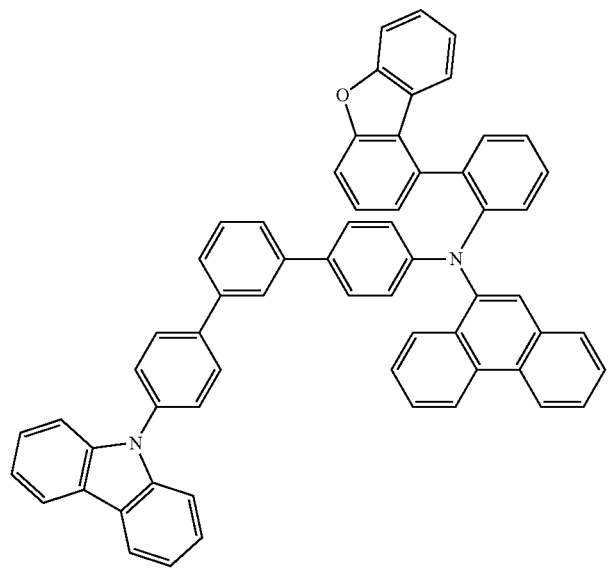
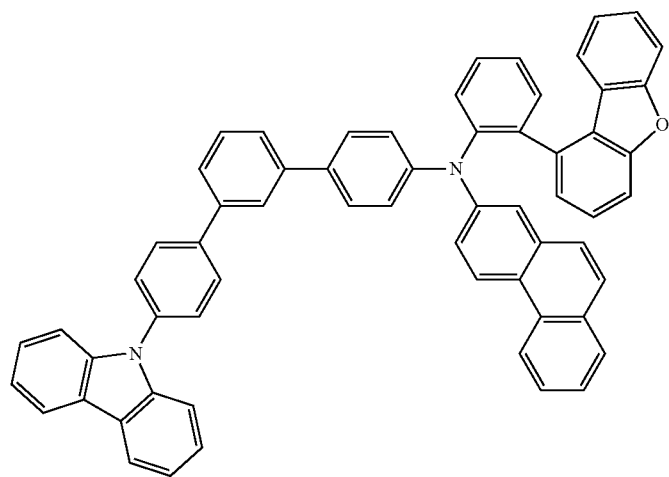

-continued
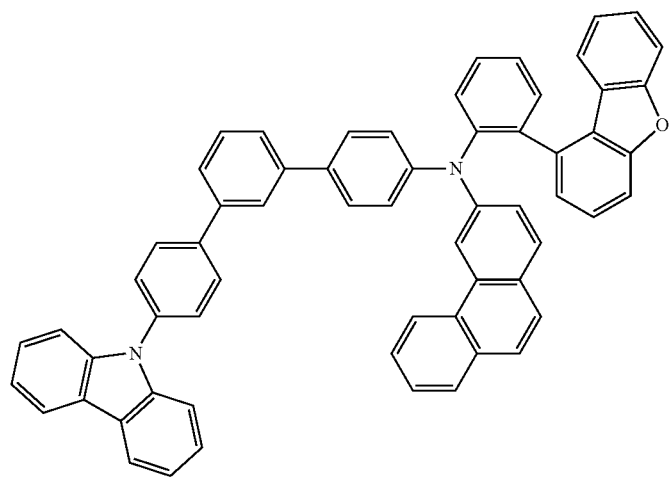
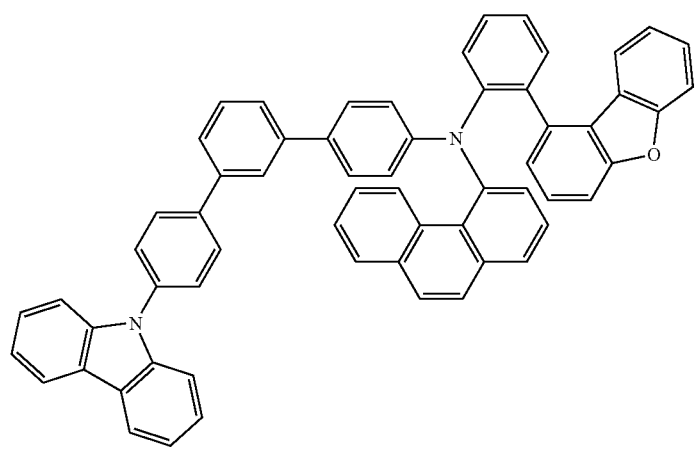
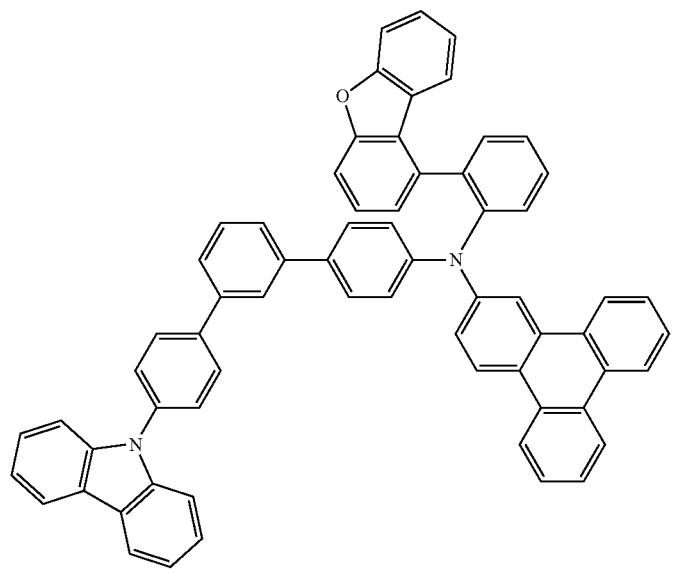

-continued
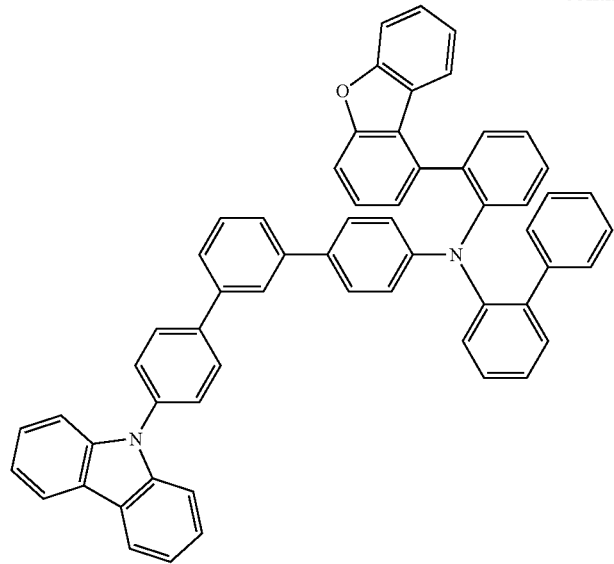
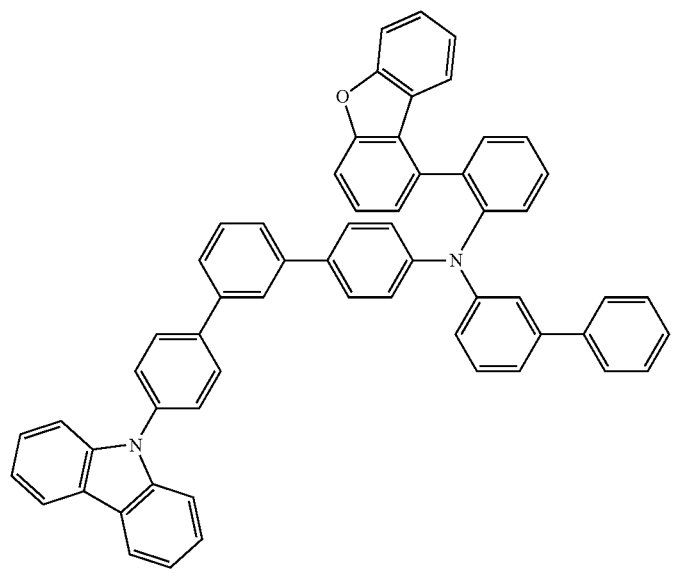
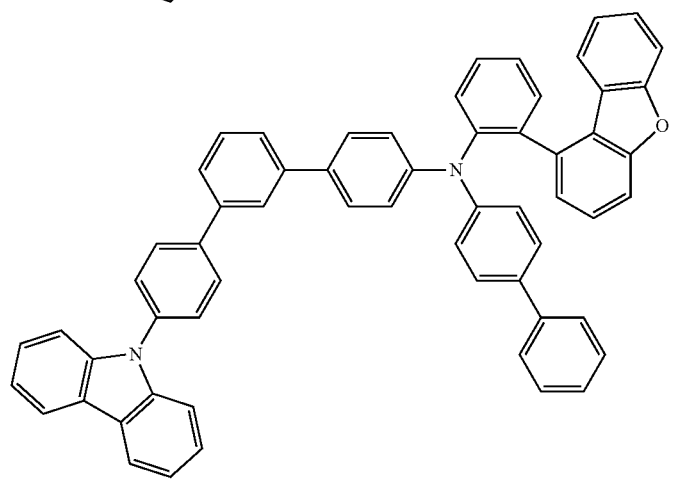

-continued
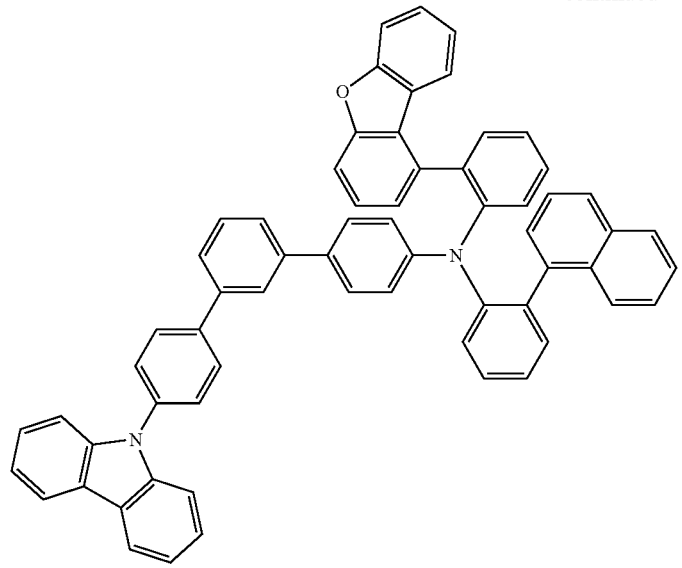
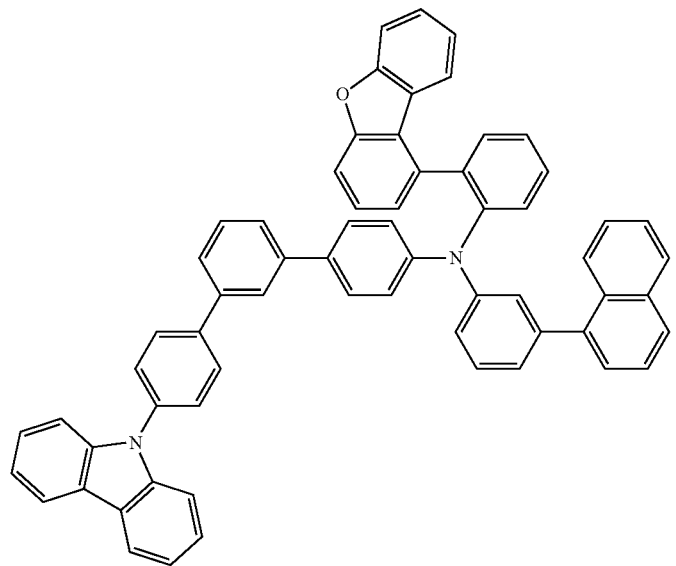
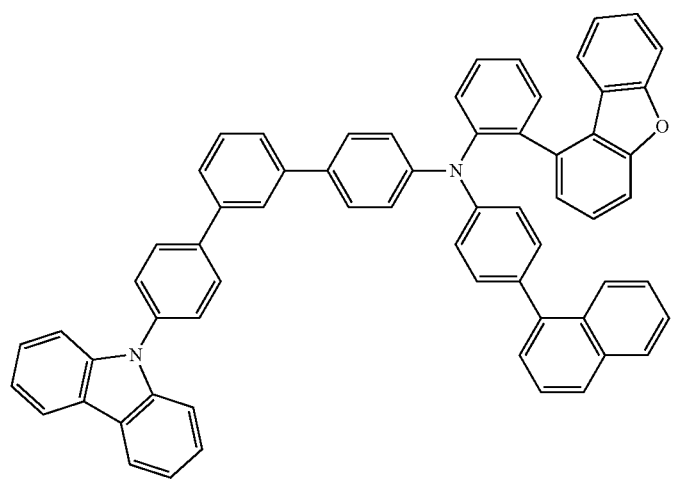

-continued
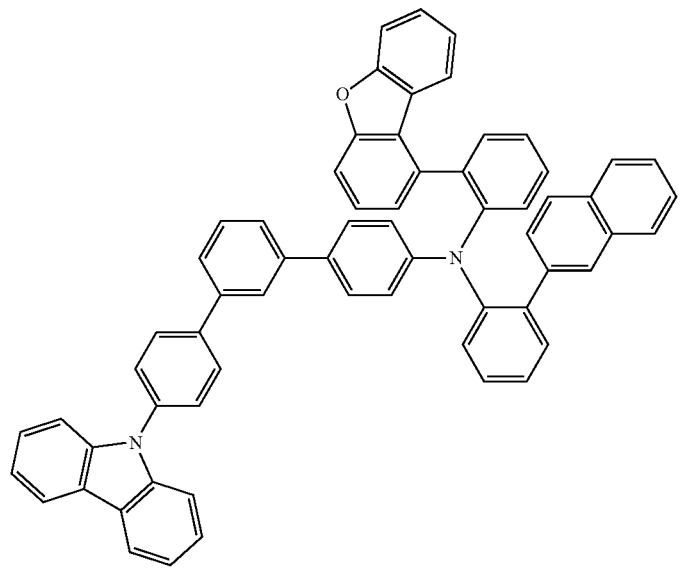
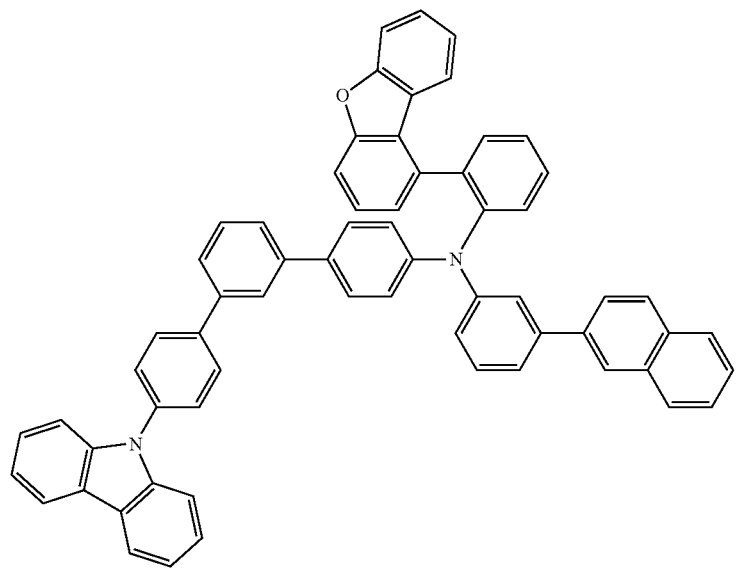
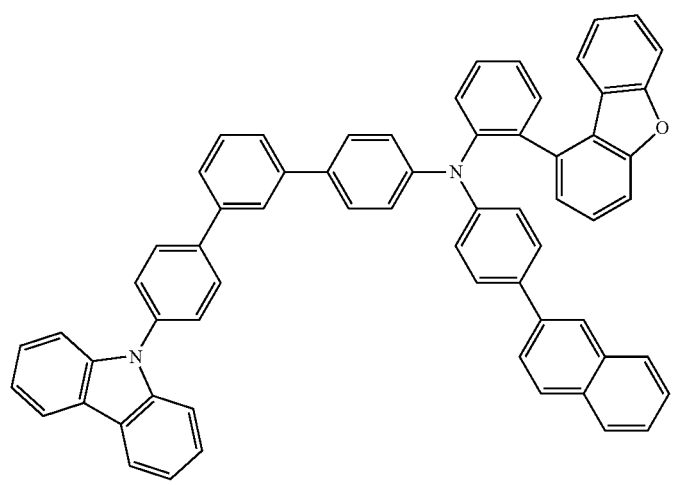

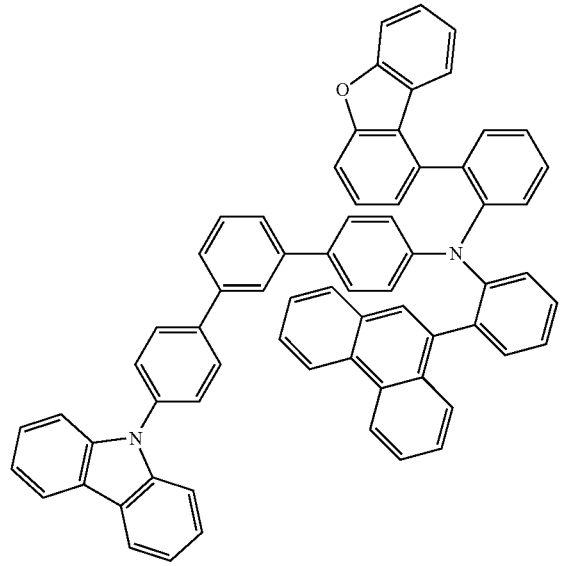
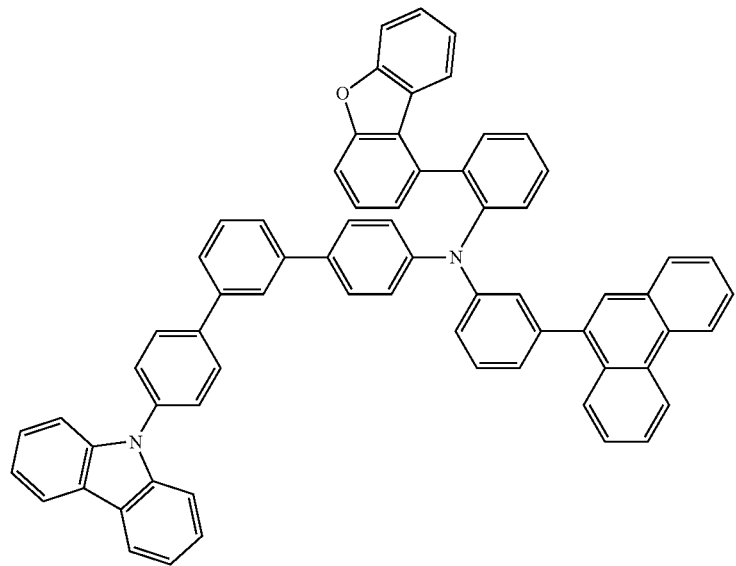
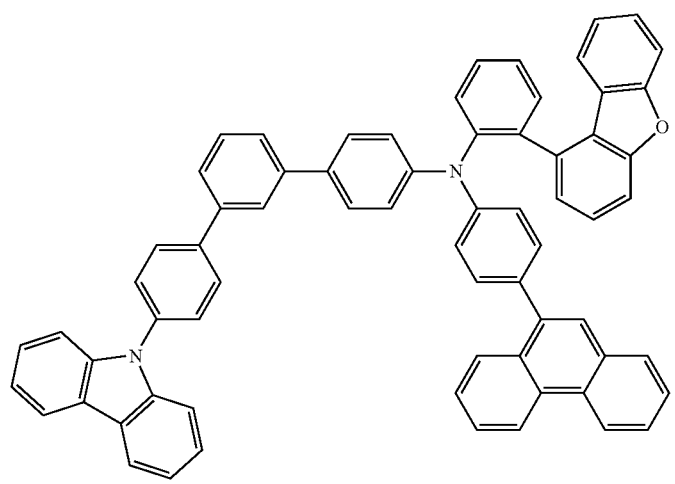

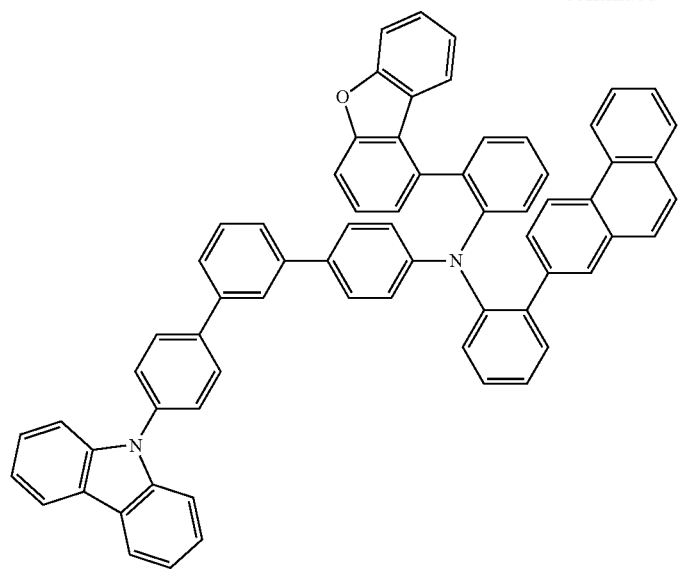
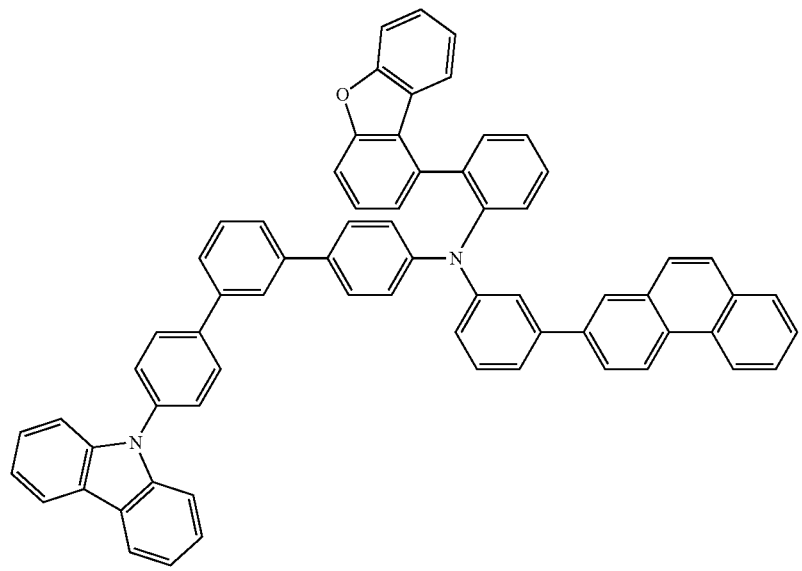
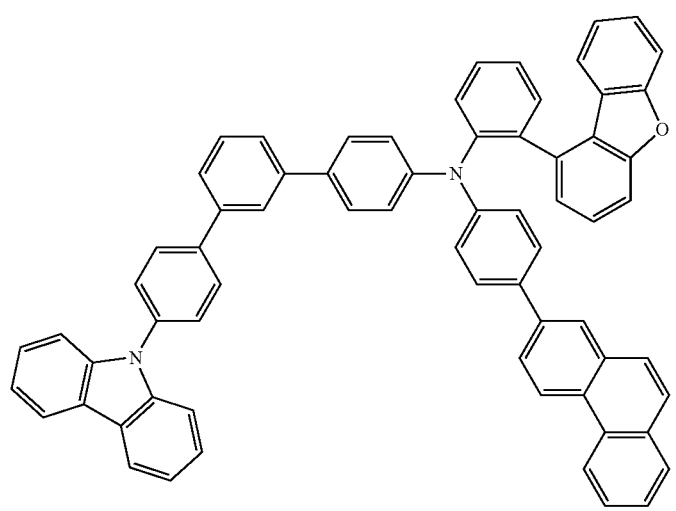

-continued
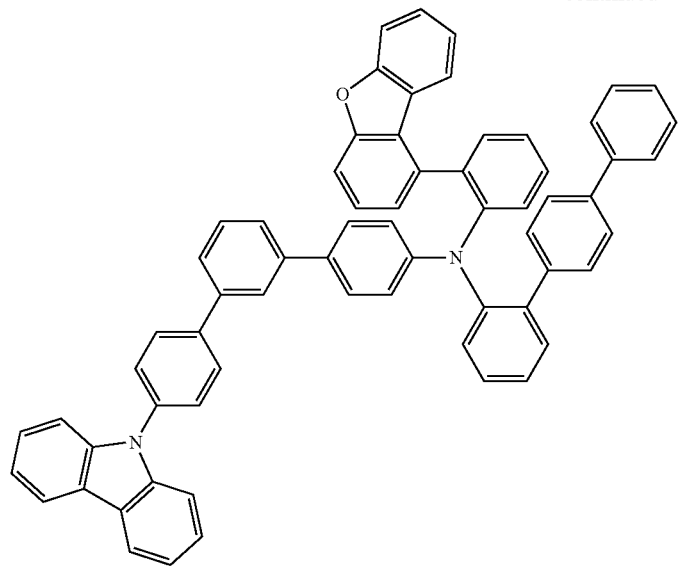
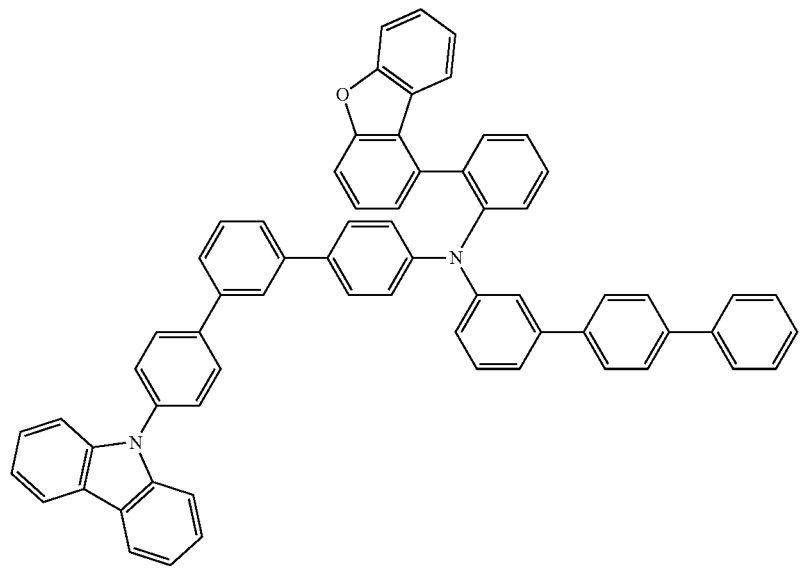
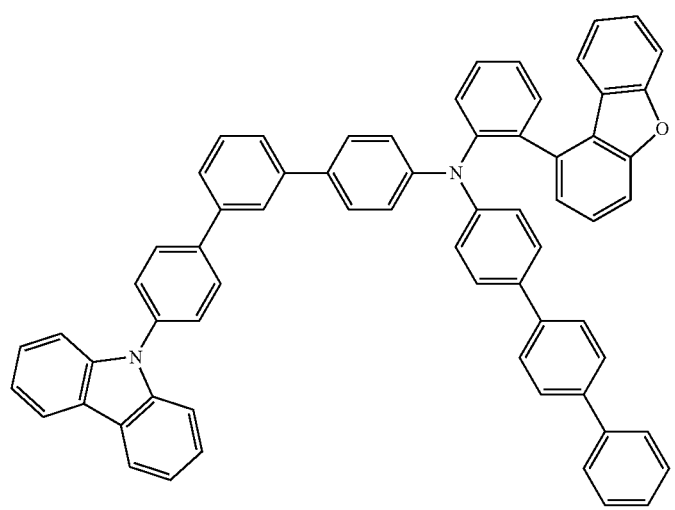

-continued
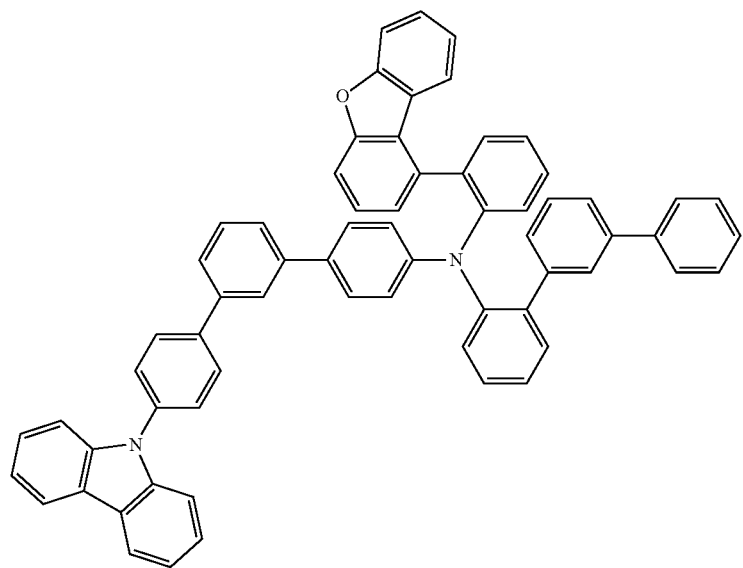
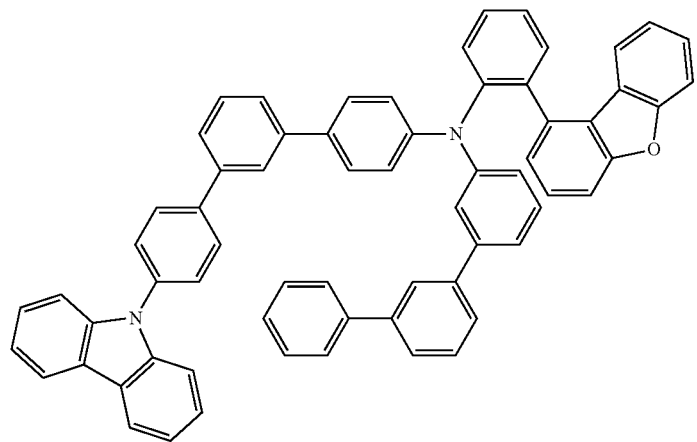
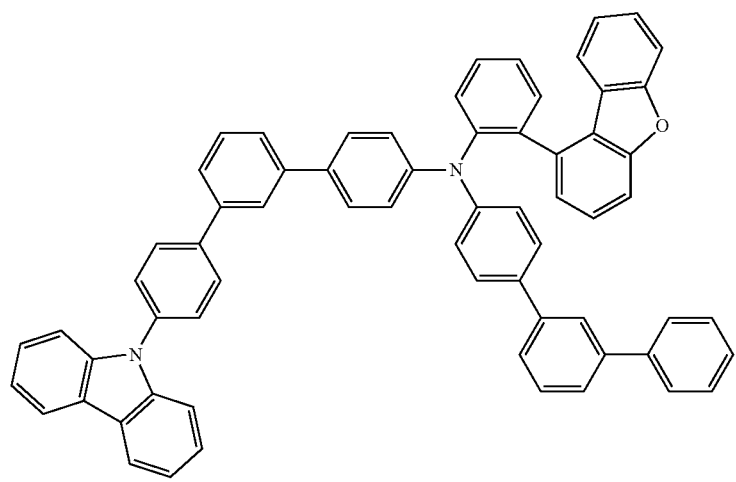

-continued
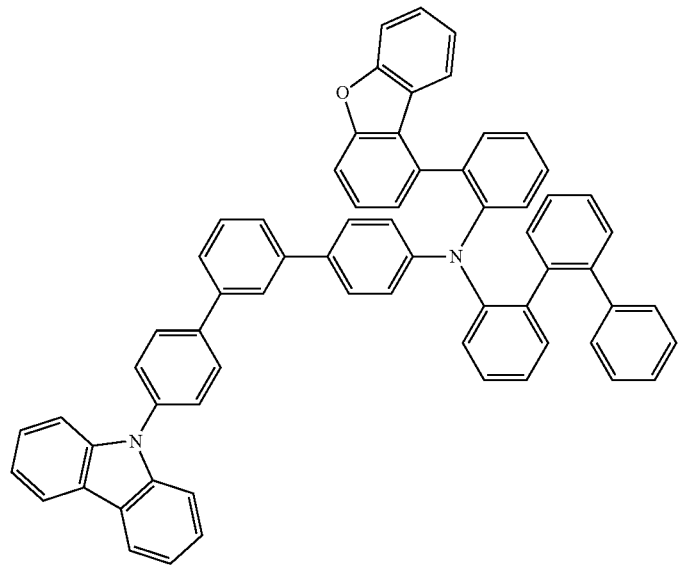
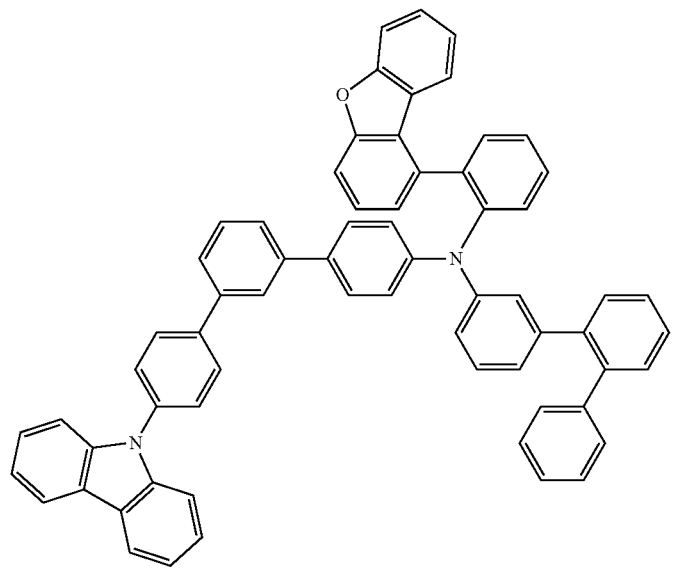
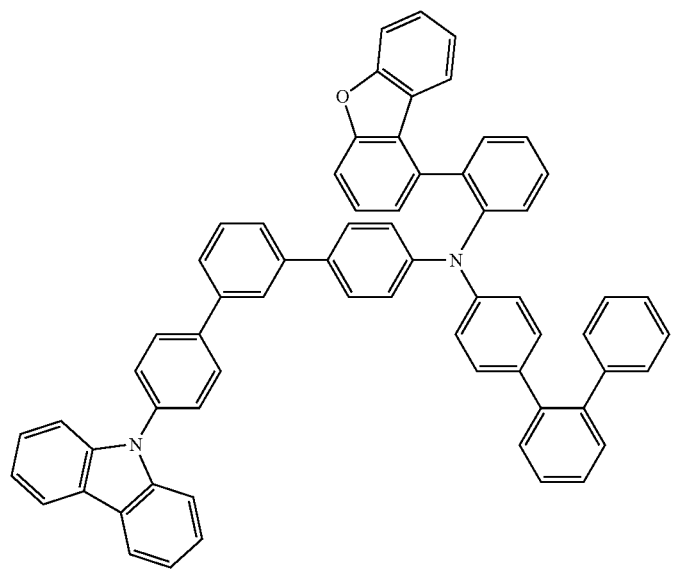

-continued
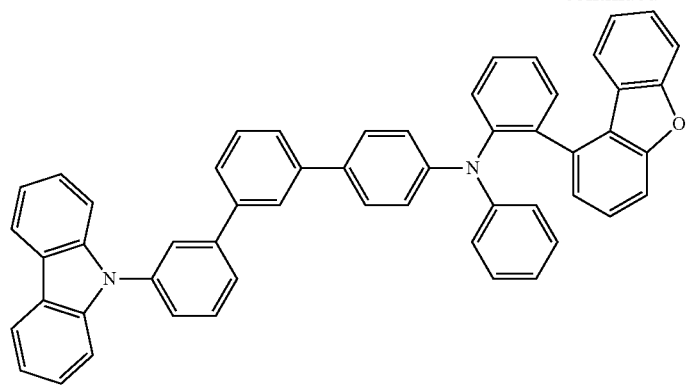
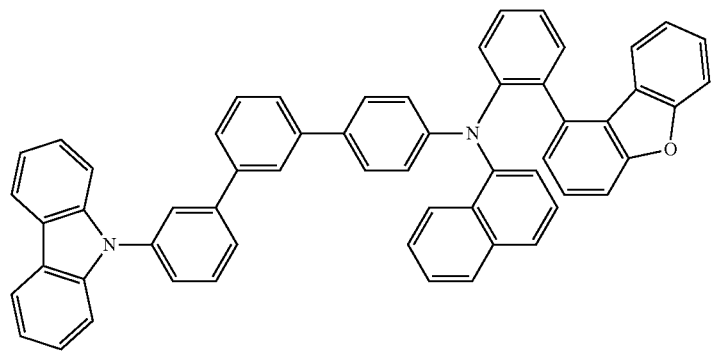
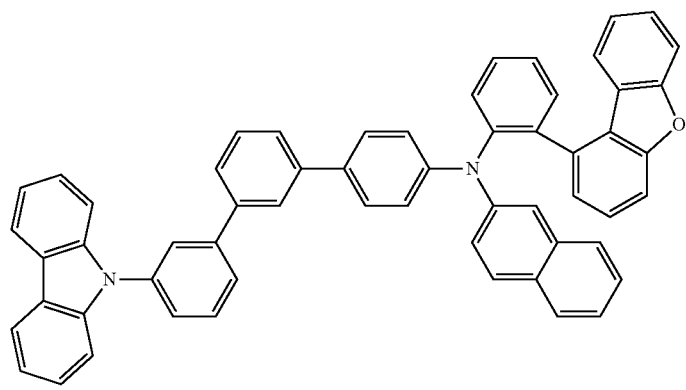
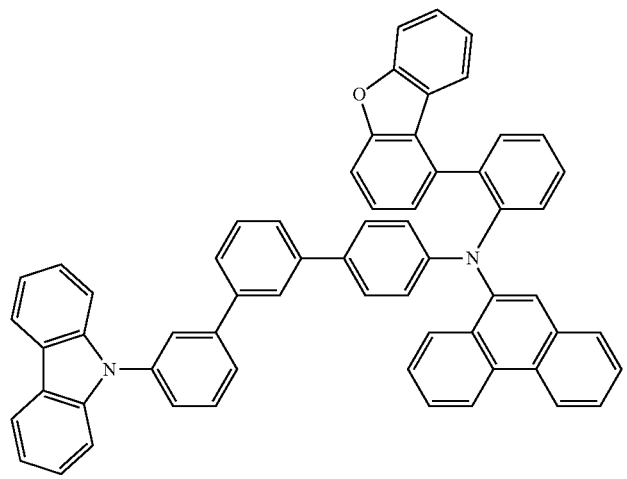

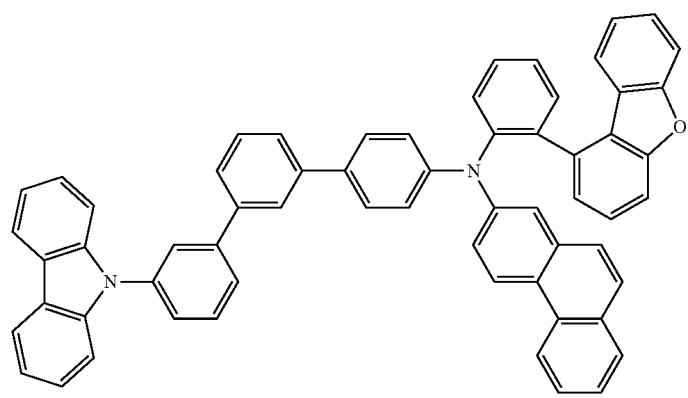
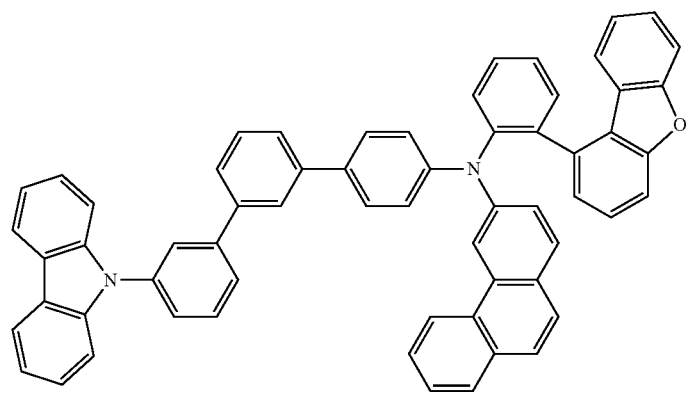
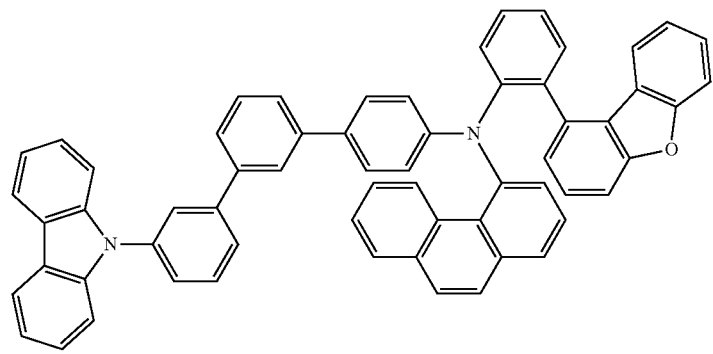
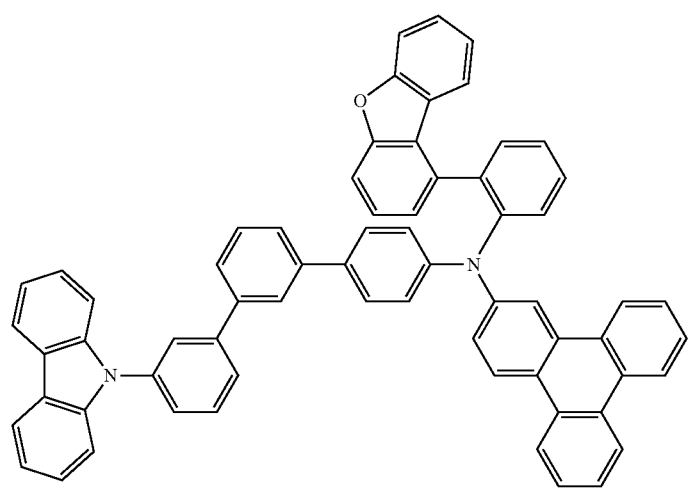

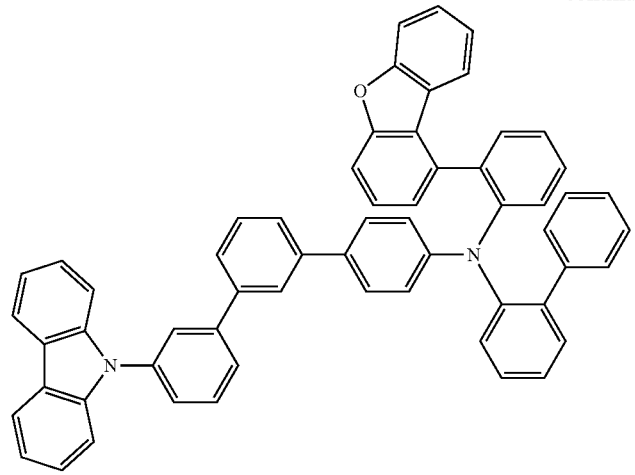
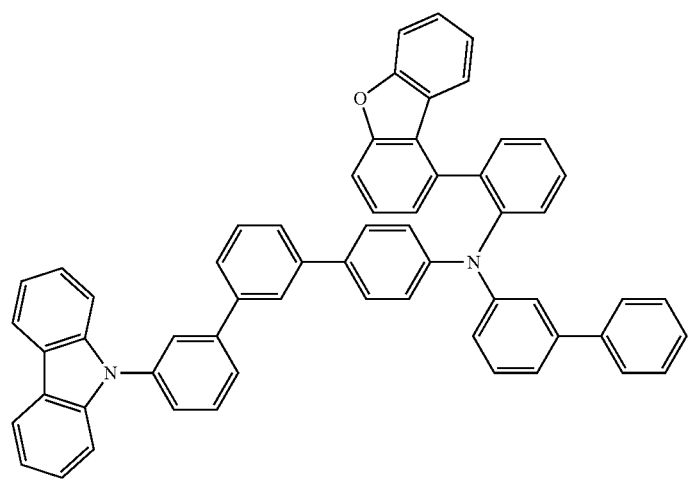
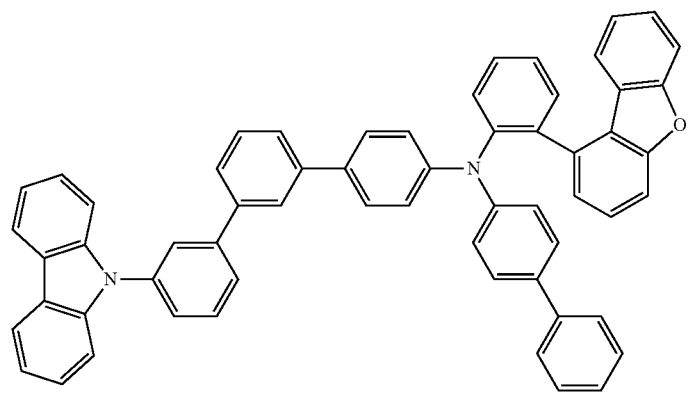

-continued
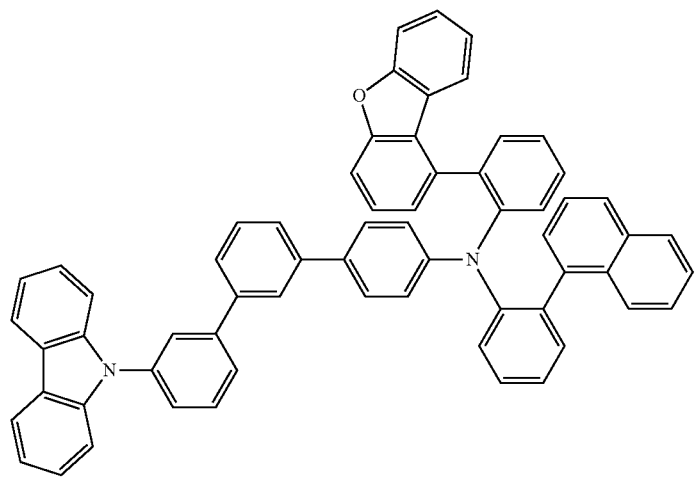

-continued
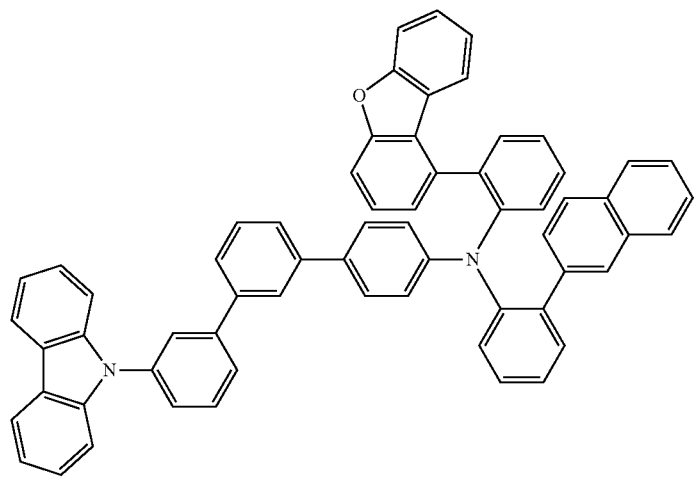
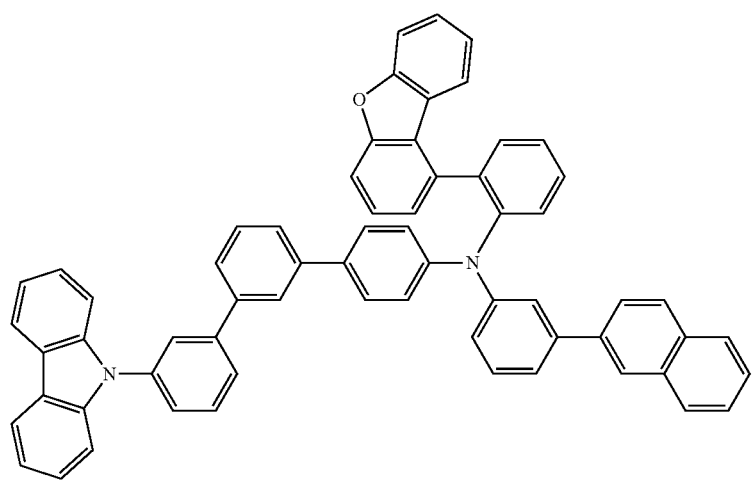
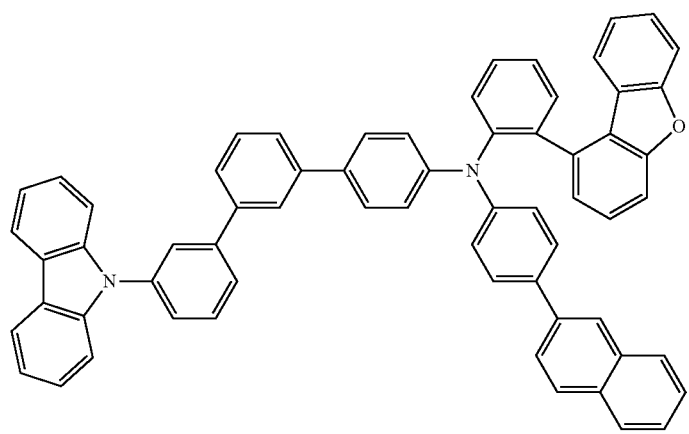

-continued
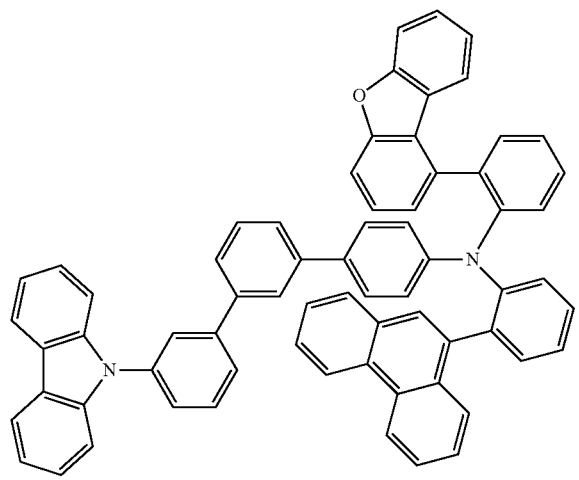
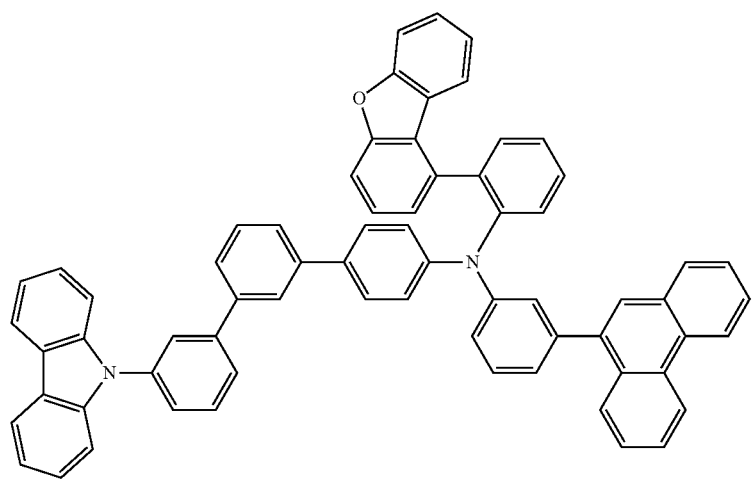
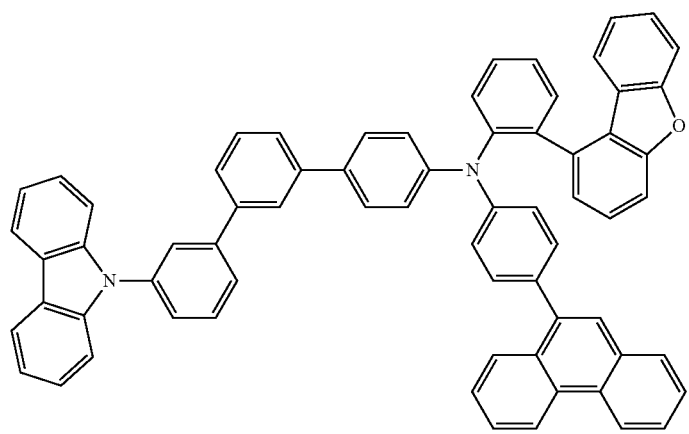

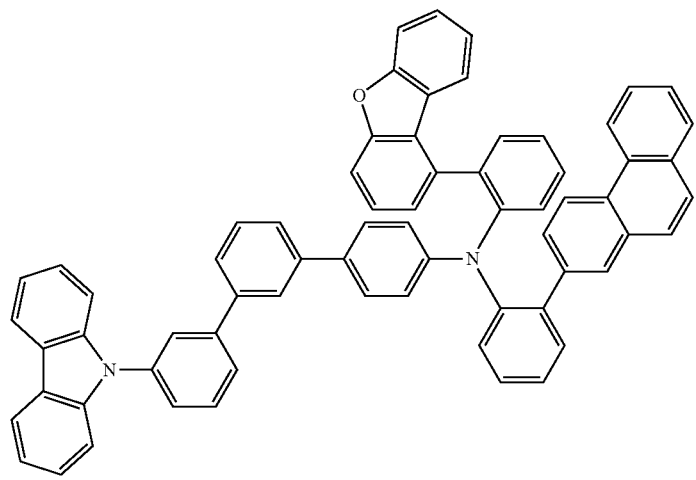
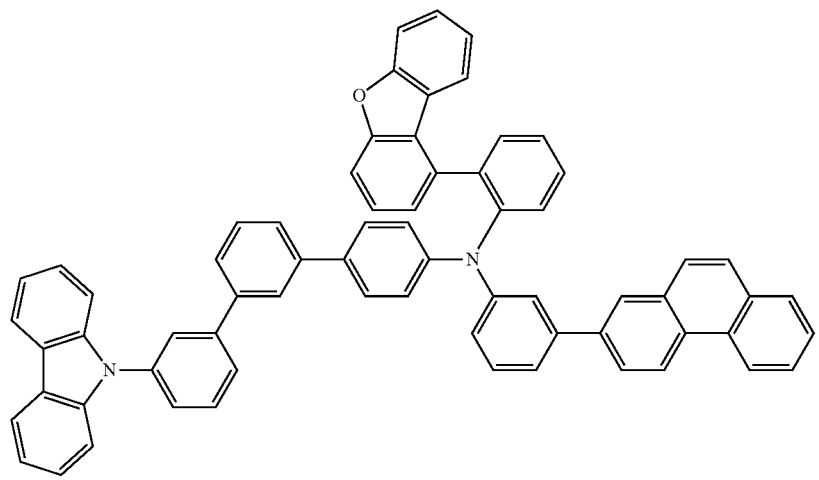
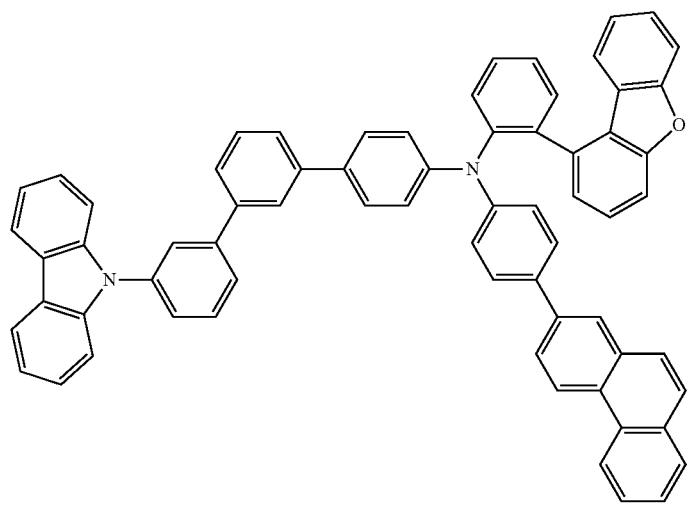

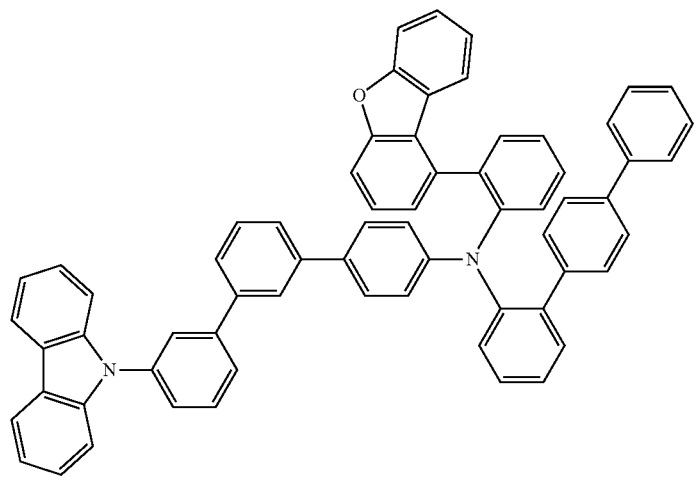
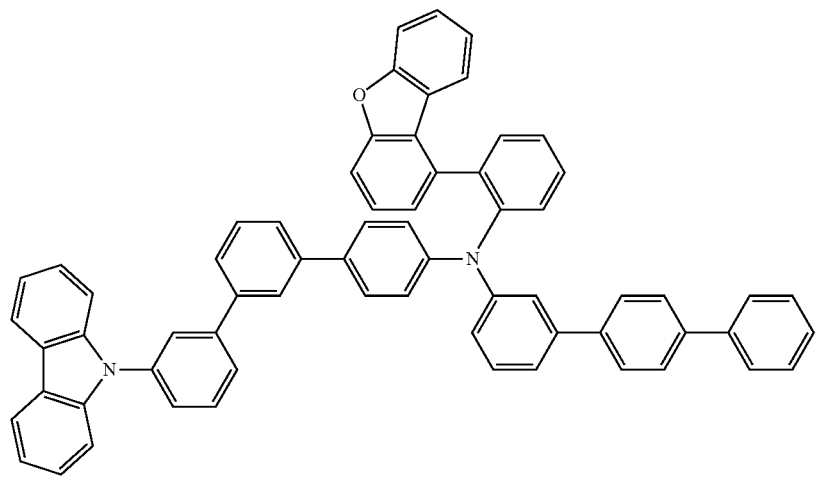
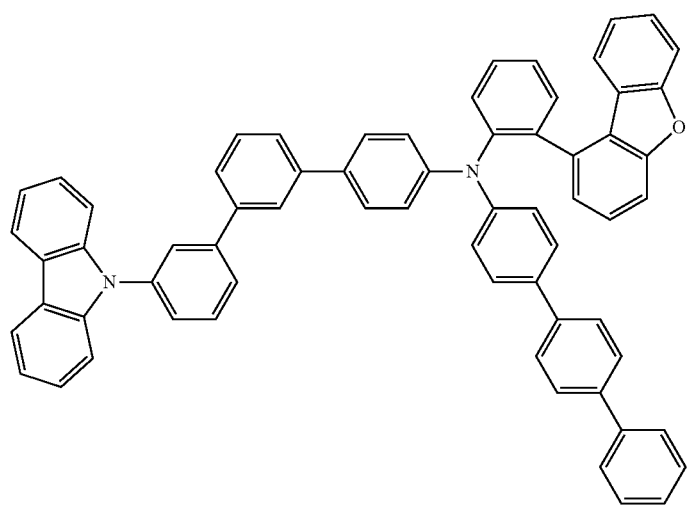

-continued
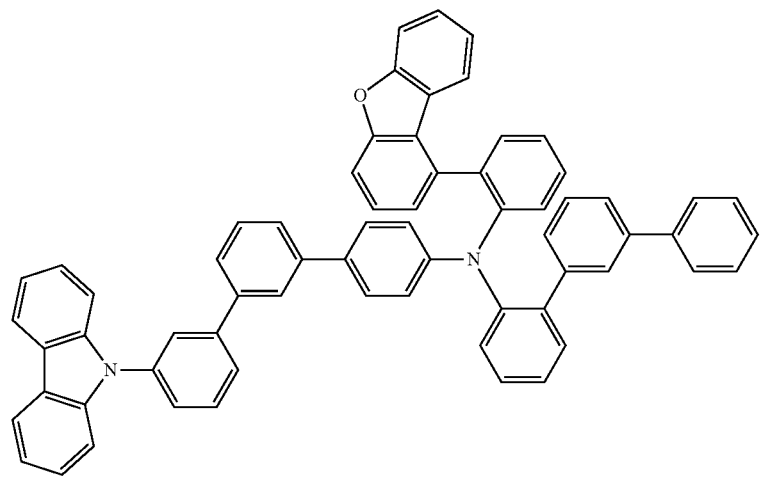
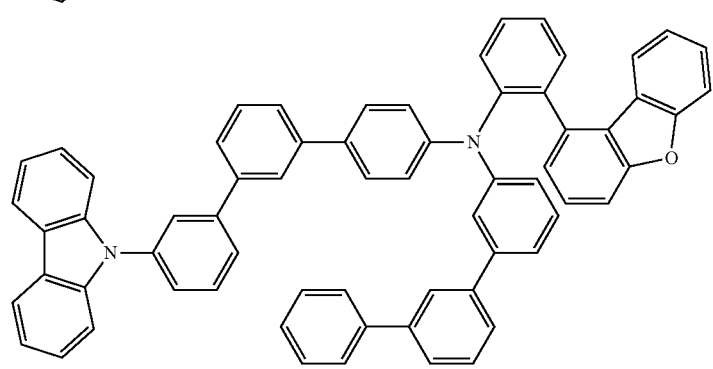
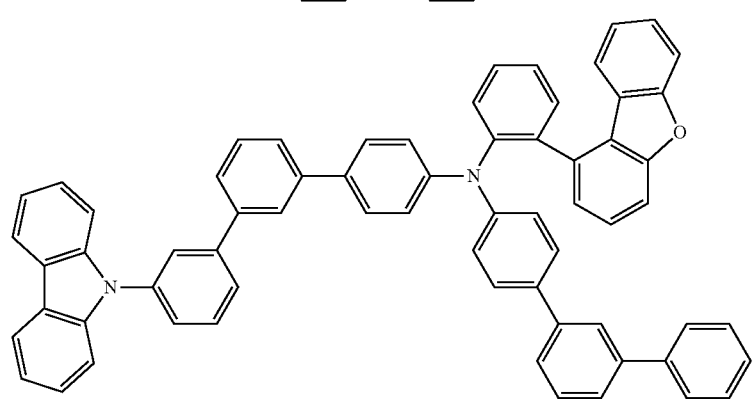
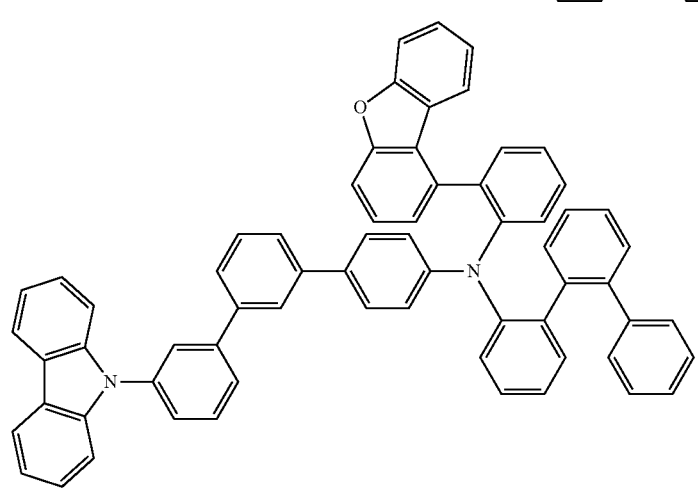

419
-continued
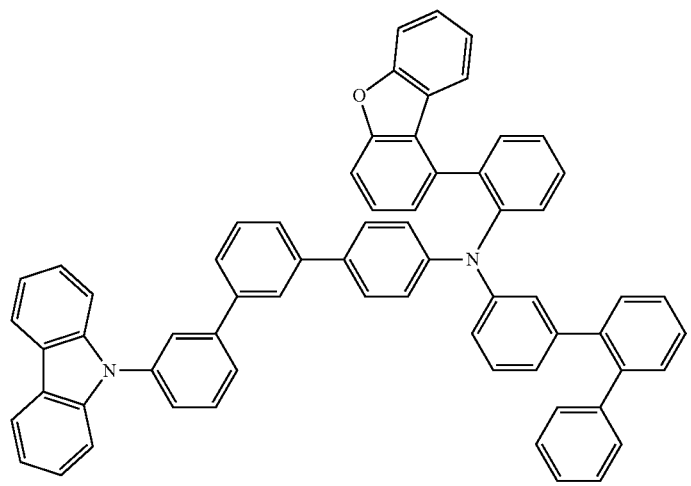
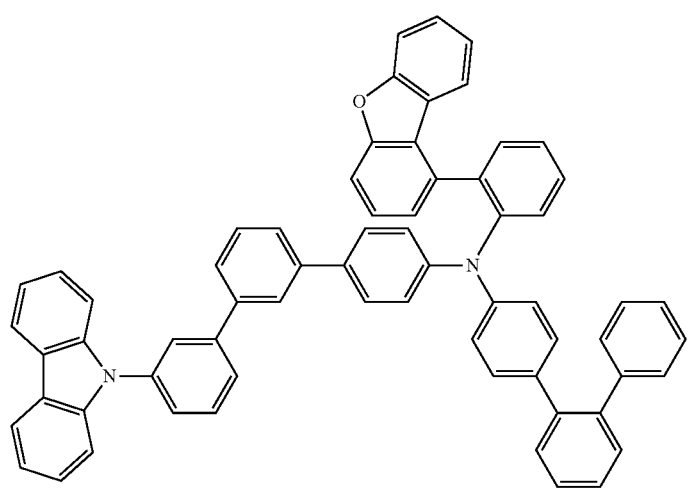
420
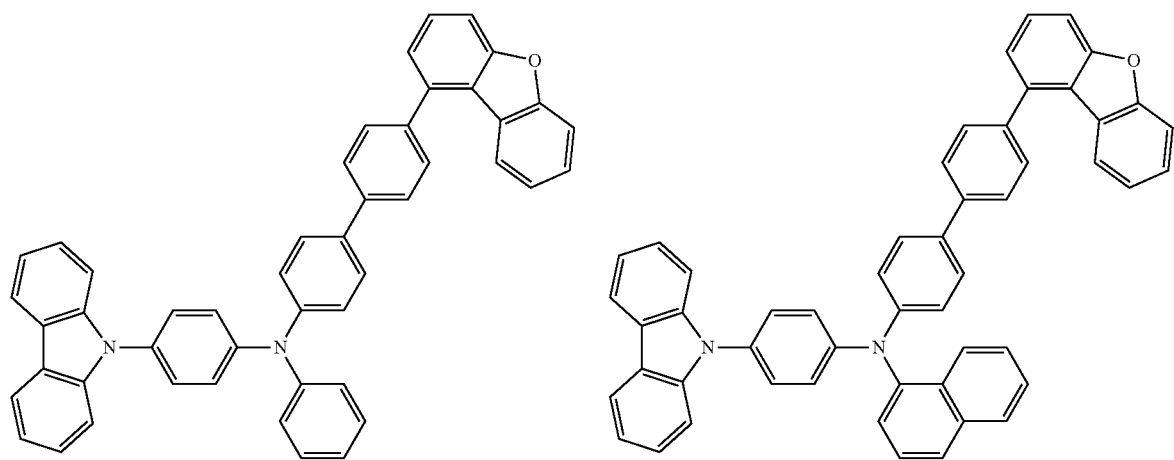

-continued
421
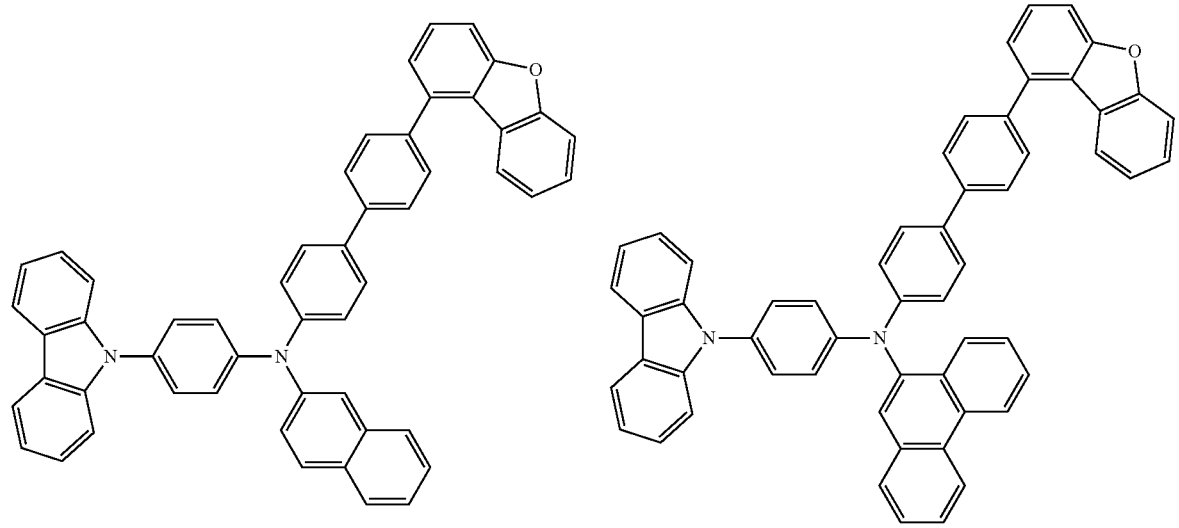
422
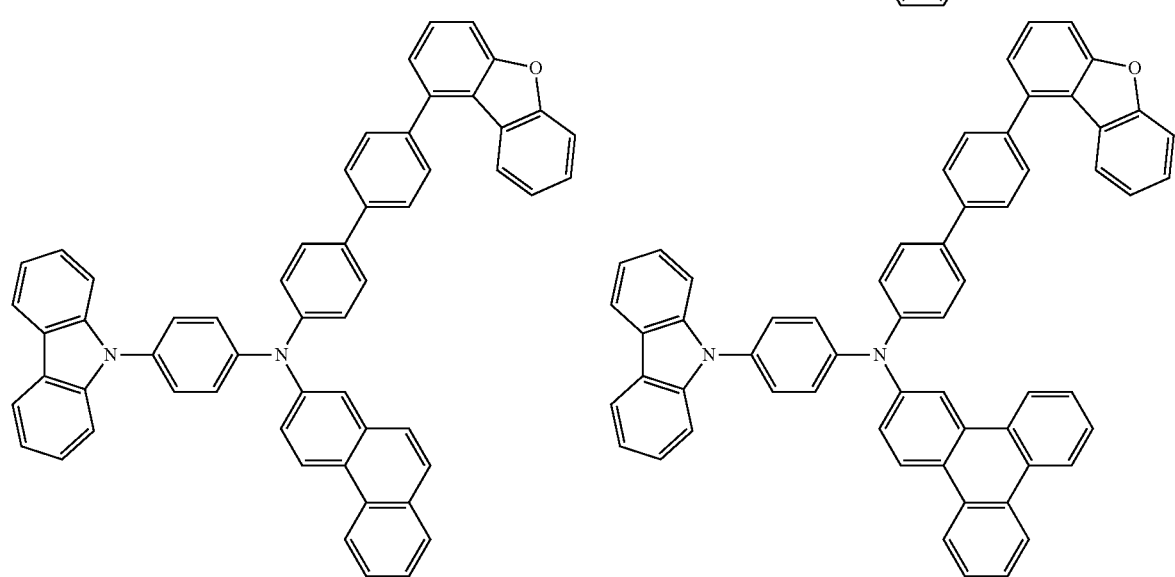
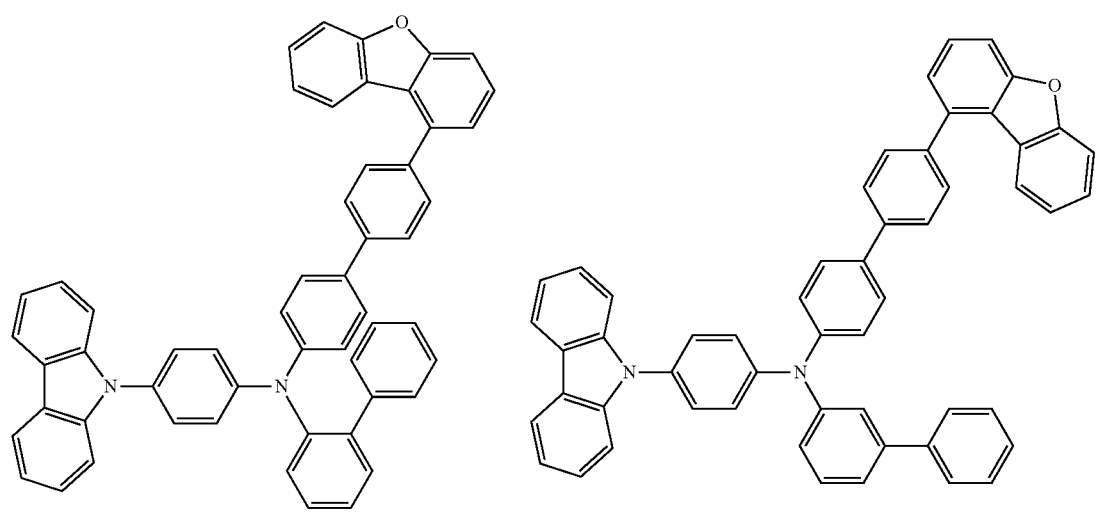

-continued
423
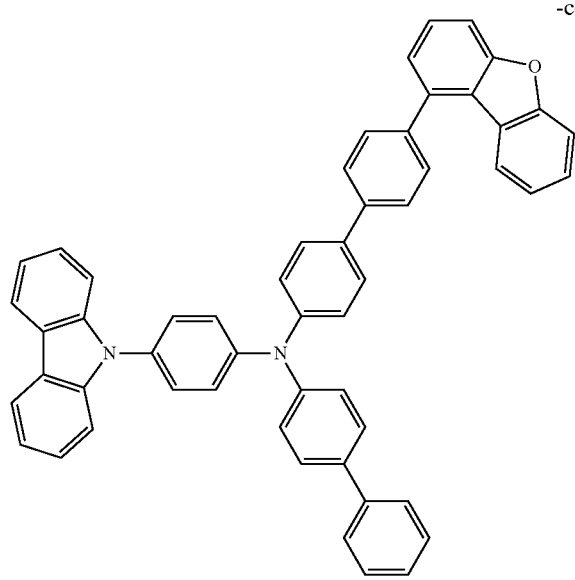
424
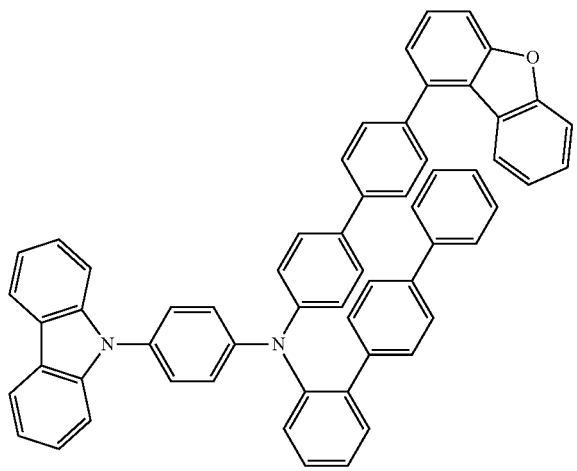
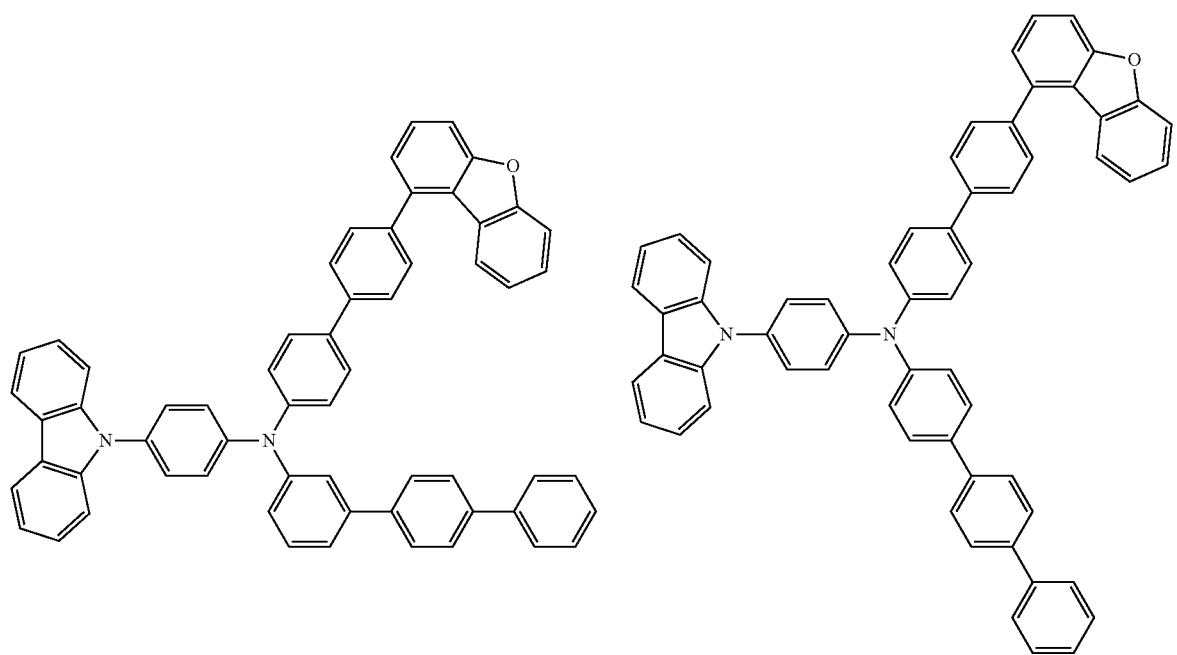

425 426
-continued
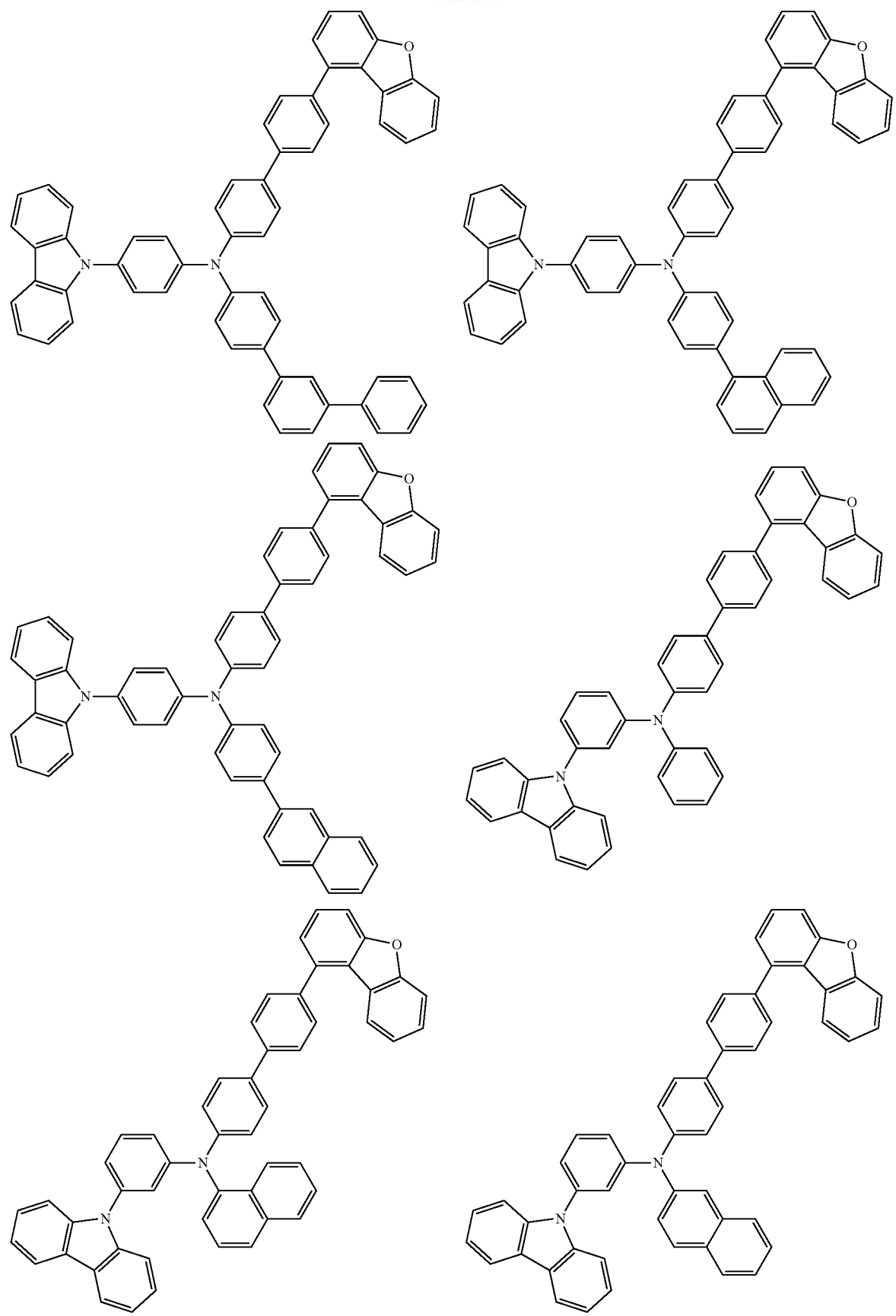

-continued
427
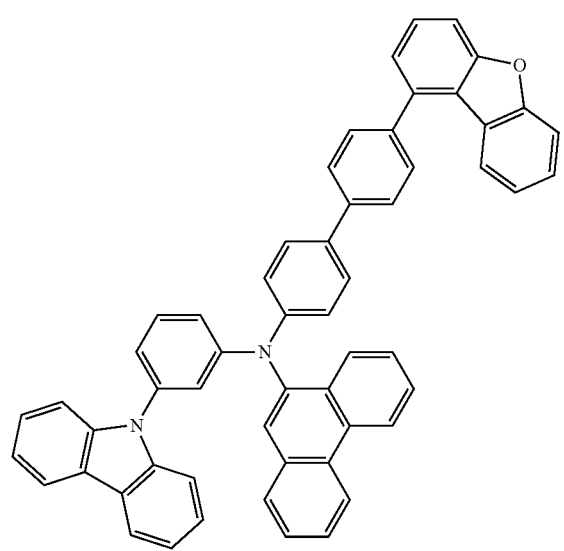
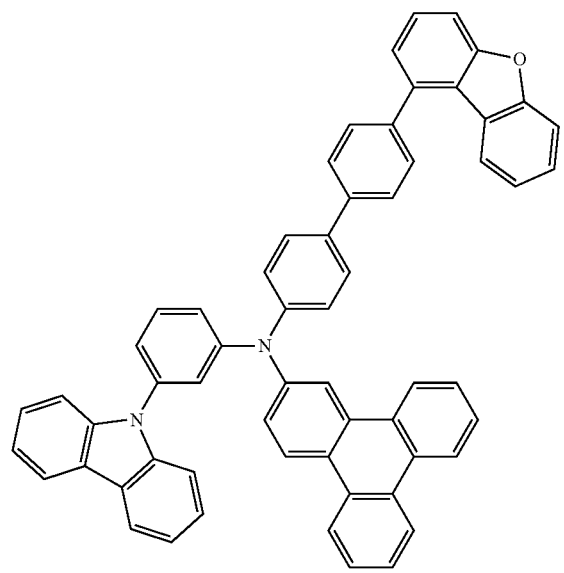
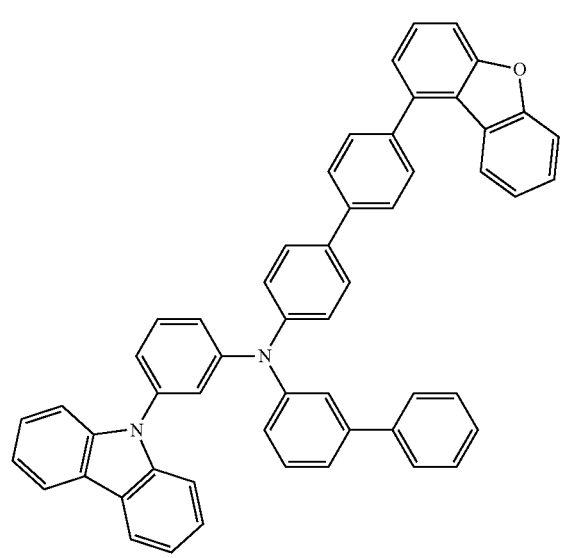
428
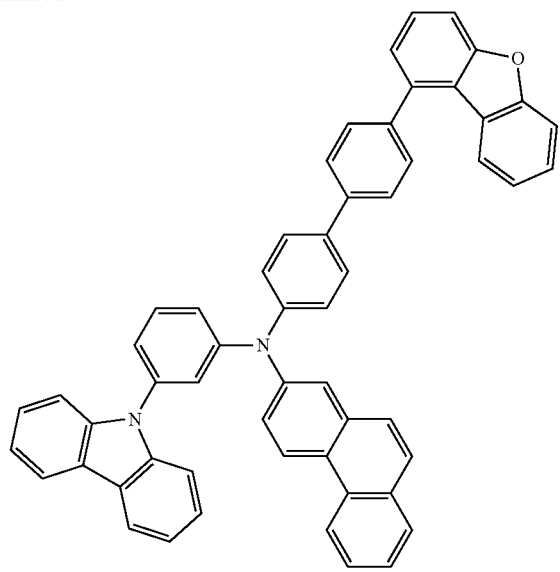
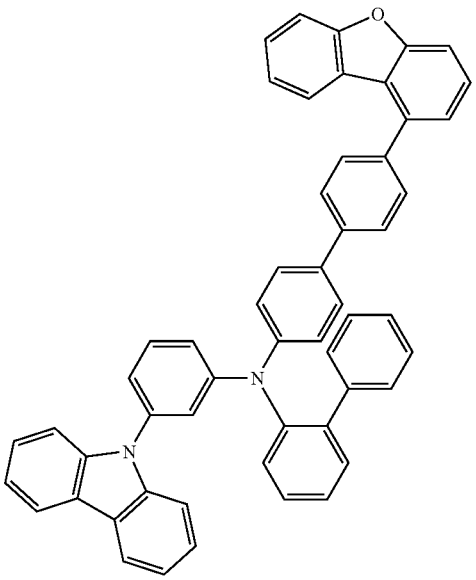
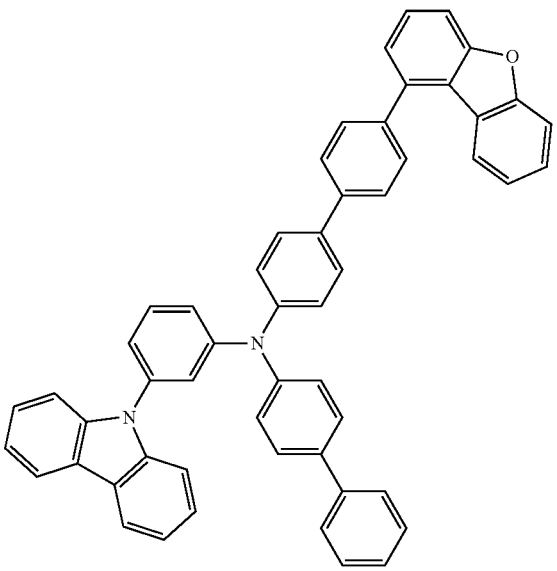

429
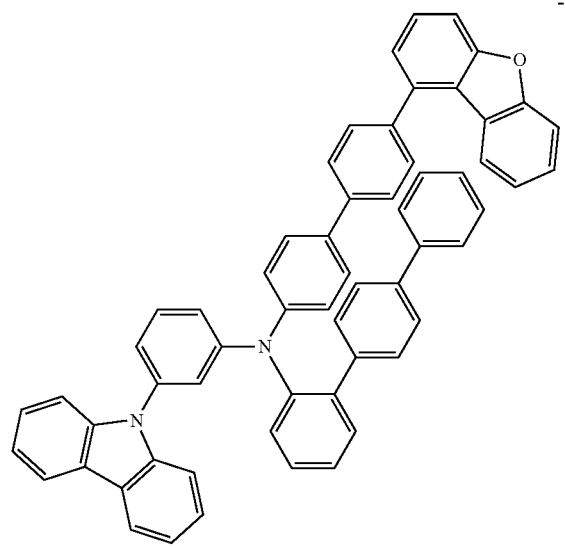
430
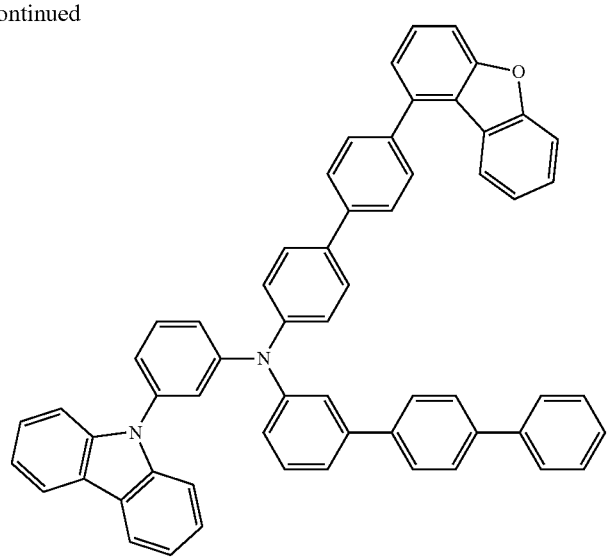
-continued
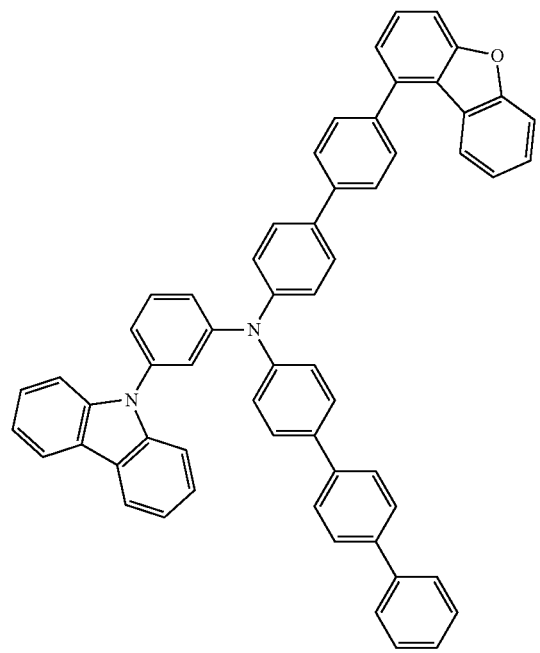
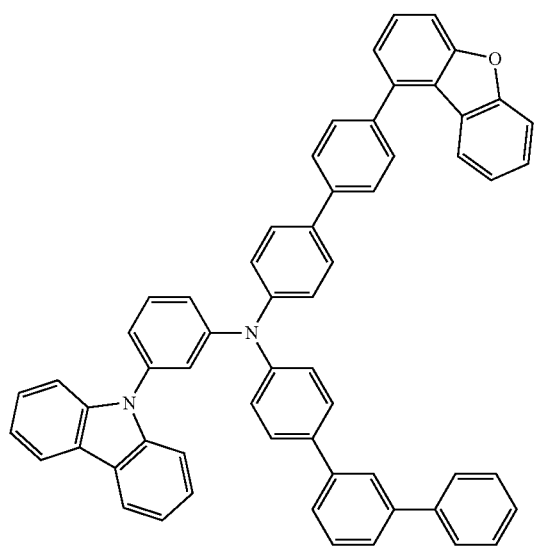

-continued
| 431 | 432 |
|---|---|
| 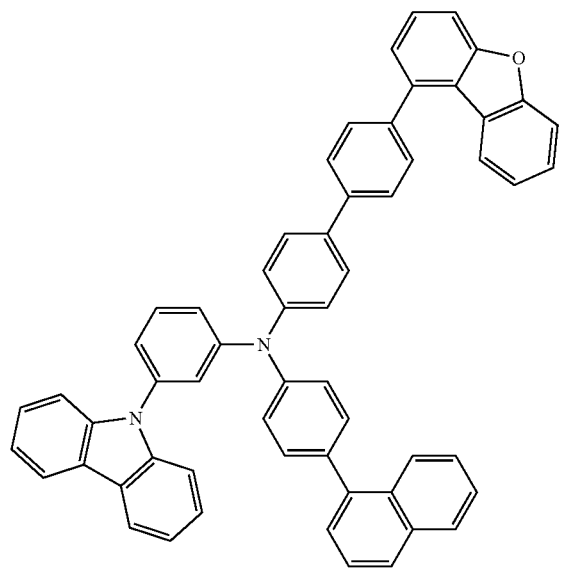 | 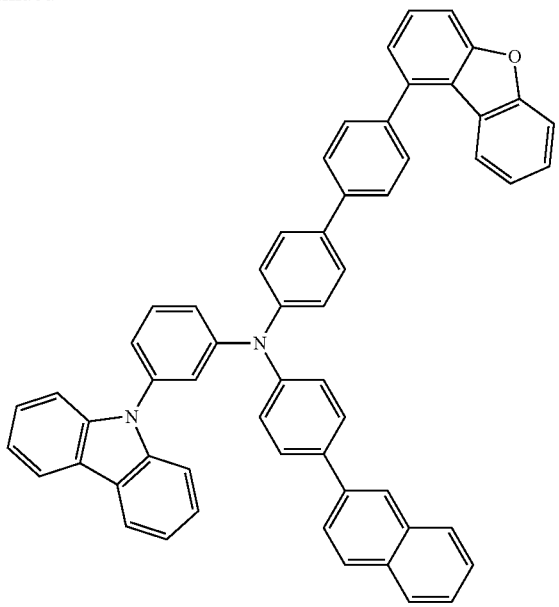 |
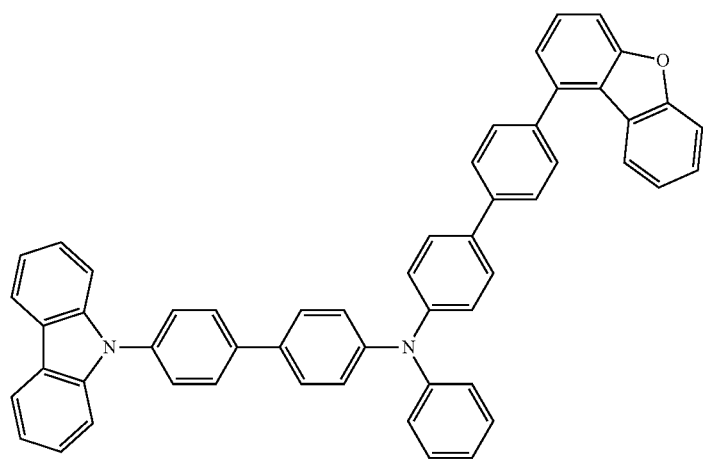
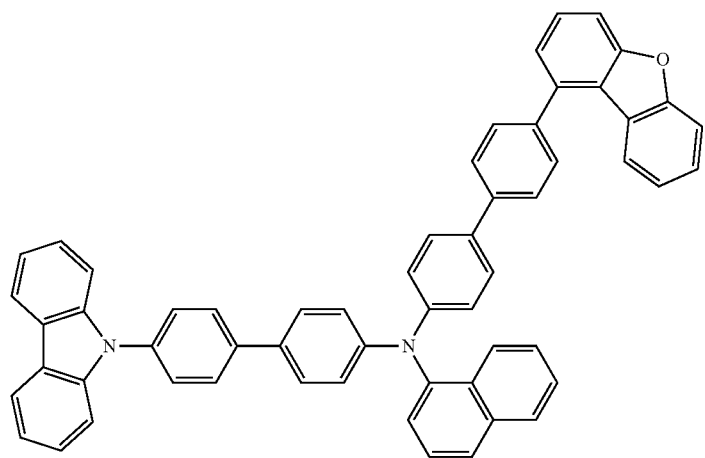

-continued
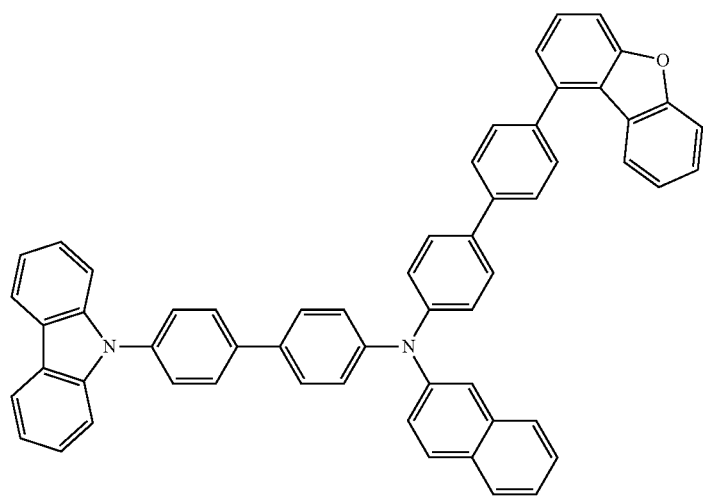
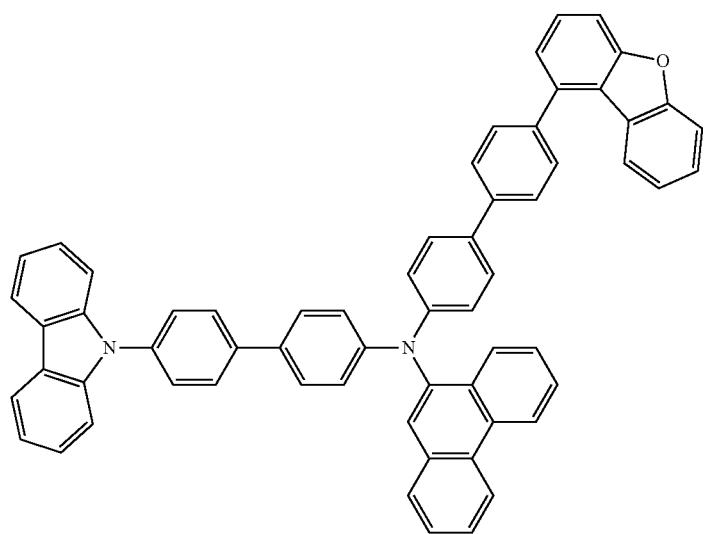
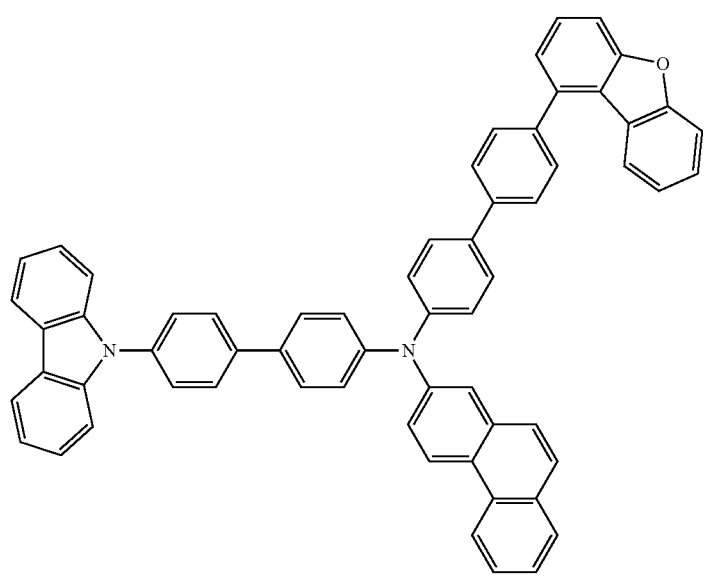

-continued
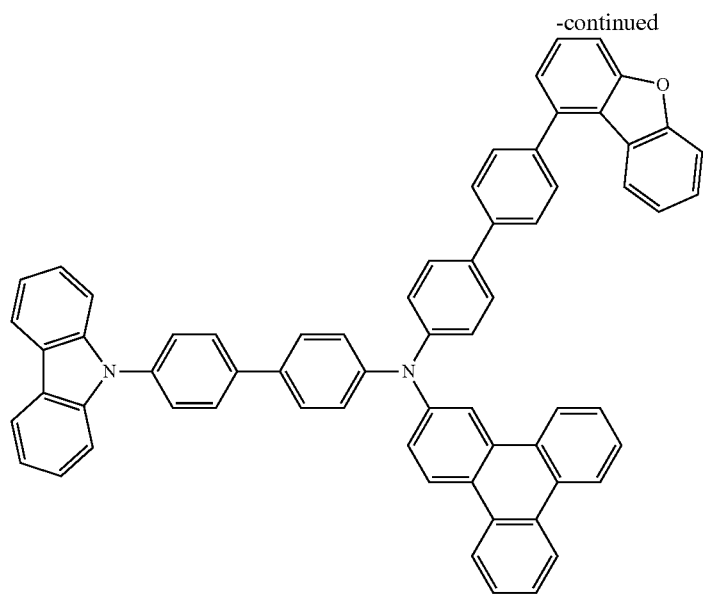
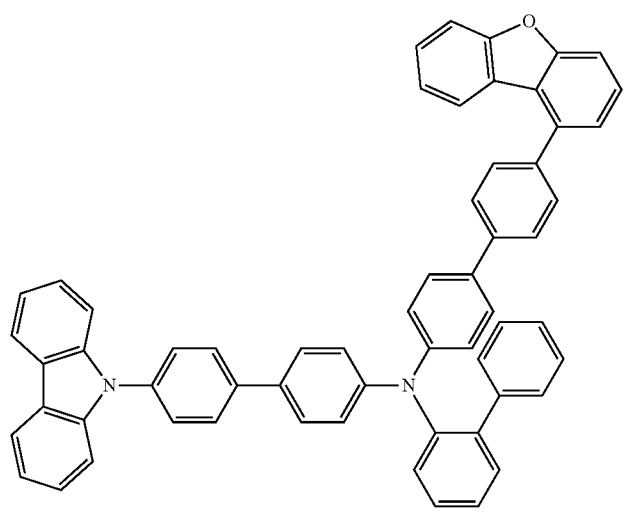
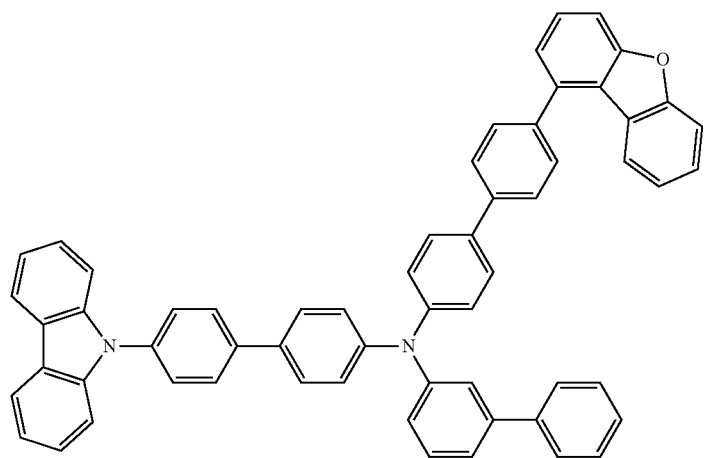

-continued
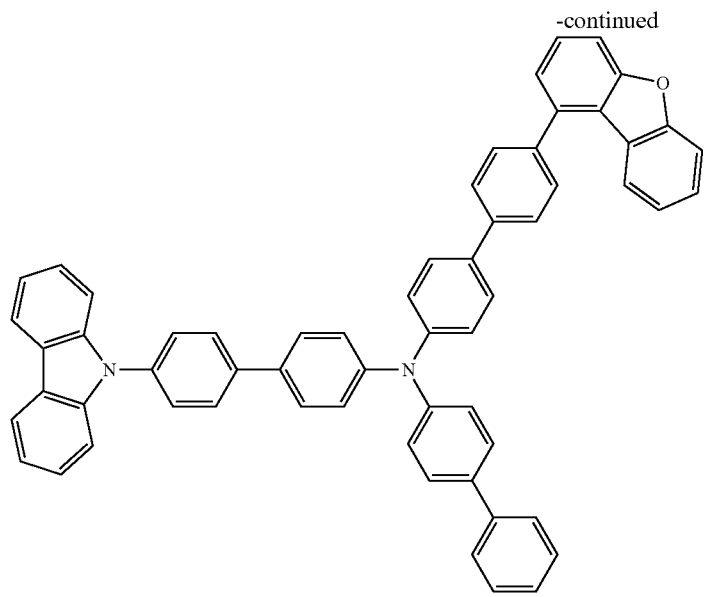
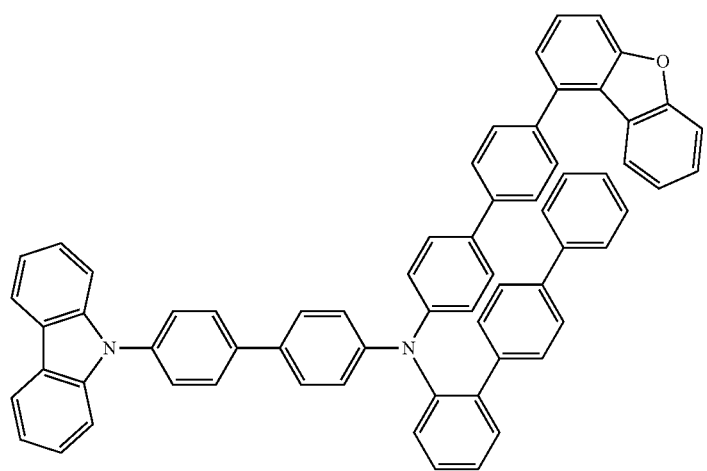
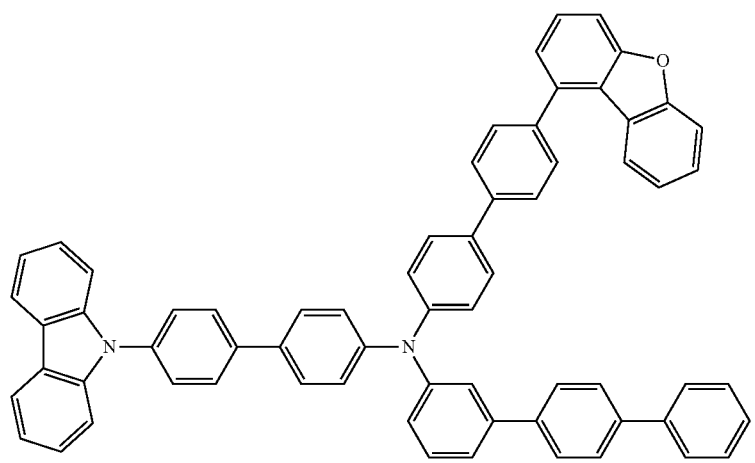

-continued
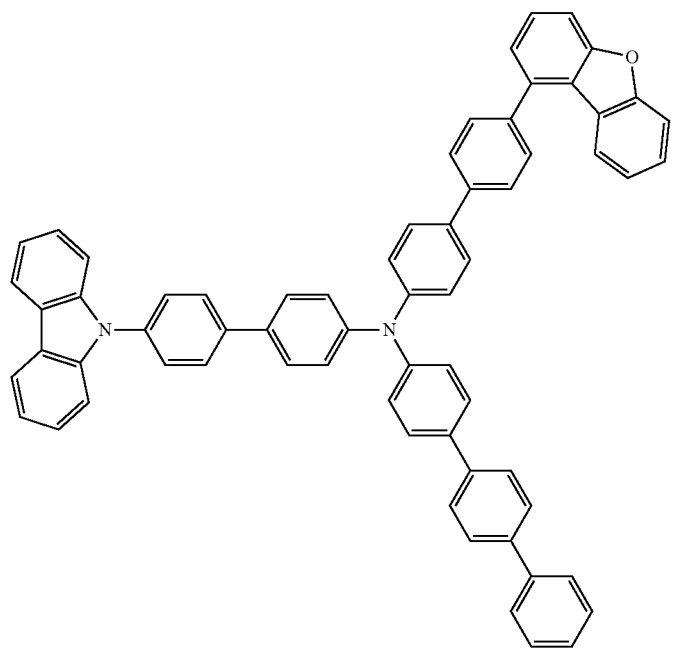
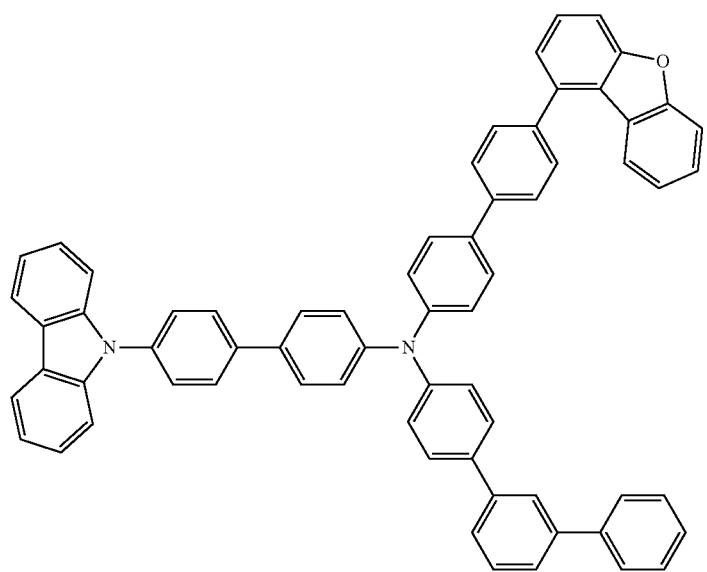

-continued
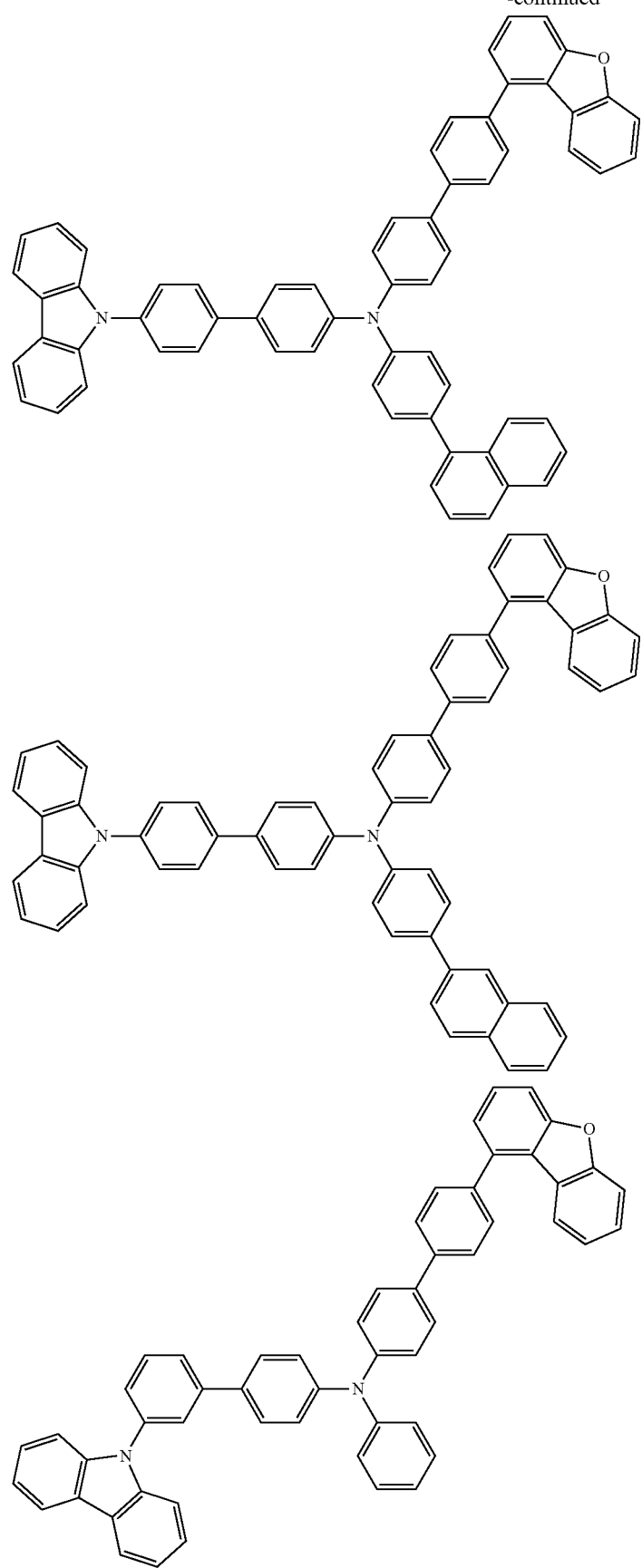

-continued
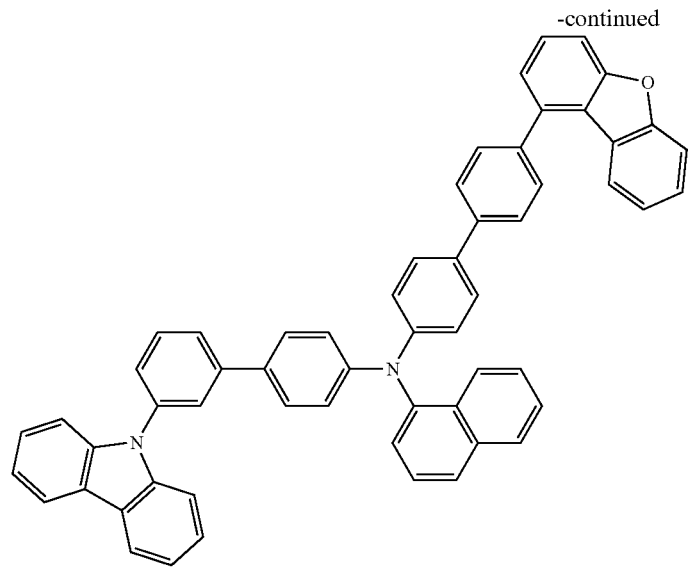
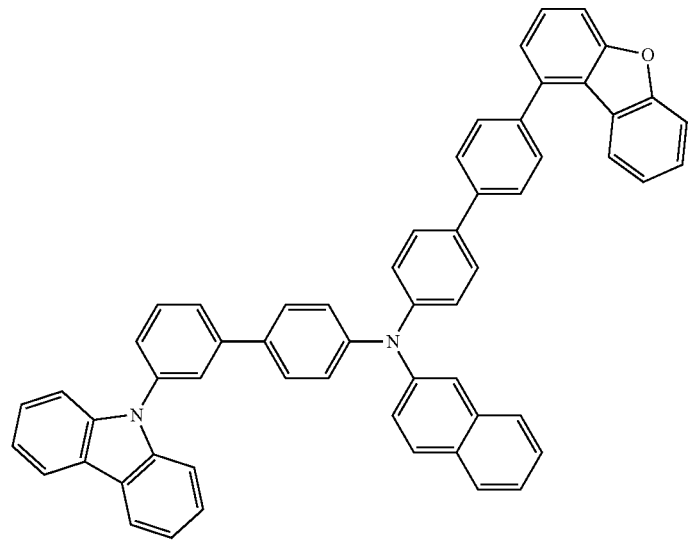
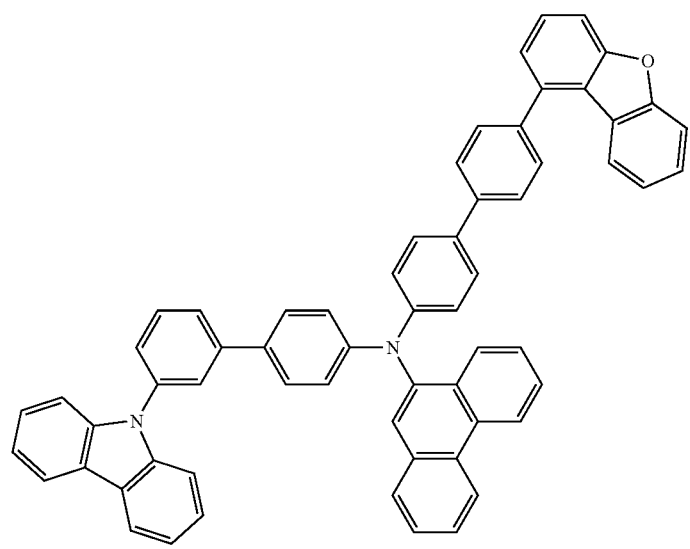

-continued
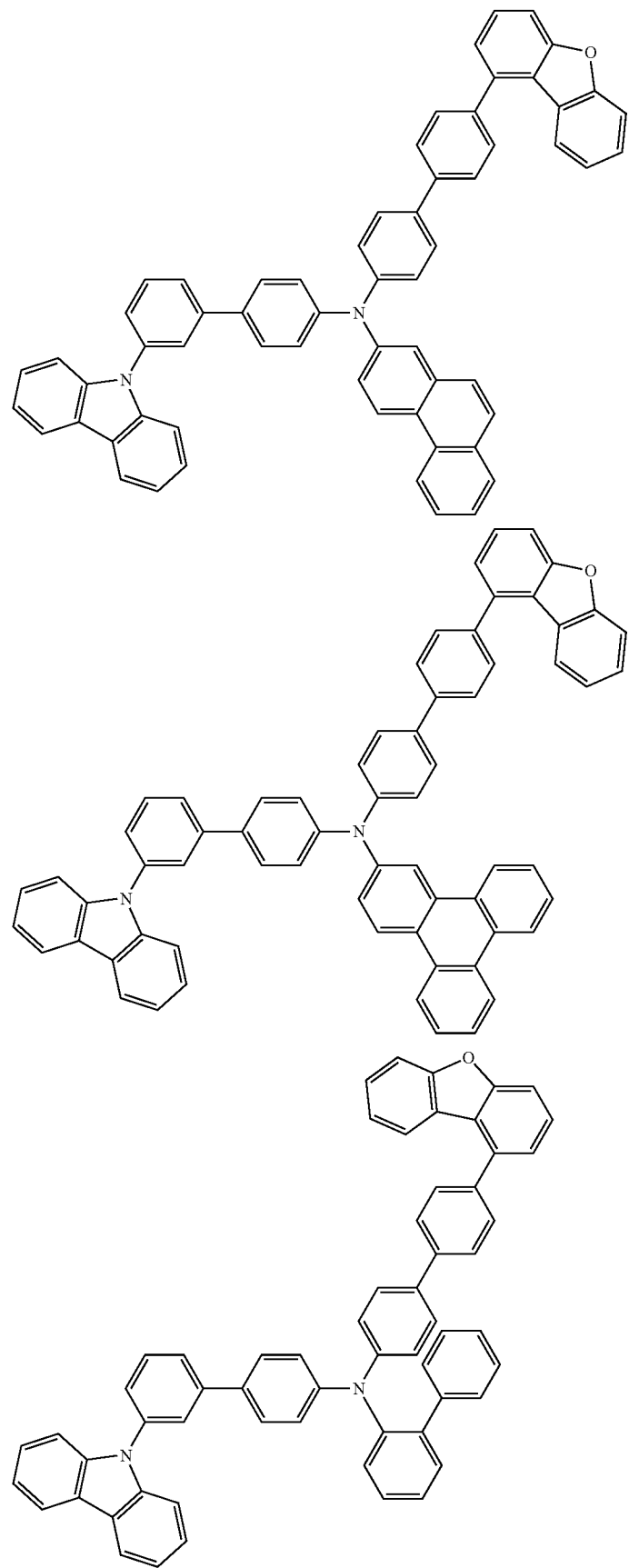

-continued
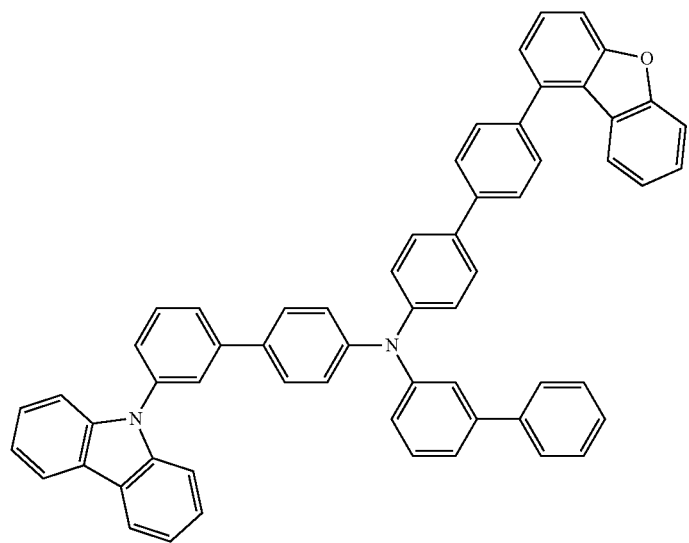
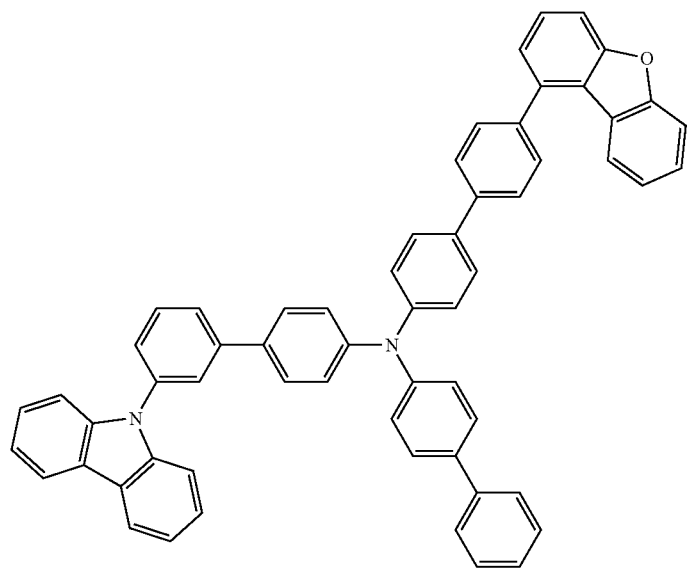
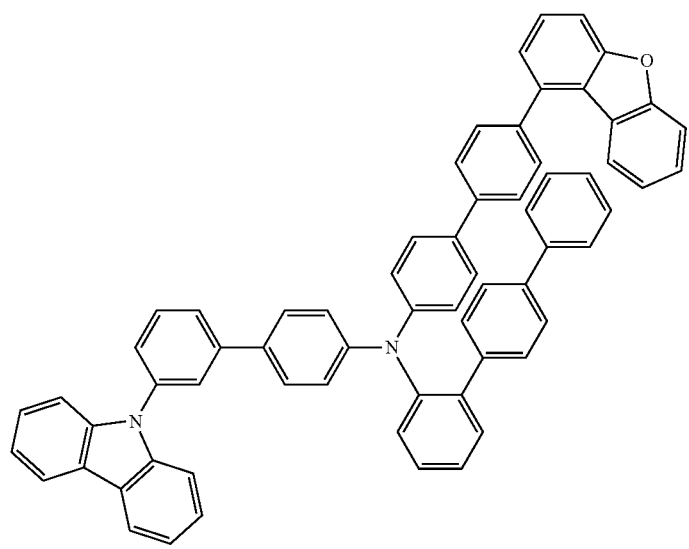

-continued
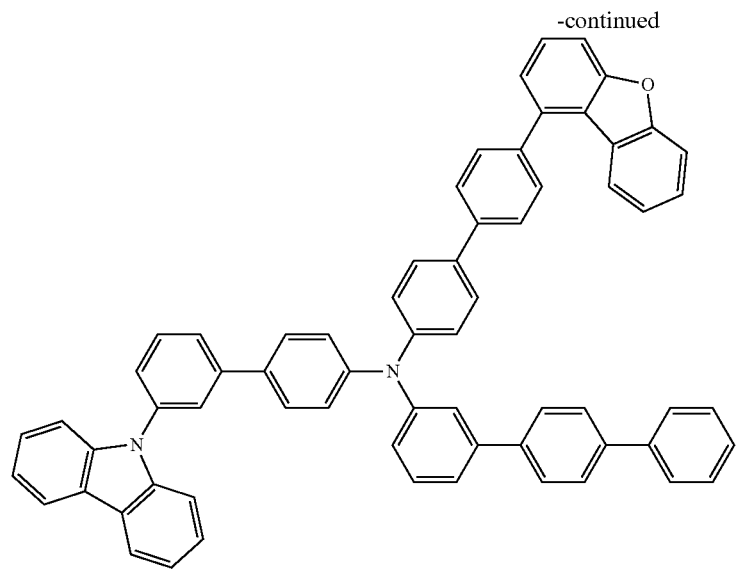
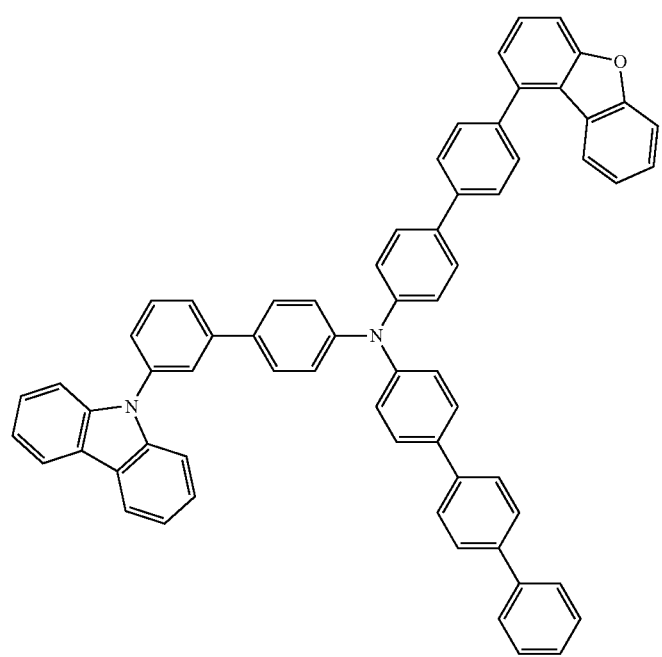

-continued
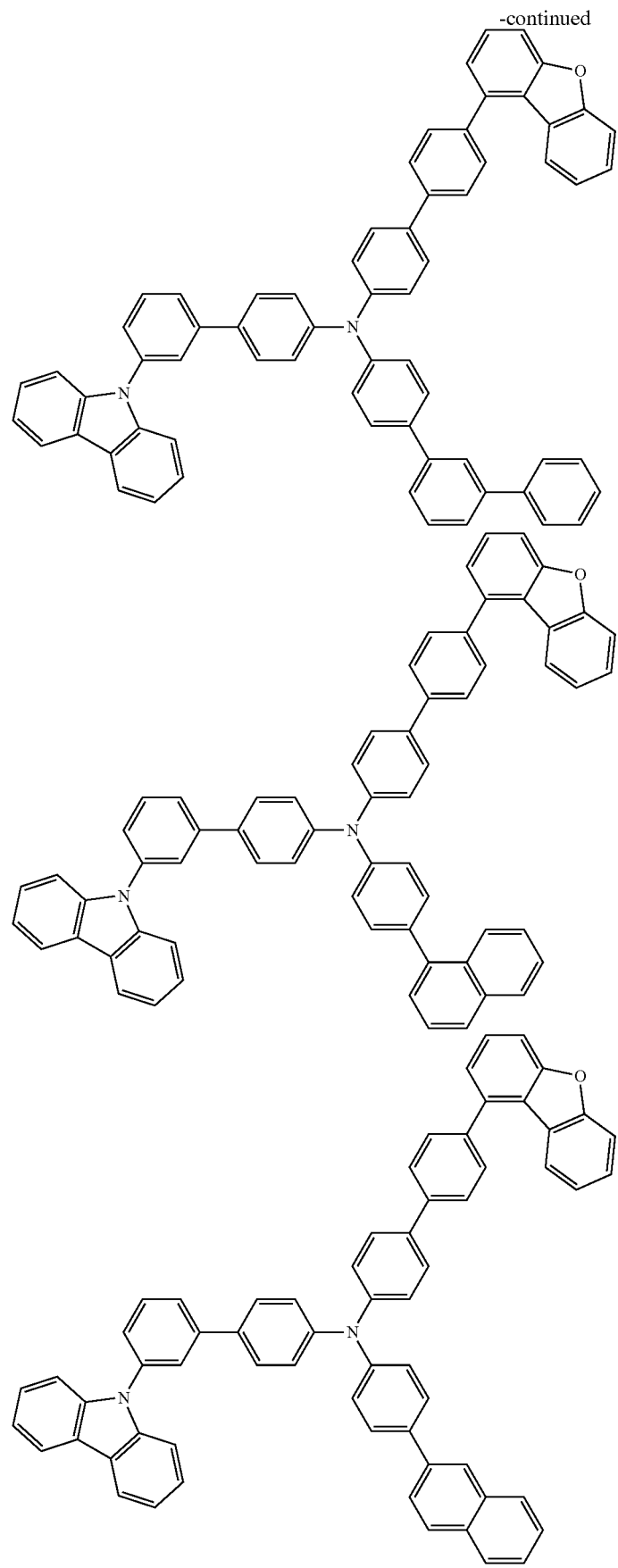

-continued
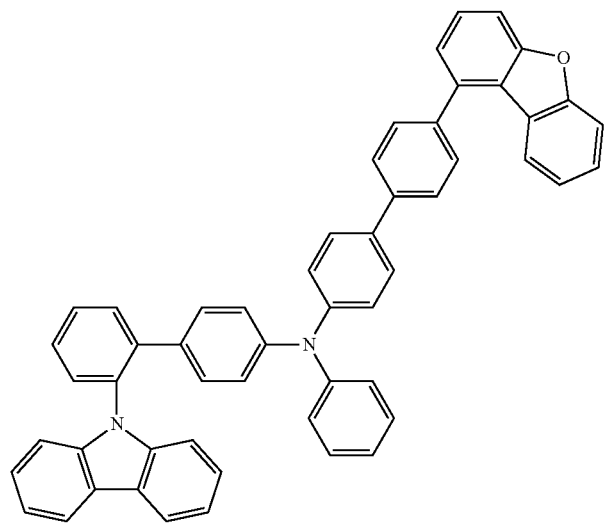
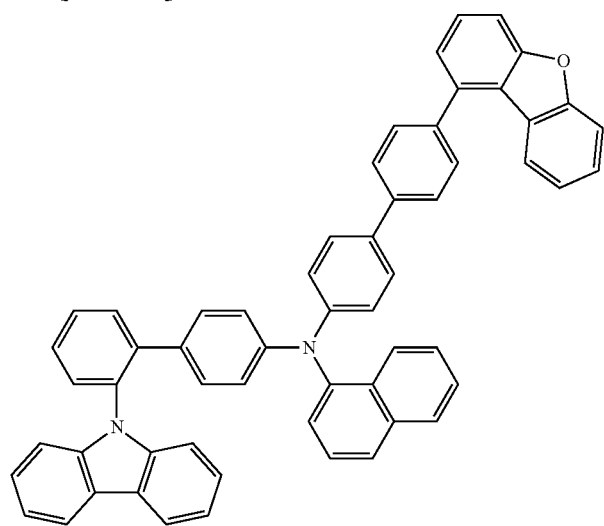
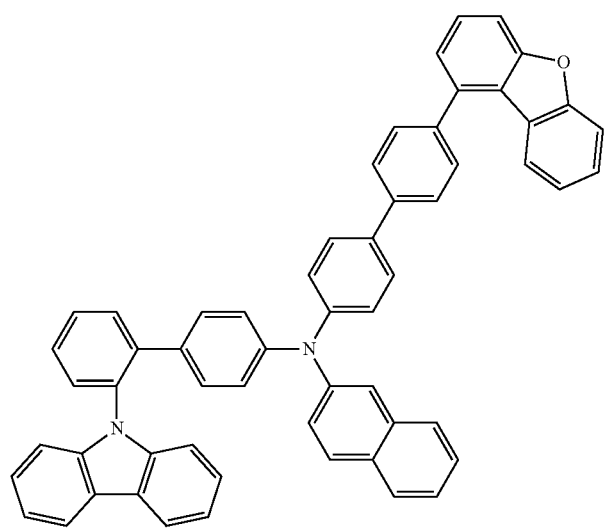

-continued
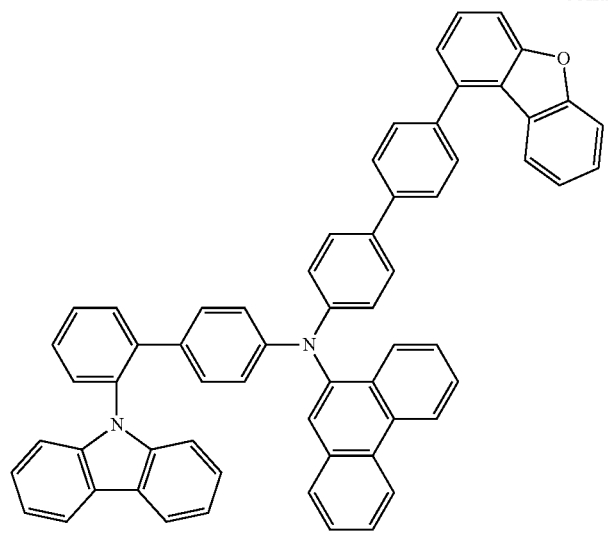
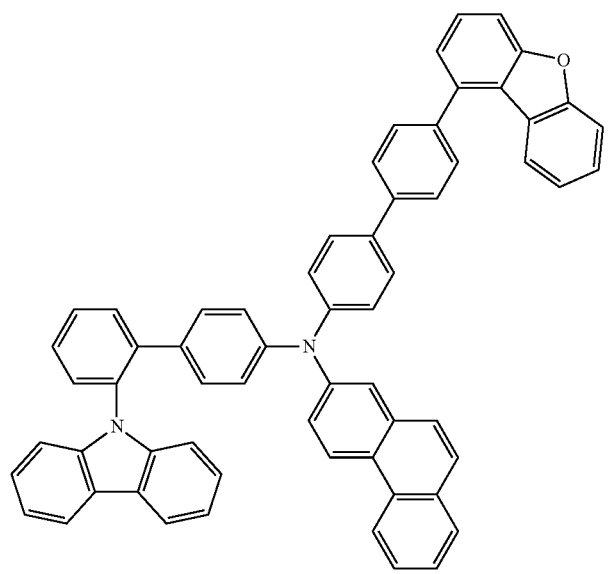
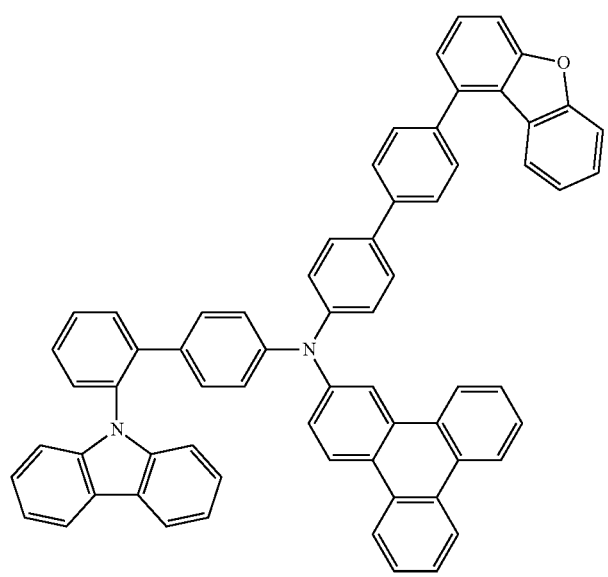

-continued
457
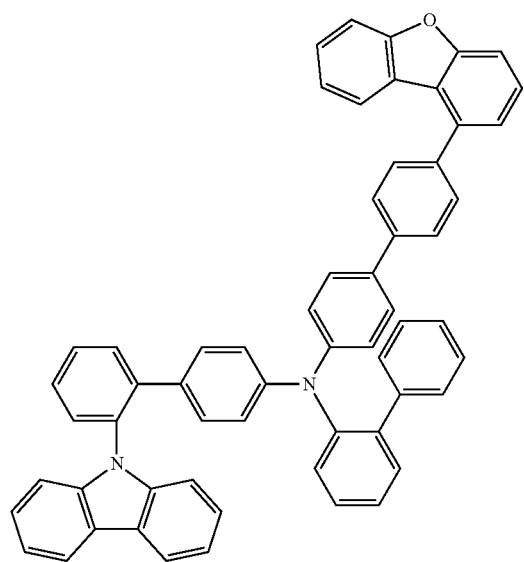
458
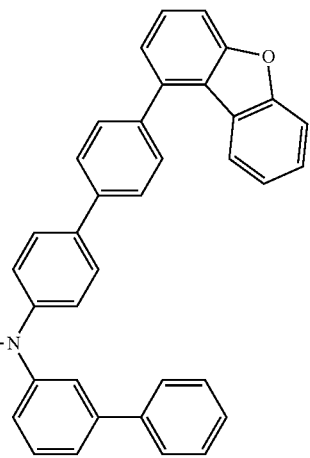
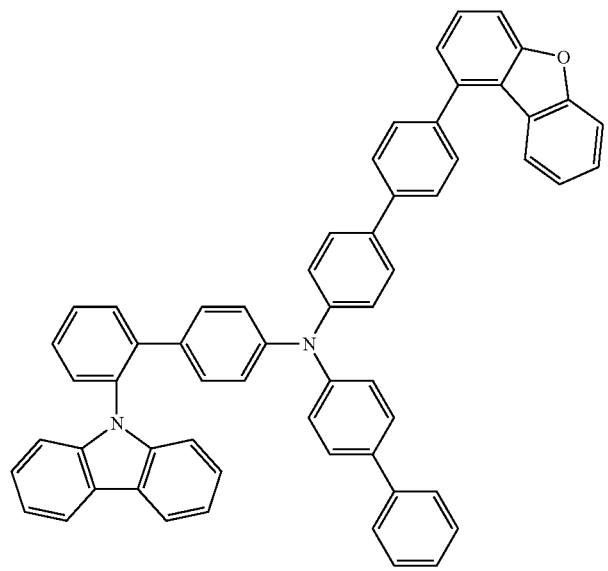
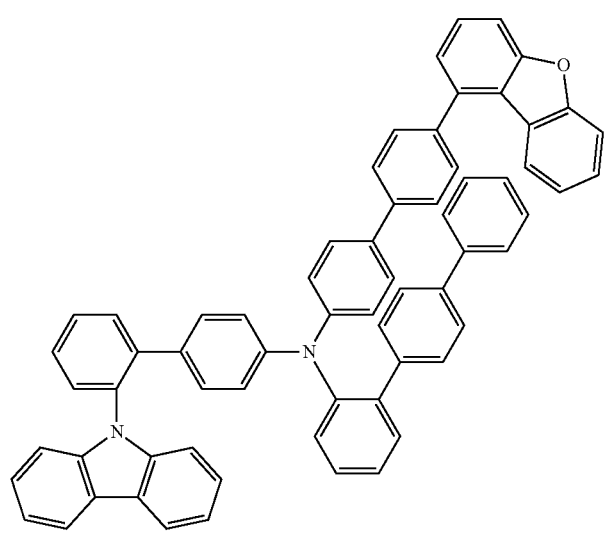

-continued
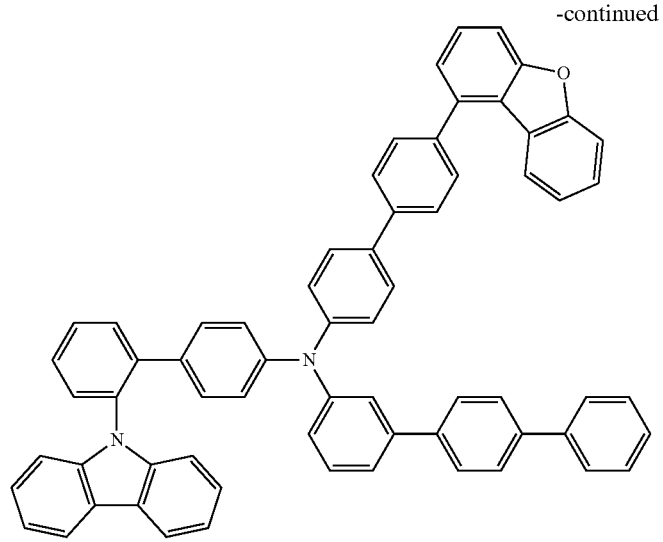
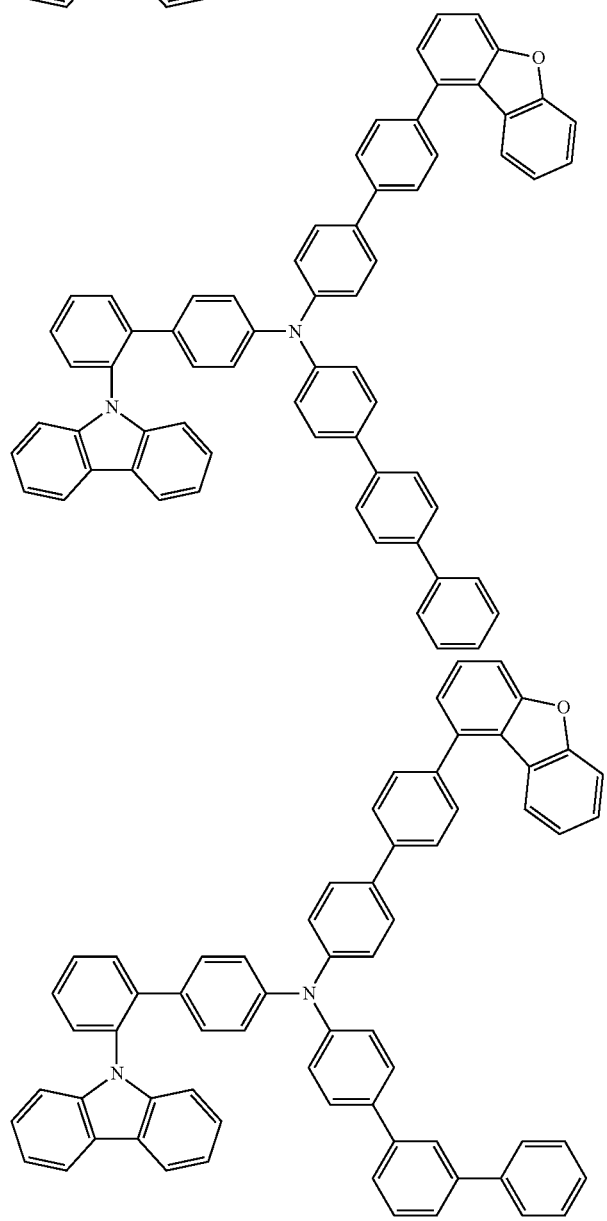

461
462
-continued
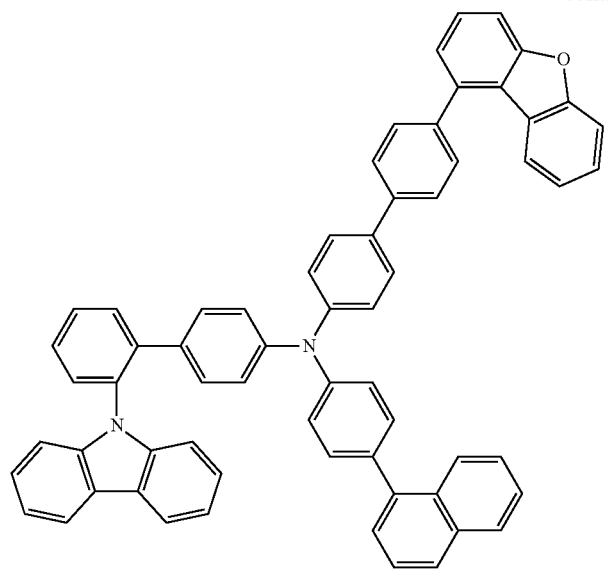
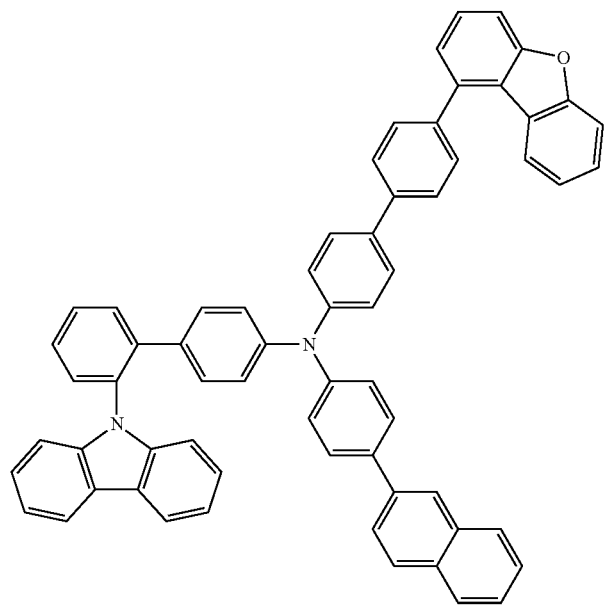
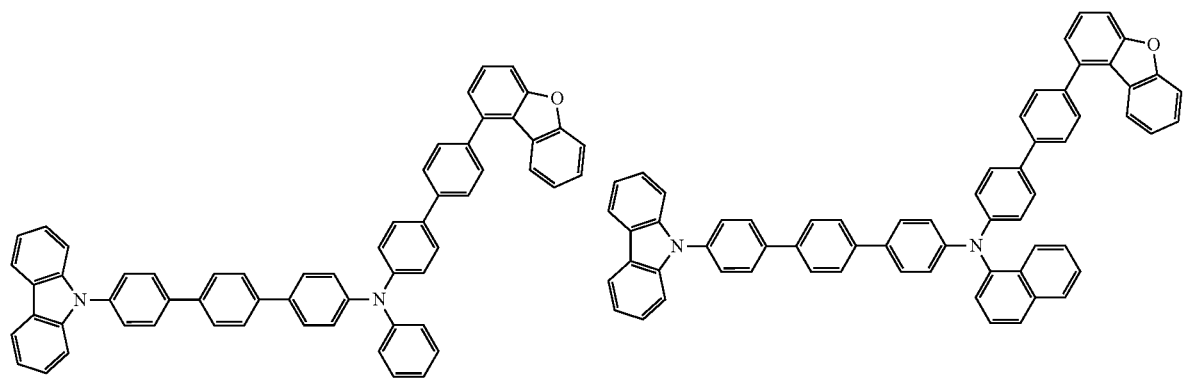

-continued
| 463 | 464 |
|---|---|
| 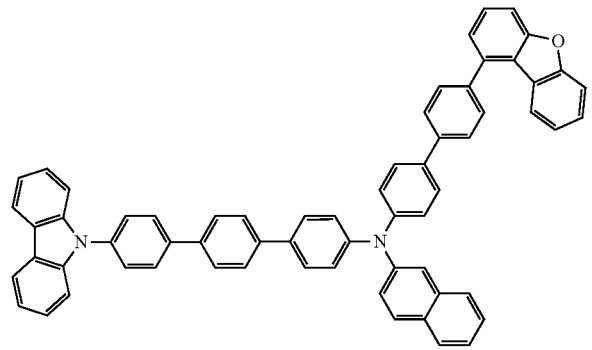 | 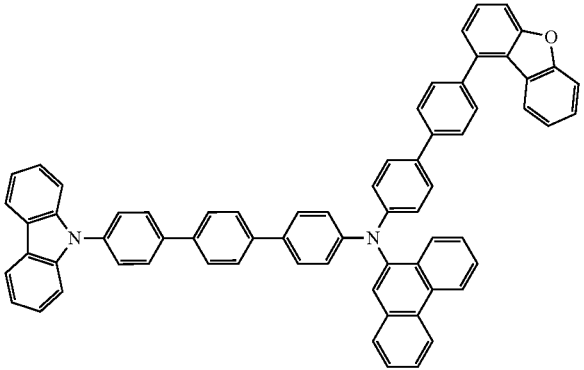 |
| 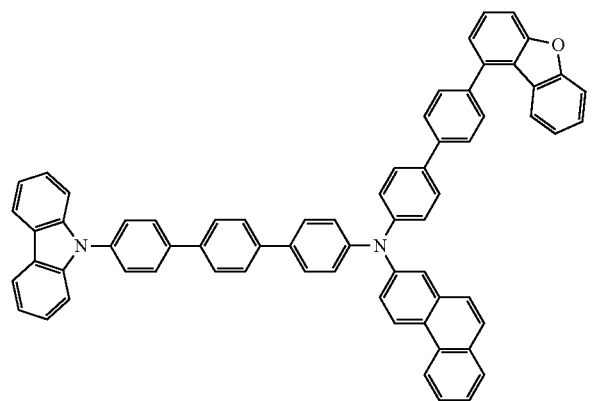 | 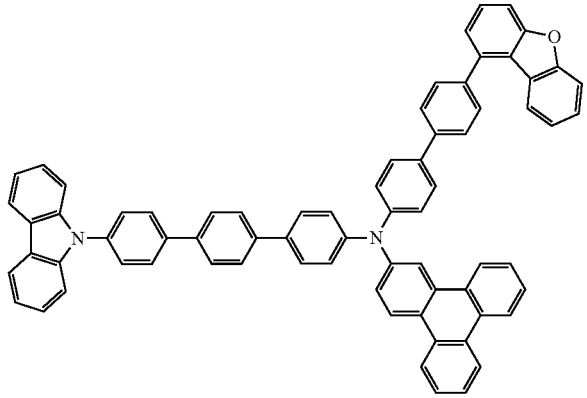 |
| 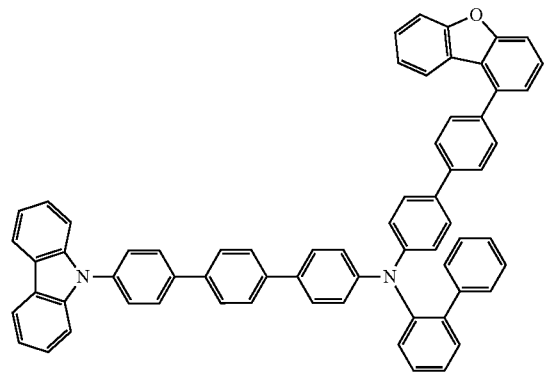 | 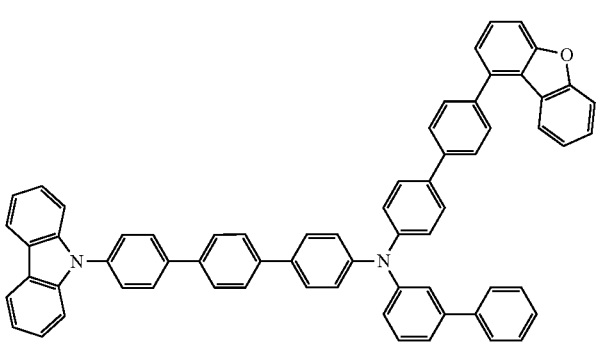 |
| 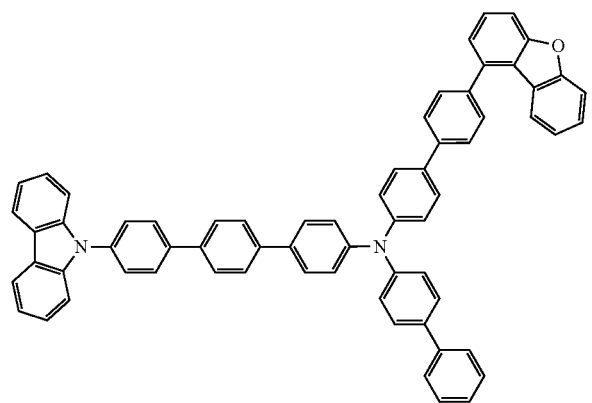 | 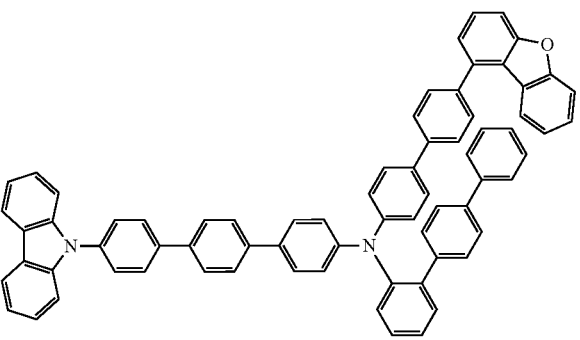 |

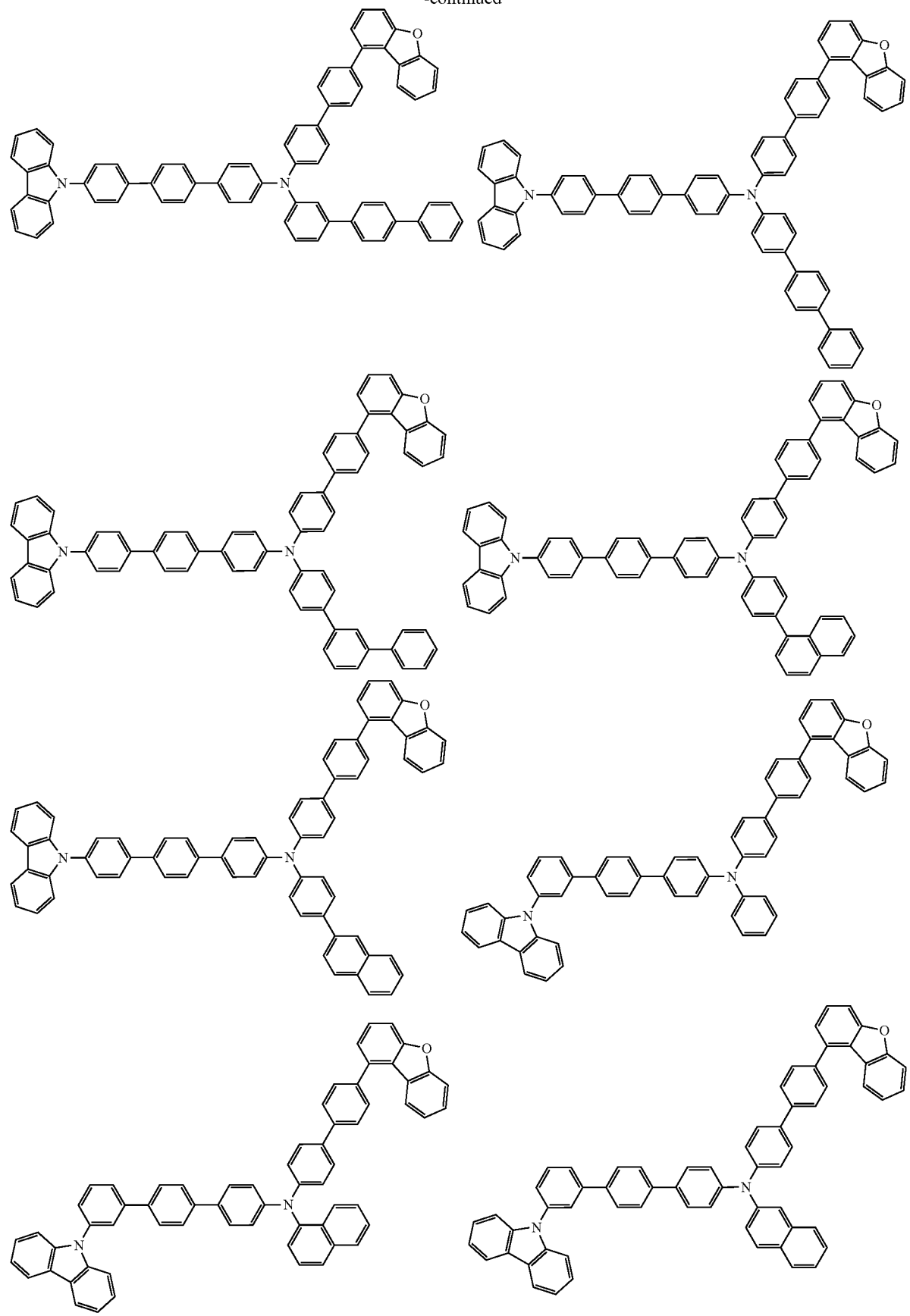

467 468
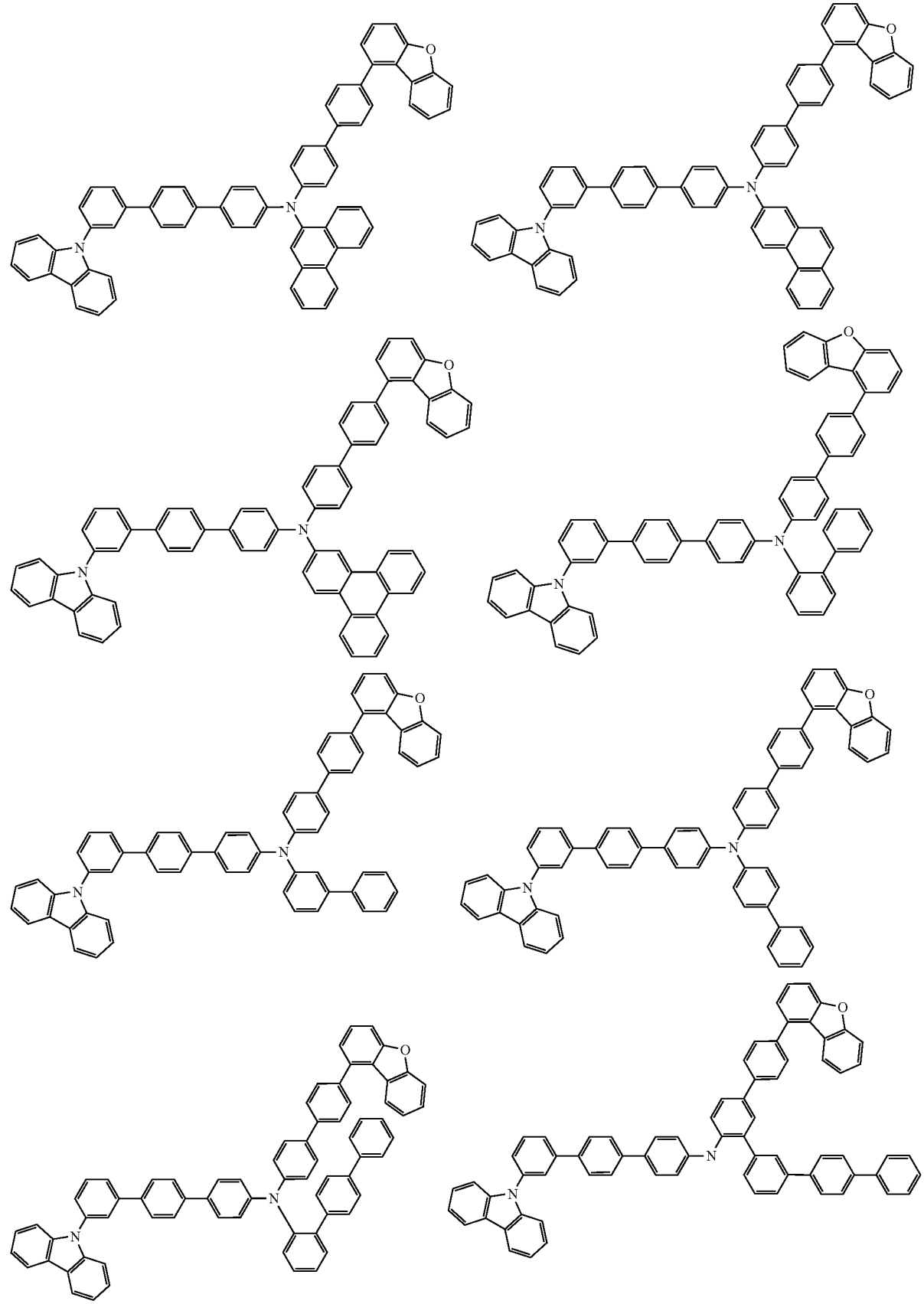

-continued
469
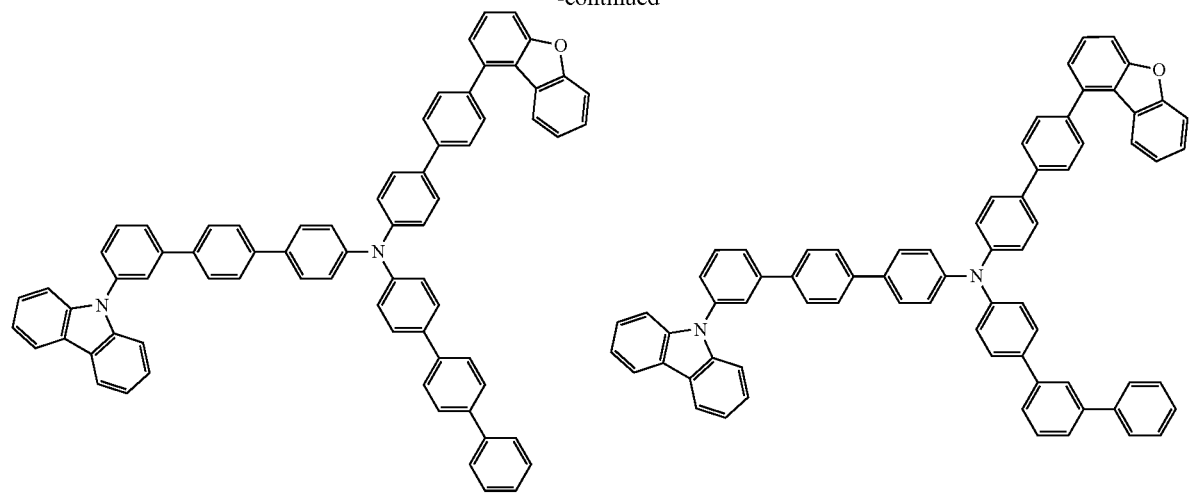
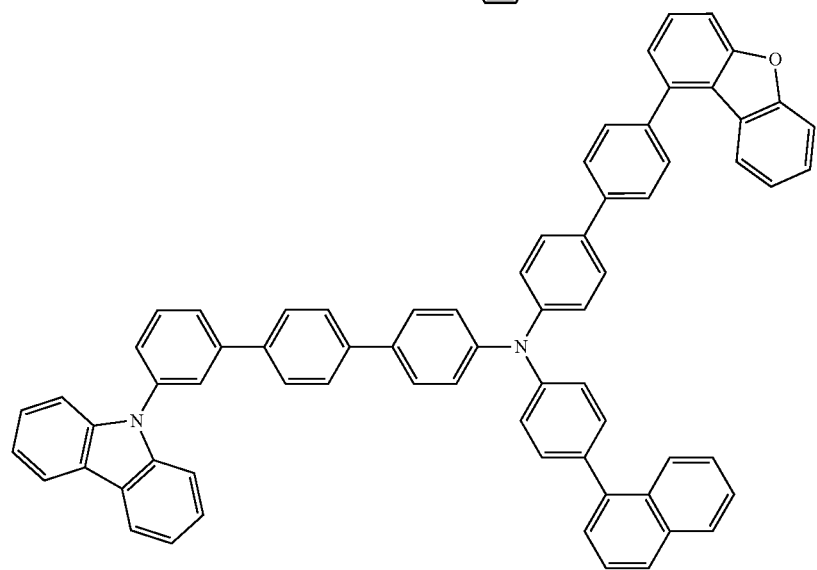
470
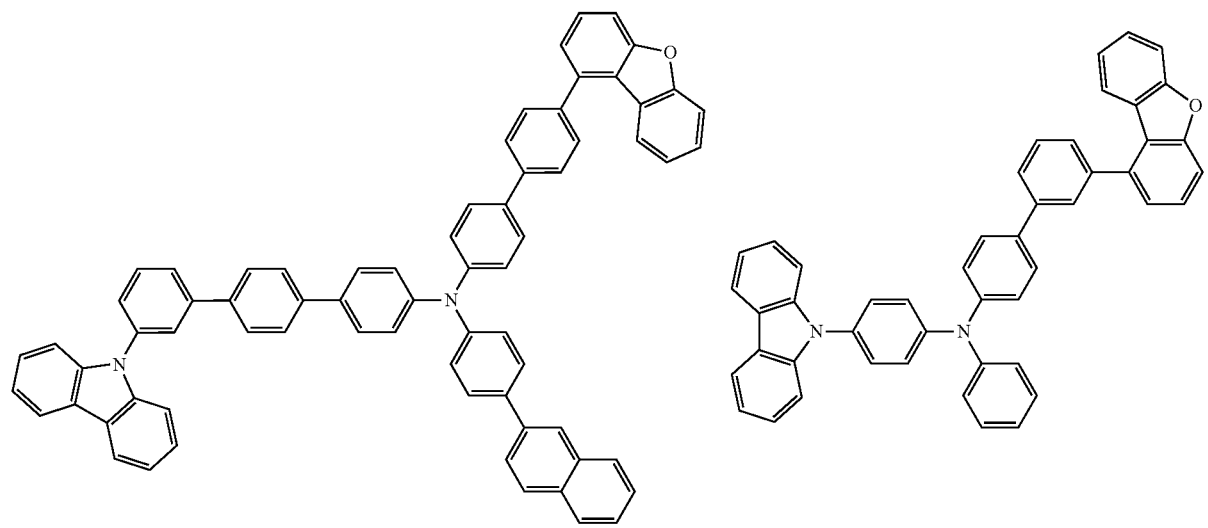

-continued
471
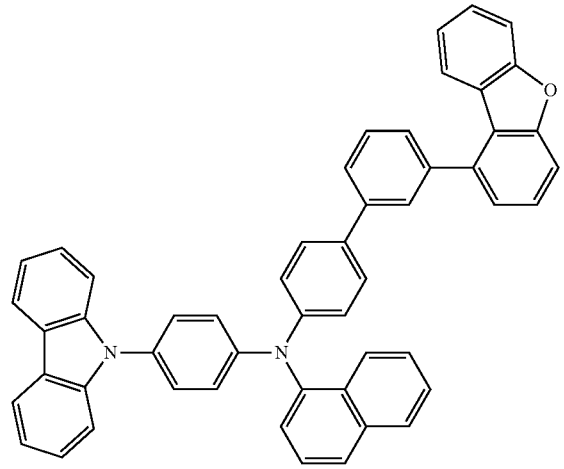
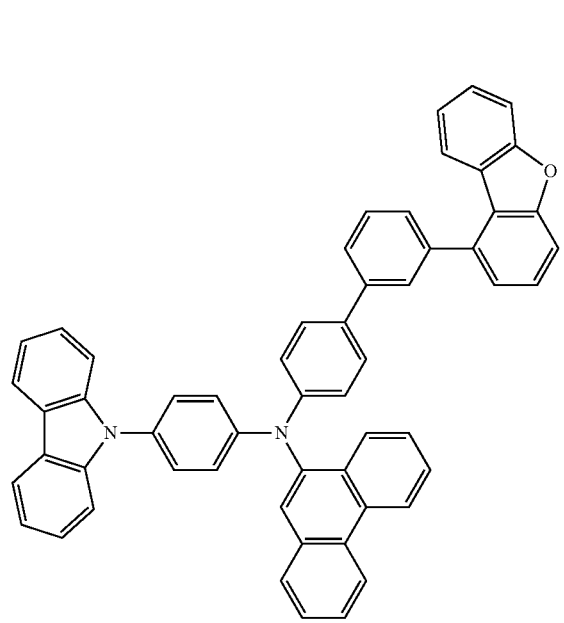
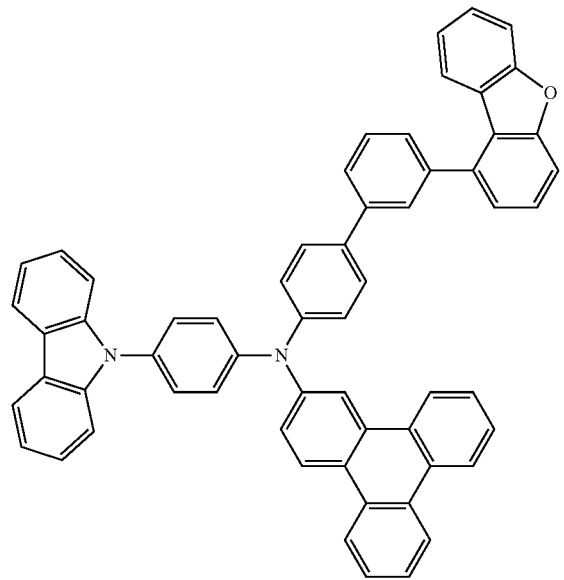
472
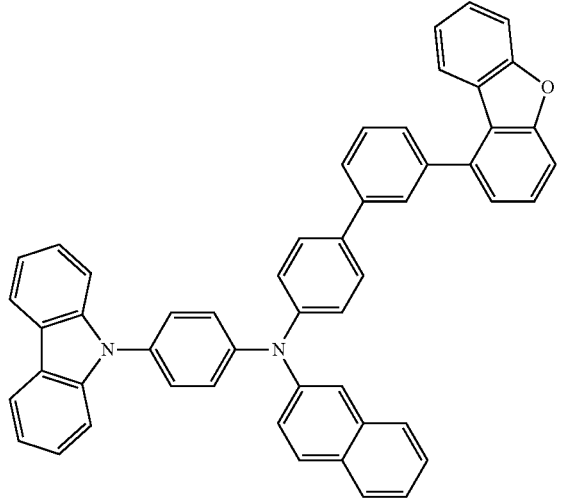
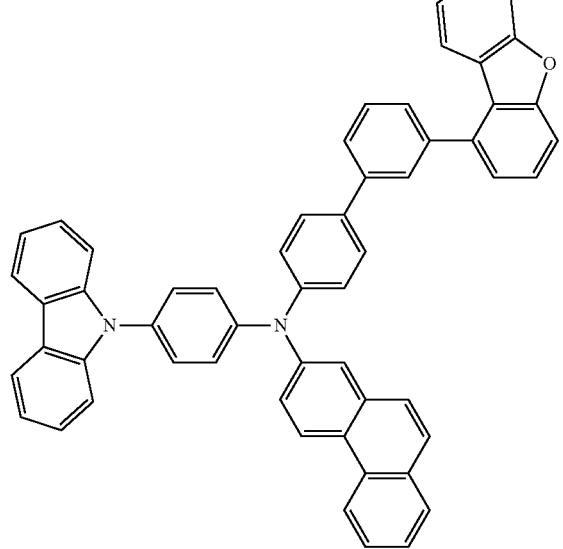
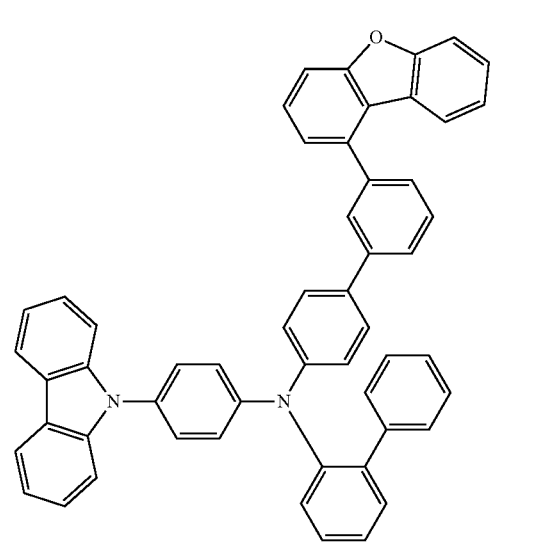

-continued
473
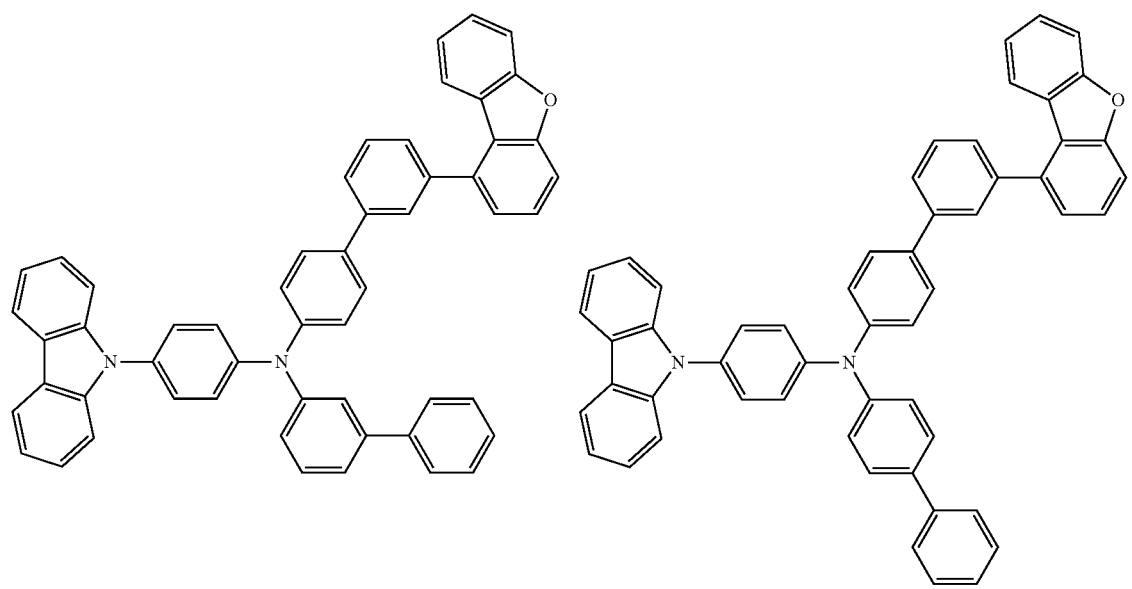
474
475
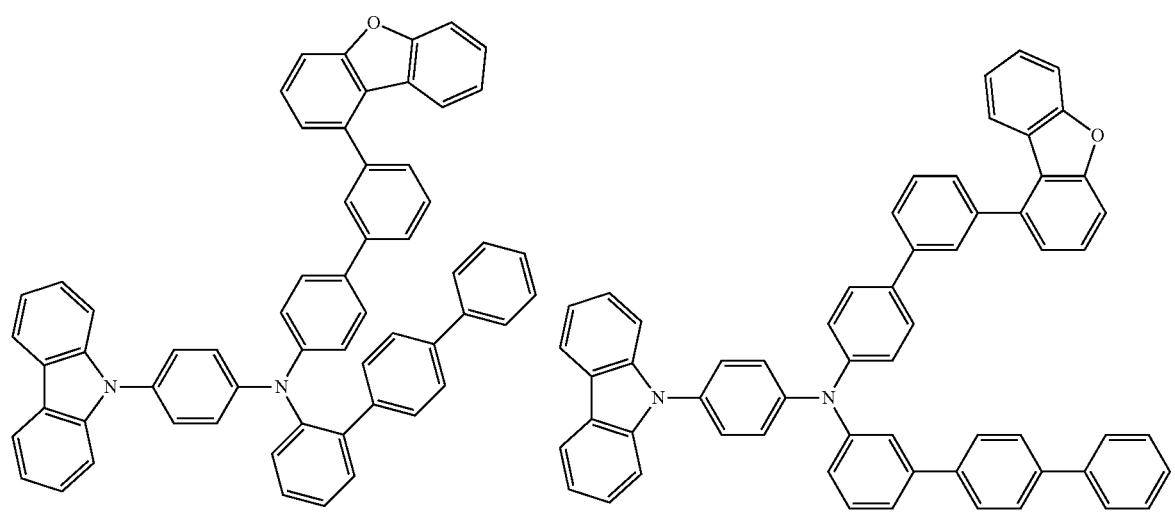
476

475
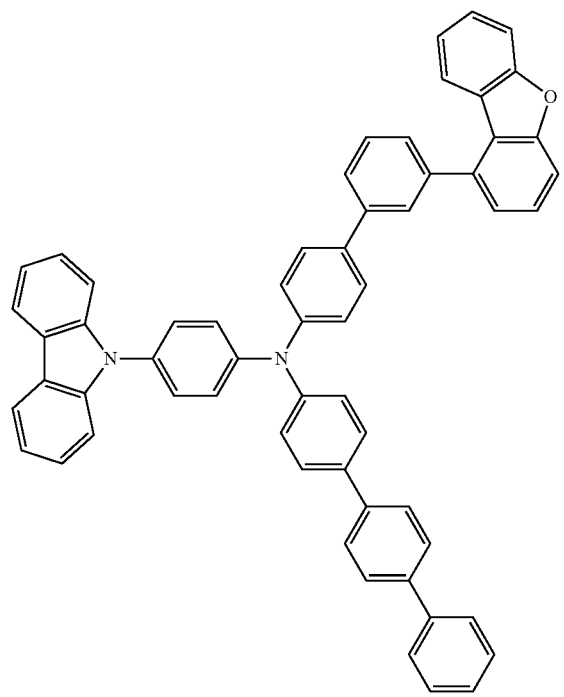
476
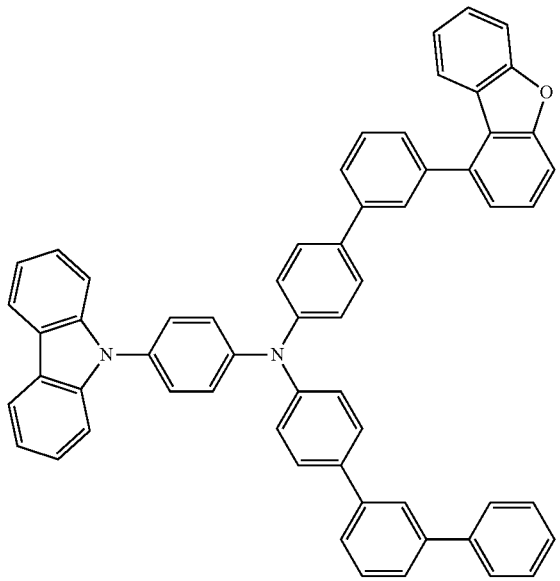
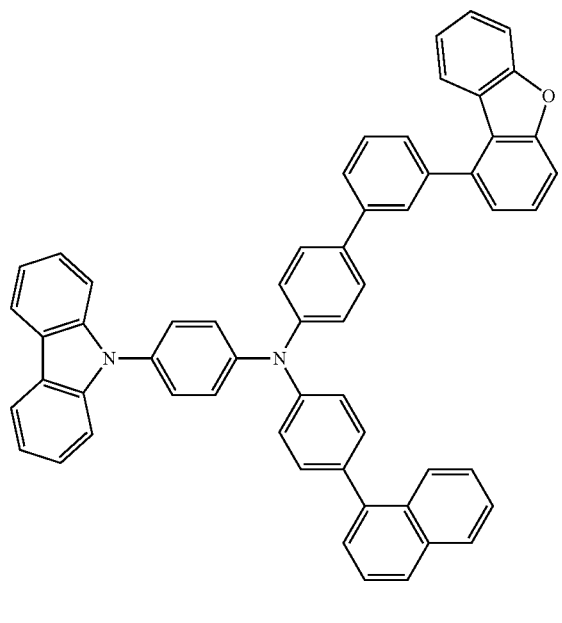
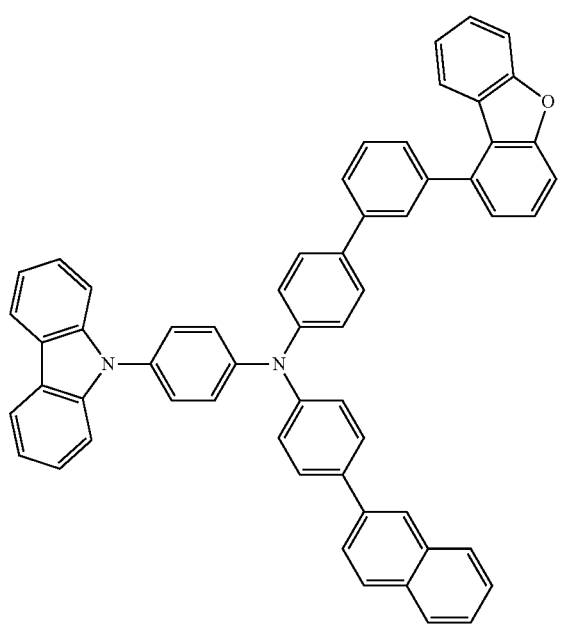

-continued
477
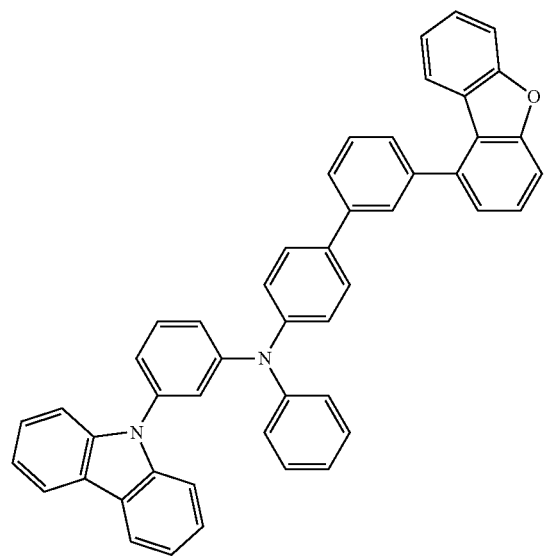
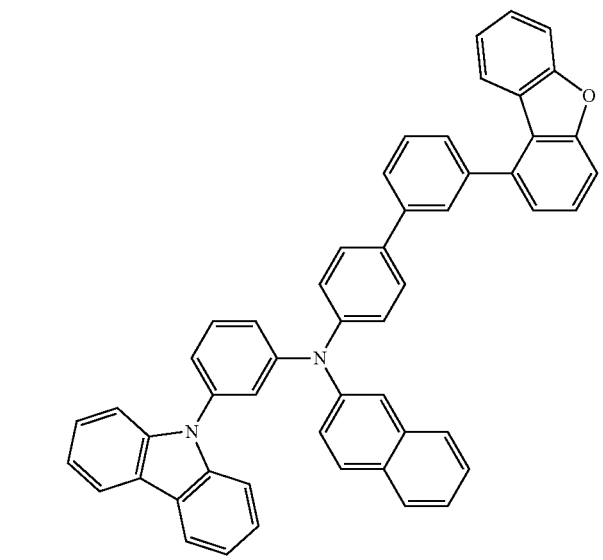
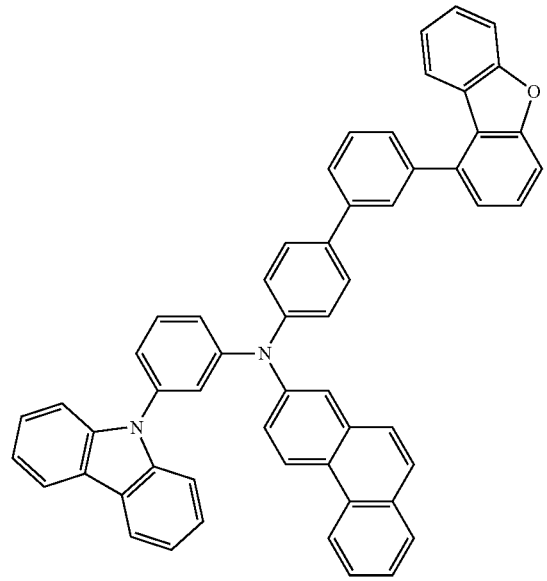
478
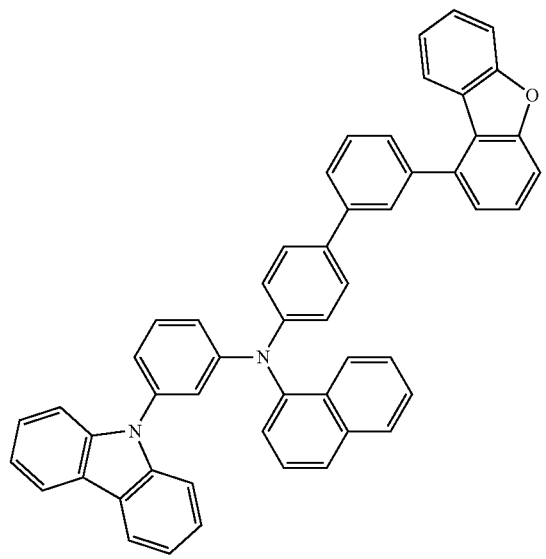
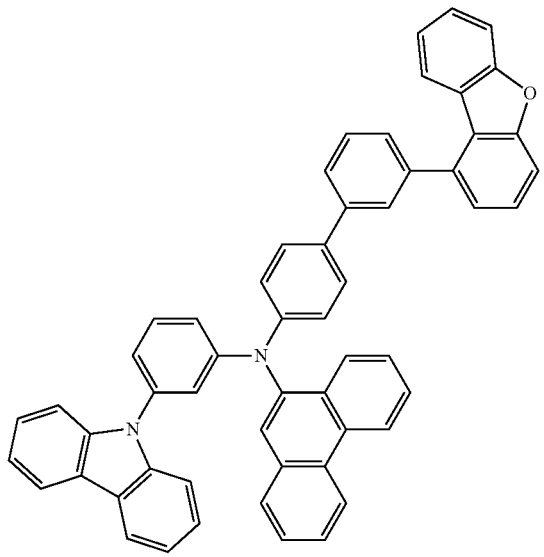
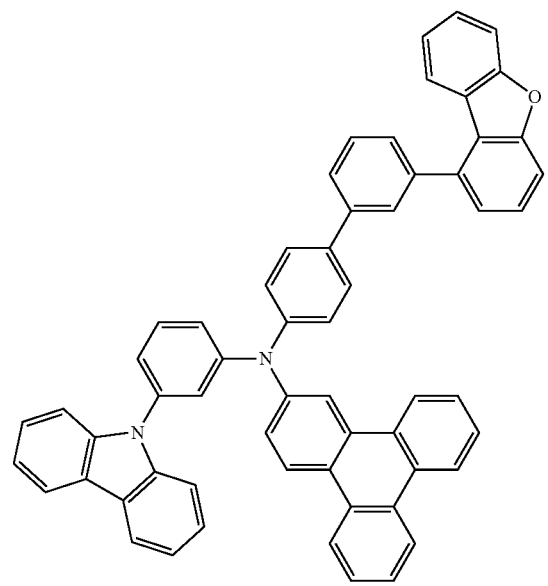

479 480
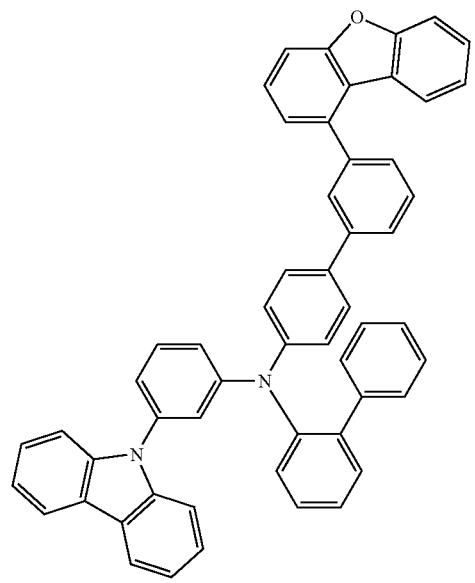
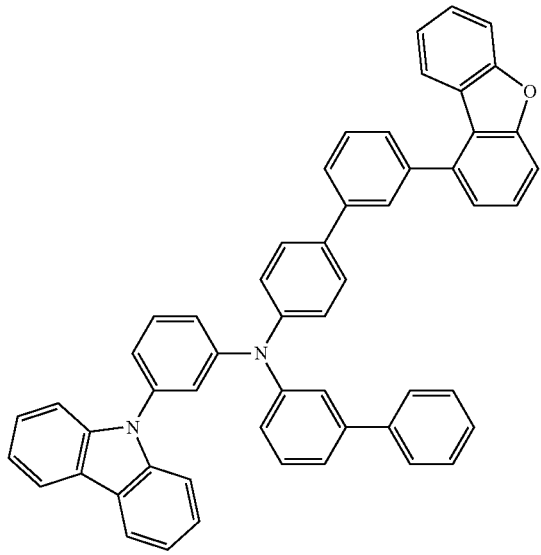
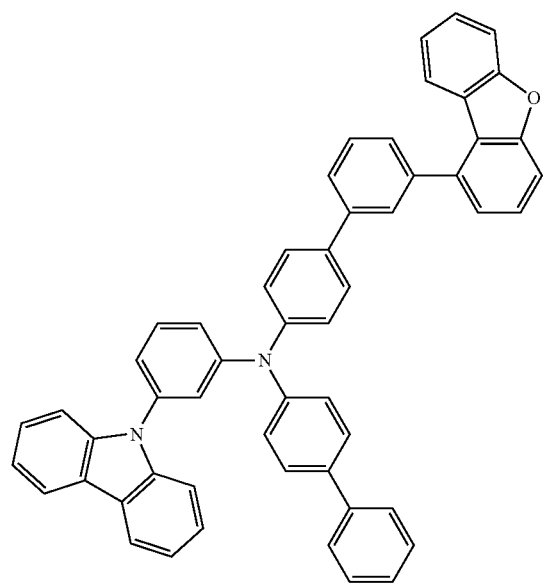
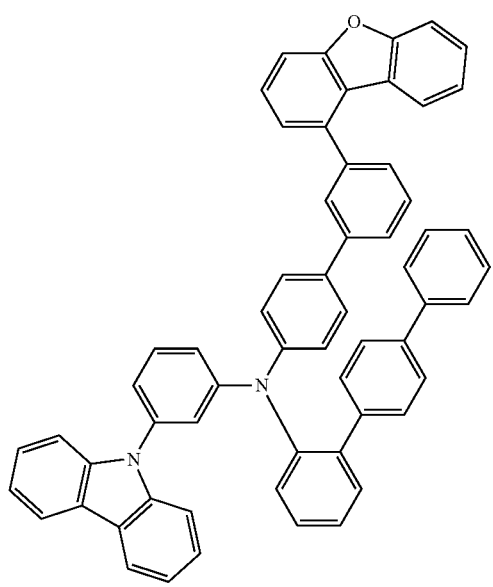

481
-continued
482
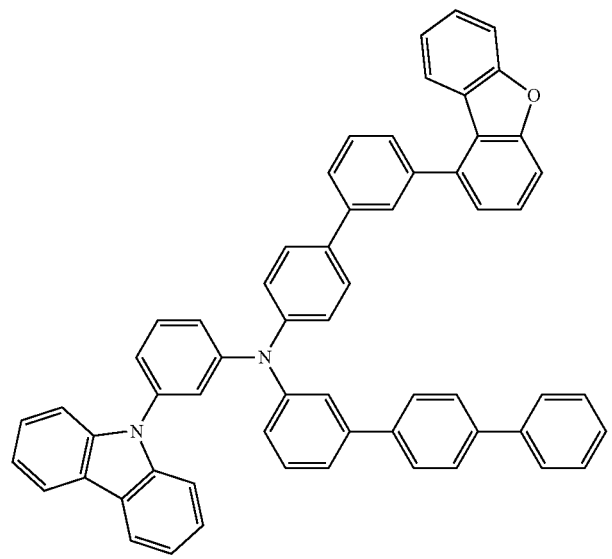
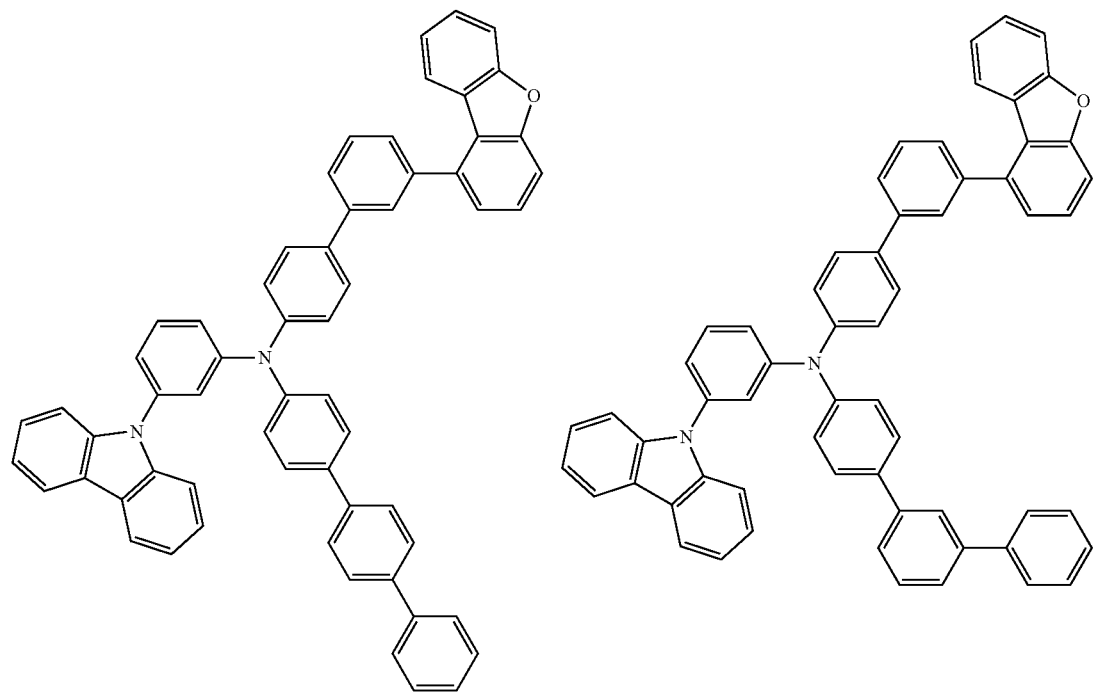

-continued
483
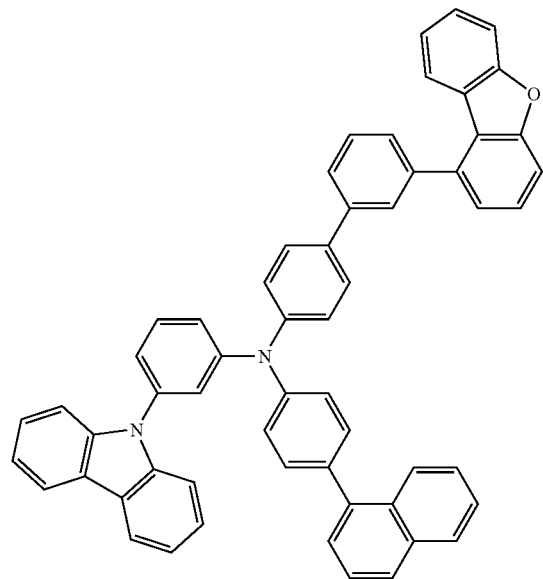
484
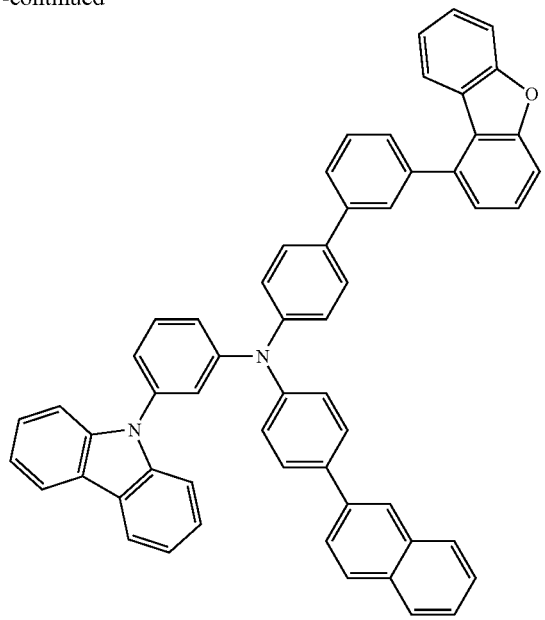
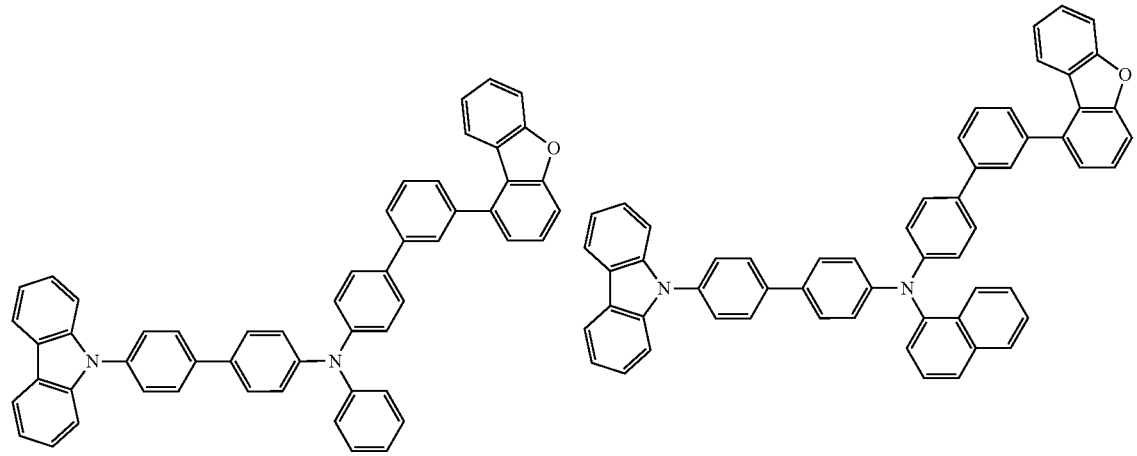
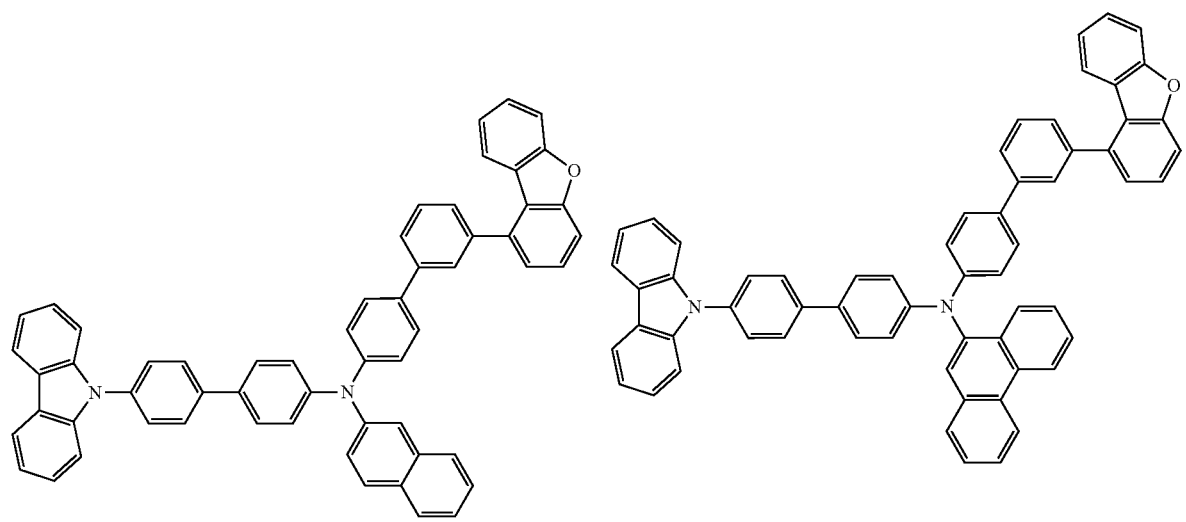

-continued
485
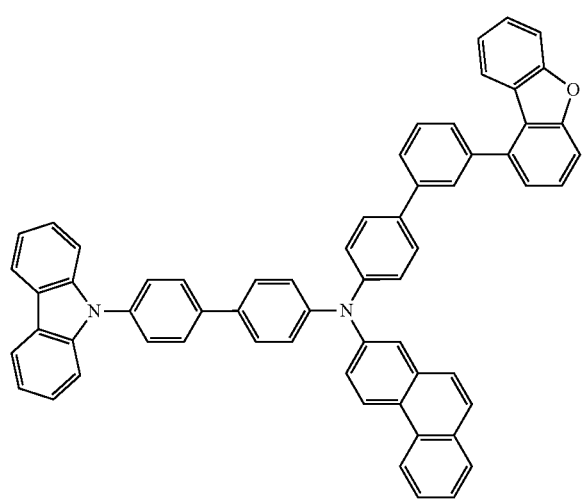
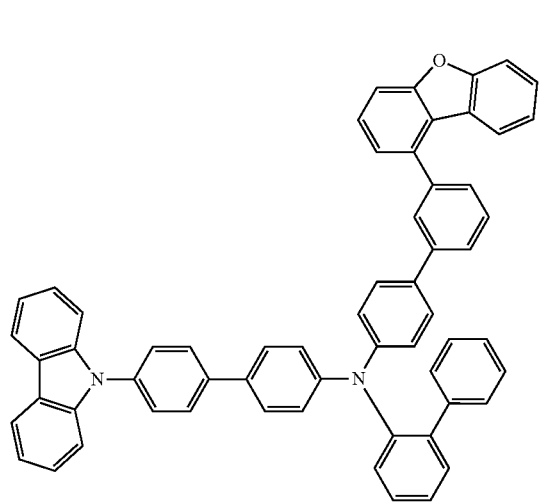
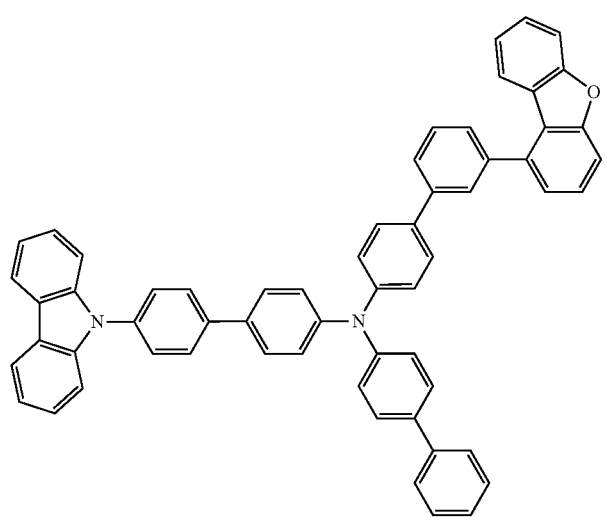
486
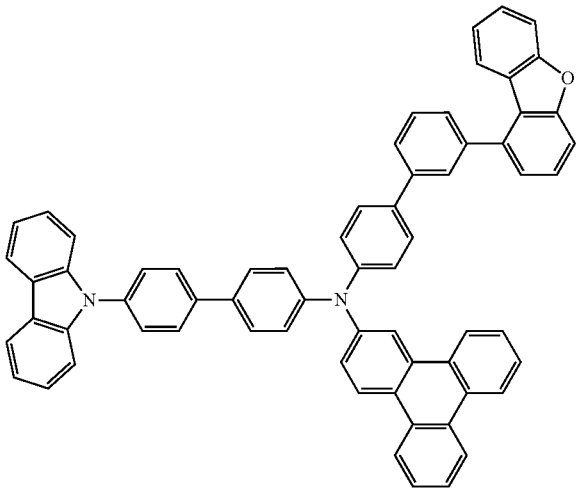
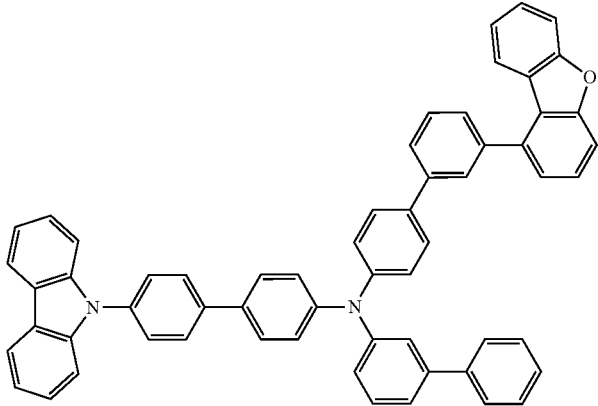
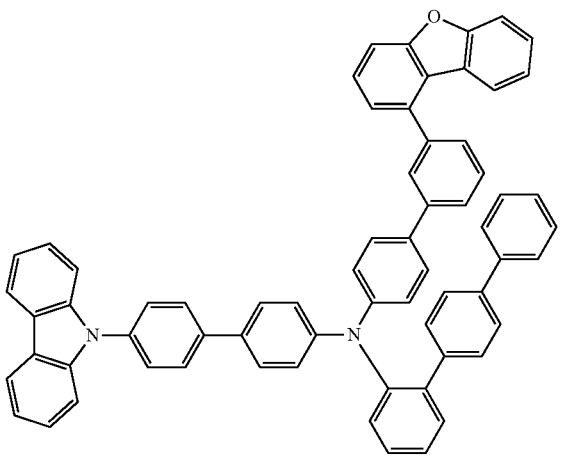

-continued
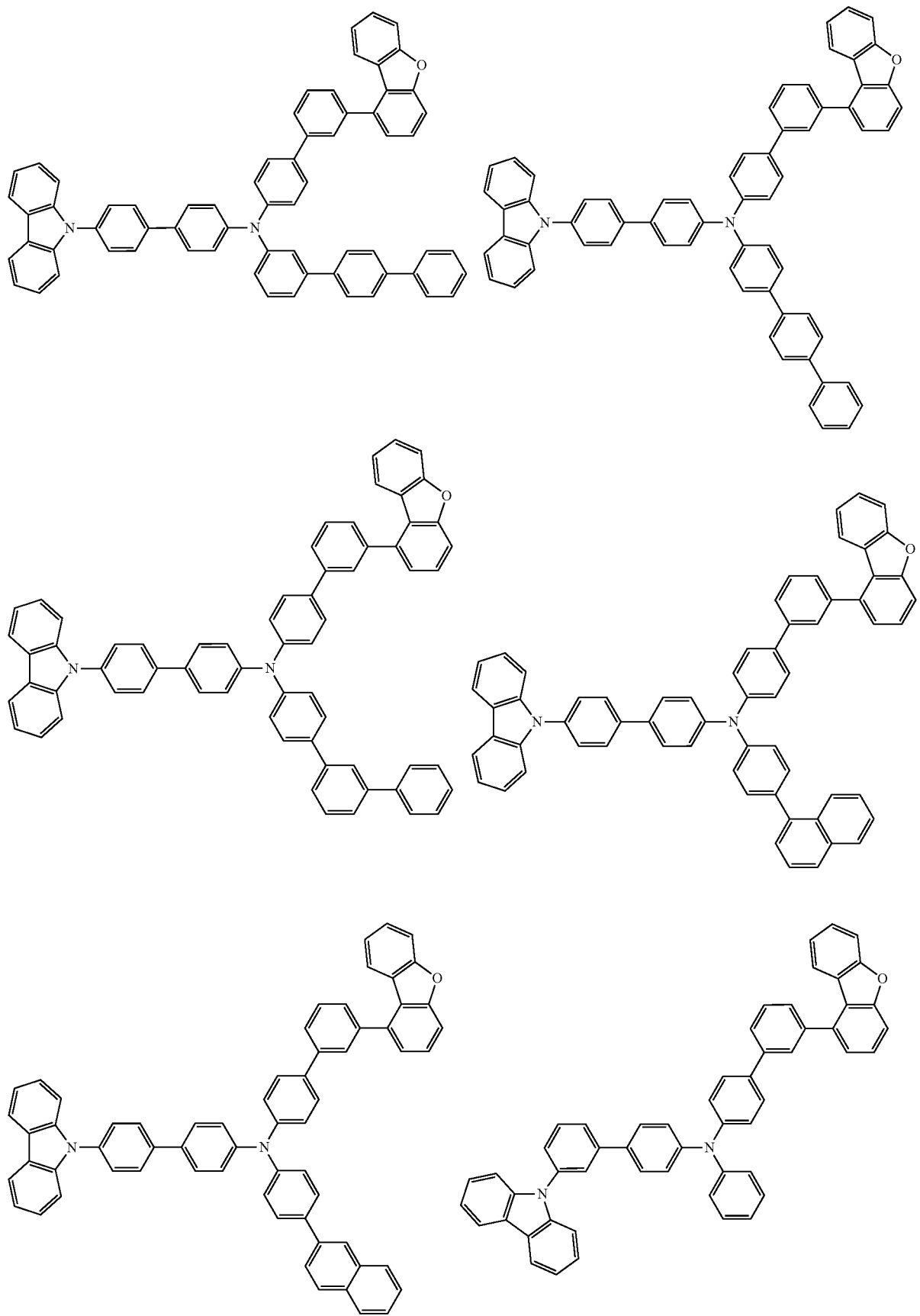

-continued
489
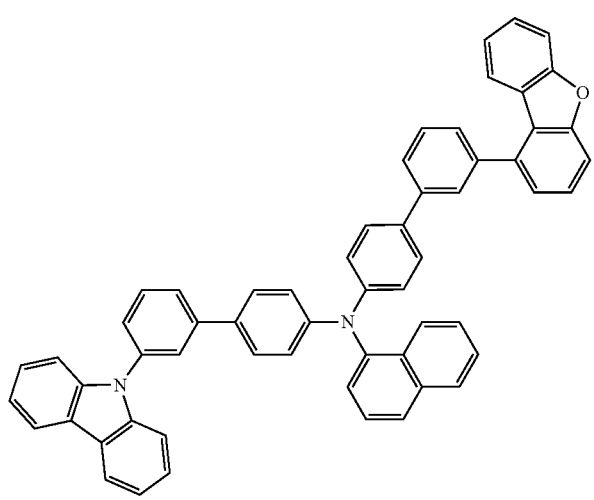
490
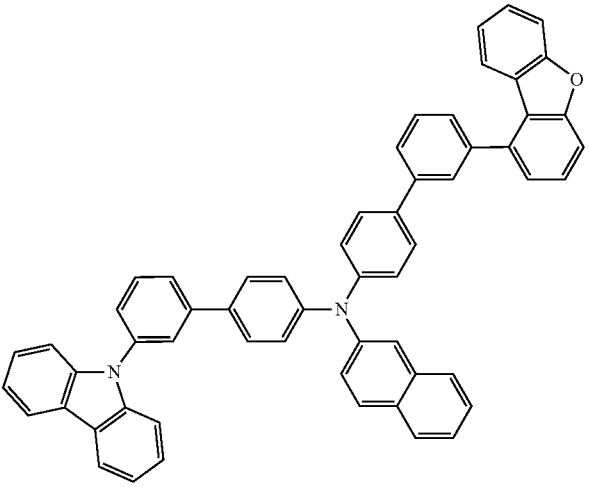
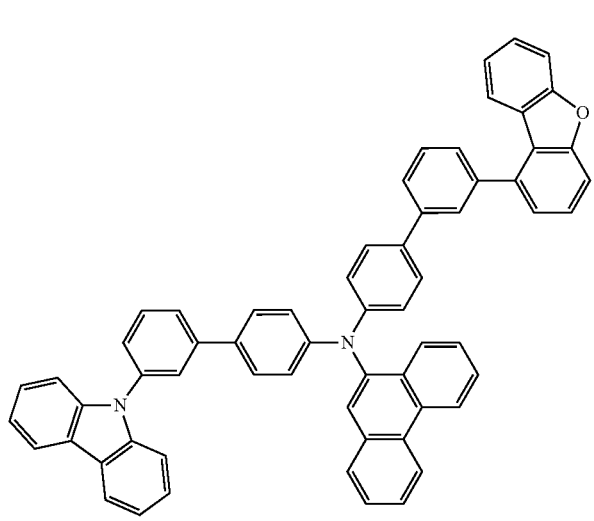
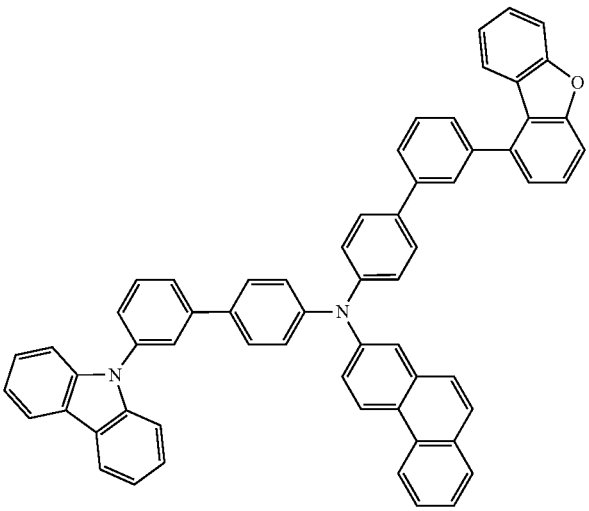
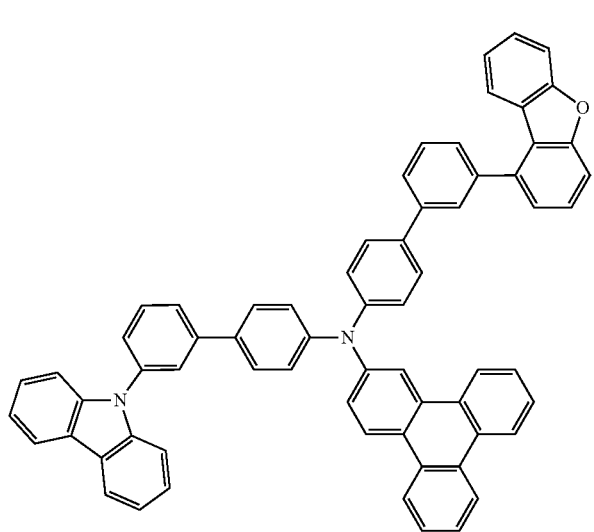
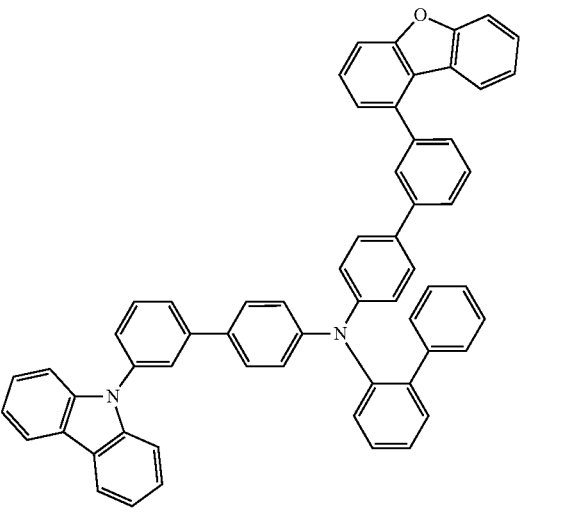

491
492
-continued
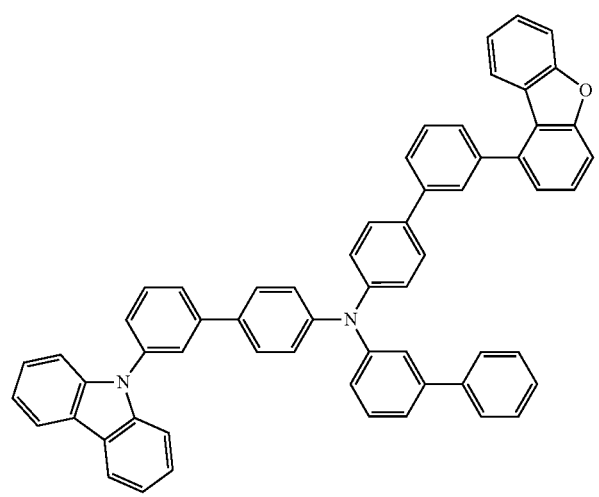
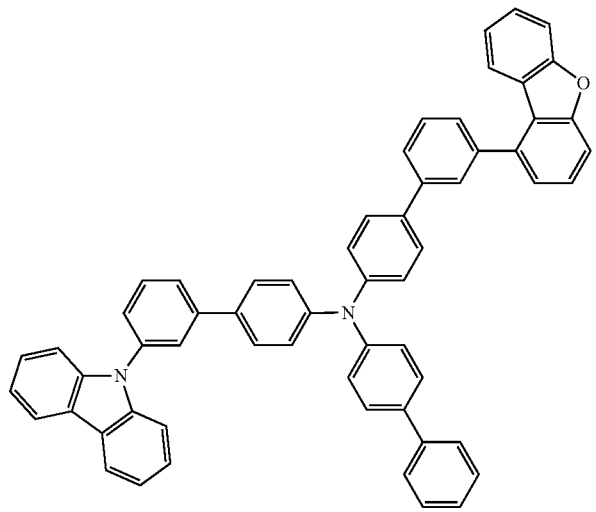
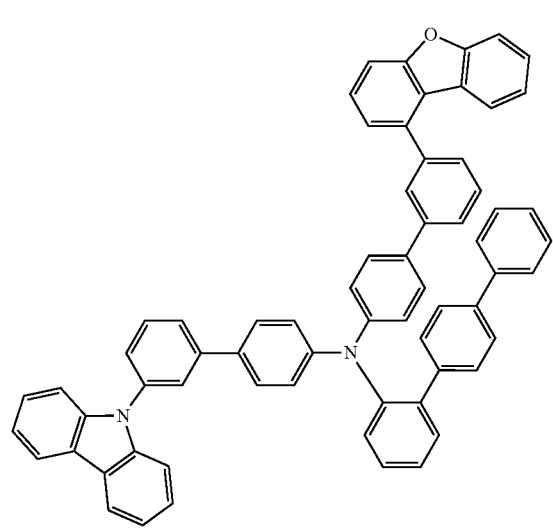
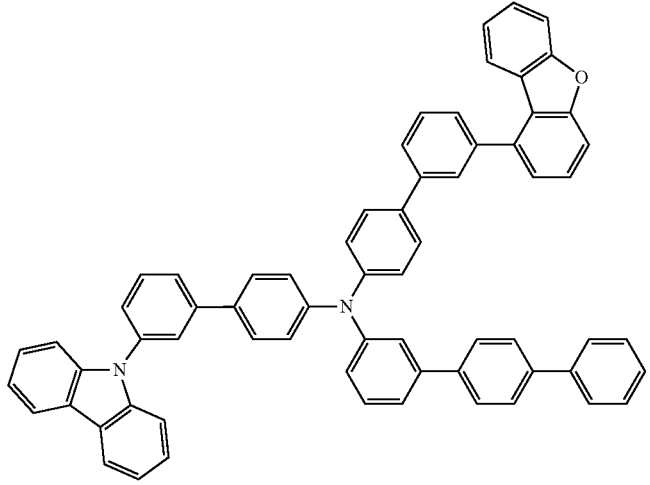
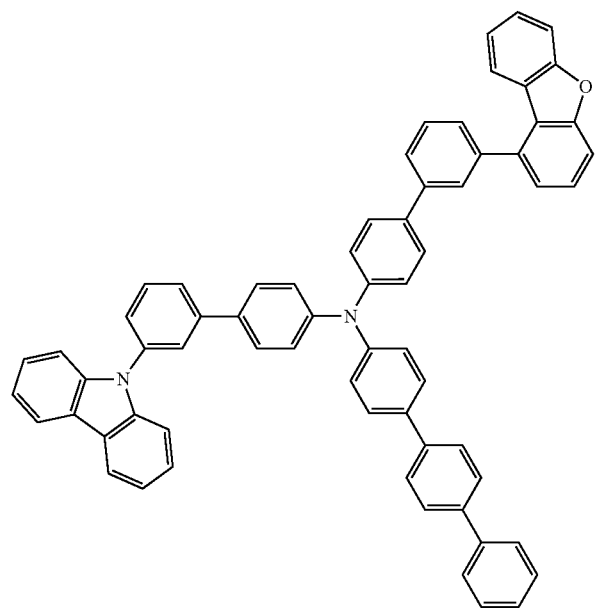
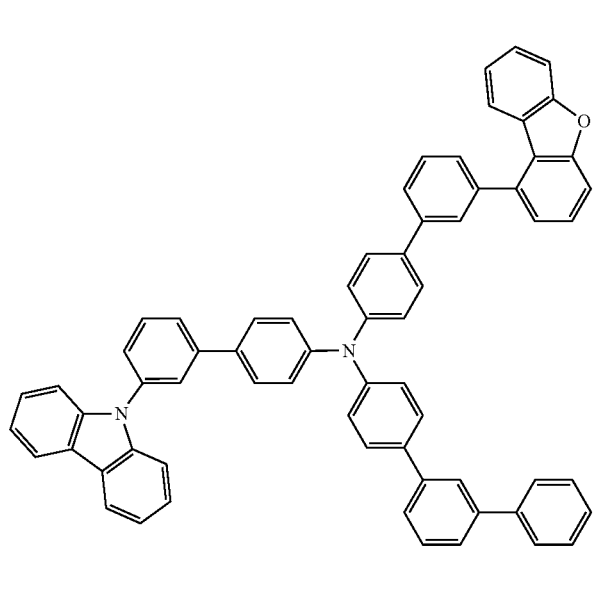

493
494
-continued
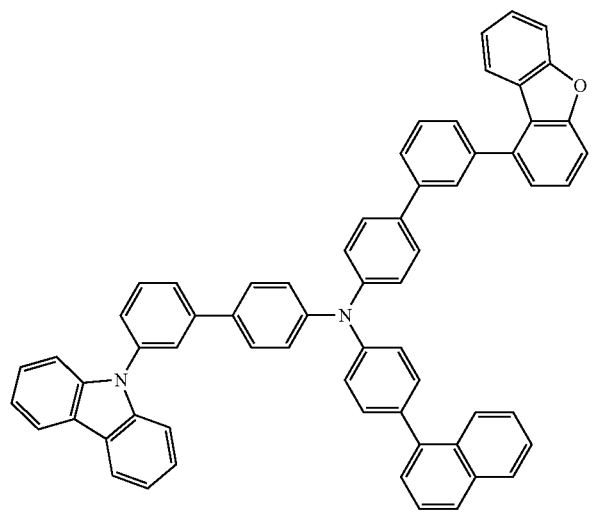
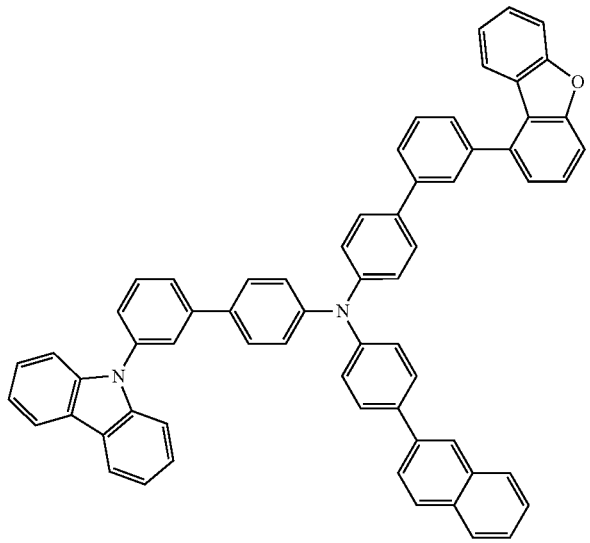
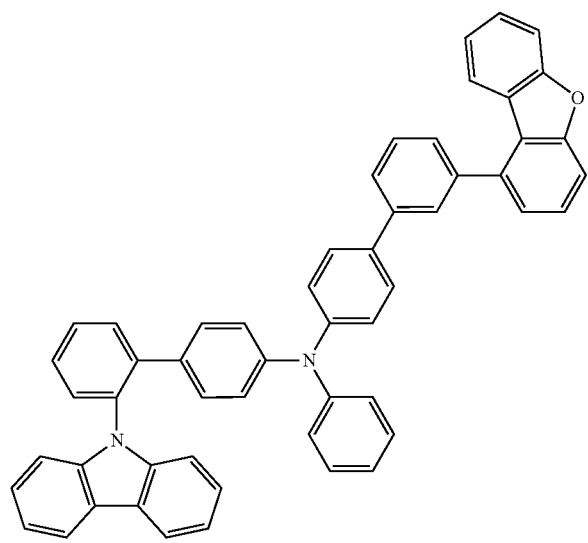
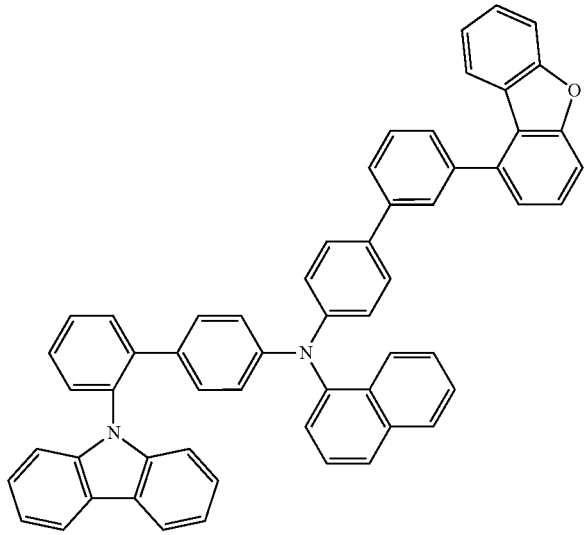
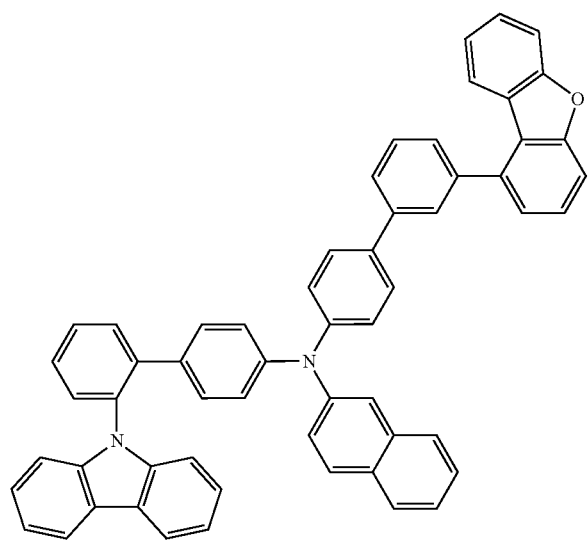
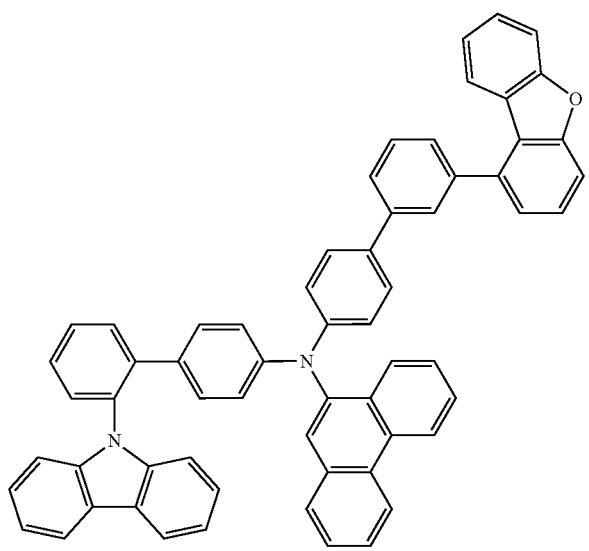

-continued
495 496
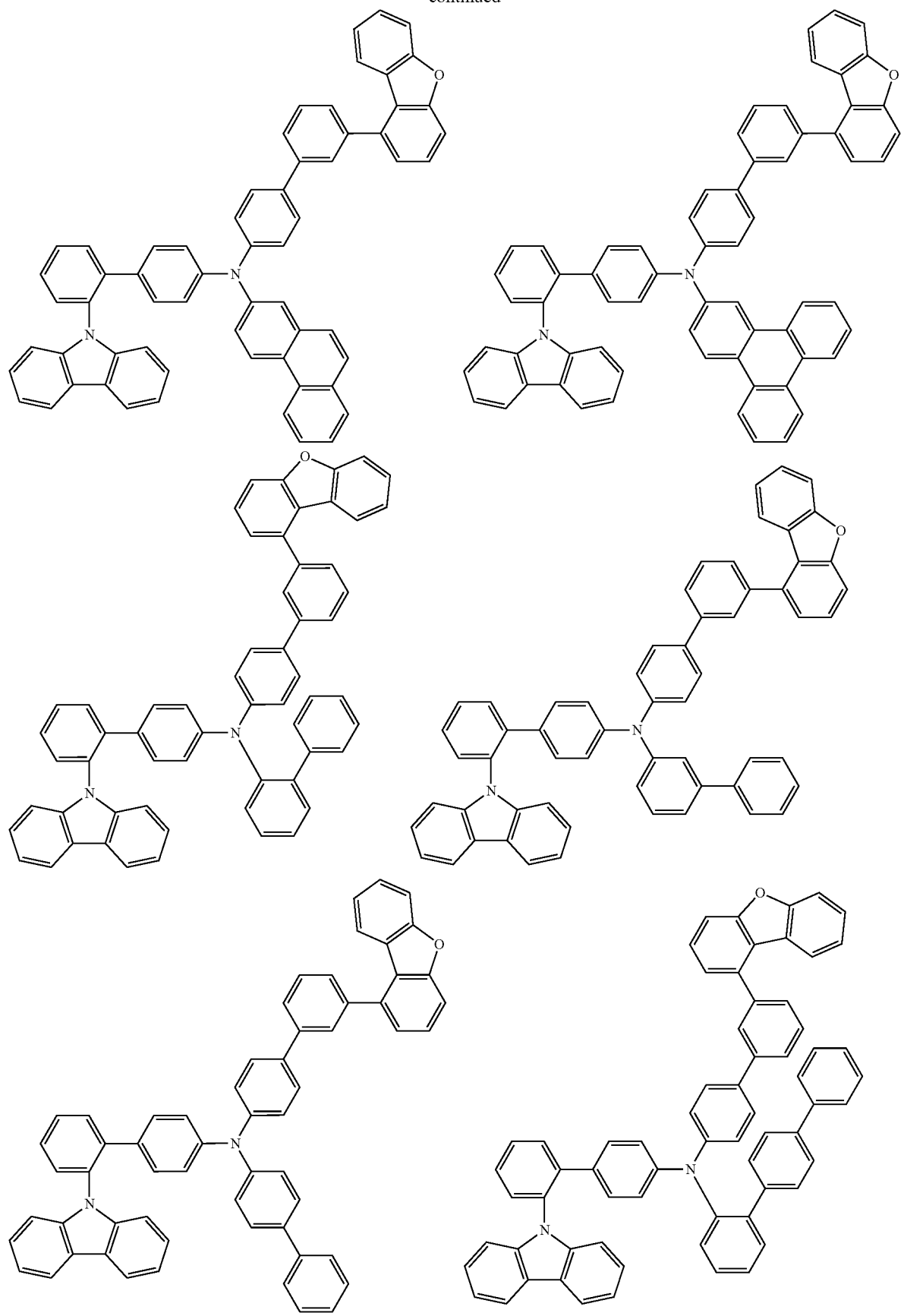

497 498
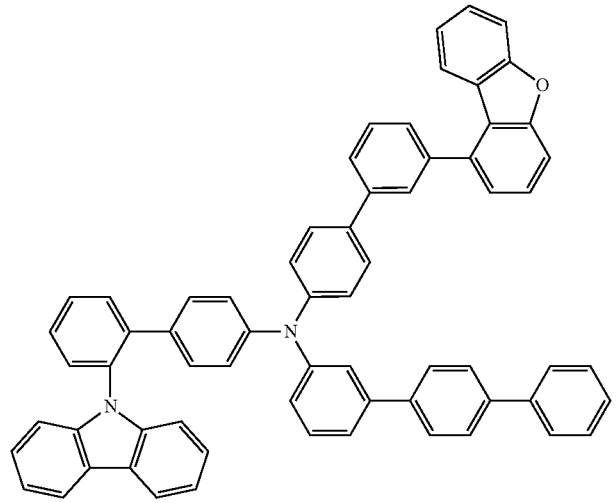
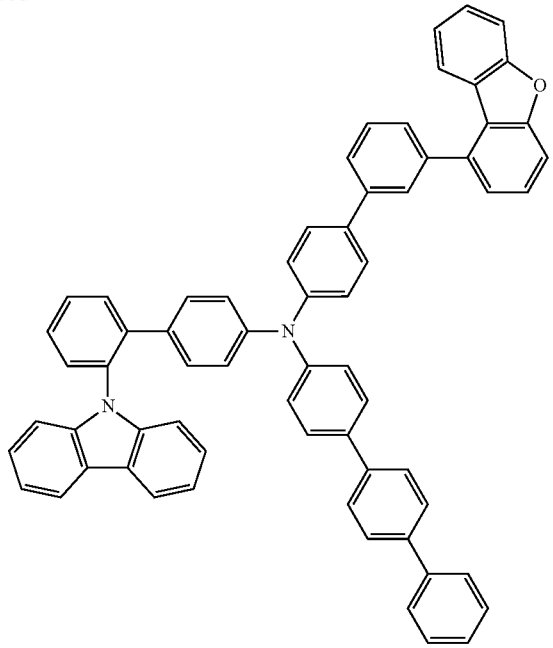
-continued
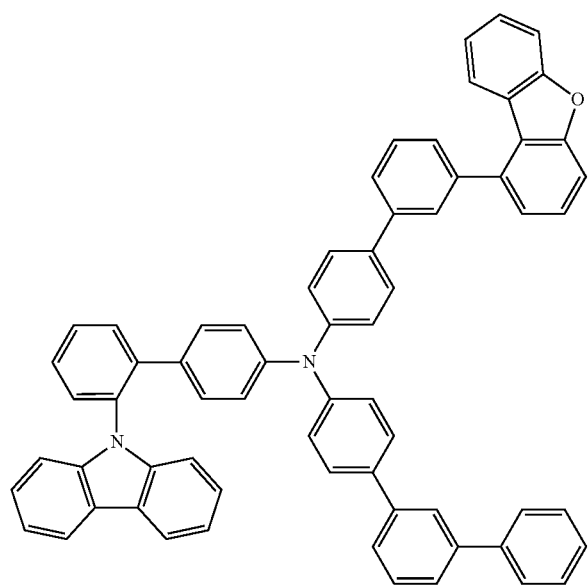
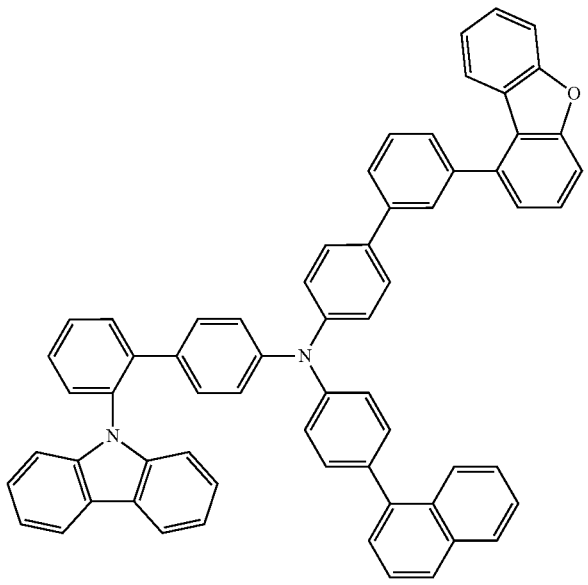

-continued
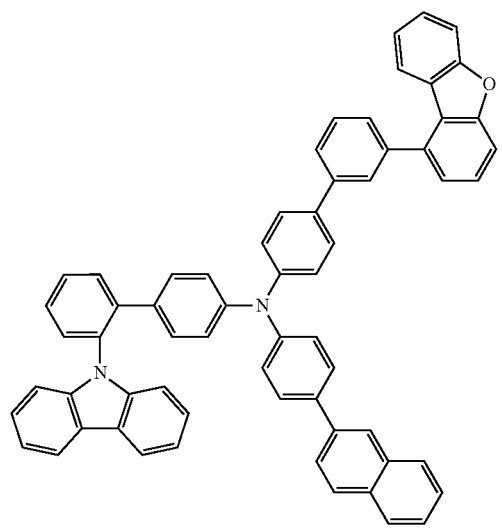
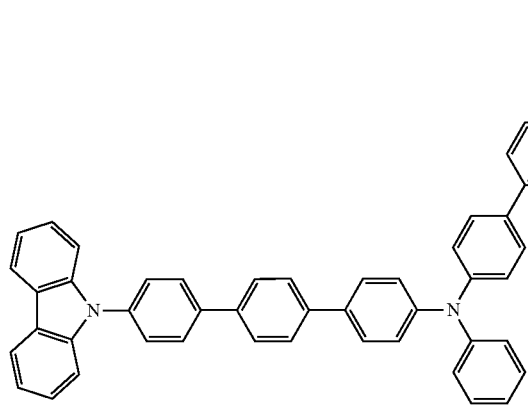
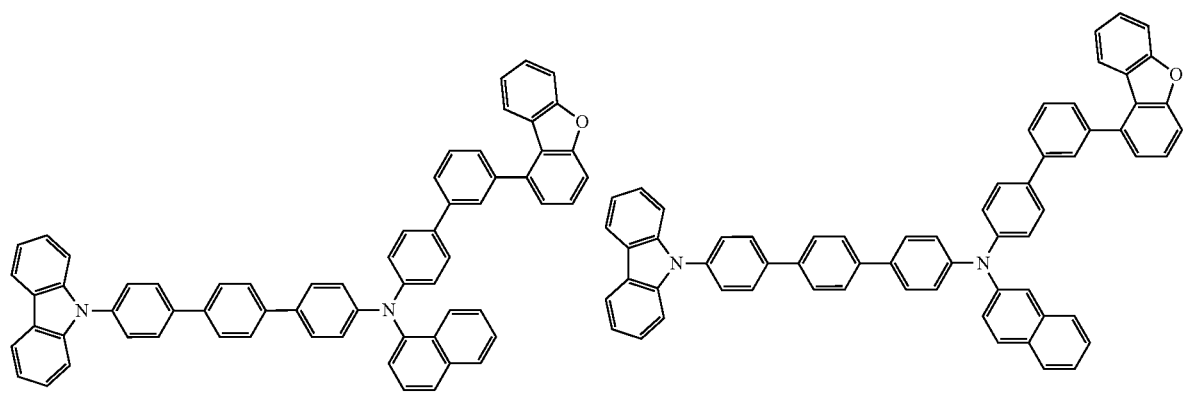
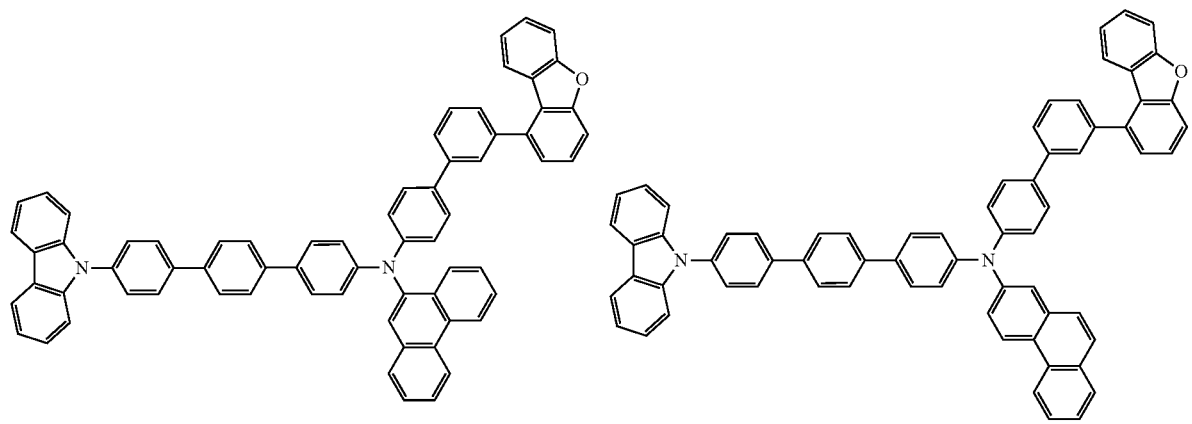

-continued
501
502
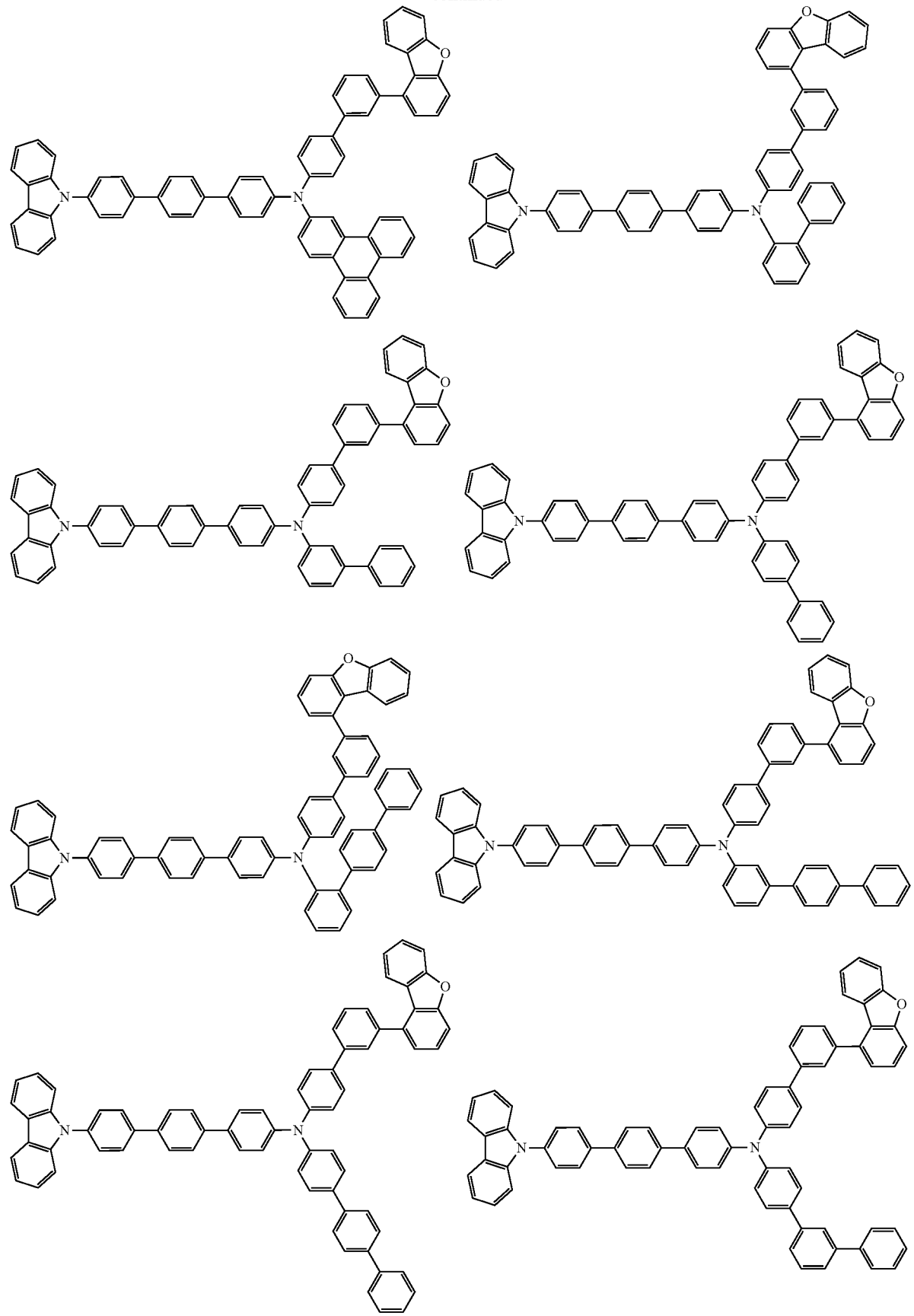

503
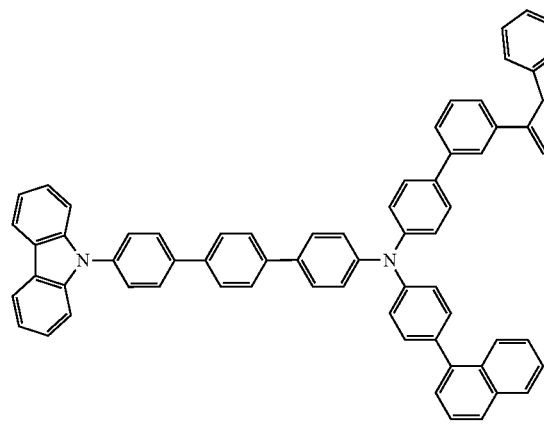
504
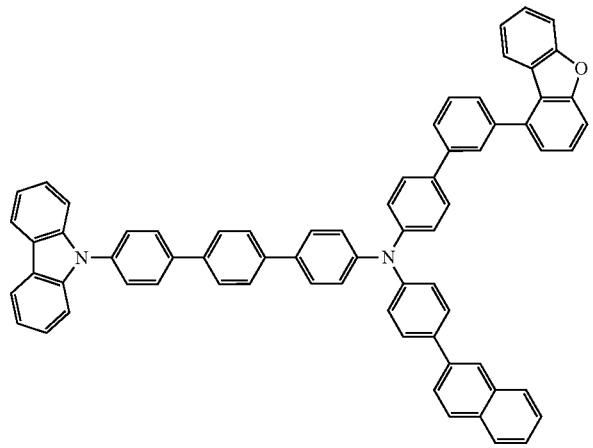
-continued
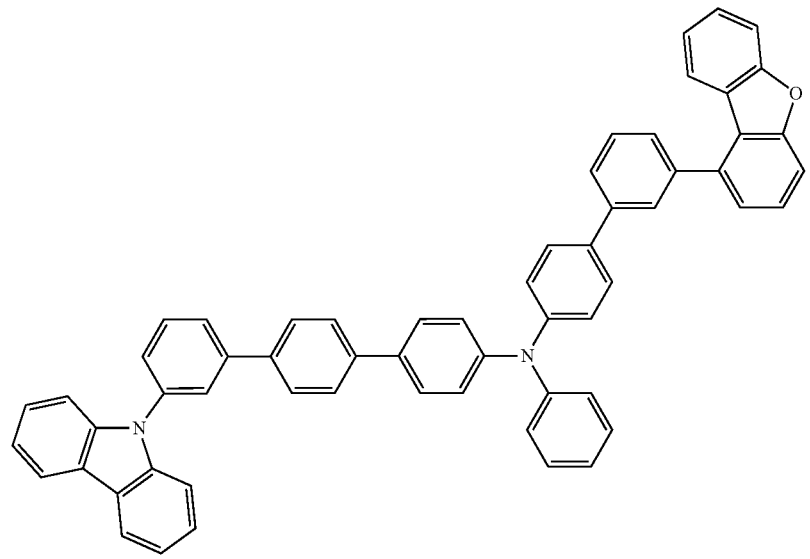 [SMILES: c1ccc(N(c2ccc(-c3ccc(-c4cccc(-n5c6ccccc6c6ccccc65)c4)cc3)cc2)c2ccc(-c3cccc(-c4cccc5oc6ccccc6c45)c3)cc2)cc1]
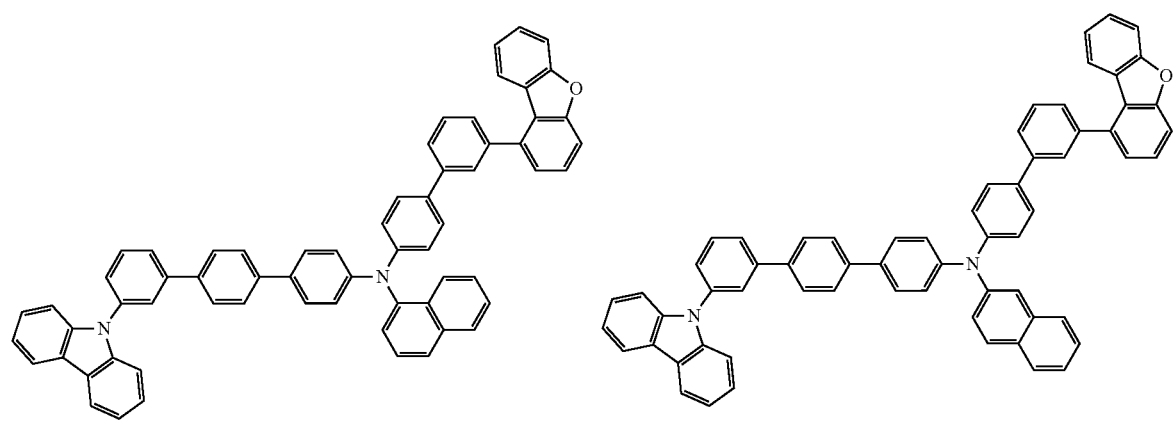

505
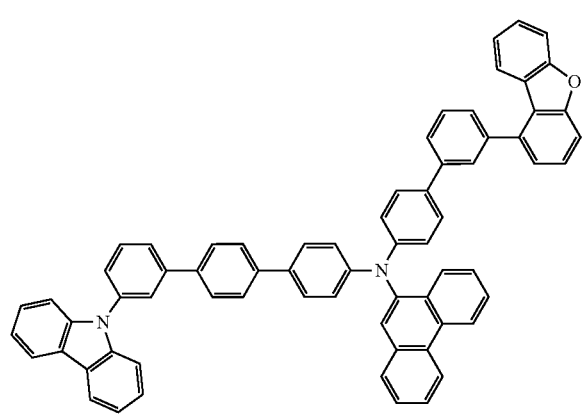
506
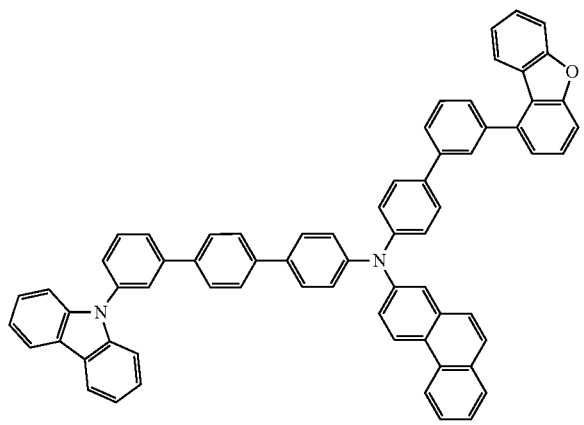
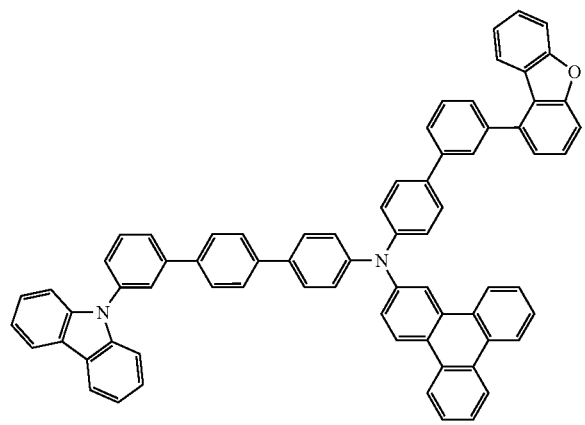
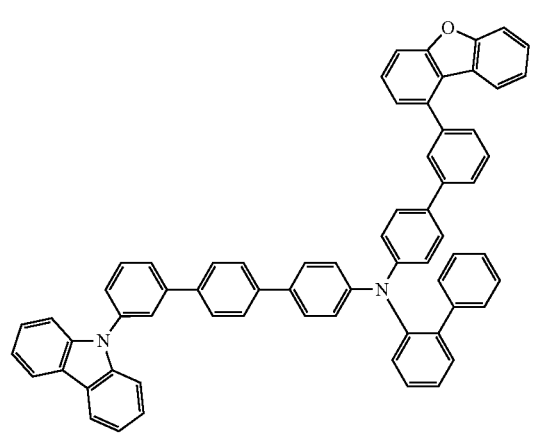
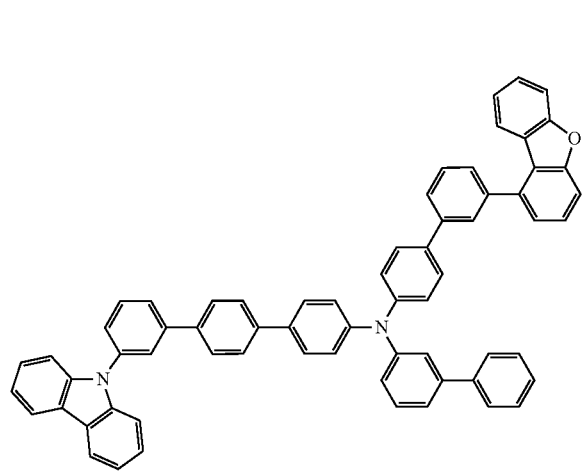
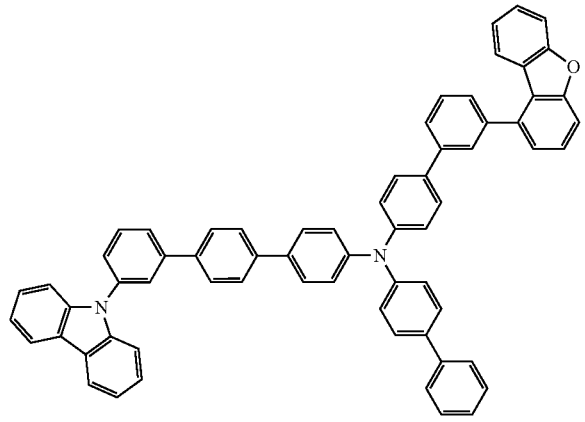

507
508
-continued
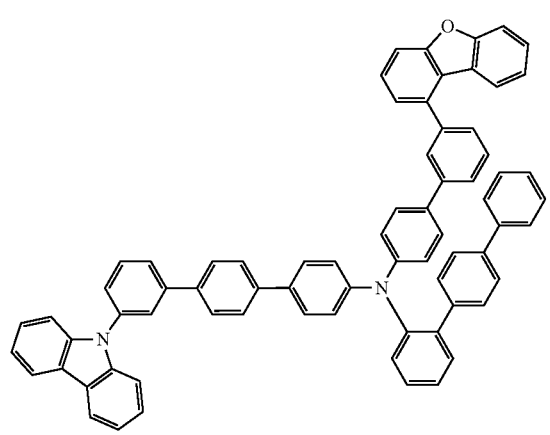
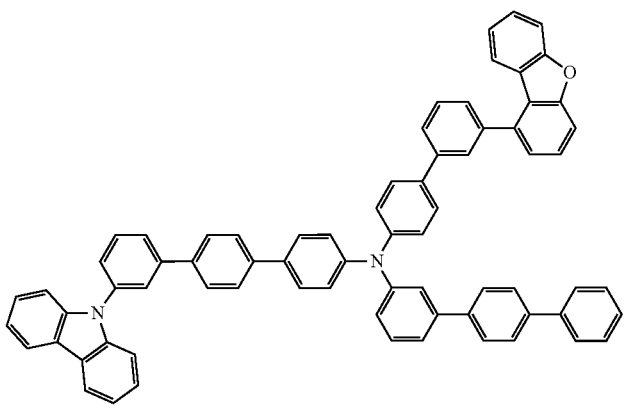
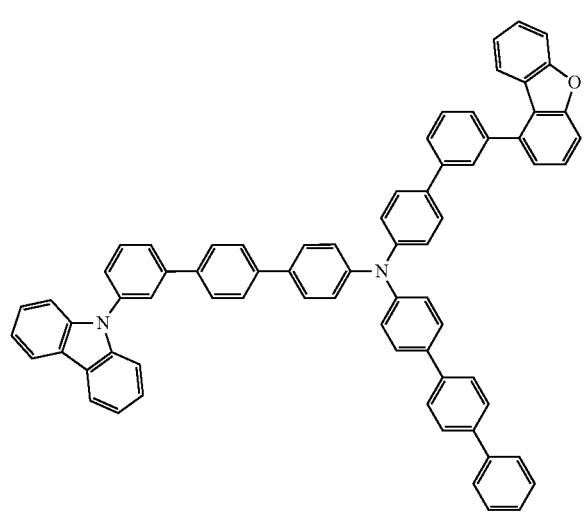
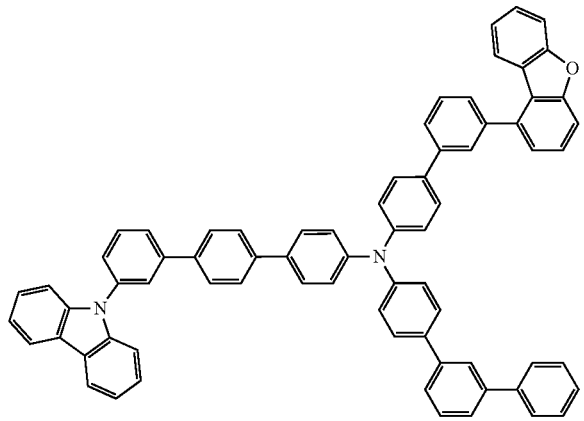
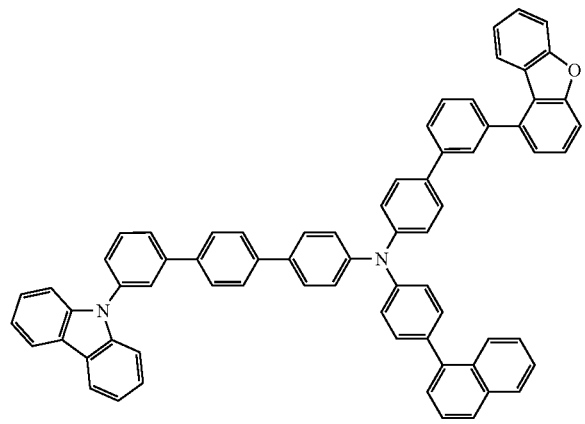
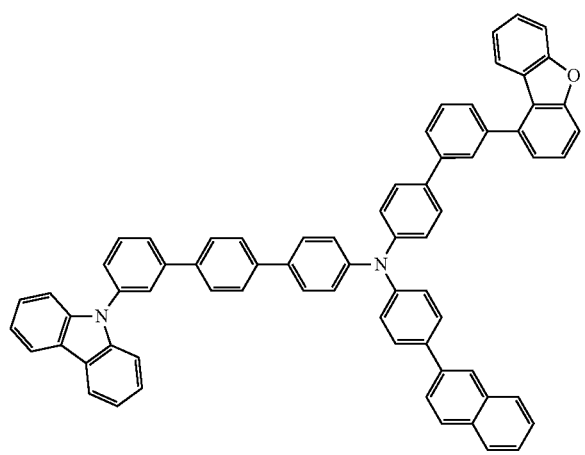

-continued
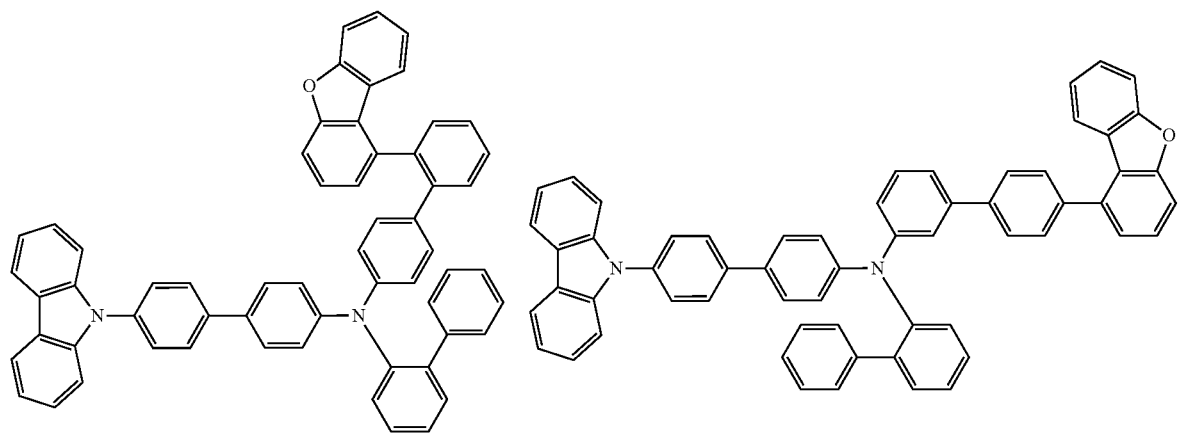
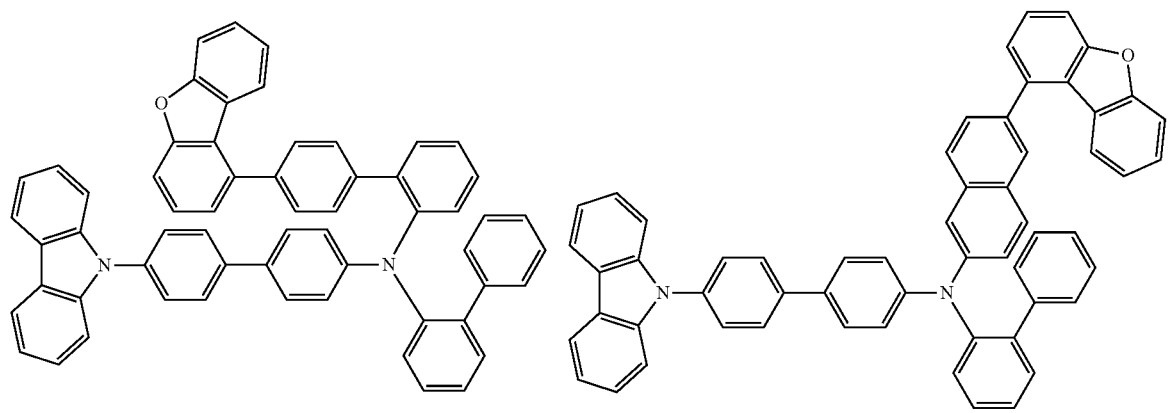
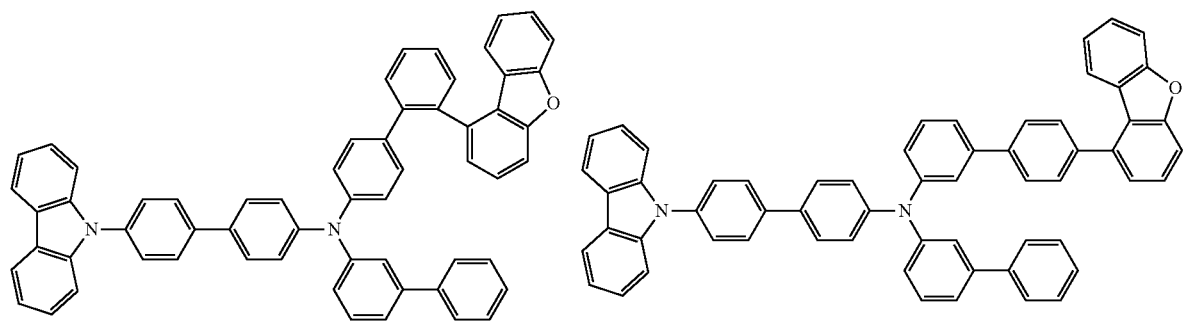
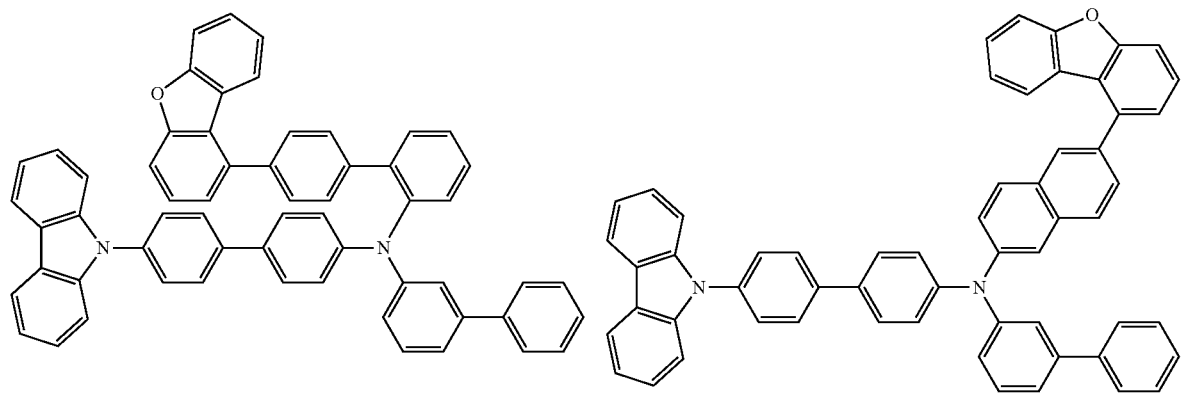

-continued
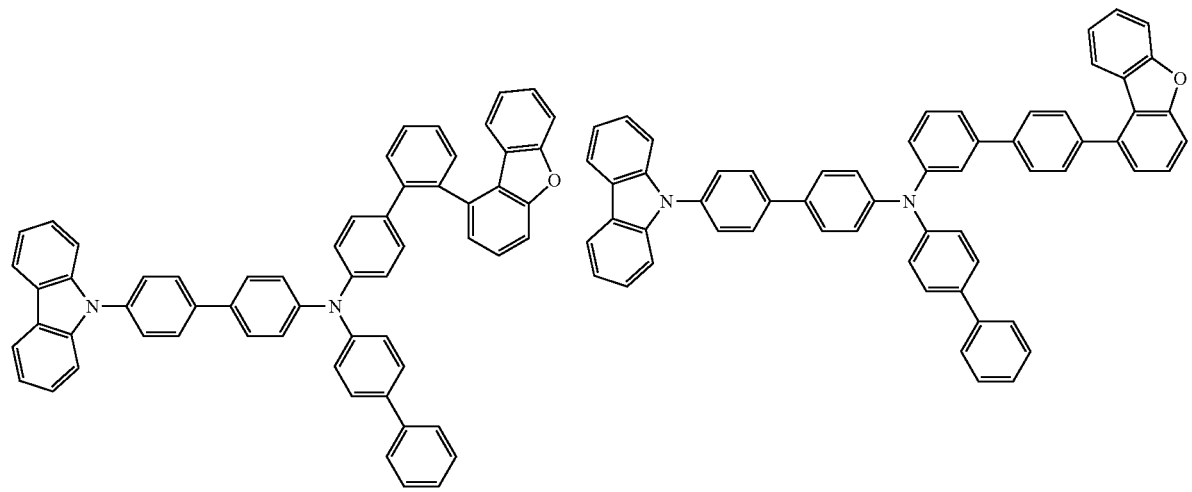
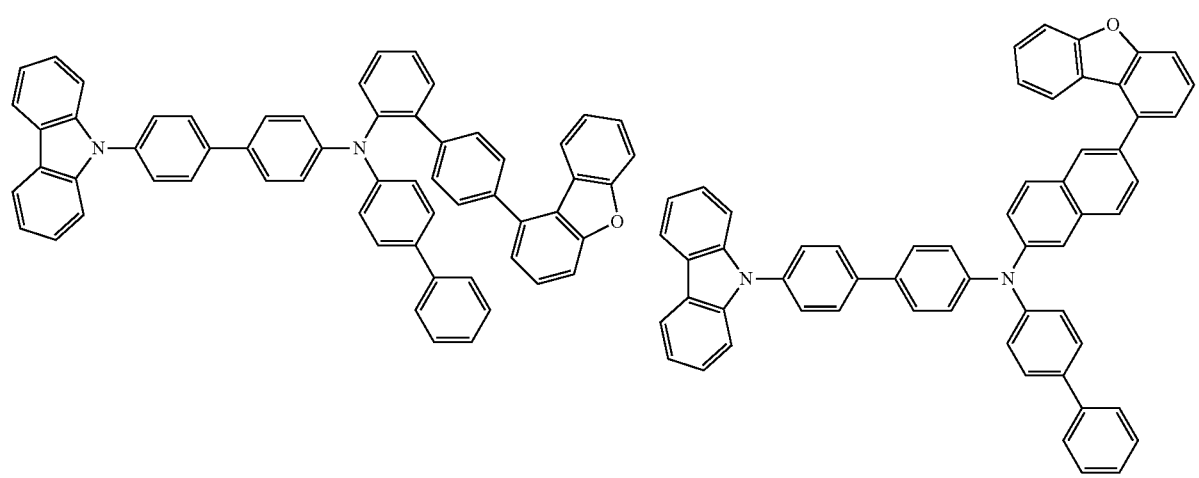
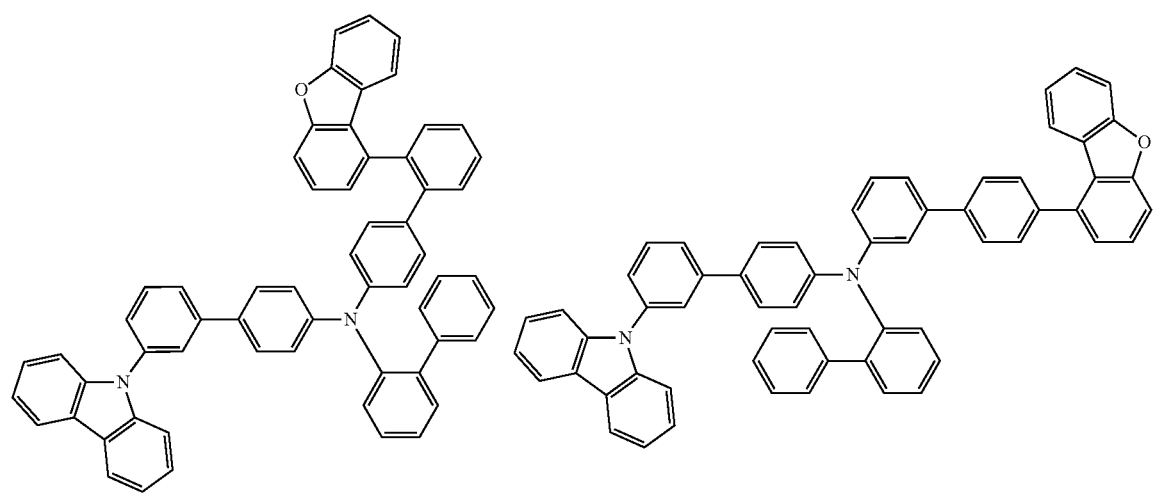

513
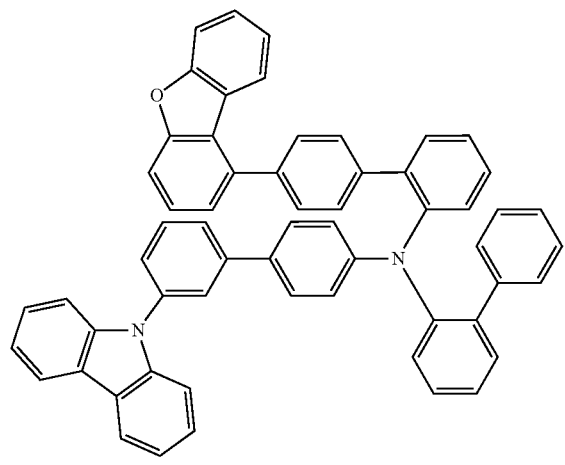
514
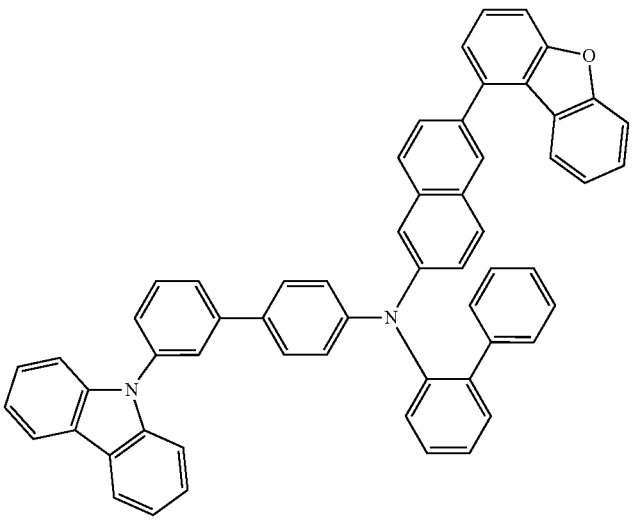
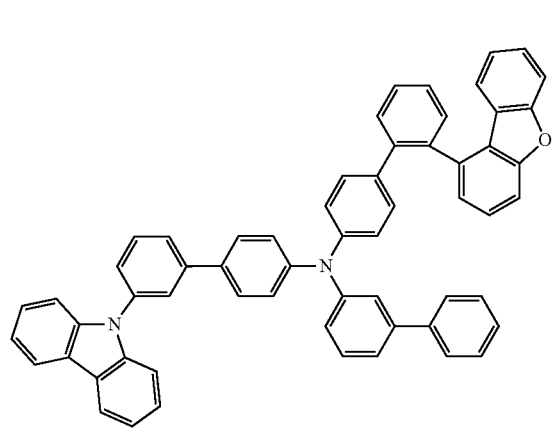
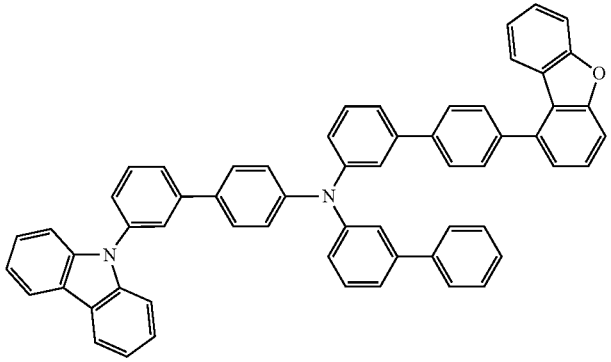
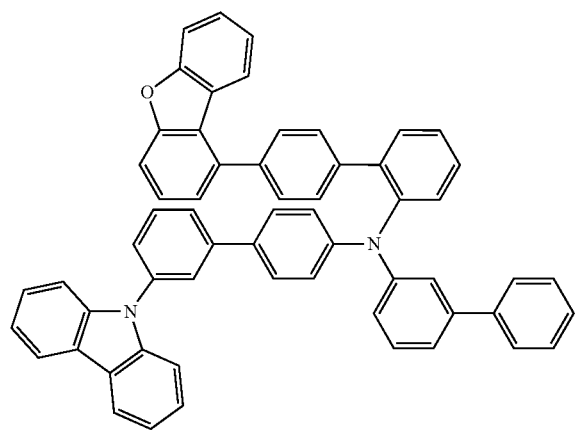
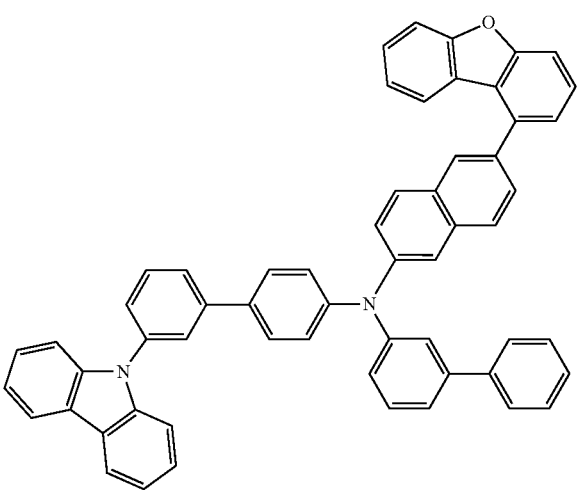

515 516
-continued
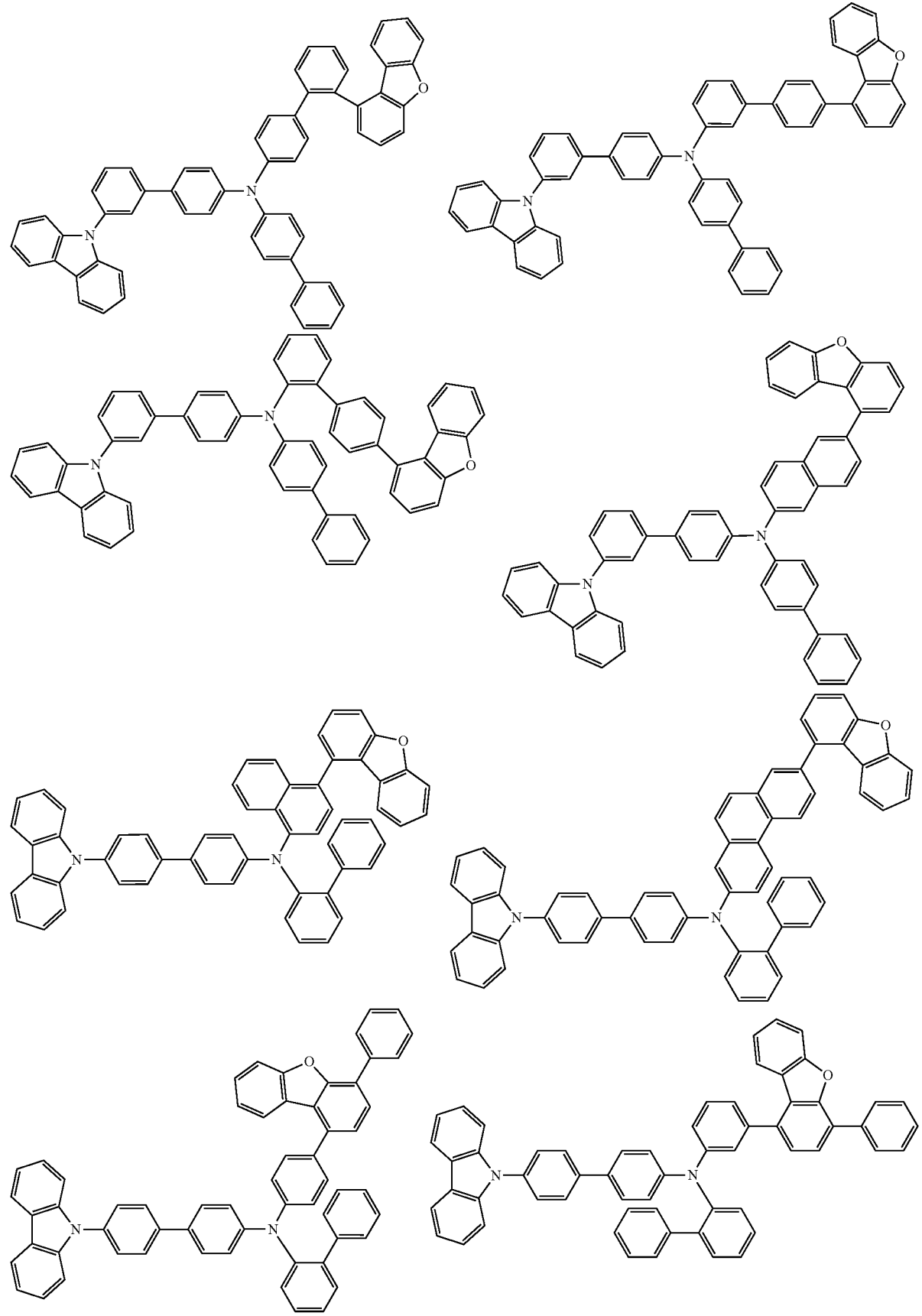

517 518
-continued
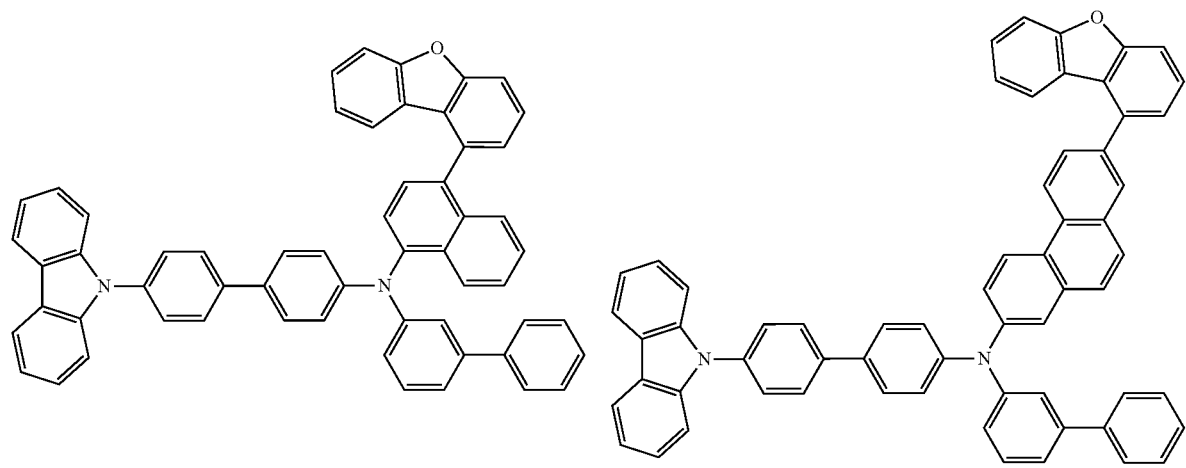
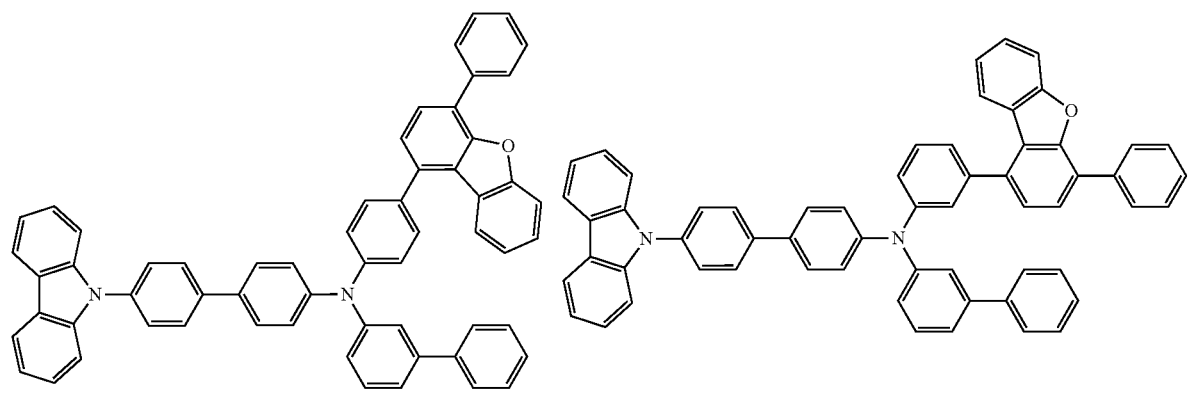
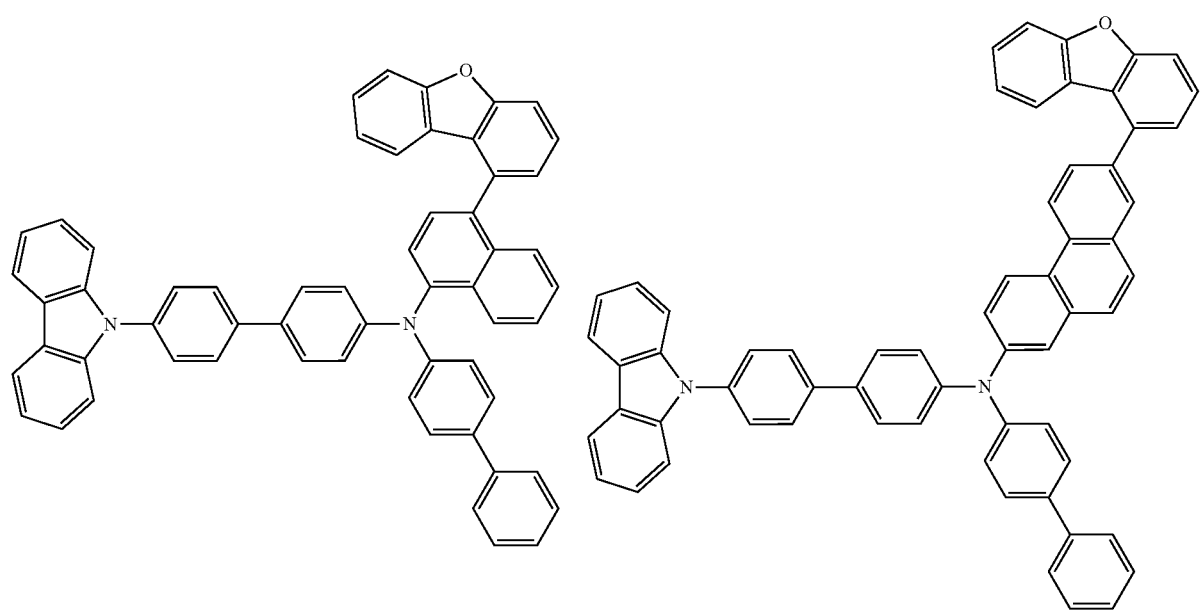

519 520
-continued
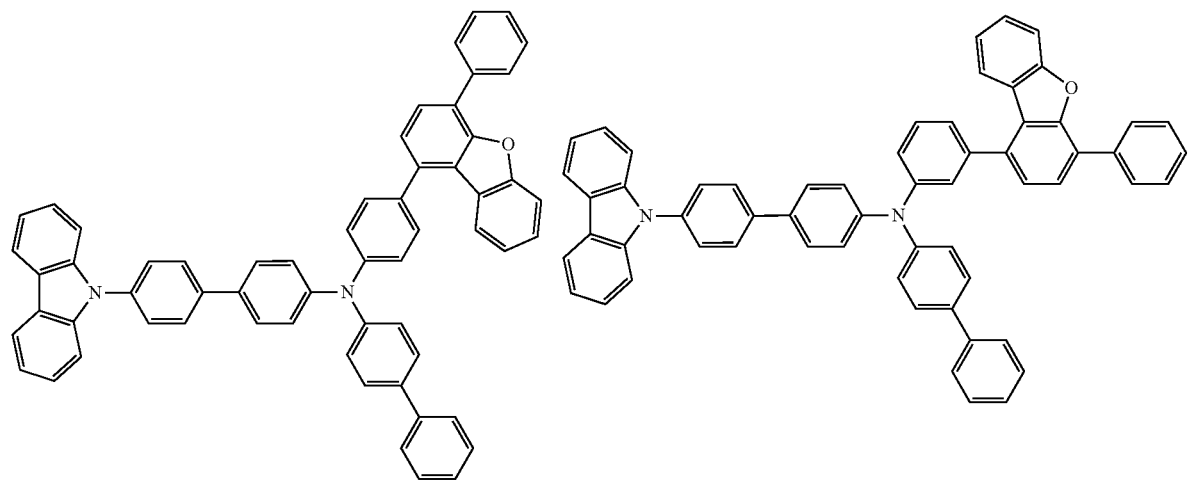
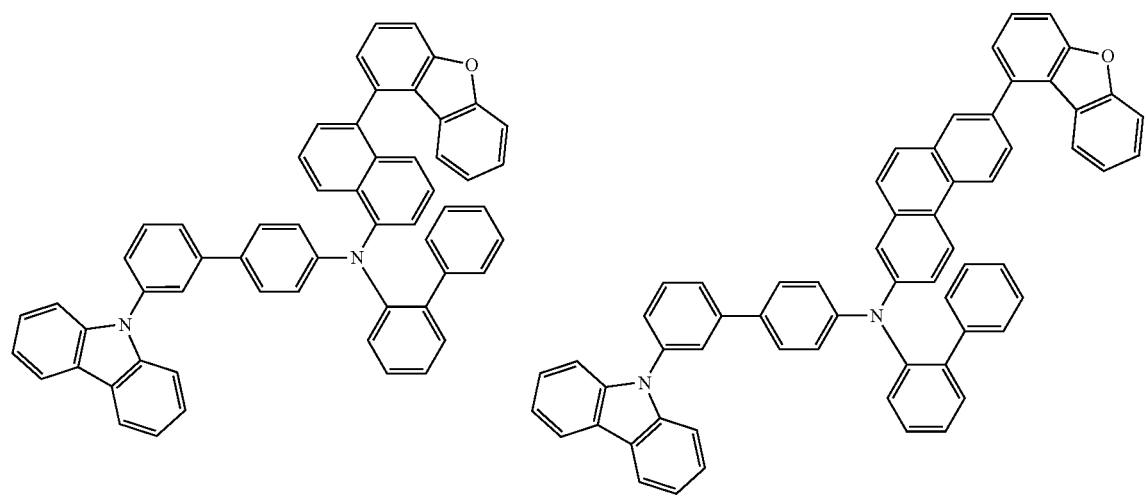
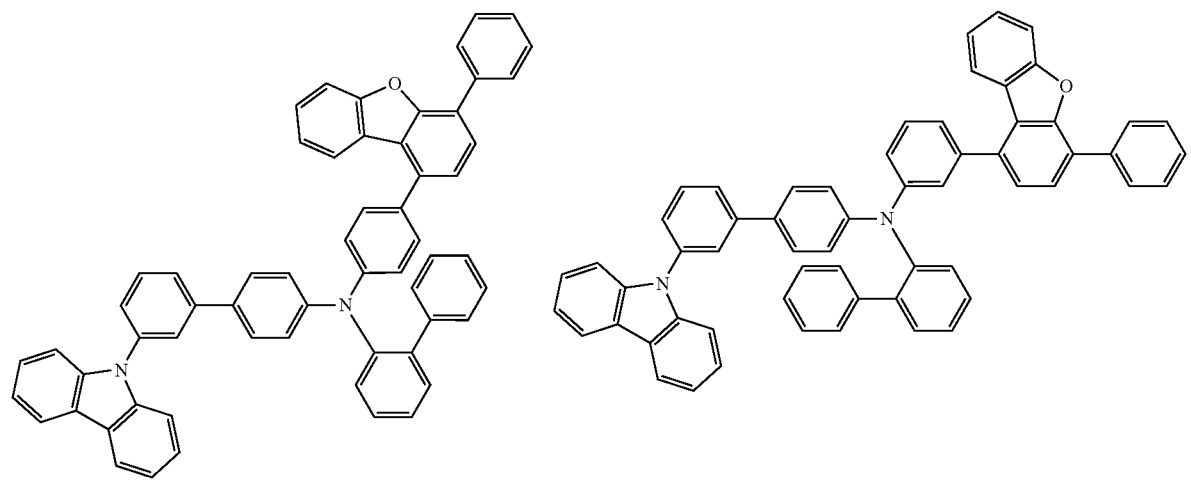

-continued
521
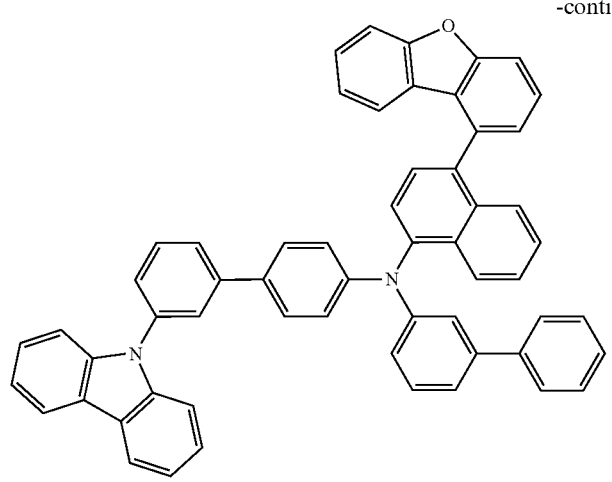
522
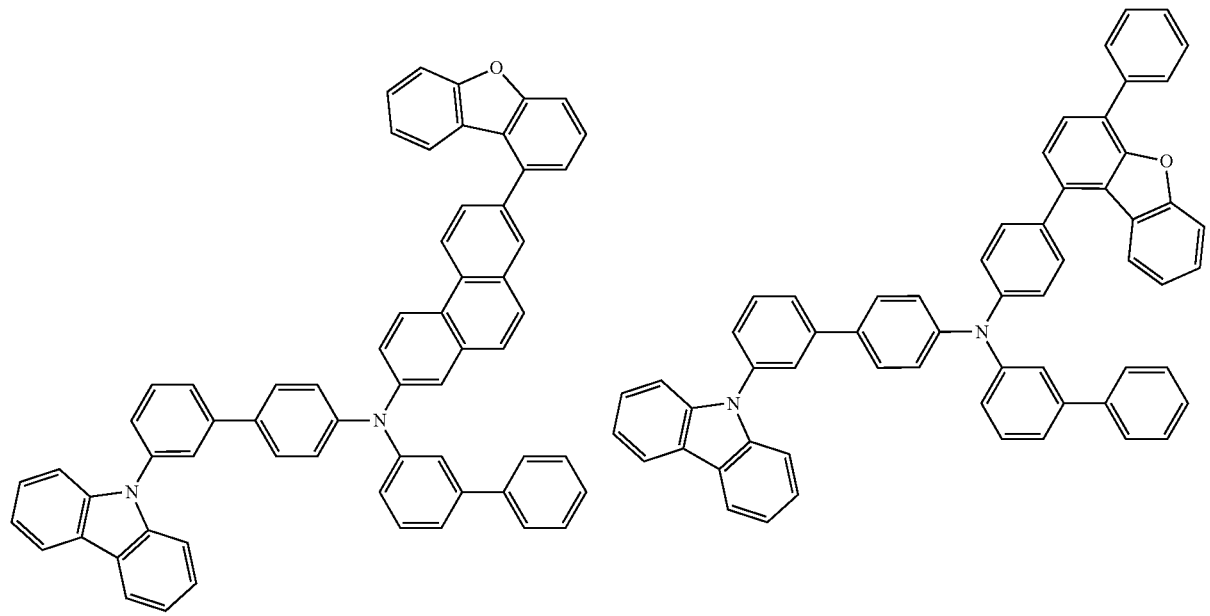
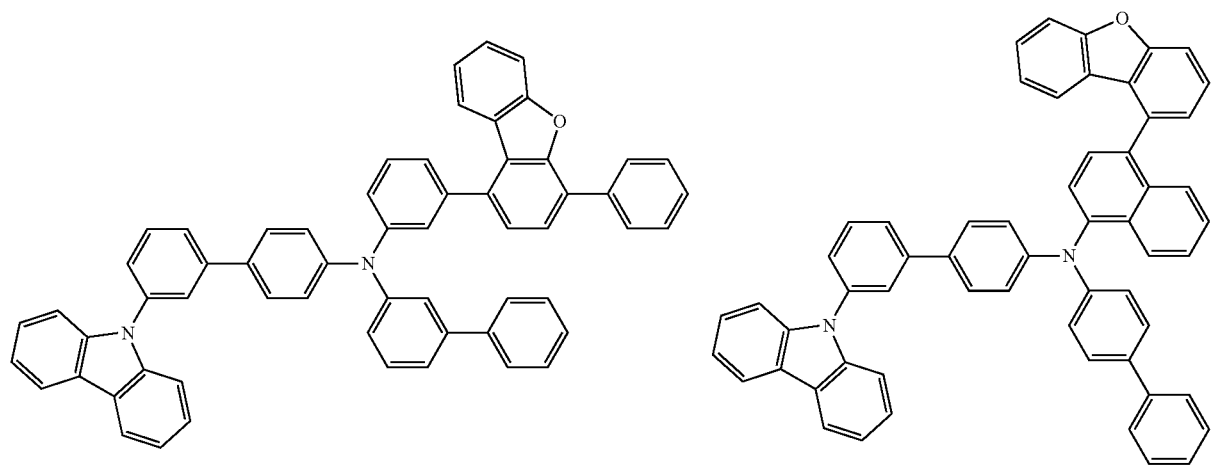

-continued
523 524
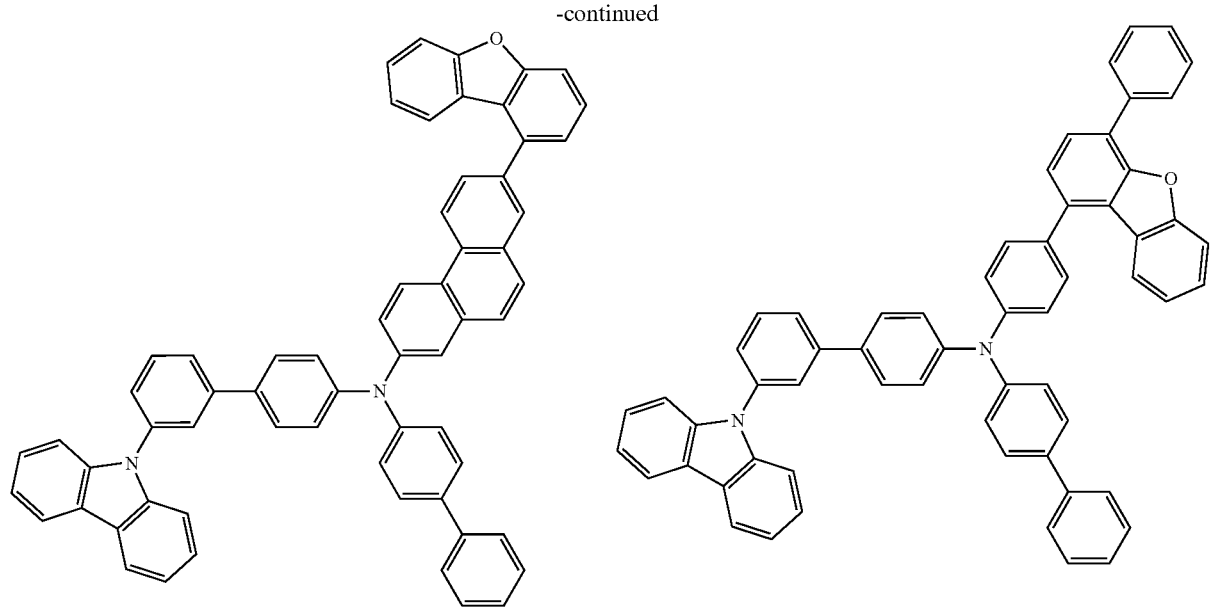
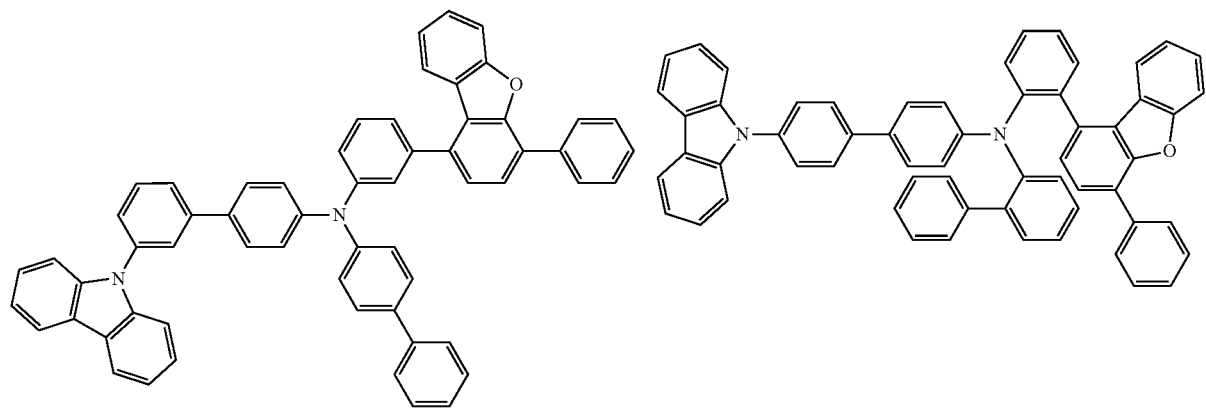
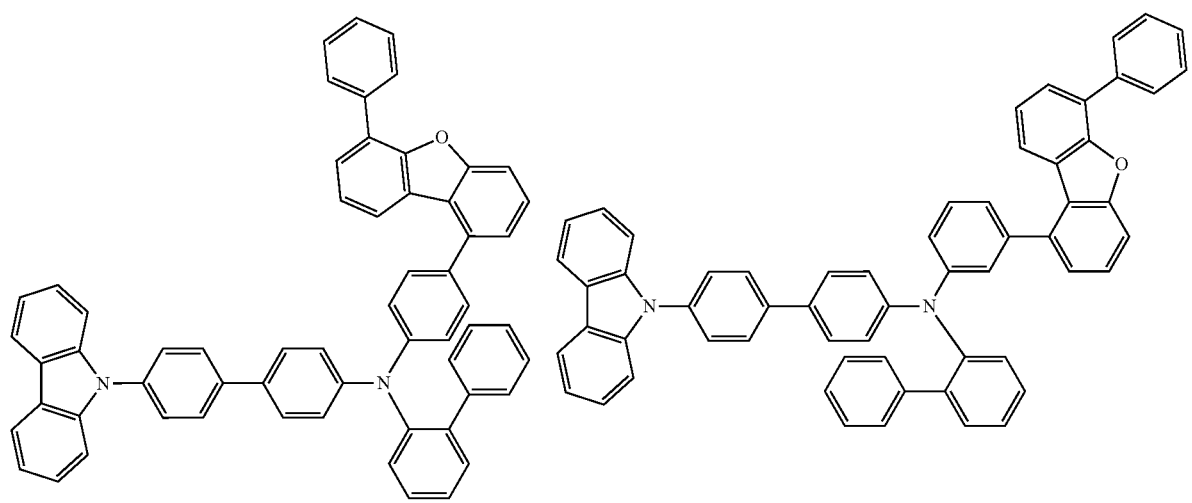

525 526
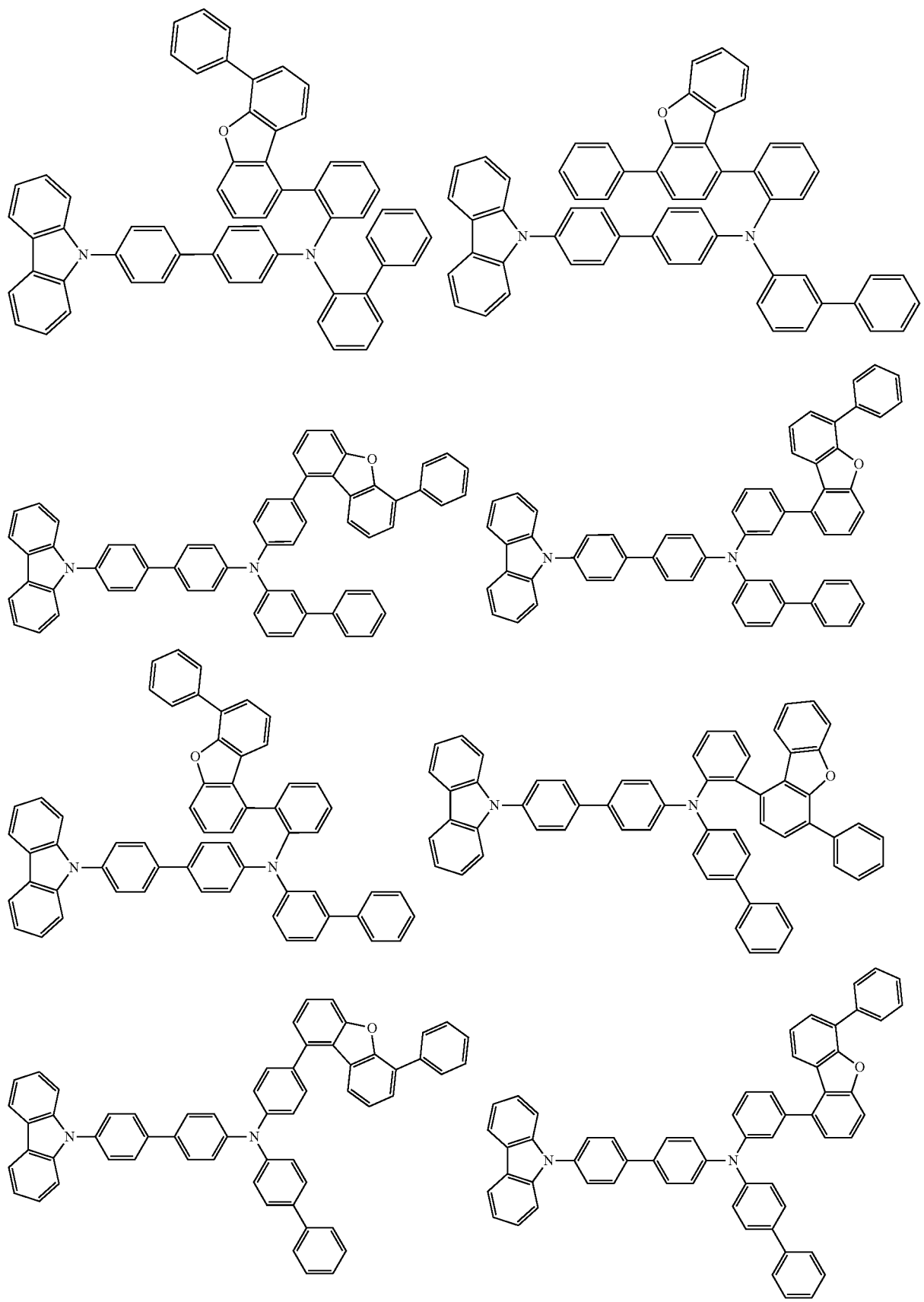
-continued

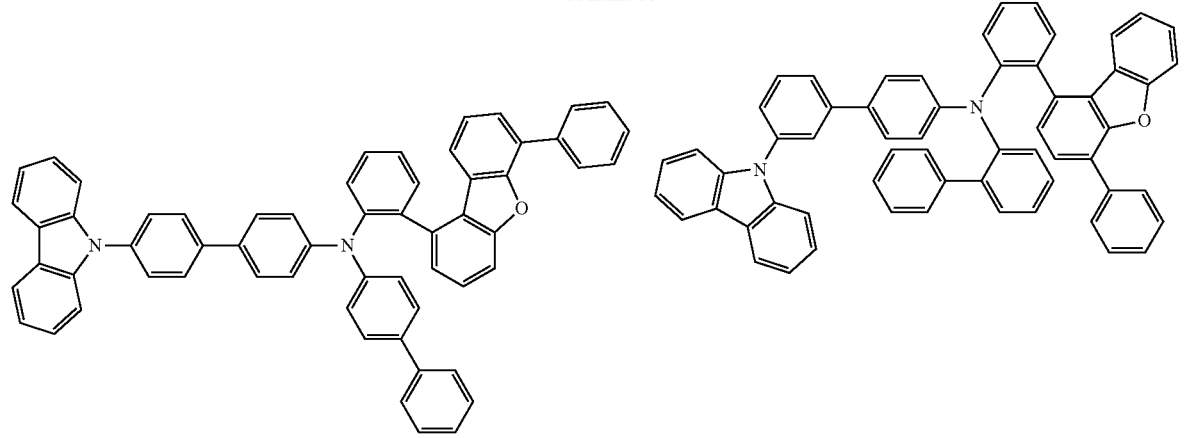

-continued
529
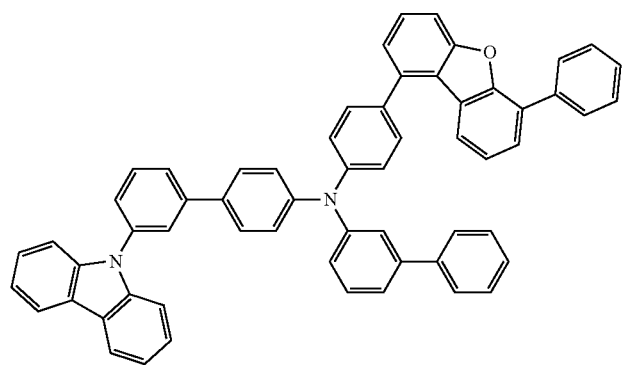
530
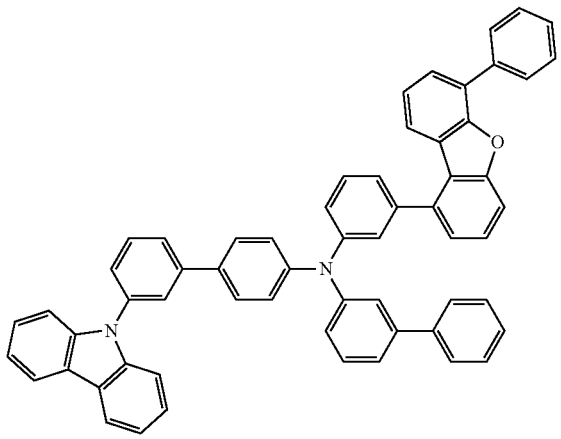
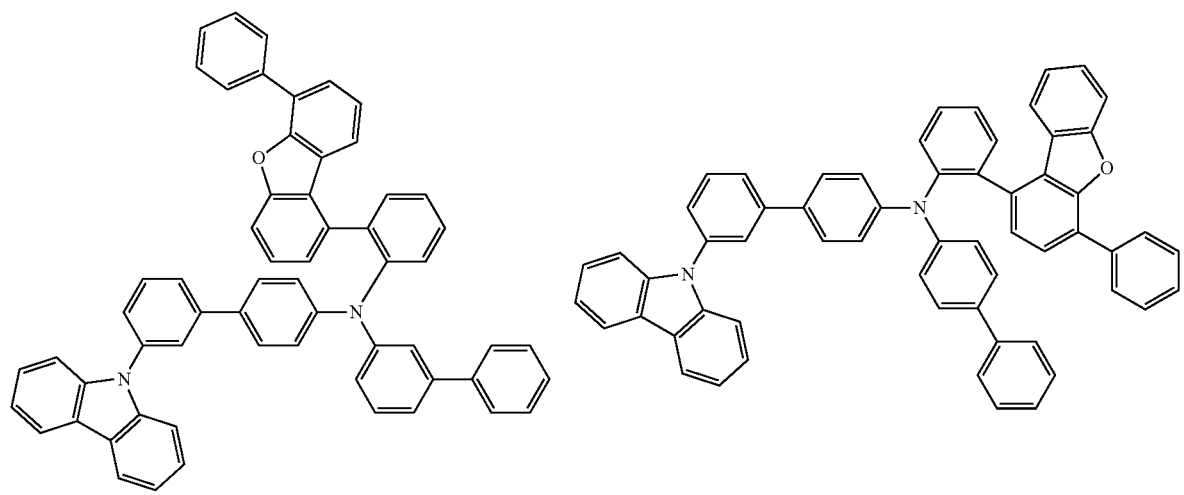
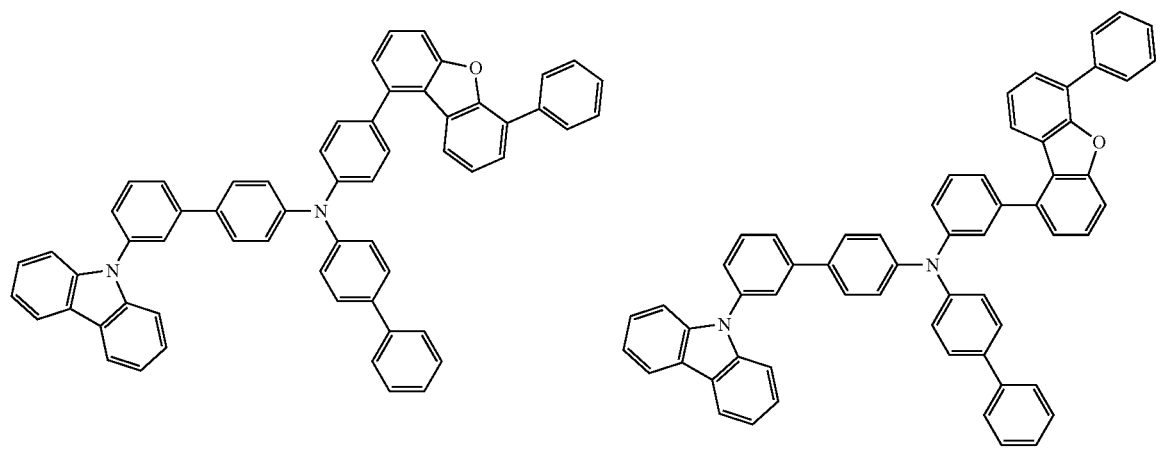

-continued
| 531 | 532 |
|---|---|
| 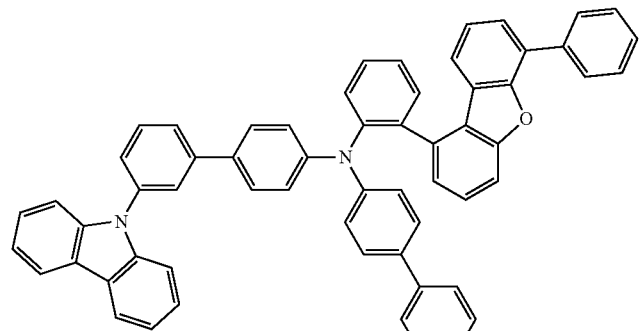 | 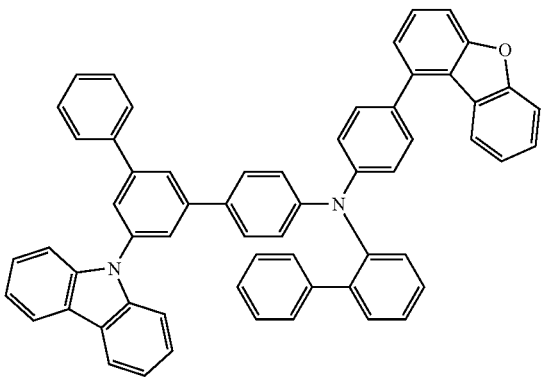 |
| 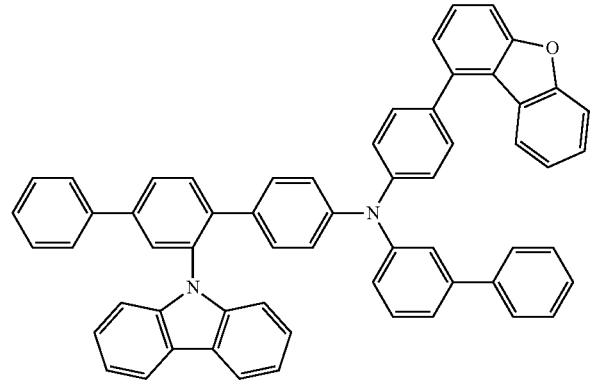 | |
| 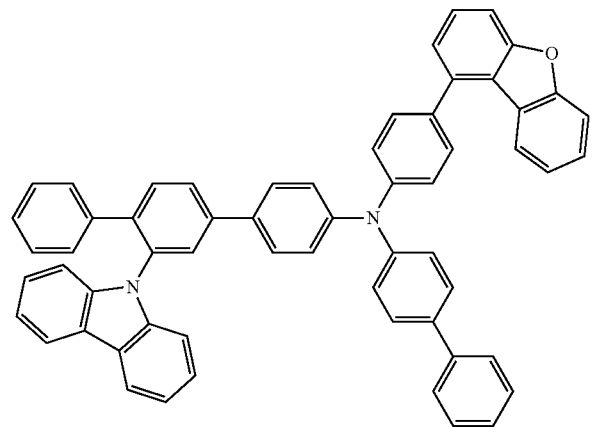 | |
| 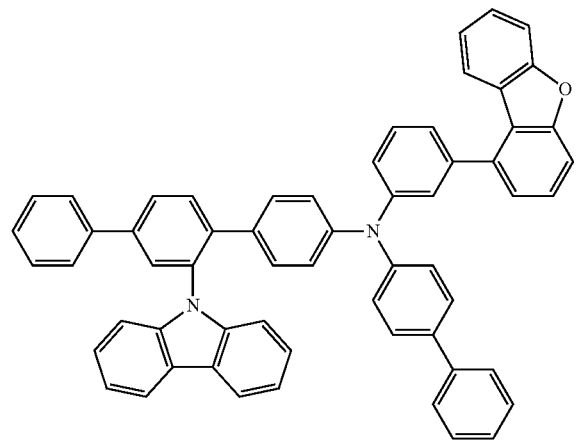 | 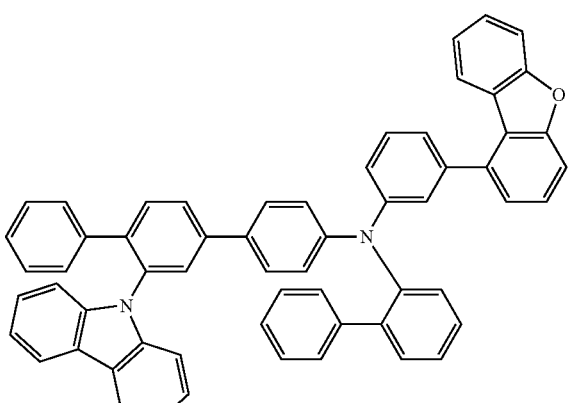 |

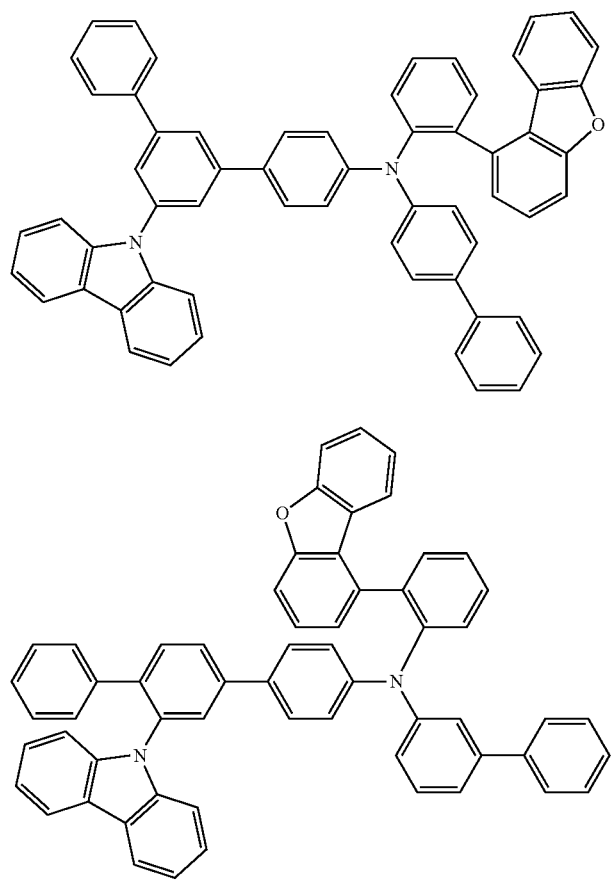
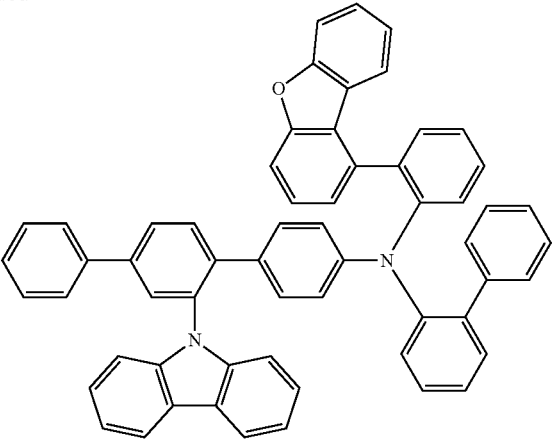

The production method of the compound (1) is not particularly limited. One of ordinary skill in the art can easily produce the compound (1) by the method described in the examples mentioned below or by a method modifying the method described in the following examples with reference to known synthesis methods.

Material for Organic Electroluminescence Device

The material for organic electroluminescence device comprises the compound (1). The content of the compound (1) in the material for organic electroluminescence devices is, but not particularly limited, 1% by mass or more (inclusive of 100% by mass), preferably 10% by mass or more (inclusive of 100% by mass), more preferably 50% by mass or more (inclusive of 100% by mass), still more preferably 80% by mass or more (inclusive of 100% by mass), and particularly preferably 90% by mass or more (inclusive of 100% by mass). The material for organic electroluminescence device is useful for the production of an organic EL device.

Organic Electroluminescence Device

The organic EL device of the invention will be described below.

The organic EL device comprises an organic layer between a cathode and an anode. The organic layer comprises a light emitting layer and at least one layer of the organic layer comprises the compound (1).

Examples of the organic layer which comprises the compound (1) include a hole transporting region formed between an anode and a light emitting layer, such as a hole transporting layer, a hole injecting layer, an electron blocking layer, and an exciton blocking layer, a light emitting layer, a space layer, and an electron transporting region formed between a cathode and a light emitting layer, such as an electron transporting layer, an electron injecting layer, and a hole blocking layer, although not limited thereto. The compound (1) is used for the production of a fluorescent or phosphorescent EL device as a material for a hole transporting region or a light emitting layer, preferably as a material for a hole transporting region, and more preferably as a material for a hole transporting layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a laminated structure comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer(/Electron transporting layer);
(b) (Hole injecting layer/)Hole transporting layer/Phosphorescent emitting layer(/Electron transporting layer);
(c) (Hole injecting layer/)Hole transporting layer/First fluorescent emitting layer/Second fluorescent emitting layer(/Electron transporting layer);
(d) (Hole injecting layer/)Hole transporting layer/First phosphorescent emitting layer/Second phosphorescent emitting layer(/Electron transporting layer);
(e) (Hole injecting layer/)Hole transporting layer/Phosphorescent emitting layer/Space layer/Fluorescent emitting layer(/Electron transporting layer);
(f) (Hole injecting layer/)Hole transporting layer/First phosphorescent emitting layer/Second phosphorescent emitting layer/Space layer/Fluorescent emitting layer(/Electron transporting layer);
(g) (Hole injecting layer/)Hole transporting layer/First phosphorescent emitting layer/Space layer/Second phosphorescent emitting layer/Space layer/Fluorescent emitting layer(/Electron transporting layer);
(h) (Hole injecting layer/)Hole transporting layer/Phosphorescent emitting layer/Space layer/First fluorescent emitting layer/Second fluorescent emitting layer(/Electron transporting layer);
(i) (Hole injecting layer/)Hole transporting layer/Electron blocking layer/Fluorescent emitting layer(/Electron transporting layer);
(j) (Hole injecting layer/)Hole transporting layer/Electron blocking layer/Phosphorescent emitting layer(/Electron transporting layer);
(k) (Hole injecting layer/)Hole transporting layer/Exciton blocking layer/Fluorescent emitting layer(/Electron transporting layer);
(l) (Hole injecting layer/)Hole transporting layer/Exciton blocking layer/Phosphorescent emitting layer(/Electron transporting layer);
(m) (Hole injecting layer/)First hole transporting layer/Second hole transporting layer/Fluorescent emitting layer(/Electron transporting layer);
(n) (Hole injecting layer/)First hole transporting layer/Second hole transporting layer/Phosphorescent emitting layer(/Electron transporting layer);
(o) (Hole injecting layer/)Hole transporting layer/Fluorescent emitting layer/Hole blocking layer(/Electron transporting layer);
(p) (Hole injecting layer/)Hole transporting layer/Phosphorescent emitting layer/Hole blocking layer(/Electron transporting layer);
(q) (Hole injecting layer/)Hole transporting layer/Fluorescent emitting layer/Triplet blocking layer(/Electron transporting layer); and
(r) (Hole injecting layer/)Hole transporting layer/Phosphorescent emitting layer/Triplet blocking layer(/Electron transporting layer).

The emission colors of the phosphorescent emitting layers or the fluorescent emitting layer may be different. For example, the emission unit (f) may be (Hole injecting layer/)Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer supplies electrons to the first emission unit and holes to the second emission unit and may be formed by known materials.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5. An anode-side organic layer 6 (for example, a hole injecting layer or a hole transporting layer) may be disposed between the light emitting layer 5 and the anode 3, and a cathode-side organic layer 7 (for example, an electron injecting layer or an electron transporting layer) may be disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

In the present invention, a host is referred to as a fluorescent host when combinedly used with a fluorescent dopant (fluorescent emitting material) and as a phosphorescent host when combinedly used with a phosphorescent dopant (phosphorescent emitting material). Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode is formed on the substrate preferably from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo, iron (Fe), cobalt (Co), copper (Cu), palladium (Pd), titanium (Ti), and a nitride of the above metal (for example, titanium nitride) are also usable.

These anode materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function belonging to a group 1 or a group 2 of the periodic table, for example, an alkali metal, such as lithium (Li) and cesium (Cs), an alkaline earth metal, such as magnesium (Mg), calcium (Ca), and strontium (Sr), and an alloy thereof, such as MgAg and AlLi, are also usable as an anode material. In addition, a rare earth metal, such as europium and ytterbium, and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer comprises a material having a high hole injecting ability (hole injecting material). The compound (1) may be used in the hole injecting layer solely or in combination with the following material.

Examples of the hole injecting material other than the compound (1) include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting layer material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly [N-(4-{N'-[4-(4-diphenylamino)phenyl]phenyl-N'-phenylamino}phenyl)methacrylamide](PTPDMA), and poly[N,N'-bis(4-butylphenyl)-N,N'-bis(phenyl)benzidine] (Poly-TPD). An acid-added macromolecular compound, such as poly(3,4-ethylenedioxythiophene)/poly(styrene-sulfonic acid) (PEDOT/PSS) and polyaniline/poly(styrene-sulfonic acid) (PAni/PSS), is also usable.

In addition, an acceptor material, such as a hexaazatriphenylene (HAT) compound represented by formula (K), is preferably used in combination with the compound (1):

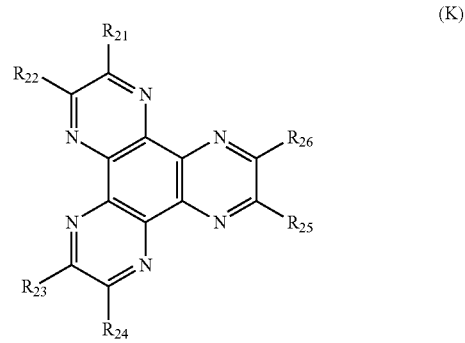

(K)

wherein:

$R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 ring carbon atoms, or adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a material having a high hole transporting ability (hole transporting material). The compound (1) is preferably used in the hole transporting layer alone or in combination with the compound mentioned below.

When used in the hole transporting layer (electron blocking layer) adjacent to the light emitting layer, the compound of the invention reduces the energy barrier for injecting holes into the light emitting layer and controls the hole mobility. Therefore, the recombination region of carriers is concentrated in the vicinity of the hole transporting layer/light emitting layer interface in the light emitting layer, allowing efficient generation of excitons to make a device more efficient. If the energy barrier for injecting holes into the light emitting layer is reduced, the accumulation of positive charges in the hole transporting layer/light emitting layer interface may be prevented to reduce the load to the device, thereby providing a device combining a high efficiency and a long lifetime.

Examples of the hole transporting material other than the compound (1) includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)

triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of 10-6 cm²/Vs or more.

Also usable in the hole transporting layer is a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA), and an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth). In addition, a macromolecular compound, such as poly(N-vinylcarbazole) (PVK) and poly(4-vinyltriphenylamine) (PVTPA) are usable.

Compounds other than those mentioned above are also usable, if their hole transporting ability is higher than their electron transporting ability.

The hole transporting layer may be a single layer or a laminate of two or more layers. For example, the hole transporting layer may be a two-layered structure comprising a first hole transporting layer (anode side) and a second hole transporting layer (cathode side). In such a two-layered structure, the compound (1) may be used in one of the first hole transporting layer and the second hole transporting layer, or used in both layers, wherein the compound (1) used in the first hole transporting layer is different from the compound (1) used in the second hole transporting layer.

In an embodiment of the invention, the compound (1) is preferably used in the first hole transporting layer. In another embodiment, the compound (1) is preferably used in the second hole transporting layer. In still another embodiment, the compound (1) is preferably used in both the first hole transporting layer and the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material usable in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material usable in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material usable in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-a]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)s(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting material.

Host Material for Light Emitting Layer

The light emitting layer may be a layer wherein the above dopant material is dispersed in another material (host material). The compound (1) may be used as a host material and other various materials may be used as a host material. The host material preferably has a lowest unoccupied molecular orbital level (LUMO level) higher than that of the dopant material and a highest occupied molecular orbital level (HOMO level) lower than that of the dopant material.

The host material other the compound (1) may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III)

(Almq₃), bis(10-hydroxybenzo[h]quinolinato)beryllium(II) (BeBc₂), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2''-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3''-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB).

The host material may be used alone or in combination of two or more.

In particular, as a host material for a blue fluorescent device, the following anthracene compound is preferably used.

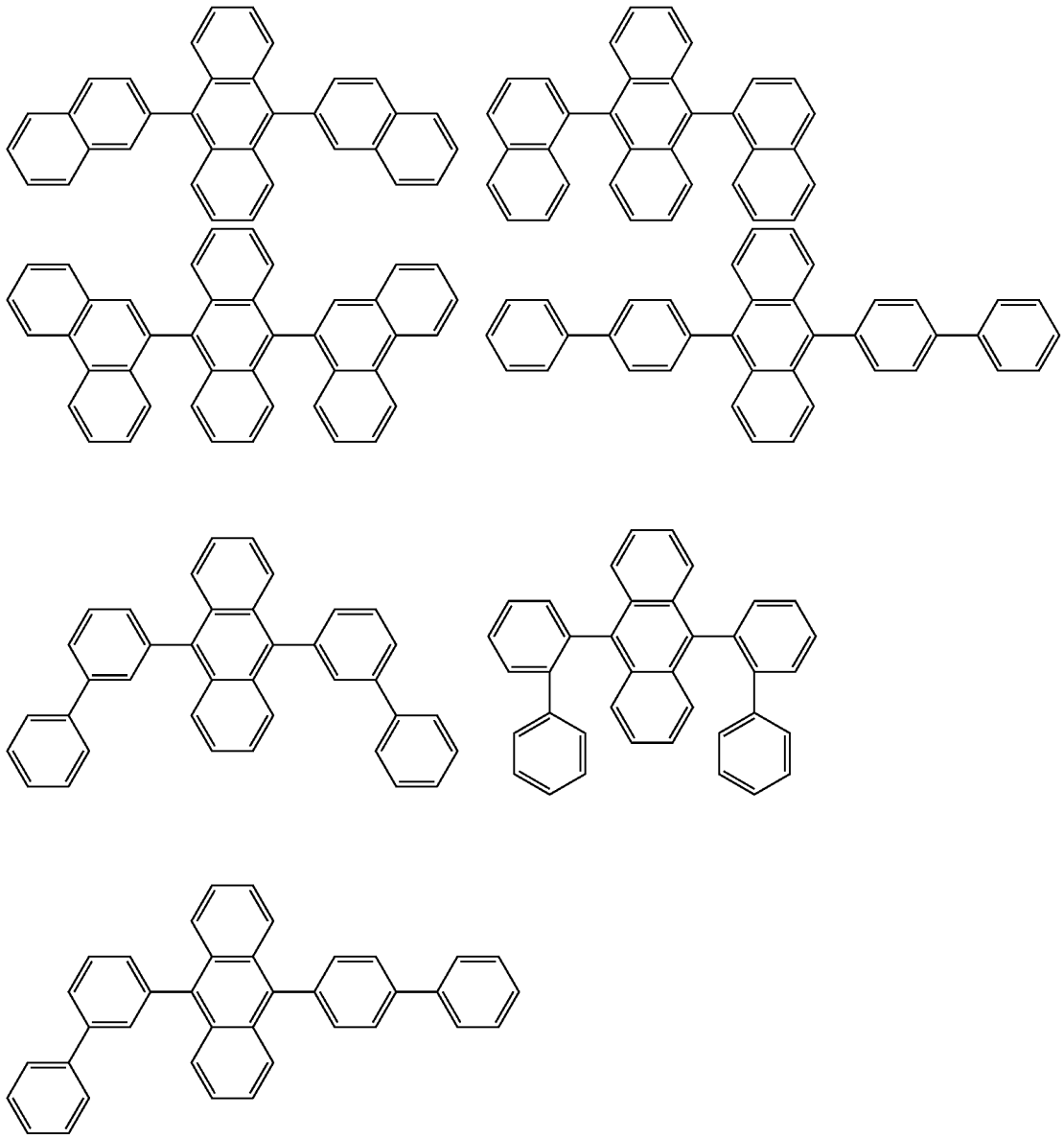

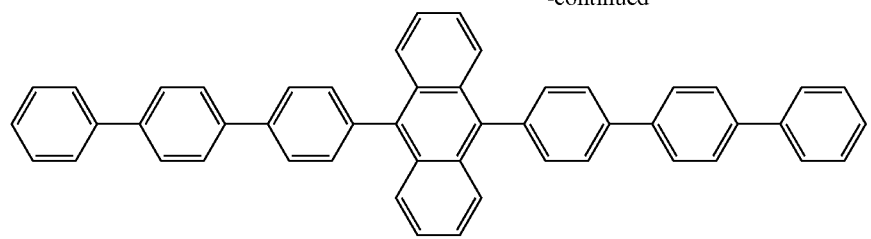
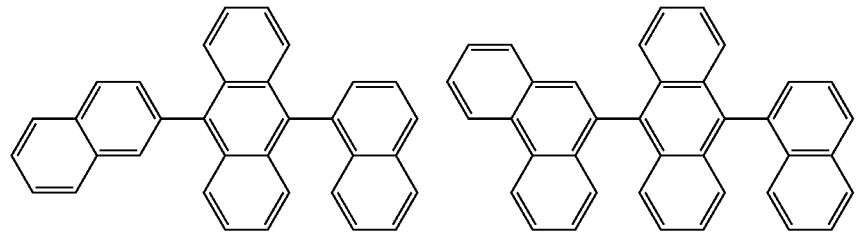
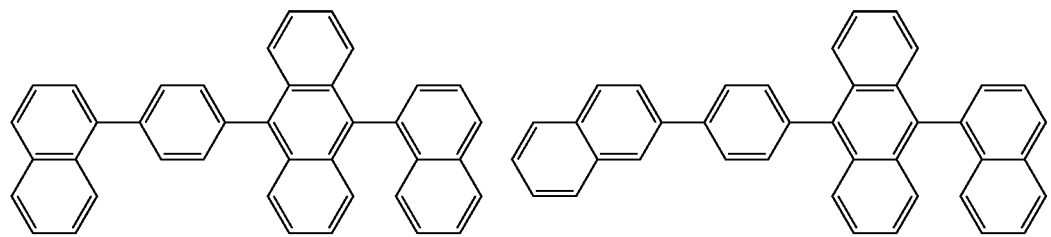
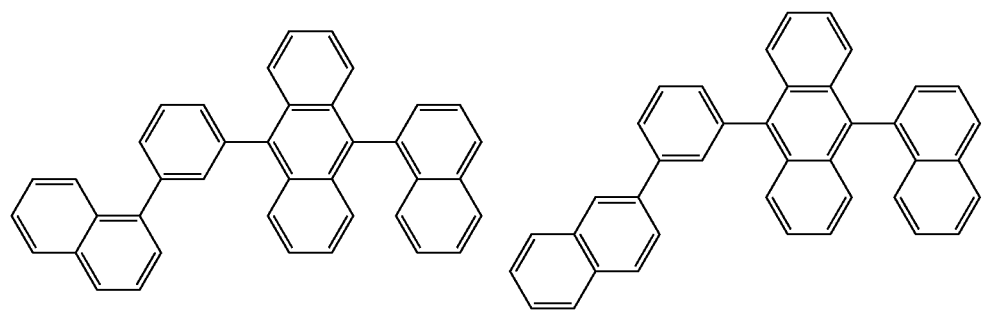
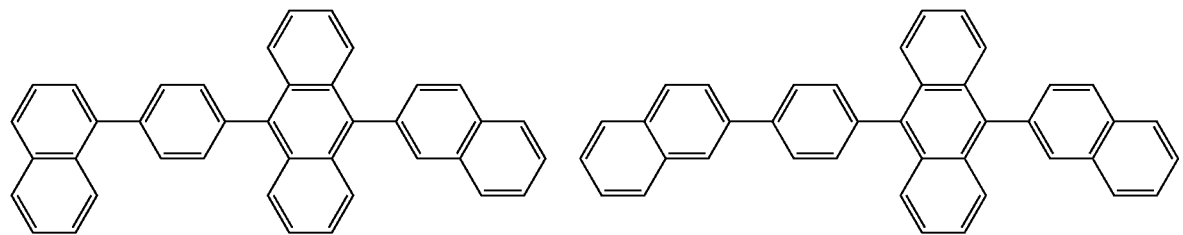
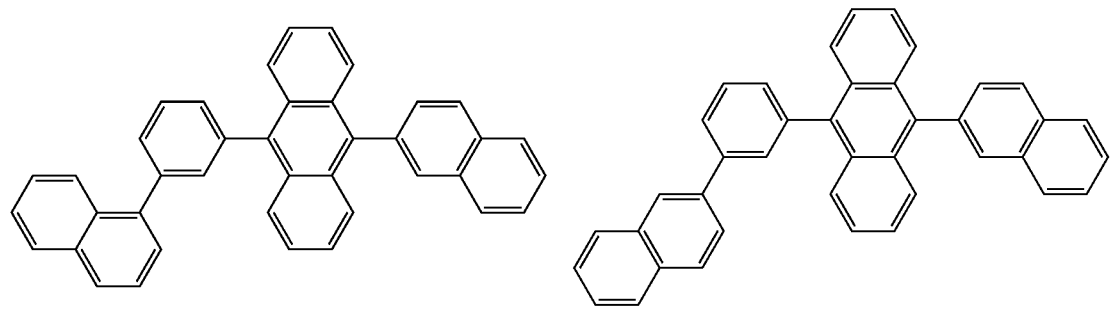

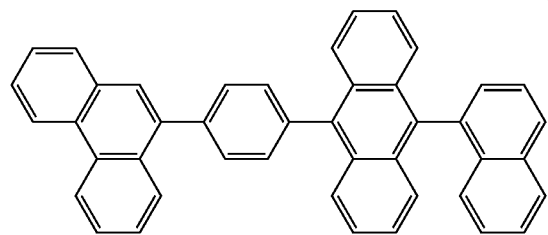
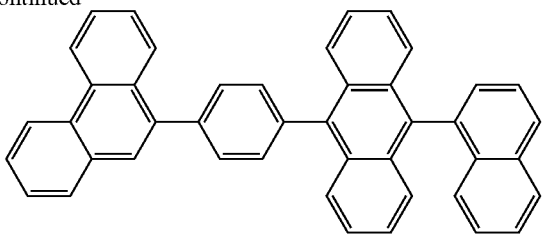
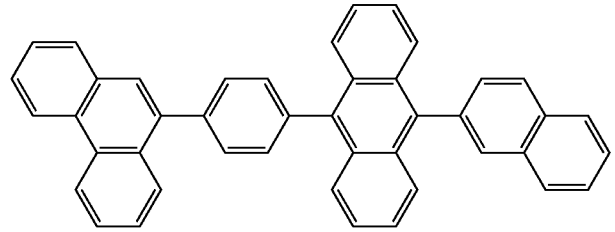
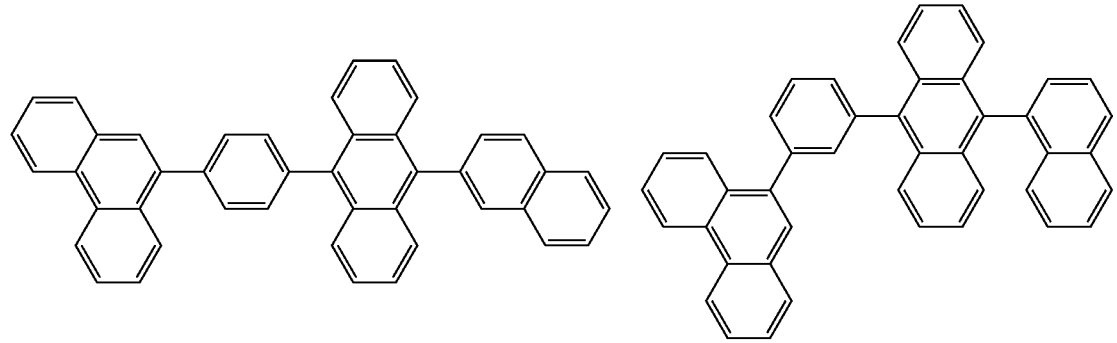
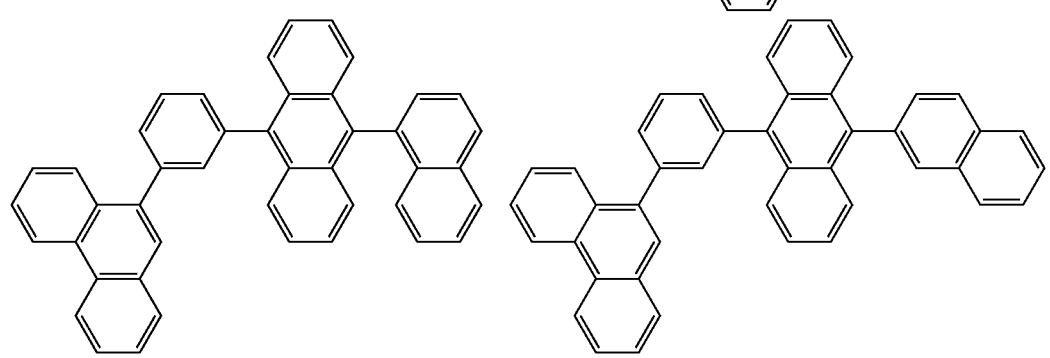
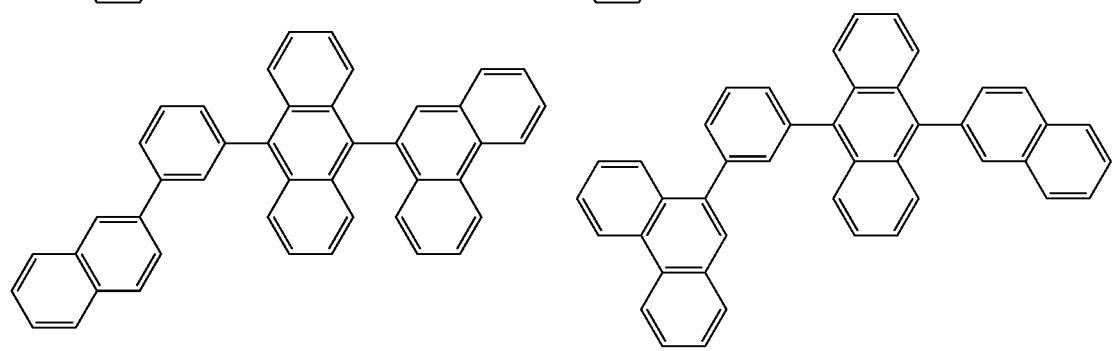
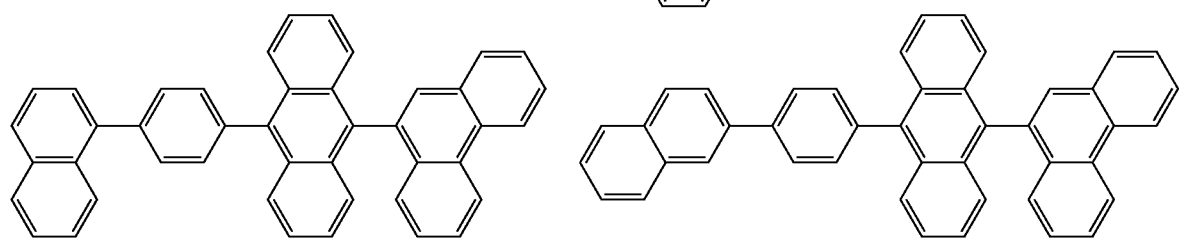

547
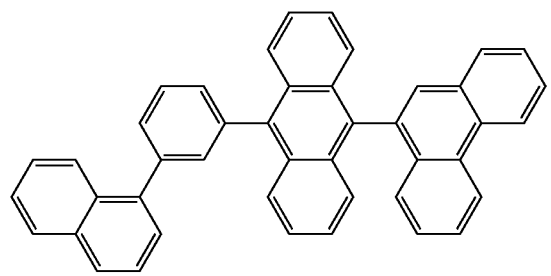
548
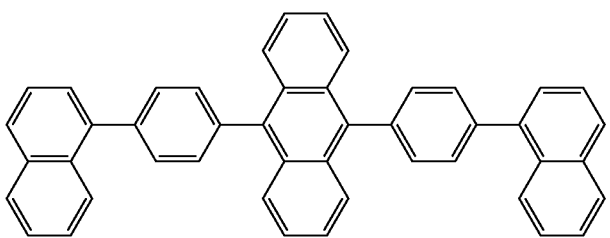
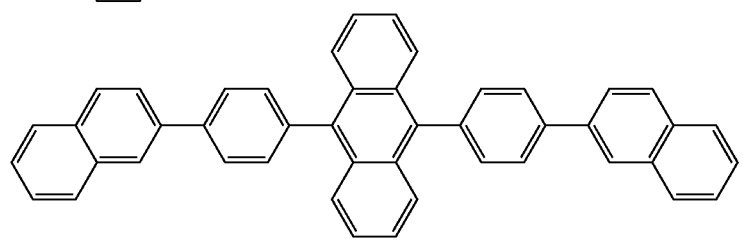
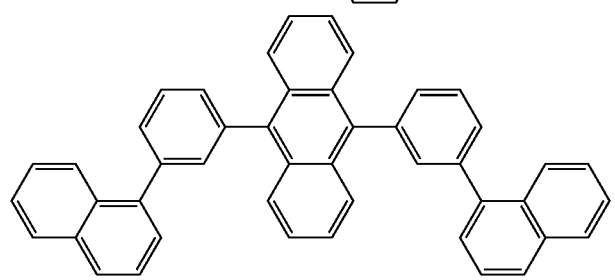
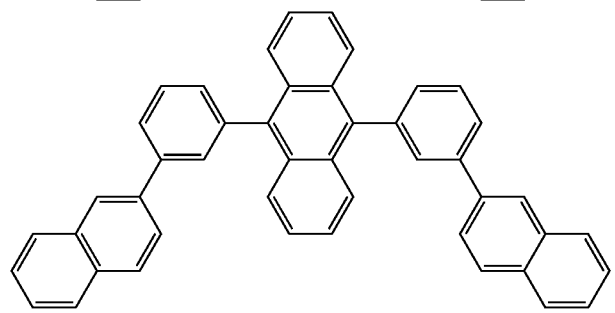
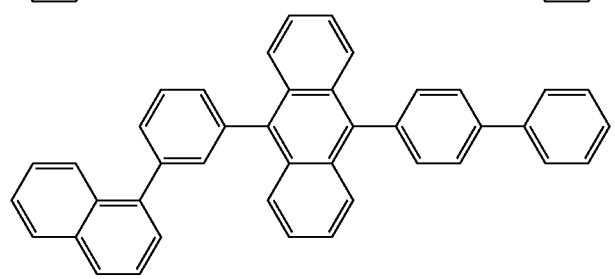
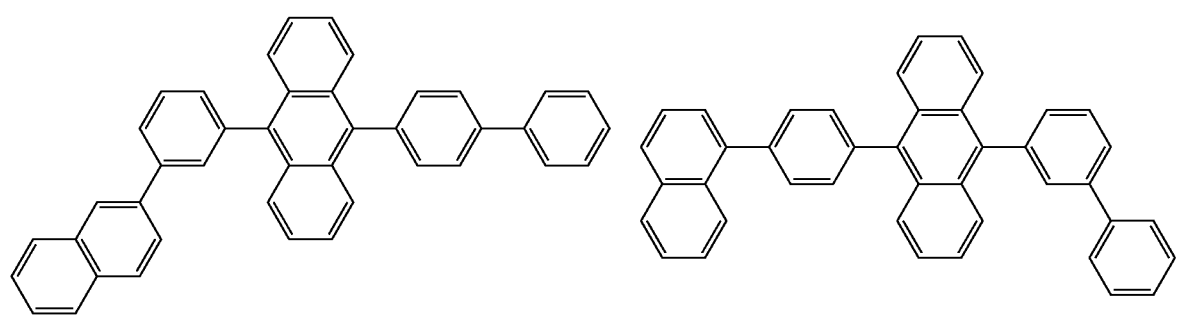

549 550
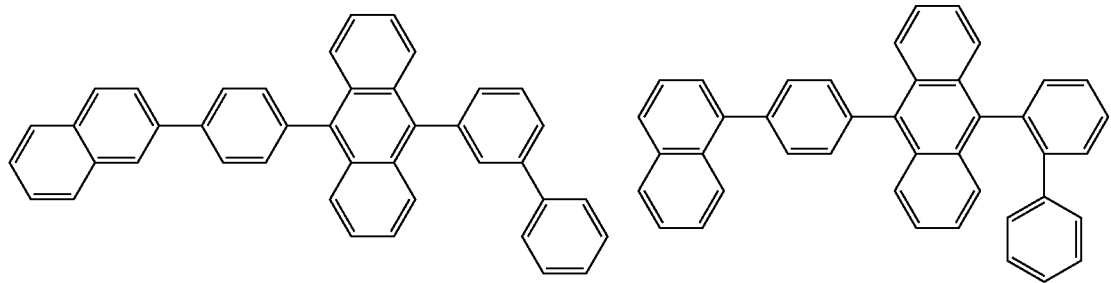 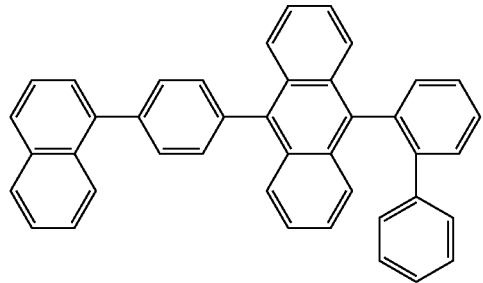
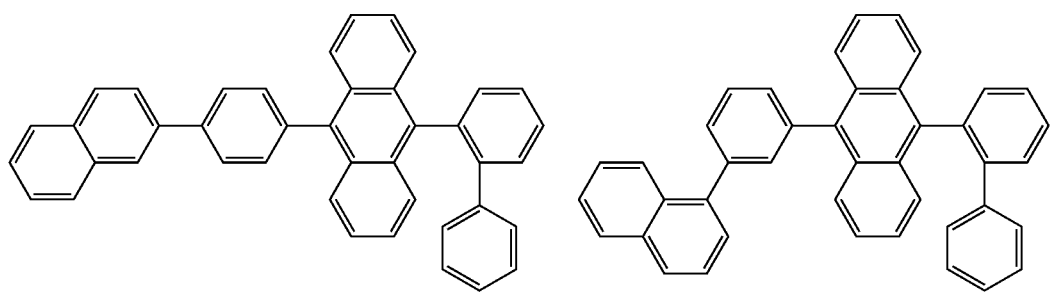 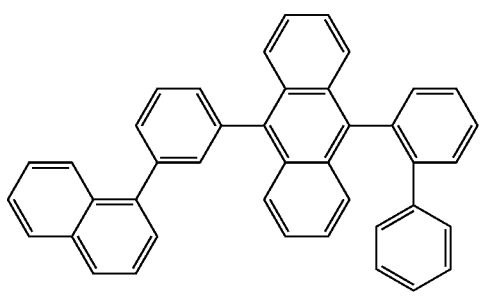
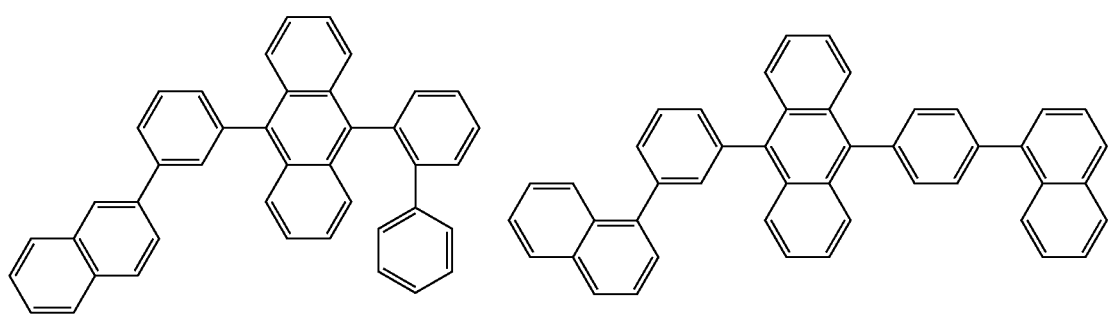 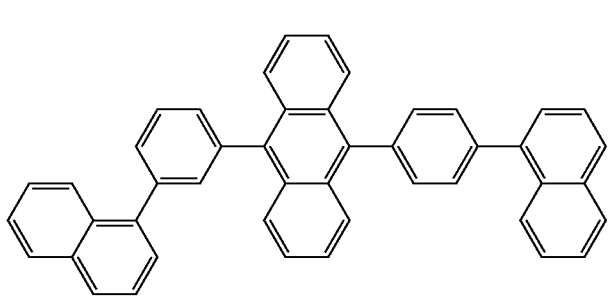
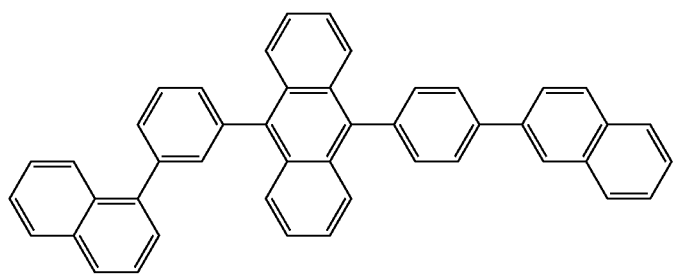 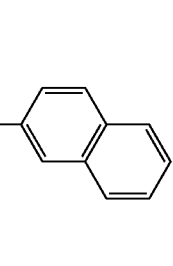
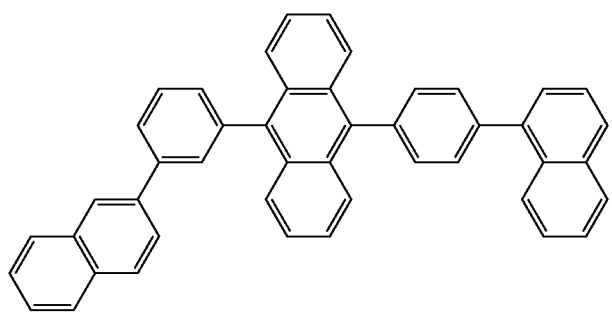 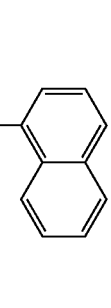

551 552
-continued
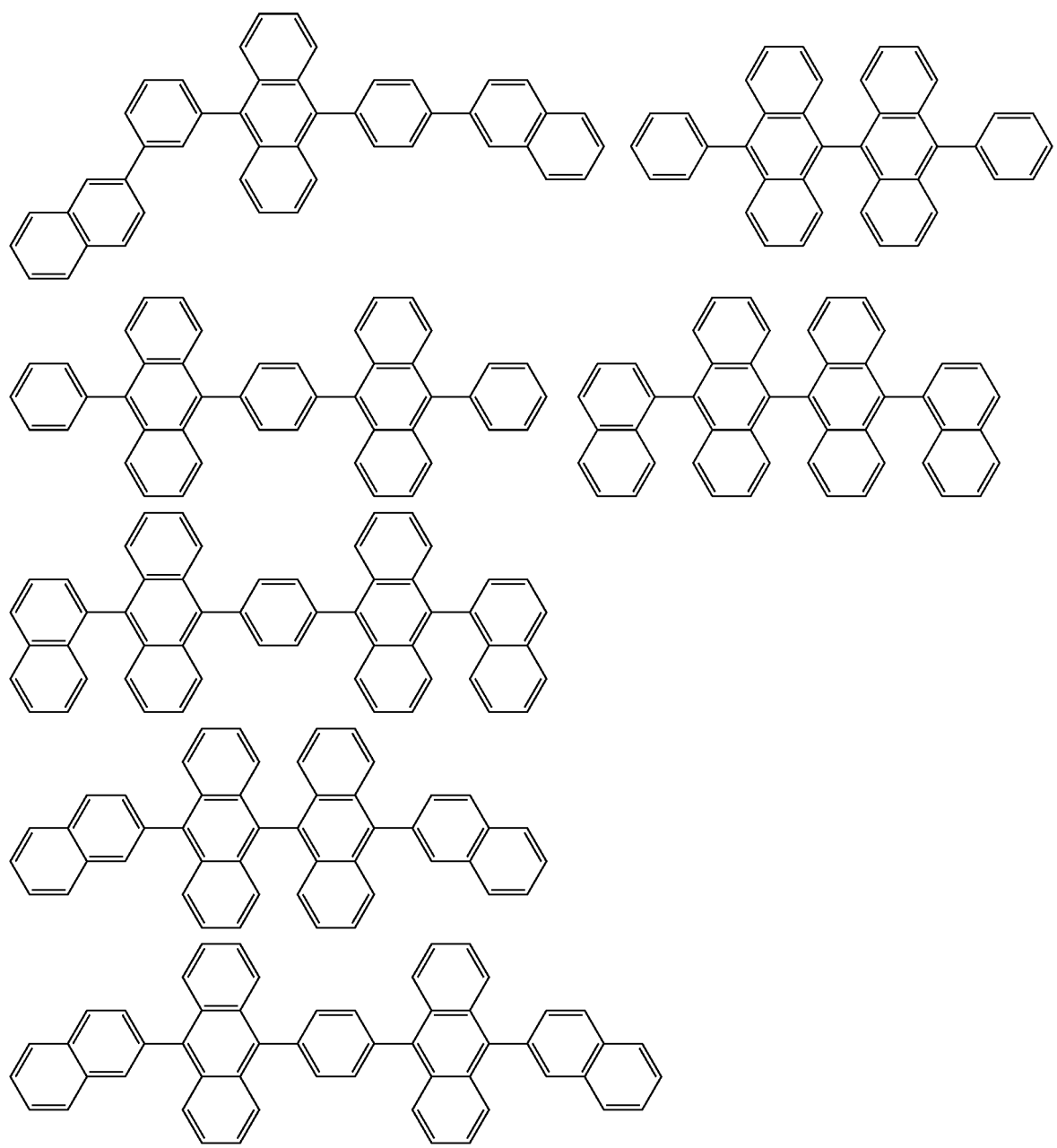
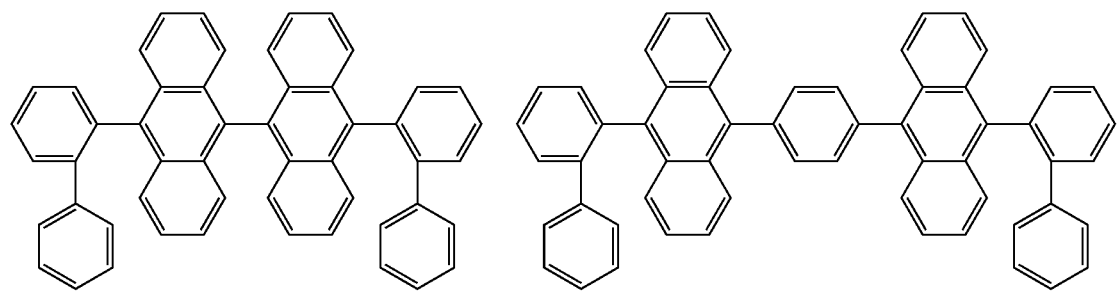

553 554
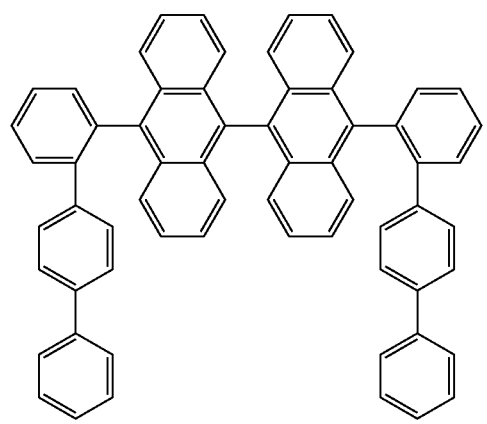 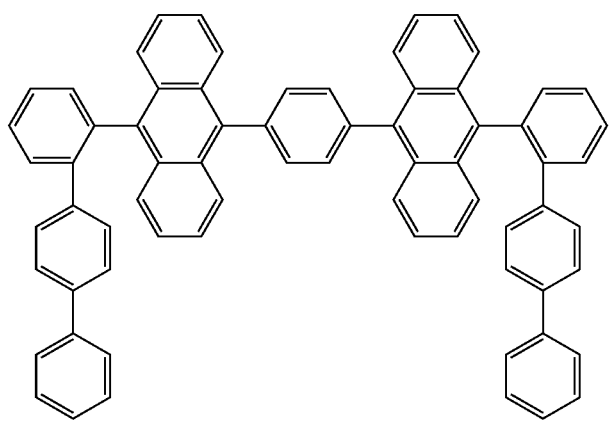
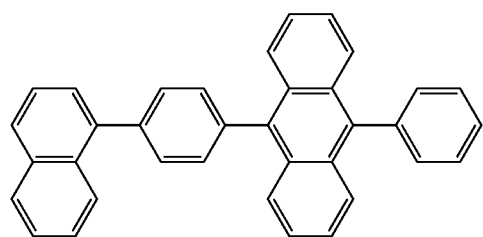 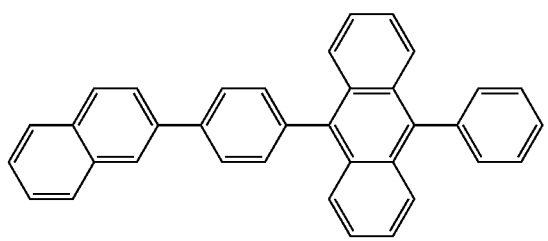
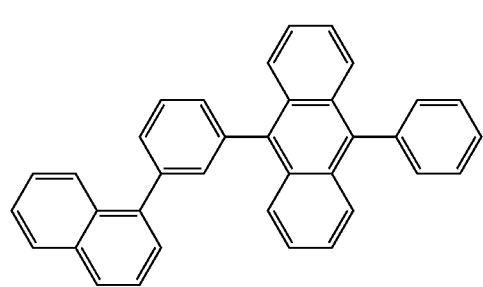 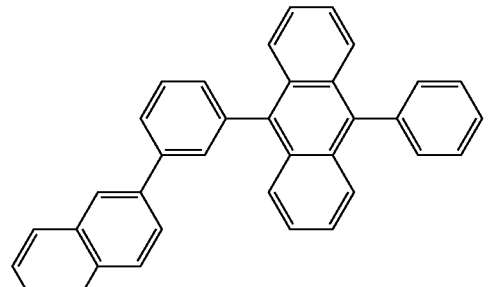
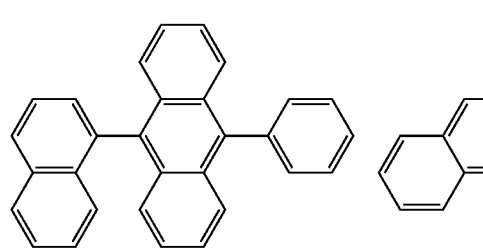 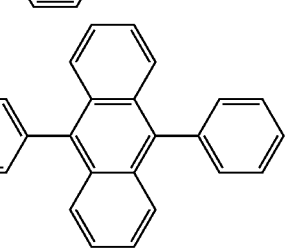
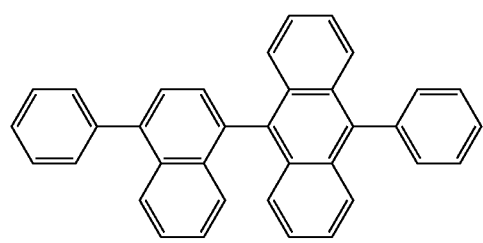 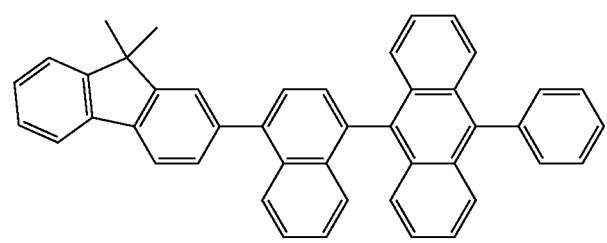
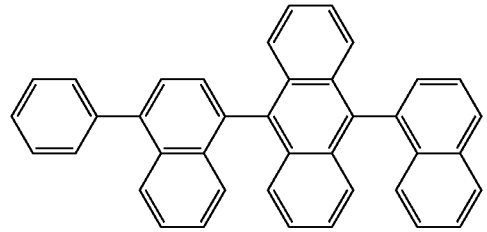 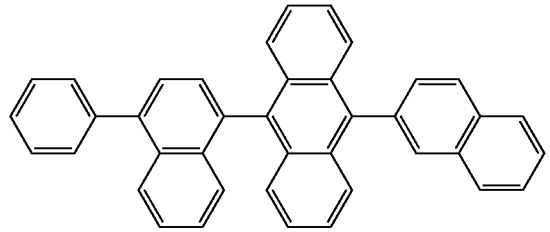

555 556
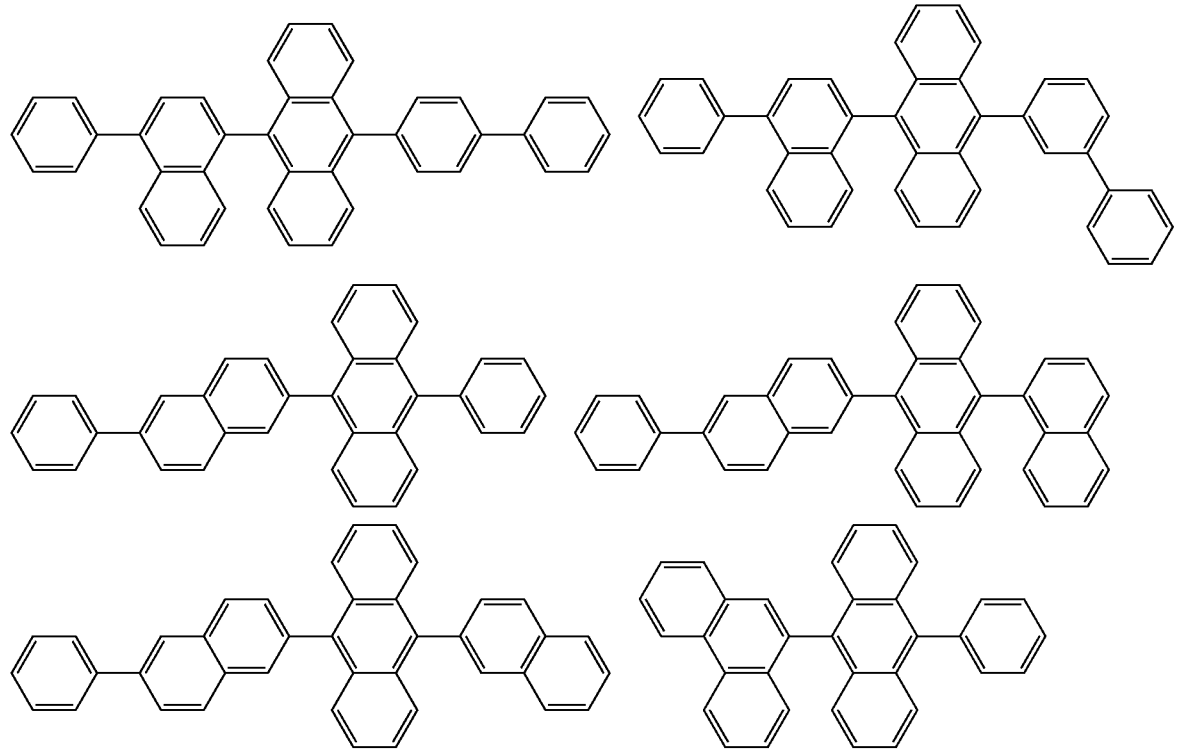
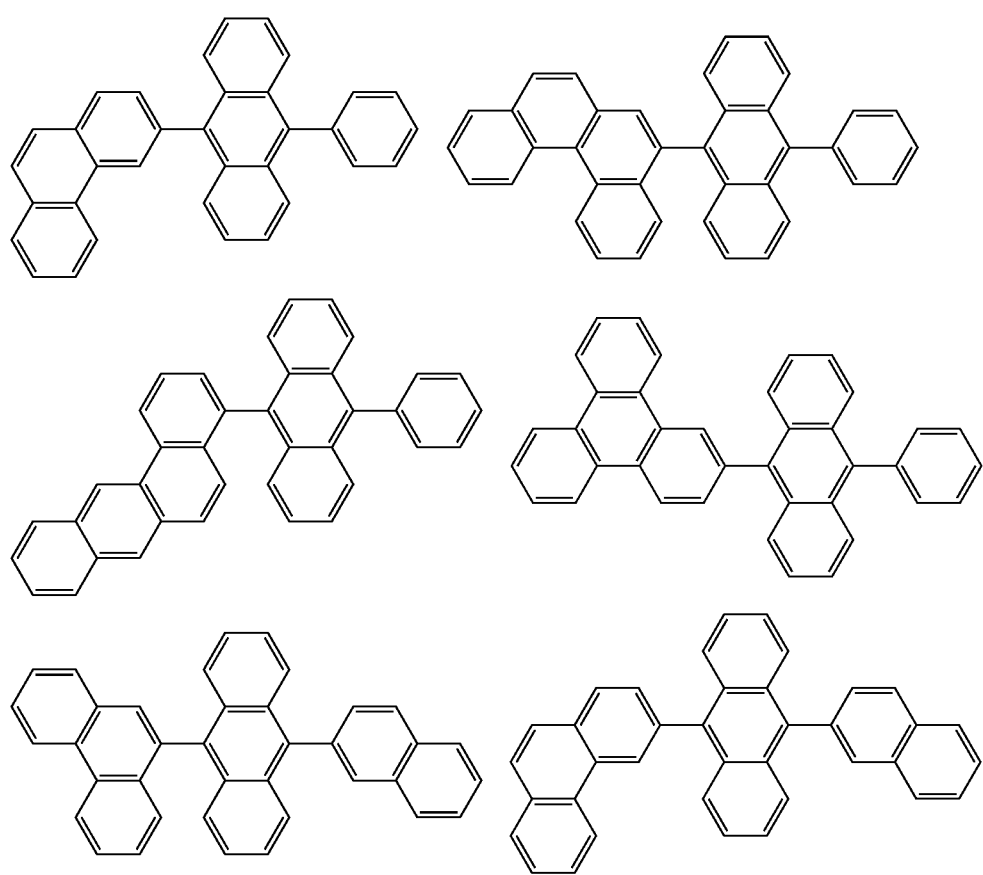

557 558
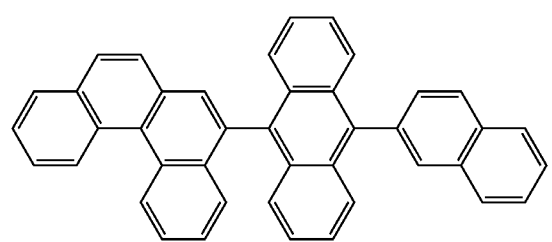
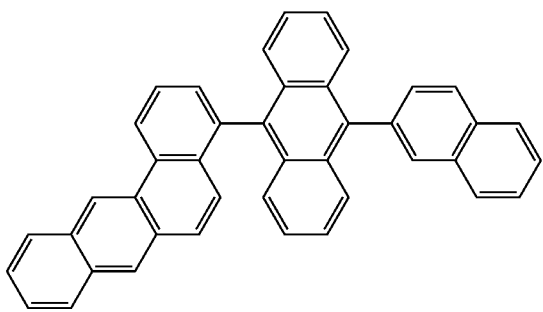
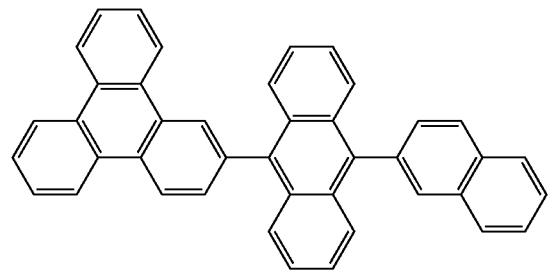
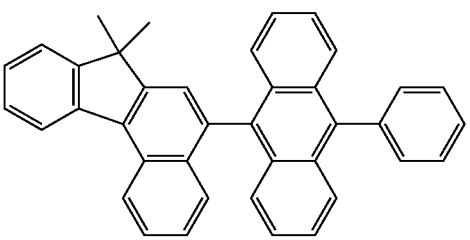
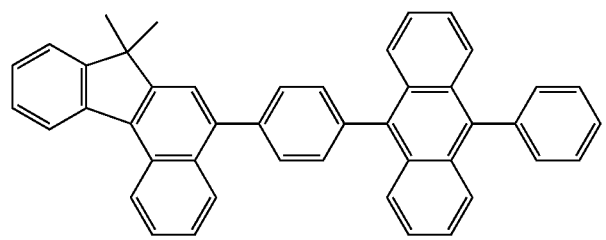
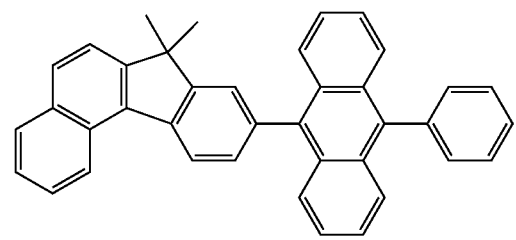
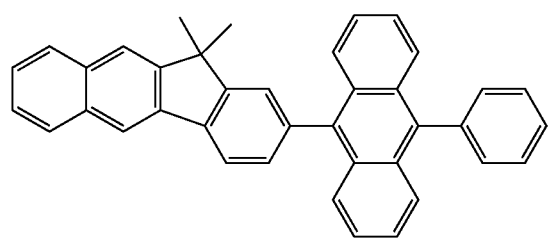
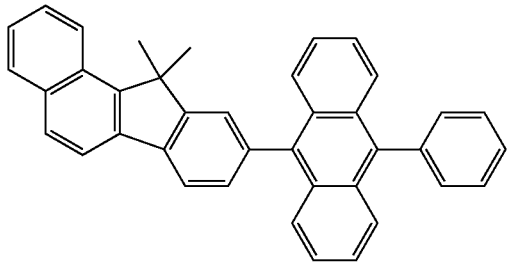
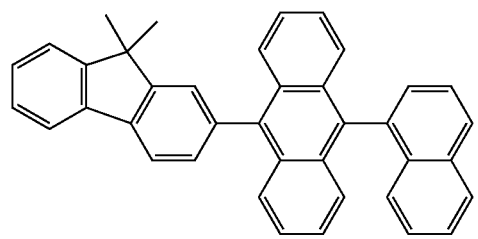
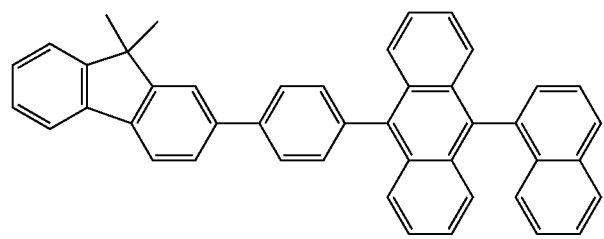
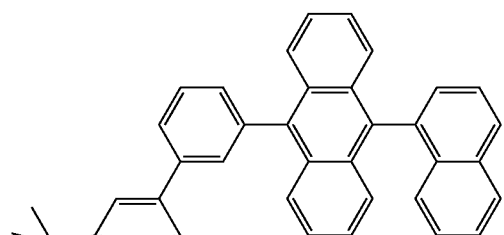
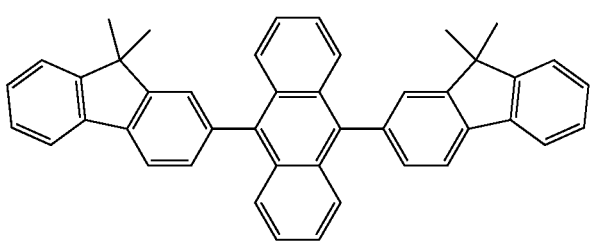

-continued
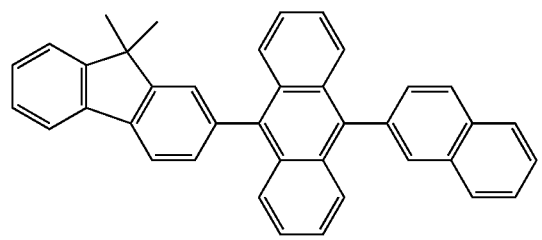
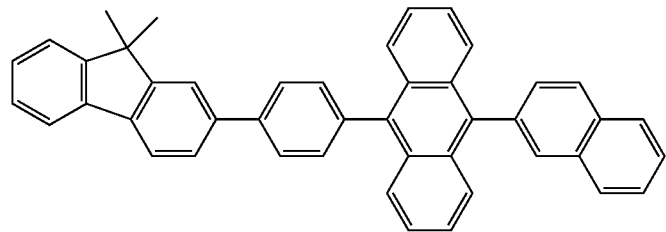
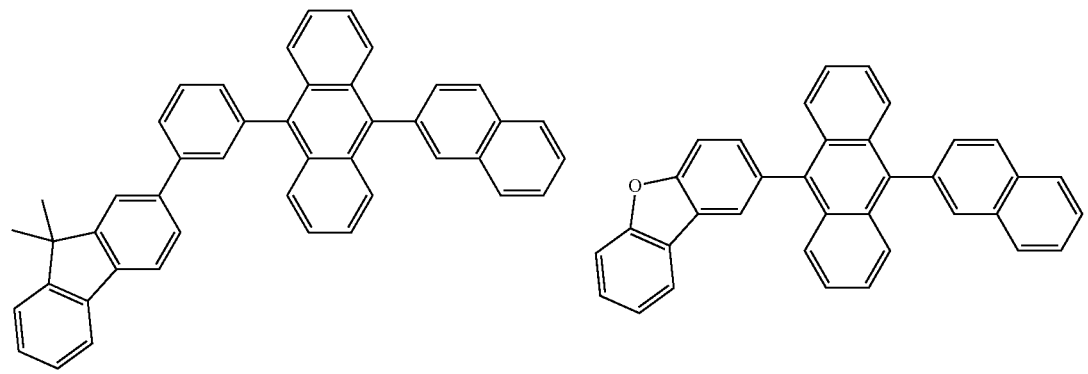
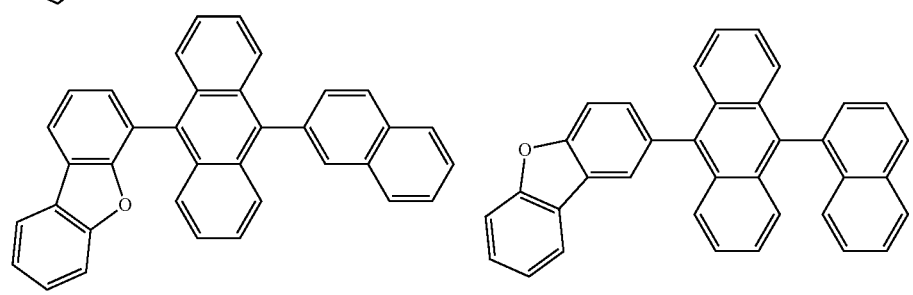
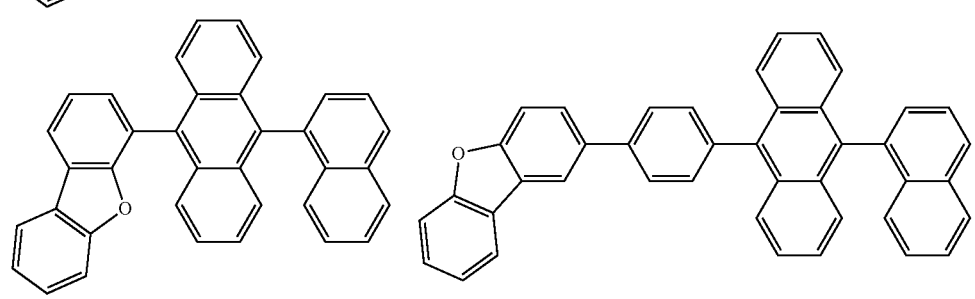
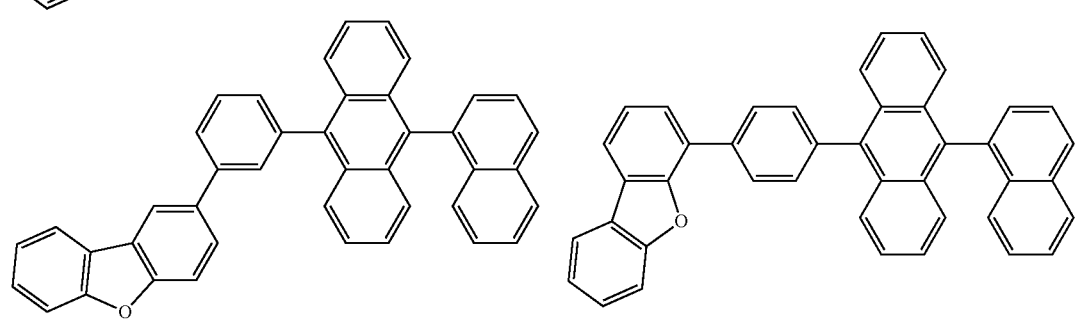

561 562
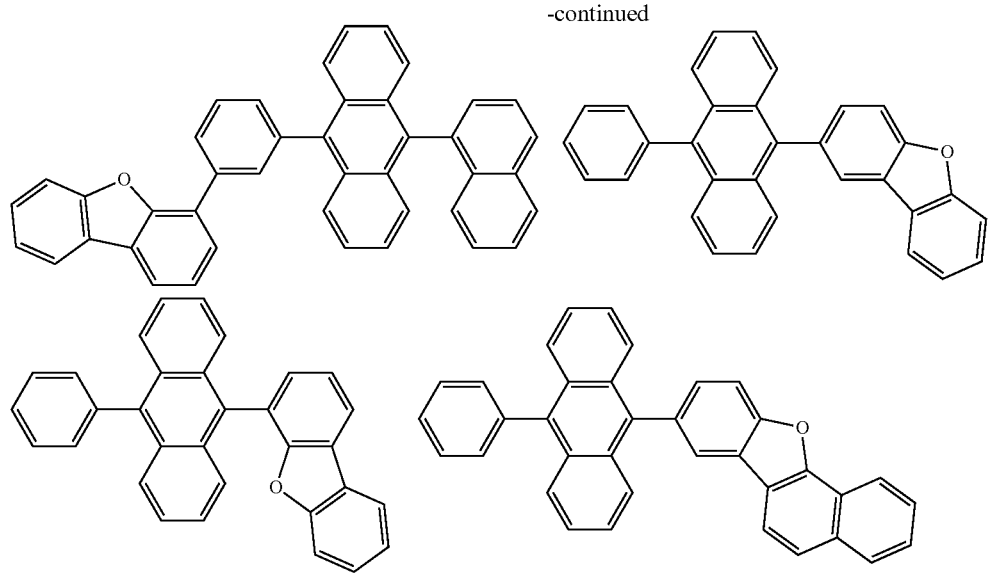
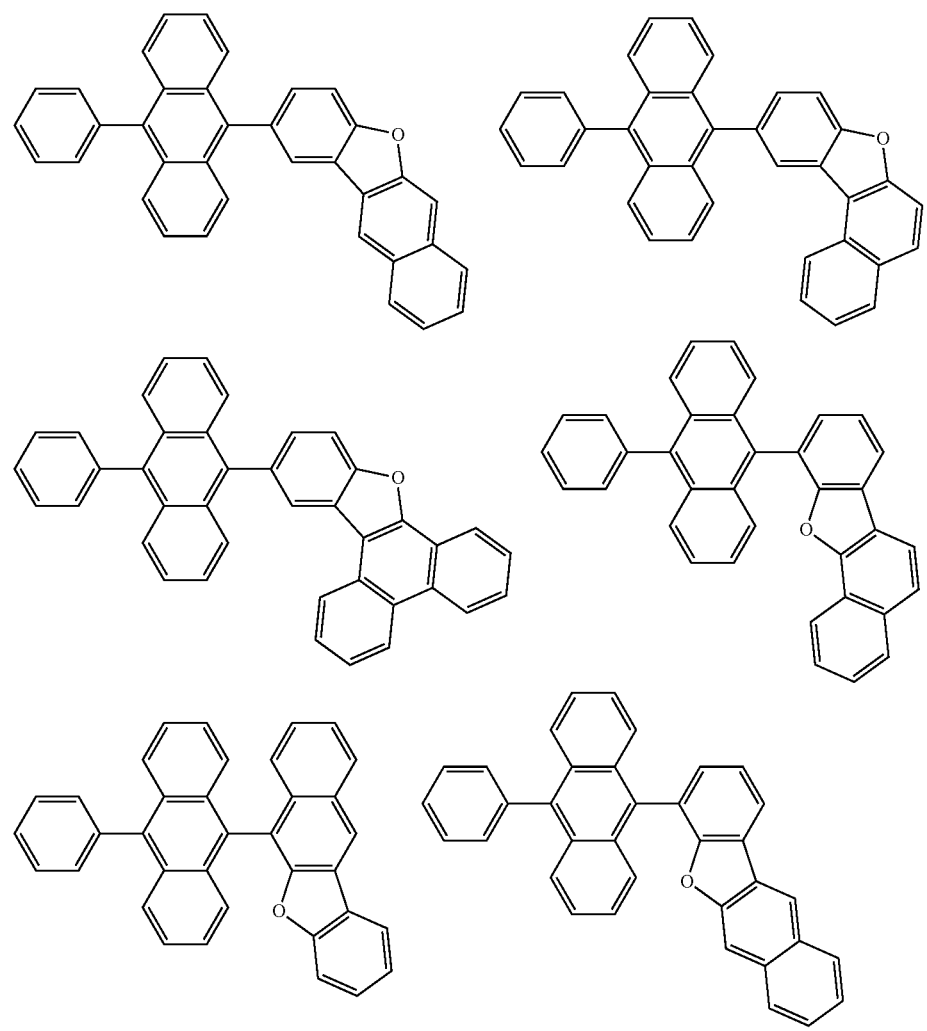

563
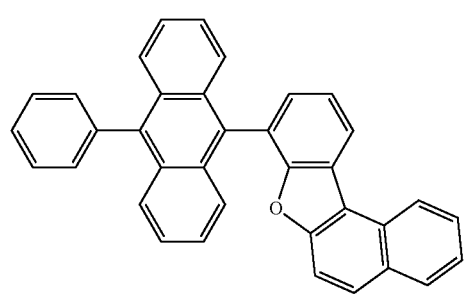
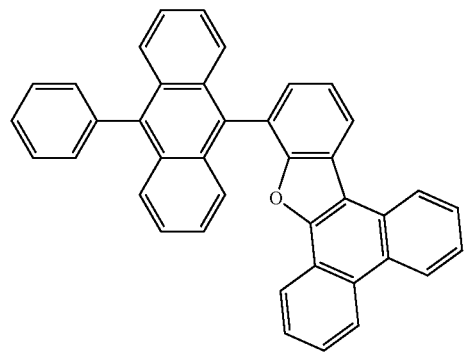
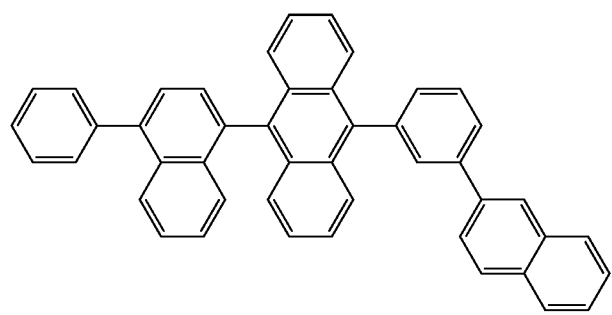
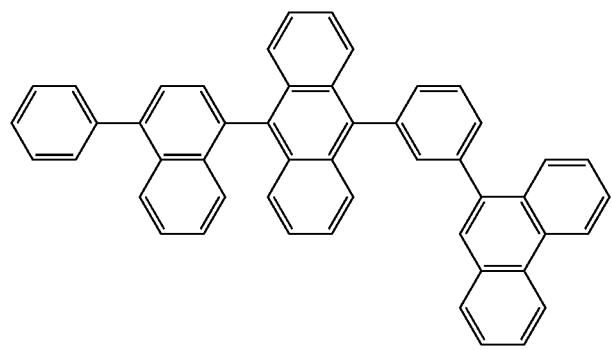
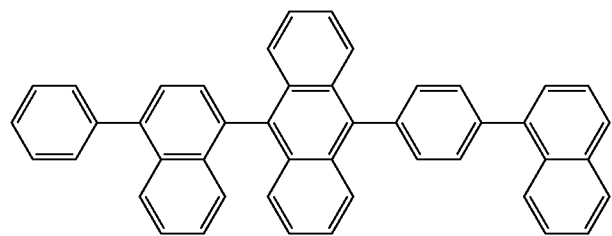
564
-continued
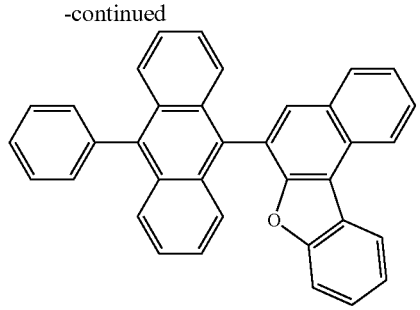
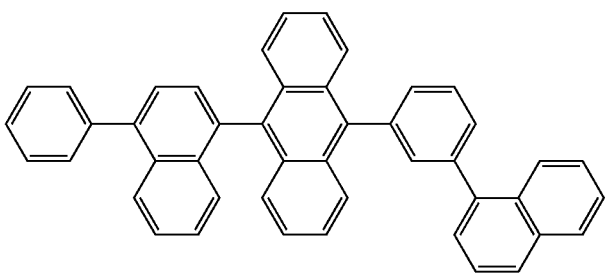

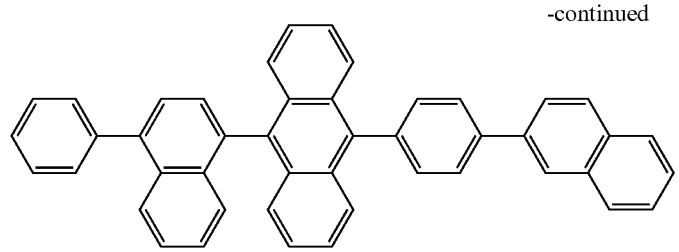
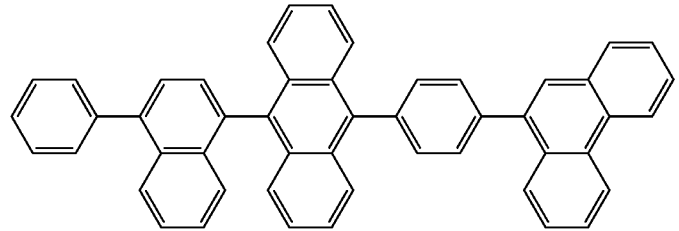
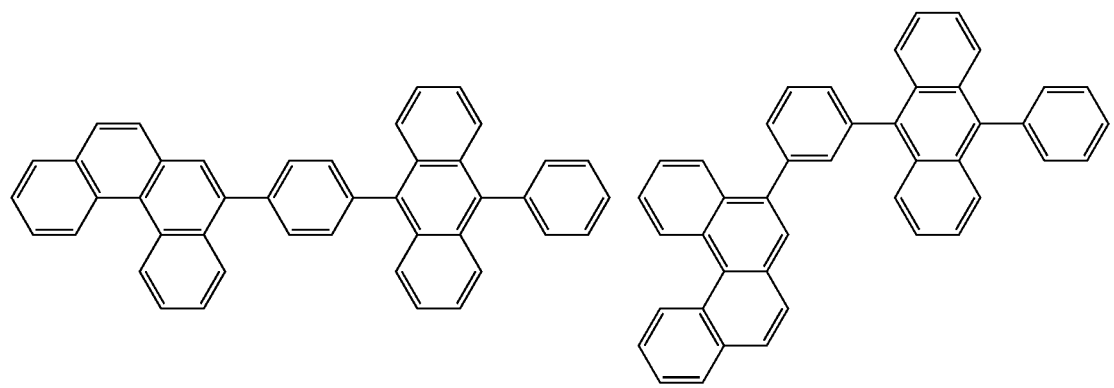
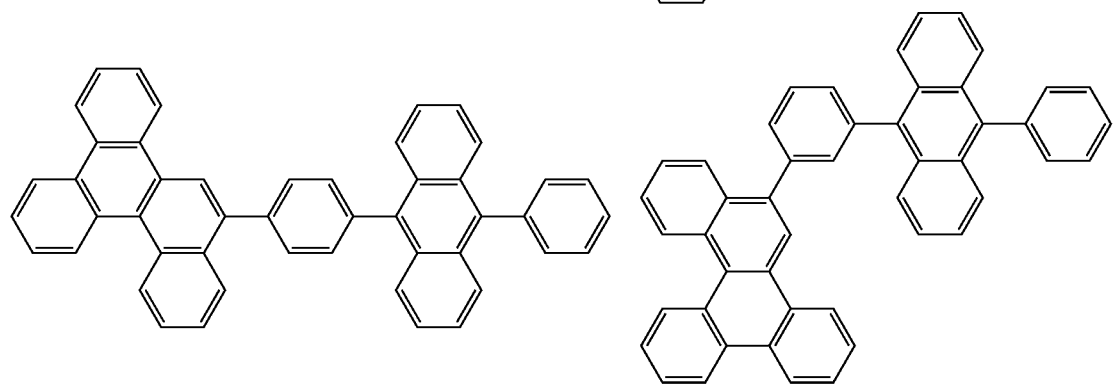
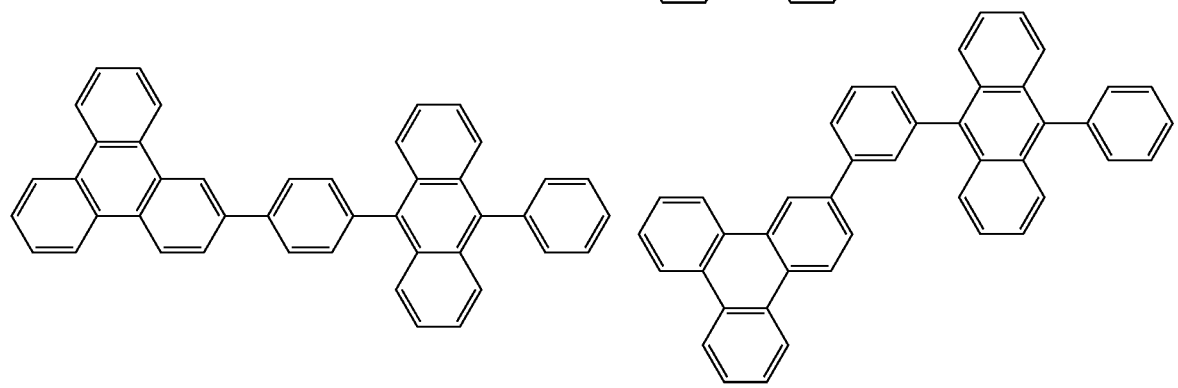

Electron Transporting Layer

The electron transporting layer comprises a material having a high electron transporting ability (electron transporting material). Examples thereof are:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato)aluminum (Almqs), bis(10-hydroxybenzo[h]quinolinato)beryllium (BeBq2), bis(2-methyl-8-quinolinato)(4-phenylphenolato)aluminum (III) (BAlq), bis(8-quinolinato)zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of 10-6 cm$^2$/Vs or more. Materials other than those mentioned above are also usable in the electron transporting layer if their electron transporting ability is higher than their hole transporting ability. The electron transporting layer may be a single layer or a laminate of two or more layers each comprising the material mentioned above.

Electron Injecting Layer

The electron injecting layer is a layer comprising a material having a high electron injecting ability, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the aromatic heterocyclic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an element belonging to a group 1 or group 2 of the periodic table, i.e., an alkali metal, such as lithium (Li) and cesium (Cs), an alkaline earth metal, such as magnesium (Mg), calcium (Ca), and strontium (Sr), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of laminated layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method using a solution of a compound for forming a layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited thereto.

Intermediate Synthesis A: Synthesis of Intermediate A

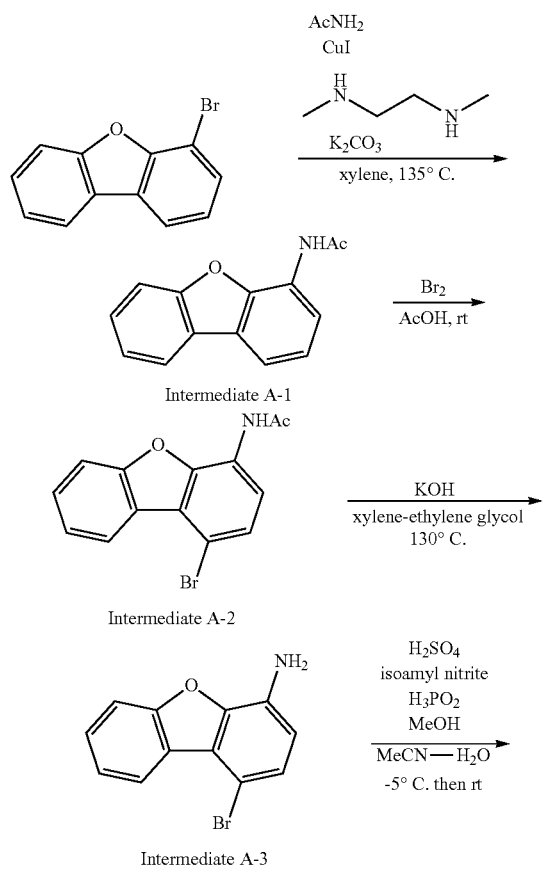

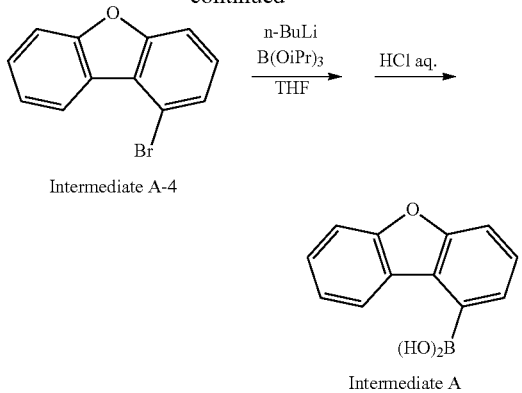

(A-1) Synthesis of Intermediate A-1

In argon atmosphere, a mixture of 4-bromodibenzaofuran (1200 g, 4.86 mol), acetamide (573 g, 9.71 mol), copper iodide (I) (184.98 g, 971 mmol), N,N'-dimethylethylenediamine (85.62 g, 971 mmol), potassium carbonate (1342 g, 97.1 mol), and xylene (6 L) was allowed to react at 135° C. for 5 h. After cooling to room temperature, water (4 L) was added and the resultant mixture was stirred for one hour. The precipitated crystal was collected by filtration and washed with water and n-heptane to obtain the intermediate A-1 (950 g) in a yield of 75%.

(A-2) Synthesis of Intermediate A-2

In argon atmosphere, into a solution of the intermediate A-1 synthesized in the step (A-1) (950 g, 4.22 mol) in acetic acid (7.1 L), bromine (809 g, 5.06 mol) was added. The resultant solution was stirred at room temperature for 6 h. After adding water (7 L) dropwise and adding sodium thiosulfate (63 g), the solution was stirred at room temperature overnight. The precipitated crystal was collected by filtration and washed with water, methanol, toluene, and n-heptane successively to obtain the intermediate A-2 (1044 g) in a yield of 78%.

(A-3) Synthesis of Intermediate A-3

Into a solution of the intermediate A-2 synthesized in the step (A-2) (1044 g, 3.43 mol) in a mixed solvent of xylene (5 L) and ethylene glycol (700 mL), potassium hydroxide (1925 g, 34.3 mol) was added. The resultant mixture was stirred at 130° C. for 24 h. After adding ethylene glycol (500 mL), the stirring was further continued at 130° C. for 3 days. After cooling, the reaction liquid was phase-separated upon the addition of water (3 L). The organic layer was concentrated and the obtained residue was purified by silica gel column chromatography to obtain the intermediate A-3 (721 g) in a yield of 80%.

(A-4) Synthesis of Intermediate A-4

In argon atmosphere, into a solution of the intermediate A-3 synthesized in the step (A-3) (721 g, 2.75 mol) in acetonitrile (3.6 L) and water (3.6 L), concentrated sulfuric acid (2698 g, 27.5 mol) was added dropwise at −5 to 15° C. The resultant solution was stirred at −5° C. for 30 min. After adding isoamyl nitrite (483 g, 4.13 mol) dropwise while maintaining the temperature at −3° C. or below, the solution was stirred at −5° C. for one hour. Then, phosphinic acid (908 g, 13.8 mol) was added dropwise while maintaining the temperature at −2° C. or below. After adding methanol (3 L), the solution was stirred at room temperature overnight. The reaction solution was phase-separated upon the addition of toluene. The toluene layer was washed with a saturated brine. The obtained residue was purified by silica gel column chromatography to obtain the intermediate A-4 (418 g) in a yield of 61.4%.

(A-5) Synthesis of Intermediate A

In argon atmosphere, into a solution of the intermediate A-4 synthesized in the step (A-4) (5 g, 20.2 mmol) in tetrahydrofuran (THF) (100 mL), a 2.7 M hexane solution of n-butyllithium (8.34 mL, 22.3 mmol) was added at −63° C. The resultant solution was stirred for 2.5 h. After adding triisopropyl borate (8.20 g, 43.6 mmol) at −65° C., the temperature was returned to room temperature and the solution was stirred for 3.3 h. The reaction solution was stirred at room temperature for one hour after adding a 4 M hydrochloric acid (50 mL). The obtained reaction solution was extracted with dichloromethane. The dichloromethane layer was washed with an aqueous solution of sodium hydrogen carbonate and a saturated brine, dried over anhydrous magnesium sulfate, and then concentrated. The obtained residue was crystallized from toluene and hexane to obtain the intermediate A (3.30 g) in a yield of 77%.

Intermediate Synthesis B: Synthesis of Intermediate B

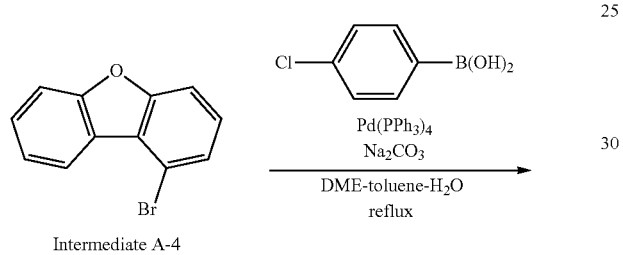

Intermediate A-4

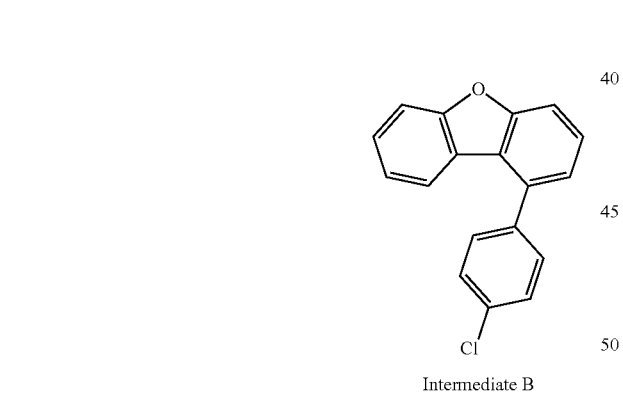

Intermediate B

In nitrogen atmosphere, a mixture of the intermediate A-4 (3.0 g, 12.1 mmol), 4-chlorophenylboronic acid (1.90 g, 12.1 mmol), tetrakis(triphenylphosphine)palladium(0) (0.281 g, 0.243 mmol), a 2 M aqueous solution of sodium carbonate (18.2 mL, 36.4 mmol), ethylene glycol dimethyl ether (DME) (30.4 mL), and toluene (30.4 mL) was refluxed for 6.5 h under heating. After cooling to room temperature, the reaction solution was phase-separated and the aqueous layer was extracted with ethyl acetate. The organic layer was washed with water, dried over anhydrous sodium sulfate, and concentrated under reduced pressure. The obtained residue was purified by silica gel column chromatography to obtain the intermediate B (3.30 g) in a yield of 98%.

Intermediate Synthesis C: Synthesis of Intermediate C

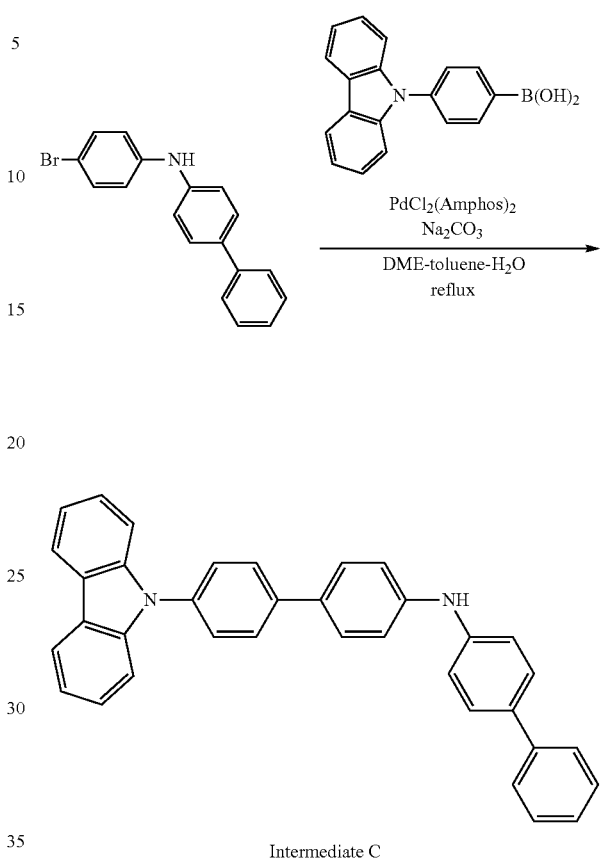

Intermediate C

In nitrogen atmosphere, a mixture of N-(4-bromophenyl)-4-biphenylamine (4.86 g, 15.0 mmol), 4-(9-carbazolyl)phenylboronic acid (4.31 g, 15.0 mmol), $PdCl_2(Amphos)_2$ (0.212 g, 0.300 mmol), a 2 M aqueous solution of sodium carbonate (22.5 mL, 45 mmol), toluene (37.5 mL), and DME (37.5 mL) was refluxed for 7 h under heating. The reaction solution was cooled to room temperature and the generated solid upon the addition of water was collected by filtration and washed with water. The obtained solid was purified by silica gel column chromatography and recrystallization to obtain the intermediate C (4.11 g) in a yield of 56%.

Intermediate Synthesis D: Synthesis of Intermediate D

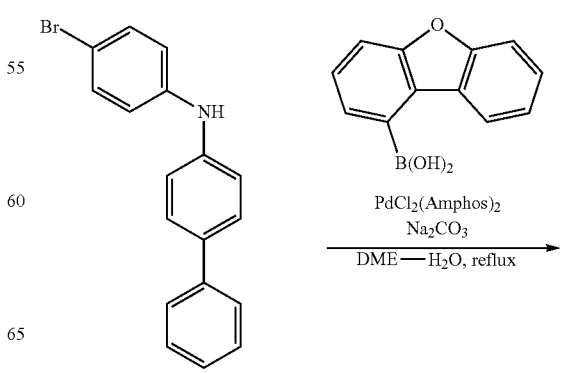

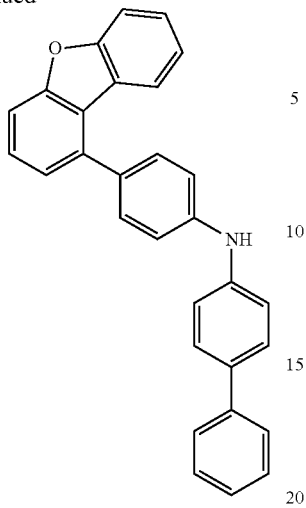

Intermediate D

In argon atmosphere, a mixture of N-(4-bromophenyl)-4-biphenylamine (5.00 g, 15.4 mmol), the intermediate A (3.27 g, 15.4 mmol), PdCl$_2$(Amphos)$_2$ (0.218 g, 0.308 mmol), a 2 M aqueous solution of sodium carbonate (23.1 mL), and DME (100 mL) was refluxed for 4 h under heating. The reaction solution was cooled to room temperature and concentrated under reduced pressure. After adding water, the resultant solution was extracted with toluene. The toluene layer was purified by silica gel column chromatography and recrystallization to obtain the intermediate D (3.2 g) in a yield of 50.4%.

Intermediate Synthesis E: Synthesis of Intermediate E

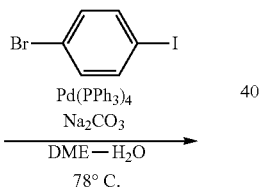

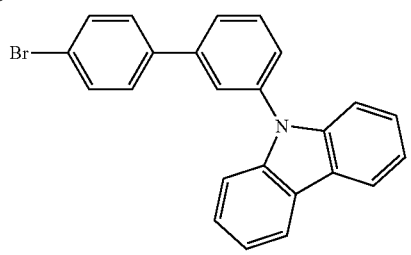

Intermediate E

In argon atmosphere, a solution of 3-(9-carbazolyl)phenylboronic acid (208 g, 725 mmol), 1-bromo-4-iodobenzene (246 g, 868 mmol), tetrakis(triphenylphosphine)palladium (0) (16.7 g, 14 mmol), and sodium carbonate (154 g, 1.45 mol) in DME (4.1 L)/water (710 mL) was stirred at 78° C. for 18 h. After cooling to room temperature, the generated solid upon the addition of methanol was collected by filtration. The obtained solid was purified by silica gel column chromatography and recrystallization to obtain the intermediate E (187 g) in a yield of 64%.

Intermediate Synthesis F: Synthesis of Intermediate F

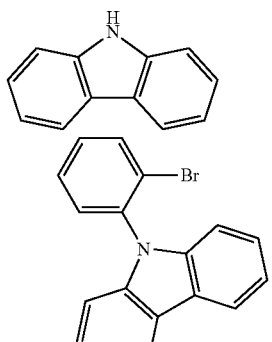
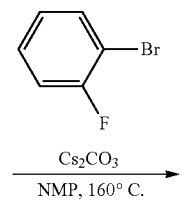
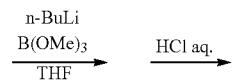

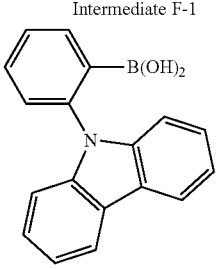

Intermediate F-1

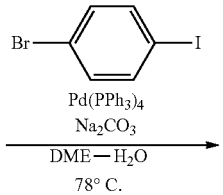

Intermediate F-2

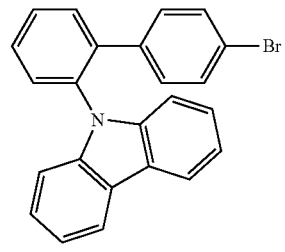

Intermediate F (F-1) Synthesis of Intermediate F-1

Into a solution of carbazole (10 g, 59.8 mmol) and cesium carbonate (39.0 g, 120 mmol) in N-methylpyrrolidone (NMP) (59.8 mL), 1-bromo-2-fluorobenzene (7.80 mL, 71.8 mmol) was added. The resultant mixture was stirred at 160° C. for 16 h under heating. The reaction solution was cooled to room temperature and toluene was added. The insoluble was removed by filtration. The obtained solution was washed with water, dried over anhydrous sodium sulfate, and purified by silica gel column chromatography. The obtained residue was crystallized to obtain the intermediate F-1 (18.3 g) in a yield of 94%.

(F-2) Synthesis of Intermediate F-2

In argon atmosphere, a solution of the intermediate F-1 synthesized in the step (F-1) (8.0 g, 24.8 mmol) in THF (124 mL) was cooled in a dry ice/acetone bath and a 1.6 M solution of n-butyllithium in hexane (17.1 mL, 27.3 mmol) was added dropwise. The resultant solution was stirred for 2 h. After adding a solution of trimethyl borate (3.33 mL, 29.8 mmol) in THF (10 mL) dropwise, the solution was further stirred for one hour. After removing the dry ice/acetone bath, the temperature was raised to room temperature. The reaction solution was cooled over an iced water bath. After adding a 2 M hydrochloric acid, the temperature was raised to room temperature and the solution was stirred for one hour. The obtained reaction solution was extracted with ethyl acetate. The organic layer was washed with water, dried over anhydrous sodium sulfate, and concentrated under reduced pressure. The obtained residue was crystallized to obtain the intermediate F-2 (4.91 g) in a yield of 69%.

(F-3) Synthesis of Intermediate F

The intermediate F was synthesized in the same manner as in Intermediate Synthesis E except for using the intermediate F-2 synthesized in the step (F-2) in place of 3-(9-carbazolyl)phenylboronic acid.

Intermediate Synthesis G: Synthesis of Intermediate G

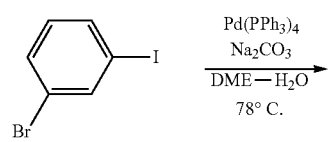

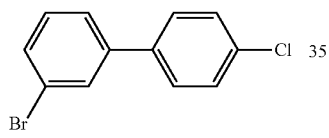

Intermediate G

In argon atmosphere, a solution of 4-chlorophenylboronic acid (200 g, 1.27 mol), 1-bromo-3-iodobenzene (362 g, 1.27 mol), tetrakis(triphenylphosphine)palladium(0) (29.5 g, 25 mmol), and sodium carbonate (407 g, 3.83 mol) in DME (5.6 L)/water (1.9 L) was stirred at 78° C. for 17 h, and then cooled to room temperature and extracted. The extract was concentrated under reduced pressure. The obtained residue was purified by silica gel column chromatography to obtain the intermediate G (172 g) in a yield of 50%.

Intermediate Synthesis H: Synthesis of Intermediate H

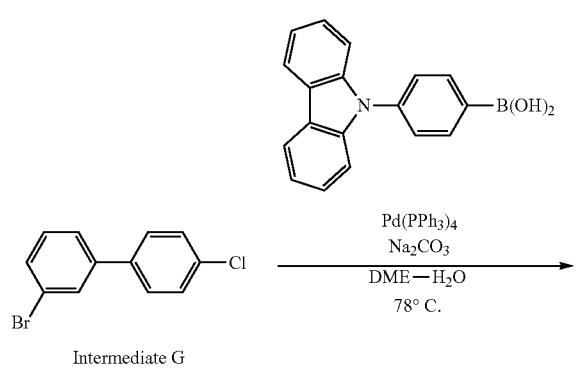

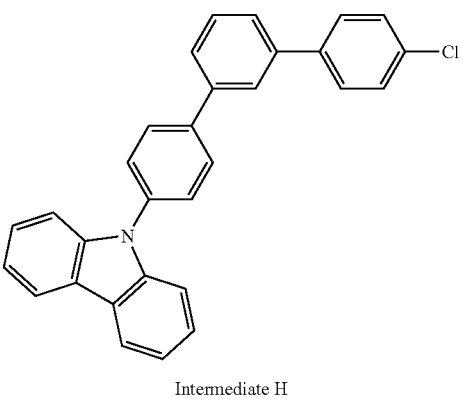

Intermediate H

The intermediate H was synthesized in the same manner as in Intermediate Synthesis E except for using 4-(9-carbazolyl)phenylboronic acid in place of 3-(9-carbazolyl)phenylboronic acid and using the intermediate G in place of 1-bromo-4-iodobenzene.

INTERMEDIATE Synthesis I: Synthesis of Intermediate I

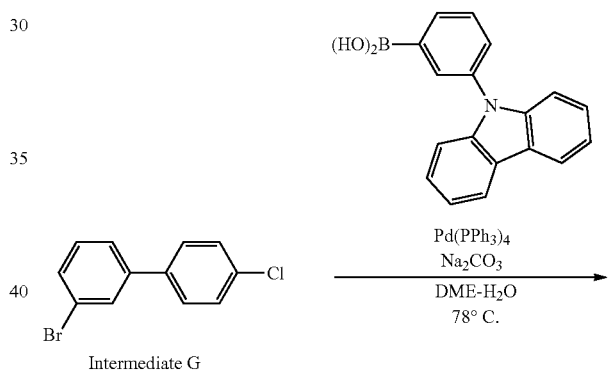

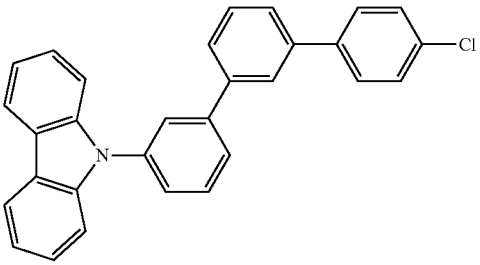

Intermediate I

The intermediate I was synthesized in the same manner as in Intermediate Synthesis E except for using the intermediate G in place of 1-bromo-4-iodobenzene.

Intermediate Synthesis J: Synthesis of Intermediate J

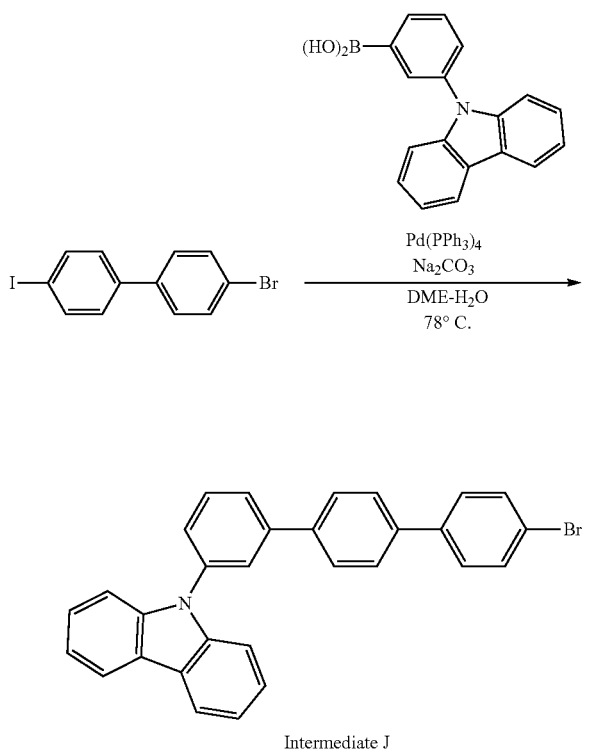 [SMILES: OB(O)c1cccc(-n2c3ccccc3c3ccccc32)c1 ; Brc1ccc(-c2ccc(I)cc2)cc1 ; Brc1ccc(-c2ccc(-c3cccc(-n4c5ccccc5c5ccccc54)c3)cc2)cc1]

Intermediate J

The intermediate J was synthesized in the same manner as in Intermediate Synthesis E except for using 4-bromo-4'-iodobiphenyl in place of 1-bromo-4-iodobenzene.

Intermediate Synthesis K: Synthesis of Intermediate K

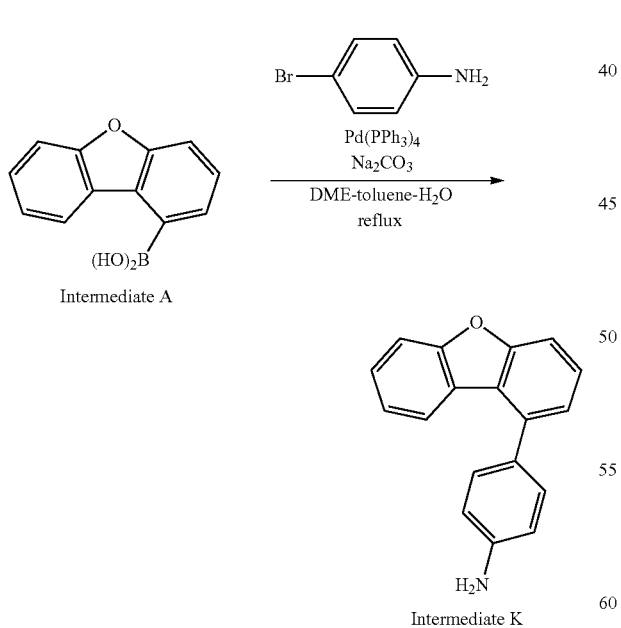

Intermediate K

In nitrogen atmosphere, a mixture of the intermediate A (5.13 g, 24.2 mmol), 4-bromoaniline (4.16 g, 24.2 mmol), tetrakis(triphenylphosphine)palladium(0) (0.562 g, 0.486 mmol), a 2 M aqueous solution of sodium carbonate (36.4 mL, 72.8 mmol), DME (60 mL), and toluene (60 mL) was refluxed for 6.5 h under heating. After cooling to room temperature, the reaction solution was phase-separated and the aqueous layer was extracted with ethyl acetate. The organic layer was washed with water, dried over anhydrous sodium sulfate, and concentrated under reduced pressure. The obtained residue was purified by silica gel column chromatography to obtain the intermediate K (5.08 g) in a yield of 81%.

Intermediate Synthesis L: Synthesis of Intermediate L

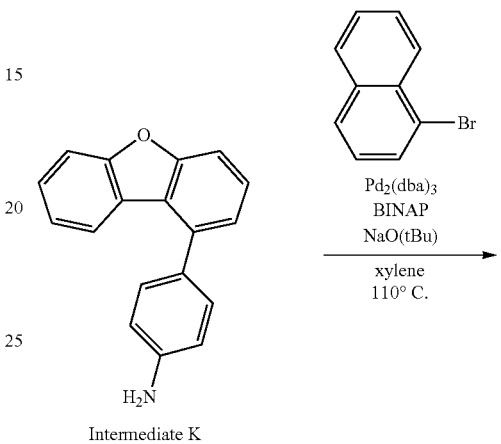

Intermediate L

In argon atmosphere, a mixture of the intermediate K (3.88 g, 15.0 mmol), 1-bromonaphthalene (3.10 g, 15.0 mmol), tris(dibenzylideneacetone)dipalladium(0) (0.206 g, 0.225 mmol), BINAP (0.280 g, 0.45 mmol), sodium t-butoxide (2.88 g, 30 mmol), and xylene (1.5 L) was stirred at 110° C. for 10 h. The reaction solution was cooled to room temperature and extracted with toluene upon the addition of water. The extract was concentrated under reduced pressure. The obtained residue was purified by silica gel column chromatography and recrystallization to obtain the intermediate L (3.35 g) in a yield of 58%.

Intermediate Synthesis M: Synthesis of Intermediate M

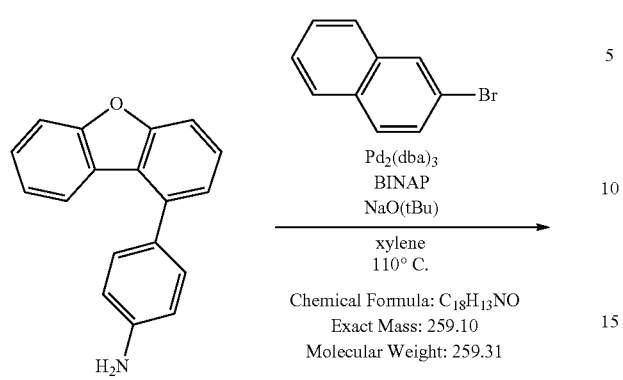

Intermediate K

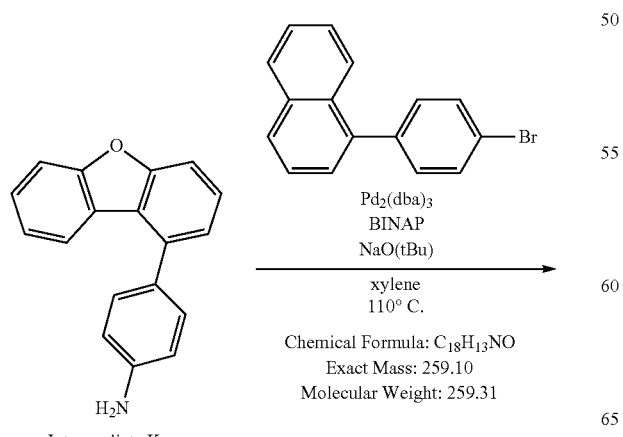

Intermediate M

The intermediate M was synthesized in the same manner as in Intermediate Synthesis L except for using 2-bromonaphthalene in place of 1-bromonaphthalene.

Intermediate Synthesis N: Synthesis of Intermediate N

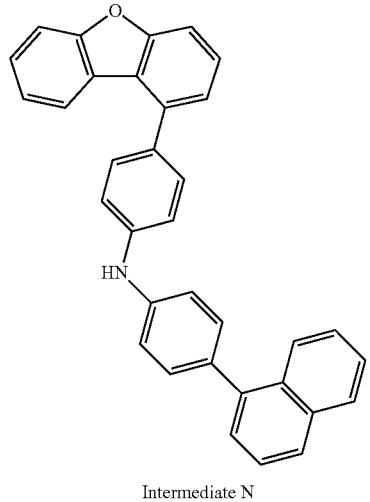

Intermediate N

The intermediate N was synthesized in the same manner as in Intermediate Synthesis L except for using 1-(4-bromophenyl)naphthalene in place of 1-bromonaphthalene.

Intermediate Synthesis O: Synthesis of Intermediate O

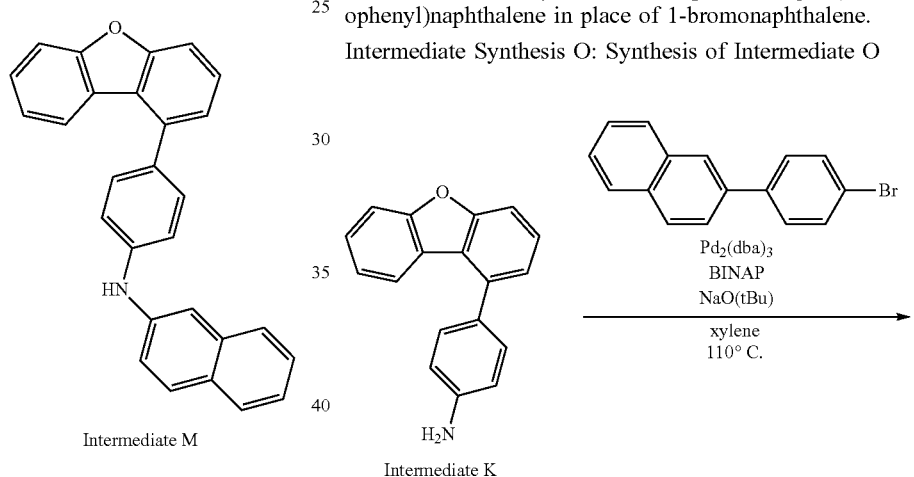

Intermediate O

The intermediate O was synthesized in the same manner as in Intermediate Synthesis L except for using 2-(4-bromophenyl)naphthalene in place of 1-bromonaphthalene.

Intermediate Synthesis P: Synthesis of Intermediate P

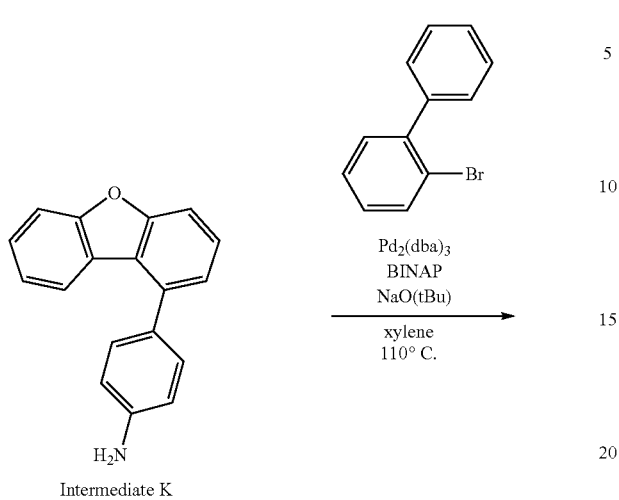

Intermediate K

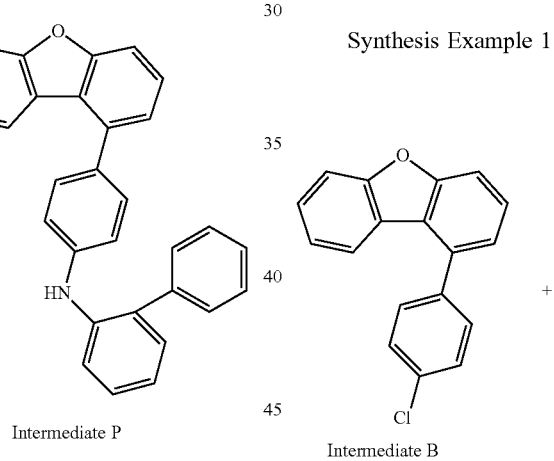

Intermediate P

The intermediate P was synthesized in the same manner as in Intermediate Synthesis L except for using 2-bromobiphenyl in place of 1-bromonaphthalene.

Intermediate Synthesis Q: Synthesis of Intermediate Q

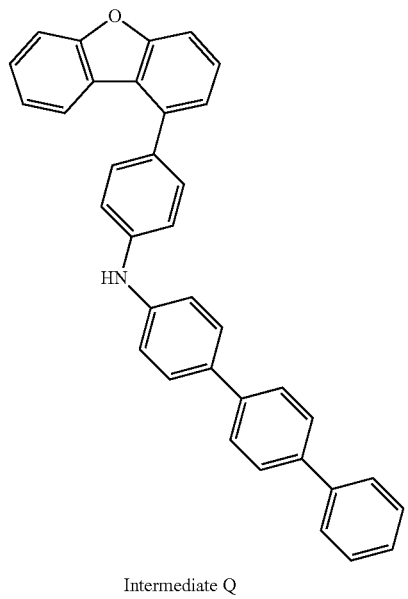

Intermediate Q

The intermediate Q was synthesized in the same manner as in Intermediate Synthesis L except for using 4-bromo-p-terphenyl in place of 1-bromonaphthalene.

Synthesis Example 1: Synthesis of Compound 1

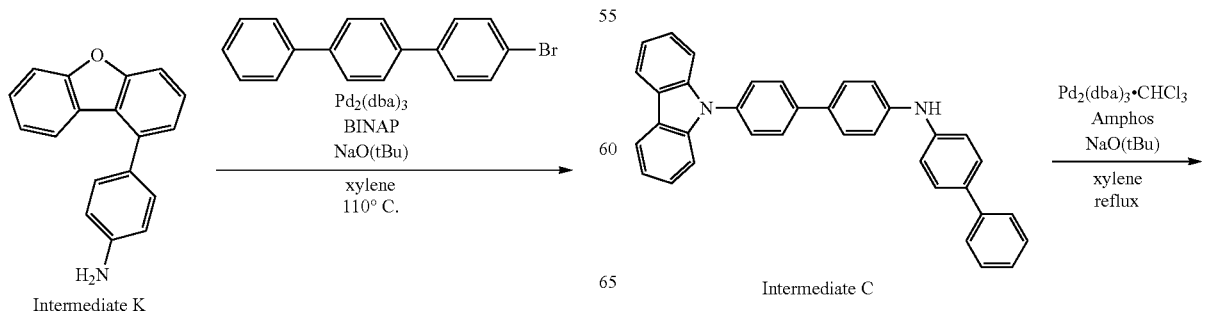

Intermediate B

Intermediate C

-continued

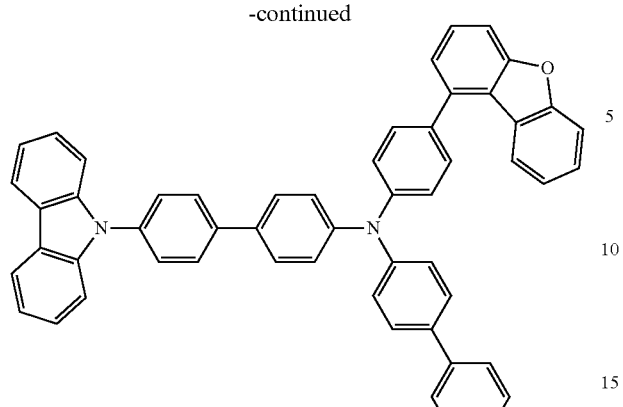

Compound 1

In nitrogen atmosphere, a mixture of the intermediate B (2.98 g, 10.7 mmol), the intermediate C (5.21 g, 10.7 mmol), tris(dibenzylideneacetone)dipalladium(0) chloroform adduct (0.222 g, 0.214 mmol), Amphos (0.227 g, 0.856 mmol), sodium t-butoxide (1.440 g, 15.0 mmol), and xylene (54 mL) was refluxed for 5 h under heating. The reaction solution was cooled to room temperature and methanol was added. The precipitated solid was removed by filtration and the filtrate was concentrated under reduced pressure. The obtained residue was purified by silica gel column chromatography to obtain a white solid (1.15 g) in a yield of 21%.

The obtained product was identified as Compound 1 by the result of mass spectrometric analysis (m/e=728 to the molecular weight of 728.28).

Synthesis Example 2: Synthesis of Compound 2

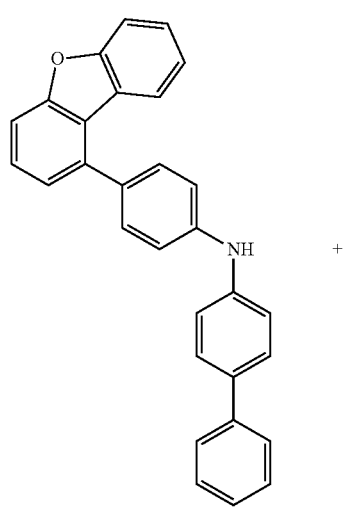

Intermediate D

-continued

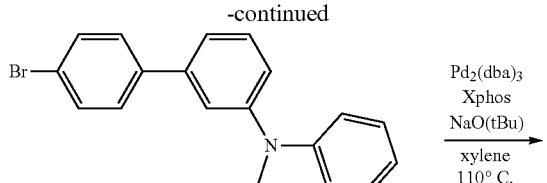

Intermediate E

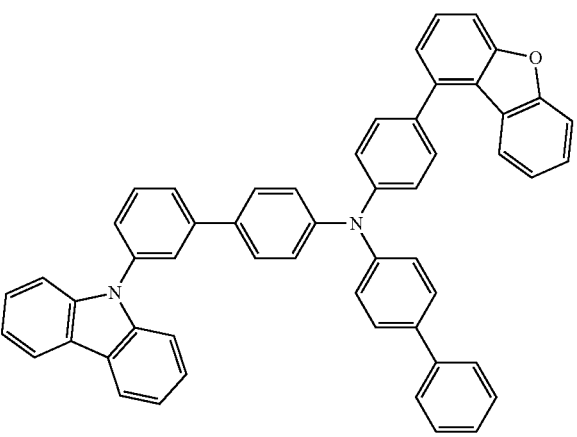

Compound 2

In argon atmosphere, a mixture of the intermediate D (3.20 g, 7.78 mmol), the intermediate E (3.10 g, 7.78 mmol), tris(dibenzylideneacetone)dipalladium(0) (0.142 g, 0.156 mmol), XPhos (0.297 g, 0.622 mmol), sodium t-butoxide (2.242 g, 23.33 mmol), and xylene (50 mL) was stirred at 110° C. for 4.5 h. The reaction liquid was cooled to room temperature and stirred upon the addition of NH silica gel, and then the silica gel was removed by filtration. The obtained solution was concentrated under reduced pressure. The obtained residue was purified by silica gel column chromatography and recrystallization to obtain a white solid (3.52 g) in a yield of 62%.

The obtained product was identified as Compound 2 by the result of mass spectrometric analysis (m/e=728 to the molecular weight of 728.28).

Synthesis Example 3: Synthesis of Compound 3

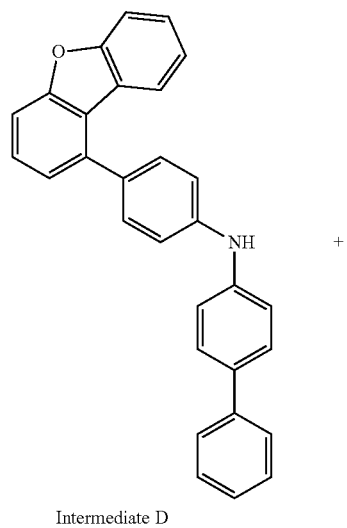

Synthesis Example 4: Synthesis of Compound 4

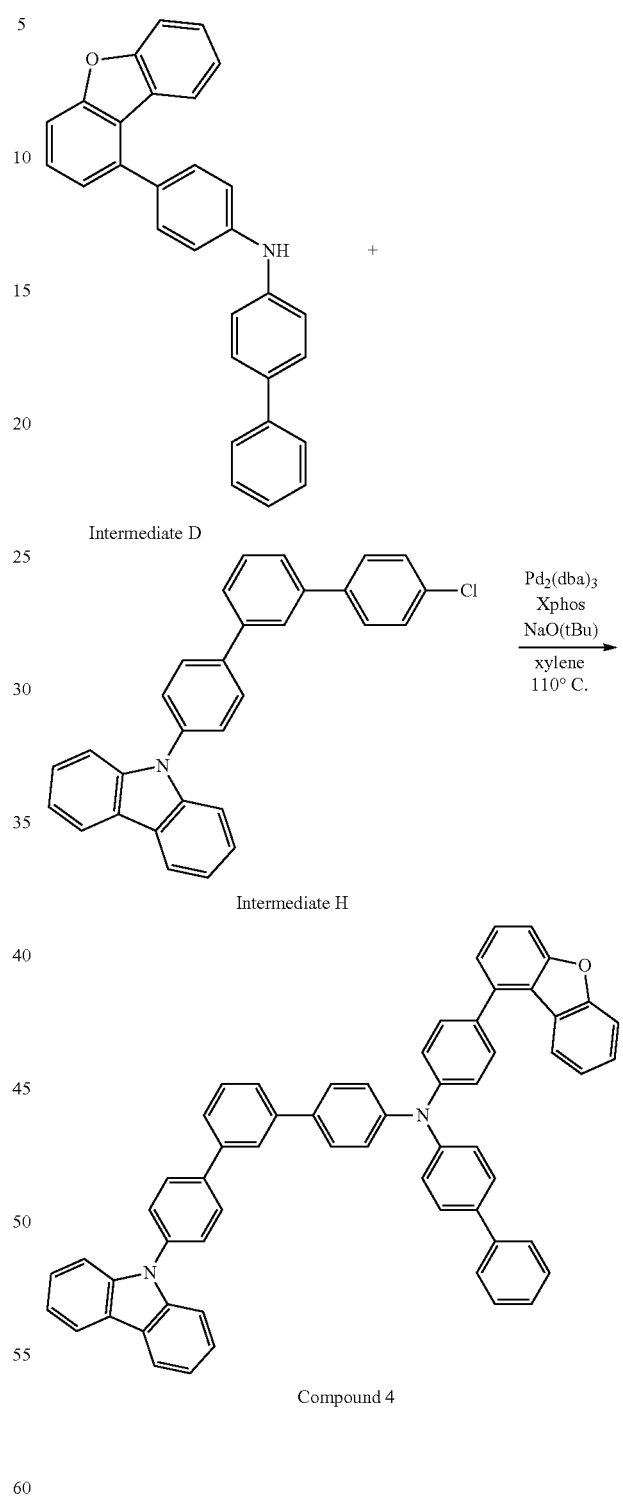

The procedure of Synthesis Example 2 was repeated except for using the intermediate F in place of the intermediate E.

The obtained product was identified as Compound 3 by the result of mass spectrometric analysis (m/e=728 to the molecular weight of 728.28).

The procedure of Synthesis Example 2 was repeated except for using the intermediate H in place of the intermediate E.

The obtained product was identified as Compound 4 by the result of mass spectrometric analysis (m/e=804 to the molecular weight of 804.31).

Synthesis Example 5: Synthesis of Compound 5

Synthesis Example 6: Synthesis of Compound 6

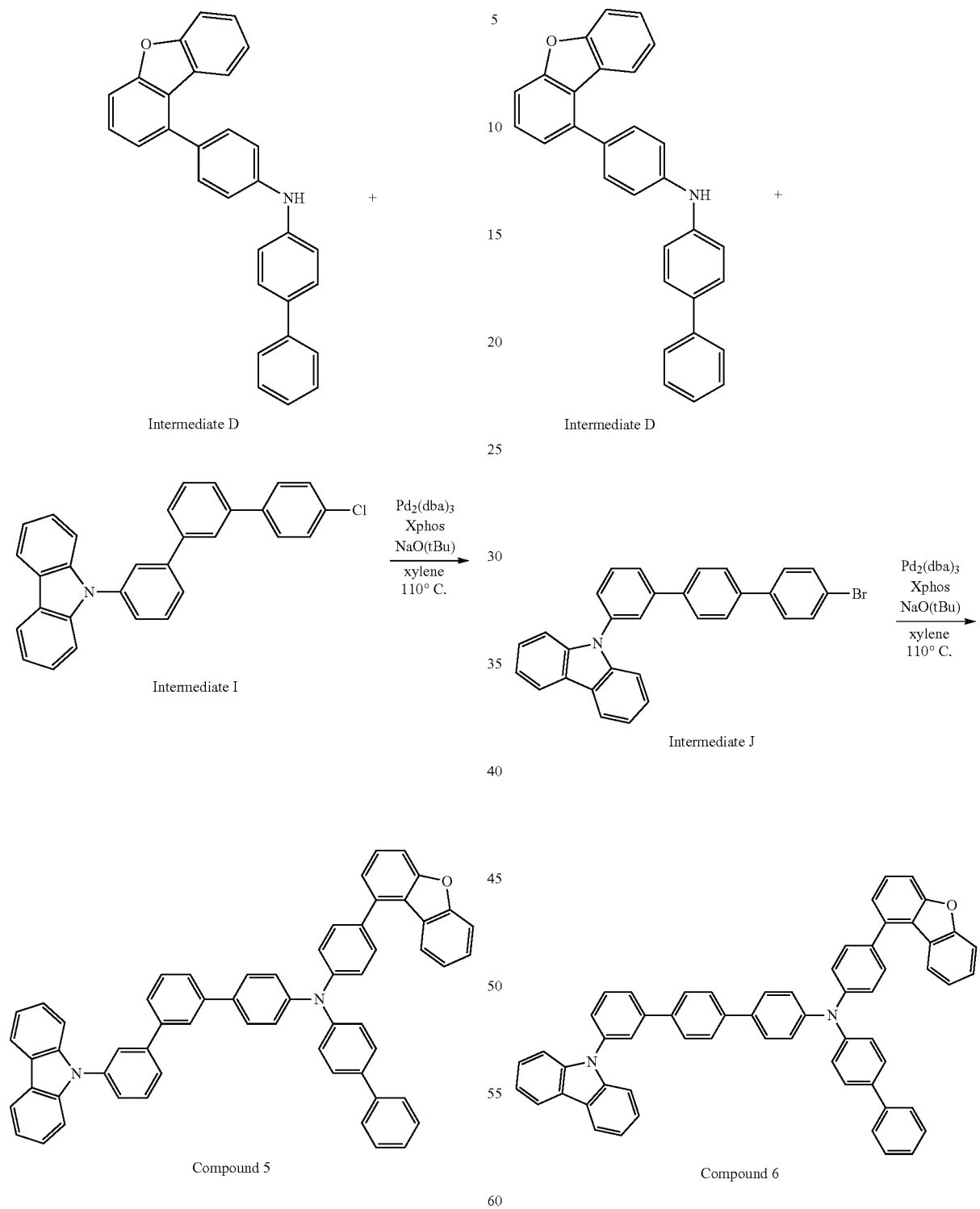

The procedure of Synthesis Example 2 was repeated except for using the intermediate I in place of the intermediate E.

The obtained product was identified as Compound 5 by the result of mass spectrometric analysis (m/e=804 to the molecular weight of 804.31).

The procedure of Synthesis Example 2 was repeated except for using the intermediate J in place of the intermediate E.

The obtained product was identified as Compound 6 by the result of mass spectrometric analysis (m/e=804 to the molecular weight of 804.31).

Synthesis Example 7: Synthesis of Compound 7

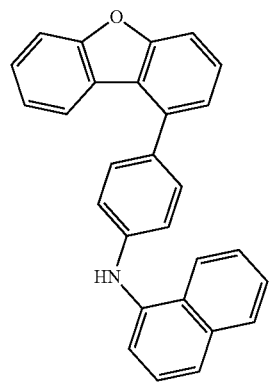

Intermediate L

+

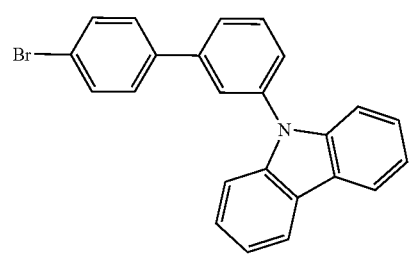

Intermediate E $\xrightarrow[\text{xylene}\ 110^\circ\text{C.}]{\text{Pd}_2(\text{dba})_3\ \text{Xphos}\ \text{NaO(tBu)}}$

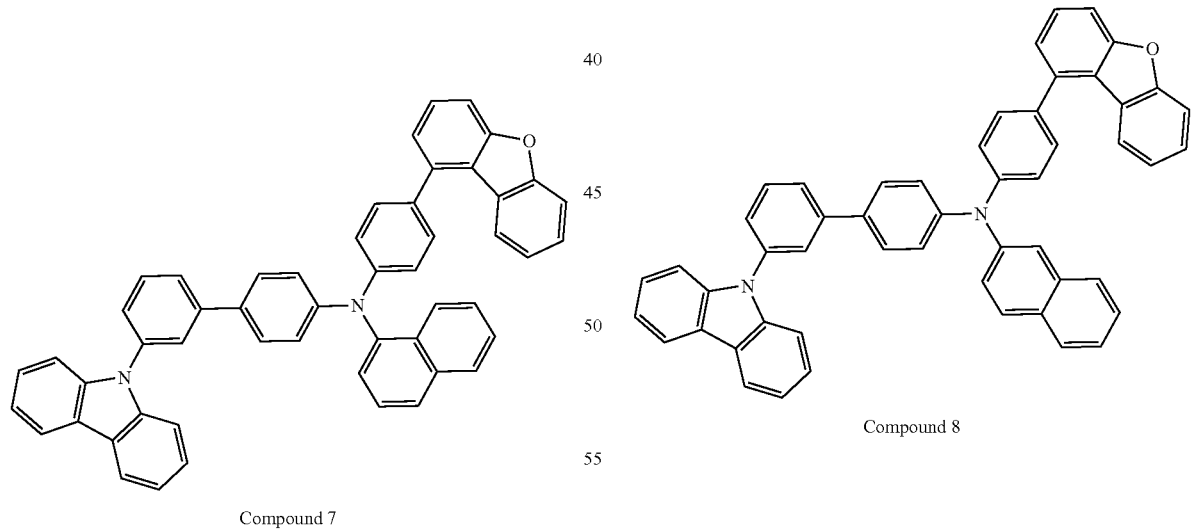

Compound 7

The procedure of Synthesis Example 2 was repeated except for using the intermediate L in place of the intermediate D.

The obtained product was identified as Compound 7 by the result of mass spectrometric analysis (m/e=702 to the molecular weight of 702.27).

Synthesis Example 8: Synthesis of Compound 8

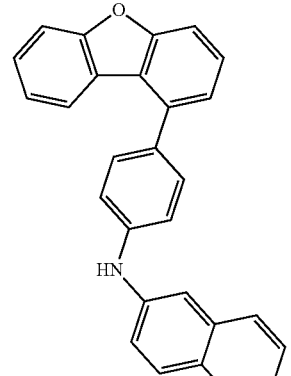

Intermediate M

+

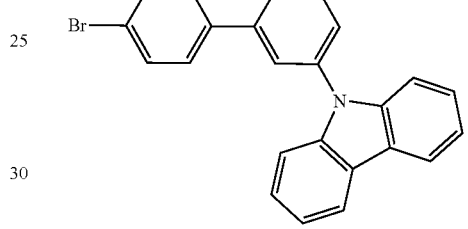

Intermediate E $\xrightarrow[\text{xylene}\ 110^\circ\text{C.}]{\text{Pd}_2(\text{dba})_3\ \text{Xphos}\ \text{NaO(tBu)}}$

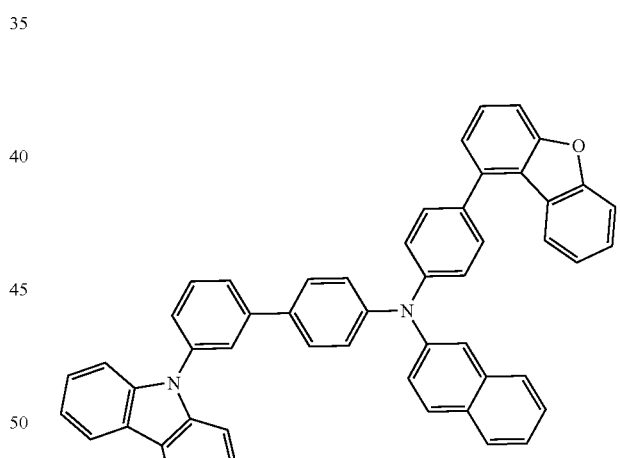

Compound 8

The procedure of Synthesis Example 2 was repeated except for using the intermediate M in place of the intermediate D.

The obtained product was identified as Compound 8 by the result of mass spectrometric analysis (m/e=702 to the molecular weight of 702.27).

Synthesis Example 9: Synthesis of Compound 9

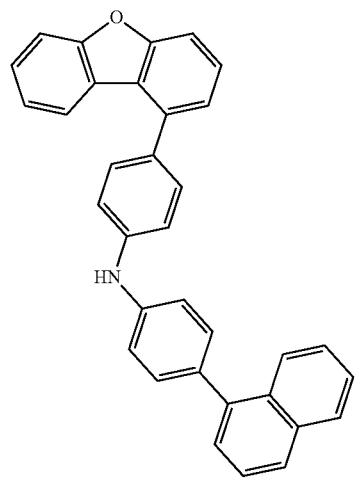

Intermediate N

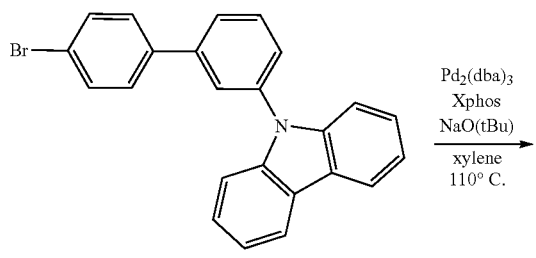

Intermediate E

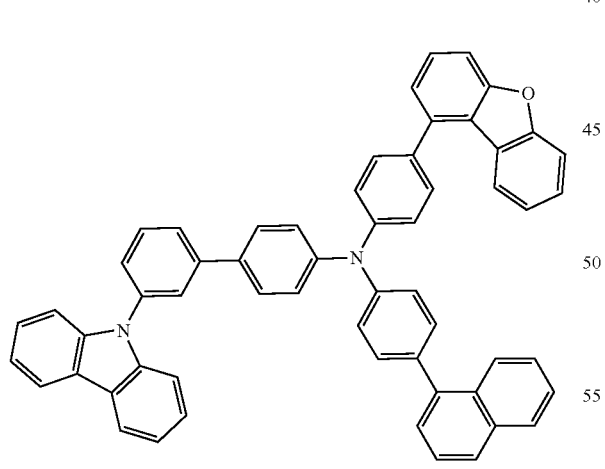

Compound 9

The procedure of Synthesis Example 2 was repeated except for using the intermediate N in place of the intermediate D.

The obtained product was identified as Compound 9 by the result of mass spectrometric analysis (m/e=778 to the molecular weight of 778.30).

Synthesis Example 10: Synthesis of Compound 10

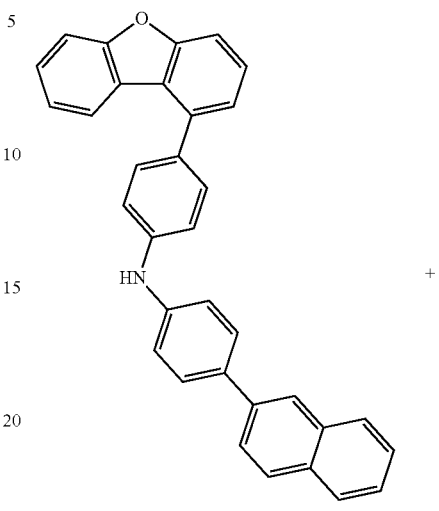

Intermediate O

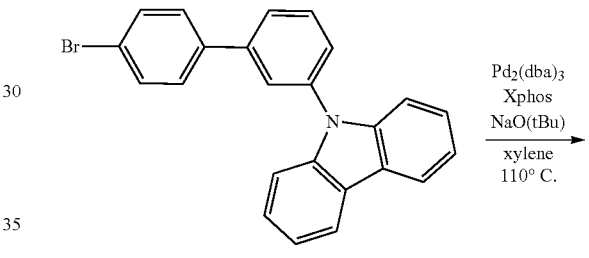

Intermediate E

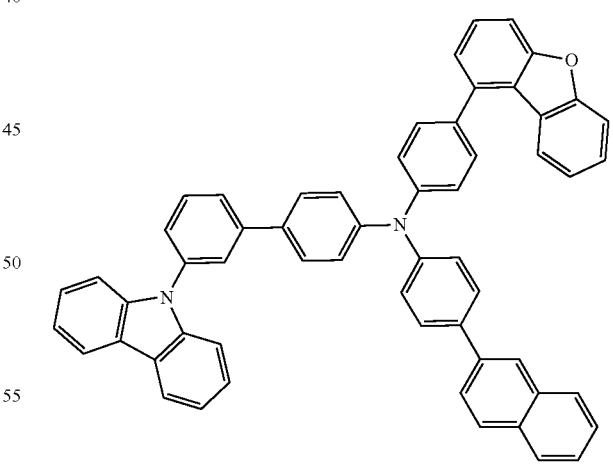

Compound 10

The procedure of Synthesis Example 2 was repeated except for using the intermediate O in place of the intermediate D.

The obtained product was identified as Compound 10 by the result of mass spectrometric analysis (m/e=778 to the molecular weight of 778.30).

Synthesis Example 11: Synthesis of Compound 11

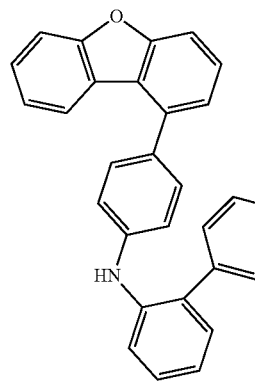

Intermediate P

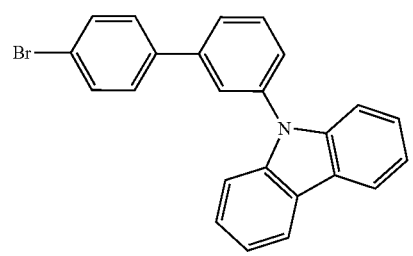

Intermediate E

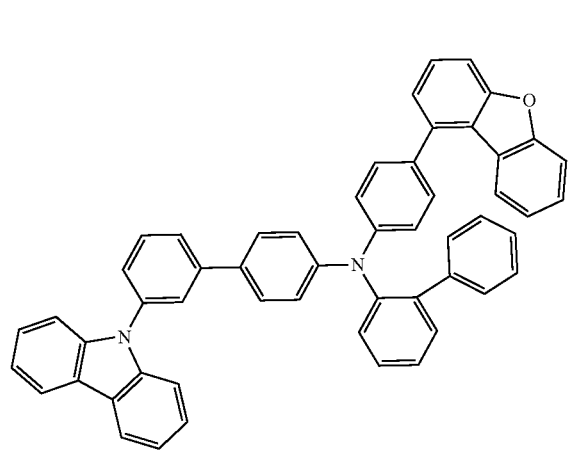

Compound 11

The procedure of Synthesis Example 2 was repeated except for using the intermediate P in place of the intermediate D.

The obtained product was identified as Compound 11 by the result of mass spectrometric analysis (m/e=728 to the molecular weight of 728.28).

Synthesis Example 12: Synthesis of Compound 12

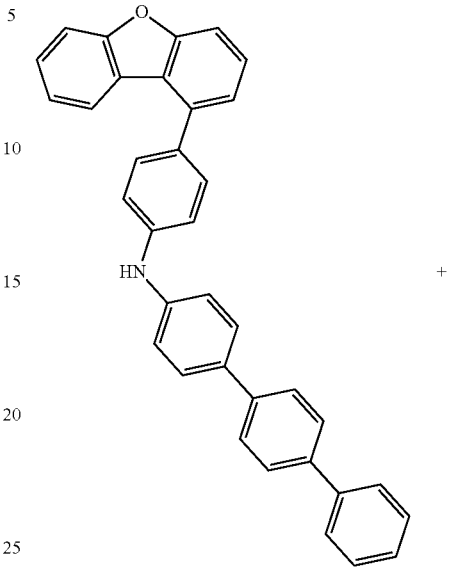

Intermediate Q

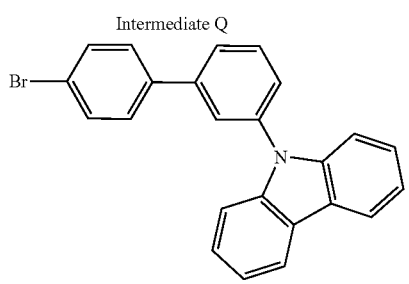

Intermediate E

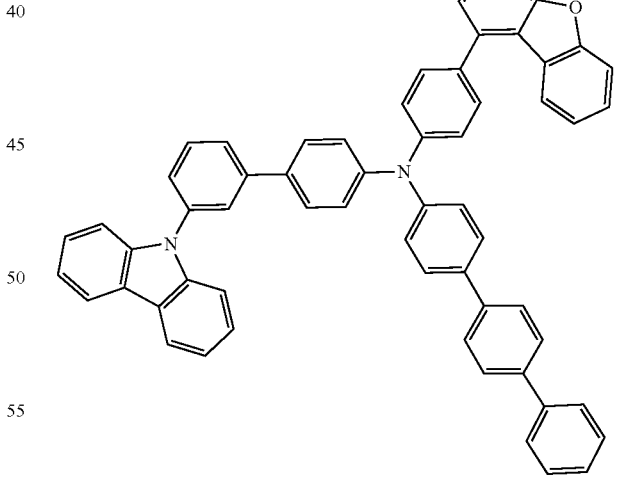

Compound 12

The procedure of Synthesis Example 2 was repeated except for using the intermediate Q in place of the intermediate D.

The obtained product was identified as Compound 12 by the result of mass spectrometric analysis (m/e=804 to the molecular weight of 804.31).

Synthesis Example 13: Synthesis of Compound 13

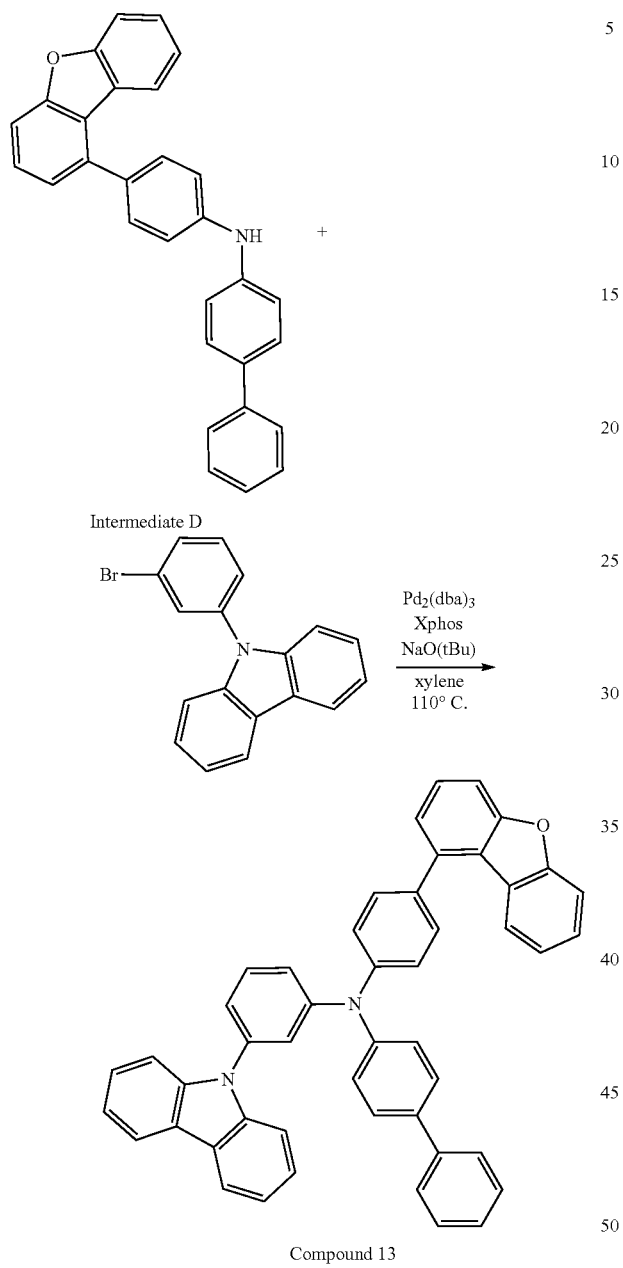

Compound 13

The procedure of Synthesis Example 2 was repeated except for using 9-3-bromophenyl)carbazole in place of the intermediate E.

The obtained product was identified as Compound 13 by the result of mass spectrometric analysis (m/e=652 to the molecular weight of 652.25).

Example 1

Production of Organic EL Device

A 25 mm×75 mm×1.1 mm glass substrate having ITO transparent electrode (product of Geomatec Company) was ultrasonically cleaned in isopropyl alcohol for 5 min and then UV/ozone cleaned for 30 min. The thickness of ITO transparent electrode was 130 nm.

The cleaned glass substrate having an ITO transparent electrode line was mounted to a substrate holder of a vacuum vapor deposition apparatus. First, the compound HI-1 was vapor-deposited on the surface having the ITO transparent electrode line so as to cover the transparent electrode to form a hole injecting layer with a thickness of 5 nm.

On the hole injecting layer, the compound HT-1 (first hole transporting material) was vapor-deposited to form a first hole transporting layer with a thickness of 80 nm.

On the first hole transporting layer, the compound 2 was vapor-deposited to form a second hole transporting layer with a thickness of 10 nm.

Then, on the second hole transporting layer, the compound BH-1 (host material) and the compound BD-1 (dopant material) were vapor co-deposited to form a co-deposited film with a thickness of 25 nm. The concentration of the compound BD-1 was 4.0% by mass. The co-deposited film works as alight emitting layer.

Then, on the light emitting layer, the compound ET-1 was vapor-deposited to form a first electron transporting layer with a thickness of 10 nm.

On the first electron transporting layer, the compound ET-2 was vapor-deposited to form a second electron transporting layer with a thickness of 15 nm.

On the second electron transporting layer, LiF was vapor-deposited to form an electron injecting electrode (cathode) with a thickness of 1 nm.

Then, metallic Al was vapor-deposited on the LiF film to form a metallic Al cathode with a thickness of 80 nm.

Evaluation of Organic EL Device

The organic EL device thus produced was operated at a current density of 10 mA/cm$^2$ to measure the external quantum efficiency (EQE). In addition, the time taken until the luminance was reduced to 95% of the initial luminance (LT95) was measured by operating the organic EL device at a current density of 50 mA/cm$^2$. The results are shown in Table 1.

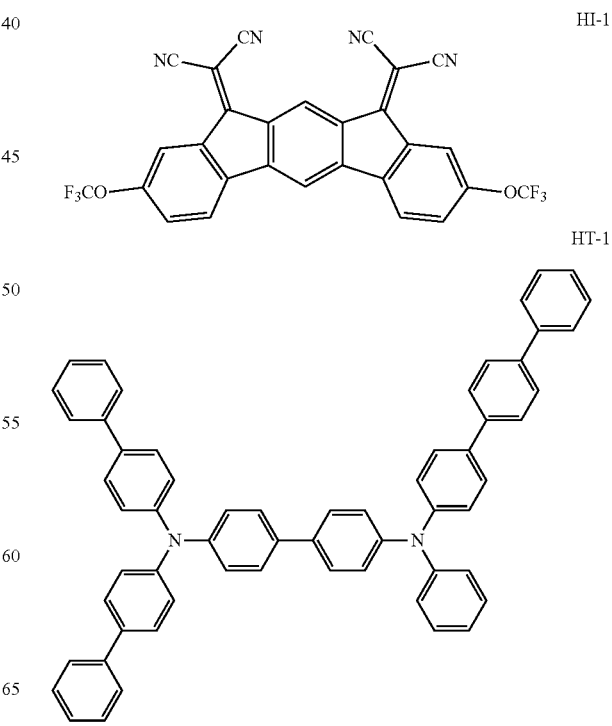

HI-1

HT-1

BH-1
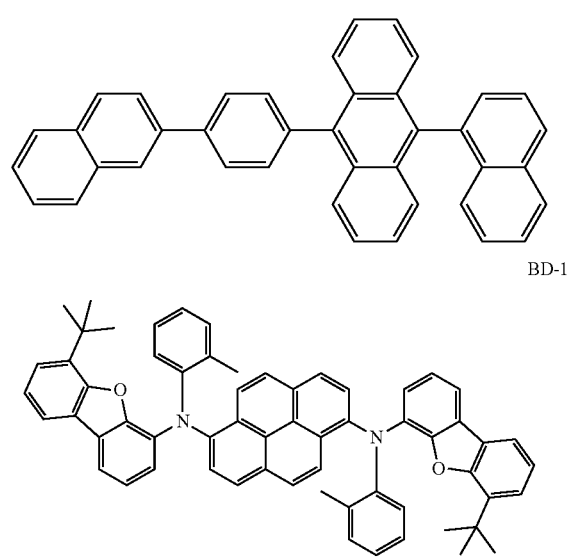
BD-1
ET-1
ET-2
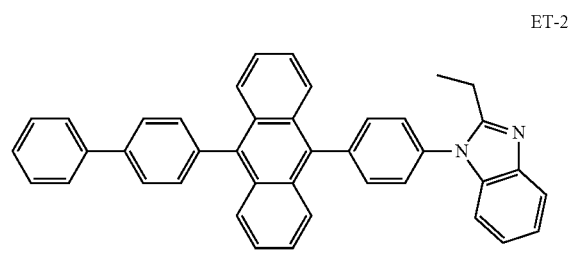 [SMILES: CCc1nc2ccccc2n1-c1ccc(-c2c3ccccc3c(-c3ccc(-c4ccccc4)cc3)c3ccccc23)cc1]
Examples 2 to 12, Comparative Examples 1 to 3
Each organic EL device was produced in the same manner as in Example 1 except for using each of the compounds 3 to 13 and the comparative compounds 1 to 3 in place of the compound 2 and evaluated in the same manner as in Example 1. The results are shown in Table 1.
Compound 2
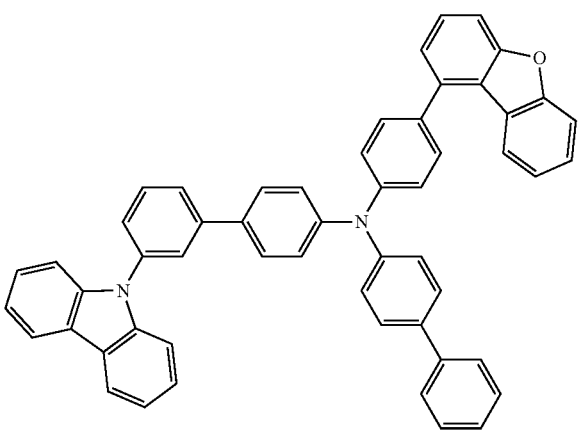
Compound 3
Compound 4
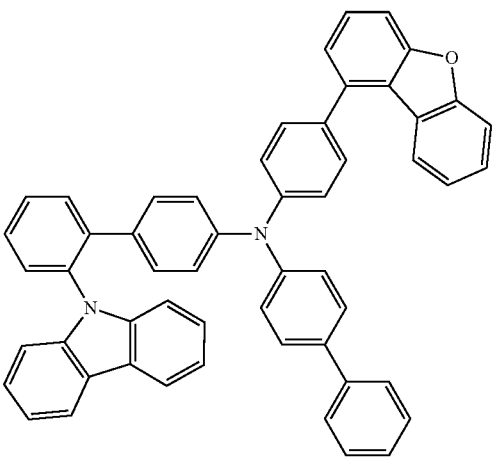

Compound 5
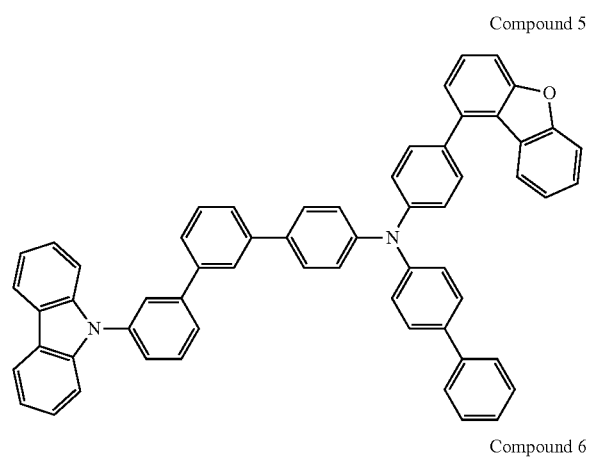
Compound 6
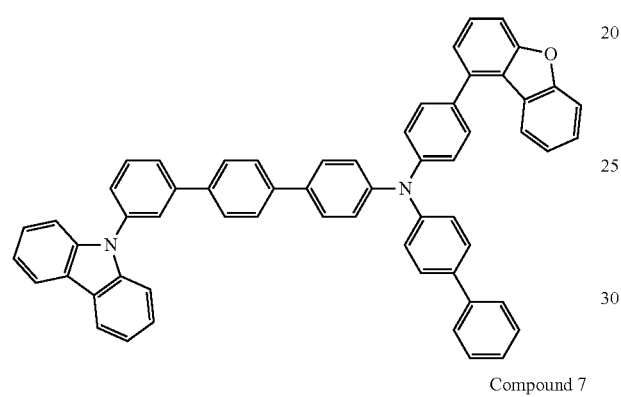
Compound 7
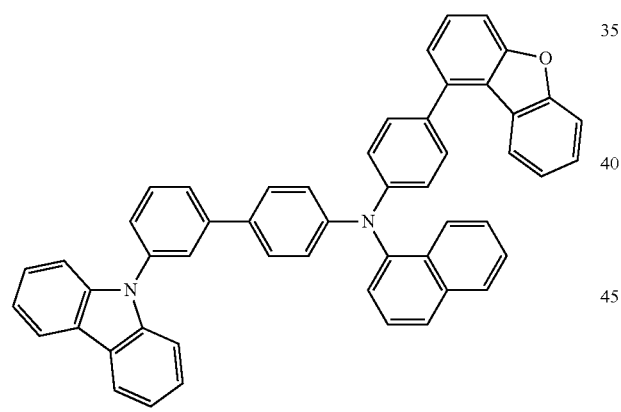
Compound 8
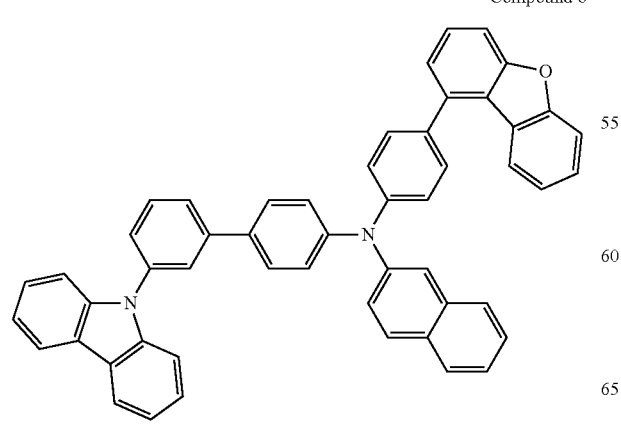
Compound 9
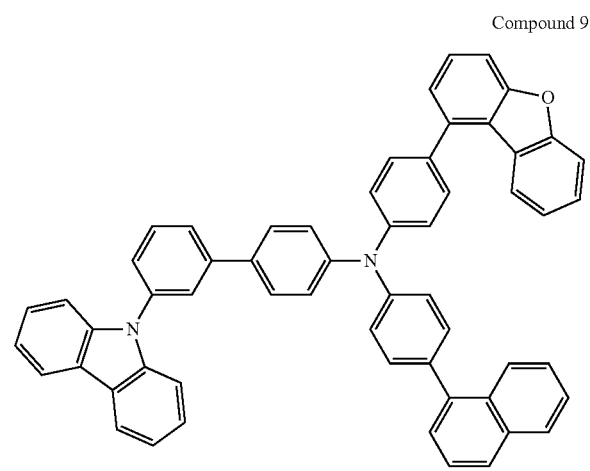
Compound 10
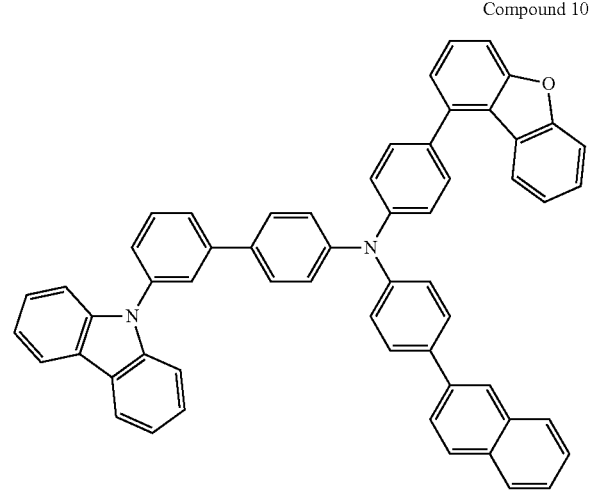
Compound 11

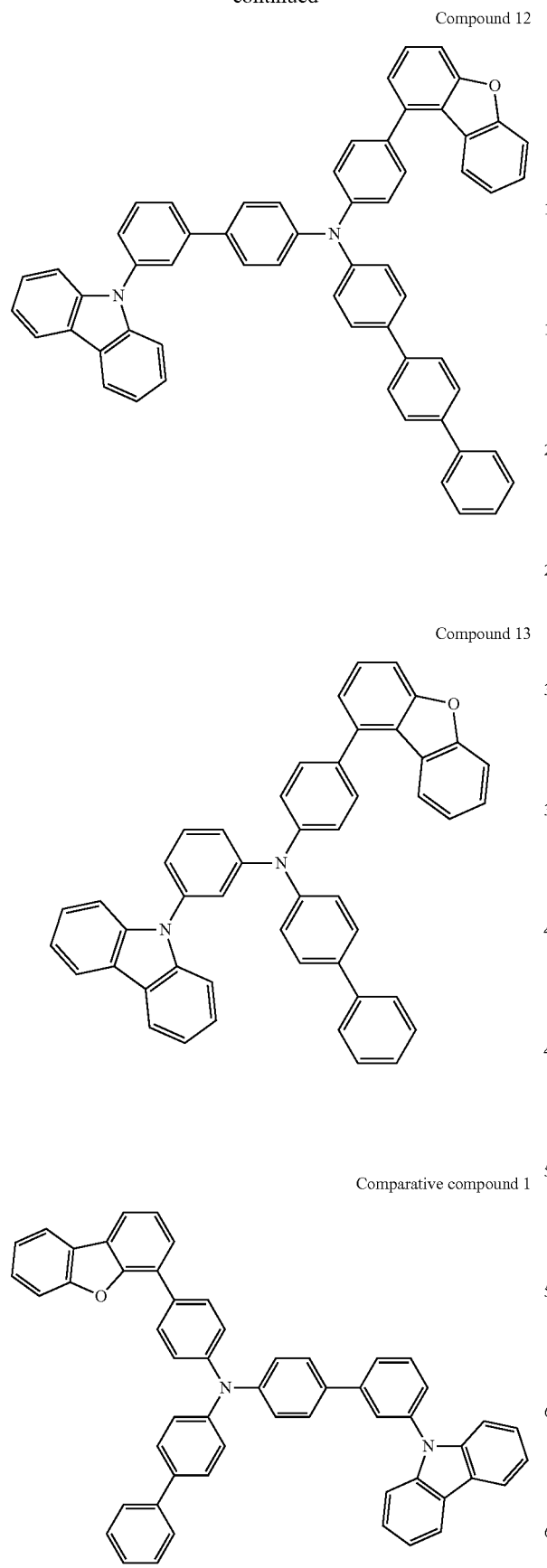

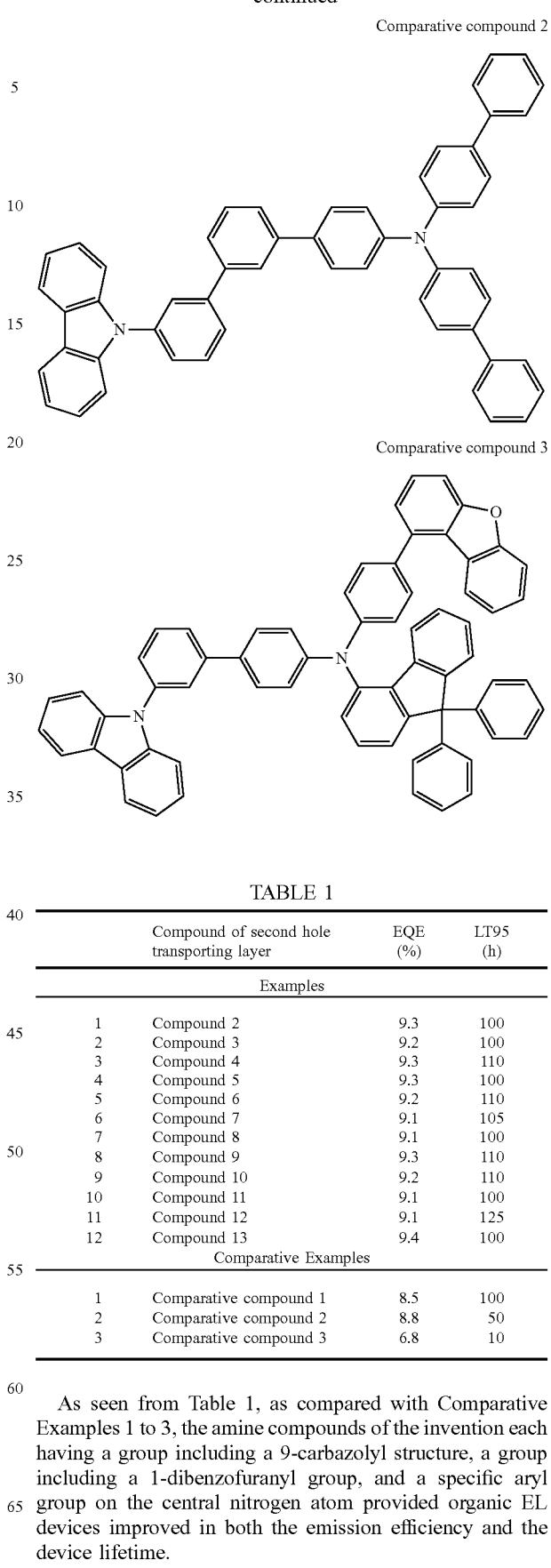

TABLE 1

| | Compound of second hole transporting layer | EQE (%) | LT95 (h) |
|---|---|---|---|
| Examples | | | |
| 1 | Compound 2 | 9.3 | 100 |
| 2 | Compound 3 | 9.2 | 100 |
| 3 | Compound 4 | 9.3 | 110 |
| 4 | Compound 5 | 9.3 | 100 |
| 5 | Compound 6 | 9.2 | 110 |
| 6 | Compound 7 | 9.1 | 105 |
| 7 | Compound 8 | 9.1 | 100 |
| 8 | Compound 9 | 9.3 | 110 |
| 9 | Compound 10 | 9.2 | 110 |
| 10 | Compound 11 | 9.1 | 100 |
| 11 | Compound 12 | 9.1 | 125 |
| 12 | Compound 13 | 9.4 | 100 |
| Comparative Examples | | | |
| 1 | Comparative compound 1 | 8.5 | 100 |
| 2 | Comparative compound 2 | 8.8 | 50 |
| 3 | Comparative compound 3 | 6.8 | 10 |

As seen from Table 1, as compared with Comparative Examples 1 to 3, the amine compounds of the invention each having a group including a 9-carbazolyl structure, a group including a 1-dibenzofuranyl group, and a specific aryl group on the central nitrogen atom provided organic EL devices improved in both the emission efficiency and the device lifetime.

REFERENCE SIGNS LIST

1: Organic EL device
2: Substrate
3: Anode
4: Cathode
5: Light emitting layer
6: Anode-side organic layer
7: Cathode-side organic layer
10: Emission unit

The invention claimed is:
1. A compound represented by formula (1):

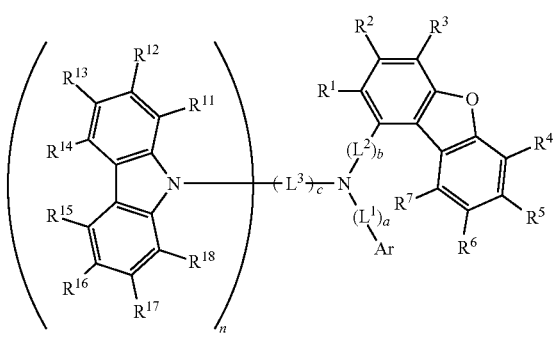

(1)

wherein:
$R^1$ to $R^7$ and $R^{11}$ to $R^{18}$ are each independently
a hydrogen atom,
a substituted or unsubstituted alkyl group having 1 to 30 carbon atoms,
a substituted or unsubstituted cycloalkyl group having 3 to 30 ring carbon atoms,
a substituted or unsubstituted aryl group having 6 to 30 ring carbon atoms,
a substituted or unsubstituted aralkyl group having 7 to 36 carbon atoms,
a substituted or unsubstituted alkoxy group having 1 to 30 carbon atoms,
a substituted or unsubstituted aryloxy group having 6 to 30 ring carbon atoms,
a mono-, di- or tri-substituted silyl group having a substituent selected from the group consisting of a substituted or unsubstituted alkyl group having 1 to 30 carbon atoms and a substituted or unsubstituted aryl group having 6 to 30 ring carbon atoms,
a substituted or unsubstituted haloalkyl group having 1 to 30 carbon atoms,
a substituted or unsubstituted haloalkoxy group having 1 to 30 carbon atoms,
a substituted or unsubstituted heteroaryl group having 5 to 30 ring atoms,
a halogen atom,
a cyano group, or
a nitro group;
adjacent two selected from $R^1$ to $R^3$, adjacent two selected from $R^4$ to $R^7$, adjacent two selected from $R^{11}$ to $R^{14}$, and adjacent two selected from $R^{15}$ to $R^{18}$ may be bonded to each other to form a ring structure;
Ar is a substituted or unsubstituted aryl group having 6 to 30 ring carbon atoms, wherein the aryl group is composed of only a six-membered ring;
a is 0, 1, 2, or 3;
when a is 0, Ar is directly bonded to the central nitrogen atom;
when a is 2 or 3, two or three $L^1$'s may be the same or different;
b is 1, 2, or 3;
when b is 2 or 3, two or three $L^2$'s may be the same or different;
c is 1, 2, or 3;
when c is 2 or 3, two or three $L^3$'s may be the same or different;
n is 1 or 2;
when n is 1, $L^1$, $L^2$, and $L^3$ are each independently a substituted or unsubstituted arylene group having 6 to 18 ring carbon atoms; and
when n is 2, $L^3$ directly bonded to the nitrogen atom of the carbazole structure is a three-valent residue of an aromatic hydrocarbon having 6 to 18 ring carbon atoms, which may have a substituent, and $L^1$, $L^2$, and $L^3$ not directly bonded to the nitrogen atom of the carbazole structure are each independently a substituted or unsubstituted arylene group having 6 to 18 ring carbon atoms.

2. The compound according to claim 1, which is represented by formula (2):

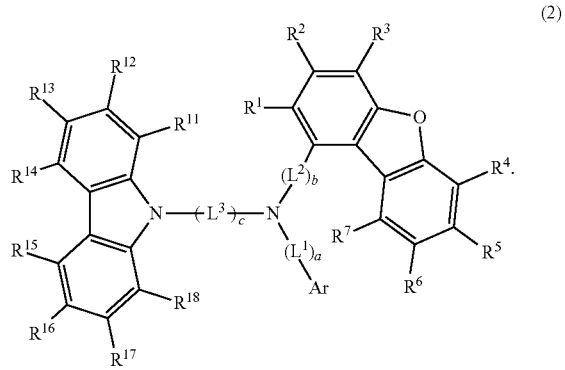

(2)

3. The compound according to claim 1, wherein the aryl group of the substituted or unsubstituted aryl group having 6 to 30 ring carbon atoms represented by Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group.

4. The compound according to claim 1, wherein the aryl group of the substituted or unsubstituted aryl group having 6 to 30 ring carbon atoms represented by Ar is a phenyl group, a biphenylyl group, a terphenylyl group, a naphthyl group, a phenanthryl group, or a triphenylenyl group.

5. The compound according to claim 1, wherein the aryl group of the substituted or unsubstituted aryl group having 6 to 30 ring carbon atoms represented by Ar is selected from the following groups:

605
-continued

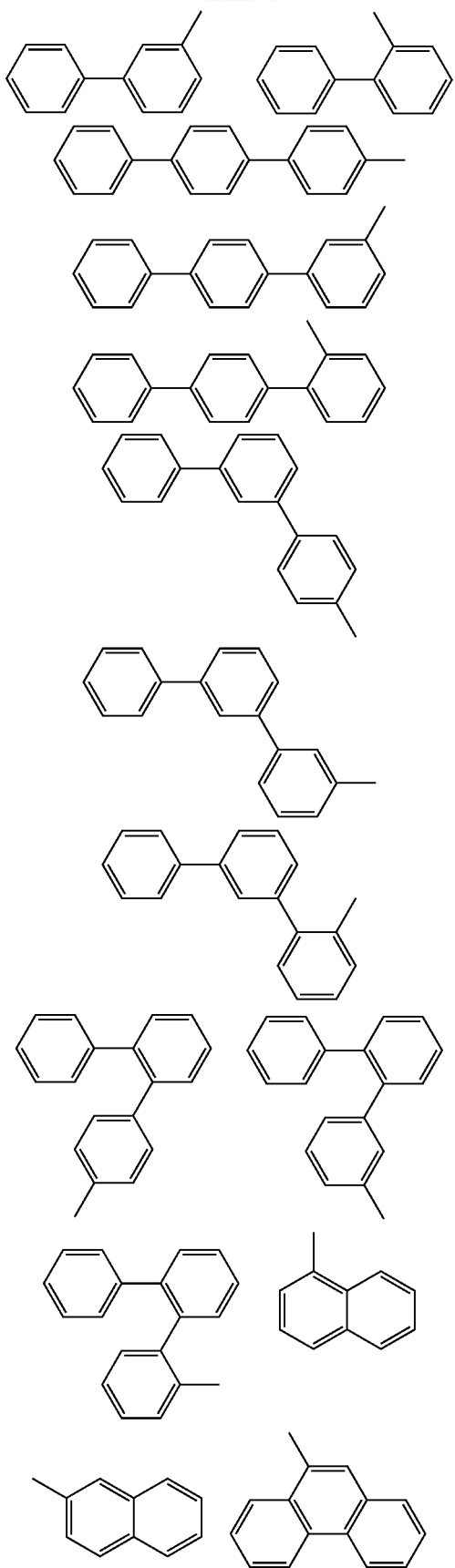

606
-continued

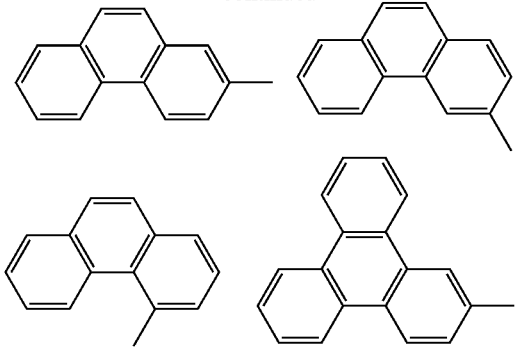

6. The compound according to claim 1, wherein the arylene group of the substituted or unsubstituted arylene group having 6 to 18 ring carbon atoms represented by each of $L^1$ to $L^3$ is independently a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, or a triphenylenylene group.

7. The compound according to claim 1, wherein the arylene group of the substituted or unsubstituted arylene group having 6 to 18 ring carbon atoms represented by each of $L^1$ to $L^3$ is independently a phenylene group, a biphenylylene group, a terphenylylene group, a naphthylene group, or a phenanthrylene group.

8. The compound according to claim 1, wherein:
the arylene group of the substituted or unsubstituted arylene group having 6 to 18 ring carbon atoms represented by each of $L^1$ and $L^2$ is independently a phenylene group, a biphenylylene group, a terphenylylene group, a naphthylene group, or a phenanthrylene group; and
the arylene group of the substituted or unsubstituted arylene group having 6 to 18 ring carbon atoms represented by $L^3$ is a phenylene group, a biphenylylene group, or a terphenylylene group.

9. The compound according to claim 1, wherein:
the arylene group of the substituted or unsubstituted arylene group having 6 to 18 ring carbon atoms represented by each of $L^1$ and $L^2$ is independently a phenylene group, a biphenylylene group, a terphenylylene group, a naphthylene group, or a phenanthrylene group; and
the arylene group of the substituted or unsubstituted arylene group having 6 to 18 ring carbon atoms represented by $L^3$ is a p-phenylene group, a 4,4'-biphenylylene group, or a 4,4''-p-terphenylylene group.

10. The compound according to claim 1, wherein:
the arylene group of the substituted or unsubstituted arylene group having 6 to 18 ring carbon atoms represented by each of $L^1$ and $L^2$ is independently an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group; and the arylene group of the substituted or unsubstituted arylene group having 6 to 18 ring carbon atoms represented by $L^3$ is a p-phenylene group, a 4,4'-biphenylylene group, or a 4,4"-p-terphenylylene group.

11. The compound according to claim 1, wherein:

the arylene group of the substituted or unsubstituted arylene group having 6 to 18 ring carbon atoms represented by each of $L^1$ and $L^2$ is independently a phenylene group, a biphenylylene group, a terphenylylene group, a naphthylene group, or a phenanthrylene group; and the arylene group of the substituted or unsubstituted arylene group having 6 to 18 ring carbon atoms represented by $L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group.

12. The compound according to claim 1, wherein:

the arylene group of the substituted or unsubstituted arylene group having 6 to 18 ring carbon atoms represented by each of $L^1$ and $L^2$ is independently an o-phenylene group, a m-phenylene group, a p-phenylene group, a 4,4'-biphenylylene group, a 4,3'-biphenylylene group, a 4,2'-biphenylylene group, a 4,4"-p-terphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, a 4,3'-m-terphenylylene group, a 1,4-naphthylene group, a 2,6-naphthylene group, or a 2,7-phenanthrylene group; and the arylene group of the substituted or unsubstituted arylene group having 6 to 18 ring carbon atoms represented by $L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group.

13. The compound according to claim 1, wherein:

the arylene group of the substituted or unsubstituted arylene group having 6 to 18 ring carbon atoms represented by $L^1$ is a phenylene group;

the arylene group of the substituted or unsubstituted arylene group having 6 to 18 ring carbon atoms represented by $L^2$ is a phenylene group, a biphenylylene group, a naphthylene group, or a phenanthrylene group; and the arylene group of the substituted or unsubstituted arylene group having 6 to 18 ring carbon atoms represented by $L^3$ is a phenylene group, a biphenylylene group, or a terphenylylene group.

14. The compound according to claim 1, wherein:

the arylene group of the substituted or unsubstituted arylene group having 6 to 18 ring carbon atoms represented by $L^1$ is a phenylene group;

the arylene group of the substituted or unsubstituted arylene group having 6 to 18 ring carbon atoms represented by $L^2$ is a phenylene group, a biphenylylene group, a naphthylene group, or a phenanthrylene group; and the arylene group of the substituted or unsubstituted arylene group having 6 to 18 ring carbon atoms represented by $L^3$ is a p-phenylene group, a 4,4'-biphenylylene group, or a 4,4"-p-terphenylylene group.

15. The compound according to claim 1, wherein:

the arylene group of the substituted or unsubstituted arylene group having 6 to 18 ring carbon atoms represented by $L^1$ is an o-phenylene group, a m-phenylene group, or a p-phenylene group;

the arylene group of the substituted or unsubstituted arylene group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group; and the arylene group of the substituted or unsubstituted arylene group having 6 to 18 ring carbon atoms represented by $L^3$ is a p-phenylene group, a 4,4'-biphenylylene group, or a 4,4"-p-terphenylylene group.

16. The compound according to claim 1, wherein:

the arylene group of the substituted or unsubstituted arylene group having 6 to 18 ring carbon atoms represented by $L^1$ is a phenylene group;

the arylene group of the substituted or unsubstituted arylene group having 6 to 18 ring carbon atoms represented by $L^2$ is a phenylene group, a biphenylylene group, a naphthylene group, or a phenanthrylene group; and the arylene group of the substituted or unsubstituted arylene group having 6 to 18 ring carbon atoms represented by $L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group.

17. The compound according to claim 1, wherein:

the arylene group of the substituted or unsubstituted arylene group having 6 to 18 ring carbon atoms represented by $L^1$ is an o-phenylene group, a m-phenylene group, or a p-phenylene group;

the arylene group of the substituted or unsubstituted arylene group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group; and the arylene group of the substituted or unsubstituted arylene group having 6 to 18 ring carbon atoms represented by $L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group.

18. The compound according to claim 1, wherein the arylene group of the substituted or unsubstituted arylene group having 6 to 18 ring carbon atoms represented by $L^3$ is selected from the following arylene groups:

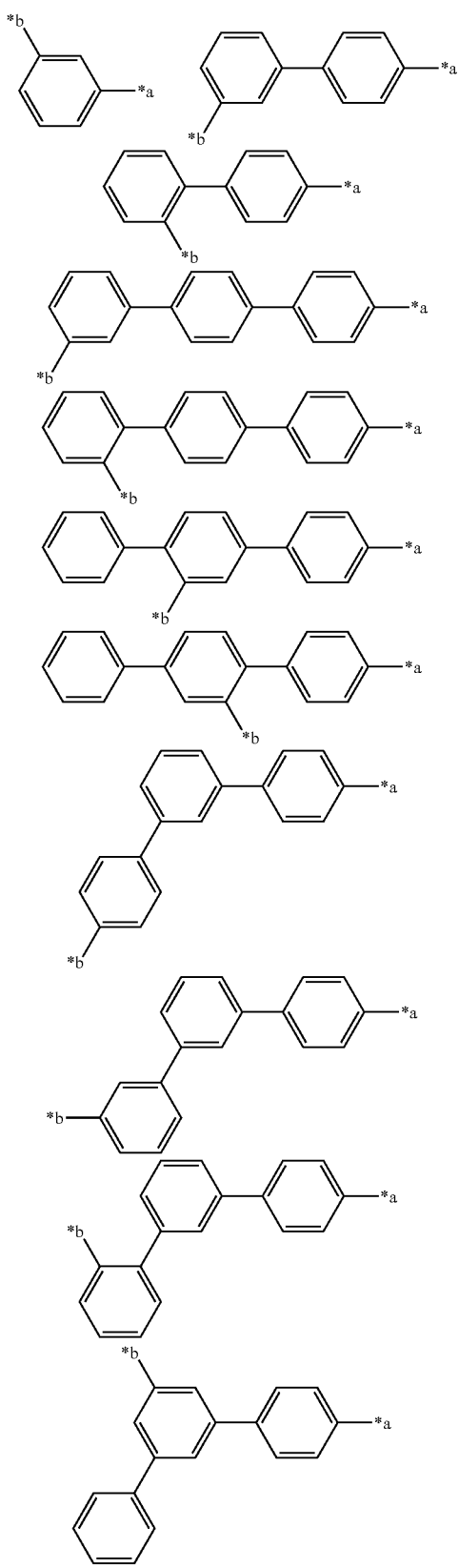

wherein *a is directly or indirectly bonded to the central nitrogen atom, and *b is directly or indirectly bonded to the nitrogen atom of the carbazole structure.

19. The compound according to claim 1, wherein a is 0, b is 1, and c is 1.

20. The compound according to claim 19, wherein:

the arylene group of the substituted or unsubstituted arylene group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group;

the arylene group of the substituted or unsubstituted arylene group having 6 to 18 ring carbon atoms represented by $L^3$ is a p-phenylene group, a 4,4'-biphenylylene group, or a 4,4''-p-terphenylylene group; and the aryl group of the substituted or unsubstituted aryl group having 6 to 30 ring carbon atoms represented by Ar is selected from the following groups:

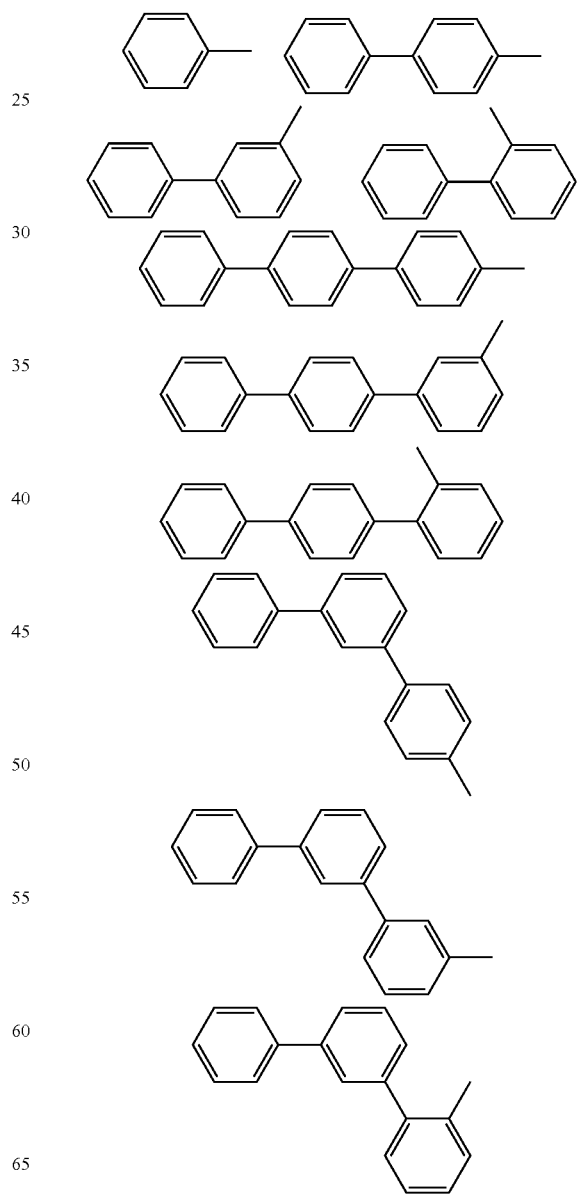

-continued

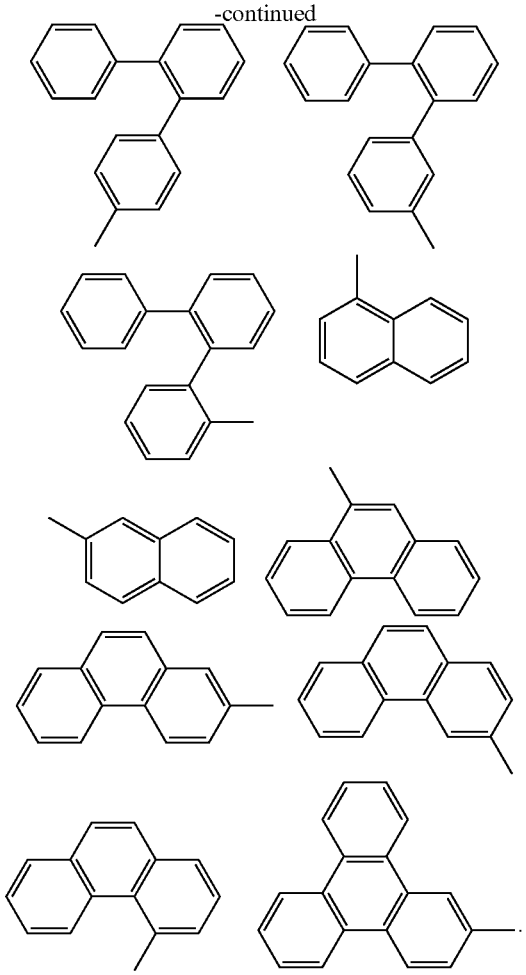

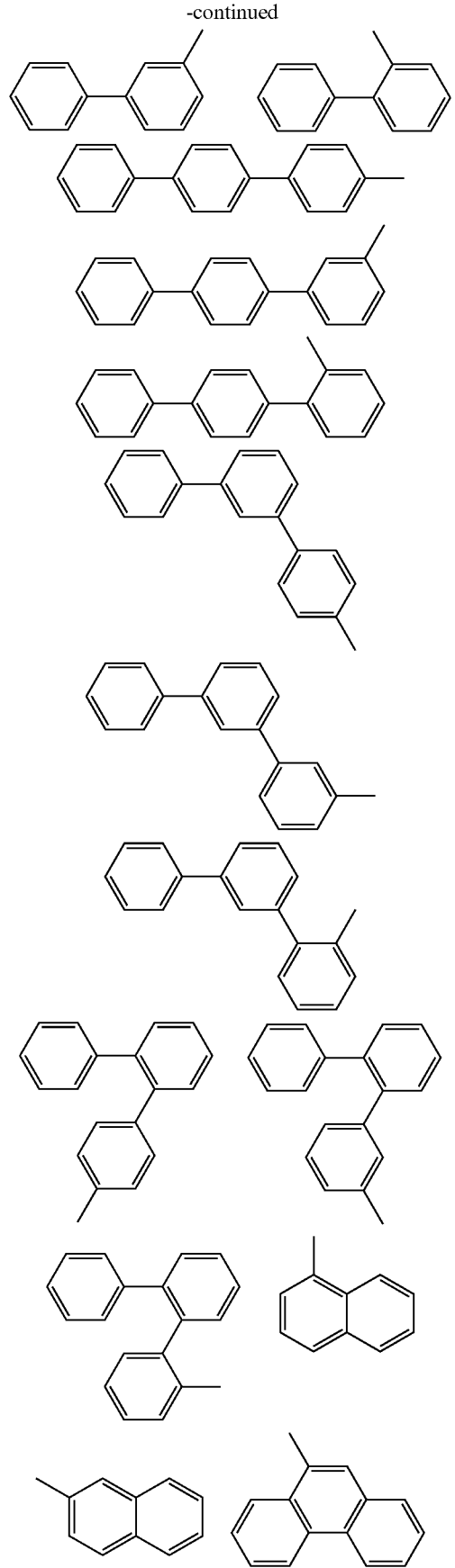

21. The compound according to claim 19, wherein:

the arylene group of the substituted or unsubstituted arylene group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group;

the arylene group of the substituted or unsubstituted arylene group having 6 to 18 ring carbon atoms represented by $L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group; and the aryl group of the substituted or unsubstituted aryl group having 6 to 30 ring carbon atoms represented by Ar is selected from the following groups:

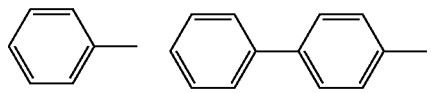

-continued

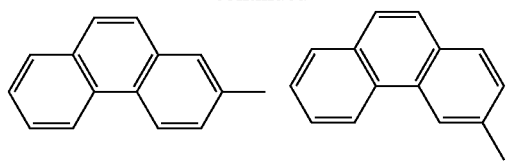

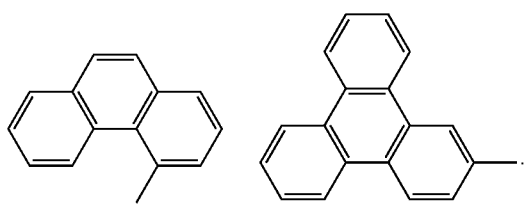

22. The compound according to claim 21, wherein the arylene group of the substituted or unsubstituted arylene group having 6 to 18 ring carbon atoms represented by $L^3$ is selected from the following arylene groups:

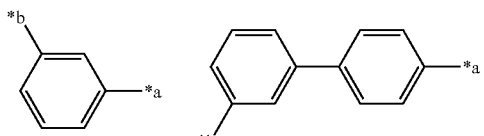

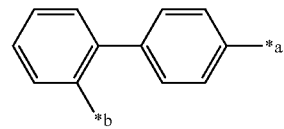

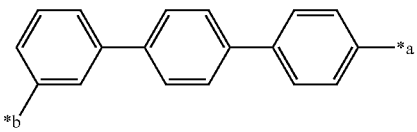

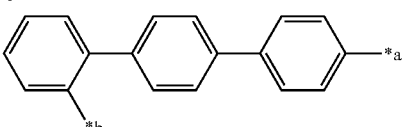

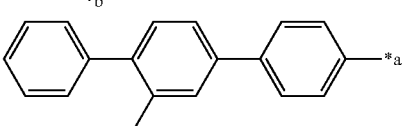

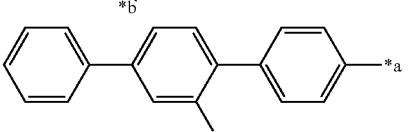

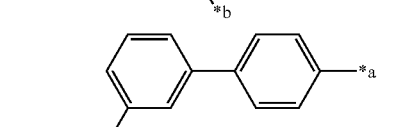

-continued

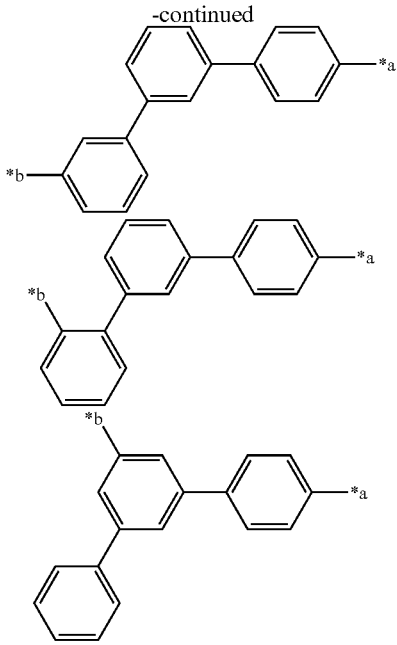

wherein *a is bonded to the central nitrogen atom, and *b is bonded to the nitrogen atom of the carbazole structure.

23. The compound according to claim 1, wherein a is 1, b is 1, and c is 1.

24. The compound according to claim 23, wherein:

the arylene group of the substituted or unsubstituted arylene group having 6 to 18 ring carbon atoms represented by $L^1$ is an o-phenylene group, a m-phenylene group, or a p-phenylene group;

the arylene group of the substituted or unsubstituted arylene group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group;

the arylene group of the substituted or unsubstituted arylene group having 6 to 18 ring carbon atoms represented by $L^3$ is a p-phenylene group, a 4,4'-biphenylylene group, or a 4,4"-p-terphenylylene group; and the aryl group of the substituted or unsubstituted aryl group having 6 to 30 ring carbon atoms represented by Ar is selected from the following groups:

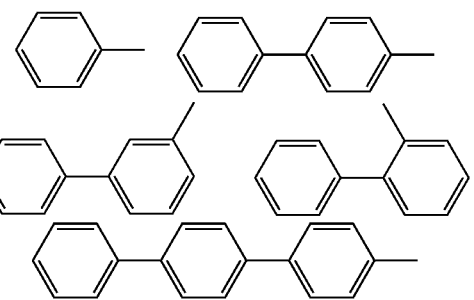

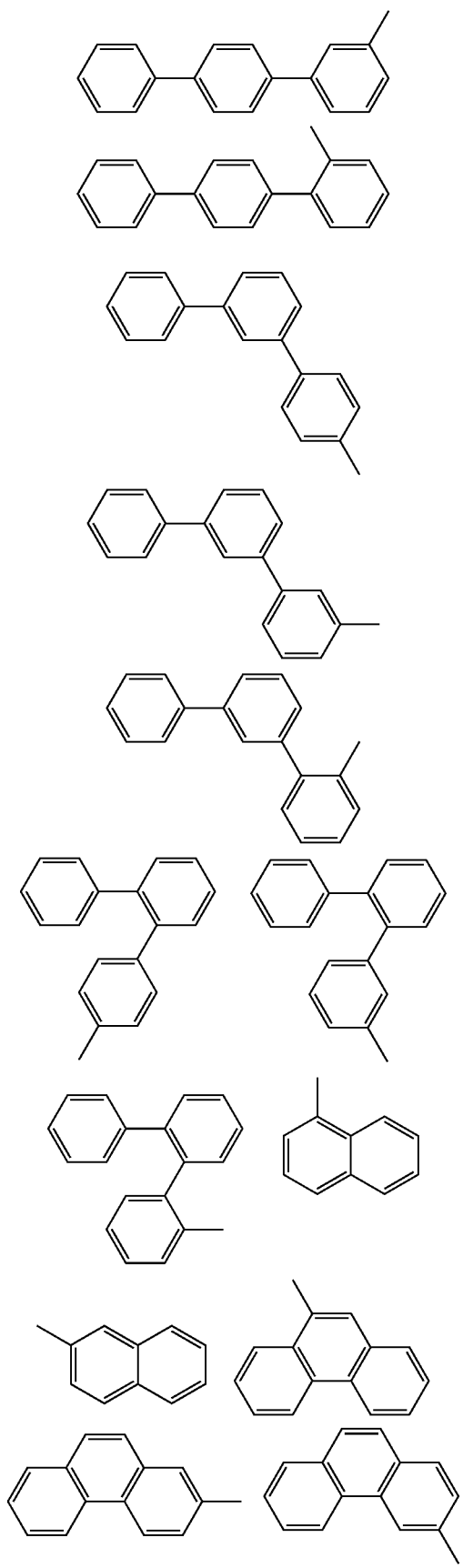

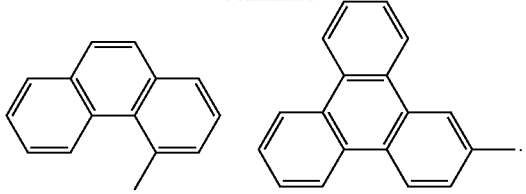

25. The compound according to claim 23, wherein:

the arylene group of the substituted or unsubstituted arylene group having 6 to 18 ring carbon atoms represented by $L^1$ is an o-phenylene group, a m-phenylene group, or a p-phenylene group;

the arylene group of the substituted or unsubstituted arylene group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group;

the arylene group of the substituted or unsubstituted arylene group having 6 to 18 ring carbon atoms represented by $L^3$ is a m-phenylene group, a 4,3'-biphenylylene group, a 4,2'-biphenylylene group, a 4,3"-p-terphenylylene group, a 4,2"-p-terphenylylene group, a 4,2'-p-terphenylylene group, a 4,3'-p-terphenylylene group, a 4,4"-m-terphenylylene group, a 4,3"-m-terphenylylene group, a 4,2"-m-terphenylylene group, or a 4,3'-m-terphenylylene group; and the aryl group of the substituted or unsubstituted aryl group having 6 to 30 ring carbon atoms represented by Ar is selected from the following groups:

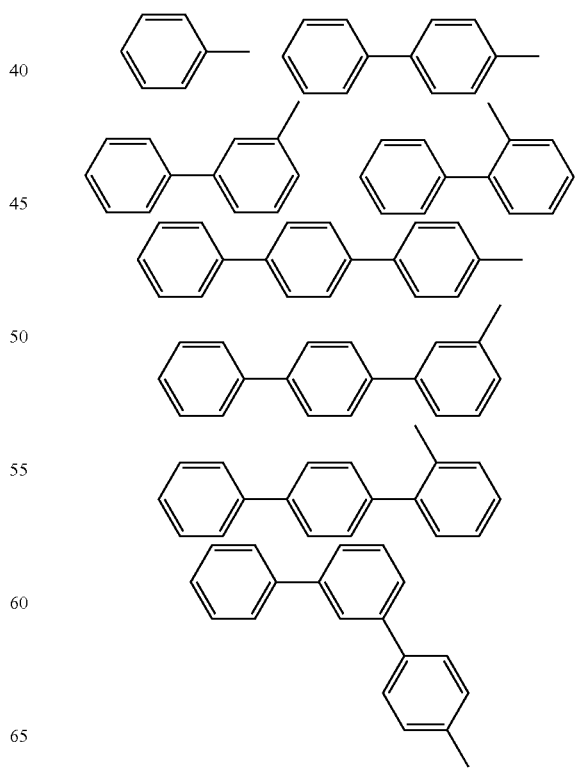

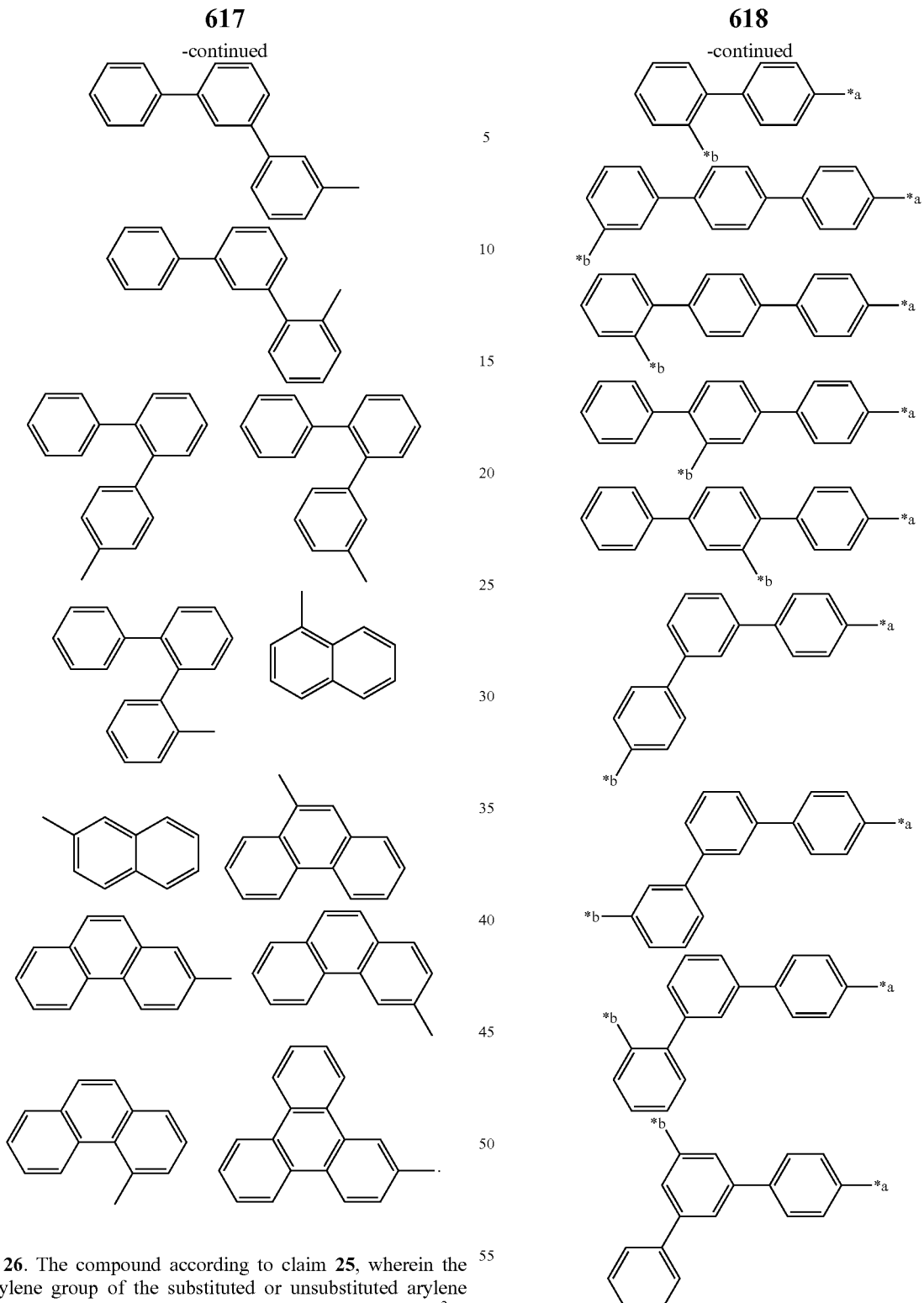

26. The compound according to claim 25, wherein the arylene group of the substituted or unsubstituted arylene group having 6 to 18 ring carbon atoms represented by $L^3$ is selected from the following arylene groups:

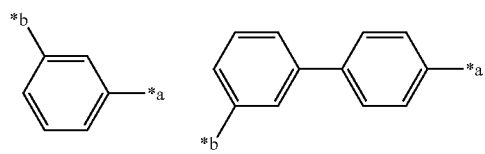

wherein *a is bonded to the central nitrogen atom, and *b is bonded to the nitrogen atom of the carbazole structure.

27. The compound according to claim 1, wherein $R^1$ to $R^7$ and $R^{11}$ to $R^{18}$ are hydrogen atoms.

28. A material for an organic electroluminescence device, the material comprising the compound according to claim 1.

29. An organic electroluminescence device, comprising a cathode, an anode, and an organic layer disposed between the cathode and the anode,
- wherein the organic layer comprises a light emitting layer and at least one layer of the organic layer comprises the compound according to claim 1.

30. The organic electroluminescence device according to claim 29, wherein the organic layer comprises a hole transporting region and the hole transporting region comprises the compound.

31. The organic electroluminescence device according to claim 29, wherein the hole transporting region comprises a first hole transporting layer at an anode side and a second hole transporting layer at a cathode side, and one or both of the first hole transporting layer and the second hole transporting layer comprises the compound.

32. An electronic device, comprising the organic electroluminescence device according to claim 29.

* * * * *